US011247965B2

(12) United States Patent
Burns et al.

(10) Patent No.: US 11,247,965 B2
(45) Date of Patent: Feb. 15, 2022

(54) HEPATITIS B CAPSID ASSEMBLY MODULATORS

(71) Applicant: VenatoRx Pharmaceuticals, Inc., Malvern, PA (US)

(72) Inventors: Christopher J. Burns, Malvern, PA (US); Glen Coburn, Bethel, CT (US); Bin Liu, Plainsboro, NJ (US); Jiangchao Yao, Princeton, NJ (US); Christopher Benetatos, Chester Springs, PA (US); Steven A. Boyd, Chester Springs, PA (US); Stephen M. Condon, Glenmoore, PA (US)

(73) Assignee: VENATORX PHARMACEUTICALS, INC., Malvern, PA (US)

( * ) Notice: Subject to any disclaimer, the term of this patent is extended or adjusted under 35 U.S.C. 154(b) by 0 days.

(21) Appl. No.: 16/771,387

(22) PCT Filed: Dec. 10, 2018

(86) PCT No.: PCT/US2018/064768
§ 371 (c)(1),
(2) Date: Jun. 10, 2020

(87) PCT Pub. No.: WO2019/118358
PCT Pub. Date: Jun. 20, 2019

(65) Prior Publication Data
US 2021/0171439 A1 Jun. 10, 2021

Related U.S. Application Data

(60) Provisional application No. 62/683,555, filed on Jun. 11, 2018, provisional application No. 62/597,370, filed on Dec. 11, 2017.

(51) Int. Cl.
| | |
|---|---|
| *C07C 233/64* | (2006.01) |
| *C07D 211/46* | (2006.01) |
| *C07D 307/66* | (2006.01) |
| *C07D 265/30* | (2006.01) |
| *C07D 309/14* | (2006.01) |
| *A61K 45/06* | (2006.01) |

(52) U.S. Cl.
CPC ............ *C07C 233/64* (2013.01); *A61K 45/06* (2013.01); *C07D 211/46* (2013.01); *C07D 265/30* (2013.01); *C07D 307/66* (2013.01); *C07D 309/14* (2013.01)

(58) Field of Classification Search
CPC ... C07C 233/64; C07D 211/46; C07D 307/66; C07D 265/30; C07D 309/14
See application file for complete search history.

(56) References Cited

U.S. PATENT DOCUMENTS

| | | |
|---|---|---|
| 10,590,076 B2 | 3/2020 | Burns et al. |
| 2009/0012075 A1 | 1/2009 | Miller et al. |
| 2015/0259324 A1 | 9/2015 | Hartman et al. |
| 2019/0292187 A1 | 9/2019 | Gutierrez et al. |
| 2020/0123105 A1 | 4/2020 | Burns et al. |

FOREIGN PATENT DOCUMENTS

| | | | |
|---|---|---|---|
| AU | 2005320134 B2 | 4/2011 | |
| WO | WO-2013006394 A1 | 1/2013 | |
| WO | WO-2015011281 A1 | 1/2015 | |
| WO | WO-2015118057 A1 | 8/2015 | |
| WO | WO-2017001655 A1 | 1/2017 | |
| WO | WO-2017156255 A1 | 9/2017 | |
| WO | WO-2018039531 A1 | 3/2018 | |
| WO | WO-2018121689 A1 * | 7/2018 | ........... C07D 231/16 |
| WO | WO-2019118358 A1 | 6/2019 | |
| WO | WO-2019165374 A1 | 8/2019 | |
| WO | WO-2019185016 A1 | 10/2019 | |
| WO | WO-2019223791 A1 | 11/2019 | |
| WO | WO-2019241292 A1 | 12/2019 | |
| WO | WO-2020156494 A1 | 8/2020 | |
| WO | WO-2021098850 A1 | 5/2021 | |
| WO | WO-2021119081 A1 | 6/2021 | |

OTHER PUBLICATIONS

PCT/US2018/64768 International Search Report and Written Opinion dated Apr. 29, 2019.
PCT/US2019/036611 International Search Report and Written Opinion dated Oct. 1, 2019.
PubChem CID 130421434. Created Oct. 7, 2017. Accessed Mar. 18, 2019 .
U.S. Appl. No. 16/438,361 Office Action dated Aug. 26, 2019.
CAS registry No. 894855-11-9; STN entry date: Jul. 20, 2006; Chemical name: 6-[(3R)-3-Amino-1-piperidinyl]-5-[(2-chlorophenyl)methyl]-N-cyclobutyl-2,3,4,5-tetrahydro-1,3-dimethyl-2,4-dioxo-1H-pyrrolo[3,2-d]pyrimidine-7-carboxamide whole document.
CAS registry No. 894855-18-6; STN entry date: Jul. 20, 2006; Chemical name: 6-[(3R)-3-Amino-1-piperidinyl]-5-[(2-chloro-5-fluorophenyl)methyl]-N-cyclopropyl-2,3,4,5-tetrahydro-1,3-dimethyl-2,4-dioxo-1H-pyrrolo[3,2-d]pyrimidine-7-carboxamide whole document.
CAS registry No. 894855-20-0; STN entry date: Jul. 20, 2006; Chemical name: 6-[(3R)-3-Amino-1-piperidinyl]-5-[(2-chloro-5-fluorophenyl)methyl]-N-cyclobutyl-2,3,4,5-tetrahydro-1,3-dimethyl-2,4-dioxo-1H-pyrrolo[3,2-d]pyrimidine-7-carboxamide whole document.

(Continued)

*Primary Examiner* — Matthew P Coughlin
(74) *Attorney, Agent, or Firm* — Wilson Sonsini Goodrich & Rosati

(57) ABSTRACT

Described herein are hepatitis B capsid assembly modulators and pharmaceutical compositions comprising said compounds. The subject compounds and compositions are useful for the treatment of hepatitis B.

18 Claims, No Drawings
Specification includes a Sequence Listing.

(56) References Cited

OTHER PUBLICATIONS

CAS registry No. 894855-23-3; STN entry date: Jul. 20, 2006; Chemical name: 6-[(3R)-3-Amino-1-piperidinyl]-5-[(2-chloro-5-fluorophenyl)methyl]-2,3,4,5-tetrahydro-N-(3-hydroxytricyclo[3.3.1.13,7]dec-1-yl)-1,3-dimethyl-2,4-dioxo-1H-pyrrolo[3,2-d]pyrimidine-7-carboxamide.
CAS registry No. 894855-25-5; STN entry date: Jul. 20, 2006; Chemical name: 6-[(3R)-3-Amino-1-piperidinyl]-5-[(2-cyanophenyl)methyl]-N-cyclobutyl-2,3,4,5-tetrahydro-1,3-dimethyl-2,4-dioxo-1H-pyrrolo[3,2-d]pyrimidine-7-carboxamide whole document.
CAS registry No. 894855-26-6; STN entry date: Jul. 20, 2006; Chemical name: 6-[(3R)-3-Amino-1-piperidinyl]-5-[(2-cyanophenyl)methyl]-N-cyclobutyl-2,3,4,5-tetrahydro-1,3-dimethyl-2,4-dioxo-1H-pyrrolo[3,2-d]pyrimidine-7-carboxamide whole document.
CAS registry No. 894855-28-8; STN entry date: Jul. 20, 2006; Chemical name: 6-[(3R)-3-Amino-1-piperidinyl]-5-(2-butyn-1-yl)-N-cyclopropyl-2,3,4,5-tetrahydro-1,3-dimethyl-2,4-dioxo-1H-pyrrolo[3,2-d]pyrimidine-7-carboxamide.
Okamoto et al.: Intramolecular cyclization of 6-amino-5-[(2-substituted-2-(cyanovinyl) amino]-1,3-dimethyluracil: synthesis of 9-deazaxanthine derivatives and 8-(cyanomethyl) theophylline. The Journal of Organic Chemistry 49(5):908-912 (1984).
PCT/US2020/063936 International Search Report and Written Opinion dated Mar. 12, 2021.
PCT/US2021/020397 International Search Report and Written Opinion dated May 14, 2021.
U.S. Appl. No. 16/671,815 Office Action dated Oct. 15, 2020.

\* cited by examiner

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic probe

<400> SEQUENCE: 1
ttggtgtctt tcggagtgtg            20

<210> SEQ ID NO 2
<211> LENGTH: 20
<212> TYPE: DNA
<213> ORGANISM: Artificial Sequence
<220> FEATURE:
<223> OTHER INFORMATION: Synthetic probe

<400> SEQUENCE: 2
aggggcattt ggtggtctat            20

HEPATITIS B CAPSID ASSEMBLY MODULATORS

CROSS-REFERENCE

This patent application is a national stage entry of PCT/US2018/064768, filed on Dec. 10, 2018, which claims the benefit of U.S. Provisional Application No. 62/597,370, filed Dec. 11, 2017 and U.S. Provisional Application No. 62/683,555, filed Jun. 11, 2018; each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 20, 2021, is named 41223-724_831_SL_ST25txt and is 745 bytes in size.

BACKGROUND OF THE INVENTION

The present invention relates to small-molecule compounds that modulate capsid assembly and block hepatitis B virus (HBV) replication with the potential to be used as a monotherapy or in combination with other antivirals for the treatment of chronic HBV infection.

HBV is a small enveloped DNA virus belonging to the Hepadnaviridae family that is distributed worldwide as ten geographically distinct genotypes. Infection with HBV is typically self-limiting in otherwise healthy adults; however, vertical transmission or exposure during early childhood often results in a chronic lifelong infection. Worldwide there are an estimated >400 million individuals chronically infected with HBV that are at risk for complications due to liver disease, including cirrhosis, fibrosis, hepatocellular carcinoma and death. Each year 500,000 to 1 million people die from end stage liver disease as a consequence of HBV infection The compact HBV genome utilizes four overlapping reading frames to encode the major structural and non-structural proteins: polymerase (F), envelope (S), core (C) and the X protein (X). HBV enters human hepatocytes via receptor mediated endocytosis, following binding of the envelope glycoprotein to its primary receptor, the bile acid transporter sodium taurocholate co-transporting polypeptide (NTCP). Following fusion with the endosome membrane, the capsid is ejected into the cytoplasm and translocated to the nucleus. The partially double-stranded, relaxed, circular HBV genome (RC DNA) is converted to a covalently closed circular DNA form (cccDNA) by host cellular DNA repair mechanisms. The HBV cccDNA serves as the template for RNA polymerase II-dependent transcription of multiple RNA species, including viral mRNAs and the 3.2-kbp pre-genomic RNA (pgRNA). During the maturation process, pgRNA is packaged into capsids along with the HBV polymerase. The pgRNA is then reverse transcribed into a negative-stranded DNA template that is subsequently converted into the partially double-stranded RC DNA species by the polymerase. Mature, enveloped HBV particles containing the RC DNA genome are secreted from the surface of the infected hepatocyte ready to initiate new cycles of infection.

The capsid is composed of 240 copies of the core protein that spontaneously self-assemble through a network of weak inter-subunit interactions. In vitro evidence suggests that a trimer of core dimers initiates the nucleation event that rapidly recruits additional dimers to form the icosahedral core structure (T=4). In addition to its structural role, encapsidation of the pgRNA is an essential step required for HBV DNA synthesis and formation of the mature capsid particle. The core protein also plays an important role in shuttling the RC DNA into the nucleus to initiate and maintain the cccDNA pools and may also play a role in regulating interferon sensitive gene expression. Thus, capsid modulators may have the unique ability to intervene at multiple points in the HBV lifecycle.

Several chemotype series of HBV capsid assembly modulators have been reported in the literature including: phenylpropenamides (PP) (e.g., AT-130), heteroarylpyrimidines (HAP) (e.g. Bay 41-4109), and sulfamoylbenzamides (SBA) (e.g. NVR 3-778). Capsid modulators exert their effects on the assembly process through one of two different mechanisms of action. The HAP series induces the aberrant assembly of large capsid aggregates that subsequently triggers the degradation of the core protein. The PP and SBA series, on the other hand, appear to accelerate capsid assembly resulting in the production of authentic empty capsid particles that have failed to incorporate pgRNA. Assembly modulators representing both mechanisms have demonstrated the ability to reduce HBV DNA levels in mouse models of infection. More recently, NVR 3-778 (SBA) demonstrated clinical proof-of-concept in a Phase 1b clinical trial, resulting in a −1.7 log 10 reduction in HBV DNA following 600 mg bid dosing for 29 days.

SUMMARY OF THE INVENTION

Described herein are compounds of Formula (I) and (II) that modulate the normal capsid assembly of hepatitis B core proteins to inhibit the hepatitis B lifecycle, and thus act as antiviral agents toward HBV.

Described herein is a compound of Formula (II), or a pharmaceutically acceptable salt, solvate, or stereoisomer thereof:

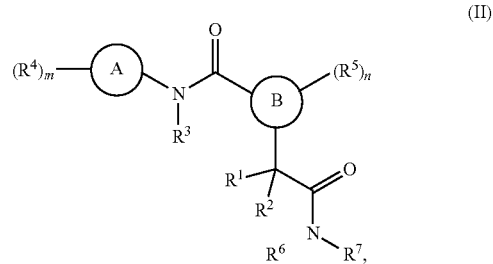

wherein:
Ring A is aryl, heteroaryl, cycloalkyl, or heterocycloalkyl;
Ring B is

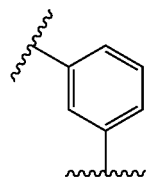 [SMILES: *c1cccc(*)c1]

or $C_{2-5}$heteroaryl;
$R^1$ is —F, —Cl, —OH, or —OR$^a$;
$R^2$ is hydrogen, —F, —Cl, —CN, —OR$^a$, $C_{1-6}$alkyl, $C_{1-6}$haloalkyl, $C_{1-6}$hydroxyalkyl, $C_{1-6}$heteroalkyl, or $C_{3-8}$cycloalkyl;
$R^3$ is hydrogen or $C_{1-6}$alkyl;

each $R^4$ is independently halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^a$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_{1-6}$alkyl, $C_{1-6}$haloalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three $R^{12}$;

or two $R^4$ on adjacent atoms are taken together with the atoms to which they are attached to form a carbocycle ring or a heterocycle ring; each optionally substituted with one, two, or three $R^{12}$;

each $R^5$ is independently hydrogen, halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_{1-6}$alkyl, $C_{1-6}$haloalkyl, $C_{1-6}$hydroxyalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three $R^{13}$;

or two $R^5$ on adjacent atoms are taken together with the atoms to which they are attached to form a carbocycle ring or a heterocycle ring; each optionally substituted with one, two, or three $R^{13}$;

$R^6$ and $R^7$ are each independently hydrogen, $C_{1-6}$alkyl, $C_{1-6}$alkoxy, $C_{2-6}$alkenyl, $C_{2-6}$alkynyl, $C_{3-15}$cycloalkyl, $C_{2-15}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkoxy, alkenyl, alkynyl, cycloalkyl, heterocycloalkyl, aryl, and heteroaryl is independently optionally substituted with one, two, or three $R^{10}$;

or $R^6$ and $R^7$ are taken together with the nitrogen atom to which they are attached to form a $C_{2-15}$heterocycloalkyl or a $C_{2-15}$heterocycloalkenyl; wherein each heterocycloalkyl and heterocycloalkenyl is independently optionally substituted with one, two, or three $R^{11}$;

m is an integer from 0 to 5;

n is an integer from 0 to 4;

each $R^{10}$ is independently oxo, halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, —B(OR$^d$)$_2$, $C_{1-6}$alkyl, $C_{1-6}$haloalkyl, $C_{1-6}$hydroxyalkyl, $C_{1-6}$heteroalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl);

each $R^{11}$ is independently oxo, halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —NR$^b$S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —CH$_2$C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, —NR$^b$C(=O)CH$_2$NR$^b$R$^c$, —C(=O)CH$_2$NR$^b$C(=O)NR$^b$R$^c$, —OP(=O)(OR$^b$)(OR$^b$), —B(OR$^d$)$_2$, $C_{1-6}$alkyl, $C_{1-6}$haloalkyl, $C_{1-6}$hydroxyalkyl, $C_{1-6}$heteroalkyl, $C_{1-6}$cyanoalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl);

each $R^{12}$ and $R^{13}$ is independently halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^a$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_{1-6}$alkyl, $C_{1-6}$haloalkyl, $C_{1-6}$hydroxyalkyl, $C_{1-6}$heteroalkyl, or $C_{3-8}$cycloalkyl;

each $R^a$ is independently $C_{1-6}$alkyl, $C_{2-6}$alkenyl, $C_{2-6}$alkynyl, $C_{1-6}$haloalkyl, $C_{1-6}$hydroxyalkyl, $C_{1-6}$heteroalkyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three oxo, halogen, —OH, $C_{1-6}$alkyl, or $C_{1-6}$haloalkyl;

each $R^b$ and $R^c$ is independently hydrogen, $C_{1-6}$alkyl, $C_{2-6}$alkenyl, $C_{2-6}$alkynyl, $C_{1-6}$haloalkyl, $C_{1-6}$hydroxyalkyl, $C_{1-6}$heteroalkyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three oxo, halogen, —OH, $C_{1-6}$alkyl, or $C_{1-6}$haloalkyl;

or $R^b$ and $R^c$ are taken together with the nitrogen atom to which they are attached to form a $C_{2-7}$heterocycloalkyl optionally substituted with one, two, or three oxo, halogen, —OH, $C_{1-6}$alkyl, or $C_{1-6}$haloalkyl; and each $R^d$ is independently hydrogen or $C_{1-6}$alkyl;

or two $R^d$ are taken together to form a $C_{2-7}$heterocycloalkyl optionally substituted with one, two, or three halogen, —OH, or $C_{1-6}$alkyl.

Described herein is a pharmaceutical composition comprising a compound of Formula (II), or a pharmaceutically acceptable salt, solvate, or stereoisomer thereof, and a pharmaceutically acceptable excipient. Described herein is a method of treating an infection in a subject, comprising administering to the subject a compound of Formula (II), or a pharmaceutically acceptable salt, solvate, or stereoisomer thereof. Described herein is a method of treating an infection in a subject, comprising administering to the subject a pharmaceutical composition comprising a compound of Formula (II), or a pharmaceutically acceptable salt, solvate, or stereoisomer thereof, and a pharmaceutically acceptable excipient.

Also described herein is a method of treating an infection in a subject, comprising administering to the subject a compound of Formula (I), or a pharmaceutically acceptable salt, solvate, or stereoisomer thereof:

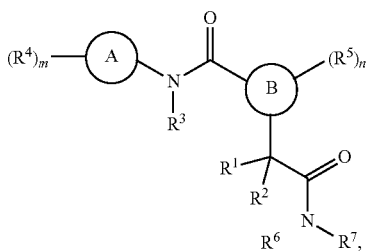

(I)

wherein:
Ring A is aryl, heteroaryl, cycloalkyl, or heterocycloalkyl;
Ring B is aryl or heteroaryl;
$R^1$ is —F, —Cl, —OH, or —OR;
$R^2$ is hydrogen, —F, —Cl, —CN, —OR$^a$, $C_{1-6}$alkyl, $C_{1-6}$haloalkyl, $C_{1-6}$hydroxyalkyl, $C_{1-6}$heteroalkyl, or $C_{3-8}$cycloalkyl;
$R^3$ is hydrogen or $C_{1-6}$alkyl;
each $R^4$ is independently halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^a$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_{1-6}$alkyl, $C_{1-6}$haloalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three $R^{12}$;
or two $R^4$ on adjacent atoms are taken together with the atoms to which they are attached to form a carbocycle ring or a heterocycle ring; each optionally substituted with one, two, or three $R^{12}$;
each $R^5$ is independently hydrogen, halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_{1-6}$alkyl, $C_{1-6}$haloalkyl, $C_{1-6}$hydroxyalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three $R^{13}$;
or two $R^5$ on adjacent atoms are taken together with the atoms to which they are attached to form a carbocycle ring or a heterocycle ring; each optionally substituted with one, two, or three $R^{13}$;
$R^6$ and $R$ are each independently hydrogen, $C_{1-6}$alkyl, $C_{1-6}$alkoxy, $C_{2-6}$alkenyl, $C_{2-6}$alkynyl, $C_{3-15}$cycloalkyl, $C_{2-15}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkoxy, alkenyl, alkynyl, cycloalkyl, heterocycloalkyl, aryl, and heteroaryl is independently optionally substituted with one, two, or three $R^{10}$;
or $R^6$ and $R^7$ are taken together with the nitrogen atom to which they are attached to form a $C_{2-15}$heterocycloalkyl or a $C_{2-15}$heterocycloalkenyl; wherein each heterocycloalkyl and heterocycloalkenyl is independently optionally substituted with one, two, or three $R^{11}$;
m is an integer from 0 to 5;
n is an integer from 0 to 4;
each $R^1$ is independently oxo, halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^a$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, —B(OR$^d$)$_2$, $C_{1-6}$alkyl, $C_{1-6}$haloalkyl, $C_{1-6}$hydroxyalkyl, $C_{1-6}$heteroalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl);
each $R^{11}$ is independently oxo, halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —NR$^b$S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —CH$_2$C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, —B(OR$^d$)$_2$, —OP(=O)(OR)(OR), $C_{1-6}$alkyl, $C_{1-6}$haloalkyl, $C_{1-6}$hydroxyalkyl, $C_{1-6}$heteroalkyl, $C_{1-6}$cyanoalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl);
each $R^{12}$ and $R^{13}$ is independently halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^a$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_{1-6}$alkyl, $C_{1-6}$haloalkyl, $C_{1-6}$hydroxyalkyl, $C_{1-6}$heteroalkyl, or $C_{3-8}$cycloalkyl;
each $R^a$ is independently $C_{1-6}$alkyl, $C_{2-6}$alkenyl, $C_{2-6}$alkynyl, $C_{1-6}$haloalkyl, $C_{1-6}$hydroxyalkyl, $C_{1-6}$heteroalkyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three oxo, halogen, —OH, $C_{1-6}$alkyl, or $C_{1-6}$haloalkyl;
each $R^b$ and $R^c$ is independently hydrogen, $C_{1-6}$alkyl, $C_{2-6}$alkenyl, $C_{2-6}$alkynyl, $C_{1-6}$haloalkyl, $C_{1-6}$hydroxyalkyl, $C_{1-6}$heteroalkyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three oxo, halogen, —OH, $C_{1-6}$alkyl, or $C_{1-6}$haloalkyl;
or $R^b$ and $R^c$ are taken together with the nitrogen atom to which they are attached to form a $C_{2-7}$heterocycloalkyl optionally substituted with one, two, or three oxo, halogen, —OH, $C_{1-6}$alkyl, or $C_{1-6}$haloalkyl; and
each $R^d$ is independently hydrogen or $C_{1-6}$alkyl;
or two $R^d$ are taken together to form a $C_{2-7}$heterocycloalkyl optionally substituted with one, two, or three halogen, —OH, or $C_{1-6}$alkyl.

INCORPORATION BY REFERENCE

All publications, patents, and patent applications mentioned in this specification are herein incorporated by ref-

DETAILED DESCRIPTION OF THE INVENTION

Chronic hepatitis B infection (CHB) is currently managed with interferon-alpha or nucleoside(tide) analog-based therapies that target the HBV encoded polymerase/reverse transcriptase. The effectiveness of interferon-alpha is limited by inadequate long term responses and severe side effects, while entecavir and tenofovir, are generally well-tolerated, possess a high barrier to resistance and potently suppress viral replication. None of the aforementioned frontline therapies are curative, however, and expensive lifelong therapy is required to maintain a virologic response and prevent the complications associated with liver disease. Novel therapies representing different treatment classes are therefore urgently required to improve functional cure rates (i.e. defined as the loss of HBsAg expression) and shorten treatment durations. Modulators of HBV capsid assembly represent one such class of antivirals with the potential to improve outcomes for chronically infected individuals.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Alkyl" refers to an optionally substituted straight-chain, or optionally substituted branched-chain saturated hydrocarbon monoradical having from one to about ten carbon atoms, more preferably one to six carbon atoms, wherein a sp3-hybridized carbon of the alkyl residue is attached to the rest of the molecule by a single bond. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_{1-10}$alkyl. In some embodiments, the alkyl is a $C_{1-6}$alkyl. In some embodiments, the alkyl is a $C_{1-5}$alkyl. In some embodiments, the alkyl is a $C_{1-4}$alkyl. In some embodiments, the alkyl is a $C_{1-3}$alkyl. Unless stated otherwise specifically in the specification, an alkyl group may be optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —OH, —OMe, —NH$_2$, or —NO$_2$. In some embodiments, the alkyl is optionally substituted with halogen, —CN, —OH, or —OMe. In some embodiments, the alkyl is optionally substituted with halogen.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms, wherein an sp2-hybridized carbon of the alkenyl residue is attached to the rest of the molecule by a single bond. The group may be in either the cis or trans conformation about the double bond(s), and should be understood to include both isomers. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "$C_2$-$C_6$ alkenyl" or "$C_{2-6}$alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkenyl is optionally substituted with oxo, halogen, —CN, —OH, —OMe, —NH$_2$, or —NO$_2$. In some embodiments, the alkenyl is optionally substituted with halogen, —CN, —OH, or —OMe. In some embodiments, the alkenyl is optionally substituted with halogen.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkynyl is optionally substituted with oxo, halogen, —CN, —OH, —OMe, —NH$_2$, or —NO$_2$. In some embodiments, the alkynyl is optionally substituted with halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkylene is optionally substituted with oxo, halogen, —CN, —OH, —OMe, —NH$_2$, or —NO$_2$. In some embodiments, the alkylene is optionally substituted with halogen, —CN, —OH, or —OMe. In some embodiments, the alkylene is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkoxy is optionally substituted with halogen, —CN, —OH, —OMe, —NH$_2$, or —NO$_2$. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted as described below, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, the aryl is optionally substituted with halogen, methyl, ethyl, —CN, —CF$_3$, —OH, —OMe, —NH$_2$, or —NO$_2$. In some embodiments, the aryl is optionally substituted with halogen, methyl, ethyl, —CN, —CF$_3$, —OH, or —OMe. In some embodiments, the aryl is optionally substituted with halogen.

"Carbocycle" refers to a saturated, a partially unsaturated, or a fully unsaturated carbocyclic ring. Carbocycles include cycloalkyls, cycloalkenyls, and aryls.

"Cycloalkyl" refers to a fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms (C$_3$-C$_{15}$ cycloalkyl), from three to ten carbon atoms (C$_3$-C$_{10}$ cycloalkyl), from three to eight carbon atoms (C$_3$-C$_8$ cycloalkyl), from three to six carbon atoms (C$_3$-C$_6$ cycloalkyl), from three to five carbon atoms (C$_3$-C$_5$ cycloalkyl), or three to four carbon atoms (C$_3$-C$_4$ cycloalkyl). Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Unless stated otherwise specifically in the specification, a cycloalkyl may be optionally substituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, the cycloalkyl is optionally substituted with oxo, halogen, methyl, ethyl, —CN, —CF$_3$, —OH, —OMe, —NH$_2$, or —NO$_2$. In some embodiments, the cycloalkyl is optionally substituted with halogen, methyl, ethyl, —CN, —CF$_3$, —OH, or —OMe. In some embodiments, the cycloalkyl is optionally substituted with halogen.

"Cycloalkenyl" refers to a partially unsaturated, monocyclic or polycyclic carbocyclic ring, which may include fused (when fused with an aryl or a heteroaryl ring, the cycloalkenyl is bonded through a non-aromatic ring atom) or bridged ring systems. Representative cycloalkenyl include, but are not limited to, cycloalkenyls having from three to fifteen carbon atoms (C$_3$-C$_{15}$ cycloalkenyl), from three to ten carbon atoms (C$_3$-C$_{10}$ cycloalkenyl), from three to eight carbon atoms (C$_3$-C$_8$ cycloalkenyl), from three to six carbon atoms (C$_3$-C$_6$ cycloalkenyl), from three to five carbon atoms (C$_3$-C$_5$ cycloalkenyl), four to six carbon atoms (C$_4$-C$_6$ cycloalkenyl), four to eight carbon atoms (C$_4$-C$_8$ cycloalkenyl), or four to ten carbon atoms (C$_4$-C$_{10}$ cycloalkenyl). Monocyclic cycloalkenyl include, for example, cyclopentene, cyclohexene, cycloheptene, cyclopentadiene, cyclohexadiene, cycloheptadiene, and cycloheptatriene. Unless stated otherwise specifically in the specification, a cycloalkenyl may be optionally substituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, the cycloalkenyl is optionally substituted with oxo, halogen, methyl, ethyl, —CN, —CF$_3$, —OH, —OMe, —NH$_2$, or —NO$_2$. In some embodiments, the cycloalkenyl is optionally substituted with halogen, methyl, ethyl, —CN, —CF$_3$, —OH, or —OMe. In some embodiments, the cycloalkenyl is optionally substituted with halogen.

"Halo" or "halogen" refers to bromo, chloro, fluoro or iodo. In some embodiments, halogen is fluoro or chloro. In some embodiments, halogen is fluoro.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, or combinations thereof. A heteroalkyl is attached to the rest of the molecule at a carbon atom of the heteroalkyl. In one aspect, a heteroalkyl is a C$_1$-C$_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$CH$_3$, or —CH(CH$_3$)OCH$_3$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Heterocycle ring" refers to a saturated, a partially unsaturated, or a fully unsaturated heterocarbocyclic ring. Heterocycles include heterocycloalkyls, heterocycloalkenyls, and heteroaryls. In some embodiments, the heterocycle comprises one to three heteroatoms selected from the group consisting of nitrogen, oxygen, and sulfur. In some embodiments, the heterocycle comprises one to three heteroatoms selected from the group consisting of nitrogen and oxygen. In some embodiments, the heterocycle comprises one to three nitrogens. In some embodiments, the heterocycle comprises one or two nitrogens.

"Heterocycloalkyl" refers to a stable 3- to 24-membered fully saturated ring radical comprising 2 to 23 carbon atoms and from one to 8 heteroatoms selected from the group consisting of nitrogen, oxygen, phosphorous and sulfur. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms ($C_2$-$C_{15}$ heterocycloalkyl), from two to ten carbon atoms ($C_2$-$C_{10}$ heterocycloalkyl), from two to eight carbon atoms ($C_2$-$C_8$ heterocycloalkyl), from two to seven carbon atoms ($C_2$-$C_7$ heterocycloalkyl), from two to six carbon atoms ($C_2$-$C_6$ heterocycloalkyl), from two to five carbon atoms ($C_2$-$C_5$ heterocycloalkyl), or two to four carbon atoms ($C_2$-$C_4$ heterocycloalkyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, the heterocycloalkyl is optionally substituted with oxo, halogen, methyl, ethyl, —CN, —CF$_3$, —OH, —OMe, —NH$_2$, or —NO$_2$. In some embodiments, the heterocycloalkyl is optionally substituted with halogen, methyl, ethyl, —CN, —CF$_3$, —OH, or —OMe. In some embodiments, the heterocycloalkyl is optionally substituted with halogen.

"Heterocycloalkenyl" refers to a stable 3- to 24-membered partially unsaturated ring radical comprising 2 to 23 carbon atoms and from one to 8 heteroatoms selected from the group consisting of nitrogen, oxygen, phosphorous and sulfur. In some embodiments, the heterocycloalkenyl comprises one to three heteroatoms selected from the group consisting of nitrogen, oxygen, and sulfur. In some embodiments, the heterocycloalkenyl comprises one to three heteroatoms selected from the group consisting of nitrogen and oxygen. In some embodiments, the heterocycloalkenyl comprises one to three nitrogens. In some embodiments, the heterocycloalkenyl comprises one or two nitrogens. Unless stated otherwise specifically in the specification, the heterocycloalkenyl may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkenyl radical may be optionally oxidized; the nitrogen atom may be optionally quaternized. Representative heterocycloalkenyls include, but are not limited to, heterocycloalkenyls having from two to fifteen carbon atoms ($C_2$-$C_{15}$ heterocycloalkenyl), from two to ten carbon atoms ($C_2$-$C_{10}$ heterocycloalkenyl), from two to eight carbon atoms ($C_2$-$C_8$ heterocycloalkenyl), from two to seven carbon atoms ($C_2$-$C_7$ heterocycloalkenyl), from two to six carbon atoms ($C_2$-$C_6$ heterocycloalkenyl), from two to five carbon atoms ($C_2$-$C_5$ heterocycloalkenyl), or two to four carbon atoms ($C_2$-$C_4$ heterocycloalkenyl). Examples of such heterocycloalkenyls include, but are not limited to, 2,3-dihydro-H-pyrrole, 1,2,3,6-tetrahydropyridine, 1,2-dihydropyridine, 1,2,3,4-tetrahydropyrazine, and 3,4-dihydro-2H-1, 4-oxazine. Unless otherwise noted, heterocycloalkenyls have from 2 to 10 carbons in the ring. It is understood that when referring to the number of carbon atoms in a heterocycloalkenyl, the number of carbon atoms in the heterocycloalkenyl is not the same as the total number of atoms (including the heteroatoms) that make up the heterocycloalkenyl (i.e. skeletal atoms of the heterocycloalkenyl ring). In some embodiments, the heterocycloalkenyl is a 3- to 8-membered heterocycloalkenyl. In some embodiments, the heterocycloalkenyl is a 3- to 7-membered heterocycloalkenyl. In some embodiments, the heterocycloalkenyl is a 3- to 6-membered heterocycloalkenyl. In some embodiments, the heterocycloalkenyl is a 4- to 6-membered heterocycloalkenyl. In some embodiments, the heterocycloalkenyl is a 5- to 6-membered heterocycloalkenyl. Unless stated otherwise specifically in the specification, a heterocycloalkenyl may be optionally substituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, the heterocycloalkenyl is optionally substituted with oxo, halogen, methyl, ethyl, —CN, —CF$_3$, —OH, —OMe, —NH$_2$, or —NO$_2$. In some embodiments, the heterocycloalkenyl is optionally substituted with halogen, methyl, ethyl, —CN, —CF$_3$, —OH, or —OMe. In some embodiments, the heterocycloalkenyl is optionally substituted with halogen.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted as described below, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, the heteroaryl is optionally substituted with halogen, methyl, ethyl, —CN, —CF$_3$, —OH, —OMe, —NH$_2$, or —NO$_2$. In some embodiments, the heteroaryl is optionally substituted with halogen, methyl, ethyl, —CN, —CF$_3$, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition. In some embodiments, treatment also includes prophylactic treatment (e.g., administration of a composition described herein when an individual is suspected to be suffering from a viral infection).

Compounds

Described herein are compounds of Formula (I) and Formula (II), or a pharmaceutically acceptable salt, solvate, or stereoisomer thereof useful in the treatment of viral infections. In some embodiments, the viral infection is a chronic hepatitis B infection.

Provided herein is a compound having the structure of Formula (I), or a pharmaceutically acceptable salt, solvate, or stereoisomer thereof:

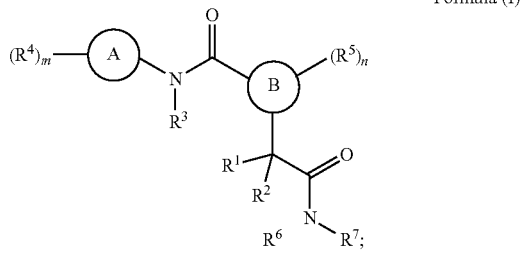

Formula (I)

wherein:
Ring A is aryl, heteroaryl, cycloalkyl, or heterocycloalkyl;
Ring B is aryl or heteroaryl;
$R^1$ is —F, —Cl, —OH, or —$OR^a$;
$R^2$ is hydrogen, —F, —Cl, —CN, —$OR^a$, $C_{1-6}$alkyl, $C_{1-6}$haloalkyl, $C_{1-6}$hydroxyalkyl, $C_{1-6}$heteroalkyl, or $C_{3-8}$cycloalkyl;
$R^3$ is hydrogen or $C_{1-6}$alkyl;
each $R^4$ is independently halogen, —CN, —OH, —$OR^a$, —SH, —$SR^a$, —S(=O)$R^a$, —$NO_2$, —$NR^bR^c$, —S(=O)$_2R^a$, —NHS(=O)$_2R^a$, —S(=O)$_2NR^bR^c$, —C(=O)$R^a$, —OC(=O)$R^a$, —C(=O)$OR^a$, —OC(=O)$OR^b$, —C(=O)$NR^bR^c$, —OC(=O)$NR^bR^c$, —$NR^bC(=O)NR^bR^c$, —$NR^bC(=O)R^a$, —$NR^bC(=O)OR^b$, $C_{1-6}$alkyl, $C_{1-6}$haloalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three $R^{12}$;
or two $R^4$ on adjacent atoms are taken together with the atoms to which they are attached to form a carbocycle ring or a heterocycle ring; each optionally substituted with one, two, or three $R^{12}$;
each $R^5$ is independently hydrogen, halogen, —CN, —OH, —$OR^a$, —SH, —$SR^a$, —S(=O)$R^a$, —$NO_2$, —$NR^bR^c$, —S(=O)$_2R^a$, —NHS(=O)$_2R^a$, —S(=O)$_2NR^bR^c$, —C(=O)$R^a$, —OC(=O)$R^a$, —C(=O)$OR^b$, —OC(=O)$OR^b$, —C(=O)$NR^bR^c$, —OC(=O)$NR^bR^c$, —$NR^bC(=O)NR^bR^c$, —$NR^bC(=O)R^a$, —$NR^bC(=O)OR^b$, $C_{1-6}$alkyl, $C_{1-6}$haloalkyl, $C_{1-6}$hydroxyalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three $R^{13}$;
or two $R^5$ on adjacent atoms are taken together with the atoms to which they are attached to form a carbocycle ring or a heterocycle ring; each optionally substituted with one, two, or three $R^{13}$;
$R^6$ and R are each independently hydrogen, $C_{1-6}$alkyl, $C_{1-6}$alkoxy, $C_{2-6}$alkenyl, $C_{2-6}$alkynyl, $C_{3-15}$cycloalkyl, $C_{2-15}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkoxy, alkenyl, alkynyl, cycloalkyl, heterocycloalkyl, aryl, and heteroaryl is independently optionally substituted with one, two, or three $R^{10}$;

or $R^6$ and $R^7$ are taken together with the nitrogen atom to which they are attached to form a $C_{2-15}$heterocycloalkyl or a $C_{2-15}$heterocycloalkenyl; wherein each heterocycloalkyl and heterocycloalkenyl is independently optionally substituted with one, two, or three $R^{11}$;
m is an integer from 0 to 5;
n is an integer from 0 to 4;
each $R^{10}$ is independently oxo, halogen, —CN, —OH, —$OR^a$, —SH, —$SR^a$, —S(=O)$R^a$, —$NO_2$, —$NR^bR^c$, —S(=O)$_2R^a$, —NHS(=O)$_2R^a$, —S(=O)$_2NR^bR^c$, —C(=O)$R^a$, —OC(=O)$R^a$, —C(=O)$OR^b$, —OC(=O)$OR^b$, —C(=O)$NR^bR^c$, —OC(=O)$NR^bR^c$, —$NR^bC(=O)NR^bR^c$, —$NR^bC(=O)R^a$, —$NR^bC(=O)OR^b$, —$B(OR^d)_2$, $C_{1-6}$alkyl, $C_{1-6}$haloalkyl, $C_{1-6}$hydroxyalkyl, $C_{1-6}$heteroalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl);
each $R^{11}$ is independently oxo, halogen, —CN, —OH, —$OR^a$, —SH, —$SR^a$, —S(=O)$R^a$, —$NO_2$, —$NR^bR^c$, —S(=O)$_2R^a$, —NHS(=O)$_2R^a$, —S(=O)$_2NR^bR^c$, —$NR^bS(=O)_2NR^bR^c$, —C(=O)$R^a$, —OC(=O)$R^a$, —C(=O)$OR^b$, —OC(=O)$OR^b$, —C(=O)$NR^bR^c$, —$CH_2C(=O)NR^bR^c$, —OC(=O)$NR^bR^c$, —$NR^bC(=O)NR^bR^c$, —$NR^bC(=O)R^a$, —$NR^bC(=O)OR^b$, —OP(=O)(OR)(OR), —$B(OR^d)_2$, $C_{1-6}$alkyl, $C_{1-6}$haloalkyl, $C_{1-6}$hydroxyalkyl, $C_{1-6}$heteroalkyl, $C_{1-6}$cyanoalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl);
each $R^{12}$ and $R^{13}$ is independently halogen, —CN, —OH, —$OR^a$, —SH, —$SR^a$, —S(=O)$R^a$, —$NO_2$, —$NR^bR^c$, —S(=O)$_2R^a$, —NHS(=O)$_2R^a$, —S(=O)$_2NR^bR^c$, —C(=O)$R^a$, —OC(=O)$R^a$, —C(=O)$OR^b$, —OC(=O)$OR^b$, —C(=O)$NR^bR^c$, —OC(=O)$NR^bR^c$, —$NR^bC(=O)NR^bR^c$, —$NR^bC(=O)R^a$, —$NR^bC(=O)OR^b$, $C_{1-6}$alkyl, $C_{1-6}$haloalkyl, $C_{1-6}$hydroxyalkyl, $C_{1-6}$heteroalkyl, or $C_{3-8}$cycloalkyl;
each $R^a$ is independently $C_{1-6}$alkyl, $C_{2-6}$alkenyl, $C_{2-6}$alkynyl, $C_{1-6}$haloalkyl, $C_{1-6}$hydroxyalkyl, $C_{1-6}$heteroalkyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three oxo, halogen, —OH, $C_{1-6}$alkyl, or $C_{1-6}$haloalkyl;
each $R^b$ and $R^c$ is independently hydrogen, $C_{1-6}$alkyl, $C_{2-6}$alkenyl, $C_{2-6}$alkynyl, $C_{1-6}$haloalkyl, $C_{1-6}$hydroxyalkyl, $C_{1-6}$heteroalkyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three oxo, halogen, —OH, $C_{1-6}$alkyl, or $C_{1-6}$haloalkyl;
or $R^b$ and $R^c$ are taken together with the nitrogen atom to which they are attached to form a $C_{2-7}$heterocycloalkyl optionally substituted with one, two, or three oxo, halogen, —OH, $C_{1-6}$alkyl, or $C_{1-6}$haloalkyl; and
each $R^d$ is independently hydrogen or $C_{1-6}$alkyl;
or two $R^d$ are taken together to form a $C_{2-7}$heterocycloalkyl optionally substituted with one, two, or three halogen, —OH, or $C_{1-6}$alkyl.

Provided herein is a compound of Formula (II), or a pharmaceutically acceptable salt, solvate, or stereoisomer thereof:

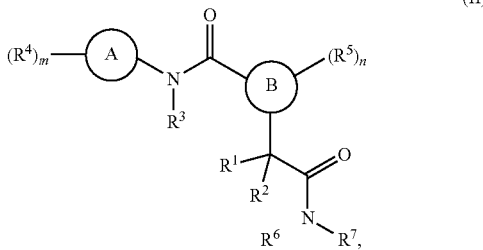

(II)

wherein:
Ring A is aryl, heteroaryl, cycloalkyl, or heterocycloalkyl;
Ring B is

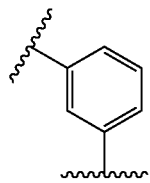 [SMILES: *c1cccc(*)c1]

or $C_{2-5}$heteroaryl;
$R^1$ is —F, —Cl, —OH, or —OR$^a$;
$R^2$ is hydrogen, —F, —Cl, —CN, —OR$^a$, $C_{1-6}$alkyl, $C_{1-6}$haloalkyl, $C_{1-6}$hydroxyalkyl, $C_{1-6}$heteroalkyl, or $C_{3-8}$cycloalkyl;
$R^3$ is hydrogen or $C_{1-6}$alkyl;
each $R^4$ is independently halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_{1-6}$alkyl, $C_{1-6}$haloalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three $R^{12}$;
or two $R^4$ on adjacent atoms are taken together with the atoms to which they are attached to form a carbocycle ring or a heterocycle ring; each optionally substituted with one, two, or three $R^{12}$;
each $R^5$ is independently hydrogen, halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_{1-6}$alkyl, $C_{1-6}$haloalkyl, $C_{1-6}$hydroxyalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three $R^{13}$;
or two $R^5$ on adjacent atoms are taken together with the atoms to which they are attached to form a carbocycle ring or a heterocycle ring; each optionally substituted with one, two, or three $R^{13}$;
$R^6$ and $R^7$ are each independently hydrogen, $C_{1-6}$alkyl, $C_{1-6}$alkoxy, $C_{2-6}$alkenyl, $C_{2-6}$alkynyl, $C_{3-15}$cycloalkyl, $C_{2-15}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkoxy, alkenyl, alkynyl, cycloalkyl, heterocycloalkyl, aryl, and heteroaryl is independently optionally substituted with one, two, or three $R^{10}$;
or $R^6$ and $R^7$ are taken together with the nitrogen atom to which they are attached to form a $C_{2-15}$heterocycloalkyl or a $C_{2-15}$heterocycloalkenyl; wherein each heterocycloalkyl and heterocycloalkenyl is independently optionally substituted with one, two, or three $R^{11}$;
m is an integer from 0 to 5;
n is an integer from 0 to 4;
each $R^{10}$ is independently oxo, halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, —B(OR$^d$)$_2$, $C_{1-6}$alkyl, $C_{1-6}$haloalkyl, $C_{1-6}$hydroxyalkyl, $C_{1-6}$heteroalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl);
each $R^{11}$ is independently oxo, halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —NR$^b$S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —CH$_2$C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, —NR$^b$C(=O)CH$_2$NR$^b$R$^c$, —C(=O)CH$_2$NR$^b$C(=O)NR$^b$R$^c$, —OP(=O)(OR)(OR), —B(OR$^d$)$_2$, $C_{1-6}$alkyl, $C_{1-6}$haloalkyl, $C_{1-6}$hydroxyalkyl, $C_{1-6}$heteroalkyl, $C_{1-6}$cyanoalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl);
each $R^{12}$ and $R^{13}$ is independently halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_{1-6}$alkyl, $C_{1-6}$haloalkyl, $C_{1-6}$hydroxyalkyl, $C_{1-6}$heteroalkyl, or $C_{3-8}$cycloalkyl;
each $R^a$ is independently $C_{1-6}$alkyl, $C_{2-6}$alkenyl, $C_{2-6}$alkynyl, $C_{1-6}$haloalkyl, $C_{1-6}$hydroxyalkyl, $C_{1-6}$heteroalkyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three oxo, halogen, —OH, $C_{1-6}$alkyl, or $C_{1-6}$haloalkyl;
each $R^b$ and $R^c$ is independently hydrogen, $C_{1-6}$alkyl, $C_{2-6}$alkenyl, $C_{2-6}$alkynyl, $C_{1-6}$haloalkyl, $C_{1-6}$hydroxyalkyl, $C_{1-6}$heteroalkyl, $C_{3-8}$cycloalkyl, $C_{2-7}$heterocycloalkyl, aryl, heteroaryl, $C_{1-6}$alkyl(aryl), $C_6$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three oxo, halogen, —OH, $C_{1-6}$alkyl, or $C_{1-6}$haloalkyl;

or $R^b$ and $R^c$ are taken together with the nitrogen atom to which they are attached to form a $C_{2-7}$heterocycloalkyl optionally substituted with one, two, or three oxo, halogen, —OH, $C_{1-6}$alkyl, or $C_{1-6}$haloalkyl; and each $R^d$ is independently hydrogen or $C_{1-6}$alkyl;

or two $R^d$ are taken together to form a $C_{2-7}$heterocycloalkyl optionally substituted with one, two, or three halogen, —OH, or $C_{1-6}$alkyl.

For any and all of the embodiments of Formula (I) or (II), substituents are selected from among a subset of the listed alternatives.

In some embodiments of a compound of Formula (I) or (II), or a pharmaceutically acceptable salt, solvate, or stereoisomer thereof, $R^1$ is —F or —OH. In some embodiments of a compound of Formula (I) or (II), or a pharmaceutically acceptable salt, solvate, or stereoisomer thereof, $R^1$ is —F or —Cl. In some embodiments of a compound of Formula (I) or (II), or a pharmaceutically acceptable salt, solvate, or stereoisomer thereof, $R^1$ is —F. In some embodiments of a compound of Formula (I) or (II), or a pharmaceutically acceptable salt, solvate, or stereoisomer thereof, $R^1$ is —OH. In some embodiments of a compound of Formula (I) or (II), or a pharmaceutically acceptable salt, solvate, or stereoisomer thereof, $R^1$ is —Cl. In some embodiments of a compound of Formula (I) or (II), or a pharmaceutically acceptable salt, solvate, or stereoisomer thereof, $R^1$ is —OR$^a$. In some embodiments of a compound of Formula (I) or (II), or a pharmaceutically acceptable salt, solvate, or stereoisomer thereof, $R^1$ is —OMe.

In some embodiments of a compound of Formula (I) or (II), or a pharmaceutically acceptable salt, solvate, or stereoisomer thereof, $R^2$ is hydrogen, —F, —Cl, —CN, —OR$^a$, $C_{1-6}$alkyl, $C_{1-6}$haloalkyl, or $C_{3-8}$cycloalkyl. In some embodiments of a compound of Formula (I) or (II), or a pharmaceutically acceptable salt, solvate, or stereoisomer thereof, $R^2$ is hydrogen, —F, —Cl, —CN, —OR$^a$, or $C_{1-6}$alkyl. In some embodiments of a compound of Formula (I) or (II), or a pharmaceutically acceptable salt, solvate, or stereoisomer thereof, $R^2$ is hydrogen, —F, —Cl, or $C_{1-6}$alkyl. In some embodiments of a compound of Formula (I) or (II), or a pharmaceutically acceptable salt, solvate, or stereoisomer thereof, $R^2$ is hydrogen, —F, or $C_{1-6}$alkyl. In some embodiments of a compound of Formula (I) or (II), or a pharmaceutically acceptable salt, solvate, or stereoisomer thereof, $R^2$ is hydrogen or —F. In some embodiments of a compound of Formula (I) or (II), or a pharmaceutically acceptable salt, solvate, or stereoisomer thereof, $R^2$ is hydrogen. In some embodiments of a compound of Formula (I) or (II), or a pharmaceutically acceptable salt, solvate, or stereoisomer thereof, $R^2$ is —F. In some embodiments of a compound of Formula (I) or (II), or a pharmaceutically acceptable salt, solvate, or stereoisomer thereof, $R^2$ is —Cl. In some embodiments of a compound of Formula (I) or (II), or a pharmaceutically acceptable salt, solvate, or stereoisomer thereof, $R^2$ is $C_{1-6}$alkyl. In some embodiments of a compound of Formula (I) or (II), or a pharmaceutically acceptable salt, solvate, or stereoisomer thereof, $R^2$ is methyl.

In some embodiments of a compound of Formula (I) or (II), or a pharmaceutically acceptable salt, solvate, or stereoisomer thereof, $R^1$ is —F; and $R^2$ is hydrogen, —F, or $C_{1-6}$alkyl. In some embodiments of a compound of Formula (I) or (II), or a pharmaceutically acceptable salt, solvate, or stereoisomer thereof, $R^1$ is —F; and $R^2$ is hydrogen or —F.

In some embodiments of a compound of Formula (I) or (II), or a pharmaceutically acceptable salt, solvate, or stereoisomer thereof, $R^1$ is —F; and $R^2$ is hydrogen. In some embodiments of a compound of Formula (I) or (II), or a pharmaceutically acceptable salt, solvate, or stereoisomer thereof, $R^1$ is —F; and $R^2$ is —F. In some embodiments of a compound of Formula (I) or (II), or a pharmaceutically acceptable salt, solvate, or stereoisomer thereof, $R^1$ is —F; and $R^2$ is $C_{1-6}$alkyl. In some embodiments of a compound of Formula (I) or (II), or a pharmaceutically acceptable salt, solvate, or stereoisomer thereof, $R^1$ is —F; and $R^2$ is methyl.

In some embodiments of a compound of Formula (I) or (II), or a pharmaceutically acceptable salt, solvate, or stereoisomer thereof, $R^1$ is —OH; and $R^2$ is $C_{1-6}$alkyl. In some embodiments of a compound of Formula (I) or (II), or a pharmaceutically acceptable salt, solvate, or stereoisomer thereof, $R^1$ is —OH; and $R^2$ is methyl.

In some embodiments of a compound of Formula (I) or (II), or a pharmaceutically acceptable salt, solvate, or stereoisomer thereof, $R^3$ is hydrogen or methyl. In some embodiments of a compound of Formula (I) or (II), or a pharmaceutically acceptable salt, solvate, or stereoisomer thereof, $R^3$ is hydrogen. In some embodiments of a compound of Formula (I) or (II), or a pharmaceutically acceptable salt, solvate, or stereoisomer thereof, $R^3$ is methyl.

In some embodiments of a compound of Formula (I) or (II), or a pharmaceutically acceptable salt, solvate, or stereoisomer thereof, Ring A is aryl, heteroaryl, $C_{3-8}$cycloalkyl, or $C_{2-7}$heterocycloalkyl.

In some embodiments of a compound of Formula (I) or (II), or a pharmaceutically acceptable salt, solvate, or stereoisomer thereof, Ring A is aryl or heteroaryl.

In some embodiments of a compound of Formula (I) or (II), or a pharmaceutically acceptable salt, solvate, or stereoisomer thereof, Ring A is aryl. In some embodiments of a compound of Formula (I) or (II), or a pharmaceutically acceptable salt, solvate, or stereoisomer thereof, Ring A is $C_{6-10}$aryl. In some embodiments of a compound of Formula (I) or (II), or a pharmaceutically acceptable salt, solvate, or stereoisomer thereof, Ring A is anthryl, naphthyl, phenanthryl, phenyl, fluoryl, indanyl, or indenyl. In some embodiments of a compound of Formula (I) or (II), or a pharmaceutically acceptable salt, solvate, or stereoisomer thereof, Ring A is naphthyl or phenyl. In some embodiments of a compound of Formula (I) or (II), or a pharmaceutically acceptable salt, solvate, or stereoisomer thereof, Ring A is phenyl.

In some embodiments of a compound of Formula (I) or (II), or a pharmaceutically acceptable salt, solvate, or stereoisomer thereof, Ring A is heteroaryl. In some embodiments of a compound of Formula (I) or (II), or a pharmaceutically acceptable salt, solvate, or stereoisomer thereof, Ring A is azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, or thiophenyl. In some embodiments of a compound of Formula (I) or (II), or a pharmaceutically acceptable salt, solvate, or stereoisomer thereof, Ring A is $C_{2-9}$heteroaryl. In some embodiments of a compound of Formula (I) or (II), or a pharmaceutically acceptable salt, solvate, or stereoisomer thereof, Ring A is pyridinyl, pyrazinyl, pyrimidinyl, pyridazinyl, triazinyl, pyrrolyl, imidazolyl, pyrazolyl, oxazolyl, isoxazolyl, thiazolyl, isothiazolyl, triazolyl, or thiophenyl. In some embodiments of a compound of Formula (I) or (II), or a pharmaceutically acceptable salt, solvate, or stereoisomer thereof, Ring A is pyridinyl, imidazolyl, pyrazolyl, thiazolyl, or thiophenyl. In some embodiments of a compound of Formula (I) or (II), or a pharmaceutically acceptable salt, solvate, or stereoisomer thereof, Ring A is pyridinyl. In some embodiments of a compound of Formula (I) or (II), or a pharmaceutically acceptable salt, solvate, or stereoisomer thereof, Ring A is imidazolyl. In some embodiments of a compound of Formula (I) or (II), or a pharmaceutically acceptable salt, solvate, or stereoisomer thereof, Ring A is pyrazolyl. In some embodiments of a compound of Formula (I) or (II), or a pharmaceutically acceptable salt, solvate, or stereoisomer thereof, Ring A is thiazolyl. In some embodiments of a compound of Formula (I) or (II), or a pharmaceutically acceptable salt, solvate, or stereoisomer thereof, Ring A is thiophenyl.

In some embodiments of a compound of Formula (I) or (II), or a pharmaceutically acceptable salt, solvate, or stereoisomer thereof, Ring A is cycloalkyl or heterocycloalkyl. In some embodiments of a compound of Formula (I) or (II), or a pharmaceutically acceptable salt, solvate, or stereoisomer thereof, Ring A is $C_{3-8}$cycloalkyl or $C_{2-7}$heterocycloalkyl.

In some embodiments of a compound of Formula (I) or (II), or a pharmaceutically acceptable salt, solvate, or stereoisomer thereof, Ring A is cycloalkyl. In some embodiments of a compound of Formula (I) or (II), or a pharmaceutically acceptable salt, solvate, or stereoisomer thereof, Ring A is $C_{3-8}$cycloalkyl. In some embodiments of a compound of Formula (I) or (II), or a pharmaceutically acceptable salt, solvate, or stereoisomer thereof, Ring A is monocyclic cycloalkyl. In some embodiments of a compound of Formula (I) or (II), or a pharmaceutically acceptable salt, solvate, or stereoisomer thereof, Ring A is cyclopropyl, cyclobutyl, cyclopentyl, cyclohexyl, cycloheptyl, or cyclooctyl. In some embodiments of a compound of Formula (I) or (II), or a pharmaceutically acceptable salt, solvate, or stereoisomer thereof, Ring A is a polycyclic cycloalkyl.

In some embodiments of a compound of Formula (I) or (II), or a pharmaceutically acceptable salt, solvate, or stereoisomer thereof, Ring A is heterocycloalkyl. In some embodiments of a compound of Formula (I) or (II), or a pharmaceutically acceptable salt, solvate, or stereoisomer thereof, Ring A is $C_{2-7}$heterocycloalkyl. In some embodiments of a compound of Formula (I) or (II), or a pharmaceutically acceptable salt, solvate, or stereoisomer thereof, Ring A is monocyclic heterocycloalkyl. In some embodiments of a compound of Formula (I) or (II), or a pharmaceutically acceptable salt, solvate, or stereoisomer thereof, Ring A is polycyclic heterocycloalkyl. In some embodiments of a compound of Formula (I) or (II), or a pharmaceutically acceptable salt, solvate, or stereoisomer thereof, Ring A is aziridinyl, azetidinyl, oxetanyl, dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, or 2-oxo-1,3-dioxol-4-yl.

In some embodiments of a compound of Formula (I) or (II), or a pharmaceutically acceptable salt, solvate, or stereoisomer thereof, each $R^4$ is independently halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_{1-6}$alkyl, $C_{1-6}$ haloalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three $R^{12}$. In some embodiments of a compound of Formula (I) or (II), or a pharmaceutically acceptable salt, solvate, or stereoisomer thereof, each $R^4$ is independently halogen, —CN, —OR$^a$, —NO$_2$, —C(=O)NR$^b$R$^c$, $C_{1-6}$alkyl, or $C_{3-8}$cycloalkyl; wherein each alkyl and cycloalkyl are independently optionally substituted with one, two, or three $R^{12}$. In some embodiments of a compound of Formula (I) or (II), or a pharmaceutically acceptable salt, solvate, or stereoisomer thereof, each $R^4$ is independently halogen, —CN, —OR$^a$, —NO$_2$, —C(=O)NR$^b$R$^c$, $C_{1-6}$alkyl, $C_{1-6}$haloalkyl, or $C_{3-8}$cycloalkyl. In some embodiments of a compound of Formula (I) or (II), or a pharmaceutically acceptable salt, solvate, or stereoisomer thereof, each $R^4$ is independently —F, —Cl, —Br, —CN, —OMe, —NO$_2$, —C(=O)NH$_2$, methyl, ethyl, propyl, butyl, pentyl, hexyl, isopropyl, isobutyl, sec-butyl, —CF$_3$, —CHF$_2$, CH$_2$F, cyclopropyl, cyclobutyl, cyclopentyl, or cyclohexyl. In some embodiments of a compound of Formula (I) or (II), or a pharmaceutically acceptable salt, solvate, or stereoisomer thereof, each $R^4$ is independently —F, —Cl, —Br, —CN, —OMe, —NO$_2$, —C(=O)NH$_2$, —CF$_3$, methyl, isopropyl, or cyclopropyl. In some embodiments of a compound of Formula (I) or (II), or a pharmaceutically acceptable salt, solvate, or stereoisomer thereof, each $R^4$ is independently —F, —Cl, —Br, —CN, —OMe, —C(=O)NH$_2$, —CF$_3$, methyl, isopropyl, or cyclopropyl. In some embodiments of a compound of Formula (I) or (II), or a pharmaceutically acceptable salt, solvate, or stereoisomer thereof, each $R^4$ is independently —F, —Cl, —Br, —CN, —OMe, —C(=O)NH$_2$, or methyl.

In some embodiments of a compound of Formula (I) or (II), or a pharmaceutically acceptable salt, solvate, or stereoisomer thereof, two $R^4$ on adjacent atoms are taken together with the atoms to which they are attached to form a heterocycle ring optionally substituted with one, two, or three $R^{12}$. In some embodiments of a compound of Formula (I) or (II), or a pharmaceutically acceptable salt, solvate, or stereoisomer thereof, two $R^4$ on adjacent atoms are taken together with the atoms to which they are attached to form a carbocycle ring optionally substituted with one, two, or three $R^{12}$.

In some embodiments of a compound of Formula (I) or (II), or a pharmaceutically acceptable salt, solvate, or stereoisomer thereof, R⁴ is defined as above and each $R^{12}$ is independently halogen, —CN, —OH, —$OR^a$, —$NR^bR^c$, —$C(=O)R^a$, —$C(=O)OR^b$, —$C(=O)NR^bR^c$, —$NR^bC(=O)R^a$, $C_{1-6}$alkyl, $C_{1-6}$haloalkyl, $C_{1-6}$hydroxyalkyl, $C_{1-6}$heteroalkyl, or $C_{3-8}$cycloalkyl. In some embodiments of a compound of Formula (I) or (II), or a pharmaceutically acceptable salt, solvate, or stereoisomer thereof, R⁴ is defined as above and each $R^{12}$ is independently halogen, —CN, —$OR^a$, —$NR^bR^c$, —$C(=O)NR^bR^c$, —$NR^bC(=O)R^a$, $C_{1-6}$alkyl, or $C_{1-6}$haloalkyl. In some embodiments of a compound of Formula (I) or (II), or a pharmaceutically acceptable salt, solvate, or stereoisomer thereof, R⁴ is defined as above and each $R^{12}$ is independently halogen, $C_{1-6}$alkyl, or $C_{1-6}$haloalkyl. In some embodiments of a compound of Formula (I) or (II), or a pharmaceutically acceptable salt, solvate, or stereoisomer thereof, R⁴ is defined as above and each $R^{12}$ is halogen. In some embodiments of a compound of Formula (I) or (II), or a pharmaceutically acceptable salt, solvate, or stereoisomer thereof, R⁴ is defined as above and each $R^{12}$ is $C_{1-6}$alkyl. In some embodiments of a compound of Formula (I) or (II), or a pharmaceutically acceptable salt, solvate, or stereoisomer thereof, R⁴ is defined as above and each $R^{12}$ is $C_{1-6}$haloalkyl.

In some embodiments of a compound of Formula (I) or (II), or a pharmaceutically acceptable salt, solvate, or stereoisomer thereof, m is 0 to 5. In some embodiments of a compound of Formula (I) or (II), or a pharmaceutically acceptable salt, solvate, or stereoisomer thereof, m is 0 to 4. In some embodiments of a compound of Formula (I) or (II), or a pharmaceutically acceptable salt, solvate, or stereoisomer thereof, m is 0 to 3. In some embodiments of a compound of Formula (I) or (II), or a pharmaceutically acceptable salt, solvate, or stereoisomer thereof, m is 0 to 2. In some embodiments of a compound of Formula (I) or (II), or a pharmaceutically acceptable salt, solvate, or stereoisomer thereof, m is 0 to 1. In some embodiments of a compound of Formula (I) or (II), or a pharmaceutically acceptable salt, solvate, or stereoisomer thereof, m is 1 to 5. In some embodiments of a compound of Formula (I) or (II), or a pharmaceutically acceptable salt, solvate, or stereoisomer thereof, m is 1 to 4. In some embodiments of a compound of Formula (I) or (II), or a pharmaceutically acceptable salt, solvate, or stereoisomer thereof, m is 1 to 3. In some embodiments of a compound of Formula (I) or (II), or a pharmaceutically acceptable salt, solvate, or stereoisomer thereof, m is 1 to 2. In some embodiments of a compound of Formula (I) or (II), or a pharmaceutically acceptable salt, solvate, or stereoisomer thereof, m is 2 to 5. In some embodiments of a compound of Formula (I) or (II), or a pharmaceutically acceptable salt, solvate, or stereoisomer thereof, m is 2 to 4. In some embodiments of a compound of Formula (I) or (II), or a pharmaceutically acceptable salt, solvate, or stereoisomer thereof, m is 2 to 3. In some embodiments of a compound of Formula (I) or (II), or a pharmaceutically acceptable salt, solvate, or stereoisomer thereof, m is 3 to 5. In some embodiments of a compound of Formula (I) or (II), or a pharmaceutically acceptable salt, solvate, or stereoisomer thereof, m is 3 to 4. In some embodiments of a compound of Formula (I) or (II), or a pharmaceutically acceptable salt, solvate, or stereoisomer thereof, m is 4 to 5. In some embodiments of a compound of Formula (I) or (II), or a pharmaceutically acceptable salt, solvate, or stereoisomer thereof, m is 0. In some embodiments of a compound of Formula (I) or (II), or a pharmaceutically acceptable salt, solvate, or stereoisomer thereof, m is 1. In some embodiments of a compound of Formula (I) or (II), or a pharmaceutically acceptable salt, solvate, or stereoisomer thereof, m is 2. In some embodiments of a compound of Formula (I) or (II), or a pharmaceutically acceptable salt, solvate, or stereoisomer thereof, m is 3. In some embodiments of a compound of Formula (I) or (II), or a pharmaceutically acceptable salt, solvate, or stereoisomer thereof, m is 4. In some embodiments of a compound of Formula (I) or (II), or a pharmaceutically acceptable salt, solvate, or stereoisomer thereof, m is 5.

In some embodiments of a compound of Formula (I) or (II), or a pharmaceutically acceptable salt, solvate, or stereoisomer thereof,

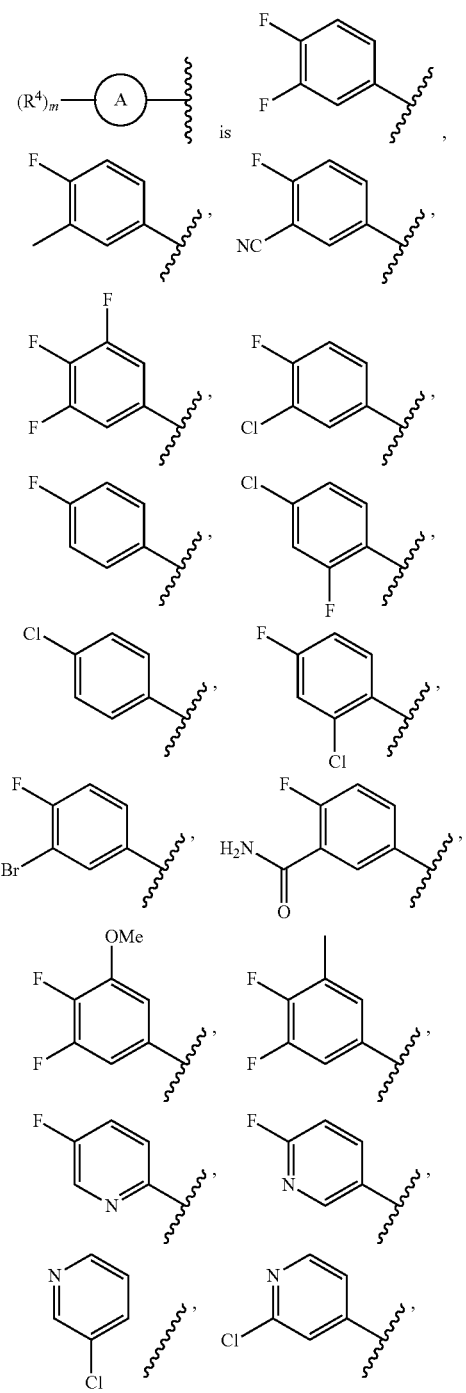

-continued
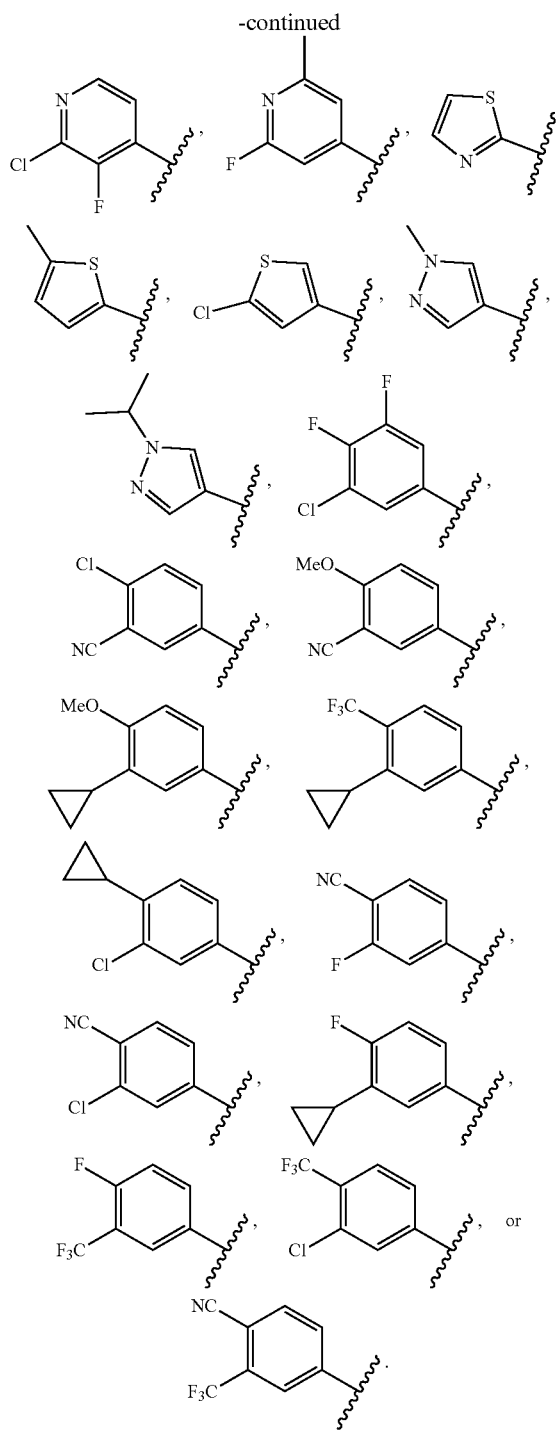
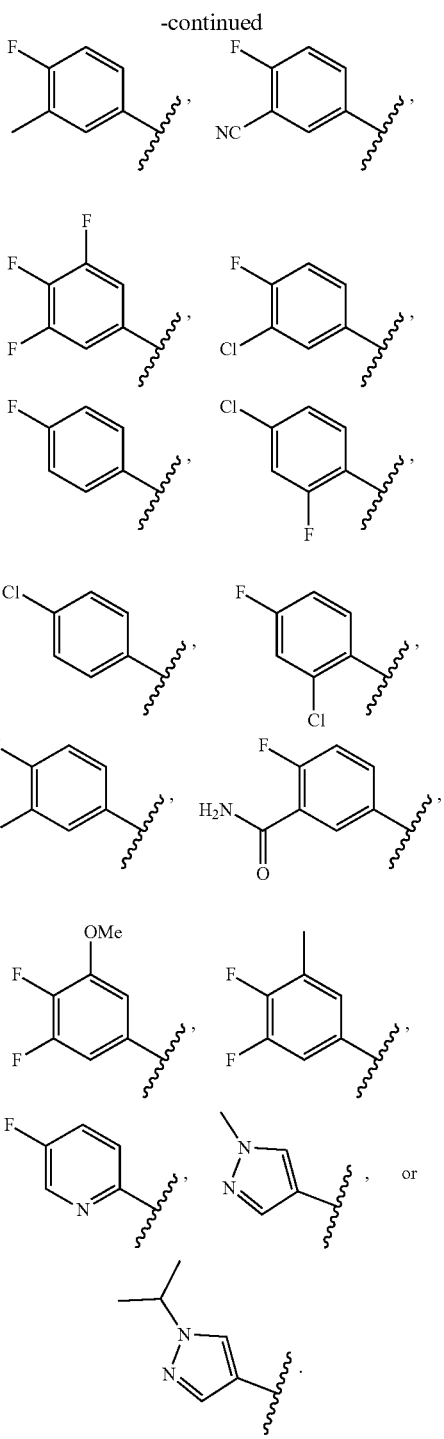
In some embodiments of a compound of Formula (I) or (II), or a pharmaceutically acceptable salt, solvate, or stereoisomer thereof,
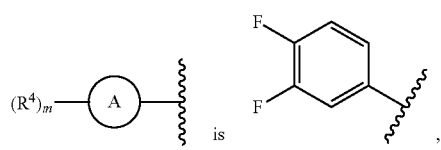
In some embodiments of a compound of Formula (I) or (II), or a pharmaceutically acceptable salt, solvate, or stereoisomer thereof,
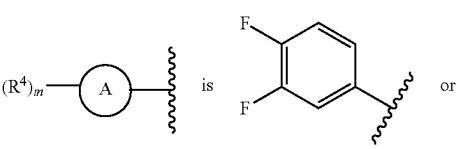

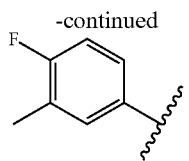

In some embodiments of a compound of Formula (I), or a pharmaceutically acceptable salt, solvate, or stereoisomer thereof, Ring B is heteroaryl. In some embodiments of a compound of Formula (I), or a pharmaceutically acceptable salt, solvate, or stereoisomer thereof, Ring B is a 6-membered heteroaryl. In some embodiments of a compound of Formula (I), or a pharmaceutically acceptable salt, solvate, or stereoisomer thereof, Ring B is a 5-membered heteroaryl. In some embodiments of a compound of Formula (I), or a pharmaceutically acceptable salt, solvate, or stereoisomer thereof, Ring B is pyridinyl, pyrazinyl, pyrimidinyl, pyridazinyl, triazinyl, pyrrolyl, imidazolyl, pyrazolyl, oxazolyl, isoxazolyl, thiazolyl, isothiazolyl, triazolyl, thiophenyl, azepinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzoxazolyl, benzodioxolyl, benzodioxinyl, benzopyranyl, benzopyranonyl, benzofuranyl, benzofuranonyl, benzothienyl (benzothiophenyl), benzotriazolyl, cinnolinyl, indazolyl, indolyl, isoindolyl, indolinyl, isoindolinyl, isoquinolyl, indolizinyl, isoxazolyl, naphthyridinyl, purinyl, quinazolinyl, quinoxalinyl, quinolinyl, isoquinolinyl, or tetrahydroquinolinyl. In some embodiments of a compound of Formula (I), or a pharmaceutically acceptable salt, solvate, or stereoisomer thereof, Ring B is pyridinyl, pyrrolyl, thiazolyl, thiophenyl, benzimidazolyl, or indolyl.

In some embodiments of a compound of Formula (I), or a pharmaceutically acceptable salt, solvate, or stereoisomer thereof, Ring B is aryl. In some embodiments of a compound of Formula (I), or a pharmaceutically acceptable salt, solvate, or stereoisomer thereof, Ring B is phenyl or naphthyl. In some embodiments of a compound of Formula (I), or a pharmaceutically acceptable salt, solvate, or stereoisomer thereof, Ring B is phenyl. In some embodiments of a compound of Formula (I) or (II), or a pharmaceutically acceptable salt, solvate, or stereoisomer thereof, Ring B is

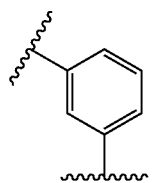 [SMILES: *c1cccc(*)c1]

or $C_{2-5}$heteroaryl.

In some embodiments of a compound of Formula (I) or (II), or a pharmaceutically acceptable salt, solvate, or stereoisomer thereof, Ring B is $C_{2-5}$heteroaryl. In some embodiments of a compound of Formula (I) or (II), or a pharmaceutically acceptable salt, solvate, or stereoisomer thereof, Ring B is pyridinyl, pyrazinyl, pyrimidinyl, pyridazinyl, triazinyl, pyrrolyl, imidazolyl, pyrazolyl, oxazolyl, isoxazolyl, thiazolyl, isothiazolyl, triazolyl, or thiophenyl. In some embodiments of a compound of Formula (I) or (II), or a pharmaceutically acceptable salt, solvate, or stereoisomer thereof, Ring B is pyridinyl, pyrrolyl, thiazolyl, or thiophenyl. In some embodiments of a compound of Formula (I) or (II), or a pharmaceutically acceptable salt, solvate, or stereoisomer thereof, Ring B is $C_{2-4}$heteroaryl. In some embodiments of a compound of Formula (I) or (II), or a pharmaceutically acceptable salt, solvate, or stereoisomer thereof, Ring B is pyrrolyl, imidazolyl, pyrazolyl, oxazolyl, isoxazolyl, thiazolyl, isothiazolyl, triazolyl, or thiophenyl. In some embodiments of a compound of Formula (I) or (II), or a pharmaceutically acceptable salt, solvate, or stereoisomer thereof, Ring B is pyrrolyl, thiazolyl, pyrazolyl, imidazolyl, or thiophenyl. In some embodiments of a compound of Formula (I) or (II), or a pharmaceutically acceptable salt, solvate, or stereoisomer thereof, Ring B is pyrrolyl, thiazolyl, pyrazolyl, or thiophenyl. In some embodiments of a compound of Formula (I) or (II), or a pharmaceutically acceptable salt, solvate, or stereoisomer thereof, Ring B is pyrrolyl, thiazolyl, or thiophenyl. In some embodiments of a compound of Formula (I) or (II), or a pharmaceutically acceptable salt, solvate, or stereoisomer thereof, Ring B is pyrrolyl or thiophenyl. In some embodiments of a compound of Formula (I) or (II), or a pharmaceutically acceptable salt, solvate, or stereoisomer thereof, Ring B is pyrrolyl.

In some embodiments of a compound of Formula (I) or (II), or a pharmaceutically acceptable salt, solvate, or stereoisomer thereof,

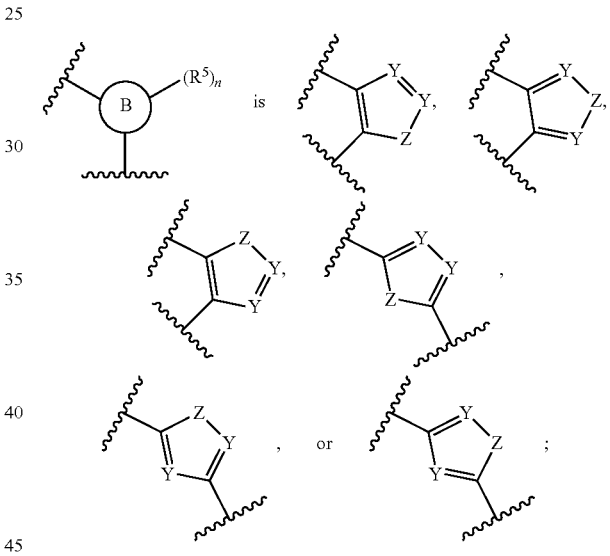

wherein,
Y is —N— or —CR$^5$—;
Z is —NR$^8$—, —S—, or —O—;
R$^8$ is hydrogen or $C_{1-6}$alkyl;
each R$^5$ is independently hydrogen, halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_{1-6}$alkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three R$^{13}$;
or two R$^5$ on adjacent atoms are taken together with the atoms to which they are attached to form a carbocycle ring or heterocycle ring; each optionally substituted with one, two, or three R$^{13}$;

or R⁵ and R⁸ on adjacent atoms are taken together with the atoms to which they are attached to form a carbocycle ring or heterocycle ring optionally substituted with one, two, or three R¹³; and each R¹³ is independently halogen, —CN, —OH, —OR<sup>a</sup>, —SH, —SR<sup>a</sup>, —S(═O)R<sup>a</sup>, —NO₂, —NR<sup>b</sup>R<sup>c</sup>, —S(═O)₂R<sup>a</sup>, —NHS(═O)₂R<sup>a</sup>, —S(═O)₂NR<sup>b</sup>R<sup>c</sup>, —C(═O)R<sup>a</sup>, —OC(═O)R<sup>a</sup>, —C(═O)OR<sup>b</sup>, —OC(═O)OR<sup>b</sup>, —C(═O)NR<sup>b</sup>R<sup>c</sup>, —OC(═O)NR<sup>b</sup>R<sup>c</sup>, —NR<sup>b</sup>C(═O)NR<sup>b</sup>R<sup>c</sup>, —NR<sup>b</sup>C(═O)R<sup>a</sup>, —NR<sup>b</sup>C(═O)OR<sup>b</sup>, C₁₋₆alkyl, C₁₋₆haloalkyl, C₁₋₆hydroxyalkyl, C₁₋₆heteroalkyl, or C₃₋₈cycloalkyl.

In some embodiments of a compound of Formula (I) or (II), or a pharmaceutically acceptable salt, solvate, or stereoisomer thereof, Y is —CR⁵—. In some embodiments of a compound of Formula (I) or (II), or a pharmaceutically acceptable salt, solvate, or stereoisomer thereof, Y is —N—.

In some embodiments of a compound of Formula (I) or (II), or a pharmaceutically acceptable salt, solvate, or stereoisomer thereof, Z is —NR⁸—. In some embodiments of a compound of Formula (I) or (II), or a pharmaceutically acceptable salt, solvate, or stereoisomer thereof, Z is —S—. In some embodiments of a compound of Formula (I) or (II), or a pharmaceutically acceptable salt, solvate, or stereoisomer thereof, Z is —O—.

In some embodiments of a compound of Formula (I) or (II), or a pharmaceutically acceptable salt, solvate, or stereoisomer thereof,

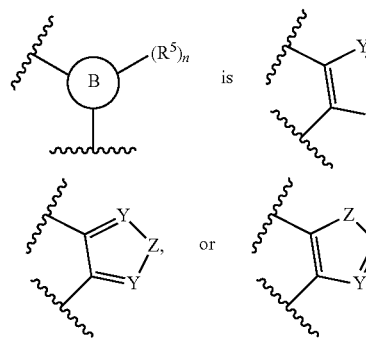

In some embodiments of a compound of Formula (I) or (II), or a pharmaceutically acceptable salt, solvate, or stereoisomer thereof,

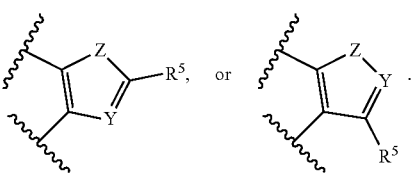

In some embodiments of a compound of Formula (I) or (II), or a pharmaceutically acceptable salt, solvate, or stereoisomer thereof,

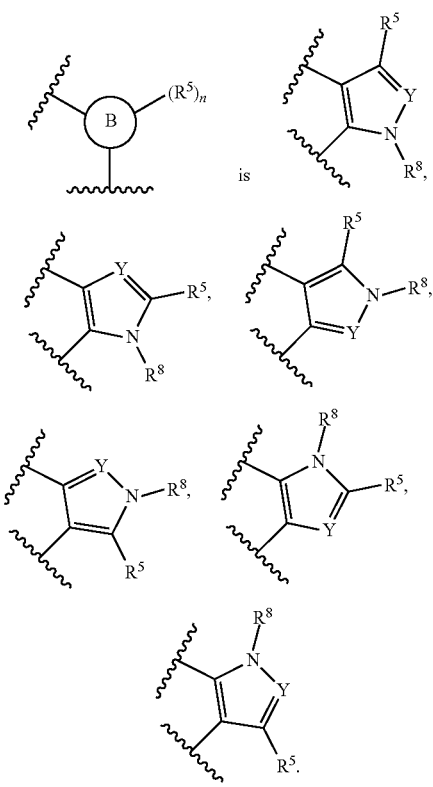

In some embodiments of a compound of Formula (I) or (II), or a pharmaceutically acceptable salt, solvate, or stereoisomer thereof,

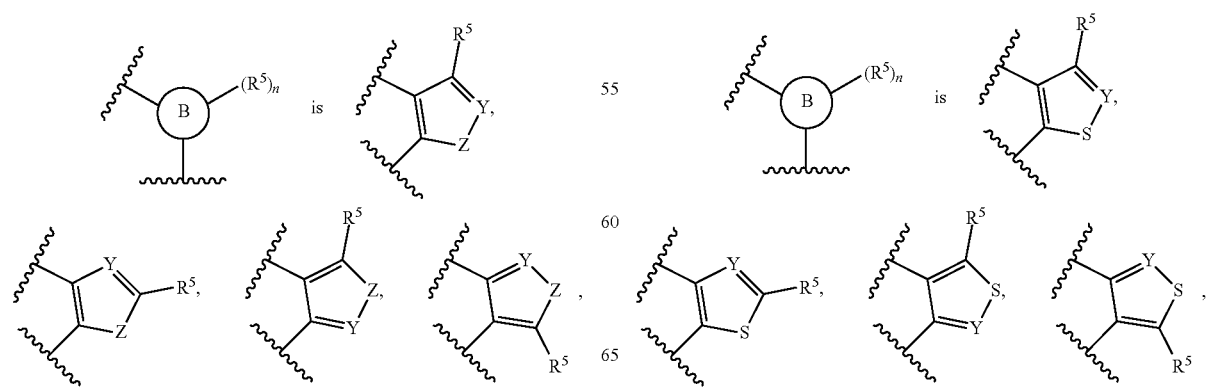

-continued

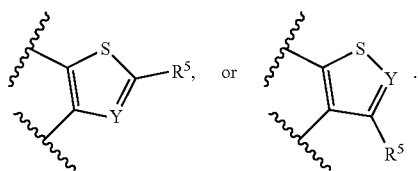

In some embodiments of a compound of Formula (I) or (II), or a pharmaceutically acceptable salt, solvate, or stereoisomer thereof,

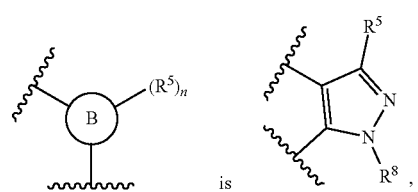

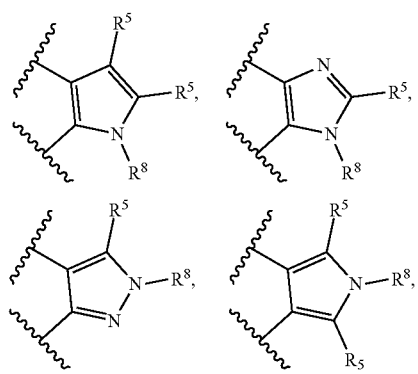

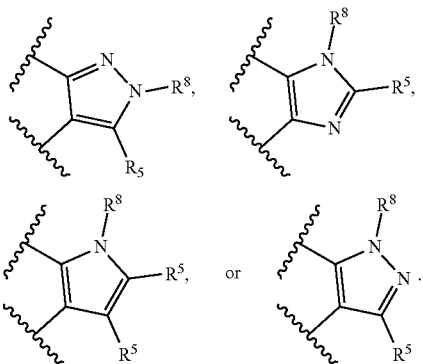

In some embodiments of a compound of Formula (I) or (II), or a pharmaceutically acceptable salt, solvate, or stereoisomer thereof,

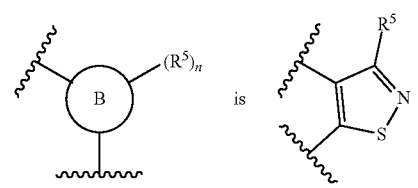

-continued

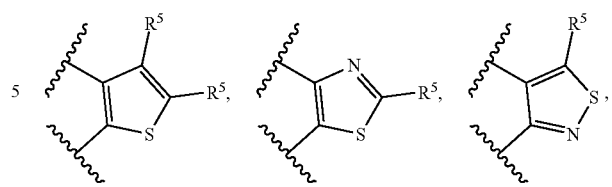

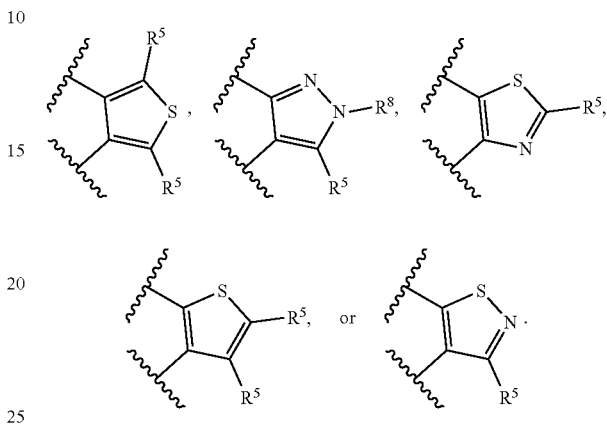

In some embodiments of a compound of Formula (I) or (II), or a pharmaceutically acceptable salt, solvate, or stereoisomer thereof,

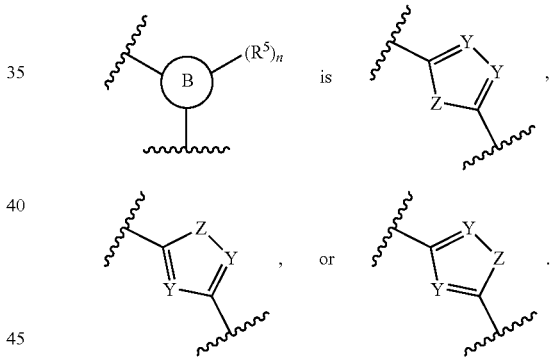

In some embodiments of a compound of Formula (I) or (II), or a pharmaceutically acceptable salt, solvate, or stereoisomer thereof,

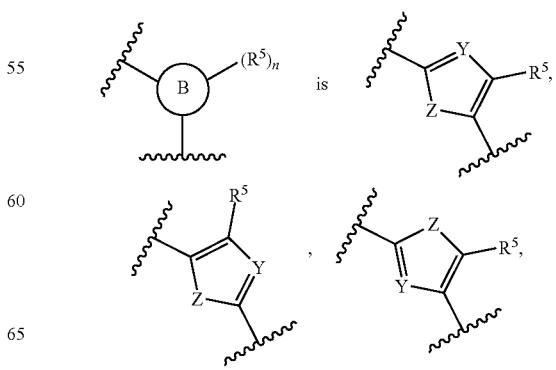

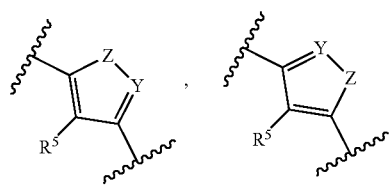 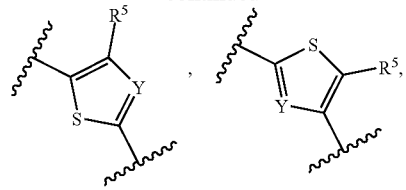

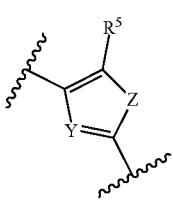 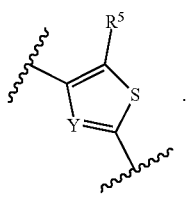

In some embodiments of a compound of Formula (I) or (II), or a pharmaceutically acceptable salt, solvate, or stereoisomer thereof,

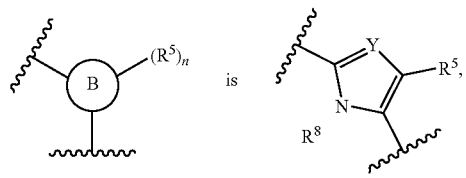 is 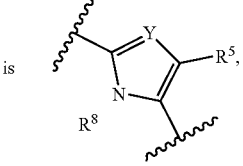,

In some embodiments of a compound of Formula (I) or (II), or a pharmaceutically acceptable salt, solvate, or stereoisomer thereof,

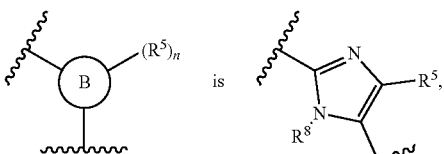 is 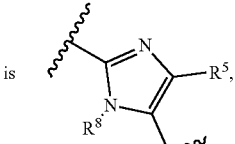,

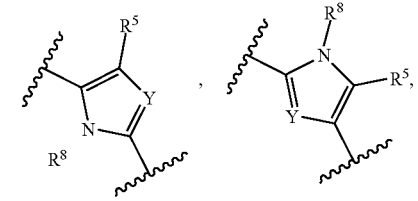, 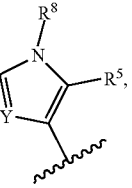,

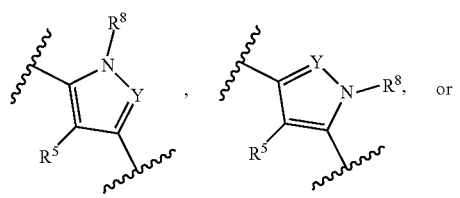, 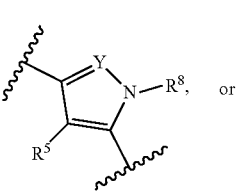,

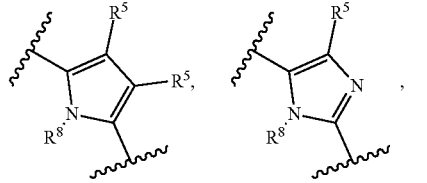, 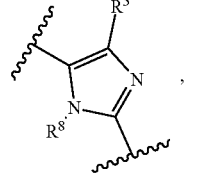,

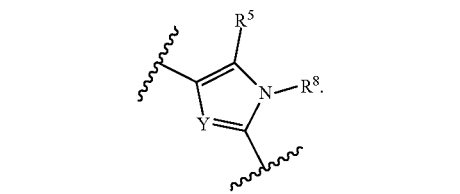, 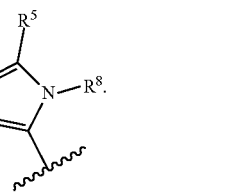, or

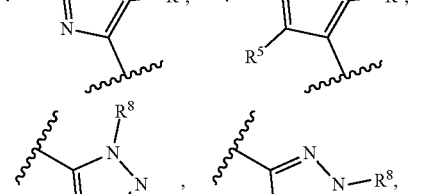, 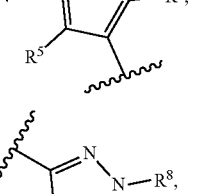,

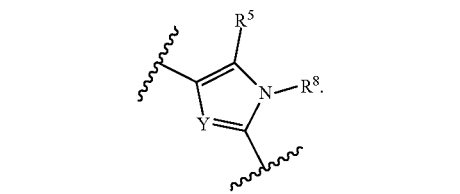.

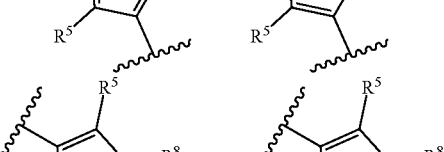, 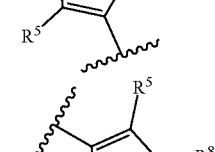, or

In some embodiments of a compound of Formula (I) or II or a pharmaceutically acceptable salt, solvate, or stereoisomer thereof,

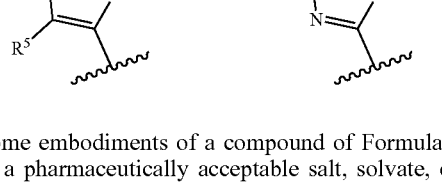.

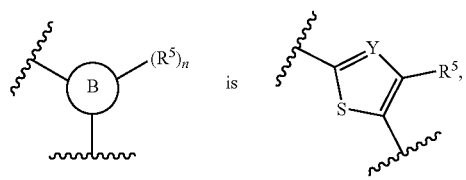 is 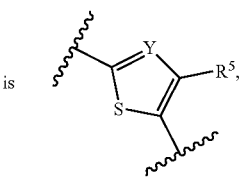,

In some embodiments of a compound of Formula (I) or (II), or a pharmaceutically acceptable salt, solvate, or stereoisomer thereof,

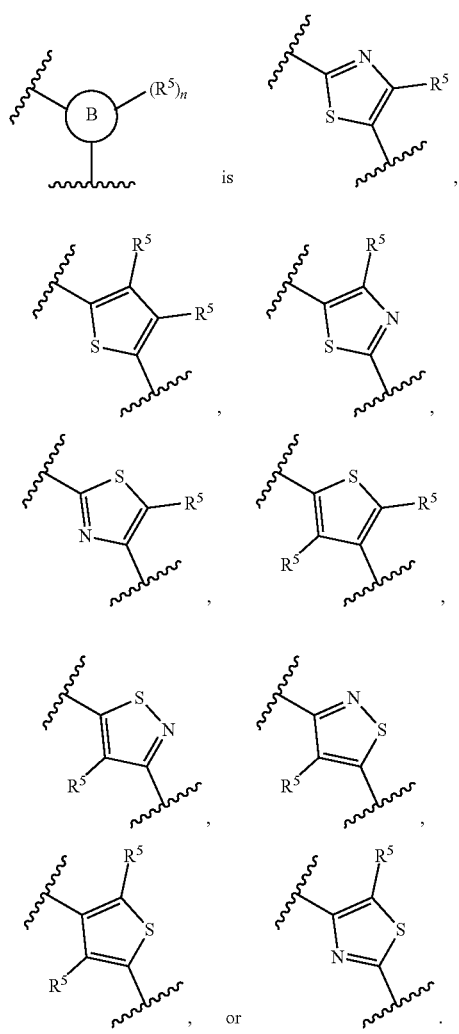

In some embodiments of a compound of Formula (I) or (II), or a pharmaceutically acceptable salt, solvate, or stereoisomer thereof,

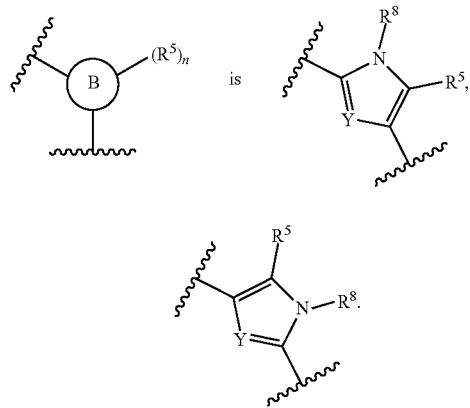

In some embodiments of a compound of Formula (I) or (II), or a pharmaceutically acceptable salt, solvate, or stereoisomer thereof,

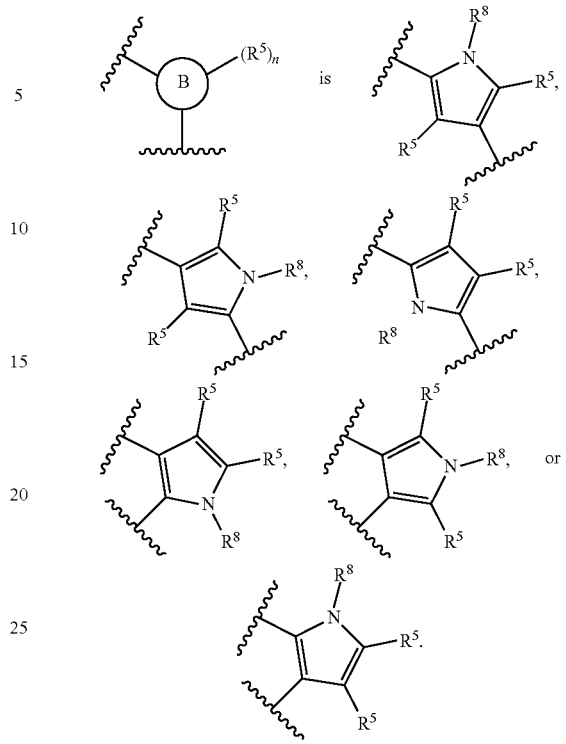

In some embodiments of a compound of Formula (I) or (II), or a pharmaceutically acceptable salt, solvate, or stereoisomer thereof,

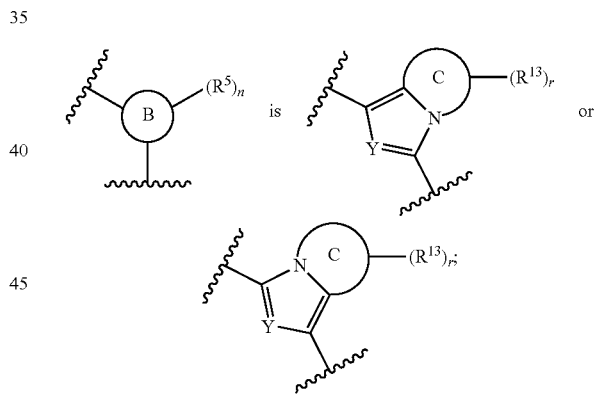

wherein
Ring C is a heterocycloalkyl or heteroaryl;
Y is —N— or —$CR^5$—;
each $R^5$ is independently hydrogen, halogen, —CN, —OH, —$OR^a$, —SH, —$SR^a$, —S(=O)$R^a$, —$NO_2$, —$NR^bR^c$, —S(=O)$_2R^a$, —NHS(=O)$_2R^a$, —S(=O)$_2NR^bR^c$, —C(=O)$R^a$, —OC(=O)$R^a$, —C(=O)$OR^b$, —OC(=O)$OR^b$, —C(=O)$NR^bR^c$, —OC(=O)$NR^bR^c$, —$NR^bC$(=O)$NR^bR^c$, —$NR^bC$(=O)$R^a$, —$NR^bC$(=O)$OR^b$, $C_{1-6}$alkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three $R^{13}$;

each $R^{13}$ is independently halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_{1-6}$alkyl, $C_{1-6}$haloalkyl, $C_{1-6}$hydroxyalkyl, $C_{1-6}$heteroalkyl, or $C_{3-8}$cycloalkyl; and
r is 0 to 3.

In some embodiments of a compound of Formula (I) or (II), or a pharmaceutically acceptable salt, solvate, or stereoisomer thereof, is In some embodiments of a compound of Formula (I) or (II), or a pharmaceutically acceptable salt, solvate, or stereoisomer thereof, r is 0. In some embodiments of a compound of Formula (I) or (II), or a pharmaceutically acceptable salt, solvate, or stereoisomer thereof, r is 1. In some embodiments of a compound of Formula (I) or (II), or a pharmaceutically acceptable salt, solvate, or stereoisomer thereof, r is 2. In some embodiments of a compound of Formula (I) or (II), or a pharmaceutically acceptable salt, solvate, or stereoisomer thereof, r is 3. In some embodiments of a compound of Formula (I) or (II), or a pharmaceutically acceptable salt, solvate, or stereoisomer thereof, r is 0 or 1. In some embodiments of a compound of Formula (I) or (II), or a pharmaceutically acceptable salt, solvate, or stereoisomer thereof, r is 0 to 2. In some embodiments of a compound of Formula (I) or (II), or a pharmaceutically acceptable salt, solvate, or stereoisomer thereof, r is 1 or 2. In some embodiments of a compound of Formula (I) or (II), or a pharmaceutically acceptable salt, solvate, or stereoisomer thereof, r is 1 to 3.

In some embodiments of a compound of Formula (I) or (II), or a pharmaceutically acceptable salt, solvate, or stereoisomer thereof, Ring C is a heterocycloalkyl.

In some embodiments of a compound of Formula (I) or (II), or a pharmaceutically acceptable salt, solvate, or stereoisomer thereof, Ring C is a 4- to 7-membered heterocycloalkyl. In some embodiments of a compound of Formula (I) or (II), or a pharmaceutically acceptable salt, solvate, or stereoisomer thereof, Ring C is a 5- to 7-membered heterocycloalkyl. In some embodiments of a compound of Formula (I) or (II), or a pharmaceutically acceptable salt, solvate, or stereoisomer thereof, Ring C is a 5- to 6-membered heterocycloalkyl. In some embodiments of a compound of Formula (I) or (II), or a pharmaceutically acceptable salt, solvate, or stereoisomer thereof, Ring C is a 5-membered heterocycloalkyl. In some embodiments of a compound of Formula (I) or (II), or a pharmaceutically acceptable salt, solvate, or stereoisomer thereof, Ring C is a 6-membered heterocycloalkyl.

In some embodiments of a compound of Formula (I) or (II), or a pharmaceutically acceptable salt, solvate, or stereoisomer thereof, Ring C is a 4- to 7-membered heterocycloalkyl having one, two, or three heteroatoms selected from nitrogen, oxygen, and sulfur. In some embodiments of a compound of Formula (I) or (II), or a pharmaceutically acceptable salt, solvate, or stereoisomer thereof, Ring C is a 5- to 7-membered heterocycloalkyl having one, two, or three heteroatoms selected from nitrogen, oxygen, and sulfur. In some embodiments of a compound of Formula (I) or (II), or a pharmaceutically acceptable salt, solvate, or stereoisomer thereof, Ring C is a 5- to 6-membered heterocycloalkyl having one, two, or three heteroatoms selected from nitrogen, oxygen, and sulfur. In some embodiments of a compound of Formula (I) or (II), or a pharmaceutically acceptable salt, solvate, or stereoisomer thereof, Ring C is a 5-membered heterocycloalkyl having one, two, or three heteroatoms selected from nitrogen, oxygen, and sulfur. In some embodiments of a compound of Formula (I) or (II), or a pharmaceutically acceptable salt, solvate, or stereoisomer thereof, Ring C is a 6-membered heterocycloalkyl having one, two, or three heteroatoms selected from nitrogen, oxygen, and sulfur.

In some embodiments of a compound of Formula (I) or (II), or a pharmaceutically acceptable salt, solvate, or stereoisomer thereof, Ring C is a 4- to 7-membered heterocycloalkyl having one or two heteroatoms selected from nitrogen or oxygen. In some embodiments of a compound of Formula (I) or (II), or a pharmaceutically acceptable salt, solvate, or stereoisomer thereof, Ring C is a 5- to 7-membered heterocycloalkyl having one or two heteroatoms selected from nitrogen or oxygen. In some embodiments of a compound of Formula (I) or (II), or a pharmaceutically acceptable salt, solvate, or stereoisomer thereof, Ring C is a 5- to 6-membered heterocycloalkyl having one or two heteroatoms selected from nitrogen or oxygen. In some embodiments of a compound of Formula (I) or (II), or a pharmaceutically acceptable salt, solvate, or stereoisomer thereof, Ring C is a 5-membered heterocycloalkyl having one or two heteroatoms selected from nitrogen or oxygen. In some embodiments of a compound of Formula (I) or (II), or a pharmaceutically acceptable salt, solvate, or stereoisomer thereof, Ring C is a 6-membered heterocycloalkyl having one or two heteroatoms selected from nitrogen or oxygen.

In some embodiments of a compound of Formula (I) or (II), or a pharmaceutically acceptable salt, solvate, or stereoisomer thereof, Ring C is a 4- to 7-membered heterocycloalkyl having one or two nitrogens. In some embodiments of a compound of Formula (I) or (II), or a pharmaceutically acceptable salt, solvate, or stereoisomer thereof, Ring C is a 5- to 7-membered heterocycloalkyl having one or two nitrogens. In some embodiments of a compound of Formula (I) or (II), or a pharmaceutically acceptable salt, solvate, or stereoisomer thereof, Ring C is a 5- to 6-membered heterocycloalkyl having one or two nitrogens. In some embodiments of a compound of Formula (I) or (II), or a pharmaceutically acceptable salt, solvate, or stereoisomer thereof, Ring C is a 5-membered heterocycloalkyl having one or two nitrogens. In some embodiments of a compound of Formula (I) or (II), or a pharmaceutically acceptable salt, solvate, or stereoisomer thereof, Ring C is a 6-membered heterocycloalkyl having one or two nitrogens.

In some embodiments of a compound of Formula (I) or (II), or a pharmaceutically acceptable salt, solvate, or stereoisomer thereof, Ring C is a 5- to 7-membered heteroaryl. In some embodiments of a compound of Formula (I) or (II), or a pharmaceutically acceptable salt, solvate, or stereoisomer thereof, Ring C is a 5- to 6-membered heteroaryl. In some embodiments of a compound of Formula (I) or (II), or a pharmaceutically acceptable salt, solvate, or stereoisomer thereof, Ring C is a 5-membered heteroaryl. In some embodiments of a compound of Formula (I) or (II), or a pharmaceutically acceptable salt, solvate, or stereoisomer thereof, Ring C is a 6-membered heteroaryl.

In some embodiments of a compound of Formula (I) or (II), or a pharmaceutically acceptable salt, solvate, or stereoisomer thereof, Ring C is a 5- to 7-membered heteroaryl having one, two, or three heteroatoms selected from nitrogen, oxygen, and sulfur. In some embodiments of a compound of Formula (I) or (II), or a pharmaceutically acceptable salt, solvate, or stereoisomer thereof, Ring C is a 5- to 6-membered heteroaryl having one, two, or three heteroatoms selected from nitrogen, oxygen, and sulfur. In some embodiments of a compound of Formula (I) or (II), or a pharmaceutically acceptable salt, solvate, or stereoisomer thereof, Ring C is a 5-membered heteroaryl having one, two, or three heteroatoms selected from nitrogen, oxygen, and sulfur. In some embodiments of a compound of Formula (I) or (II), or a pharmaceutically acceptable salt, solvate, or stereoisomer thereof, Ring C is a 6-membered heteroaryl having one, two, or three heteroatoms selected from nitrogen, oxygen, and sulfur.

In some embodiments of a compound of Formula (I) or (II), or a pharmaceutically acceptable salt, solvate, or stereoisomer thereof, Ring C is a 5- to 7-membered heteroaryl having one or two heteroatoms selected from nitrogen and oxygen. In some embodiments of a compound of Formula (I) or (II), or a pharmaceutically acceptable salt, solvate, or stereoisomer thereof, Ring C is a 5- to 6-membered heteroaryl having one or two heteroatoms selected from nitrogen and oxygen. In some embodiments of a compound of Formula (I) or (II), or a pharmaceutically acceptable salt, solvate, or stereoisomer thereof, Ring C is a 5-membered heteroaryl having one or two heteroatoms selected from nitrogen and oxygen. In some embodiments of a compound of Formula (I) or (II), or a pharmaceutically acceptable salt, solvate, or stereoisomer thereof, Ring C is a 6-membered heteroaryl having one or two heteroatoms selected from nitrogen and oxygen.

In some embodiments of a compound of Formula (I) or (II), or a pharmaceutically acceptable salt, solvate, or stereoisomer thereof, Ring C is a 5- to 7-membered heteroaryl having one or two nitrogens. In some embodiments of a compound of Formula (I) or (II), or a pharmaceutically acceptable salt, solvate, or stereoisomer thereof, Ring C is a 5- to 6-membered heteroaryl having one or two nitrogens. In some embodiments of a compound of Formula (I) or (II), or a pharmaceutically acceptable salt, solvate, or stereoisomer thereof, Ring C is a 5-membered heteroaryl having one or two nitrogens. In some embodiments of a compound of Formula (I) or (II), or a pharmaceutically acceptable salt, solvate, or stereoisomer thereof, Ring C is a 6-membered heteroaryl having one or two nitrogens.

In some embodiments of a compound of Formula (I) or (II), or a pharmaceutically acceptable salt, solvate, or stereoisomer thereof, Ring B is

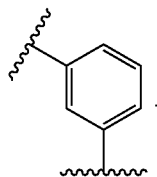 [SMILES: *c1cccc(*)c1]

In some embodiments of a compound of Formula (I) or (II), or a pharmaceutically acceptable salt, solvate, or stereoisomer thereof, each $R^5$ is independently hydrogen, halogen, —CN, —OH, —$OR^a$, —SH, —$SR^a$, —$S(=O)R^a$, —$NO_2$, —$NR^bR^c$, —$S(=O)_2R^a$, —$NHS(=O)_2R^a$, —$S(=O)_2NR^bR^c$, —$C(=O)R^a$, —$OC(=O)R^a$, —$C(=O)OR^b$, —$OC(=O)OR^b$, —$C(=O)NR^bR^c$, —$OC(=O)$ $NR^bR^c$, —$NR^bC(=O)NR^bR^c$, —$NR^bC(=O)R^a$, —$NR^bC(=O)OR^b$, $C_{1-6}$alkyl, $C_{1-6}$haloalkyl, $C_{1-6}$hydroxyalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three $R^{13}$. In some embodiments of a compound of Formula (I) or (II), or a pharmaceutically acceptable salt, solvate, or stereoisomer thereof, each $R^5$ is independently hydrogen, halogen, —CN, —$OR^a$, $C_{1-6}$hydroxyalkyl, $C_{2-6}$alkenyl, or $C_{1-6}$alkyl optionally substituted with one, two, or three $R^{13}$. In some embodiments of a compound of Formula (I) or (II), or a pharmaceutically acceptable salt, solvate, or stereoisomer thereof, each $R^5$ is independently hydrogen, halogen, —CN, —$OR^a$, $C_{1-6}$haloalkyl, $C_{1-6}$hydroxyalkyl, $C_{2-6}$alkenyl, or $C_{1-6}$alkyl. In some embodiments of a compound of Formula (I) or (II), or a pharmaceutically acceptable salt, solvate, or stereoisomer thereof, each $R^5$ is independently hydrogen, —F, —Cl, —Br, —OMe, —$CH_3$, —$CH=CH_2$, —$CH(OH)CH_2OH$, —$CH_2F$, —$CHF_2$, or —$CF_3$. In some embodiments of a compound of Formula (I) or (II), or a pharmaceutically acceptable salt, solvate, or stereoisomer thereof, each $R^5$ is independently hydrogen, —F, —Cl, —Br, —OMe, —$CH=CH_2$, —$CH(OH)CH_2OH$, or —$CH_3$. In some embodiments of a compound of Formula (I) or (II), or a pharmaceutically acceptable salt, solvate, or stereoisomer thereof, each $R^5$ is independently hydrogen, —F, —Cl, —Br, —$CH=CH_2$, —$CH(OH)CH_2OH$, or —$CH_3$. In some embodiments of a compound of Formula (I) or (II), or a pharmaceutically acceptable salt, solvate, or stereoisomer thereof, each R is hydrogen or halogen. In some embodiments of a compound of Formula (I) or (II), or a pharmaceutically acceptable salt, solvate, or stereoisomer thereof, each R is hydrogen or $C_{1-6}$alkyl optionally substituted with one, two, or three $R^{13}$. In some embodiments of a compound of Formula (I) or (II), or a pharmaceutically acceptable salt, solvate, or stereoisomer thereof, each $R^5$ is hydrogen.

In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a heterocycle ring optionally substituted with one, two, or three $R^{13}$.

In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 4- to 7-membered heterocycloalkyl optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 5- to 6-membered heterocycloalkyl optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 5-membered heterocycloalkyl optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 6-membered heterocycloalkyl optionally substituted with one, two, or three $R^{13}$.

In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 4- to 7-membered heterocycloalkyl having one, two, or three heteroatoms selected from nitrogen, oxygen, and sulfur and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 5- to 6-membered heterocycloalkyl having one, two, or three heteroatoms selected from nitrogen, oxygen, and sulfur and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 5-membered heterocycloalkyl having one, two, or three heteroatoms selected from nitrogen, oxygen, and sulfur and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 6-membered heterocycloalkyl having one, two, or three heteroatoms selected from nitrogen, oxygen, and sulfur and optionally substituted with one, two, or three $R^{13}$.

In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 4- to 7-membered heterocycloalkyl having one or two heteroatoms selected from nitrogen or oxygen and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 5- to 6-membered heterocycloalkyl having one or two heteroatoms selected from nitrogen or oxygen and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 5-membered heterocycloalkyl having one or two heteroatoms selected from nitrogen or oxygen and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 6-membered heterocycloalkyl having one or two heteroatoms selected from nitrogen or oxygen and optionally substituted with one, two, or three $R^{13}$.

In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 4- to 7-membered heterocycloalkyl having one or two nitrogens and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 5- to 6-membered heterocycloalkyl having one or two nitrogens and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 5-membered heterocycloalkyl having one or two nitrogens and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 6-membered heterocycloalkyl having one or two nitrogens and optionally substituted with one, two, or three $R^{13}$.

In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 4- to 7-membered heteroaryl and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 5- to 6-membered heteroaryl and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 5-membered heteroaryl and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 6-membered heteroaryl and optionally substituted with one, two, or three $R^{13}$.

In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 4- to 7-membered heteroaryl having one, two, or three heteroatoms selected from nitrogen, oxygen, and sulfur and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 5- to 6-membered heteroaryl having one, two, or three heteroatoms selected from nitrogen, oxygen, and sulfur and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 5-membered heteroaryl having one, two, or three heteroatoms selected from nitrogen, oxygen, and sulfur and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 6-membered heteroaryl having one, two, or three heteroatoms selected from nitrogen, oxygen, and sulfur and optionally substituted with one, two, or three $R^{13}$.

In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 4- to 7-membered heteroaryl having one or two heteroatoms selected from nitrogen and oxygen and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 5- to 6-membered heteroaryl having one or two heteroatoms selected from nitrogen and oxygen and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 5-membered heteroaryl having one or two heteroatoms selected from nitrogen and oxygen and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 6-membered heteroaryl having one or two heteroatoms selected from nitrogen and oxygen and optionally substituted with one, two, or three $R^{13}$.

In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 4- to 7-membered heteroaryl having one or two nitrogens and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 5- to 6-membered heteroaryl having one or two nitrogens and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 5-membered heteroaryl having one or two nitrogens and optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 6-membered heteroaryl having one or two nitrogens and optionally substituted with one, two, or three $R^{13}$.

In some embodiments of a compound of Formula (I) or (II), or a pharmaceutically acceptable salt, solvate, or stereoisomer thereof, two $R^5$ on adjacent atoms or R and R on adjacent atoms are taken together with the atoms to which they are attached to form a carbocycle optionally substituted with one, two, or three $R^{13}$.

In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 4- to 7-membered cycloalkyl optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 5- to 6-membered cycloalkyl optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 5-membered cycloalkyl optionally substituted with one, two, or three $R^{13}$. In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form a 6-membered cycloalkyl optionally substituted with one, two, or three $R^{13}$.

In some embodiments of a compound of Formula (I) or (II), or a pharmaceutically acceptable salt, solvate, or stereoisomer thereof, two $R^5$ on adjacent atoms or $R^5$ and $R^8$ on adjacent atoms are taken together with the atoms to which they are attached to form phenyl optionally substituted with one, two, or three $R^{13}$.

In some embodiments of a compound of Formula (I) or (II), or a pharmaceutically acceptable salt, solvate, or stereoisomer thereof, $R^5$ is defined as above and each $R^{13}$ is independently halogen, —CN, —OH, —OR$^a$, —NR$^b$R$^c$, —C(=O)R$^a$, —C(=O)OR$^b$, —C(=O)NR$^b$R$^c$, —NR$^b$C(=O)R$^a$, $C_{1-6}$alkyl, $C_{1-6}$haloalkyl, $C_{1-6}$hydroxyalkyl, $C_{1-6}$heteroalkyl, or $C_{3-8}$cycloalkyl. In some embodiments of a compound of Formula (I) or (II), or a pharmaceutically acceptable salt, solvate, or stereoisomer thereof, $R^5$ is defined as above and each $R^{13}$ is independently halogen, —CN, —OR$^a$, —NR$^b$R$^c$, —C(=O)NR$^b$R$^c$, —NR$^b$C(=O)R$^a$, $C_{1-6}$alkyl, or $C_{1-6}$haloalkyl. In some embodiments of a compound of Formula (I) or (II), or a pharmaceutically acceptable salt, solvate, or stereoisomer thereof, $R^5$ is defined as above and each $R^{13}$ is independently halogen, $C_{1-6}$alkyl, or $C_{1-6}$haloalkyl. In some embodiments of a compound of Formula (I) or (II), or a pharmaceutically acceptable salt, solvate, or stereoisomer thereof, $R^5$ is defined as above and each $R^{13}$ is halogen. In some embodiments of a compound of Formula (I) or (II), or a pharmaceutically acceptable salt, solvate, or stereoisomer thereof, $R^5$ is defined as above and each $R^{13}$ is $C_{1-6}$alkyl. In some embodiments of a compound of Formula (I) or (II), or a pharmaceutically acceptable salt, solvate, or stereoisomer thereof, $R^5$ is defined as above and each $R^{13}$ is $C_{1-6}$haloalkyl.

In some embodiments of a compound of Formula (I) or (II), or a pharmaceutically acceptable salt, solvate, or stereoisomer thereof, n is 0 to 4. In some embodiments of a compound of Formula (I) or (II), or a pharmaceutically acceptable salt, solvate, or stereoisomer thereof, n is 0 to 3. In some embodiments of a compound of Formula (I) or (II), or a pharmaceutically acceptable salt, solvate, or stereoisomer thereof, n is 0 to 2. In some embodiments of a compound of Formula (I) or (II), or a pharmaceutically acceptable salt, solvate, or stereoisomer thereof, n is 0 to 1.

In some embodiments of a compound of Formula (I) or (II), or a pharmaceutically acceptable salt, solvate, or stereoisomer thereof, n is 1 to 4. In some embodiments of a compound of Formula (I) or (II), or a pharmaceutically acceptable salt, solvate, or stereoisomer thereof, n is 1 to 3. In some embodiments of a compound of Formula (I) or (II), or a pharmaceutically acceptable salt, solvate, or stereoisomer thereof, n is 1 to 2. In some embodiments of a compound of Formula (I) or (II), or a pharmaceutically acceptable salt, solvate, or stereoisomer thereof, n is 2 to 4. In some embodiments of a compound of Formula (I) or (II), or a pharmaceutically acceptable salt, solvate, or stereoisomer thereof, n is 2 to 3. In some embodiments of a compound of Formula (I) or (II), or a pharmaceutically acceptable salt, solvate, or stereoisomer thereof, n is 0. In some embodiments of a compound of Formula (I) or (II), or a pharmaceutically acceptable salt, solvate, or stereoisomer thereof, n is 1. In some embodiments of a compound of Formula (I) or (II), or a pharmaceutically acceptable salt, solvate, or stereoisomer thereof, n is 2. In some embodiments of a compound of Formula (I) or (II), or a pharmaceutically acceptable salt, solvate, or stereoisomer thereof, n is 3. In some embodiments of a compound of Formula (I) or (II), or a pharmaceutically acceptable salt, solvate, or stereoisomer thereof, n is 4.

In some embodiments of a compound of Formula (I) or (II), or a pharmaceutically acceptable salt, solvate, or stereoisomer thereof,

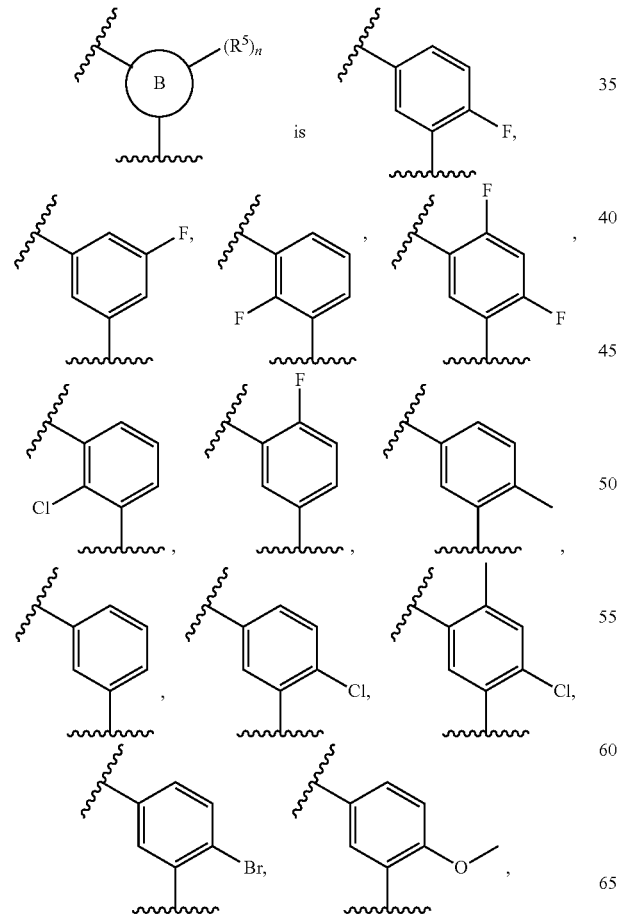

-continued

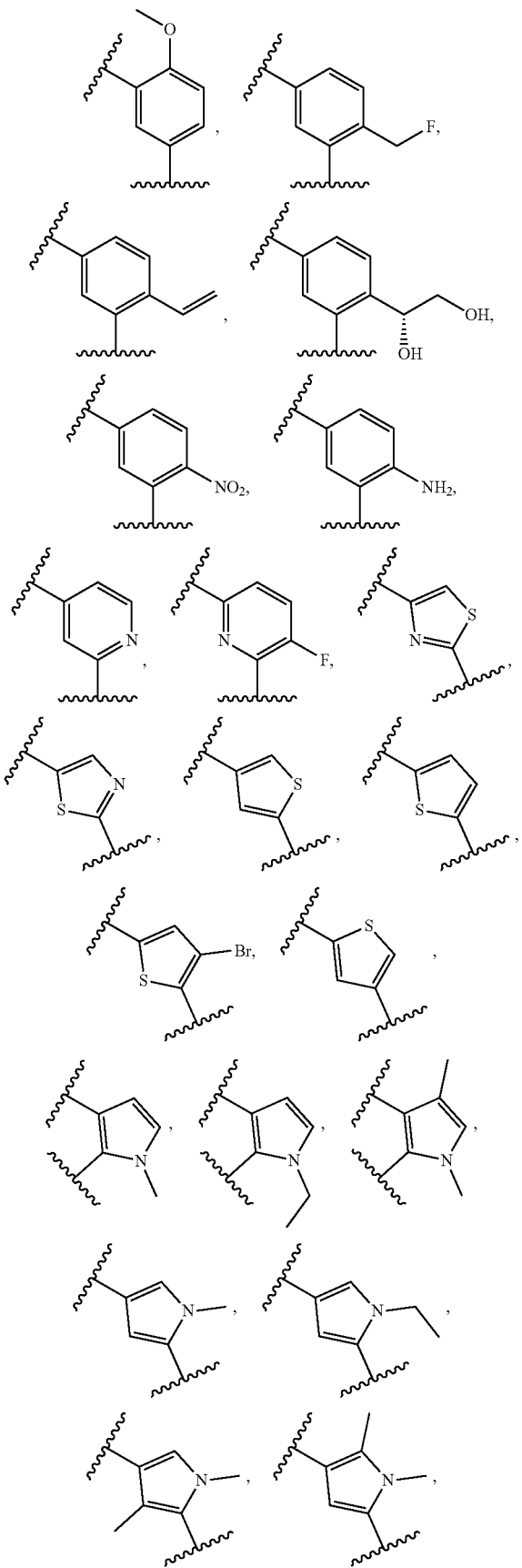

-continued
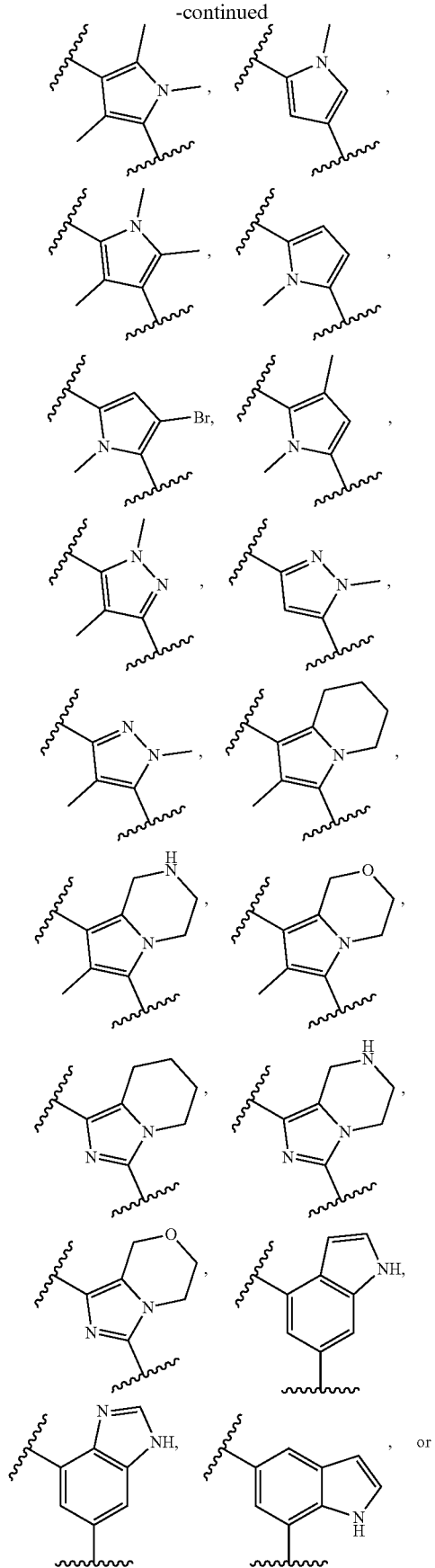
-continued
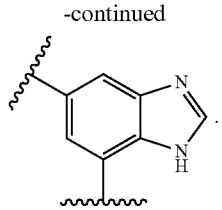
In some embodiments of a compound of Formula (I) or (II), or a pharmaceutically acceptable salt, solvate, or stereoisomer thereof,
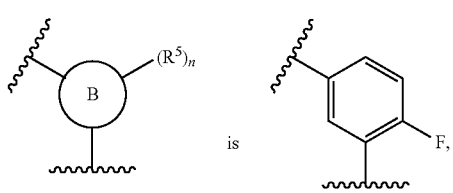
is
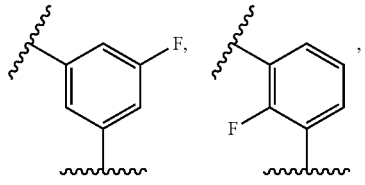
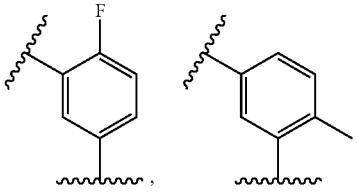
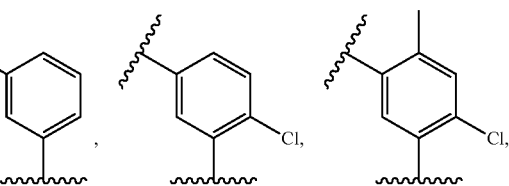
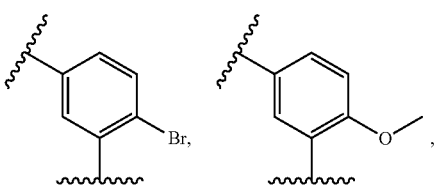
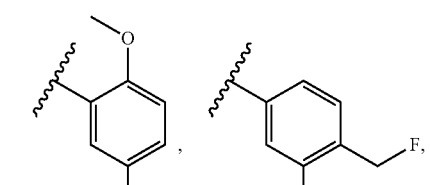
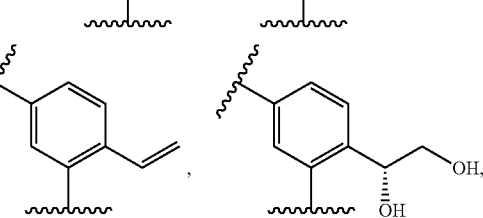

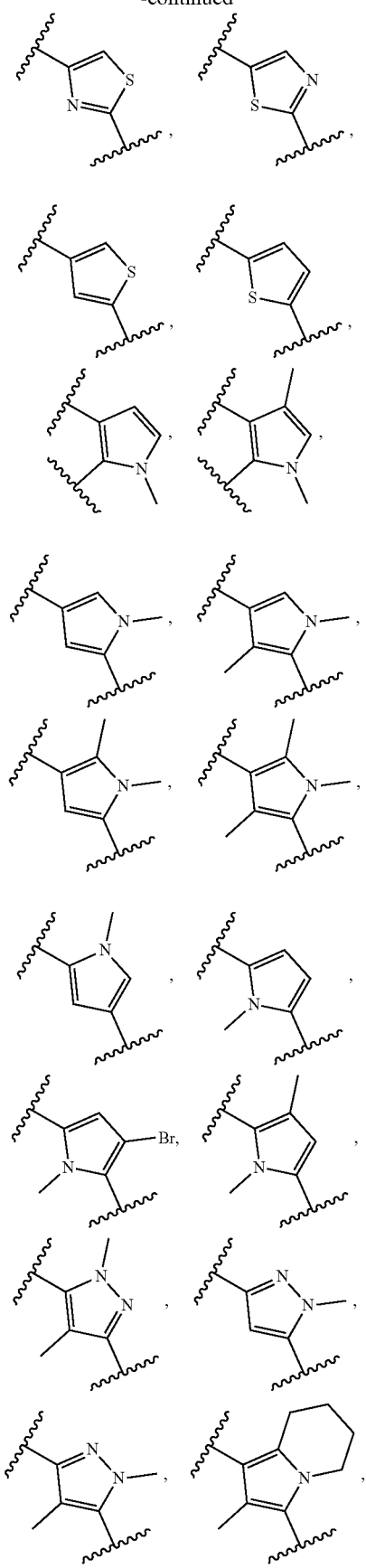
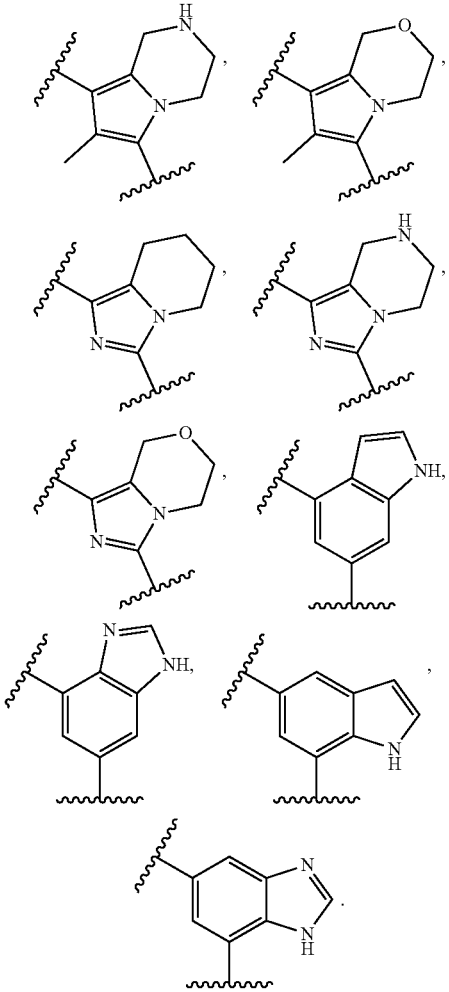
In some embodiments of a compound of Formula (I) or (II) or a pharmaceutically acceptable salt, solvate, or stereoisomer thereof,
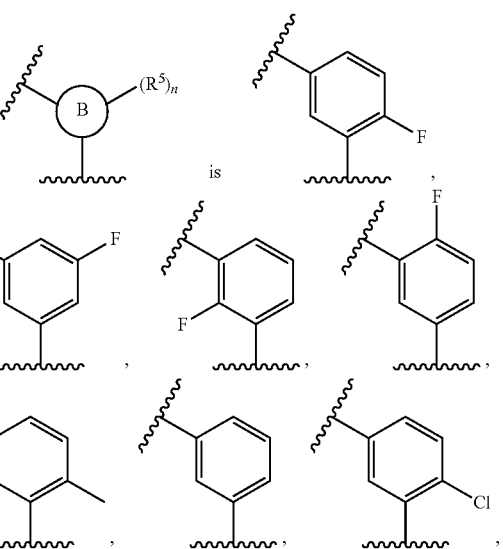

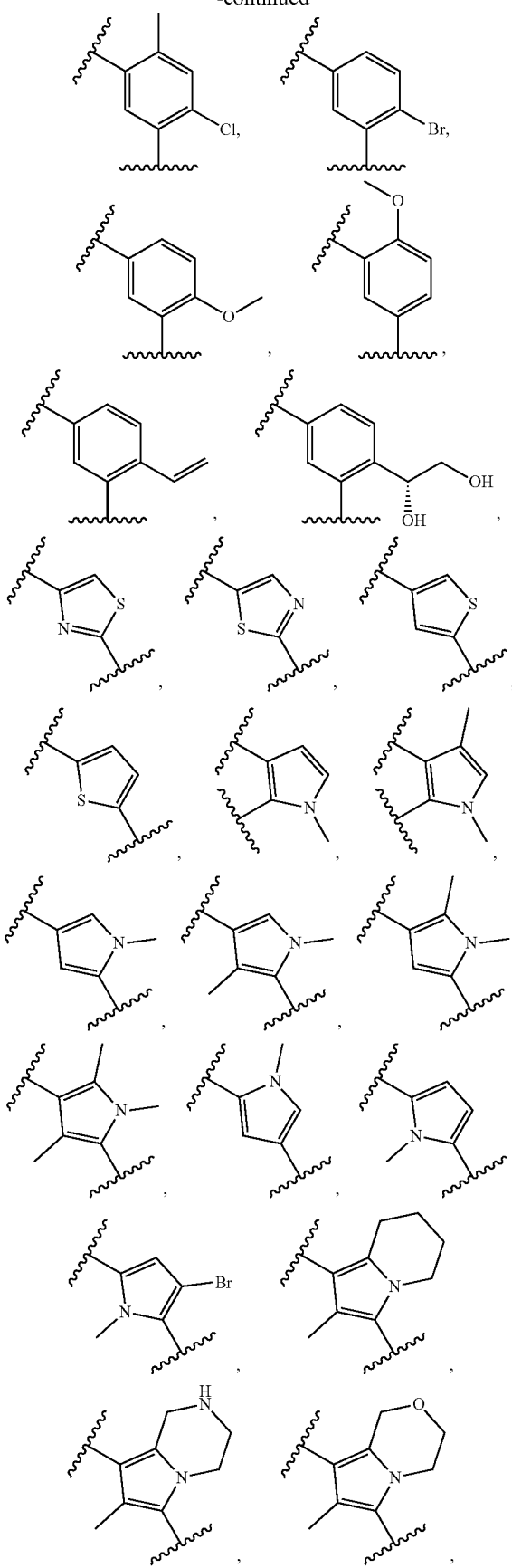
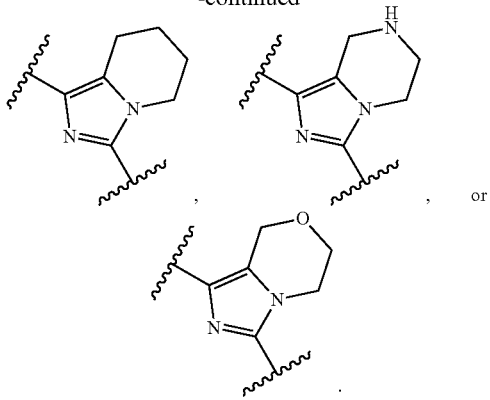
In some embodiments of a compound of Formula (I) or (II) or a pharmaceutically acceptable salt, solvate, or stereoisomer thereof,
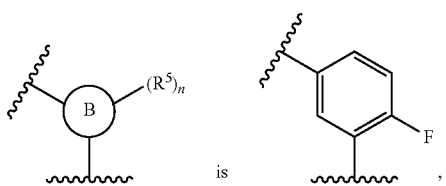
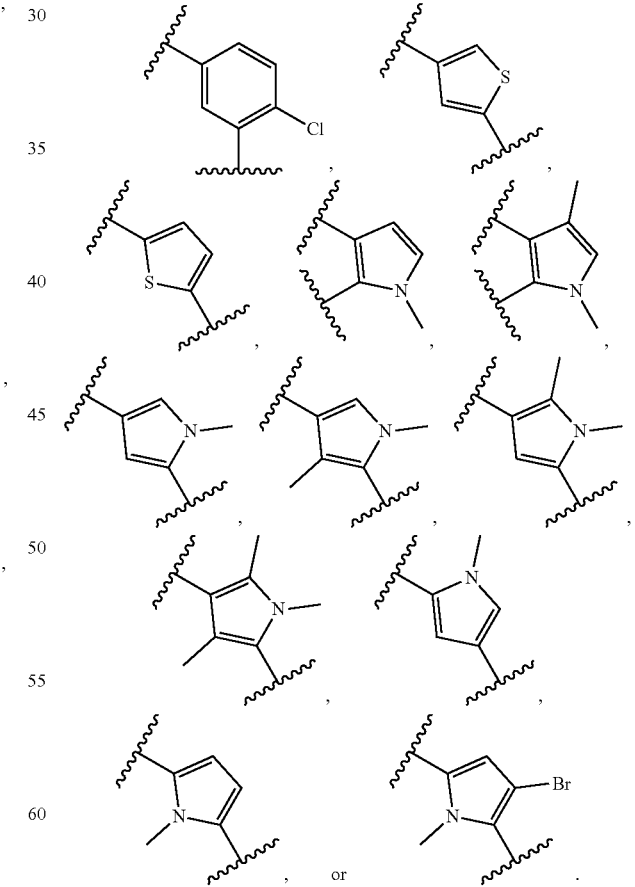
In some embodiments of a compound of Formula (I) or (II), or a pharmaceutically acceptable salt, solvate, or stereoisomer thereof,

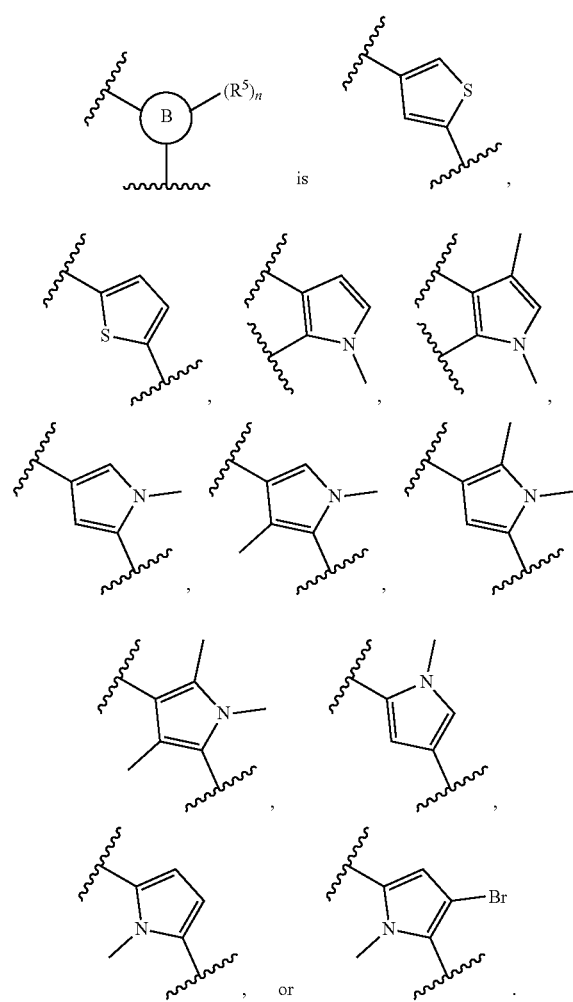

In some embodiments of a compound of Formula (I) or (II), or a pharmaceutically acceptable salt, solvate, or stereoisomer thereof,

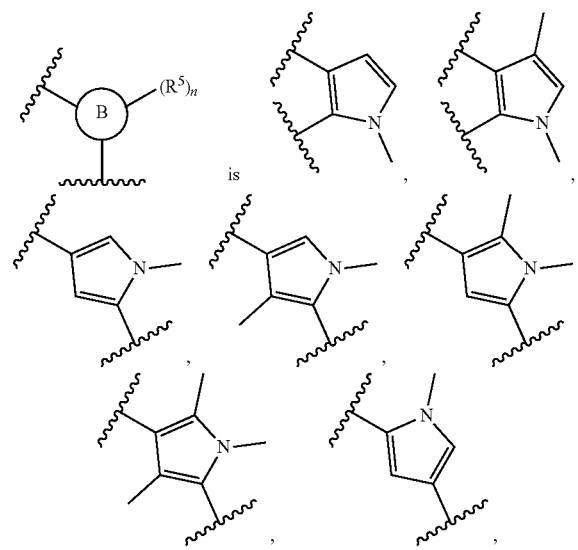

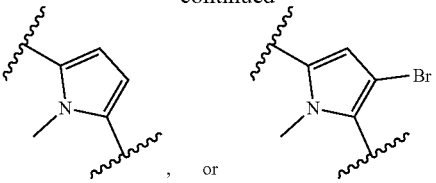

In some embodiments of a compound of Formula (I) or (II), or a pharmaceutically acceptable salt, solvate, or stereoisomer thereof, $R^6$ and $R^7$ are each independently hydrogen, $C_{1-6}$alkyl, $C_{1-6}$alkoxy, $C_{2-6}$alkenyl, $C_{2-6}$alkynyl, $C_{3-15}$cycloalkyl, $C_{2-15}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkoxy, alkenyl, alkynyl, cycloalkyl, heterocycloalkyl, aryl, and heteroaryl is independently optionally substituted with one, two, or three $R^{10}$.

In some embodiments of a compound of Formula (I) or (II), or a pharmaceutically acceptable salt, solvate, or stereoisomer thereof, $R^6$ is hydrogen, $C_{1-6}$alkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl ($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three $R^{10}$. In some embodiments of a compound of Formula (I) or (II), or a pharmaceutically acceptable salt, solvate, or stereoisomer thereof, $R^6$ is hydrogen or $C_{1-6}$alkyl; wherein the alkyl is optionally substituted with one, two, or three $R^{10}$. In some embodiments of a compound of Formula (I) or (II), or a pharmaceutically acceptable salt, solvate, or stereoisomer thereof, $R^6$ is hydrogen, $C_{1-6}$alkyl, or $C_{1-6}$hydroxyalkyl. In some embodiments of a compound of Formula (I) or (II), or a pharmaceutically acceptable salt, solvate, or stereoisomer thereof, $R^6$ is hydrogen, methyl, ethyl, propyl, or —CH$_2$CH$_2$OH. In some embodiments of a compound of Formula (I) or (II), or a pharmaceutically acceptable salt, solvate, or stereoisomer thereof, $R^6$ is hydrogen. In some embodiments of a compound of Formula (I) or (II), or a pharmaceutically acceptable salt, solvate, or stereoisomer thereof, $R^6$ is methyl. In some embodiments of a compound of Formula (I) or (II), or a pharmaceutically acceptable salt, solvate, or stereoisomer thereof, $R^6$ is ethyl. In some embodiments of a compound of Formula (I) or (II), or a pharmaceutically acceptable salt, solvate, or stereoisomer thereof, $R^6$ is propyl. In some embodiments of a compound of Formula (I) or (II), or a pharmaceutically acceptable salt, solvate, or stereoisomer thereof, $R^6$ is —CH$_2$CH$_2$OH.

In some embodiments of a compound of Formula (I) or (II), or a pharmaceutically acceptable salt, solvate, or stereoisomer thereof, $R^7$ is hydrogen, $C_{1-6}$alkyl, $C_{2-6}$alkenyl, $C_{2-6}$alkynyl, $C_{3-15}$cycloalkyl, $C_{2-15}$heterocycloalkyl, aryl, heteroaryl, $C_{1-6}$alkyl(aryl), $C_{1-6}$alkyl(heteroaryl), $C_{1-6}$alkyl ($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three $R^{10}$. In some embodiments of a compound of Formula (I) or (II), or a pharmaceutically acceptable salt, solvate, or stereoisomer thereof, $R^7$ is hydrogen, $C_{1-6}$alkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl (aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three $R^{10}$. In some embodiments of a compound of Formula (I) or (II), or a pharmaceutically acceptable salt, solvate, or stereoisomer thereof, $R^7$ is $C_{1-6}$alkyl, $C_{1-6}$alkoxy, $C_{3-15}$cycloalkyl, $C_{2-15}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, cycloalkyl, heterocycloalkyl, aryl, and heteroaryl is independently optionally substituted with one, two, or three $R^{10}$. In some embodiments of a compound of Formula (I) or (II), or a pharmaceutically acceptable salt, solvate, or stereoisomer thereof, $R^7$ is $C_{1-6}$alkyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, cycloalkyl, heterocycloalkyl, aryl, and heteroaryl is independently optionally substituted with one, two, or three $R^{10}$.

In some embodiments of a compound of Formula (I) or (II), or a pharmaceutically acceptable salt, solvate, or stereoisomer thereof, $R^7$ is $C_{1-6}$alkyl. In some embodiments of a compound of Formula (I) or (II), or a pharmaceutically acceptable salt, solvate, or stereoisomer thereof, $R^7$ is $C_{1-6}$alkyl substituted with one, two, or three $R^{10}$. In some embodiments of a compound of Formula (I) or (II), or a pharmaceutically acceptable salt, solvate, or stereoisomer thereof, $R^7$ is $C_{1-6}$alkyl substituted with three $R^{10}$. In some embodiments of a compound of Formula (I) or (II), or a pharmaceutically acceptable salt, solvate, or stereoisomer thereof, $R^7$ is $C_{1-6}$alkyl substituted with one or two $R^{10}$. In some embodiments of a compound of Formula (I) or (II), or a pharmaceutically acceptable salt, solvate, or stereoisomer thereof, $R^7$ is $C_{1-6}$alkyl substituted with one $R^{10}$. In some embodiments of a compound of Formula (I) or (II), or a pharmaceutically acceptable salt, solvate, or stereoisomer thereof, $R^7$ is $C_{1-6}$alkyl substituted with two $R^{10}$.

In some embodiments of a compound of Formula (I) or (II), or a pharmaceutically acceptable salt, solvate, or stereoisomer thereof, $R^7$ is $C_{3-15}$cycloalkyl. In some embodiments of a compound of Formula (I) or (II), or a pharmaceutically acceptable salt, solvate, or stereoisomer thereof, $R^7$ is $C_{3-8}$cycloalkyl. In some embodiments of a compound of Formula (I) or (II), or a pharmaceutically acceptable salt, solvate, or stereoisomer thereof, $R^7$ is a monocyclic cycloalkyl. In some embodiments of a compound of Formula (I) or (II), or a pharmaceutically acceptable salt, solvate, or stereoisomer thereof, $R^7$ is cyclopropyl, cyclobutyl, cyclopentyl, cyclohexyl, cycloheptyl, or cyclooctyl. In some embodiments of a compound of Formula (I) or (II), or a pharmaceutically acceptable salt, solvate, or stereoisomer thereof, $R^7$ is cyclopropyl. In some embodiments of a compound of Formula (I) or (II), or a pharmaceutically acceptable salt, solvate, or stereoisomer thereof, $R^7$ is cyclobutyl. In some embodiments of a compound of Formula (I) or (II), or a pharmaceutically acceptable salt, solvate, or stereoisomer thereof, $R^7$ is cyclopentyl. In some embodiments of a compound of Formula (I) or (II), or a pharmaceutically acceptable salt, solvate, or stereoisomer thereof, $R^7$ is cyclohexyl. In some embodiments of a compound of Formula (I) or (II), or a pharmaceutically acceptable salt, solvate, or stereoisomer thereof, $R^7$ is polycyclic cycloalkyl.

In some embodiments of a compound of Formula (I) or (II), or a pharmaceutically acceptable salt, solvate, or stereoisomer thereof, $R^7$ is $C_{3-15}$cycloalkyl substituted with one, two, or three $R^{10}$. In some embodiments of a compound of Formula (I) or (II), or a pharmaceutically acceptable salt, solvate, or stereoisomer thereof, $R^7$ is $C_{3-8}$cycloalkyl substituted with one $R^{10}$. In some embodiments of a compound of Formula (I) or (II), or a pharmaceutically acceptable salt, solvate, or stereoisomer thereof, $R^7$ is $C_{3-15}$cycloalkyl substituted with two $R^{10}$. In some embodiments of a compound of Formula (I) or (II), or a pharmaceutically acceptable salt, solvate, or stereoisomer thereof, $R^7$ is $C_{3-15}$cycloalkyl substituted with three $R^{10}$.

In some embodiments of a compound of Formula (I) or (II), or a pharmaceutically acceptable salt, solvate, or stereoisomer thereof, $R^7$ is $C_{3-8}$cycloalkyl substituted with one, two, or three $R^{10}$. In some embodiments of a compound of Formula (I) or (II), or a pharmaceutically acceptable salt, solvate, or stereoisomer thereof, $R^7$ is $C_{3-8}$cycloalkyl substituted with one $R^{10}$. In some embodiments of a compound of Formula (I) or (II), or a pharmaceutically acceptable salt, solvate, or stereoisomer thereof, $R^7$ is $C_{3-8}$cycloalkyl substituted with two $R^{10}$. In some embodiments of a compound of Formula (I) or (II), or a pharmaceutically acceptable salt, solvate, or stereoisomer thereof, $R^7$ is $C_{3-8}$cycloalkyl substituted with three $R^{10}$.

In some embodiments of a compound of Formula (I) or (II), or a pharmaceutically acceptable salt, solvate, or stereoisomer thereof, $R^7$ is cyclohexyl substituted with one, two, or three $R^{10}$. In some embodiments of a compound of Formula (I) or (II), or a pharmaceutically acceptable salt, solvate, or stereoisomer thereof, $R^7$ is cyclohexyl substituted with one $R^{10}$. In some embodiments of a compound of Formula (I) or (II), or a pharmaceutically acceptable salt, solvate, or stereoisomer thereof, $R^7$ is cyclohexyl substituted with two $R^{10}$. In some embodiments of a compound of Formula (I) or (II), or a pharmaceutically acceptable salt, solvate, or stereoisomer thereof, $R^7$ is cyclohexyl substituted with three $R^{10}$.

In some embodiments of a compound of Formula (I) or (II), or a pharmaceutically acceptable salt, solvate, or stereoisomer thereof, $R^7$ is cyclopropyl substituted with one, two, or three $R^{10}$. In some embodiments of a compound of Formula (I) or (II), or a pharmaceutically acceptable salt, solvate, or stereoisomer thereof, $R^7$ is cyclopropyl substituted with one $R^{10}$. In some embodiments of a compound of Formula (I) or (II), or a pharmaceutically acceptable salt, solvate, or stereoisomer thereof, $R^7$ is cyclopropyl substituted with two $R^{10}$. In some embodiments of a compound of Formula (I) or (II), or a pharmaceutically acceptable salt, solvate, or stereoisomer thereof, $R^7$ is cyclopropyl substituted with three $R^{13}$.

In some embodiments of a compound of Formula (I) or (II), or a pharmaceutically acceptable salt, solvate, or stereoisomer thereof, $R^7$ is $C_{2-15}$heterocycloalkyl. In some embodiments of a compound of Formula (I) or (II), or a pharmaceutically acceptable salt, solvate, or stereoisomer thereof, $R^7$ is $C_{2-7}$heterocycloalkyl. In some embodiments of a compound of Formula (I) or (II), or a pharmaceutically acceptable salt, solvate, or stereoisomer thereof, $R^7$ is monocyclic $C_{2-7}$heterocycloalkyl. In some embodiments of a compound of Formula (I) or (II), or a pharmaceutically acceptable salt, solvate, or stereoisomer thereof, $R^7$ is polycyclic $C_{2-15}$heterocycloalkyl. In some embodiments of a compound of Formula (I) or (II), or a pharmaceutically acceptable salt, solvate, or stereoisomer thereof, $R^7$ is polycyclic $C_{2-7}$heterocycloalkyl. In some embodiments of a compound of Formula (I) or (II), or a pharmaceutically acceptable salt, solvate, or stereoisomer thereof, $R^7$ is aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, or 2-oxo-1,3-dioxol-4-yl. In some embodiments of a compound of Formula (I) or (II), or a pharmaceutically acceptable salt, solvate, or stereoisomer thereof, $R^7$ is aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, or 2-oxo-1,3-dioxol-4-yl. In some embodiments of a compound of Formula (I) or (II), or a pharmaceutically acceptable salt, solvate, or stereoisomer thereof, $R^7$ is oxetanyl, tetrahydrofuryl, or tetrahydropyranyl. In some embodiments of a compound of Formula (I) or (II), or a pharmaceutically acceptable salt, solvate, or stereoisomer thereof, $R^7$ is oxetanyl. In some embodiments of a compound of Formula (I) or (II), or a pharmaceutically acceptable salt, solvate, or stereoisomer thereof, $R^7$ is tetrahydrofuryl. In some embodiments of a compound of Formula (I) or (II), or a pharmaceutically acceptable salt, solvate, or stereoisomer thereof, $R^7$ is tetrahydropyranyl.

In some embodiments of a compound of Formula (I) or (II), or a pharmaceutically acceptable salt, solvate, or stereoisomer thereof, $R^7$ is $C_{2-15}$heterocycloalkyl substituted with one, two, or three $R^{10}$. In some embodiments of a compound of Formula (I) or (II), or a pharmaceutically acceptable salt, solvate, or stereoisomer thereof, $R^7$ is $C_{2-15}$heterocycloalkyl substituted with one $R^{10}$. In some embodiments of a compound of Formula (I) or (II), or a pharmaceutically acceptable salt, solvate, or stereoisomer thereof, $R^7$ is $C_{2-15}$heterocycloalkyl substituted with two $R^{10}$. In some embodiments of a compound of Formula (I) or (II), or a pharmaceutically acceptable salt, solvate, or stereoisomer thereof, $R^7$ is $C_{2-7}$heterocycloalkyl substituted with three $R^{10}$.

In some embodiments of a compound of Formula (I) or (II), or a pharmaceutically acceptable salt, solvate, or stereoisomer thereof, $R^7$ is $C_{2-7}$heterocycloalkyl substituted with one, two, or three $R^{10}$. In some embodiments of a compound of Formula (I) or (II), or a pharmaceutically acceptable salt, solvate, or stereoisomer thereof, $R^7$ is $C_{2-7}$heterocycloalkyl substituted with one $R^{10}$. In some embodiments of a compound of Formula (I) or (II), or a pharmaceutically acceptable salt, solvate, or stereoisomer thereof, $R^7$ is $C_{2-7}$heterocycloalkyl substituted with two $R^{10}$. In some embodiments of a compound of Formula (I) or (II), or a pharmaceutically acceptable salt, solvate, or stereoisomer thereof, $R^7$ is $C_{2-7}$heterocycloalkyl substituted with three $R^{10}$.

In some embodiments of a compound of Formula (I) or (II), or a pharmaceutically acceptable salt, solvate, or stereoisomer thereof, $R^7$ is aryl. In some embodiments of a compound of Formula (I) or (II), or a pharmaceutically acceptable salt, solvate, or stereoisomer thereof, $R^7$ is $C_{6-10}$aryl. In some embodiments of a compound of Formula (I) or (II), or a pharmaceutically acceptable salt, solvate, or stereoisomer thereof, Ring A is anthryl, naphthyl, phenanthryl, phenyl, fluoryl, indanyl, or indenyl. In some embodiments of a compound of Formula (I) or (II), or a pharmaceutically acceptable salt, solvate, or stereoisomer thereof, $R^7$ is naphthyl or phenyl. In some embodiments of a compound of Formula (I) or (II), or a pharmaceutically acceptable salt, solvate, or stereoisomer thereof, $R^7$ is phenyl. In some embodiments of a compound of Formula (I) or (II), or a pharmaceutically acceptable salt, solvate, or stereoisomer thereof, $R^7$ is aryl substituted by one, two, or three $R^{10}$. In some embodiments of a compound of Formula (I) or (II), or a pharmaceutically acceptable salt, solvate, or stereoisomer thereof, $R^7$ is aryl substituted by one $R^{10}$. In some embodiments of a compound of Formula (I) or (II), or a pharmaceutically acceptable salt, solvate, or stereoisomer thereof, $R^7$ is phenyl substituted by one $R^{10}$.

In some embodiments of a compound of Formula (I) or (II), or a pharmaceutically acceptable salt, solvate, or stereoisomer thereof, $R^7$ is heteroaryl. In some embodiments of a compound of Formula (I) or (II), or a pharmaceutically acceptable salt, solvate, or stereoisomer thereof, $R^7$ is azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, or thiophenyl. In some embodiments of a compound of Formula (I) or (II), or a pharmaceutically acceptable salt, solvate, or stereoisomer thereof, $R^7$ is pyridinyl, pyrazinyl, pyrimidinyl, pyridazinyl, triazinyl, pyrrolyl, imidazolyl, pyrazolyl, oxazolyl, isoxazolyl, thiazolyl, isothiazolyl, triazolyl, or thiophenyl. In some embodiments of a compound of Formula (I) or (II), or a pharmaceutically acceptable salt, solvate, or stereoisomer thereof, $R^7$ is $C_{2-9}$heteroaryl. In some embodiments of a compound of Formula (I) or (II), or a pharmaceutically acceptable salt, solvate, or stereoisomer thereof, $R^7$ is pyridinyl, imidazolyl, pyrazolyl, thiazolyl, or thiophenyl. In some embodiments of a compound of Formula (I) or (II), or a pharmaceutically acceptable salt, solvate, or stereoisomer thereof, $R^7$ is pyridinyl. In some embodiments of a compound of Formula (I) or (II), or a pharmaceutically acceptable salt, solvate, or stereoisomer thereof, $R^7$ is heteroaryl substituted by one, two, or three $R^{10}$. In some embodiments of a compound of Formula (I) or (II), or a pharmaceutically acceptable salt, solvate, or stereoisomer thereof, $R^7$ is pyridinyl substituted by one, two, or three $R^{10}$. In some embodiments of a compound of Formula (I) or (II), or a pharmaceutically acceptable salt, solvate, or stereoisomer thereof, $R^7$ is pyridinyl substituted by one $R^{10}$.

In some embodiments of a compound of Formula (I) or (II), or a pharmaceutically acceptable salt, solvate, or stereoisomer thereof, $R^7$ is $C_{1-6}$alkyl(aryl). In some embodiments of a compound of Formula (I) or (II), or a pharmaceutically acceptable salt, solvate, or stereoisomer thereof, R⁷ is $C_{1-6}$alkyl(aryl); wherein alkyl and aryl are independently optionally substituted with one, two, or three R¹⁰.

In some embodiments of a compound of Formula (I) or (II), or a pharmaceutically acceptable salt, solvate, or stereoisomer thereof, R⁷ is $C_{1-6}$alkyl(heteroaryl). In some embodiments of a compound of Formula (I) or (II), or a pharmaceutically acceptable salt, solvate, or stereoisomer thereof, R⁷ is $C_{1-6}$alkyl(heteroaryl); wherein alkyl and heteroaryl are independently optionally substituted with one, two, or three R¹⁰.

In some embodiments of a compound of Formula (I) or (II), or a pharmaceutically acceptable salt, solvate, or stereoisomer thereof, R⁷ is $C_{1-6}$alkyl(cycloalkyl). In some embodiments of a compound of Formula (I) or (II), or a pharmaceutically acceptable salt, solvate, or stereoisomer thereof, R⁷ is $C_{1-6}$alkyl(cycloalkyl); wherein alkyl and cycloalkyl are independently optionally substituted with one, two, or three R¹⁰.

In some embodiments of a compound of Formula (I) or (II), or a pharmaceutically acceptable salt, solvate, or stereoisomer thereof, R⁷ is $C_{1-6}$alkyl(heterocycloalkyl). In some embodiments of a compound of Formula (I) or (II), or a pharmaceutically acceptable salt, solvate, or stereoisomer thereof, R⁷ is $C_{1-6}$alkyl(heterocycloalkyl); wherein alkyl and heterocycloalkyl are independently optionally substituted with one, two, or three R¹⁰.

In some embodiments of a compound of Formula (I) or (II), or a pharmaceutically acceptable salt, solvate, or stereoisomer thereof, R⁶ and R⁷ are defined as above and each R¹⁰ is independently oxo, halogen, —CN, —OH, —OR$^a$, —NR$^b$R$^c$, —NHS(=O)₂R$^a$, —S(=O)₂NR$^b$R$^c$, —C(=O)R$^a$, —OC(=O)R$^a$, —C(=O)OR$^b$, —B(OR$^d$)₂, —$C_{1-6}$alkyl, or $C_{1-6}$haloalkyl. In some embodiments of a compound of Formula (I) or (II), or a pharmaceutically acceptable salt, solvate, or stereoisomer thereof, R⁶ and R⁷ are defined as above and each R¹⁰ is independently —F, —Cl, —Br, —CN, —OH, —OMe, —OEt, —OiPr, —NH₂, —NHMe, —NMe₂, —NHS(=O)₂Me, —NHS(=O)₂Et, —NHS(=O)₂Pr, —NHS(=O)₂iPr, —S(=O)₂NH₂, —S(=O)₂NHMe, —S(=O)₂NMe₂, —C(=O)Me, —C(=O)Et, —C(=O)Pr, —C(=O)iPr, —OC(=O)Me, —OC(=O)Et, —OC(=O)iPr, —C(=O)OMe, —C(=O)OEt, —C(=O)OiPr, —B(OH)₂, methyl, ethyl, propyl, isopropyl, —CF₃, —CHF₂, or —CH₂F. In some embodiments of a compound of Formula (I) or (II), or a pharmaceutically acceptable salt, solvate, or stereoisomer thereof, R⁶ and R⁷ are defined as above and each R¹⁰ is independently —F, —Cl, —Br, —CN, —OH, —OMe, —OEt, —OiPr, —NH₂, —NHMe, —NMe₂, —B(OH)₂, methyl, ethyl, propyl, isopropyl, —CF₃, —CHF₂, or —CH₂F. In some embodiments of a compound of Formula (I) or (II), or a pharmaceutically acceptable salt, solvate, or stereoisomer thereof, R⁶ and R are defined as above and each R¹⁰ is independently —F, —Cl, —OH, —OMe, methyl, or —CF₃. In some embodiments of a compound of Formula (I), or a pharmaceutically acceptable salt, solvate, or stereoisomer thereof, R⁶ and R⁷ are defined as above and each R¹⁰ is independently —F, —OH, —OMe, methyl, or —CF₃. In some embodiments of a compound of Formula (I), or a pharmaceutically acceptable salt, solvate, or stereoisomer thereof, R⁶ and R⁷ are defined as above and each R¹⁰ is halogen or —OH. In some embodiments of a compound of Formula (I), or a pharmaceutically acceptable salt, solvate, or stereoisomer thereof, R⁶ and R⁷ are defined as above and each R¹⁰ is —F or —OH. In some embodiments of a compound of Formula (I), or a pharmaceutically acceptable salt, solvate, or stereoisomer thereof, R⁶ and R⁷ are defined as above and each R¹⁰ is —F. In some embodiments of a compound of Formula (I), or a pharmaceutically acceptable salt, solvate, or stereoisomer thereof, R⁶ and R⁷ are defined as above and each R¹⁰ is —OH. In some embodiments of a compound of Formula (I), or a pharmaceutically acceptable salt, solvate, or stereoisomer thereof, R⁶ and R⁷ are defined as above and each R¹⁰ is $C_{1-6}$alkyl.

In some embodiments of a compound of Formula (I) or (II), or a pharmaceutically acceptable salt, solvate, or stereoisomer thereof, R⁷ is

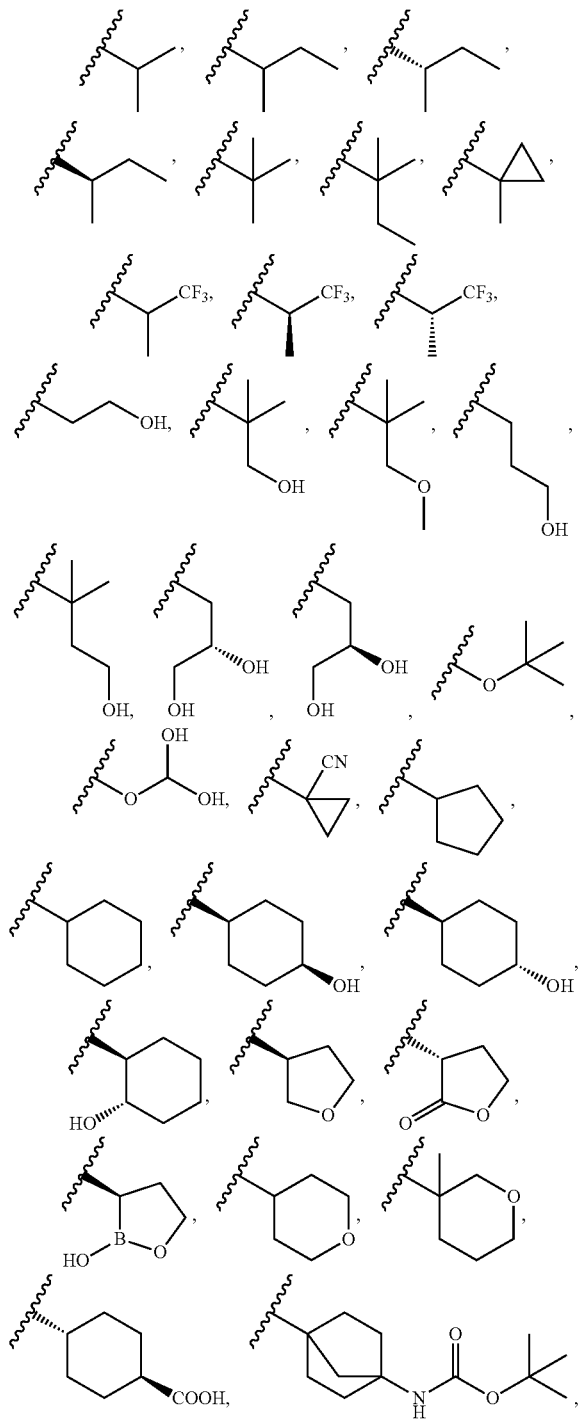

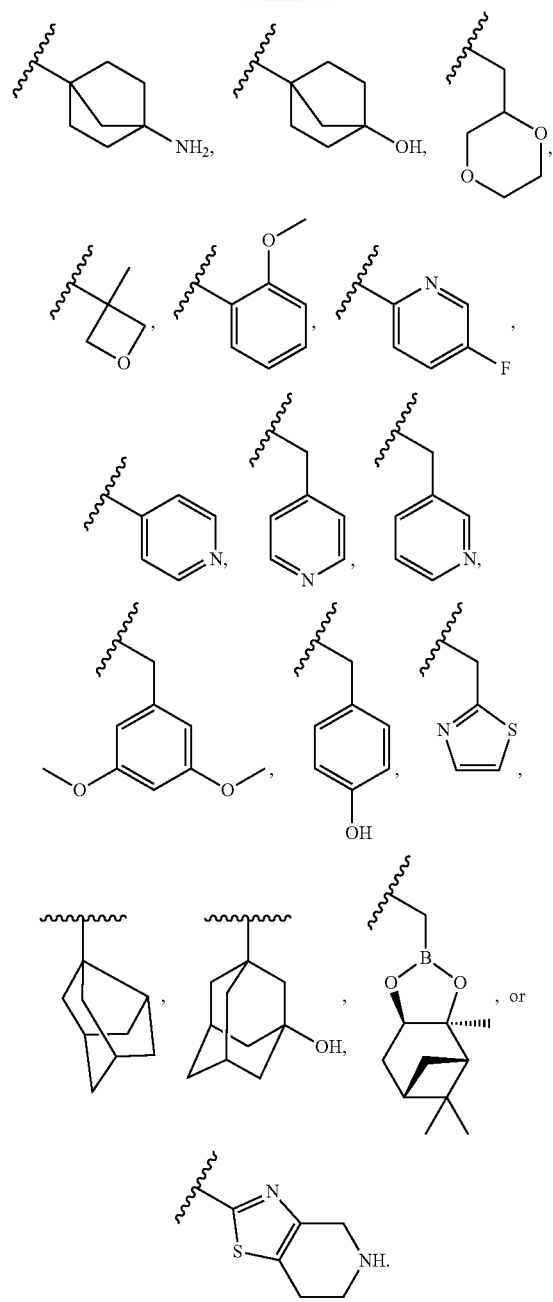
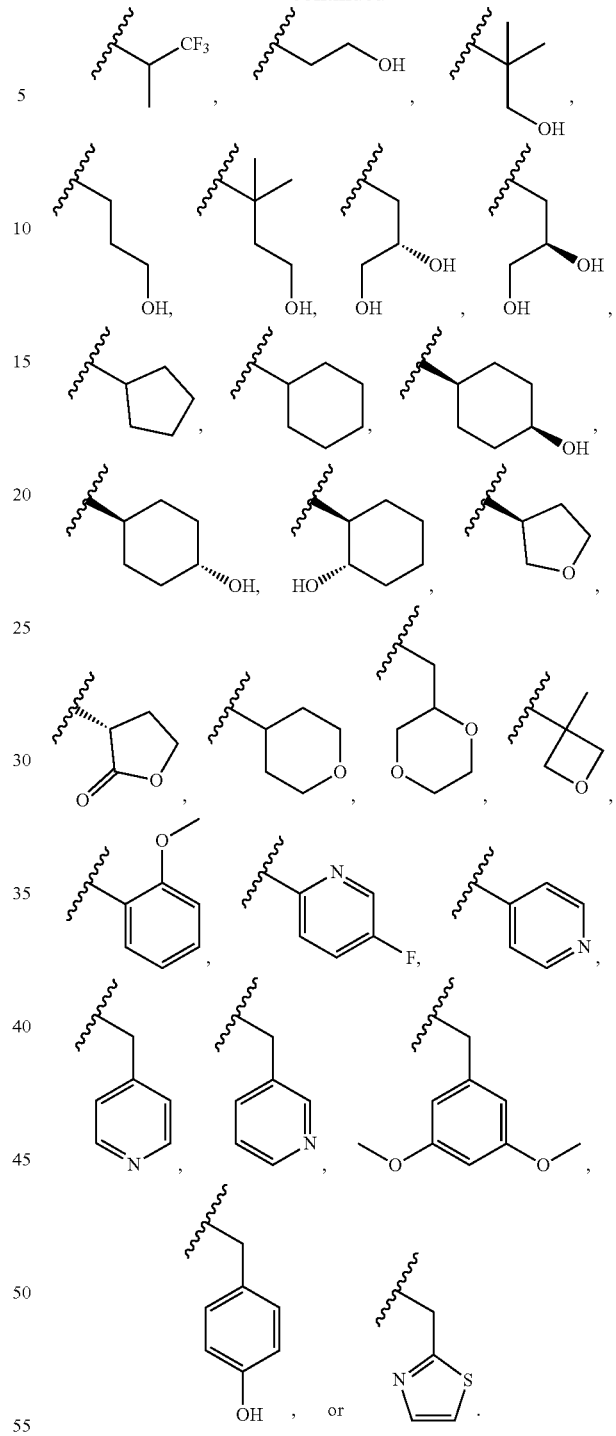

In some embodiments of a compound of Formula (I) or (II), or a pharmaceutically acceptable salt, solvate, or stereoisomer thereof, $R^7$ is In some embodiments of a compound of Formula (I) or (II), or a pharmaceutically acceptable salt, solvate, or stereoisomer thereof, $R^6$ and $R^7$ are taken together with the nitrogen atom to which they are attached to form a $C_{2-15}$heterocycloalkyl or a $C_{2-15}$heterocycloalkenyl; wherein each heterocycloalkyl and heterocycloalkenyl is independently optionally substituted with one, two, or three $R^{11}$. In some embodiments of a compound of Formula (I) or (II), or a pharmaceutically acceptable salt, solvate, or stereoisomer thereof, $R^6$ and $R^7$ are taken together with the nitrogen atom to which they are attached to form a $C_{2-7}$heterocycloalkyl or a C$_{2-7}$heterocycloalkenyl; wherein each heterocycloalkyl and heterocycloalkenyl is independently optionally substituted with one, two, or three R$^{11}$. In some embodiments of a compound of Formula (I) or (II), or a pharmaceutically acceptable salt, solvate, or stereoisomer thereof, R$^6$ and R$^7$ are taken together with the nitrogen atom to which they are attached to form a C$_{2-15}$heterocycloalkyl optionally substituted with one, two, or three R$^{11}$. In some embodiments of a compound of Formula (I) or (II), or a pharmaceutically acceptable salt, solvate, or stereoisomer thereof, R$^6$ and R$^7$ are taken together with the nitrogen atom to which they are attached to form a C$_{2-7}$heterocycloalkyl optionally substituted with one, two, or three R$^{11}$. In some embodiments of a compound of Formula (I) or (II), or a pharmaceutically acceptable salt, solvate, or stereoisomer thereof, R$^6$ and R$^7$ are taken together with the nitrogen atom to which they are attached to form aziridine, azetidine, pyrrolidine, piperidine, azepane, morpholine, oxazepane, 8-azabicyclo[3.2.1]octane, 3-azabicyclo[5.1.0]octane, or tetrahydropyridine; which is optionally substituted with one, two, or three R$^{11}$. In some embodiments of a compound of Formula (I) or (II), or a pharmaceutically acceptable salt, solvate, or stereoisomer thereof, R$^6$ and R$^7$ are taken together with the nitrogen atom to which they are attached to form pyrrolidine, piperidine, azepane, or morpholine; which is optionally substituted with one, two, or three R$^{11}$. In some embodiments of a compound of Formula (I) or (II), or a pharmaceutically acceptable salt, solvate, or stereoisomer thereof, R$^6$ and R$^7$ are taken together with the nitrogen atom to which they are attached to form piperidine; which is optionally substituted with one, two, or three R$^{11}$.

In some embodiments of a compound of Formula (I) or (II), or a pharmaceutically acceptable salt, solvate, or stereoisomer thereof, R$^6$ and R$^7$ are taken together with the nitrogen atom to which they are attached as defined above and each R$^{11}$ is independently oxo, halogen, —CN, —OH, —OR$^a$, —NR$^b$R$^c$, —S(=O)$_2$R$^a$, —NHS(=O)$_2$R$^a$, —S(=O)$_2$NR$^b$R$^c$, —NR$^b$S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —CH$_2$C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, —OP(=O)(OR$^b$)(OR$^b$), —B(OR$^d$)$_2$, C$_{1-6}$alkyl, C$_{1-6}$haloalkyl, C$_{1-6}$hydroxyalkyl, C$_{1-6}$cyanoalkyl, C$_{1-6}$heteroalkyl, or C$_{3-8}$cycloalkyl.

In some embodiments of a compound of Formula (I) or (II), or a pharmaceutically acceptable salt, solvate, or stereoisomer thereof, R$^6$ and R$^7$ are taken together with the nitrogen atom to which they are attached as defined above and each R$^{11}$ is independently halogen, —CN, —OH, —OR$^a$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, —OP(=O)(OR$^b$)(OR$^b$), C$_{1-6}$alkyl, C$_{1-6}$haloalkyl, C$_{1-6}$hydroxyalkyl, C$_{1-6}$heteroalkyl, or C$_{3-8}$cycloalkyl.

In some embodiments of a compound of Formula (I) or (II), or a pharmaceutically acceptable salt, solvate, or stereoisomer thereof, R$^6$ and R$^7$ are taken together with the nitrogen atom to which they are attached as defined above and each R$^{11}$ is independently oxo, halogen, —CN, —OH, —OR$^a$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, —CH$_2$C(=O)NR$^b$R$^c$, —NR$^b$C(=O)R$^a$, —NR$^b$C(=O)OR$^b$, —OP(=O)(OR$^b$)(OR$^b$), —B(OR$^d$)$_2$, $_{-6}$alkyl, C$_{1-6}$haloalkyl, C$_{1-6}$hydroxyalkyl, C$_{1-6}$heteroalkyl, C$_{1-6}$cyanoalkyl, or C$_{3-8}$cycloalkyl.

In some embodiments of a compound of Formula (I) or (II), or a pharmaceutically acceptable salt, solvate, or stereoisomer thereof, R$^6$ and R$^7$ are taken together with the nitrogen atom to which they are attached as defined above and each R$^{11}$ is independently halogen, —CN, —OH, —OR$^a$, —NR$^b$R$^c$, —C(=O)R$^a$, —OC(=O)R$^a$, —C(=O)OR$^b$, —C(=O)NR$^b$R$^c$, —NR$^b$C(=O)R$^a$, —OP(=O)(OR$^b$)(OR$^b$), C$_{1-6}$alkyl, C$_{1-6}$haloalkyl, C$_{1-6}$hydroxyalkyl, C$_{1-6}$heteroalkyl, or C$_{3-8}$cycloalkyl.

In some embodiments of a compound of Formula (I) or (II), or a pharmaceutically acceptable salt, solvate, or stereoisomer thereof, R$^6$ and R$^7$ are taken together with the nitrogen atom to which they are attached as defined above and each R$^{11}$ is independently oxo, —F, —Cl, —CN, —OH, —OMe, —NH$_2$, —NMe$_2$, —C(=O)Me, —OC(=O)Me, —C(=O)OH, —C(=O)OMe, —C(=O)OEt, —C(=O)OtBu, —C(=O)NH$_2$, —CH$_2$C(=O)NH$_2$, —NHS(=O)$_2$Me, —NHS(=O)$_2$NH$_2$, —S(=O)$_2$NH$_2$, —S(=O)$_2$NHMe, —S(=O)$_2$Me, —NHC(=O)Me, —OP(=O)(OH)(OH), —B(OH)$_2$, methyl, ethyl, iso-propyl, —CF$_3$, —CHF$_2$, —CH$_2$F, —CH$_2$OH, —CH$_2$CH$_2$OH, —CH$_2$CH$_2$CH$_2$OH, —CH$_2$OCH$_3$, —CH$_2$CH$_2$OCH$_3$, cyclopropyl, cyclobutyl, cyclopentyl, or cyclohexyl.

In some embodiments of a compound of Formula (I) or (II), or a pharmaceutically acceptable salt, solvate, or stereoisomer thereof, R$^6$ and R$^7$ are taken together with the nitrogen atom to which they are attached as defined above and each R$^{11}$ is independently —F, —Cl, —CN, —OH, —OMe, —NH$_2$, —C(=O)Me, —OC(=O)Me, —C(=O)OH, —C(=O)OMe, —C(=O)OEt, —C(=O)NH$_2$, —OP(=O)(OH)(OH), methyl, ethyl, iso-propyl, —CF$_3$, —CHF$_2$, —CH$_2$F, —CH$_2$OH, —CH$_2$CH$_2$OH, —CH$_2$CH$_2$CH$_2$OH, —CH$_2$OCH$_3$, —CH$_2$CH$_2$OCH$_3$, cyclopropyl, cyclobutyl, cyclopentyl, or cyclohexyl. In some embodiments of a compound of Formula (I) or (II), or a pharmaceutically acceptable salt, solvate, or stereoisomer thereof, R$^6$ and R$^7$ are taken together with the nitrogen atom to which they are attached as defined above and each R$^{11}$ is independently —F, —OH, —NH$_2$, —OC(=O)Me, —C(=O)OH, —OP(=O)(OH)(OH), methyl, ethyl, —CH$_2$OH, —CH$_2$CH$_2$OH, —CH$_2$OCH$_3$, or cyclopropyl. In some embodiments of a compound of Formula (I) or (II), or a pharmaceutically acceptable salt, solvate, or stereoisomer thereof, R$^6$ and R$^7$ are taken together with the nitrogen atom to which they are attached as defined above and each R$^{11}$ is independently —F, —OH, —NH$_2$, —C(=O)OH, methyl, or —CH$_2$OH. In some embodiments of a compound of Formula (I) or (II), or a pharmaceutically acceptable salt, solvate, or stereoisomer thereof, R$^6$ and R$^7$ are taken together with the nitrogen atom to which they are attached as defined above and each R$^{11}$ is independently —OH or —CH$_2$OH.

In some embodiments of a compound of Formula (I) or (II), or a pharmaceutically acceptable salt, solvate, or stereoisomer thereof,

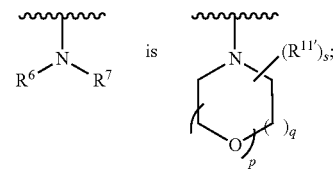

wherein each R$^{11'}$ is independently oxo, halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$ NR$^b$R$^c$, —NR$^b$S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —CH$_2$C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, —OP(=O)(OR$^b$)(OR$^b$), —B(OR$^d$)$_2$, C$_{1-6}$alkyl, C$_{1-6}$haloalkyl, C$_{1-6}$hydroxyalkyl, C$_{1-6}$heteroalkyl, C$_{1-6}$cyanoalkyl, C$_{2-6}$alkenyl, C$_{2-6}$alkynyl, C$_{3-8}$cycloalkyl, C$_{2-7}$heterocycloalkyl, aryl, heteroaryl, C$_{1-6}$alkyl(aryl), C$_{1-6}$alkyl(heteroaryl), C$_{1-6}$alkyl(C$_{3-8}$cycloalkyl), or C$_{1-6}$alkyl(C$_{2-7}$heterocycloalkyl); p is 0 or 1; q is 0 to 4; and s is 0 to 3.

In some embodiments of a compound of Formula (I) or (II), or a pharmaceutically acceptable salt, solvate, or stereoisomer thereof,

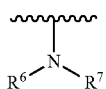

is as defined above and p is 0. In some embodiments of a compound of Formula (I) or (II), or a pharmaceutically acceptable salt, solvate, or stereoisomer thereof,

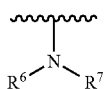

is as defined above and p is 1.

In some embodiments of a compound of Formula (I) or (II), or a pharmaceutically acceptable salt, solvate, or stereoisomer thereof,

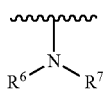

is as defined above and q is 0. In some embodiments of a compound of Formula (I) or (II), or a pharmaceutically acceptable salt, solvate, or stereoisomer thereof,

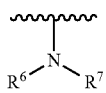

is as defined above and q is 1. In some embodiments of a compound of Formula (I) or (II), or a pharmaceutically acceptable salt, solvate, or stereoisomer thereof,

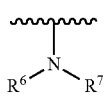

is as defined above and

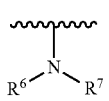

is as defined above and q is 2. In some embodiments of a compound of Formula (I) or (II), or a pharmaceutically acceptable salt, solvate, or stereoisomer thereof,

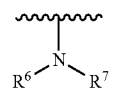

is as defined above and q is 3. In some embodiments of a compound of Formula (I) or (II), or a pharmaceutically acceptable salt, solvate, or stereoisomer thereof, q is 4.

In some embodiments of a compound of Formula (I) or (II), or a pharmaceutically acceptable salt, solvate, or stereoisomer thereof,

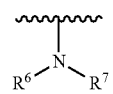

is as defined above; p is 0; and q is 0. In some embodiments of a compound of Formula (I) or (II), or a pharmaceutically acceptable salt, solvate, or stereoisomer thereof,

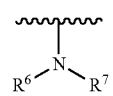

is as defined above; p is 0; and q is 1. In some embodiments of a compound of Formula (I) or (II), or a pharmaceutically acceptable salt, solvate, or stereoisomer thereof,

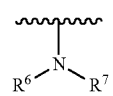

is as defined above; p is 0; and q is 2. In some embodiments of a compound of Formula (I) or (II), or a pharmaceutically acceptable salt, solvate, or stereoisomer thereof,

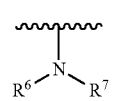

is as defined above; p is 0; and q is 3. In some embodiments of a compound of Formula (I) or (II), or a pharmaceutically acceptable salt, solvate, or stereoisomer thereof,

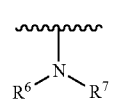

is as defined above; p is 0; and q is 4. In some embodiments of a compound of Formula (I) or (II), or a pharmaceutically acceptable salt, solvate, or stereoisomer thereof,

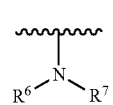

is as defined above; p is 1; and q is 0. In some embodiments of a compound of Formula (I) or (II), or a pharmaceutically acceptable salt, solvate, or stereoisomer thereof,

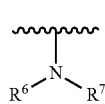

is as defined above; p is 1; and q is 1. In some embodiments of a compound of Formula (I) or (II), or a pharmaceutically acceptable salt, solvate, or stereoisomer thereof,

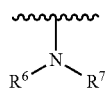

is as defined above; p is 1; and q is 2. In some embodiments of a compound of Formula (I) or (II), or a pharmaceutically acceptable salt, solvate, or stereoisomer thereof,

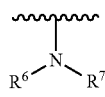

is as defined above; p is 1; and q is 3. In some embodiments of a compound of Formula (I) or (II), or a pharmaceutically acceptable salt, solvate, or stereoisomer thereof,

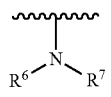

is as defined above; p is 1; and q is 4.

In some embodiments of a compound of Formula (I) or (II), or a pharmaceutically acceptable salt, solvate, or stereoisomer thereof,

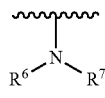

is as defined above and each $R^{11'}$ is independently oxo, halogen, —CN, —OH, —OR$^a$, —NR$^b$R$^c$, —S(=O)$_2$R$^a$, —NHS(=O)$_2$R$^a$, —S(=O)$_2$NR$^b$R$^c$, —NR$^b$S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —CH$_2$C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, —OP(=O)(OR$^b$)(OR$^b$), —B(OR$^d$)$_2$, C$_{1-6}$alkyl, C$_{1-6}$haloalkyl, C$_{1-6}$hydroxyalkyl, C$_{1-6}$heteroalkyl, C$_{1-6}$cyanoalkyl, or C$_{3-8}$cycloalkyl.

In some embodiments of a compound of Formula (I) or (II), or a pharmaceutically acceptable salt, solvate, or stereoisomer thereof,

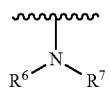

is as defined above and each $R^{11'}$ is independently halogen, —CN, —OH, —OR$^a$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, —OP(=O)(OR)(OR), C$_{1-6}$alkyl, C$_{1-6}$haloalkyl, C$_{1-6}$hydroxyalkyl, C$_{1-6}$heteroalkyl, or C$_{3-8}$cycloalkyl.

In some embodiments of a compound of Formula (I) or (II), or a pharmaceutically acceptable salt, solvate, or stereoisomer thereof,

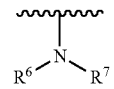

is as defined above and each $R^{11'}$ is independently oxo, halogen, —CN, —OH, —OR$^a$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, —CH$_2$C(=O)NR$^b$R$^c$, —NR$^b$C(=O)R$^a$, —NR$^b$C(=O)OR$^b$, —OP(=O)(OR)(OR), —B(OR$^d$)$_2$, $_{-6}$alkyl, C$_{1-6}$haloalkyl, C$_{1-6}$hydroxyalkyl, C$_{1-6}$heteroalkyl, C$_{1-6}$cyanoalkyl, C$_{3-8}$cycloalkyl.

In some embodiments of a compound of Formula (I) or (II), or a pharmaceutically acceptable salt, solvate, or stereoisomer thereof,

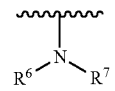

is as defined above and each $R^{11'}$ is independently halogen, —CN, —OH, —OR$^a$, —NR$^b$R$^c$, —C(=O)R$^a$, —OC(=O)R$^a$, —C(=O)OR$^b$, —C(=O)NR$^b$R$^c$, —NR$^b$C(=O)R$^a$, —OP(=O)(OR$^b$)(OR$^b$), C$_{1-6}$alkyl, C$_{1-6}$haloalkyl, C$_{1-6}$hydroxyalkyl, C$_{1-6}$heteroalkyl, or C$_{3-8}$cycloalkyl.

In some embodiments of a compound of Formula (I) or (II), or a pharmaceutically acceptable salt, solvate, or stereoisomer thereof,

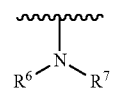

is as defined above and each $R^{11'}$ is independently oxo, —F, —Cl, —CN, —OH, —OMe, —NH$_2$, —NMe$_2$, —C(=O)Me, —OC(=O)Me, —C(=O)OH, —C(=O)OMe, —C(=O)OEt, —C(=O)OtBu, —C(=O)NH$_2$, —CH$_2$C(=O)NH$_2$, —NHS(=O)$_2$Me, —NHS(=O)$_2$NH$_2$, —S(=O)$_2$NH$_2$, —S(=O)$_2$NHMe, —S(=O)$_2$Me, —NHC(=O)Me, —OP(=O)(OH)(OH), —B(OH)$_2$, methyl, ethyl, iso-propyl, —CF$_3$, —CHF$_2$, —CH$_2$F, —CH$_2$OH, —CH$_2$CH$_2$OH, —CH$_2$CH$_2$CH$_2$OH, —CH$_2$OCH$_3$, —CH$_2$CH$_2$OCH$_3$, cyclopropyl, cyclobutyl, cyclopentyl, or cyclohexyl.

In some embodiments of a compound of Formula (I) or (II), or a pharmaceutically acceptable salt, solvate, or stereoisomer thereof,

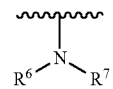

is as defined above and each $R^{11'}$ is independently —F, —Cl, —CN, —OH, —OMe, —NH$_2$, —C(=O)Me, —OC(=O)

Me, —C(=O)OH, —C(=O)OMe, —C(=O)OEt, —C(=O)NH$_2$, —OP(=O)(OH)(OH), methyl, ethyl, isopropyl, —CF$_3$, —CHF$_2$, —CH$_2$F, —CH$_2$OH, —CH$_2$CH$_2$OH, —CH$_2$CH$_2$CH$_2$OH, —CH$_2$OCH$_3$, —CH$_2$CH$_2$OCH$_3$, cyclopropyl, cyclobutyl, cyclopentyl, or cyclohexyl.

In some embodiments of a compound of Formula (I) or (II), or a pharmaceutically acceptable salt, solvate, or stereoisomer thereof,

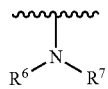

is as defined above and each R$^{11'}$ is independently —F, —OH, —NH$_2$, —OC(=O)Me, —C(=O)OH, —OP(=O)(OH)(OH), methyl, ethyl, —CH$_2$OH, —CH$_2$CH$_2$OH, —CH$_2$OCH$_3$, or cyclopropyl. In some embodiments of a compound of Formula (I) or (II), or a pharmaceutically acceptable salt, solvate, or stereoisomer thereof,

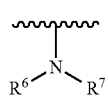

is as defined above and each R$^{11'}$ is independently —F, —OH, —NH$_2$, —C(=O)OH, methyl, or —CH$_2$OH. In some embodiments of a compound of Formula (I) or (II), or a pharmaceutically acceptable salt, solvate, or stereoisomer thereof,

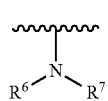

is as defined above and each R$^{11'}$ is independently —OH, or —CH$_2$OH.

In some embodiments of a compound of Formula (I) or (II), or a pharmaceutically acceptable salt, solvate, or stereoisomer thereof,

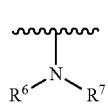

is as defined above and s is 0. In some embodiments of a compound of Formula (I) or (II), or a pharmaceutically acceptable salt, solvate, or stereoisomer thereof,

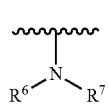

is as defined above and s is 1. In some embodiments of a compound of Formula (I) or (II), or a pharmaceutically acceptable salt, solvate, or stereoisomer thereof,

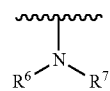

is as defined above and s is 2. In some embodiments of a compound of Formula (I) or (II), or a pharmaceutically acceptable salt, solvate, or stereoisomer thereof,

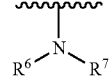

is as defined above and s is 3.

In some embodiments of a compound of Formula (I) or (II), or a pharmaceutically acceptable salt, solvate, or stereoisomer thereof,

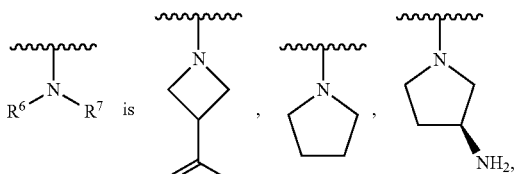

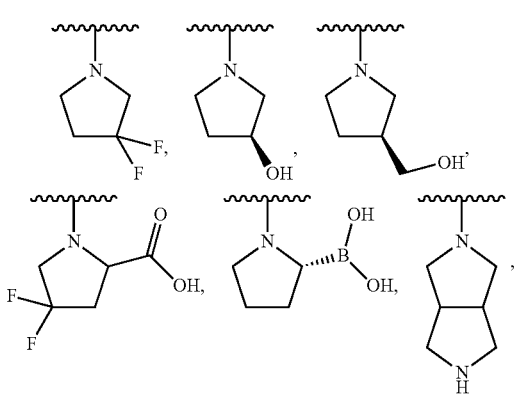

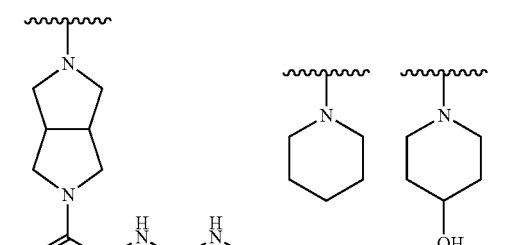

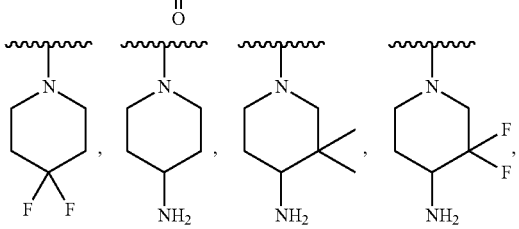

-continued
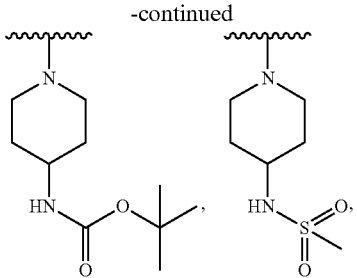
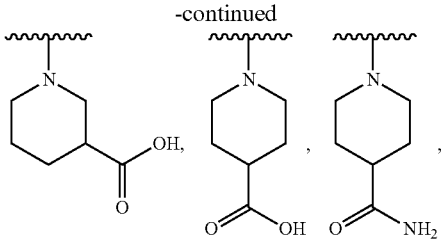
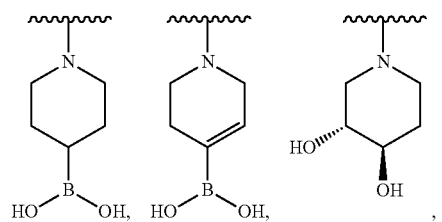
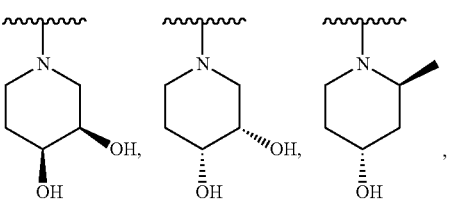
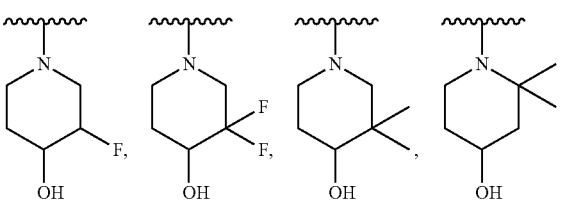
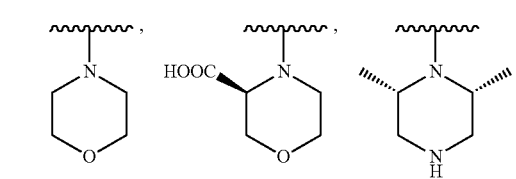
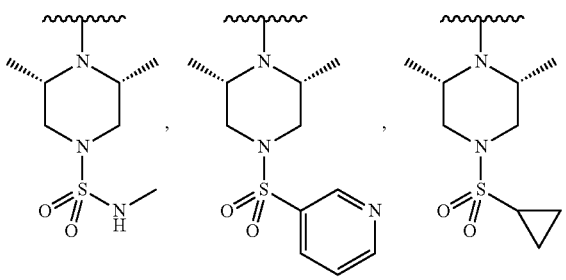
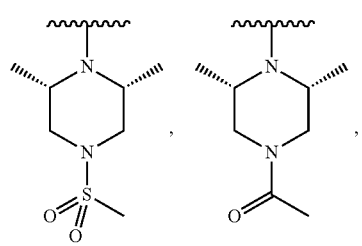

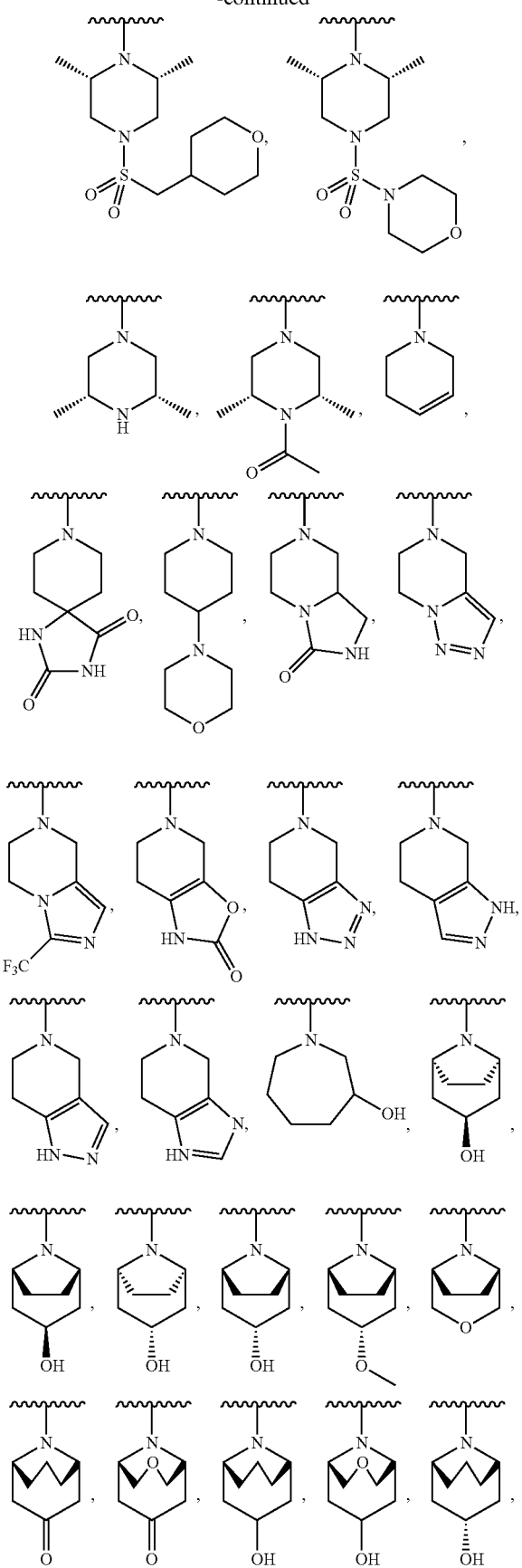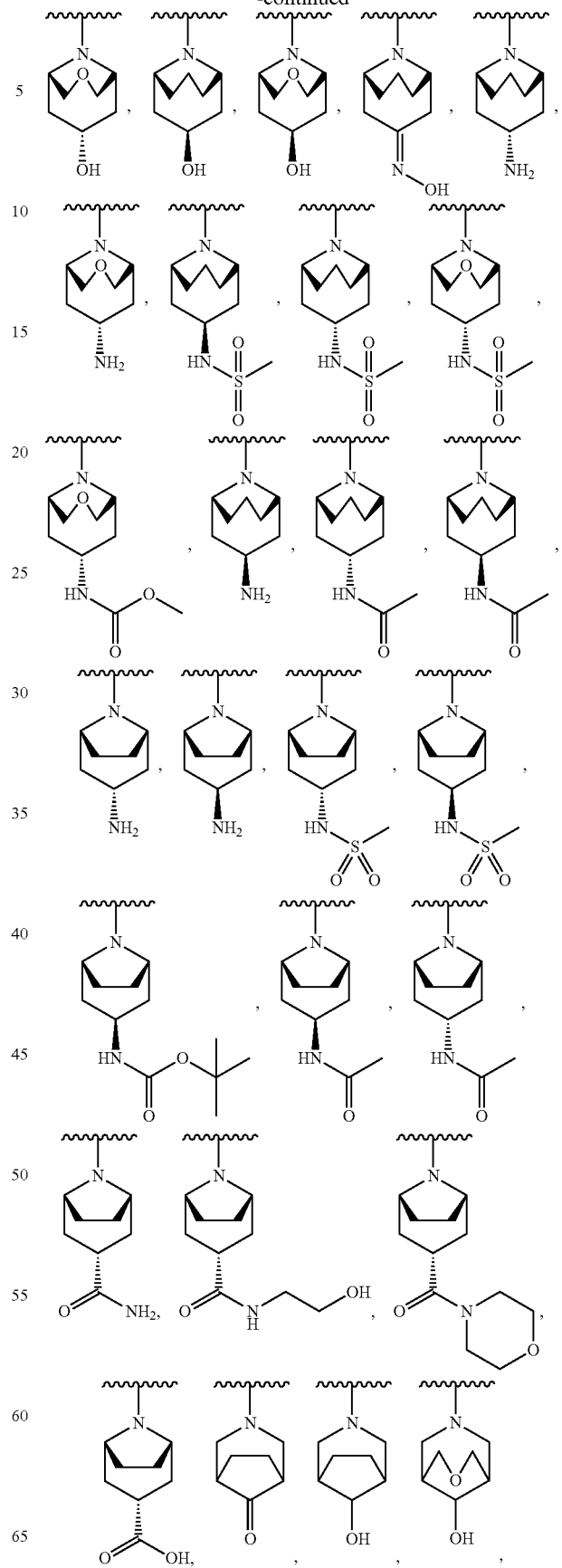

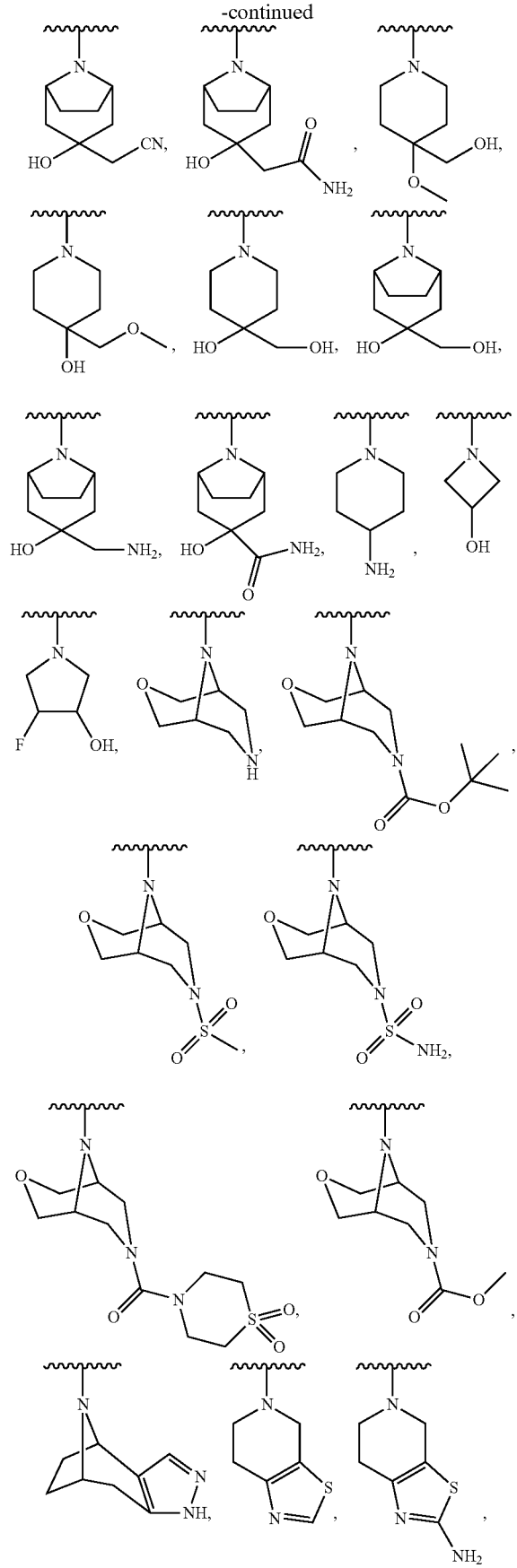
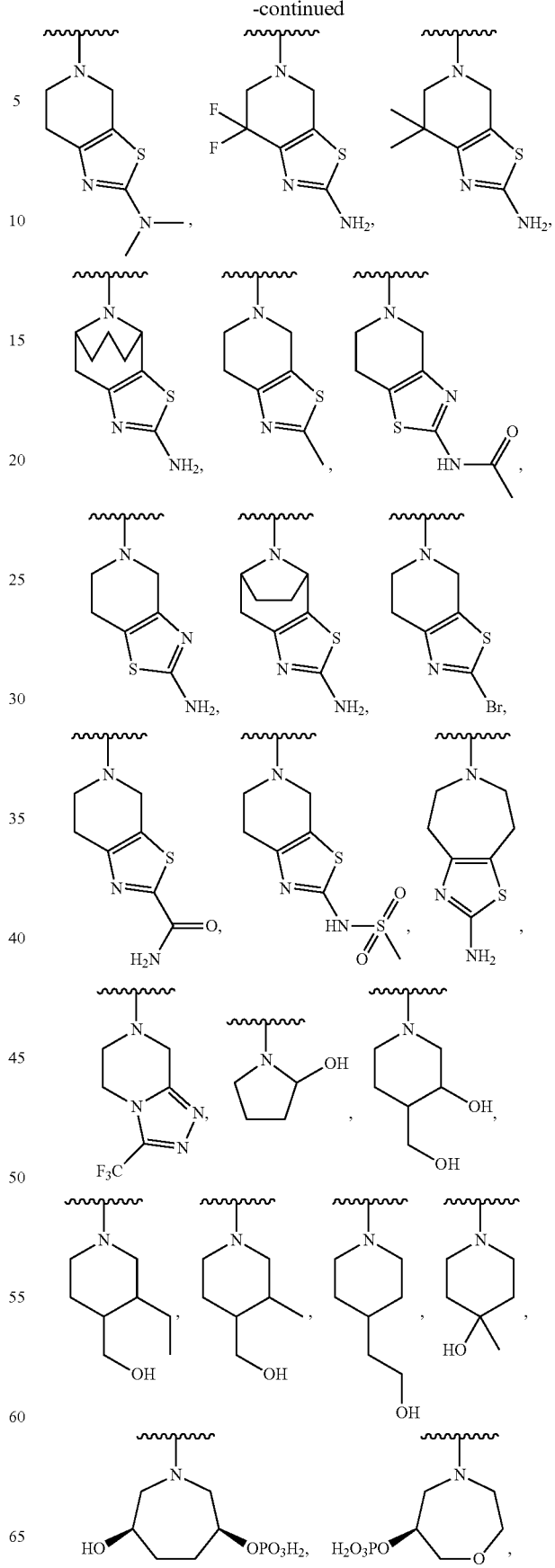

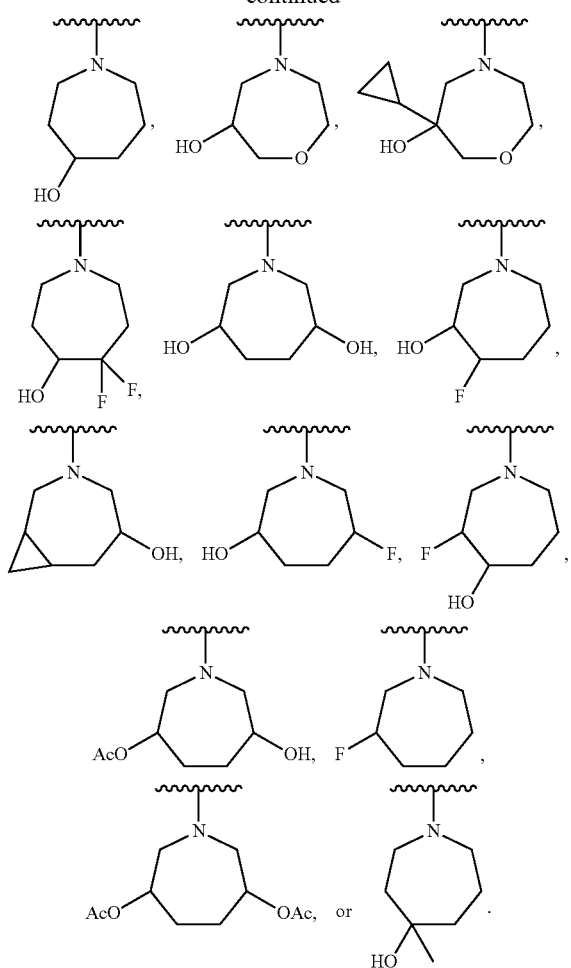
In some embodiments of a compound of Formula (I) or (II), or a pharmaceutically acceptable salt, solvate, or stereoisomer thereof,
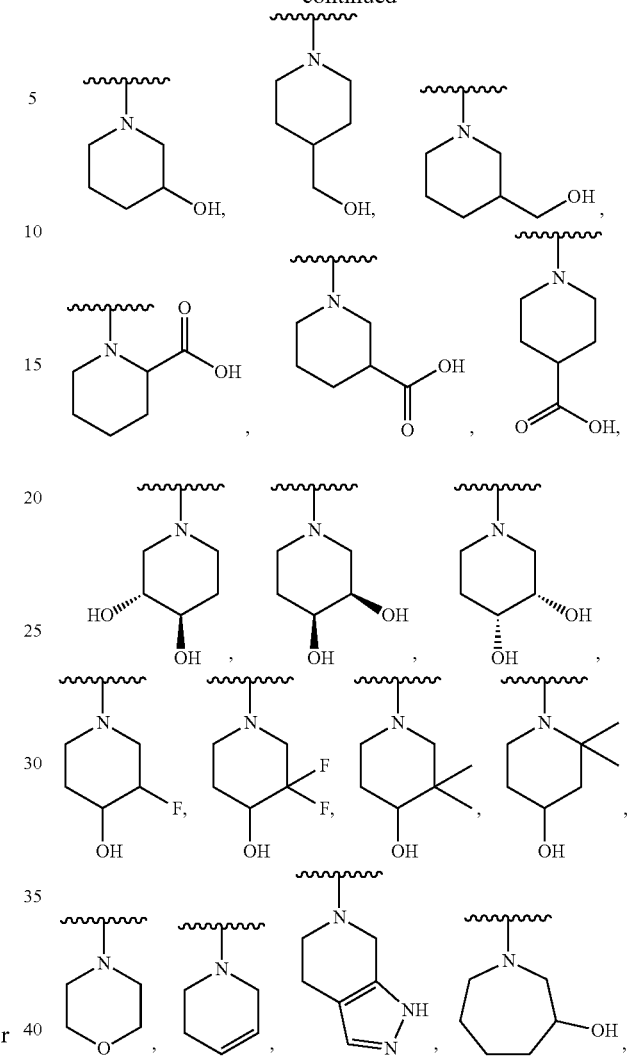

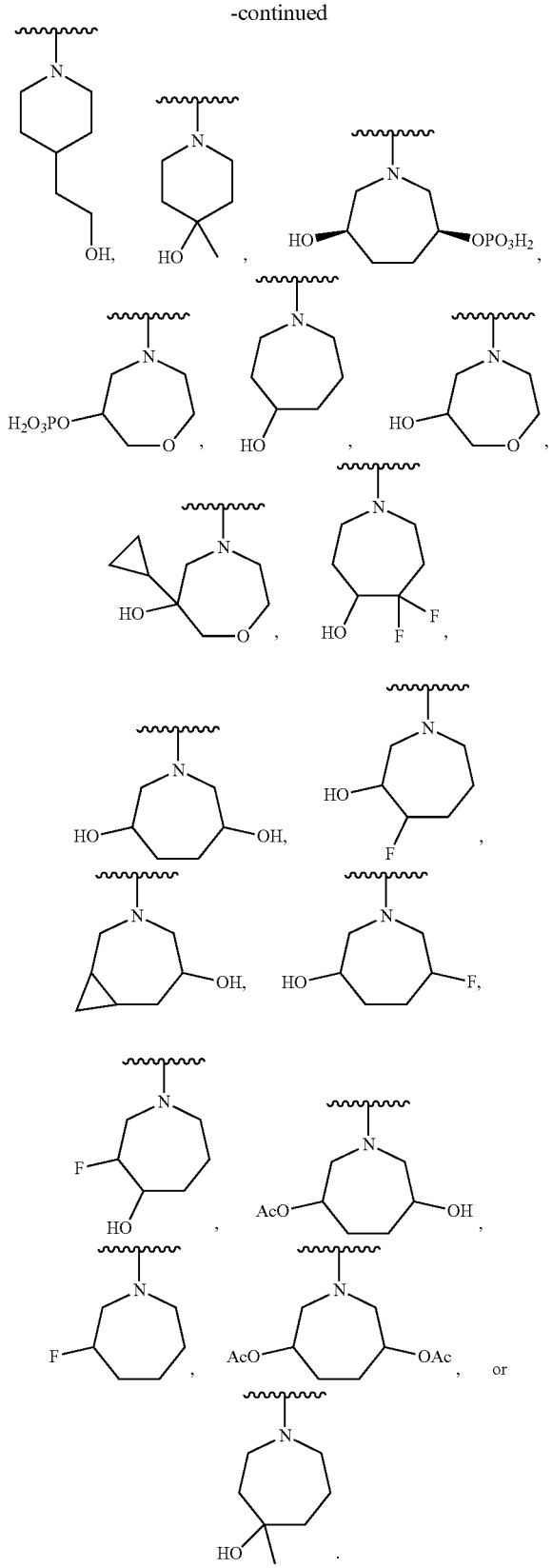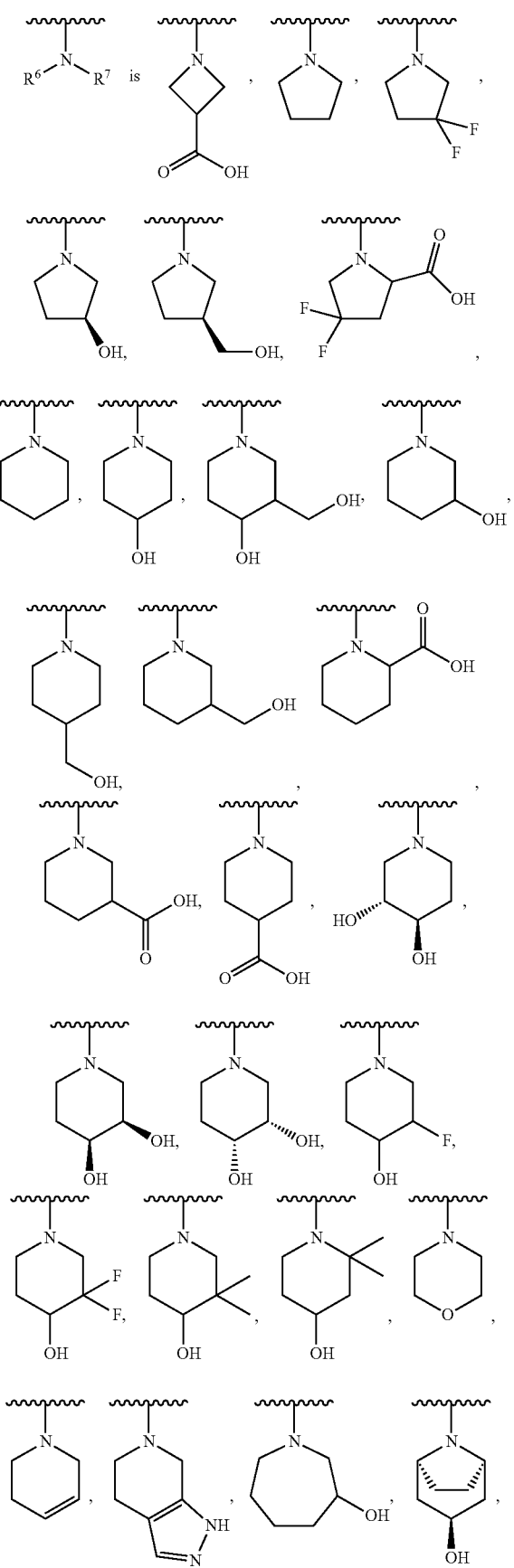
In some embodiments of a compound of Formula (I) or (II), or a pharmaceutically acceptable salt, solvate, or stereoisomer thereof,

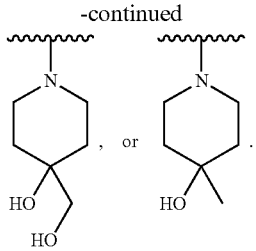

In some embodiments of a compound of Formula (I) or (II), or a pharmaceutically acceptable salt, solvate, or stereoisomer thereof,

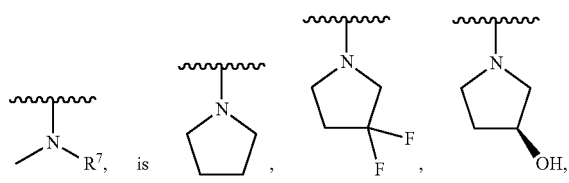

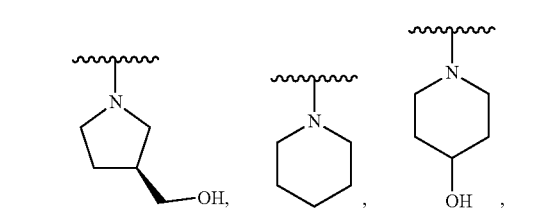

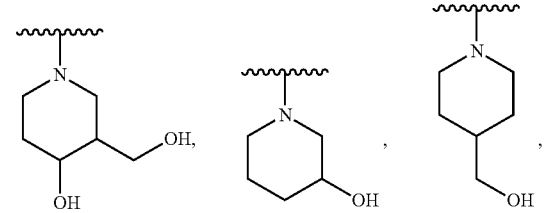

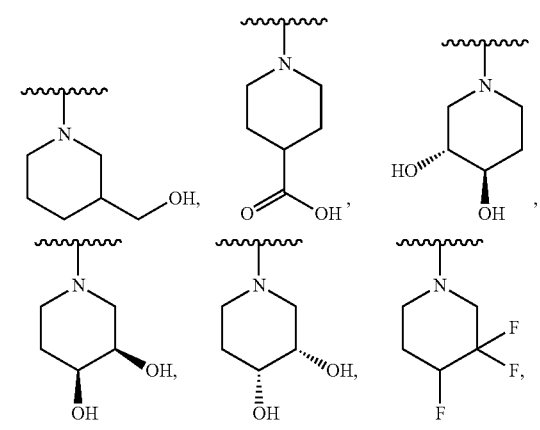

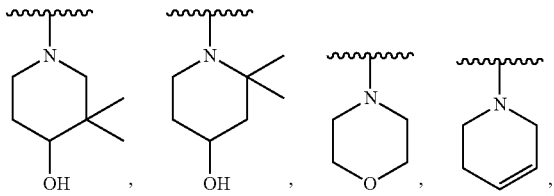

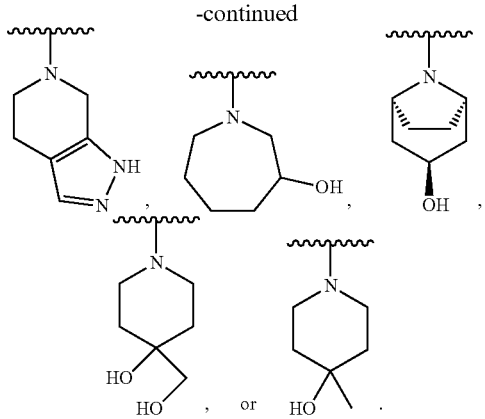

In some embodiments of a compound of Formula (I) or (II), or a pharmaceutically acceptable salt, solvate, or stereoisomer thereof,

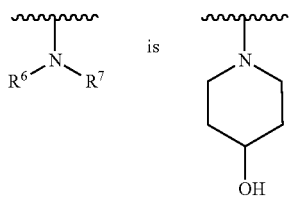

In some embodiments of a compound of Formula (I) or (II), or a pharmaceutically acceptable salt, solvate, or stereoisomer thereof,

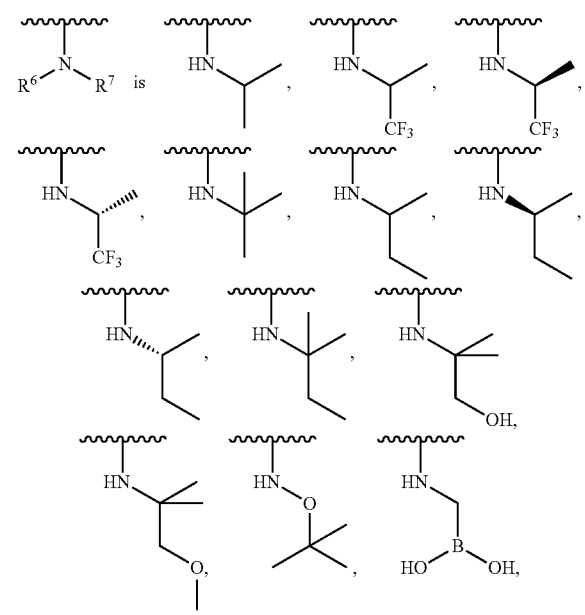

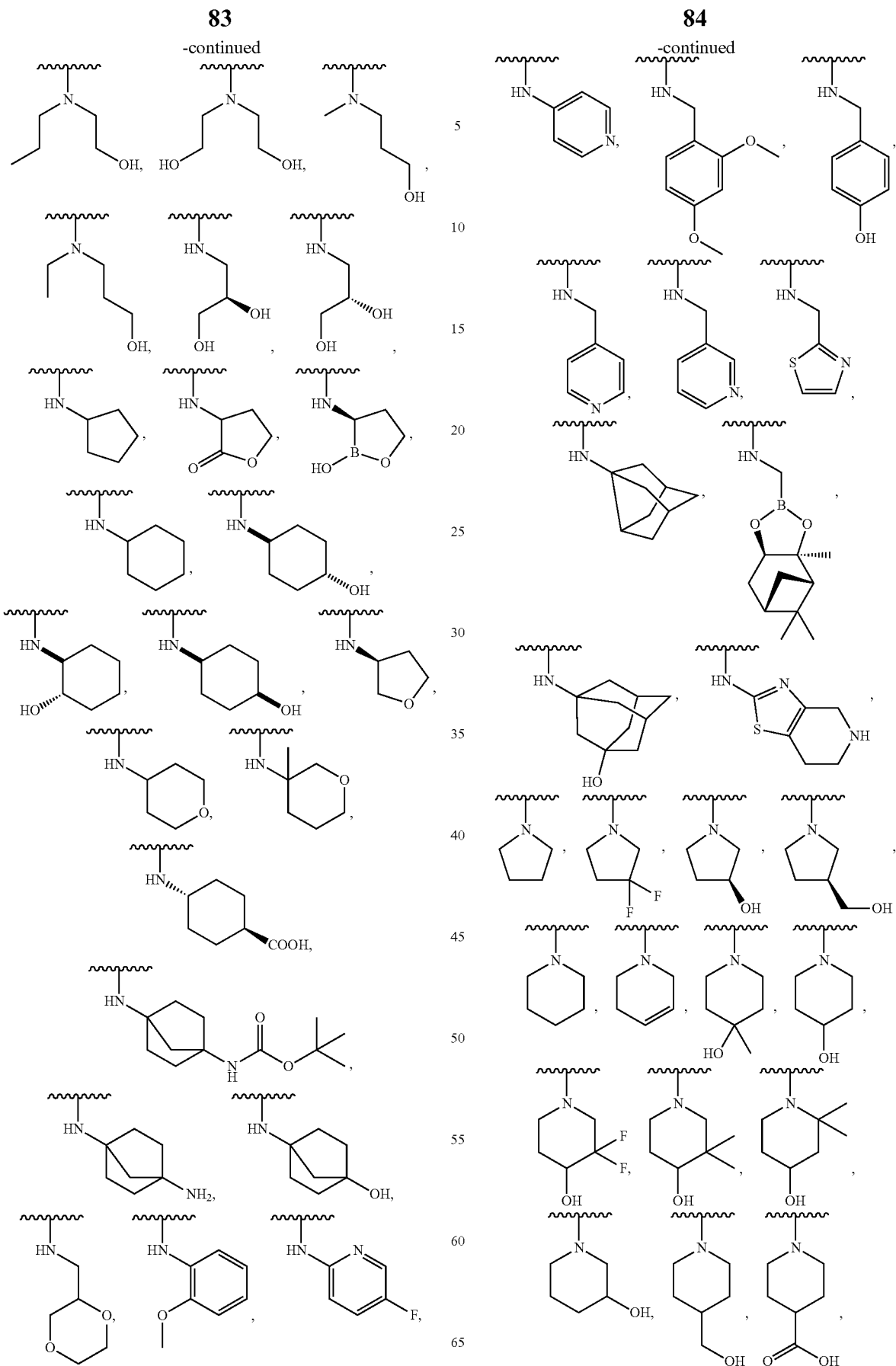

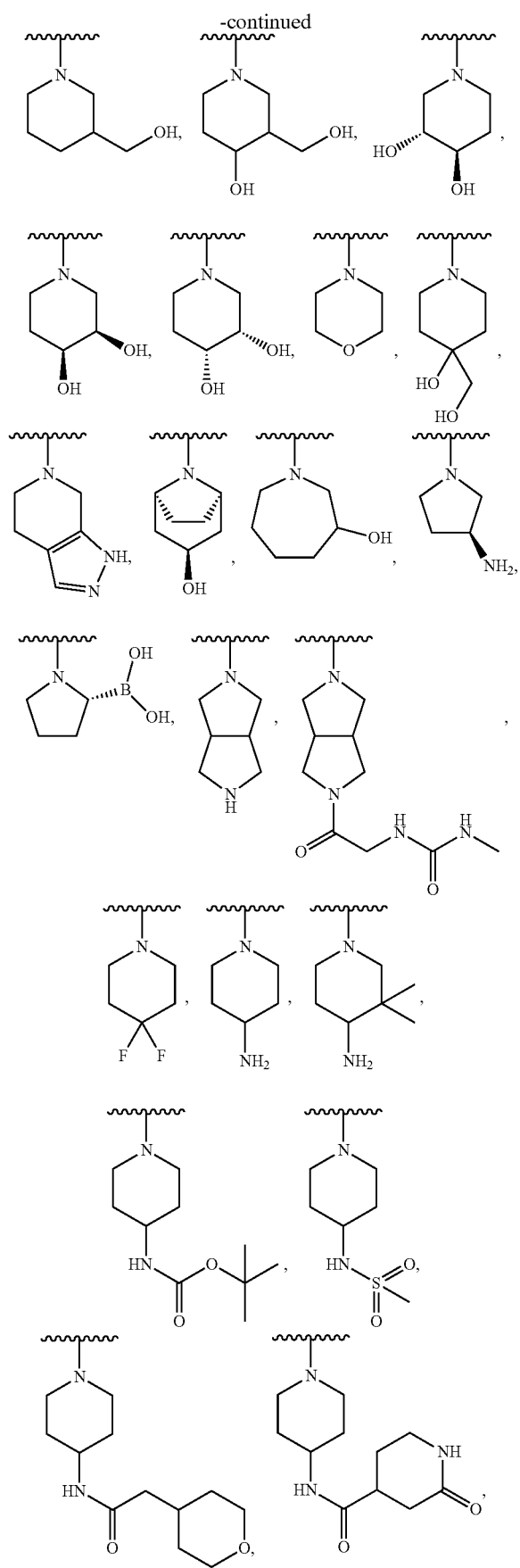
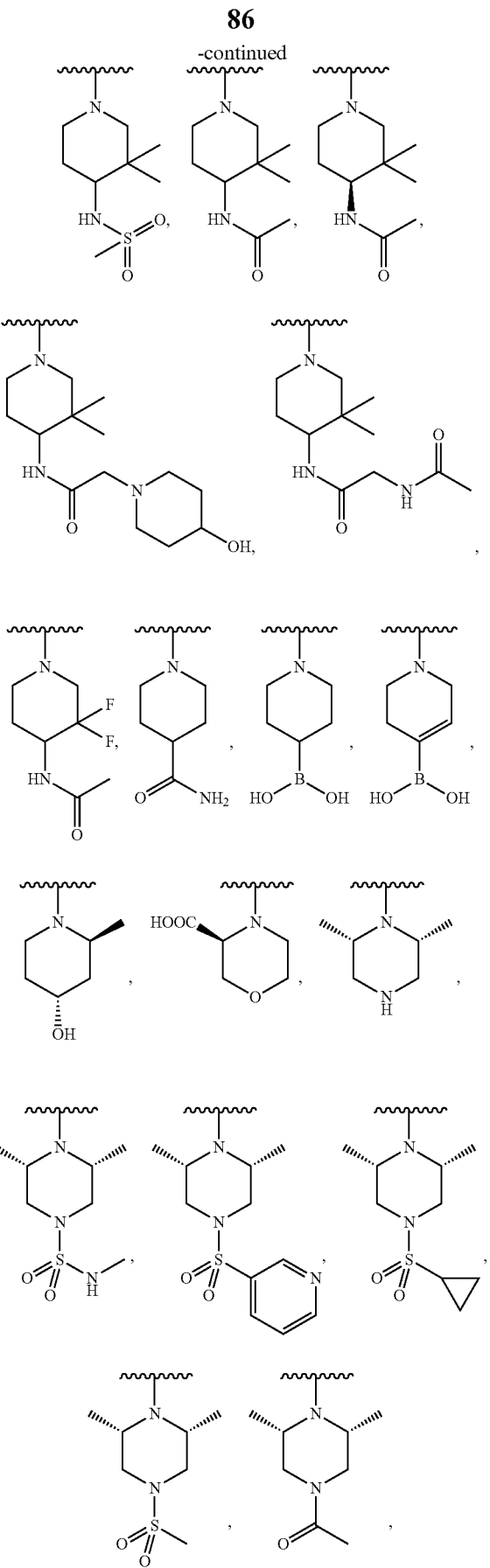

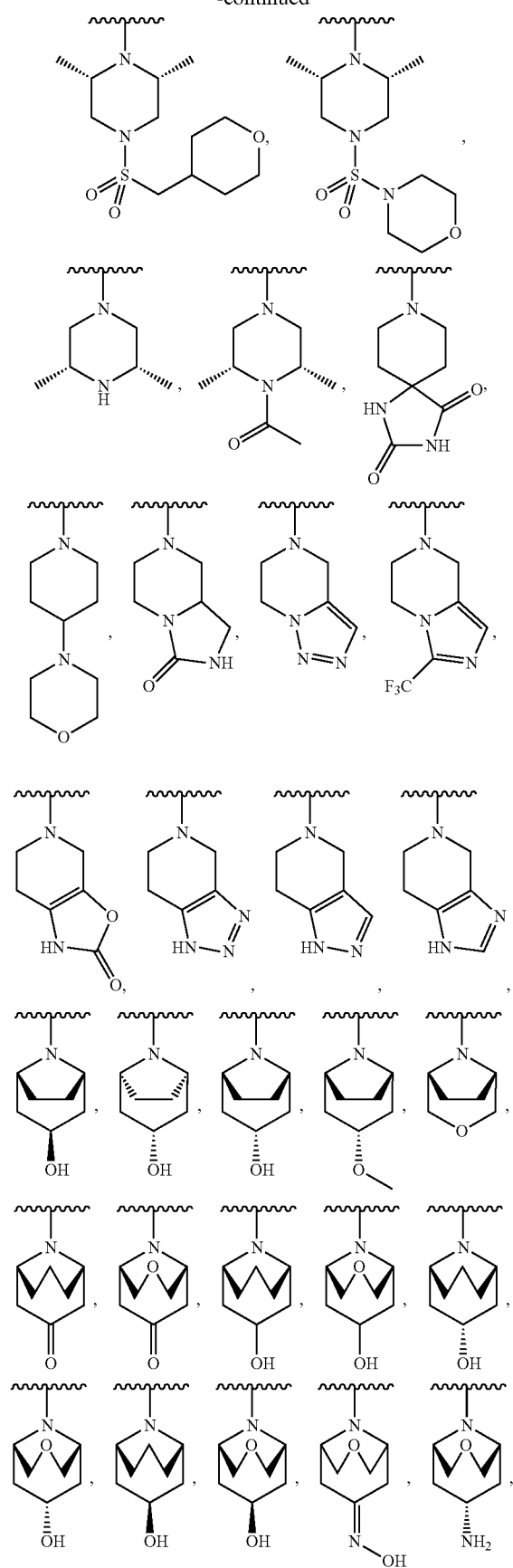
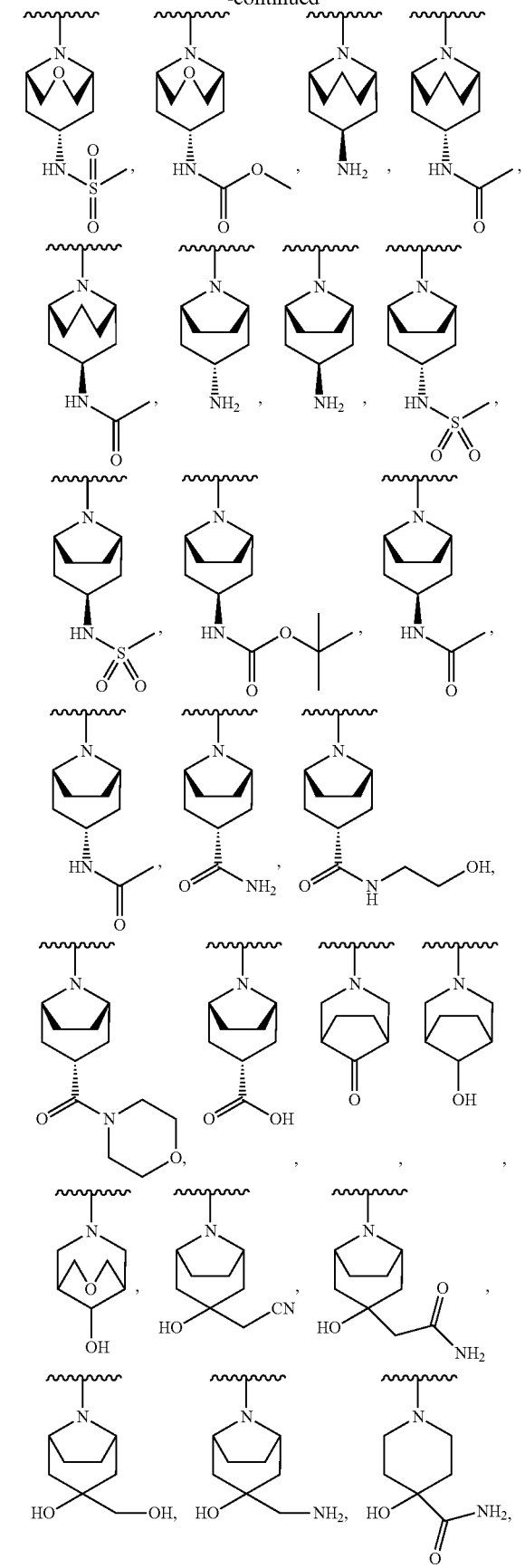

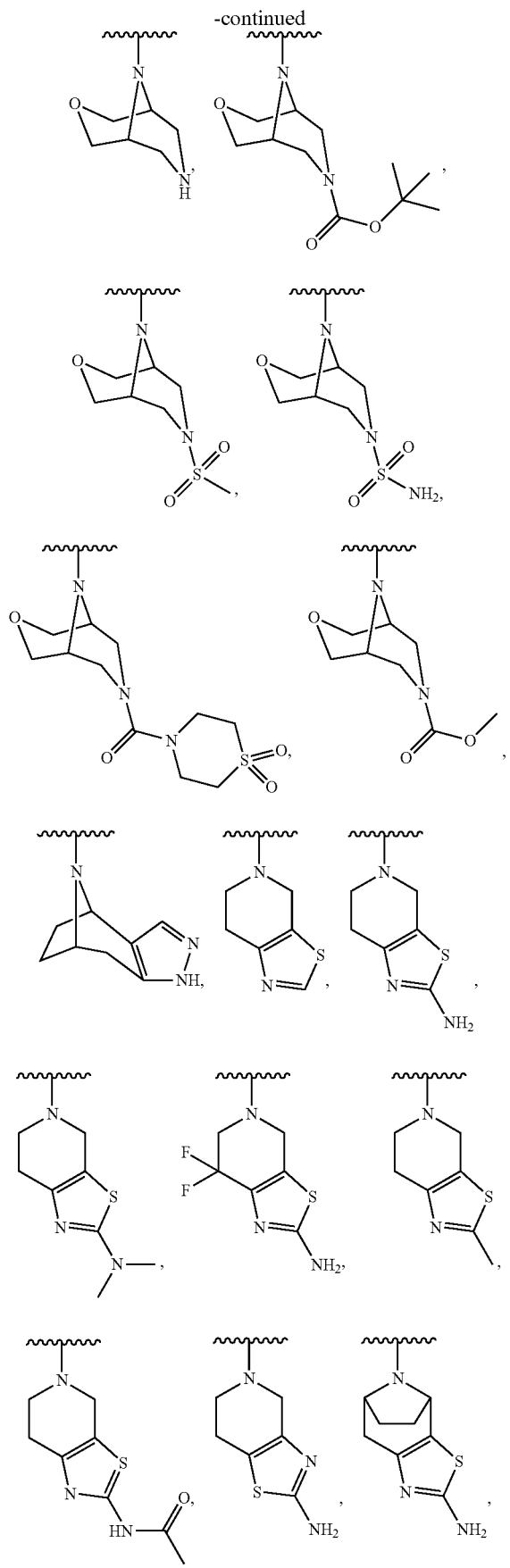

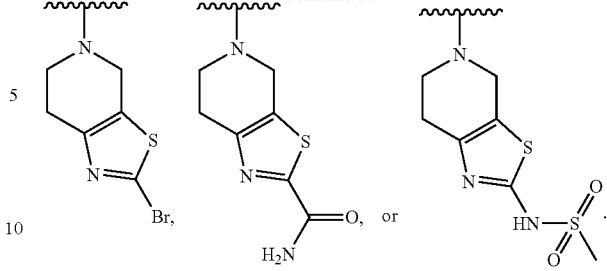

In some embodiments of a compound of Formula (I) or (II), or a pharmaceutically acceptable salt, solvate, or stereoisomer thereof, each $R^a$ is independently $C_{1-6}$alkyl, $C_{1-6}$haloalkyl, $C_{1-6}$hydroxyalkyl, $C_{1-6}$heteroalkyl, $C_{3-8}$cycloalkyl, $C_{2-7}$heterocycloalkyl, aryl, or heteroaryl. In some embodiments of a compound of Formula (I) or (II), or a pharmaceutically acceptable salt, solvate, or stereoisomer thereof, each $R^a$ is independently $C_{1-6}$alkyl, $C_{1-6}$haloalkyl, $C_{3-8}$cycloalkyl, or $C_{2-7}$heterocycloalkyl. In some embodiments of a compound of Formula (I) or (II), or a pharmaceutically acceptable salt, solvate, or stereoisomer thereof, each $R^a$ is independently $C_{1-6}$alkyl, $C_{1-6}$haloalkyl, or $C_{3-8}$cycloalkyl. In some embodiments of a compound of Formula (I) or (II), or a pharmaceutically acceptable salt, solvate, or stereoisomer thereof, each $R^a$ is independently $C_{1-6}$alkyl or $C_{1-6}$haloalkyl. In some embodiments of a compound of Formula (I) or (II), or a pharmaceutically acceptable salt, solvate, or stereoisomer thereof, each $R^a$ is independently $C_{1-6}$alkyl.

In some embodiments of a compound of Formula (I) or (II), or a pharmaceutically acceptable salt, solvate, or stereoisomer thereof, each $R^b$ and $R^c$ is independently hydrogen, $C_{1-6}$alkyl, $C_{1-6}$haloalkyl, $C_{1-6}$hydroxyalkyl, $C_{1-6}$heteroalkyl, $C_{3-8}$cycloalkyl, $C_{2-7}$heterocycloalkyl, aryl, or heteroaryl. In some embodiments of a compound of Formula (I) or (II), or a pharmaceutically acceptable salt, solvate, or stereoisomer thereof, each $R^b$ and $R^c$ is independently hydrogen, $C_{1-6}$alkyl, $C_{1-6}$haloalkyl, $C_{3-8}$cycloalkyl, or $C_{2-7}$heterocycloalkyl. In some embodiments of a compound of Formula (I) or (II), or a pharmaceutically acceptable salt, solvate, or stereoisomer thereof, each $R^b$ and $R^c$ is independently hydrogen, $C_{1-6}$alkyl, $C_{1-6}$haloalkyl, or $C_{3-8}$cycloalkyl. In some embodiments of a compound of Formula (I) or (II), or a pharmaceutically acceptable salt, solvate, or stereoisomer thereof, each $R^b$ and $R^c$ is independently hydrogen, $C_{1-6}$alkyl, or $C_{1-6}$haloalkyl. In some embodiments of a compound of Formula (I) or (II), or a pharmaceutically acceptable salt, solvate, or stereoisomer thereof, each $R^b$ and $R^c$ is independently hydrogen or $C_{1-6}$alkyl.

In some embodiments of a compound of Formula (I) or (II), or a pharmaceutically acceptable salt, solvate, or stereoisomer thereof, $R^b$ and $R^c$ are taken together with the nitrogen atom to which they are attached to form a $C_{2-7}$heterocycloalkyl optionally substituted with one, two, or three halogen, $C_{1-6}$alkyl, or $C_{1-6}$haloalkyl.

In some embodiments of a compound of Formula (I) or (II), or a pharmaceutically acceptable salt, solvate, or stereoisomer thereof, each R are hydrogen.

Any combination of the groups described above for the various variables is contemplated herein. Throughout the specification, groups and substituents thereof are chosen by one skilled in the field to provide stable moieties and compounds.

Described herein is a compound of Formula (I) or (II), or a pharmaceutically acceptable salt, solvate, or stereoisomer thereof, selected from a compound in Table 1.

TABLE 1

| Example | Structure | Chemical Name |
|---|---|---|
| 1 | 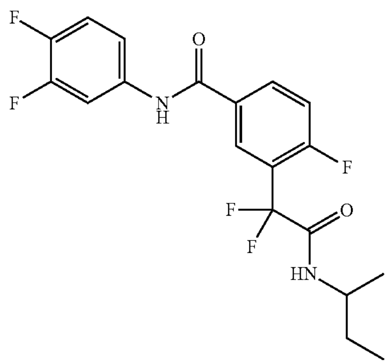 [SMILES: CCC(C)NC(=O)C(F)(F)c1cc(C(=O)Nc2ccc(F)c(F)c2)ccc1F] | 3-(2-(sec-butylamino)-1,1-difluoro-2-oxoethyl)-N-(3,4-difluorophenyl)-4-fluorobenzamide |
| 2 | 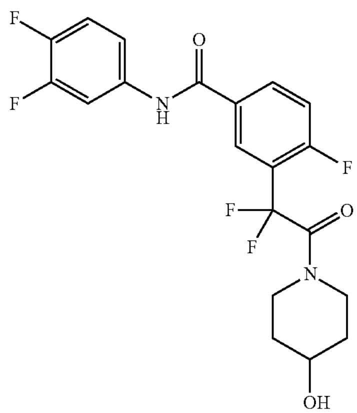 | 3-(1,1-difluoro-2-(4-hydroxypiperidin-1-yl)-2-oxoethyl)-N-(3,4-difluorophenyl)-4-fluorobenzamide |
| 3 | 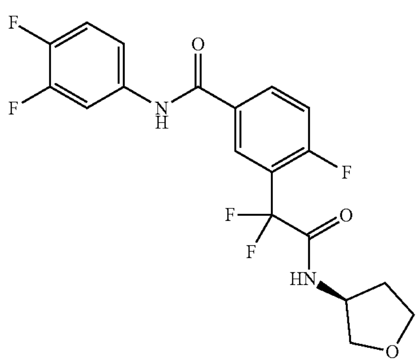 [SMILES: O=C(Nc1ccc(F)c(F)c1)c1ccc(F)c(C(F)(F)C(=O)N[C@H]2CCOC2)c1] | (S)-3-(1,1-difluoro-2-oxo-2-((tetrahydrofuran-3-yl)amino)ethyl)-N-(3,4-difluorophenyl)-4-fluorobenzamide |
| 4 | 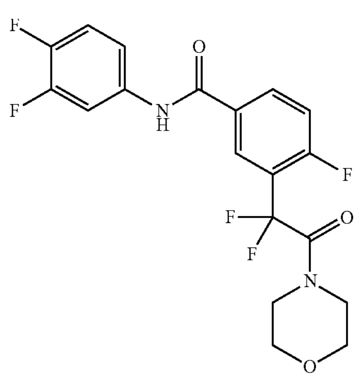 [SMILES: O=C(Nc1ccc(F)c(F)c1)c1ccc(F)c(C(F)(F)C(=O)N2CCOCC2)c1] | 3-(1,1-difluoro-2-morpholino-2-oxoethyl)-N-(3,4-difluorophenyl)-4-fluorobenzamide |

TABLE 1-continued

Exemplary compounds.

| Example | Structure | Chemical Name |
|---|---|---|
| 5 | 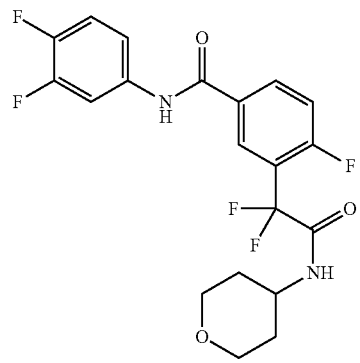 [SMILES: O=C(Nc1ccc(F)c(F)c1)c1ccc(F)c(C(F)(F)C(=O)NC2CCOCC2)c1] | 3-(1,1-difluoro-2-oxo-2-((tetrahydro-2H-pyran-4-yl)amino)ethyl)-N-(3,4-difluorophenyl)-4-fluorobenzamide |
| 6 | 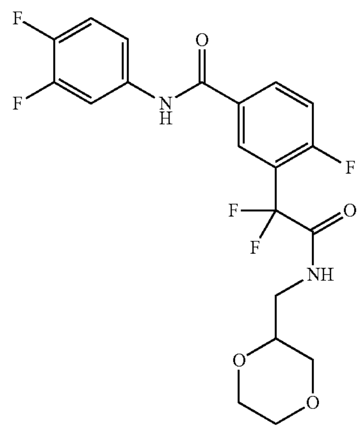 [SMILES: O=C(Nc1ccc(F)c(F)c1)c1ccc(F)c(C(F)(F)C(=O)NCC2COCCO2)c1] | 3-(2-(((1,4-dioxan-2-yl)methyl)amino)-1,1-difluoro-2-oxoethyl)-N-(3,4-difluorophenyl)-4-fluorobenzamide |
| 7 | 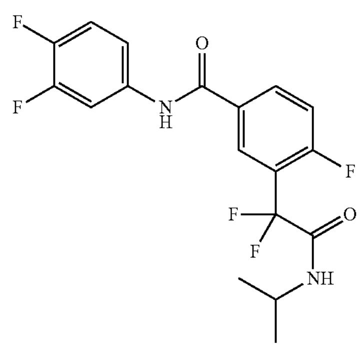 [SMILES: CC(C)NC(=O)C(F)(F)c1cc(C(=O)Nc2ccc(F)c(F)c2)ccc1F] | 3-(1,1-difluoro-2-(isopropylamino)-2-oxoethyl)-N-(3,4-difluorophenyl)-4-fluorobenzamide |
| 8 | 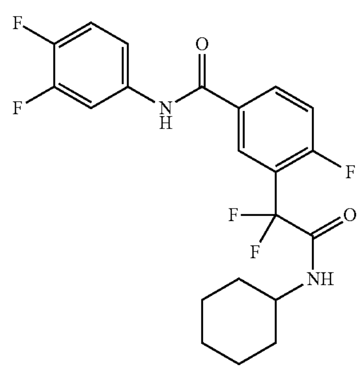 [SMILES: O=C(Nc1ccc(F)c(F)c1)c1ccc(F)c(C(F)(F)C(=O)NC2CCCCC2)c1] | 3-(2-(cyclohexylamino)-1,1-difluoro-2-oxoethyl)-N-(3,4-difluorophenyl)-4-fluorobenzamide |

TABLE 1-continued

Exemplary compounds.

| Example | Structure | Chemical Name |
|---|---|---|
| 9 | 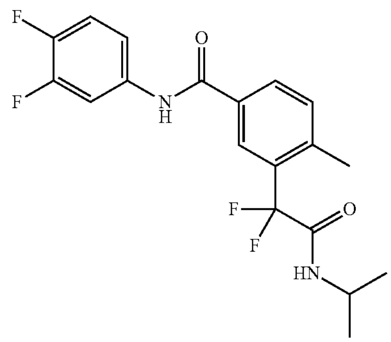 [SMILES: Cc1ccc(C(=O)Nc2ccc(F)c(F)c2)cc1C(F)(F)C(=O)NC(C)C] | 3-(1,1-difluoro-2-(isopropylamino)-2-oxoethyl)-N-(3,4-difluorophenyl)-4-methylbenzamide |
| 10 | 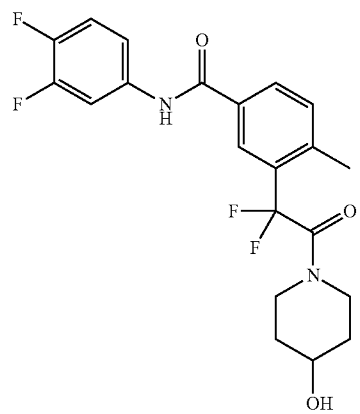 | 3-(1,1-difluoro-2-(4-hydroxypiperidin-1-yl)-2-oxoethyl)-N-(3,4-difluorophenyl)-4-methylbenzamide |
| 11 | 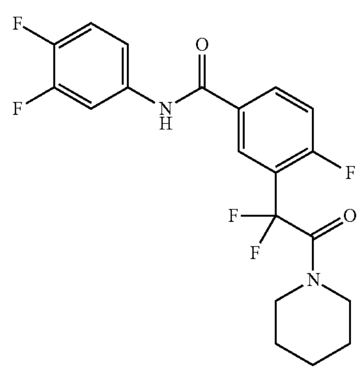 [SMILES: O=C(Nc1ccc(F)c(F)c1)c1ccc(F)c(C(F)(F)C(=O)N2CCCCC2)c1] | 3-(1,1-difluoro-2-oxo-2-(piperidin-1-yl)ethyl)-N-(3,4-difluorophenyl)-4-fluorobenzamide |
| 12 | 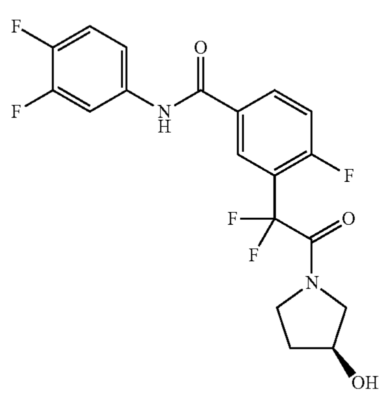 [SMILES: O=C(Nc1ccc(F)c(F)c1)c1ccc(F)c(C(F)(F)C(=O)N2CC[C@H](O)C2)c1] | (S)-3-(1,1-difluoro-2-(3-hydroxypyrrolidin-1-yl)-2-oxoethyl)-N-(3,4-difluorophenyl)-4-fluorobenzamide |

TABLE 1-continued

Exemplary compounds.

| Example | Structure | Chemical Name |
|---|---|---|
| 13 | 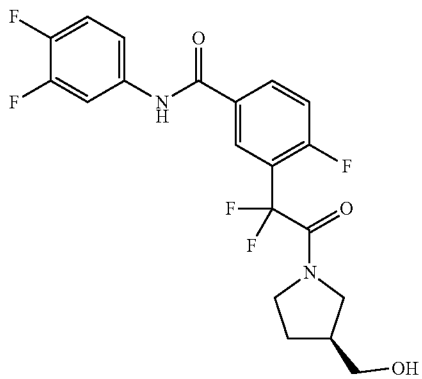 [SMILES: O=C(Nc1ccc(F)c(F)c1)c1ccc(F)c(C(F)(F)C(=O)N2CC[C@H](CO)C2)c1] | (S)-3-(1,1-difluoro-2-(3-(hydroxymethyl)pyrrolidin-1-yl)-2-oxoethyl)-N-(3,4-difluorophenyl)-4-fluorobenzamide |
| 14 | 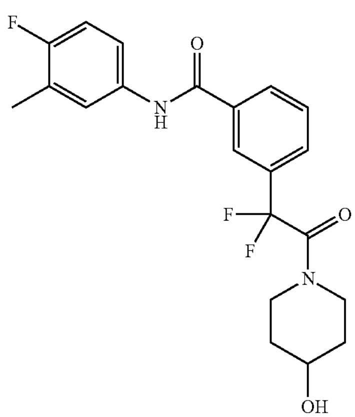 [SMILES: Cc1cc(NC(=O)c2cccc(C(F)(F)C(=O)N3CCC(O)CC3)c2)ccc1F] | 3-(1,1-difluoro-2-(4-hydroxypiperidin-1-yl)-2-oxoethyl)-N-(4-fluoro-3-methylphenyl)benzamide |
| 15 | 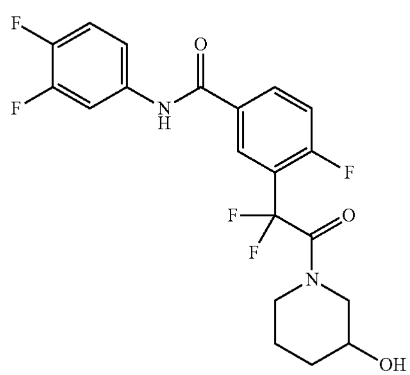 [SMILES: O=C(Nc1ccc(F)c(F)c1)c1ccc(F)c(C(F)(F)C(=O)N2CCCC(O)C2)c1] | 3-(1,1-difluoro-2-(3-hydroxypiperidin-1-yl)-2-oxoethyl)-N-(3,4-difluorophenyl)-4-fluorobenzamide |
| 16 | 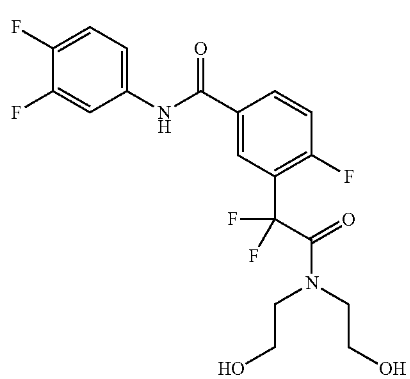 [SMILES: O=C(Nc1ccc(F)c(F)c1)c1ccc(F)c(C(F)(F)C(=O)N(CCO)CCO)c1] | 3-(2-(bis(2-hydroxyethyl)amino)-1,1-difluoro-2-oxoethyl)-N-(3,4-difluorophenyl)-4-fluorobenzamide |

TABLE 1-continued

Exemplary compounds.

| Example | Structure | Chemical Name |
|---|---|---|
| 17 | 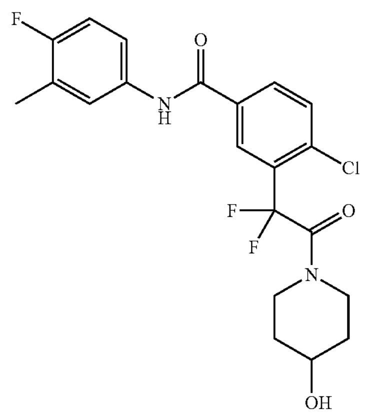 | 4-chloro-3-(1,1-difluoro-2-(4-hydroxypiperidin-1-yl)-2-oxoethyl)-N-(4-fluoro-3-methylphenyl)benzamide |
| 18 | 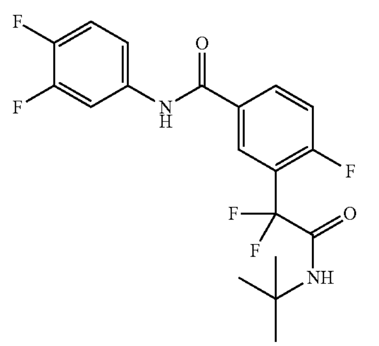 [SMILES: CC(C)(C)NC(=O)C(F)(F)c1cc(C(=O)Nc2ccc(F)c(F)c2)ccc1F] | 3-(2-(tert-butylamino)-1,1-difluoro-2-oxoethyl)-N-(3,4-difluorophenyl)-4-fluorobenzamide |
| 19 | 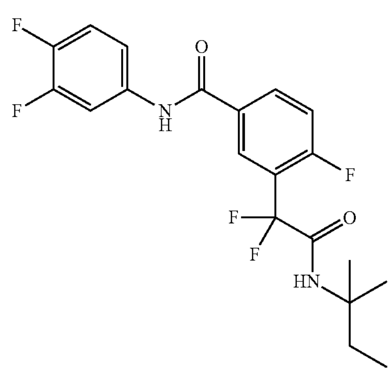 [SMILES: CCC(C)(C)NC(=O)C(F)(F)c1cc(C(=O)Nc2ccc(F)c(F)c2)ccc1F] | 3-(1,1-difluoro-2-oxo-2-(tert-pentylamino)ethyl)-N-(3,4-difluorophenyl)-4-fluorobenzamide |
| 20 | 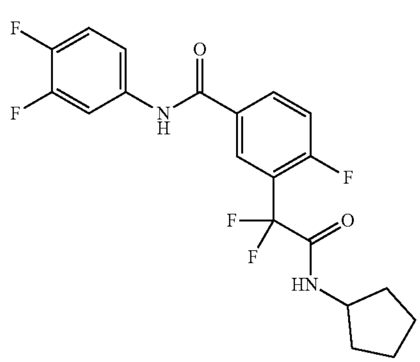 [SMILES: O=C(Nc1ccc(F)c(F)c1)c1ccc(F)c(C(F)(F)C(=O)NC2CCCC2)c1] | 3-(2-(cyclopentylamino)-1,1-difluoro-2-oxoethyl)-N-(3,4-difluorophenyl)-4-fluorobenzamide |

TABLE 1-continued

Exemplary compounds.

| Example | Structure | Chemical Name |
|---|---|---|
| 21 | 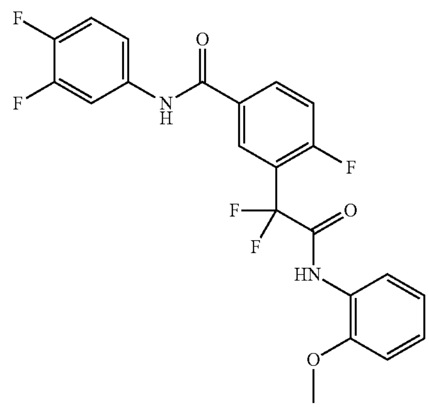 [SMILES: COc1ccccc1NC(=O)C(F)(F)c1cc(C(=O)Nc2ccc(F)c(F)c2)ccc1F] | 3-(1,1-difluoro-2-((2-methoxyphenyl)amino)-2-oxoethyl)-N-(3,4-difluorophenyl)-4-fluorobenzamide |
| 22 | 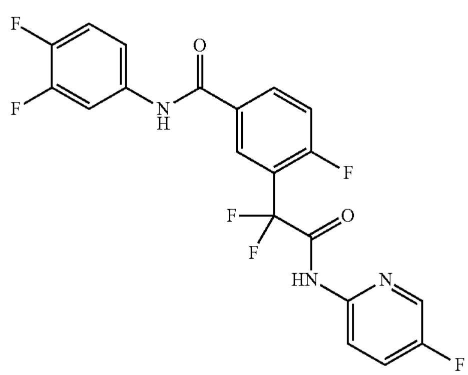 [SMILES: O=C(Nc1ccc(F)c(F)c1)c1ccc(F)c(C(F)(F)C(=O)Nc2ccc(F)cn2)c1] | 3-(1,1-difluoro-2-((5-fluoropyridin-2-yl)amino)-2-oxoethyl)-N-(3,4-difluorophenyl)-4-fluorobenzamide |
| 23 | 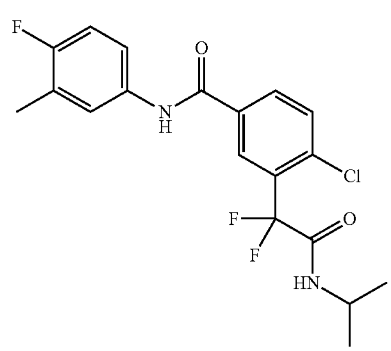 [SMILES: Cc1cc(NC(=O)c2ccc(Cl)c(C(F)(F)C(=O)NC(C)C)c2)ccc1F] | 4-chloro-3-(1,1-difluoro-2-(isopropylamino)-2-oxoethyl)-N-(4-fluoro-3-methylphenyl)benzamide |
| 24 | 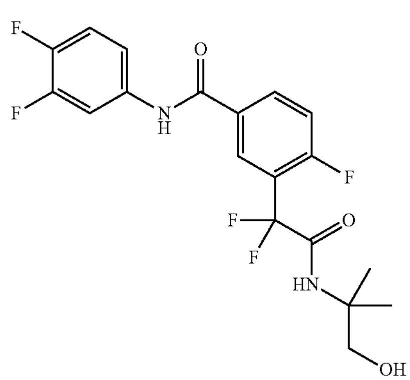 [SMILES: CC(C)(CO)NC(=O)C(F)(F)c1cc(C(=O)Nc2ccc(F)c(F)c2)ccc1F] | 3-(1,1-difluoro-2-((1-hydroxy-2-methylpropan-2-yl)amino)-2-oxoethyl)-N-(3,4-difluorophenyl)-4-fluorobenzamide |

TABLE 1-continued

Exemplary compounds.

| Example | Structure | Chemical Name |
|---|---|---|
| 25 | 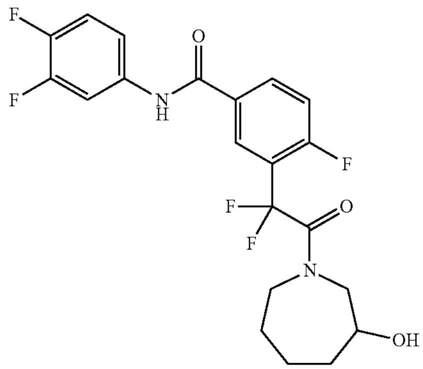 [SMILES: O=C(Nc1ccc(F)c(F)c1)c1ccc(F)c(C(F)(F)C(=O)N2CCCCC(O)C2)c1] | 3-(1,1-difluoro-2-(3-hydroxyazepan-1-yl)-2-oxoethyl)-N-(3,4-difluorophenyl)-4-fluorobenzamide |
| 26 | 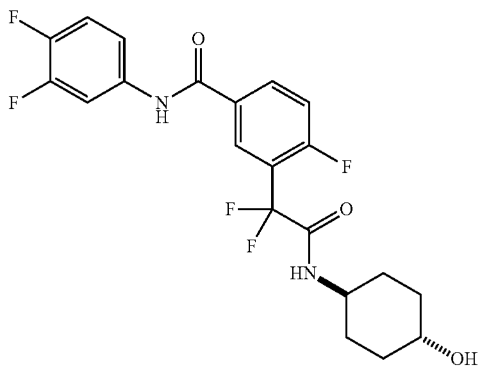 | 3-(1,1-difluoro-2-(((1r,4r)-4-hydroxycyclohexyl)amino)-2-oxoethyl)-N-(3,4-difluorophenyl)-4-fluorobenzamide |
| 27 | 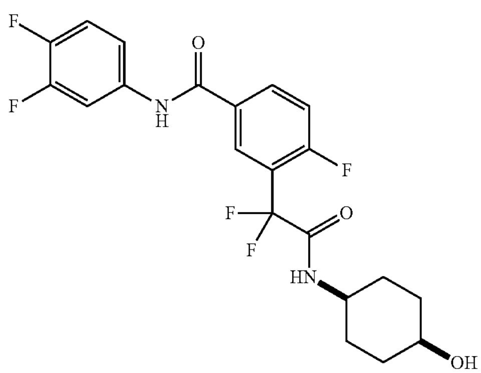 | 3-(1,1-difluoro-2-(((1s,4s)-4-hydroxycyclohexyl)amino)-2-oxoethyl)-N-(3,4-difluorophenyl)-4-fluorobenzamide |
| 28 | 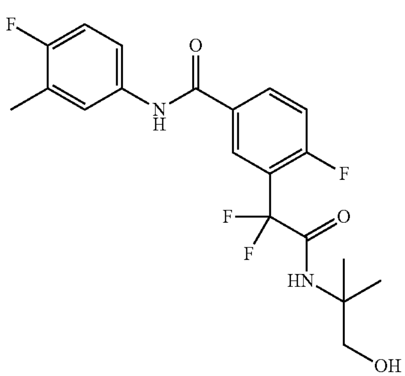 [SMILES: Cc1cc(NC(=O)c2ccc(F)c(C(F)(F)C(=O)NC(C)(C)CO)c2)ccc1F] | 3-(1,1-difluoro-2-((1-hydroxy-2-methylpropan-2-yl)amino)-2-oxoethyl)-4-fluoro-N-(4-fluoro-3-methylphenyl)benzamide |

TABLE 1-continued

Exemplary compounds.

| Example | Structure | Chemical Name |
|---|---|---|
| 29 | 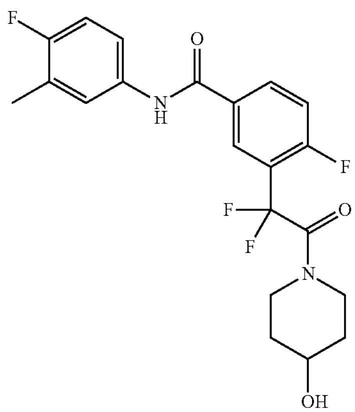 | 3-(1,1-difluoro-2-(4-hydroxypiperidin-1-yl)-2-oxoethyl)-4-fluoro-N-(4-fluoro-3-methylphenyl)benzamide |
| 30 | 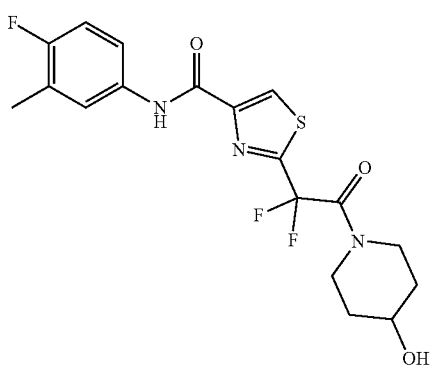 [SMILES: Cc1cc(NC(=O)c2csc(C(F)(F)C(=O)N3CCC(O)CC3)n2)ccc1F] | 2-(1,1-difluoro-2-(4-hydroxypiperidin-1-yl)-2-oxoethyl)-N-(4-fluoro-3-methylphenyl)thiazole-4-carboxamide |
| 31 | 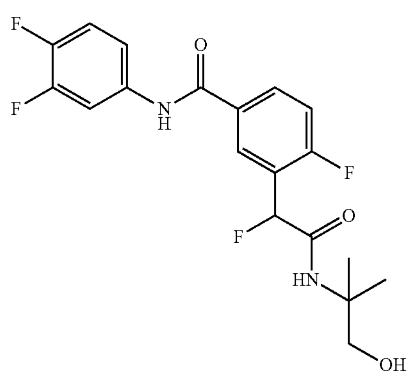 [SMILES: CC(C)(CO)NC(=O)C(F)c1cc(C(=O)Nc2ccc(F)c(F)c2)ccc1F] | N-(3,4-difluorophenyl)-4-fluoro-3-(1-fluoro-2-((1-hydroxy-2-methylpropan-2-yl)amino)-2-oxoethyl)benzamide |
| 32 | 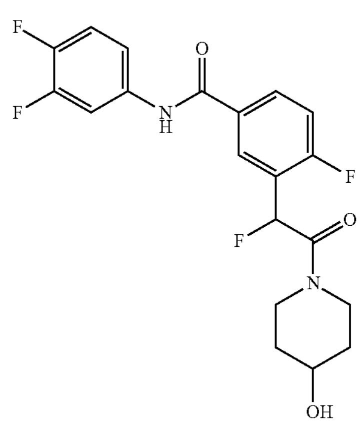 [SMILES: O=C(Nc1ccc(F)c(F)c1)c1ccc(F)c(C(F)C(=O)N2CCC(O)CC2)c1] | N-(3,4-difluorophenyl)-4-fluoro-3-(1-fluoro-2-(4-hydroxypiperidin-1-yl)-2-oxoethyl)benzamide |

TABLE 1-continued

| Example | Structure | Chemical Name |
|---------|-----------|---------------|
| 33 | 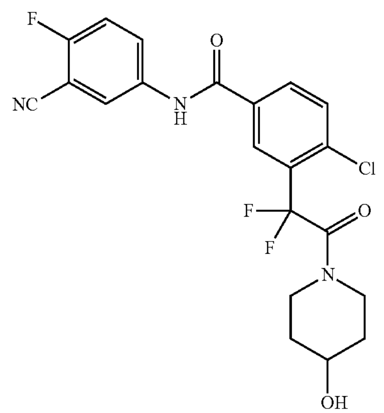 [SMILES: N#Cc1cc(NC(=O)c2ccc(Cl)c(C(F)(F)C(=O)N3CCC(O)CC3)c2)ccc1F] | 4-chloro-N-(3-cyano-4-fluorophenyl)-3-(1,1-difluoro-2-(4-hydroxypiperidin-1-yl)-2-oxoethyl)benzamide |
| 34 | 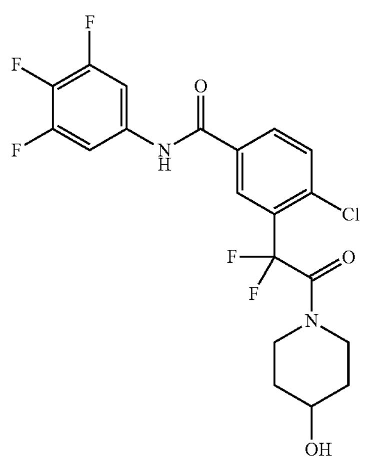 [SMILES: O=C(Nc1cc(F)c(F)c(F)c1)c1ccc(Cl)c(C(F)(F)C(=O)N2CCC(O)CC2)c1] | 4-chloro-3-(1,1-difluoro-2-(4-hydroxypiperidin-1-yl)-2-oxoethyl)-N-(3,4,5-trifluorophenyl)benzamide |
| 35 | 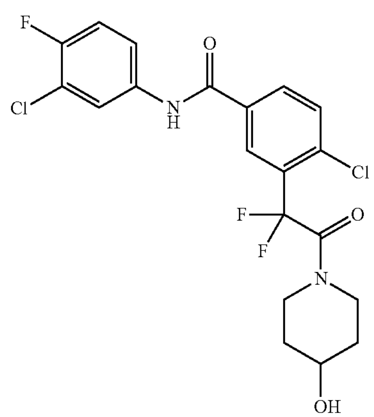 [SMILES: O=C(Nc1ccc(F)c(Cl)c1)c1ccc(Cl)c(C(F)(F)C(=O)N2CCC(O)CC2)c1] | 4-chloro-N-(3-chloro-4-fluorophenyl)-3-(1,1-difluoro-2-(4-hydroxypiperidin-1-yl)-2-oxoethyl)benzamide |

TABLE 1-continued

Exemplary compounds.

| Example | Structure | Chemical Name |
|---|---|---|
| 36 | 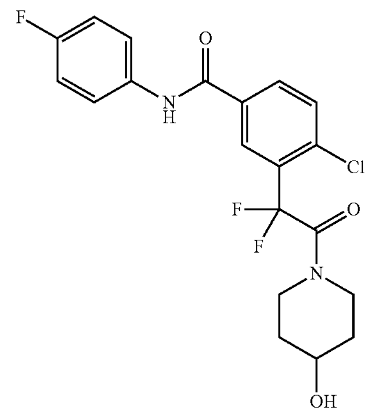 | 4-chloro-3-(1,1-difluoro-2-(4-hydroxypiperidin-1-yl)-2-oxoethyl)-N-(4-fluorophenyl)benzamide |
| 37 | 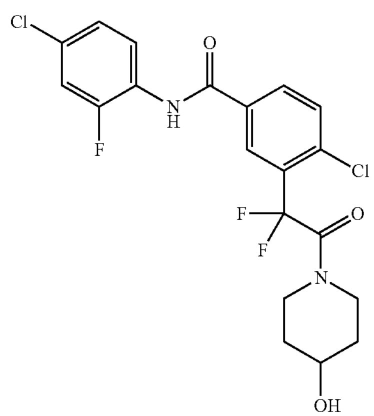 [SMILES: O=C(Nc1ccc(Cl)cc1F)c1ccc(Cl)c(C(F)(F)C(=O)N2CCC(O)CC2)c1] | 4-chloro-N-(4-chloro-2-fluorophenyl)-3-(1,1-difluoro-2-(4-hydroxypiperidin-1-yl)-2-oxoethyl)benzamide |
| 38 | 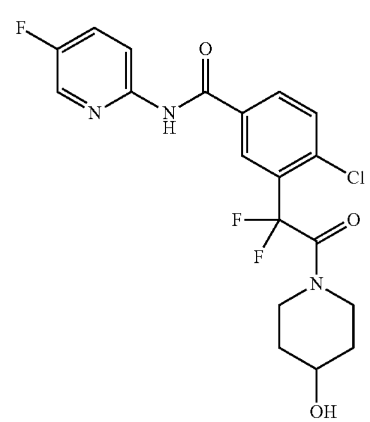 | 4-chloro-3-(1,1-difluoro-2-(4-hydroxypiperidin-1-yl)-2-oxoethyl)-N-(5-fluoropyridin-2-yl)benzamide |

TABLE 1-continued

Exemplary compounds.

| Example | Structure | Chemical Name |
|---|---|---|
| 39 | 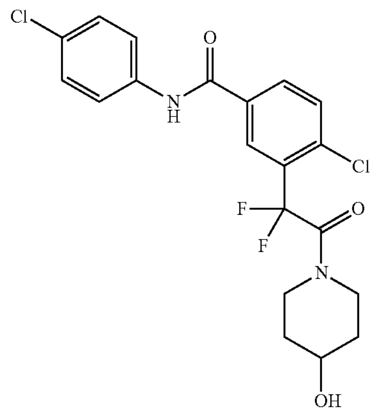 [SMILES: O=C(Nc1ccc(Cl)cc1)c1ccc(Cl)c(C(F)(F)C(=O)N2CCC(O)CC2)c1] | 4-chloro-N-(4-chlorophenyl)-3-(1,1-difluoro-2-(4-hydroxypiperidin-1-yl)-2-oxoethyl)benzamide |
| 40 | 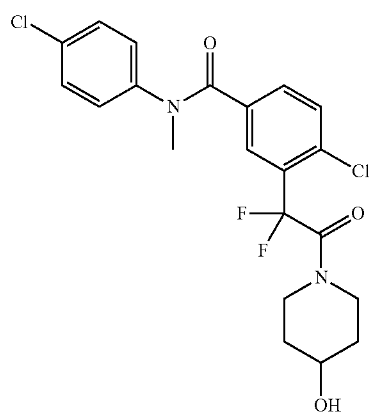 [SMILES: CN(C(=O)c1ccc(Cl)c(C(F)(F)C(=O)N2CCC(O)CC2)c1)c1ccc(Cl)cc1] | 4-chloro-N-(4-chlorophenyl)-3-(1,1-difluoro-2-(4-hydroxypiperidin-1-yl)-2-oxoethyl)-N-methylbenzamide |
| 41 | 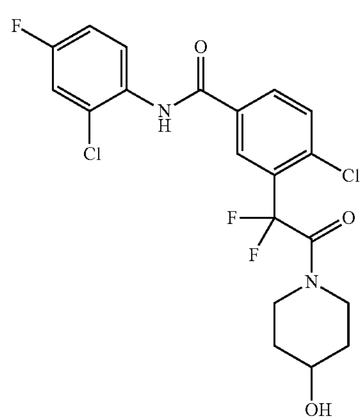 [SMILES: O=C(Nc1ccc(F)cc1Cl)c1ccc(Cl)c(C(F)(F)C(=O)N2CCC(O)CC2)c1] | 4-chloro-N-(2-chloro-4-fluorophenyl)-3-(1,1-difluoro-2-(4-hydroxypiperidin-1-yl)-2-oxoethyl)benzamide |

TABLE 1-continued

Exemplary compounds.

| Example | Structure | Chemical Name |
|---|---|---|
| 42 | 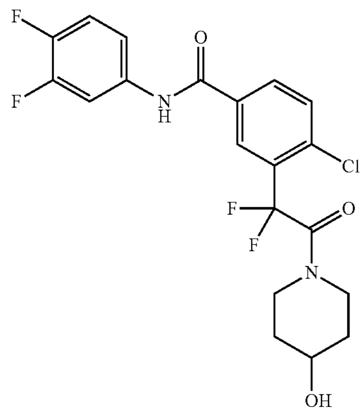 | 4-chloro-3-(1,1-difluoro-2-(4-hydroxypiperidin-1-yl)-2-oxoethyl)-N-(3,4-difluorophenyl)benzamide |
| 43 | 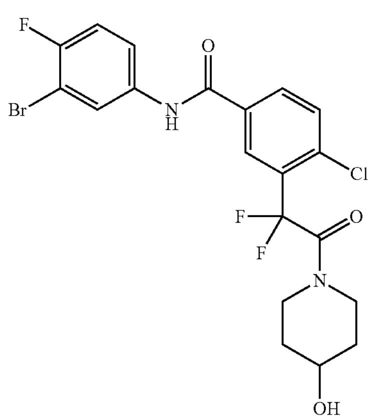 | N-(3-bromo-4-fluorophenyl)-4-chloro-3-(1,1-difluoro-2-(4-hydroxypiperidin-1-yl)-2-oxoethyl)benzamide |
| 44 | 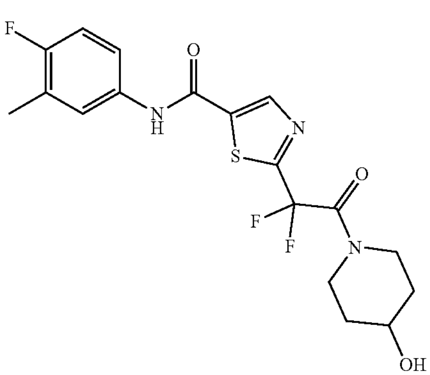 [SMILES: Cc1cc(NC(=O)c2cnc(C(F)(F)C(=O)N3CCC(O)CC3)s2)ccc1F] | 2-(1,1-difluoro-2-(4-hydroxypiperidin-1-yl)-2-oxoethyl)-N-(4-fluoro-3-methylphenyl)thiazole-5-carboxamide |

TABLE 1-continued
Exemplary compounds.
| Example | Structure | Chemical Name |
|---|---|---|
| 45 | 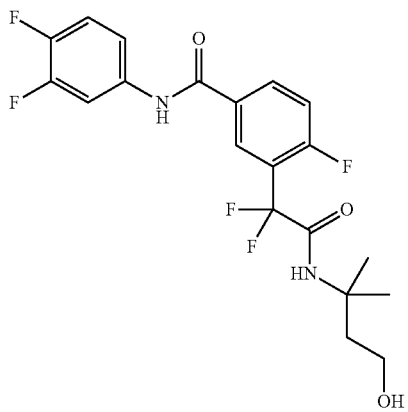 [SMILES: CC(C)(CCO)NC(=O)C(F)(F)c1cc(C(=O)Nc2ccc(F)c(F)c2)ccc1F] | 3-(1,1-difluoro-2-((4-hydroxy-2-methylbutan-2-yl)amino)-2-oxoethyl)-N-(3,4-difluorophenyl)-4-fluorobenzamide |
| 46 | 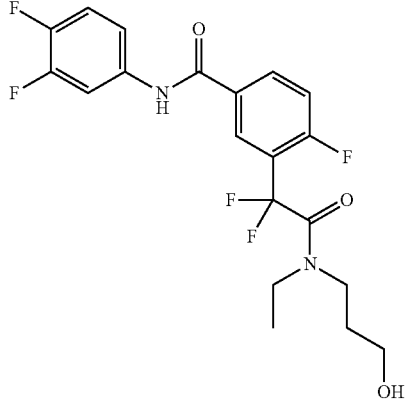 [SMILES: CCN(CCCO)C(=O)C(F)(F)c1cc(C(=O)Nc2ccc(F)c(F)c2)ccc1F] | N-(3,4-difluorophenyl)-3-(2-(ethyl(3-hydroxypropyl)amino)-1,1-difluoro-2-oxoethyl)-4-fluorobenzamide |
| 47 | 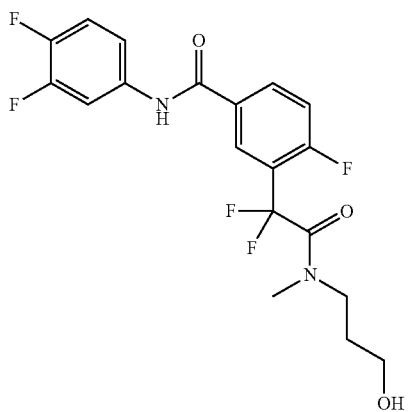 [SMILES: CN(CCCO)C(=O)C(F)(F)c1cc(C(=O)Nc2ccc(F)c(F)c2)ccc1F] | 3-(1,1-difluoro-2-((3-hydroxypropyl)(methyl)amino)-2-oxoethyl)-N-(3,4-difluorophenyl)-4-fluorobenzamide |

TABLE 1-continued

Exemplary compounds.

| Example | Structure | Chemical Name |
|---|---|---|
| 48 | 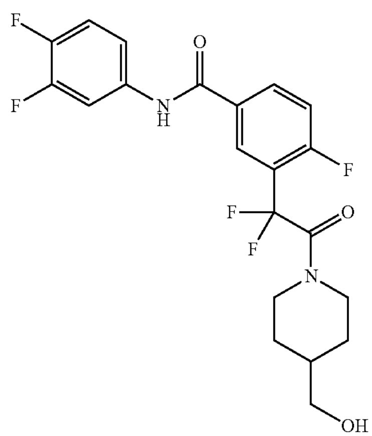 [SMILES: O=C(Nc1ccc(F)c(F)c1)c1ccc(F)c(C(F)(F)C(=O)N2CCC(CO)CC2)c1] | 3-(1,1-difluoro-2-(4-(hydroxymethyl)piperidin-1-yl)-2-oxoethyl)-N-(3,4-difluorophenyl)-4-fluorobenzamide |
| 49 | 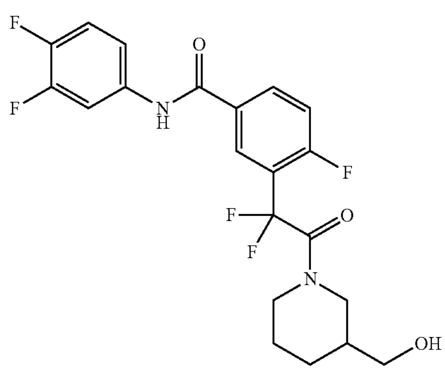 [SMILES: O=C(Nc1ccc(F)c(F)c1)c1ccc(F)c(C(F)(F)C(=O)N2CCCC(CO)C2)c1] | 3-(1,1-difluoro-2-(3-(hydroxymethyl)piperidin-1-yl)-2-oxoethyl)-N-(3,4-difluorophenyl)-4-fluorobenzamide |
| 50 | 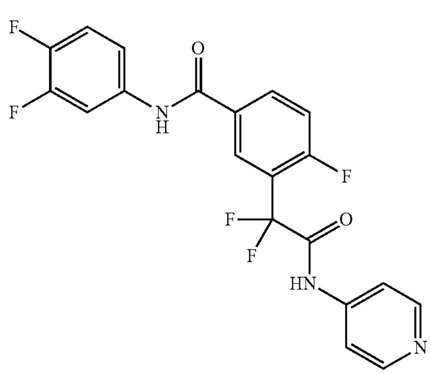 [SMILES: O=C(Nc1ccc(F)c(F)c1)c1ccc(F)c(C(F)(F)C(=O)Nc2ccncc2)c1] | 3-(1,1-difluoro-2-oxo-2-(pyridin-4-ylamino)ethyl)-N-(3,4-difluorophenyl)-4-fluorobenzamide |

TABLE 1-continued
Exemplary compounds.
| Example | Structure | Chemical Name |
|---|---|---|
| 51 | 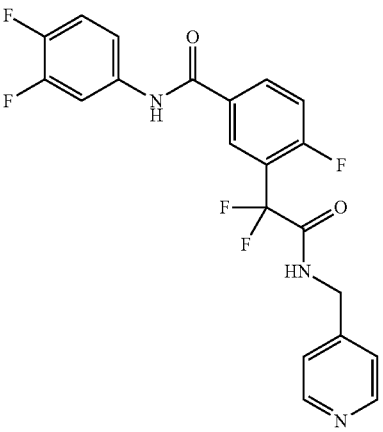 [SMILES: O=C(Nc1ccc(F)c(F)c1)c1ccc(F)c(C(F)(F)C(=O)NCc2ccncc2)c1] | 3-(1,1-difluoro-2-oxo-2-((pyridin-4-ylmethyl)amino)ethyl)-N-(3,4-difluorophenyl)-4-fluorobenzamide |
| 52 | 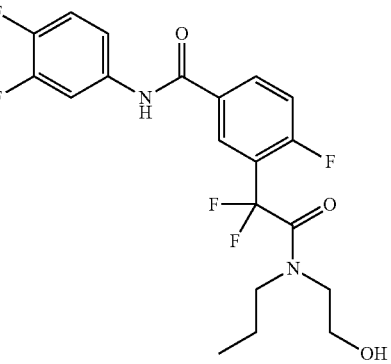 | 3-(1,1-difluoro-2-((2-hydroxyethyl)(propyl)amino)-2-oxoethyl)-N-(3,4-difluorophenyl)-4-fluorobenzamide |
| 53 | 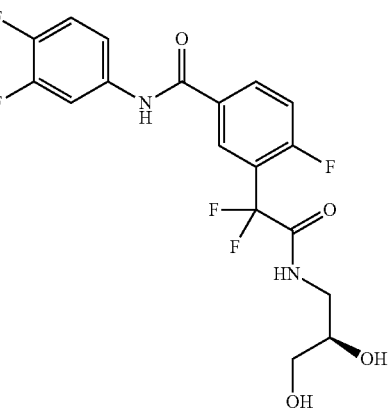 | (R)-N-(3,4-difluorophenyl)-3-(2-((2,3-dihydroxypropyl)amino)-1,1-difluoro-2-oxoethyl)-4-fluorobenzamide |

TABLE 1-continued

Exemplary compounds.

| Example | Structure | Chemical Name |
|---|---|---|
| 54 | 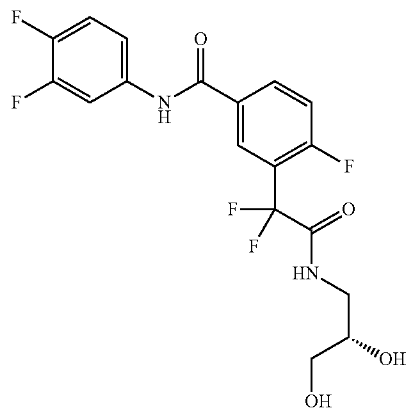 [SMILES: O=C(Nc1ccc(F)c(F)c1)c1ccc(F)c(C(F)(F)C(=O)NC[C@H](O)CO)c1] | (S)-N-(3,4-difluorophenyl)-3-(2-((2,3-dihydroxypropyl)amino)-1,1-difluoro-2-oxoethyl)-4-fluorobenzamide |
| 55 | 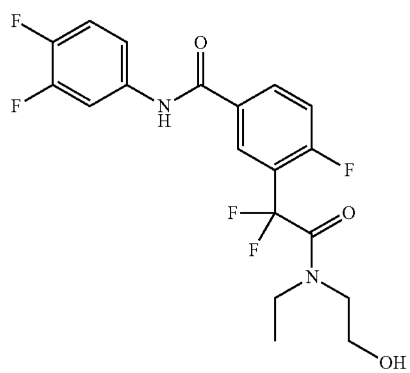 [SMILES: CCN(CCO)C(=O)C(F)(F)c1cc(C(=O)Nc2ccc(F)c(F)c2)ccc1F] | N-(3,4-difluorophenyl)-3-(2-(ethyl(2-hydroxyethyl)amino)-1,1-difluoro-2-oxoethyl)-4-fluorobenzamide |
| 56 | 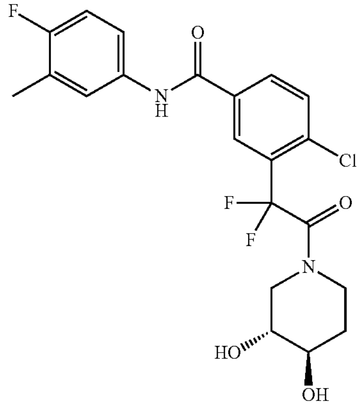 [SMILES: Cc1cc(NC(=O)c2ccc(Cl)c(C(F)(F)C(=O)N3CC[C@@H](O)[C@H](O)C3)c2)ccc1F] | 4-chloro-3-(2-((3R,4R)-3,4-dihydroxypiperidin-1-yl)-1,1-difluoro-2-oxoethyl)-N-(4-fluoro-3-methylphenyl)benzamide |

TABLE 1-continued

| Example | Structure | Chemical Name |
|---|---|---|
| 57 | 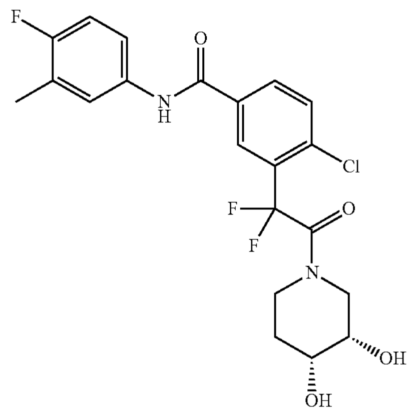 [SMILES: Cc1cc(NC(=O)c2ccc(Cl)c(C(F)(F)C(=O)N3CC[C@@H](O)[C@@H](O)C3)c2)ccc1F] | 4-chloro-3-(2-((3S,4R)-3,4-dihydroxypiperidin-1-yl)-1,1-difluoro-2-oxoethyl)-N-(4-fluoro-3-methylphenyl)benzamide |
| 58 | 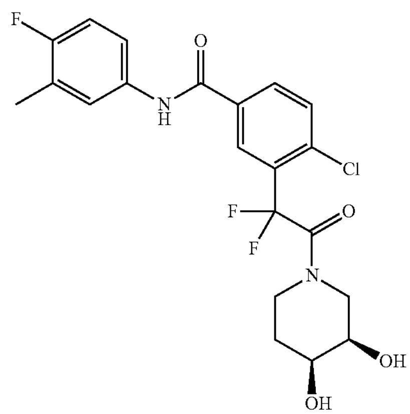 [SMILES: Cc1cc(NC(=O)c2ccc(Cl)c(C(F)(F)C(=O)N3CC[C@H](O)[C@H](O)C3)c2)ccc1F] | 4-chloro-3-(2-((3R,4S)-3,4-dihydroxypiperidin-1-yl)-1,1-difluoro-2-oxoethyl)-N-(4-fluoro-3-methylphenyl)benzamide |
| 59 | 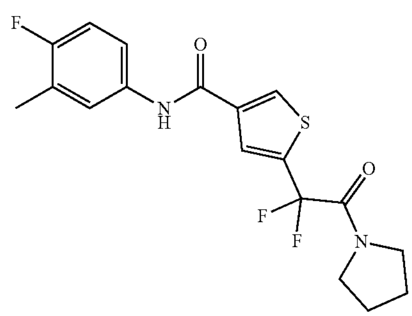 [SMILES: Cc1cc(NC(=O)c2csc(C(F)(F)C(=O)N3CCCC3)c2)ccc1F] | 5-(1,1-difluoro-2-oxo-2-(pyrrolidin-1-yl)ethyl)-N-(4-fluoro-3-methylphenyl)thiophene-3-carboxamide |
| 60 | 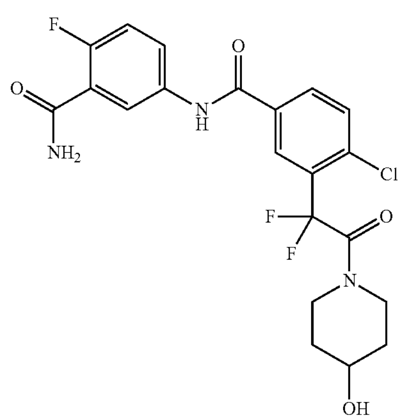 [SMILES: NC(=O)c1cc(NC(=O)c2ccc(Cl)c(C(F)(F)C(=O)N3CCC(O)CC3)c2)ccc1F] | N-(3-carbamoyl-4-fluorophenyl)-4-chloro-3-(1,1-difluoro-2-(4-hydroxypiperidin-1-yl)-2-oxoethyl)benzamide |

TABLE 1-continued
Exemplary compounds.
| Example | Structure | Chemical Name |
|---|---|---|
| 61 | 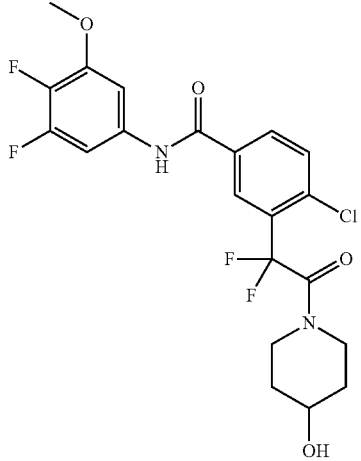 [SMILES: COc1cc(NC(=O)c2ccc(Cl)c(C(F)(F)C(=O)N3CCC(O)CC3)c2)cc(F)c1F] | 4-chloro-3-(1,1-difluoro-2-(4-hydroxypiperidin-1-yl)-2-oxoethyl)-N-(3,4-difluoro-5-methoxyphenyl)benzamide |
| 62 | 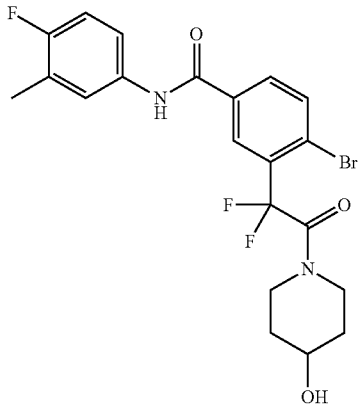 [SMILES: Cc1cc(NC(=O)c2ccc(Br)c(C(F)(F)C(=O)N3CCC(O)CC3)c2)ccc1F] | 4-bromo-3-(1,1-difluoro-2-(4-hydroxypiperidin-1-yl)-2-oxoethyl)-N-(4-fluoro-3-methylphenyl)benzamide |
| 63 | 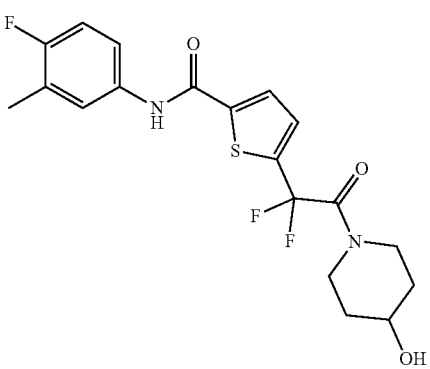 [SMILES: Cc1cc(NC(=O)c2ccc(C(F)(F)C(=O)N3CCC(O)CC3)s2)ccc1F] | 5-(1,1-difluoro-2-(4-hydroxypiperidin-1-yl)-2-oxoethyl)-N-(4-fluoro-3-methylphenyl)thiophene-2-carboxamide |

TABLE 1-continued

Exemplary compounds.

| Example | Structure | Chemical Name |
|---|---|---|
| 64 | 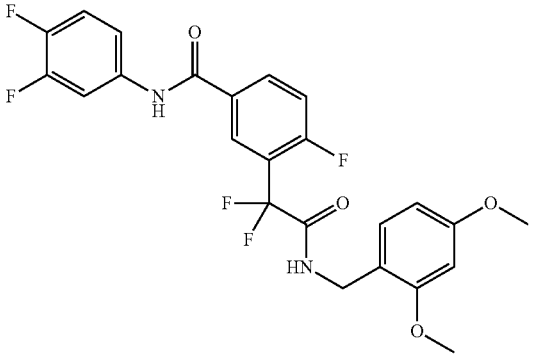 [SMILES: COc1ccc(CNC(=O)C(F)(F)c2cc(C(=O)Nc3ccc(F)c(F)c3)ccc2F)c(OC)c1] | N-(3,4-difluorophenyl)-3-(2-((2,4-dimethoxybenzyl)amino)-1,1-difluoro-2-oxoethyl)-4-fluorobenzamide |
| 65 | 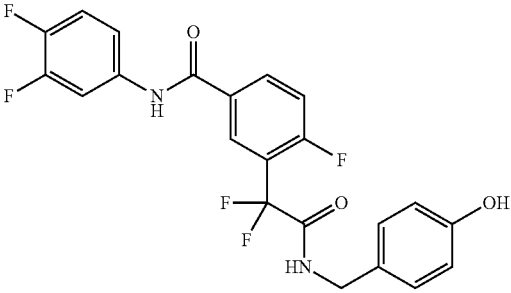 [SMILES: O=C(Nc1ccc(F)c(F)c1)c1ccc(F)c(C(F)(F)C(=O)NCc2ccc(O)cc2)c1] | 3-(1,1-difluoro-2-((4-hydroxybenzyl)amino)-2-oxoethyl)-N-(3,4-difluorophenyl)-4-fluorobenzamide |
| 66 | 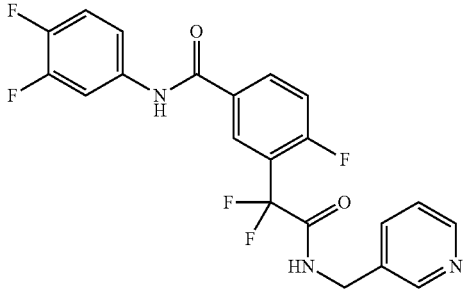 [SMILES: O=C(Nc1ccc(F)c(F)c1)c1ccc(F)c(C(F)(F)C(=O)NCc2cccnc2)c1] | 3-(1,1-difluoro-2-oxo-2-((pyridin-3-ylmethyl)amino)ethyl)-N-(3,4-difluorophenyl)-4-fluorobenzamide |
| 67 | 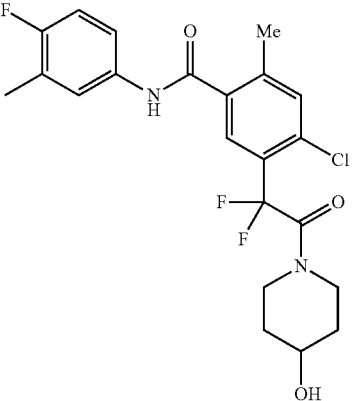 [SMILES: Cc1cc(NC(=O)c2cc(C(F)(F)C(=O)N3CCC(O)CC3)c(Cl)cc2C)ccc1F] | 4-chloro-5-(1,1-difluoro-2-(4-hydroxypiperidin-1-yl)-2-oxoethyl)-N-(4-fluoro-3-methylphenyl)-2-methylbenzamide |

TABLE 1-continued

Exemplary compounds.

| Example | Structure | Chemical Name |
|---|---|---|
| 68 | 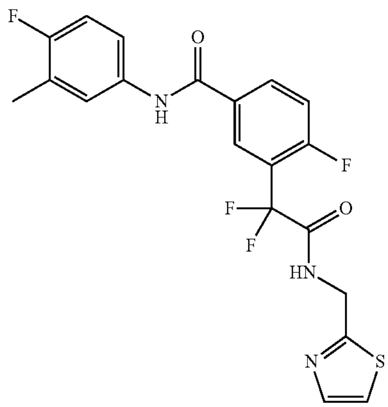 [SMILES: Cc1cc(NC(=O)c2ccc(F)c(C(F)(F)C(=O)NCc3nccs3)c2)ccc1F] | 3-(1,1-difluoro-2-oxo-2-((thiazol-2-ylmethyl)amino)ethyl)-4-fluoro-N-(4-fluoro-3-methylphenyl)benzamide |
| 69 | 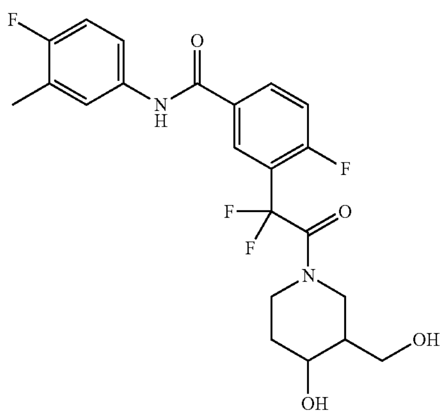 | 3-(1,1-difluoro-2-(4-hydroxy-3-(hydroxymethyl)piperidin-1-yl)-2-oxoethyl)-4-fluoro-N-(4-fluoro-3-methylphenyl)benzamide |
| 70 | 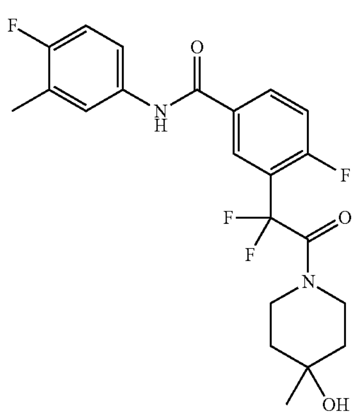 [SMILES: Cc1cc(NC(=O)c2ccc(F)c(C(F)(F)C(=O)N3CCC(C)(O)CC3)c2)ccc1F] | 3-(1,1-difluoro-2-(4-hydroxy-4-methylpiperidin-1-yl)-2-oxoethyl)-4-fluoro-N-(4-fluoro-3-methylphenyl)benzamide |

TABLE 1-continued

Exemplary compounds.

| Example | Structure | Chemical Name |
|---|---|---|
| 71 | 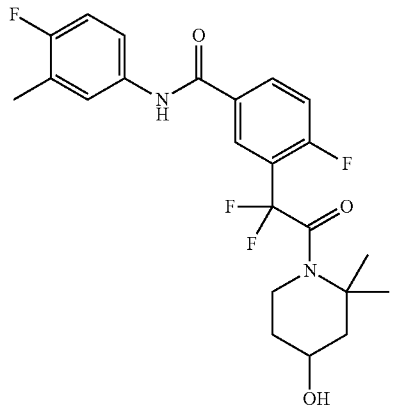 [SMILES: Cc1cc(NC(=O)c2ccc(F)c(C(F)(F)C(=O)N3CCC(O)CC3(C)C)c2)ccc1F] | 3-(1,1-difluoro-2-(4-hydroxy-2,2-dimethylpiperidin-1-yl)-2-oxoethyl)-4-fluoro-N-(4-fluoro-3-methylphenyl)benzamide |
| 72 | 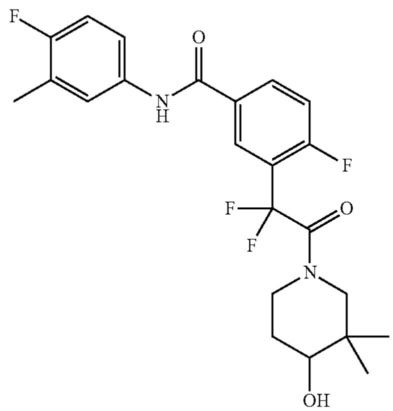 [SMILES: Cc1cc(NC(=O)c2ccc(F)c(C(F)(F)C(=O)N3CCC(O)C(C)(C)C3)c2)ccc1F] | 3-(1,1-difluoro-2-(4-hydroxy-3,3-dimethylpiperidin-1-yl)-2-oxoethyl)-4-fluoro-N-(4-fluoro-3-methylphenyl)benzamide |
| 73 | 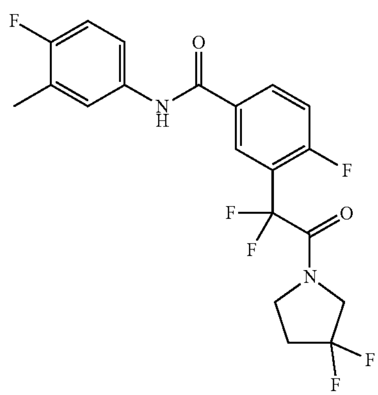 [SMILES: Cc1cc(NC(=O)c2ccc(F)c(C(F)(F)C(=O)N3CCC(F)(F)C3)c2)ccc1F] | 3-(2-(3,3-difluoropyrrolidin-1-yl)-1,1-difluoro-2-oxoethyl)-4-fluoro-N-(4-fluoro-3-methylphenyl)benzamide |
| 74 | 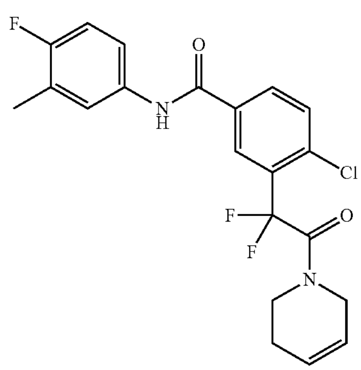 [SMILES: Cc1cc(NC(=O)c2ccc(Cl)c(C(F)(F)C(=O)N3CC=CCC3)c2)ccc1F] | 4-chloro-3-(2-(3,6-dihydropyridin-1(2H)-yl)-1,1-difluoro-2-oxoethyl)-N-(4-fluoro-3-methylphenyl)benzamide |

TABLE 1-continued

Exemplary compounds.

| Example | Structure | Chemical Name |
|---|---|---|
| 75 | 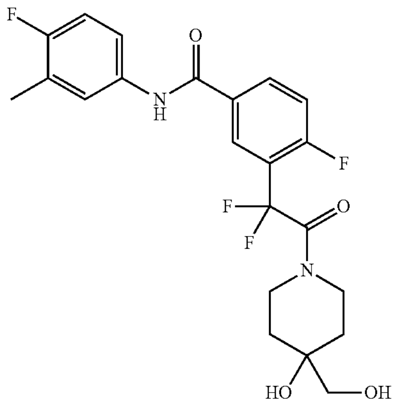 [SMILES: Cc1cc(NC(=O)c2ccc(F)c(C(F)(F)C(=O)N3CCC(O)(CO)CC3)c2)ccc1F] | 3-(1,1-difluoro-2-(4-hydroxy-4-(hydroxymethyl)piperidin-1-yl)-2-oxoethyl)-4-fluoro-N-(4-fluoro-3-methylphenyl)benzamide |
| 76 | 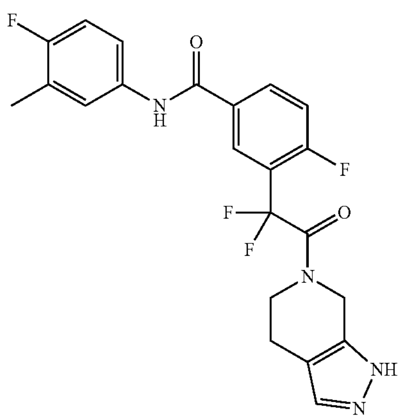 | 3-(1,1-difluoro-2-oxo-2-(1,4,5,7-tetrahydro-6H-pyrazolo[3,4-c]pyridin-6-yl)ethyl)-4-fluoro-N-(4-fluoro-3-methylphenyl)benzamide |
| 77 | 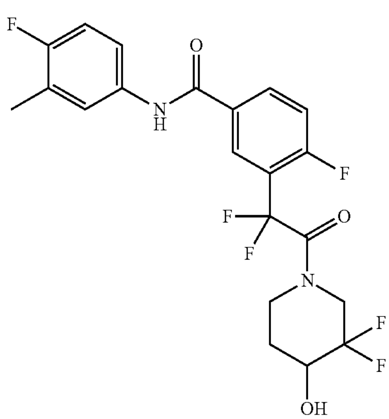 [SMILES: Cc1cc(NC(=O)c2ccc(F)c(C(F)(F)C(=O)N3CCC(O)C(F)(F)C3)c2)ccc1F] | 3-(2-(3,3-difluoro-4-hydroxypiperidin-1-yl)-1,1-difluoro-2-oxoethyl)-4-fluoro-N-(4-fluoro-3-methylphenyl)benzamide |

TABLE 1-continued

Exemplary compounds.

| Example | Structure | Chemical Name |
|---|---|---|
| 78 | 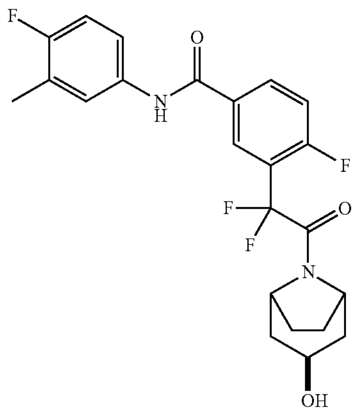 | 3-(1,1-difluoro-2-((1R,3r,5S)-3-hydroxy-8-azabicyclo[3.2.1]octan-8-yl)-2-oxoethyl)-4-fluoro-N-(4-fluoro-3-methylphenyl)benzamide |
| 79 | 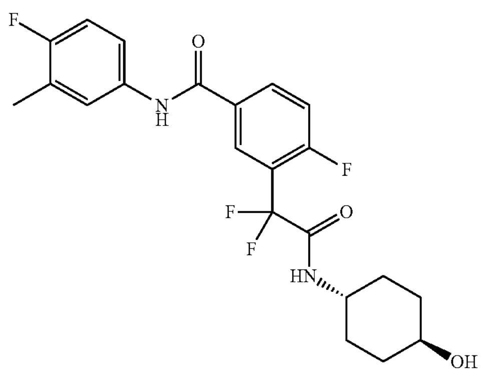 [SMILES: Cc1cc(NC(=O)c2ccc(F)c(C(F)(F)C(=O)N[C@H]3CC[C@H](O)CC3)c2)ccc1F] | 3-(1,1-difluoro-2-(((1r,4r)-4-hydroxycyclohexyl)amino)-2-oxoethyl)-4-fluoro-N-(4-fluoro-3-methylphenyl)benzamide |
| 80 | 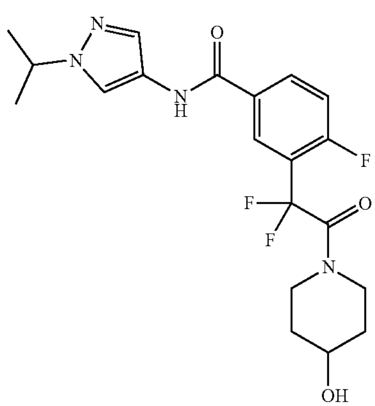 [SMILES: CC(C)n1cc(NC(=O)c2ccc(F)c(C(F)(F)C(=O)N3CCC(O)CC3)c2)cn1] | 3-(1,1-difluoro-2-(4-hydroxypiperidin-1-yl)-2-oxoethyl)-4-fluoro-N-(1-isopropyl-1H-pyrazol-4-yl)benzamide |
| 81 | 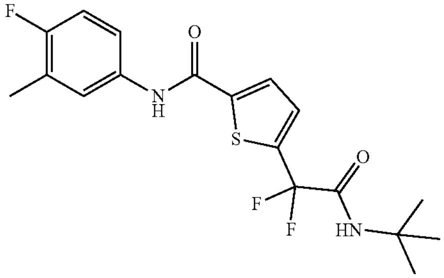 [SMILES: Cc1cc(NC(=O)c2ccc(C(F)(F)C(=O)NC(C)(C)C)s2)ccc1F] | 5-(2-(tert-butylamino)-1,1-difluoro-2-oxoethyl)-N-(4-fluoro-3-methylphenyl)thiophene-2-carboxamide |

TABLE 1-continued

Exemplary compounds.

| Example | Structure | Chemical Name |
|---|---|---|
| 82 | 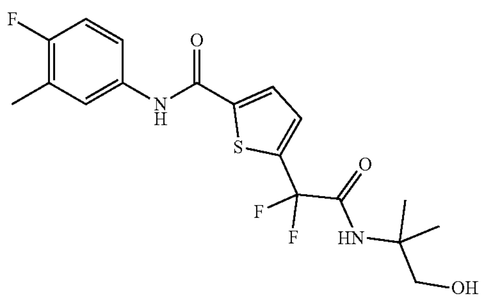 [SMILES: Cc1cc(NC(=O)c2ccc(C(F)(F)C(=O)NC(C)(C)CO)s2)ccc1F] | 5-(1,1-difluoro-2-((1-hydroxy-2-methylpropan-2-yl)amino)-2-oxoethyl)-N-(4-fluoro-3-methylphenyl)thiophene-2-carboxamide |
| 83 | 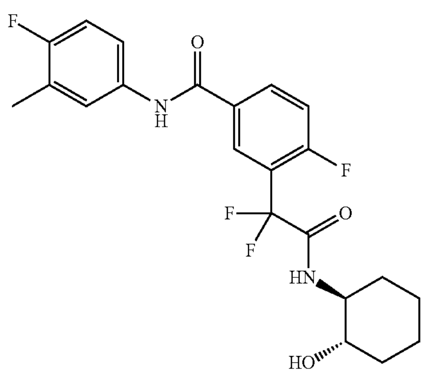 [SMILES: Cc1cc(NC(=O)c2ccc(F)c(C(F)(F)C(=O)N[C@H]3CCCC[C@@H]3O)c2)ccc1F] | 3-(1,1-difluoro-2-(((1S,2S)-2-hydroxycyclohexyl)amino)-2-oxoethyl)-4-fluoro-N-(4-fluoro-3-methylphenyl)benzamide |
| 84 | 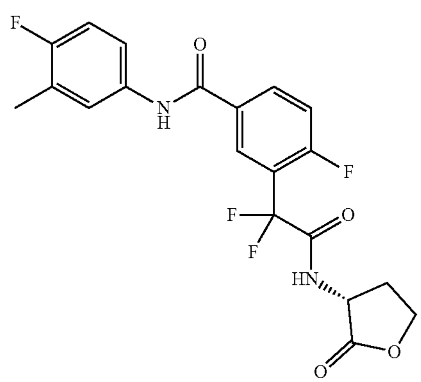 [SMILES: Cc1cc(NC(=O)c2ccc(F)c(C(F)(F)C(=O)N[C@@H]3CCOC3=O)c2)ccc1F] | (R)-3-(1,1-difluoro-2-oxo-2-((2-oxotetrahydrofuran-3-yl)amino)ethyl)-4-fluoro-N-(4-fluoro-3-methylphenyl)benzamide |
| 85 | 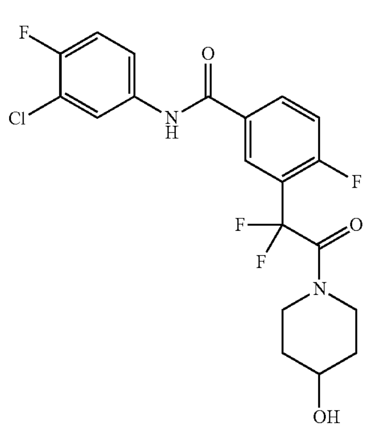 [SMILES: O=C(Nc1ccc(F)c(Cl)c1)c1ccc(F)c(C(F)(F)C(=O)N2CCC(O)CC2)c1] | N-(3-chloro-4-fluorophenyl)-3-(1,1-difluoro-2-(4-hydroxypiperidin-1-yl)-2-oxoethyl)-4-fluorobenzamide |

TABLE 1-continued

Exemplary compounds.

| Example | Structure | Chemical Name |
|---|---|---|
| 86 | 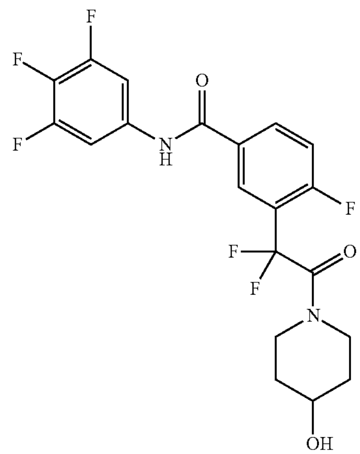 [SMILES: O=C(Nc1cc(F)c(F)c(F)c1)c1ccc(F)c(C(F)(F)C(=O)N2CCC(O)CC2)c1] | 3-(1,1-difluoro-2-(4-hydroxypiperidin-1-yl)-2-oxoethyl)-4-fluoro-N-(3,4,5-trifluorophenyl)benzamide |
| 87 | 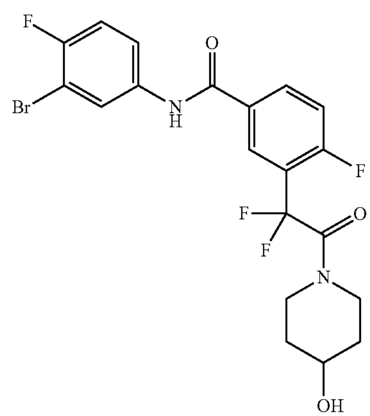 | N-(3-bromo-4-fluorophenyl)-3-(1,1-difluoro-2-(4-hydroxypiperidin-1-yl)-2-oxoethyl)-4-fluorobenzamide |
| 88 | 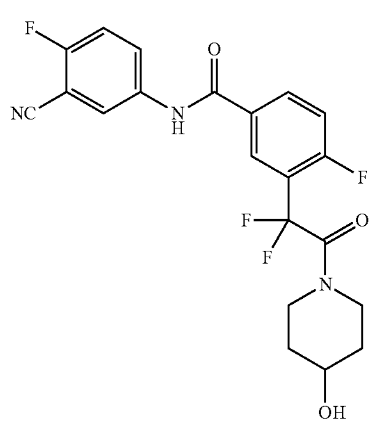 [SMILES: N#Cc1cc(NC(=O)c2ccc(F)c(C(F)(F)C(=O)N3CCC(O)CC3)c2)ccc1F] | N-(3-cyano-4-fluorophenyl)-3-(1,1-difluoro-2-(4-hydroxypiperidin-1-yl)-2-oxoethyl)-4-fluorobenzamide |

TABLE 1-continued

| Example | Structure | Chemical Name |
|---|---|---|
| 89 | 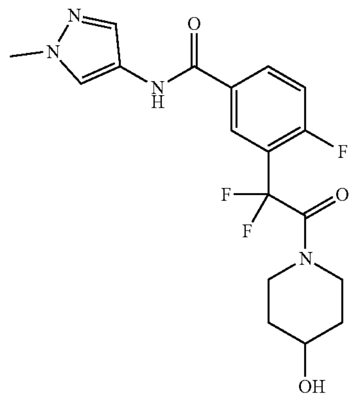 [SMILES: Cn1cc(NC(=O)c2ccc(F)c(C(F)(F)C(=O)N3CCC(O)CC3)c2)cn1] | 3-(1,1-difluoro-2-(4-hydroxypiperidin-1-yl)-2-oxoethyl)-4-fluoro-N-(1-methyl-1H-pyrazol-4-yl)benzamide |
| 90 | 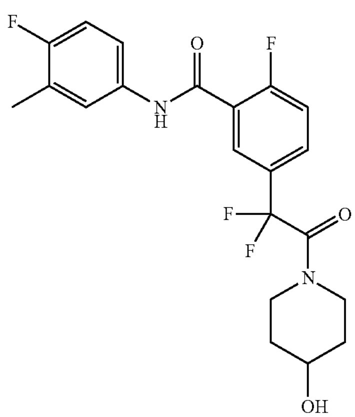 [SMILES: Cc1cc(NC(=O)c2cc(C(F)(F)C(=O)N3CCC(O)CC3)ccc2F)ccc1F] | 5-(1,1-difluoro-2-(4-hydroxypiperidin-1-yl)-2-oxoethyl)-2-fluoro-N-(4-fluoro-3-methylphenyl)benzamide |
| 91 | 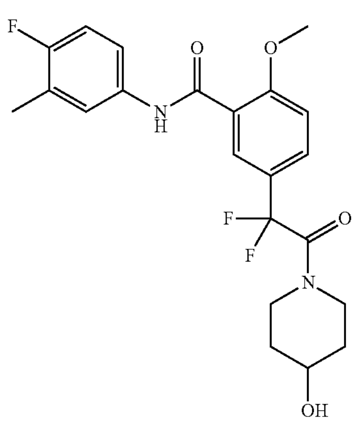 [SMILES: COc1ccc(C(F)(F)C(=O)N2CCC(O)CC2)cc1C(=O)Nc1ccc(F)c(C)c1] | 5-(1,1-difluoro-2-(4-hydroxypiperidin-1-yl)-2-oxoethyl)-N-(4-fluoro-3-methylphenyl)-2-methoxybenzamide |

TABLE 1-continued

Exemplary compounds.

| Example | Structure | Chemical Name |
| --- | --- | --- |
| 92 | 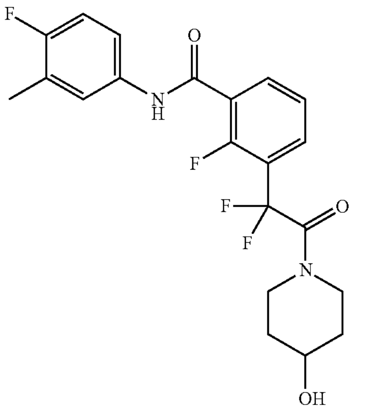 [SMILES: Cc1cc(NC(=O)c2cccc(C(F)(F)C(=O)N3CCC(O)CC3)c2F)ccc1F] | 3-(1,1-difluoro-2-(4-hydroxypiperidin-1-yl)-2-oxoethyl)-2-fluoro-N-(4-fluoro-3-methylphenyl)benzamide |
| 93 | 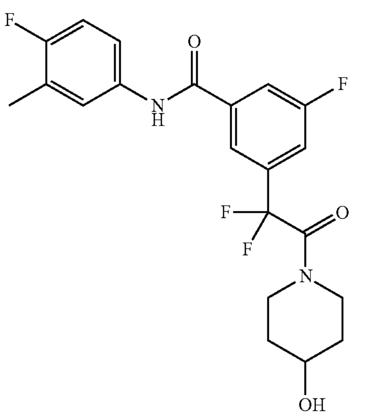 [SMILES: Cc1cc(NC(=O)c2cc(F)cc(C(F)(F)C(=O)N3CCC(O)CC3)c2)ccc1F] | 3-(1,1-difluoro-2-(4-hydroxypiperidin-1-yl)-2-oxoethyl)-5-fluoro-N-(4-fluoro-3-methylphenyl)benzamide |
| 94 | 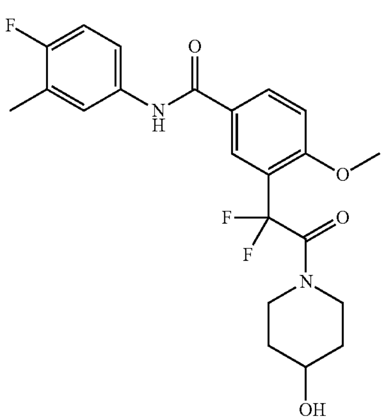 [SMILES: COc1ccc(C(=O)Nc2ccc(F)c(C)c2)cc1C(F)(F)C(=O)N1CCC(O)CC1] | 3-(1,1-difluoro-2-(4-hydroxypiperidin-1-yl)-2-oxoethyl)-N-(4-fluoro-3-methylphenyl)-4-methoxybenzamide |

TABLE 1-continued

Exemplary compounds.

| Example | Structure | Chemical Name |
|---|---|---|
| 95 | 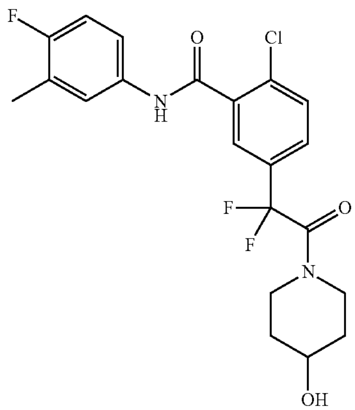 [SMILES: Cc1cc(NC(=O)c2cc(C(F)(F)C(=O)N3CCC(O)CC3)ccc2Cl)ccc1F] | 2-chloro-5-(1,1-difluoro-2-(4-hydroxypiperidin-1-yl)-2-oxoethyl)-N-(4-fluoro-3-methylphenyl)benzamide |
| 96 | 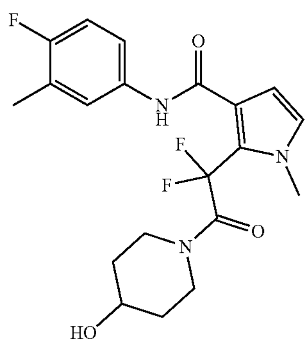 [SMILES: Cc1cc(NC(=O)c2ccn(C)c2C(F)(F)C(=O)N2CCC(O)CC2)ccc1F] | 2-(1,1-difluoro-2-(4-hydroxypiperidin-1-yl)-2-oxoethyl)-N-(4-fluoro-3-methylphenyl)-1-methyl-1H-pyrrole-3-carboxamide |
| 97 | 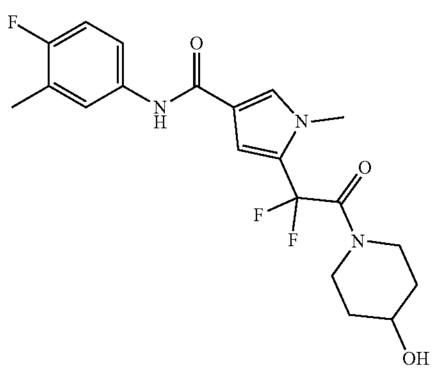 [SMILES: Cc1cc(NC(=O)c2cc(C(F)(F)C(=O)N3CCC(O)CC3)n(C)c2)ccc1F] | 5-(1,1-difluoro-2-(4-hydroxypiperidin-1-yl)-2-oxoethyl)-N-(4-fluoro-3-methylphenyl)-1-methyl-1H-pyrrole-3-carboxamide |
| 98 | 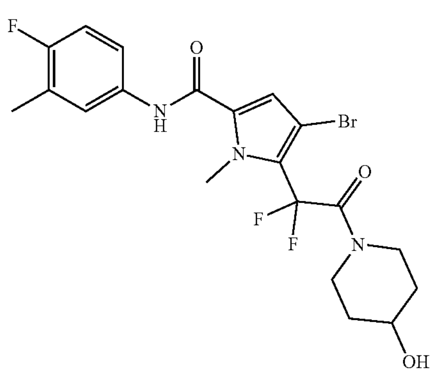 [SMILES: Cc1cc(NC(=O)c2cc(Br)c(C(F)(F)C(=O)N3CCC(O)CC3)n2C)ccc1F] | 4-bromo-5-(1,1-difluoro-2-(4-hydroxypiperidin-1-yl)-2-oxoethyl)-N-(4-fluoro-3-methylphenyl)-1-methyl-1H-pyrrole-2-carboxamide |

TABLE 1-continued

Exemplary compounds.

| Example | Structure | Chemical Name |
|---|---|---|
| 99 | 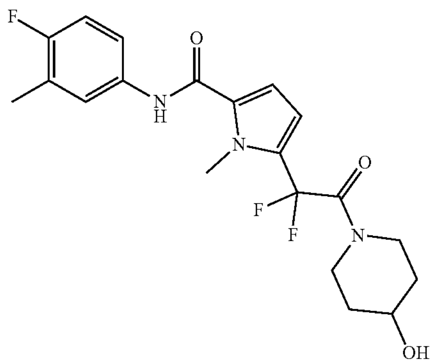 [SMILES: Cc1cc(NC(=O)c2ccc(C(F)(F)C(=O)N3CCC(O)CC3)n2C)ccc1F] | 5-(1,1-difluoro-2-(4-hydroxypiperidin-1-yl)-2-oxoethyl)-N-(4-fluoro-3-methylphenyl)-1-methyl-1H-pyrrole-2-carboxamide |
| 100 | 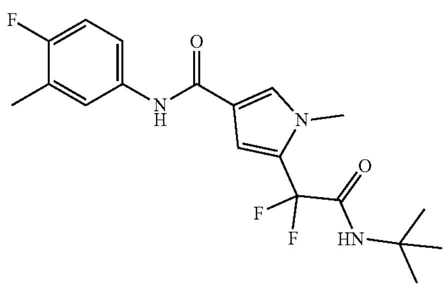 [SMILES: Cc1cc(NC(=O)c2cc(C(F)(F)C(=O)NC(C)(C)C)n(C)c2)ccc1F] | 5-(2-(tert-butylamino)-1,1-difluoro-2-oxoethyl)-N-(4-fluoro-3-methylphenyl)-1-methyl-1H-pyrrole-3-carboxamide |
| 101 | 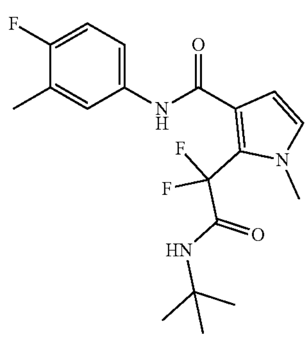 [SMILES: Cc1cc(NC(=O)c2ccn(C)c2C(F)(F)C(=O)NC(C)(C)C)ccc1F] | 2-(2-(tert-butylamino)-1,1-difluoro-2-oxoethyl)-N-(4-fluoro-3-methylphenyl)-1-methyl-1H-pyrrole-3-carboxamide |
| 102 | 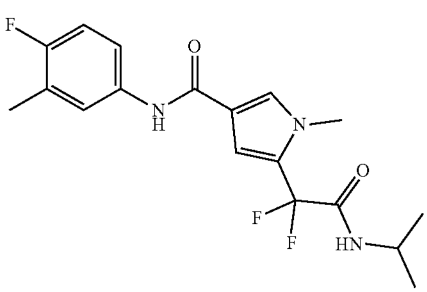 [SMILES: Cc1cc(NC(=O)c2cc(C(F)(F)C(=O)NC(C)C)n(C)c2)ccc1F] | 5-(1,1-difluoro-2-(isopropylamino)-2-oxoethyl)-N-(4-fluoro-3-methylphenyl)-1-methyl-1H-pyrrole-3-carboxamide |

TABLE 1-continued

Exemplary compounds.

| Example | Structure | Chemical Name |
|---|---|---|
| 103 | 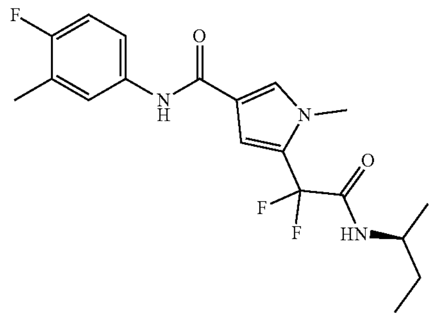 [SMILES: CC[C@H](C)NC(=O)C(F)(F)c1cc(C(=O)Nc2ccc(F)c(C)c2)cn1C] | (S)-5-(2-(sec-butylamino)-1,1-difluoro-2-oxoethyl)-N-(4-fluoro-3-methylphenyl)-1-methyl-1H-pyrrole-3-carboxamide |
| 104 | 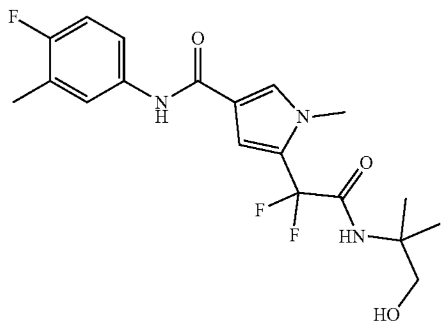 [SMILES: Cc1cc(NC(=O)c2cc(C(F)(F)C(=O)NC(C)(C)CO)n(C)c2)ccc1F] | 5-(1,1-difluoro-2-((1-hydroxy-2-methylpropan-2-yl)amino)-2-oxoethyl)-N-(4-fluoro-3-methylphenyl)-1-methyl-1H-pyrrole-3-carboxamide |
| 105 | 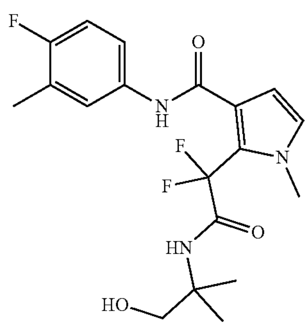 [SMILES: Cc1cc(NC(=O)c2ccn(C)c2C(F)(F)C(=O)NC(C)(C)CO)ccc1F] | 2-(1,1-difluoro-2-((1-hydroxy-2-methylpropan-2-yl)amino)-2-oxoethyl)-N-(4-fluoro-3-methylphenyl)-1-methyl-1H-pyrrole-3-carboxamide |
| 106 | 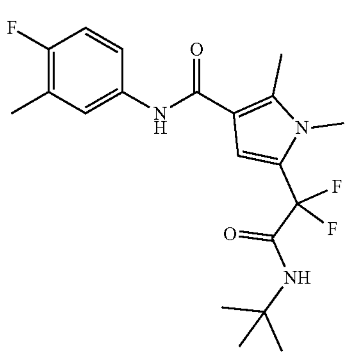 [SMILES: Cc1cc(NC(=O)c2cc(C(F)(F)C(=O)NC(C)(C)C)n(C)c2C)ccc1F] | 5-(2-(tert-butylamino)-1,1-difluoro-2-oxoethyl)-N-(4-fluoro-3-methylphenyl)-1,2-dimethyl-1H-pyrrole-3-carboxamide |

TABLE 1-continued

Exemplary compounds.

| Example | Structure | Chemical Name |
|---|---|---|
| 107 | 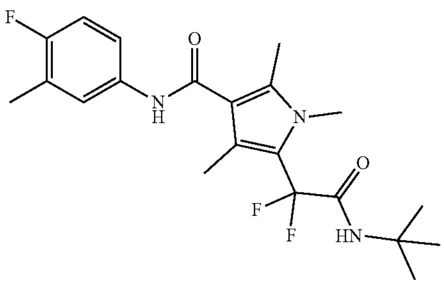 [SMILES: Cc1cc(NC(=O)c2c(C)c(C(F)(F)C(=O)NC(C)(C)C)n(C)c2C)ccc1F] | 5-(2-(tert-butylamino)-1,1-difluoro-2-oxoethyl)-N-(4-fluoro-3-methylphenyl)-1,2,4-trimethyl-1H-pyrrole-3-carboxamide |
| 108 | 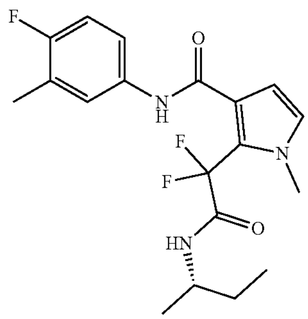 [SMILES: CC[C@H](C)NC(=O)C(F)(F)c1c(C(=O)Nc2ccc(F)c(C)c2)ccn1C] | (S)-2-(2-(sec-butylamino)-1,1-difluoro-2-oxoethyl)-N-(4-fluoro-3-methylphenyl)-1-methyl-1H-pyrrole-3-carboxamide |
| 109 | 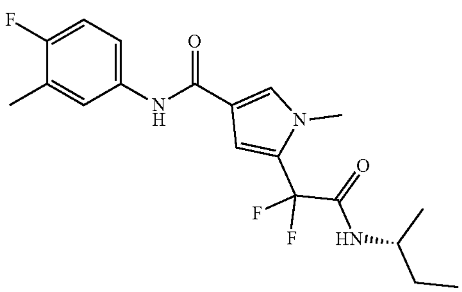 [SMILES: CC[C@@H](C)NC(=O)C(F)(F)c1cc(C(=O)Nc2ccc(F)c(C)c2)cn1C] | (R)-5-(2-(sec-butylamino)-1,1-difluoro-2-oxoethyl)-N-(4-fluoro-3-methylphenyl)-1-methyl-1H-pyrrole-3-carboxamide |
| 110 | 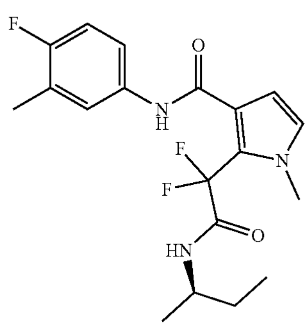 [SMILES: CC[C@@H](C)NC(=O)C(F)(F)c1c(C(=O)Nc2ccc(F)c(C)c2)ccn1C] | (R)-2-(2-(sec-butylamino)-1,1-difluoro-2-oxoethyl)-N-(4-fluoro-3-methylphenyl)-1-methyl-1H-pyrrole-3-carboxamide |
| 111 | 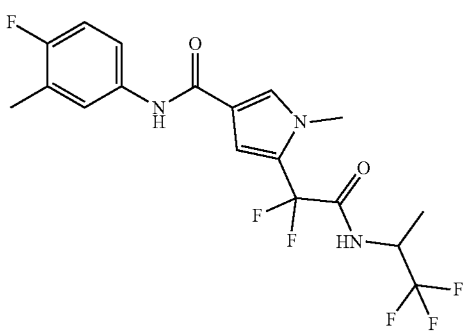 [SMILES: Cc1cc(NC(=O)c2cc(C(F)(F)C(=O)NC(C)C(F)(F)F)n(C)c2)ccc1F] | 5-(1,1-difluoro-2-oxo-2-((1,1,1-trifluoropropan-2-yl)amino)ethyl)-N-(4-fluoro-3-(methylphenyl)-1-methyl-1H-pyrrole-3-carboxamide |

TABLE 1-continued

Exemplary compounds.

| Example | Structure | Chemical Name |
|---|---|---|
| 112 | 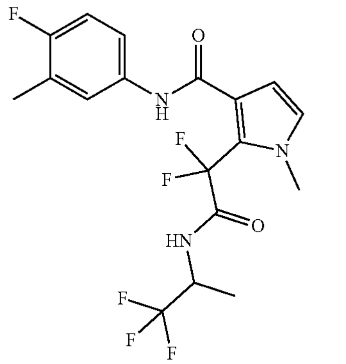 [SMILES: Cc1cc(NC(=O)c2ccn(C)c2C(F)(F)C(=O)NC(C)C(F)(F)F)ccc1F] | 2-(1,1-difluoro-2-oxo-2-((1,1,1-trifluoropropan-2-yl)amino)ethyl)-N-(4-fluoro-3-methylphenyl)-1-methyl-1H-pyrrole-3-carboxamide |
| 113 | 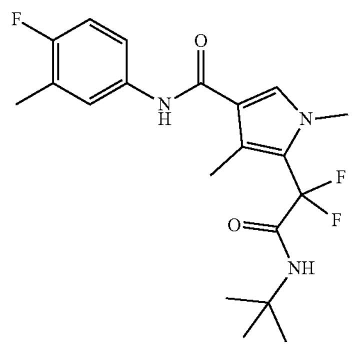 [SMILES: Cc1cc(NC(=O)c2cn(C)c(C(F)(F)C(=O)NC(C)(C)C)c2C)ccc1F] | 5-(2-(tert-butylamino)-1,1-difluoro-2-oxoethyl)-N-(4-fluoro-3-methylphenyl)-1,4-dimethyl-1H-pyrrole-3-carboxamide |
| 114 | 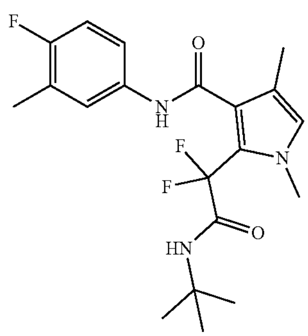 [SMILES: Cc1cc(NC(=O)c2c(C)cn(C)c2C(F)(F)C(=O)NC(C)(C)C)ccc1F] | 2-(2-(tert-butylamino)-1,1-difluoro-2-oxoethyl)-N-(4-fluoro-3-methylphenyl)-1,4-dimethyl-1H-pyrrole-3-carboxamide |
| 115 | 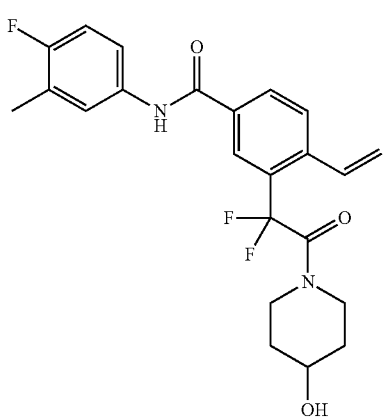 [SMILES: C=Cc1ccc(C(=O)Nc2ccc(F)c(C)c2)cc1C(F)(F)C(=O)N1CCC(O)CC1] | 3-(1,1-difluoro-2-(4-hydroxypiperidin-1-yl)-2-oxoethyl)-N-(4-fluoro-3-methylphenyl)-4-vinylbenzamide |

TABLE 1-continued

Exemplary compounds.

| Example | Structure | Chemical Name |
|---|---|---|
| 116 | 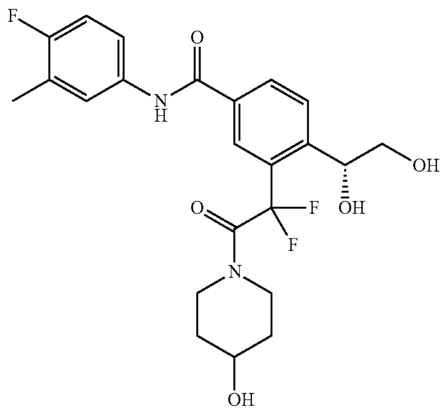 [SMILES: Cc1cc(NC(=O)c2ccc([C@@H](O)CO)c(C(F)(F)C(=O)N3CCC(O)CC3)c2)ccc1F] | (R)-3-(1,1-difluoro-2-(4-hydroxypiperidin-1-yl)-2-oxoethyl)-4-(1,2-dihydroxyethyl)-N-(4-fluoro-3-methylphenyl)benzamide |
| 117 | 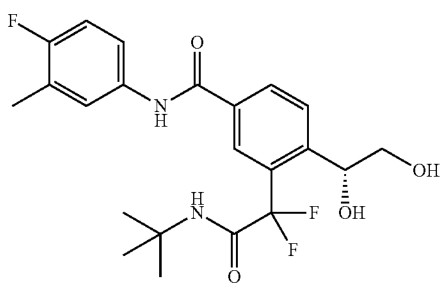 [SMILES: Cc1cc(NC(=O)c2ccc([C@@H](O)CO)c(C(F)(F)C(=O)NC(C)(C)C)c2)ccc1F] | (R)-3-(2-(tert-butylamino)-1,1-difluoro-2-oxoethyl)-4-(1,2-dihydroxyethyl)-N-(4-fluoro-3-methylphenyl)benzamide |
| 118 | 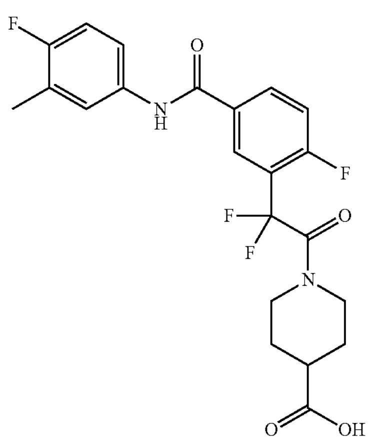 [SMILES: Cc1cc(NC(=O)c2ccc(F)c(C(F)(F)C(=O)N3CCC(C(=O)O)CC3)c2)ccc1F] | 1-(2,2-difluoro-2-(2-fluoro-5-((4-fluoro-3-methylphenyl)carbamoyl)phenyl)acetyl)piperidine-4-carboxylic acid |
| 119 | 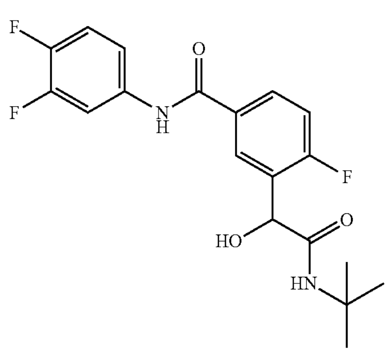 [SMILES: CC(C)(C)NC(=O)C(O)c1cc(C(=O)Nc2ccc(F)c(F)c2)ccc1F] | 3-(2-(tert-butylamino)-1-hydroxy-2-oxoethyl)-N-(3,4-difluorophenyl)-4-fluorobenzamide |

TABLE 1-continued

Exemplary compounds.

| Example | Structure | Chemical Name |
|---|---|---|
| 120 | 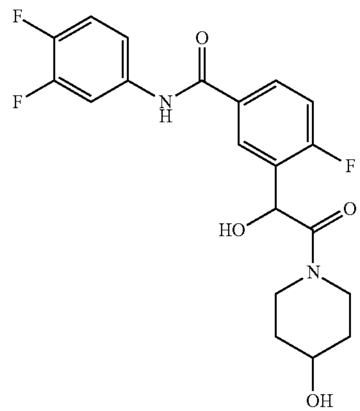 | N-(3,4-difluorophenyl)-4-fluoro-3-(1-hydroxy-2-(4-hydroxypiperidin-1-yl)-2-oxoethyl)benzamide |
| 121 | 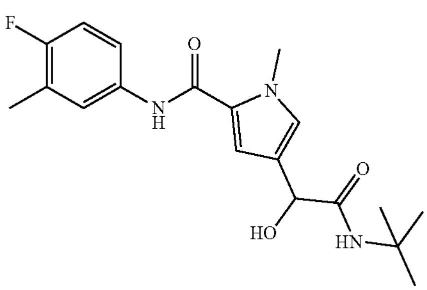 [SMILES: Cc1cc(NC(=O)c2cc(C(O)C(=O)NC(C)(C)C)cn2C)ccc1F] | 4-(2-(tert-butylamino)-1-hydroxy-2-oxoethyl)-N-(4-fluoro-3-methylphenyl)-1-methyl-1H-pyrrole-2-carboxamide |
| 122 | 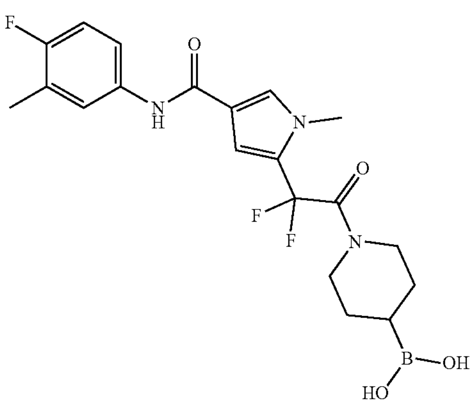 [SMILES: Cc1cc(NC(=O)c2cc(C(F)(F)C(=O)N3CCC(B(O)O)CC3)n(C)c2)ccc1F] | (1-(2,2-difluoro-2-(4-((4-fluoro-3-methylphenyl)carbamoyl)-1-methyl-1H-pyrrol-2-yl)acetyl)piperidin-4-yl)boronic acid |
| 123 | 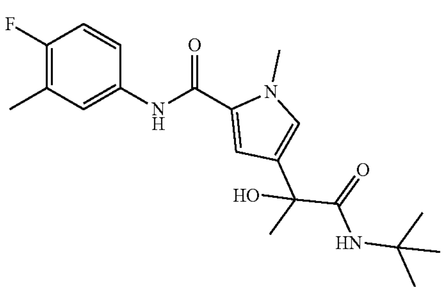 [SMILES: Cc1cc(NC(=O)c2cc(C(C)(O)C(=O)NC(C)(C)C)cn2C)ccc1F] | 4-(1-(tert-butylamino)-2-hydroxy-1-oxopropan-2-yl)-N-(4-fluoro-3-methylphenyl)-1-methyl-1H-pyrrole-2-carboxamide |

TABLE 1-continued

| Exemplary compounds. | | |
|---|---|---|
| Example | Structure | Chemical Name |
| 124 | | 4-(1-(tert-butylamino)-2-hydroxy-3-methyl-1-oxobutan-2-yl)-N-(4-fluoro-3-methylphenyl)-1-methyl-1H-pyrrole-2-carboxamide |
| 125 | | 5-(1,1-difluoro-2-(((1s,4s)-4-hydroxycyclohexyl)amino)-2-oxoethyl)-N-(4-fluoro-3-methylphenyl)-1-methyl-1H-pyrrole-3-carboxamide |
| 126 | | 2-(1,1-difluoro-2-(((1s,4s)-4-hydroxycyclohexyl)amino)-2-oxoethyl)-N-(4-fluoro-3-methylphenyl)-1-methyl-1H-pyrrole-3-carboxamide |
| 127 | | 5-(1,1-difluoro-2-(((1R,2R)-2-hydroxycyclohexyl)amino)-2-oxoethyl)-N-(4-fluoro-3-methylphenyl)-1-methyl-1H-pyrrole-3-carboxamide |

TABLE 1-continued

Exemplary compounds.

| Example | Structure | Chemical Name |
|---|---|---|
| 128 | 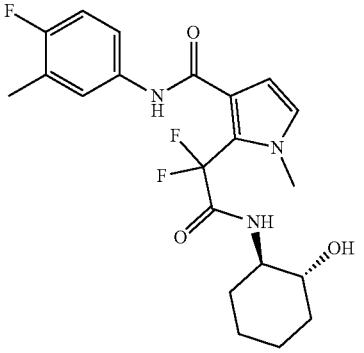 [SMILES: Cc1cc(NC(=O)c2ccn(C)c2C(F)(F)C(=O)N[C@@H]2CCCC[C@H]2O)ccc1F] | 2-(1,1-difluoro-2-(((1R,2R)-2-hydroxycyclohexyl)amino)-2-oxoethyl)-N-(4-fluoro-3-methylphenyl)-1-methyl-1H-pyrrole-3-carboxamide |
| 129 | 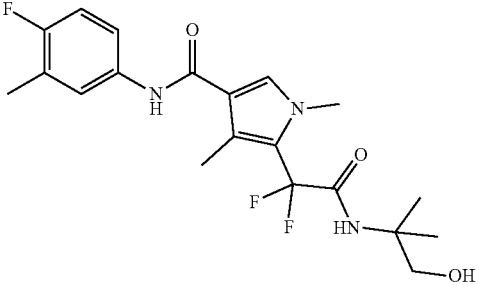 [SMILES: Cc1cc(NC(=O)c2cn(C)c(C(F)(F)C(=O)NC(C)(C)CO)c2C)ccc1F] | 5-(1,1-difluoro-2-((1-hydroxy-2-methylpropan-2-yl)amino)-2-oxoethyl)-N-(4-fluoro-3-methylphenyl)-1,4-dimethyl-1H-pyrrole-3-carboxamide |
| 131 | 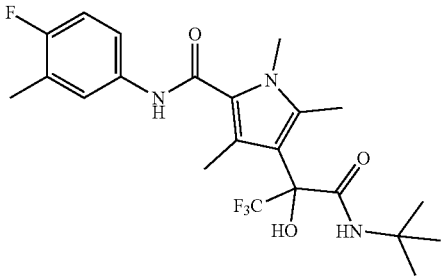 [SMILES: Cc1cc(NC(=O)c2c(C)c(C(O)(C(=O)NC(C)(C)C)C(F)(F)F)c(C)n2C)ccc1F] | 4-(3-(tert-butylamino)-1,1,1-trifluoro-2-hydroxy-3-oxopropan-2-yl)-N-(4-fluoro-3-methylphenyl)-1,3,5-trimethyl-1H-pyrrole-2-carboxamide |
| 132 | 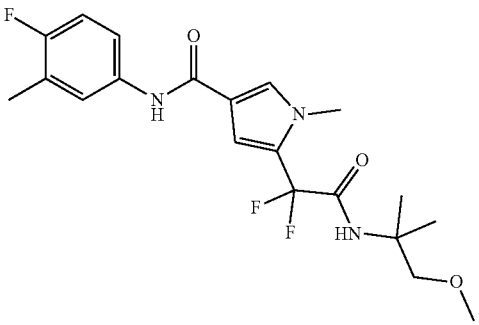 [SMILES: COCC(C)(C)NC(=O)C(F)(F)c1cc(C(=O)Nc2ccc(F)c(C)c2)cn1C] | 5-(1,1-difluoro-2-((1-methoxy-2-methylpropan-2-yl)amino)-2-oxoethyl)-N-(4-fluoro-3-methylphenyl)-1-methyl-1H-pyrrole-3-carboxamide |
| 133 | 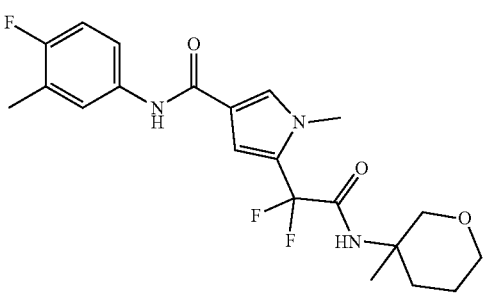 [SMILES: Cc1cc(NC(=O)c2cc(C(F)(F)C(=O)NC3(C)CCCOC3)n(C)c2)ccc1F] | 5-(1,1-difluoro-2-((3-methyltetrahydro-2H-pyran-3-yl)amino)-2-oxoethyl)-N-(4-fluoro-3-methylphenyl)-1-methyl-1H-pyrrole-3-carboxamide |

TABLE 1-continued

Exemplary compounds.

| Example | Structure | Chemical Name |
|---|---|---|
| 134 | 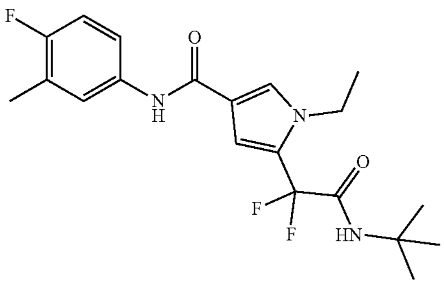 [SMILES: CCn1cc(C(=O)Nc2ccc(F)c(C)c2)cc1C(F)(F)C(=O)NC(C)(C)C] | 5-(2-(tert-butylamino)-1,1-difluoro-2-oxoethyl)-1-ethyl-N-(4-fluoro-3-methylphenyl)-1H-pyrrole-3-carboxamide |
| 135 | 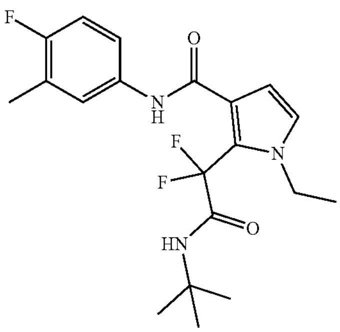 [SMILES: CCn1ccc(C(=O)Nc2ccc(F)c(C)c2)c1C(F)(F)C(=O)NC(C)(C)C] | 2-(2-(tert-butylamino)-1,1-difluoro-2-oxoethyl)-1-ethyl-N-(4-fluoro-3-methylphenyl)-1H-pyrrole-3-carboxamide |
| 136 | 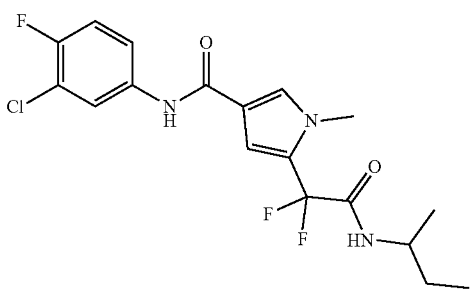 [SMILES: CCC(C)NC(=O)C(F)(F)c1cc(C(=O)Nc2ccc(F)c(Cl)c2)cn1C] | 5-(2-(sec-butylamino)-1,1-difluoro-2-oxoethyl)-N-(3-chloro-4-fluorophenyl)-1-methyl-1H-pyrrole-3-carboxamide |
| 137 | 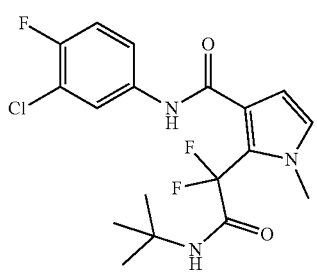 [SMILES: Cn1ccc(C(=O)Nc2ccc(F)c(Cl)c2)c1C(F)(F)C(=O)NC(C)(C)C] | 2-(2-(tert-butylamino)-1,1-difluoro-2-oxoethyl)-N-(3-chloro-4-fluorophenyl)-1-methyl-1H-pyrrole-3-carboxamide |
| 138 | 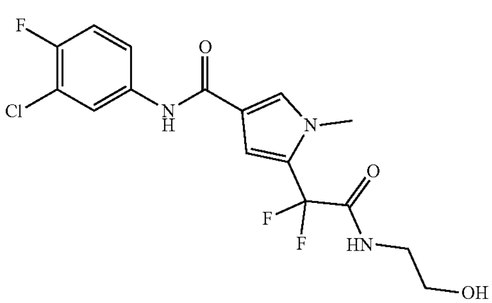 [SMILES: Cn1cc(C(=O)Nc2ccc(F)c(Cl)c2)cc1C(F)(F)C(=O)NCCO] | N-(3-chloro-4-fluorophenyl)-5-(1,1-difluoro-2-((2-hydroxyethyl)amino)-2-oxoethyl)-1-methyl-1H-pyrrole-3-carboxamide |

TABLE 1-continued

Exemplary compounds.

| Example | Structure | Chemical Name |
|---|---|---|
| 139 | 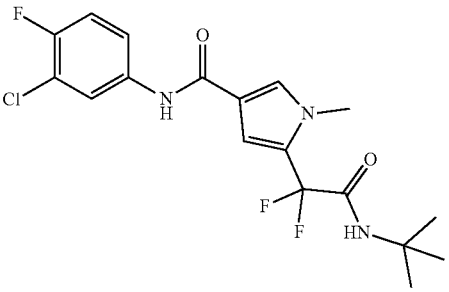 [SMILES: Cn1cc(C(=O)Nc2ccc(F)c(Cl)c2)cc1C(F)(F)C(=O)NC(C)(C)C] | 5-(2-(tert-butylamino)-1,1-difluoro-2-oxoethyl)-N-(3-chloro-4-fluorophenyl)-1-methyl-1H-pyrrole-3-carboxamide |
| 140 | 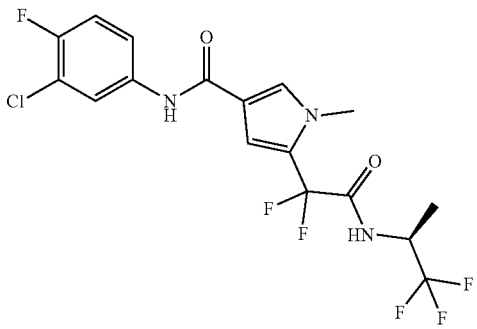 [SMILES: C[C@H](NC(=O)C(F)(F)c1cc(C(=O)Nc2ccc(F)c(Cl)c2)cn1C)C(F)(F)F] | (S)-N-(3-chloro-4-fluorophenyl)-5-(1,1-difluoro-2-oxo-2-((1,1,1-trifluoropropan-2-yl)amino)ethyl)-1-methyl-1H-pyrrole-3-carboxamide |
| 141 | 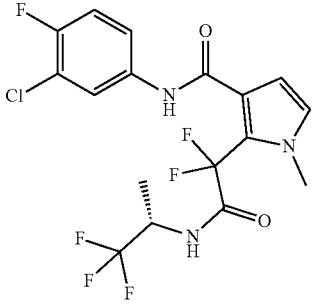 [SMILES: C[C@H](NC(=O)C(F)(F)c1c(C(=O)Nc2ccc(F)c(Cl)c2)ccn1C)C(F)(F)F] | (S)-N-(3-chloro-4-fluorophenyl)-2-((1,1-difluoro-2-oxo-2-((1,1,1-trifluoropropan-2-yl)amino)ethyl)-1-methyl-1H-pyrrole-3-carboxamide |
| 142 | 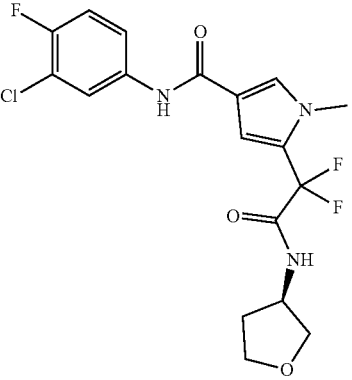 [SMILES: Cn1cc(C(=O)Nc2ccc(F)c(Cl)c2)cc1C(F)(F)C(=O)N[C@@H]1CCOC1] | (R)-N-(3-chloro-4-fluorophenyl)-5-(1,1-difluoro-2-oxo-2-((tetrahydrofuran-3-yl)amino)ethyl)-1-methyl-1H-pyrrole-3-carboxamide |

TABLE 1-continued

Exemplary compounds.

| Example | Structure | Chemical Name |
|---|---|---|
| 143 | 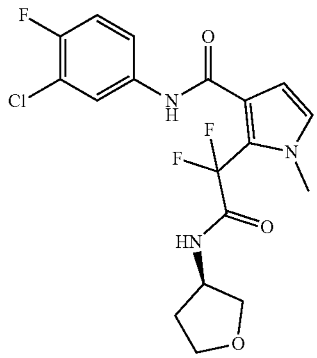 [SMILES: Cn1ccc(C(=O)Nc2ccc(F)c(Cl)c2)c1C(F)(F)C(=O)N[C@@H]1CCOC1] | (R)-N-(3-chloro-4-fluorophenyl)-2-(1,1-difluoro-2-oxo-2-((tetrahydrofuran-3-yl)amino)ethyl)-1-methyl-1H-pyrrole-3-carboxamide |
| 144 | 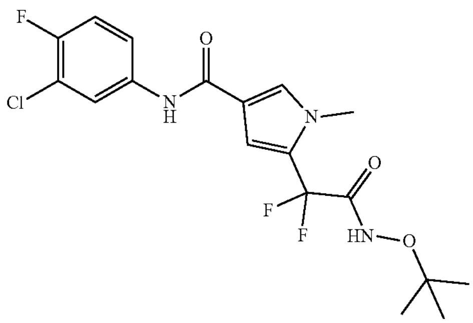 [SMILES: Cn1cc(C(=O)Nc2ccc(F)c(Cl)c2)cc1C(F)(F)C(=O)NOC(C)(C)C] | 5-(2-(tert-butoxyamino)-1,1-difluoro-2-oxoethyl)-N-(3-chloro-4-fluorophenyl)-1-methyl-1H-pyrrole-3-carboxamide |
| 145 | 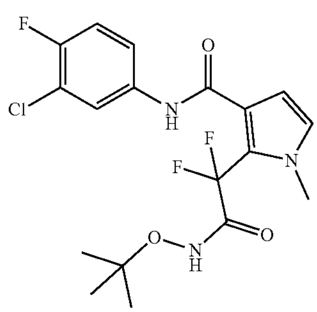 [SMILES: Cn1ccc(C(=O)Nc2ccc(F)c(Cl)c2)c1C(F)(F)C(=O)NOC(C)(C)C] | 2-(2-(tert-butoxyamino)-1,1-difluoro-2-oxoethyl)-N-(3-chloro-4-fluorophenyl)-1-methyl-1H-pyrrole-3-carboxamide |
| 146 | 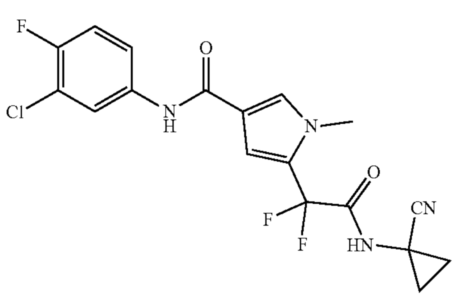 [SMILES: Cn1cc(C(=O)Nc2ccc(F)c(Cl)c2)cc1C(F)(F)C(=O)NC1(C#N)CC1] | N-(3-chloro-4-fluorophenyl)-5-(2-((1-cyanocyclopropyl)amino)-1,1-difluoro-2-oxoethyl)-1-methyl-1H-pyrrole-3-carboxamide |
| 147 | 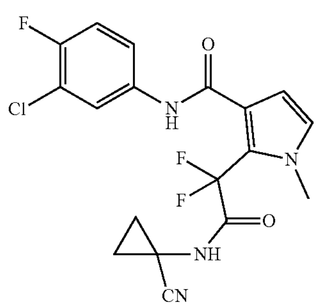 [SMILES: Cn1ccc(C(=O)Nc2ccc(F)c(Cl)c2)c1C(F)(F)C(=O)NC1(C#N)CC1] | N-(3-chloro-4-fluorophenyl)-2-(2-((1-cyanocyclopropyl)amino)-1,1-difluoro-2-oxoethyl)-1-methyl-1H-pyrrole-3-carboxamide |

TABLE 1-continued

Exemplary compounds.

| Example | Structure | Chemical Name |
|---|---|---|
| 148 | 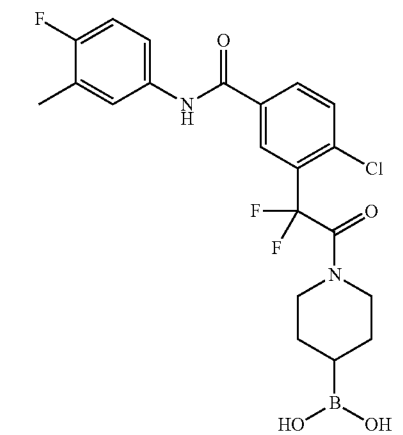 [SMILES: Cc1cc(NC(=O)c2ccc(Cl)c(C(F)(F)C(=O)N3CCC(B(O)O)CC3)c2)ccc1F] | (1-(2-(2-chloro-5-((4-fluoro-3-methylphenyl)carbamoyl)phenyl)-2,2-difluoroacetyl)piperidin-4-yl)boronic acid |
| 149 | 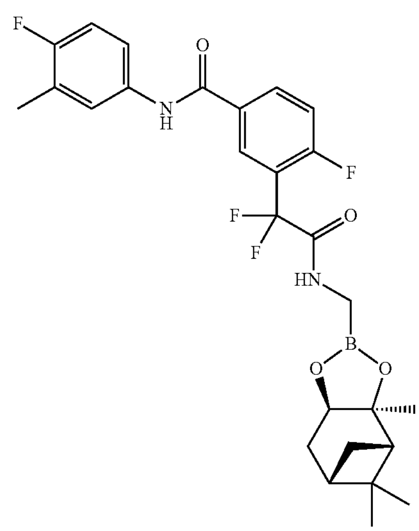 [SMILES: Cc1cc(NC(=O)c2ccc(F)c(C(F)(F)C(=O)NCB3O[C@@H]4C[C@@H]5C[C@@H](C5(C)C)[C@]4(C)O3)c2)ccc1F] | 3-(1,1-difluoro-2-oxo-2-((((3aS,4S,6S,7aR)-3a,5,5-trimethylhexahydro-4,6-methanobenzo[d][1,3,2]dioxaborol-2-yl)methyl)amino)ethyl)-4-fluoro-N-(4-fluoro-3-methylphenyl)benzamide |
| 150 | 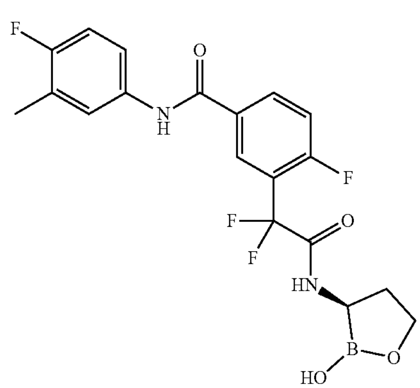 [SMILES: Cc1cc(NC(=O)c2ccc(F)c(C(F)(F)C(=O)N[C@H]3CCOB3O)c2)ccc1F] | (R)-3-(1,1-difluoro-2-((2-hydroxy-1,2-oxaborolan-3-yl)amino)-2-oxoethyl)-4-fluoro-N-(4-fluoro-3-methylphenyl)benzamide |

TABLE 1-continued

Exemplary compounds.

| Example | Structure | Chemical Name |
|---|---|---|
| 151 | 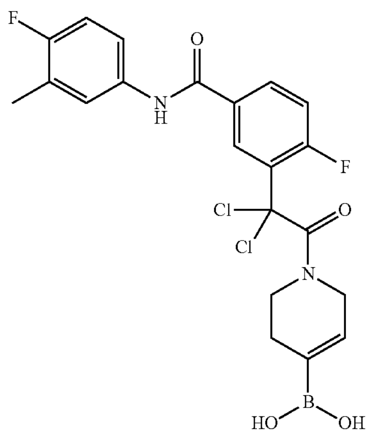 [SMILES: Cc1cc(NC(=O)c2ccc(F)c(C(Cl)(Cl)C(=O)N3CC=C(B(O)O)CC3)c2)ccc1F] | (1-(2,2-dichloro-2-(2-fluoro-5-((4-fluoro-3-methylphenyl)carbamoyl)phenyl)acetyl)-1,2,3,6-tetrahydropyridin-4-yl)boronic acid |
| 152 | 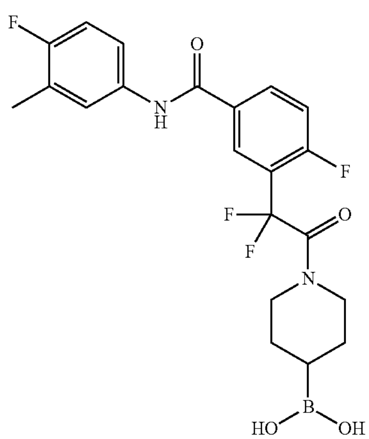 [SMILES: Cc1cc(NC(=O)c2ccc(F)c(C(F)(F)C(=O)N3CCC(B(O)O)CC3)c2)ccc1F] | (1-(2,2-difluoro-2-(2-fluoro-5-((4-fluoro-3-methylphenyl)carbamoyl)phenyl)acetyl)piperidin-4-yl)boronic acid |
| 153 | 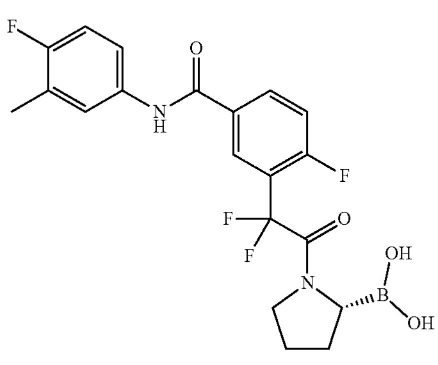 [SMILES: Cc1cc(NC(=O)c2ccc(F)c(C(F)(F)C(=O)N3CCC[C@H]3B(O)O)c2)ccc1F] | (R)-(1-(2,2-difluoro-2-(2-fluoro-5-((4-fluoro-3-methylphenyl)carbamoyl)phenyl)acetyl)pyrrolidin-2-yl)boronic acid |

TABLE 1-continued

Exemplary compounds.

| Example | Structure | Chemical Name |
|---|---|---|
| 154 | 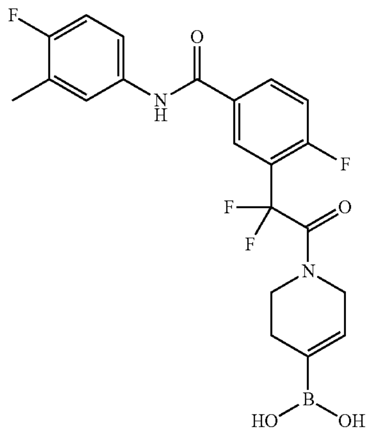 [SMILES: Cc1cc(NC(=O)c2ccc(F)c(C(F)(F)C(=O)N3CC=C(B(O)O)CC3)c2)ccc1F] | (1-(2,2-difluoro-2-(2-fluoro-5-((4-fluoro-3-methylphenyl)carbamoyl)phenyl)acetyl)-1,2,3,6-tetrahydropyridin-4-yl)boronic acid |
| 155 | 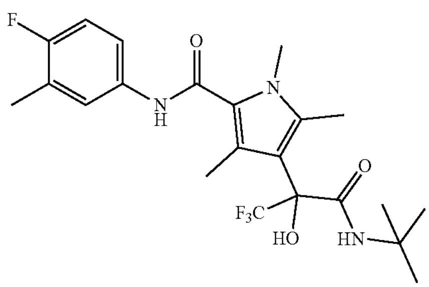 [SMILES: Cc1cc(NC(=O)c2c(C)c(C(O)(C(=O)NC(C)(C)C)C(F)(F)F)c(C)n2C)ccc1F] | 4-(3-(tert-butylamino)-1,1,1-trifluoro-2-hydroxy-3-oxopropan-2-yl)-N-(4-fluoro-3-methylphenyl)-1,3,5-trimethyl-1H-pyrrole-2-carboxamide |
| 156 | 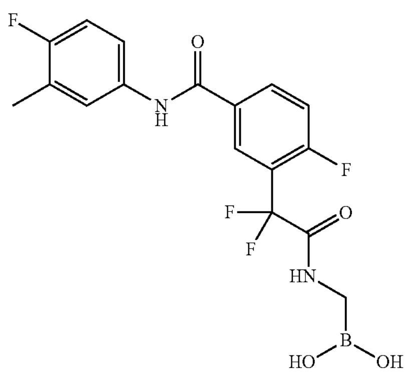 [SMILES: Cc1cc(NC(=O)c2ccc(F)c(C(F)(F)C(=O)NCB(O)O)c2)ccc1F] | ((2,2-difluoro-2-(2-fluoro-5-((4-fluoro-3-methylphenyl)carbamoyl)phenyl)acetamido)methyl)boronic acid |
| 157 | 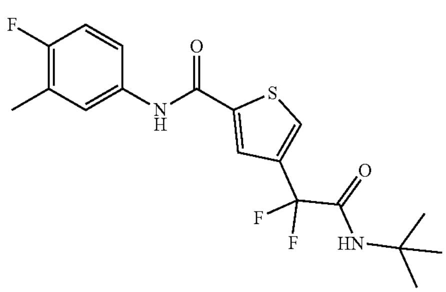 [SMILES: Cc1cc(NC(=O)c2cc(C(F)(F)C(=O)NC(C)(C)C)cs2)ccc1F] | 4-(2-(tert-butylamino)-1,1-difluoro-2-oxoethyl)-N-(4-fluoro-3-methylphenyl)thiophene-2-carboxamide |

TABLE 1-continued

Exemplary compounds.

| Example | Structure | Chemical Name |
|---|---|---|
| 158 | 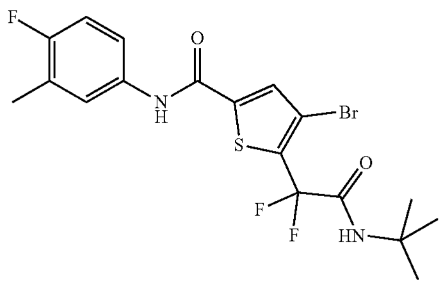 [SMILES: Cc1cc(NC(=O)c2cc(Br)c(C(F)(F)C(=O)NC(C)(C)C)s2)ccc1F] | 4-bromo-5-(2-(tert-butylamino)-1,1-difluoro-2-oxoethyl)-N-(4-fluoro-3-methylphenyl)thiophene-2-carboxamide |
| 159 | 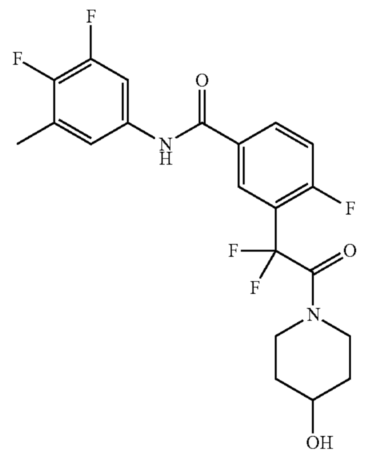 [SMILES: Cc1cc(NC(=O)c2ccc(F)c(C(F)(F)C(=O)N3CCC(O)CC3)c2)cc(F)c1F] | 3-(1,1-difluoro-2-(4-hydroxypiperidin-1-yl)-2-oxoethyl)-N-(3,4-difluoro-5-methylphenyl)-4-fluorobenzamide |
| 160 | 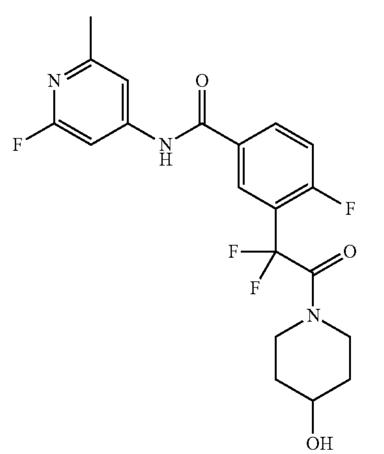 [SMILES: Cc1cc(NC(=O)c2ccc(F)c(C(F)(F)C(=O)N3CCC(O)CC3)c2)cc(F)n1] | 3-(1,1-difluoro-2-(4-hydroxypiperidin-1-yl)-2-oxoethyl)-4-fluoro-N-(2-fluoro-6-methylpyridin-4-yl)benzamide |
| 161 | 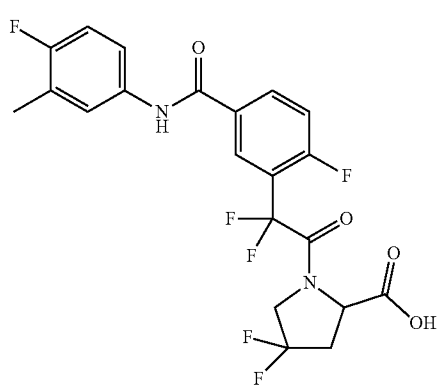 [SMILES: Cc1cc(NC(=O)c2ccc(F)c(C(F)(F)C(=O)N3CC(F)(F)CC3C(=O)O)c2)ccc1F] | 1-(2,2-difluoro-2-(2-fluoro-5-((4-fluoro-3-methylphenyl)carbamoyl)phenyl)acetyl)-4,4-difluoropyrrolidine-2-carboxylic acid |

TABLE 1-continued

Exemplary compounds.

| Example | Structure | Chemical Name |
|---|---|---|
| 162 | 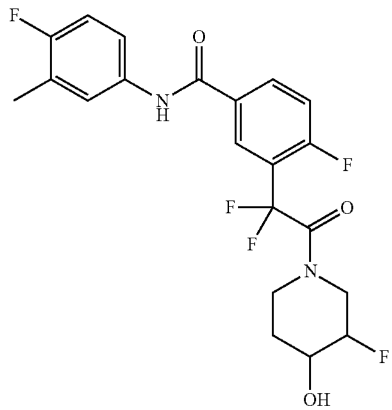 [SMILES: Cc1cc(NC(=O)c2ccc(F)c(C(F)(F)C(=O)N3CCC(O)C(F)C3)c2)ccc1F] | 3-(1,1-difluoro-2-(3-fluoro-4-hydroxypiperidin-1-yl)-2-oxoethyl)-4-fluoro-N-(4-fluoro-3-methylphenyl)benzamide |
| 163 | 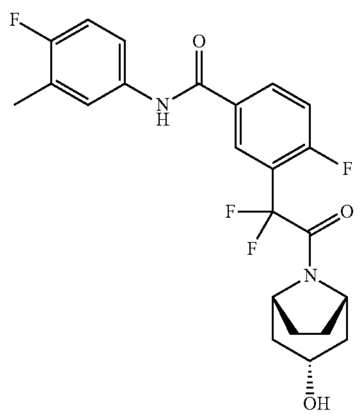 [SMILES: Cc1cc(NC(=O)c2ccc(F)c(C(F)(F)C(=O)N3[C@@H]4CC[C@H]3C[C@H](O)C4)c2)ccc1F] | 3-(1,1-difluoro-2-((1R,3s,5S)-3-hydroxy-8-azabicyclo[3.2.1]octan-8-yl)-2-oxoethyl)-4-fluoro-N-(4-fluoro-3-methylphenyl)benzamide |
| 164 | 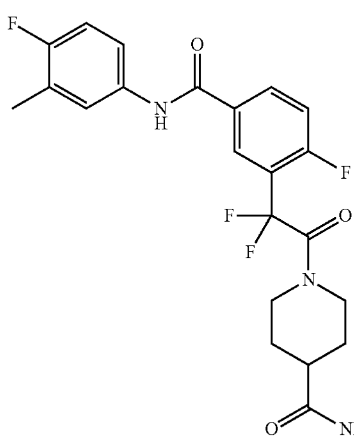 | 1-(2,2-difluoro-2-(2-fluoro-5-((4-fluoro-3-methylphenyl)carbamoyl)phenyl)acetyl)piperidine-4-carboxamide |
| 165 | 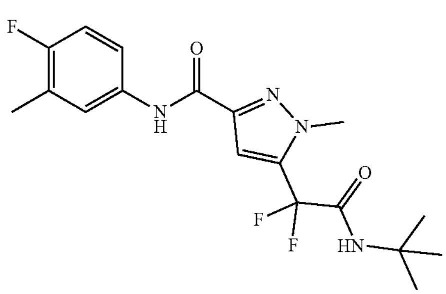 [SMILES: Cc1cc(NC(=O)c2cc(C(F)(F)C(=O)NC(C)(C)C)n(C)n2)ccc1F] | 5-(2-(tert-butylamino)-1,1-difluoro-2-oxoethyl)-N-(4-fluoro-3-methylphenyl)-1-methyl-1H-pyrazole-3-carboxamide |

TABLE 1-continued

Exemplary compounds.

| Example | Structure | Chemical Name |
|---|---|---|
| 166 | 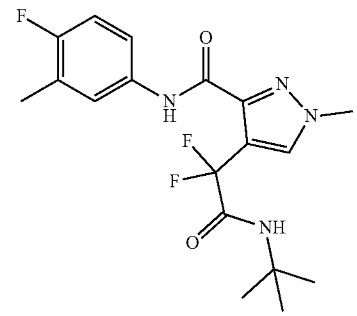 [SMILES: Cc1cc(NC(=O)c2nn(C)cc2C(F)(F)C(=O)NC(C)(C)C)ccc1F] | 4-(2-(tert-butylamino)-1,1-difluoro-2-oxoethyl)-N-(4-fluoro-3-methylphenyl)-1-methyl-1H-pyrazole-3-carboxamide |
| 167 | 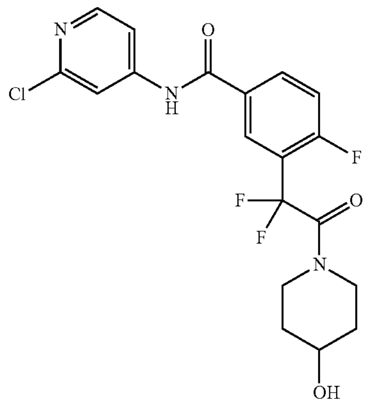 [SMILES: O=C(Nc1ccnc(Cl)c1)c1ccc(F)c(C(F)(F)C(=O)N2CCC(O)CC2)c1] | N-(2-chloropyridin-4-yl)-3-(1,1-difluoro-2-(4-hydroxypiperidin-1-yl)-2-oxoethyl)-4-fluorobenzamide |
| 168 | 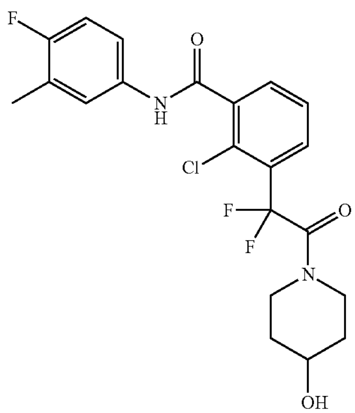 [SMILES: Cc1cc(NC(=O)c2cccc(C(F)(F)C(=O)N3CCC(O)CC3)c2Cl)ccc1F] | 2-chloro-3-(1,1-difluoro-2-(4-hydroxypiperidin-1-yl)-2-oxoethyl)-N-(4-fluoro-3-methylphenyl)benzamide |
| 169 | 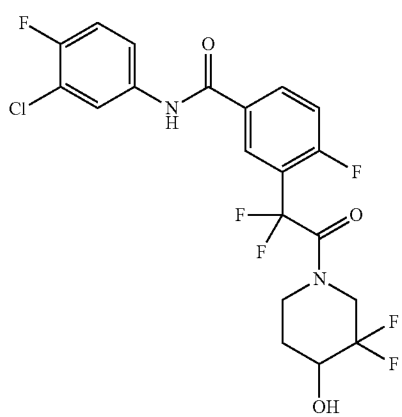 [SMILES: O=C(Nc1ccc(F)c(Cl)c1)c1ccc(F)c(C(F)(F)C(=O)N2CCC(O)C(F)(F)C2)c1] | N-(3-chloro-4-fluorophenyl)-3-(2-(3,3-difluoro-4-hydroxypiperidin-1-yl)-1,1-difluoro-2-oxoethyl)-4-fluorobenzamide |

TABLE 1-continued

Exemplary compounds.

| Example | Structure | Chemical Name |
|---|---|---|
| 170 | 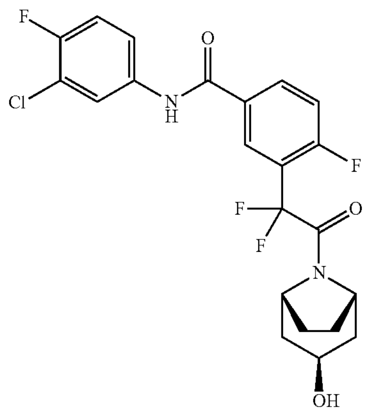 [SMILES: O=C(Nc1ccc(F)c(Cl)c1)c1ccc(F)c(C(F)(F)C(=O)N2[C@@H]3CC[C@H]2C[C@@H](O)C3)c1] | N-(3-chloro-4-fluorophenyl)-3-(1,1-difluoro-2-((1R,3r,5S)-3-hydroxy-8-azabicyclo[3.2.1]octan-8-yl)-2-oxoethyl)-4-fluorobenzamide |
| 171 | 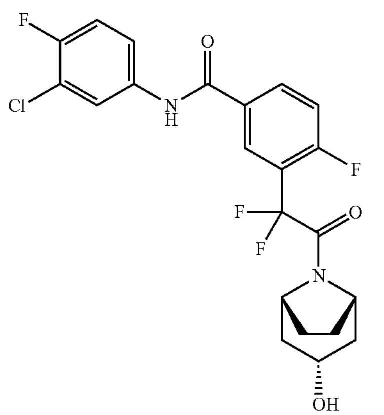 [SMILES: O=C(Nc1ccc(F)c(Cl)c1)c1ccc(F)c(C(F)(F)C(=O)N2[C@@H]3CC[C@H]2C[C@H](O)C3)c1] | N-(3-chloro-4-fluorophenyl)-3-(1,1-difluoro-2-((1R,3s,5S)-3-hydroxy-8-azabicyclo[3.2.1]octan-8-yl)-2-oxoethyl)-4-fluorobenzamide |
| 172 | 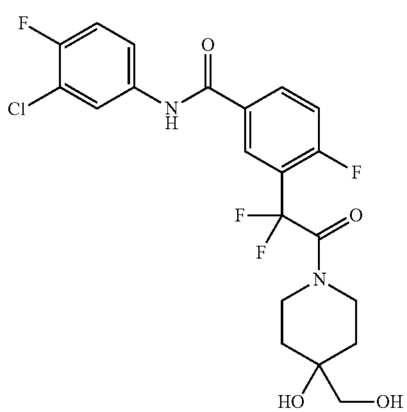 [SMILES: O=C(Nc1ccc(F)c(Cl)c1)c1ccc(F)c(C(F)(F)C(=O)N2CCC(O)(CO)CC2)c1] | N-(3-chloro-4-fluorophenyl)-3-(1,1-difluoro-2-(4-hydroxy-4-(hydroxymethyl)piperidin-1-yl)-2-oxoethyl)-4-fluorobenzamide |

TABLE 1-continued

Exemplary compounds.

| Example | Structure | Chemical Name |
|---|---|---|
| 173 | 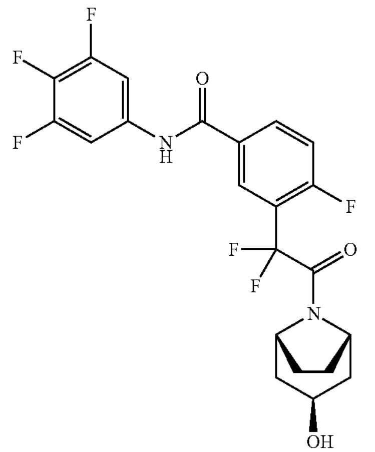 [SMILES: O=C(Nc1cc(F)c(F)c(F)c1)c1ccc(F)c(C(F)(F)C(=O)N2[C@@H]3CC[C@H]2C[C@@H](O)C3)c1] | 3-(1,1-difluoro-2-((1R,3r,5S)-3-hydroxy-8-azabicyclo[3.2.1]octan-8-yl)-2-oxoethyl)-4-fluoro-N-(3,4,5-trifluorophenyl)benzamide |
| 174 | 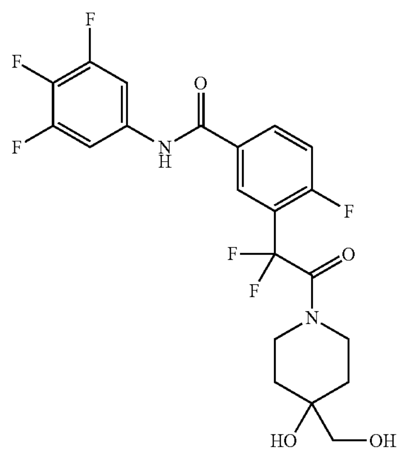 [SMILES: O=C(Nc1cc(F)c(F)c(F)c1)c1ccc(F)c(C(F)(F)C(=O)N2CCC(O)(CO)CC2)c1] | 3-(1,1-difluoro-2-(4-hydroxy-4-(hydroxymethyl)piperidin-1-yl)-2-oxoethyl)-4-fluoro-N-(3,4,5-trifluorophenyl)benzamide |
| 175 | 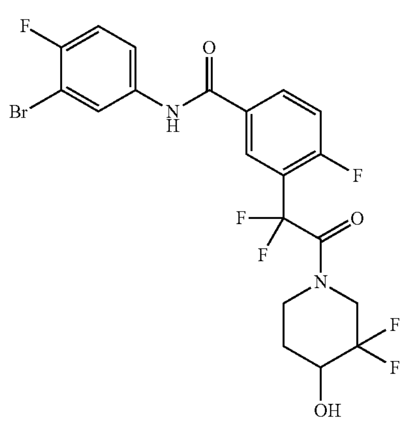 | N-(3-bromo-4-fluorophenyl)-3-(2-(3,3-difluoro-4-hydroxypiperidin-1-yl)-1,1-difluoro-2-oxoethyl)-4-fluorobenzamide |

TABLE 1-continued

Exemplary compounds.

| Example | Structure | Chemical Name |
|---|---|---|
| 176 | 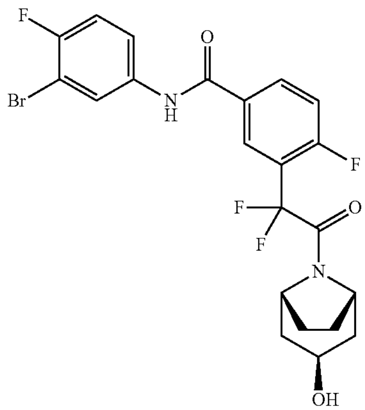 | N-(3-bromo-4-fluorophenyl)-3-(1,1-difluoro-2-((1R,3r,5S)-3-hydroxy-8-azabicyclo[3.2.1]octan-8-yl)-2-oxoethyl)-4-fluorobenzamide |
| 177 | 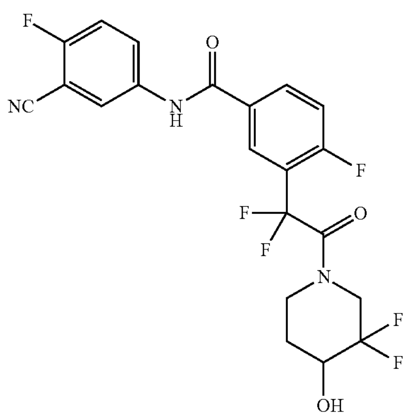 [SMILES: N#Cc1cc(NC(=O)c2ccc(F)c(C(F)(F)C(=O)N3CCC(O)C(F)(F)C3)c2)ccc1F] | N-(3-cyano-4-fluorophenyl)-3-(2-(3,3-difluoro-4-hydroxypiperidin-1-yl)-1,1-difluoro-2-oxoethyl)-4-fluorobenzamide |
| 178 | 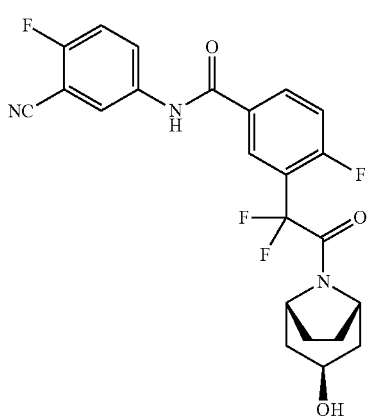 [SMILES: N#Cc1cc(NC(=O)c2ccc(F)c(C(F)(F)C(=O)N3[C@@H]4CC[C@H]3C[C@@H](O)C4)c2)ccc1F] | N-(3-cyano-4-fluorophenyl)-3-(1,1-difluoro-2-((1R,3r,5S)-3-hydroxy-8-azabicyclo[3.2.1]octan-8-yl)-2-oxoethyl)-4-fluorobenzamide |

TABLE 1-continued

Exemplary compounds.

| Example | Structure | Chemical Name |
|---|---|---|
| 179 | 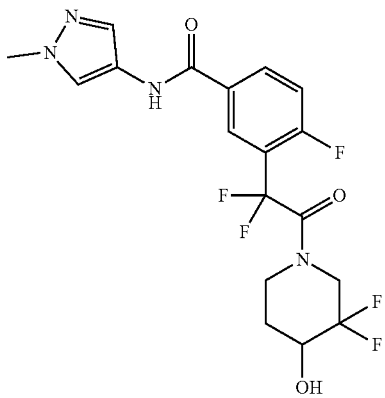 [SMILES: Cn1cc(NC(=O)c2ccc(F)c(C(F)(F)C(=O)N3CCC(O)C(F)(F)C3)c2)cn1] | 3-(2-(3,3-difluoro-4-hydroxypiperidin-1-yl)-1,1-difluoro-2-oxoethyl)-4-fluoro-N-(1-methyl-1H-pyrazol-4-yl)benzamide |
| 180 | 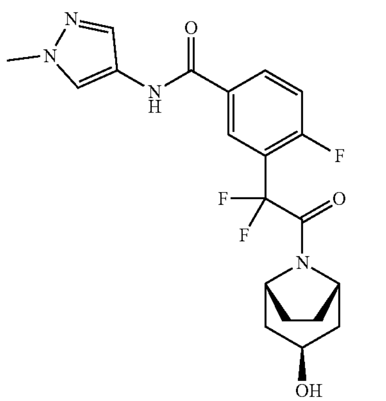 [SMILES: Cn1cc(NC(=O)c2ccc(F)c(C(F)(F)C(=O)N3[C@@H]4CC[C@H]3C[C@@H](O)C4)c2)cn1] | 3-(1,1-difluoro-2-((1R,3r,5S)-3-hydroxy-8-azabicyclo[3.2.1]octan-8-yl)-2-oxoethyl)-4-fluoro-N-(1-methyl-1H-pyrazol-4-yl)benzamide |
| 181 | 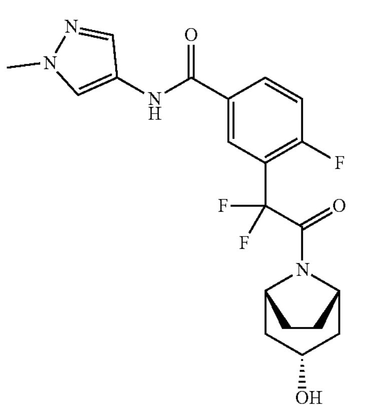 [SMILES: Cn1cc(NC(=O)c2ccc(F)c(C(F)(F)C(=O)N3[C@@H]4CC[C@H]3C[C@H](O)C4)c2)cn1] | 3-(1,1-difluoro-2-((1R,3s,5S)-3-hydroxy-8-azabicyclo[3.2.1]octan-8-yl)-2-oxoethyl)-4-fluoro-N-(1-methyl-1H-pyrazol-4-yl)benzamide |

TABLE 1-continued

Exemplary compounds.

| Example | Structure | Chemical Name |
|---|---|---|
| 182 | 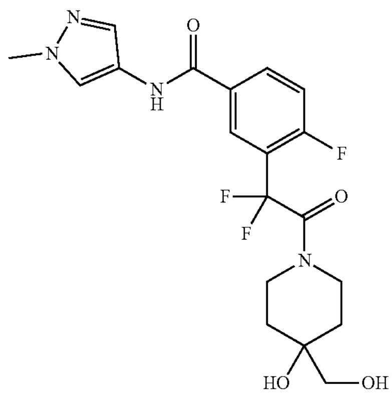 [SMILES: Cn1cc(NC(=O)c2ccc(F)c(C(F)(F)C(=O)N3CCC(O)(CO)CC3)c2)cn1] | 3-(1,1-difluoro-2-(4-hydroxy-4-(hydroxymethyl)piperidin-1-yl)-2-oxoethyl)-4-fluoro-N-(1-methyl-1H-pyrazol-4-yl)benzamide |
| 183 | 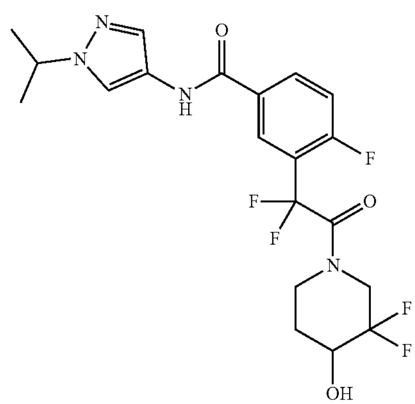 [SMILES: CC(C)n1cc(NC(=O)c2ccc(F)c(C(F)(F)C(=O)N3CCC(O)C(F)(F)C3)c2)cn1] | 3-(2-(3,3-difluoro-4-hydroxypiperidin-1-yl)-1,1-difluoro-2-oxoethyl)-4-fluoro-N-(1-isopropyl-1H-pyrazol-4-yl)benzamide |
| 184 | 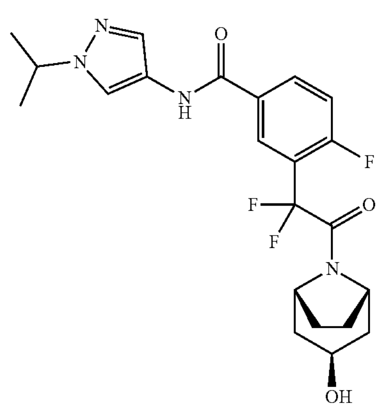 [SMILES: CC(C)n1cc(NC(=O)c2ccc(F)c(C(F)(F)C(=O)N3[C@@H]4CC[C@H]3C[C@@H](O)C4)c2)cn1] | 3-(1,1-difluoro-2-((1R,3r,5S)-3-hydroxy-8-azabicyclo[3.2.1]octan-8-yl)-2-oxoethyl)-4-fluoro-N-(1-isopropyl-1H-pyrazol-4-yl)benzamide |

TABLE 1-continued

Exemplary compounds.

| Example | Structure | Chemical Name |
|---|---|---|
| 185 | 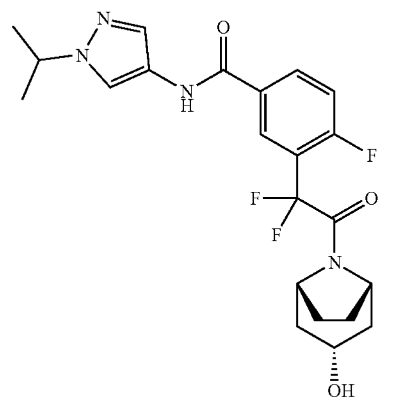 [SMILES: CC(C)n1cc(NC(=O)c2ccc(F)c(C(F)(F)C(=O)N3[C@@H]4CC[C@H]3C[C@H](O)C4)c2)cn1] | 3-(1,1-difluoro-2-((1R,3s,5S)-3-hydroxy-8-azabicyclo[3.2.1]octan-8-yl)-2-oxoethyl)-4-fluoro-N-(1-isopropyl-1H-pyrazol-4-yl)benzamide |
| 186 | 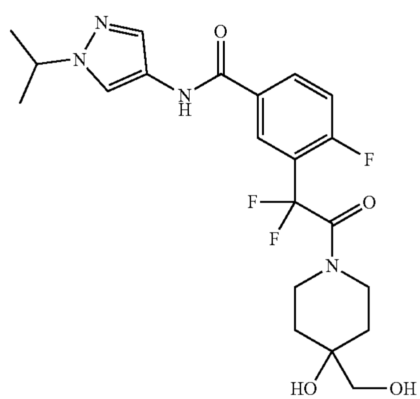 [SMILES: CC(C)n1cc(NC(=O)c2ccc(F)c(C(F)(F)C(=O)N3CCC(O)(CO)CC3)c2)cn1] | 3-(1,1-difluoro-2-(4-hydroxy-4-(hydroxymethyl)piperidin-1-yl)-2-oxoethyl)-4-fluoro-N-(1-isopropyl-1H-pyrazol-4-yl)benzamide |
| 187 | 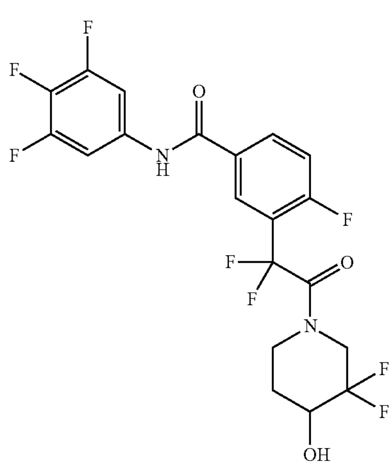 [SMILES: O=C(Nc1cc(F)c(F)c(F)c1)c1ccc(F)c(C(F)(F)C(=O)N2CCC(O)C(F)(F)C2)c1] | 3-(2-(3,3-difluoro-4-hydroxypiperidin-1-yl)-1,1-difluoro-2-oxoethyl)-4-fluoro-N-(3,4,5-trifluorophenyl)benzamide |

TABLE 1-continued

Exemplary compounds.

| Example | Structure | Chemical Name |
|---|---|---|
| 188 | 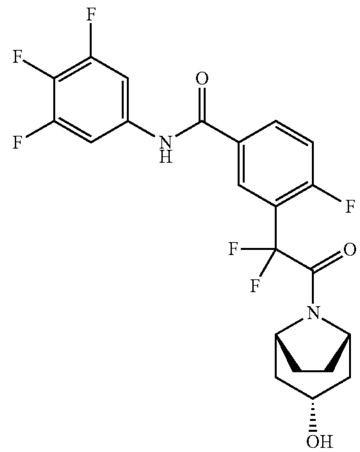 [SMILES: O=C(Nc1cc(F)c(F)c(F)c1)c1ccc(F)c(C(F)(F)C(=O)N2[C@@H]3CC[C@H]2C[C@H](O)C3)c1] | 3-(1,1-difluoro-2-((1R,3s,5S)-3-hydroxy-8-azabicyclo[3.2.1]octan-8-yl)-2-oxoethyl)-4-fluoro-N-(3,4,5-trifluorophenyl)benzamide |
| 189 | 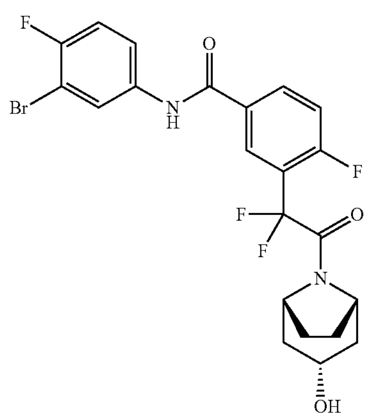 | N-(3-bromo-4-fluorophenyl)-3-(1,1-difluoro-2-((1R,3s,5S)-3-hydroxy-8-azabicyclo[3.2.1]octan-8-yl)-2-oxoethyl)-4-fluorobenzamide |
| 190 | 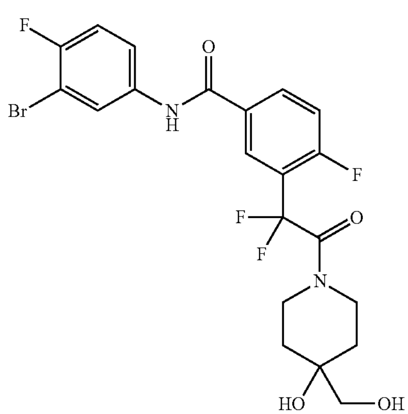 | N-(3-bromo-4-fluorophenyl)-3-(1,1-difluoro-2-(4-hydroxy-4-(hydroxymethyl)piperidin-1-yl)-2-oxoethyl)-4-fluorobenzamide |

TABLE 1-continued

Exemplary compounds.

| Example | Structure | Chemical Name |
|---|---|---|
| 191 | 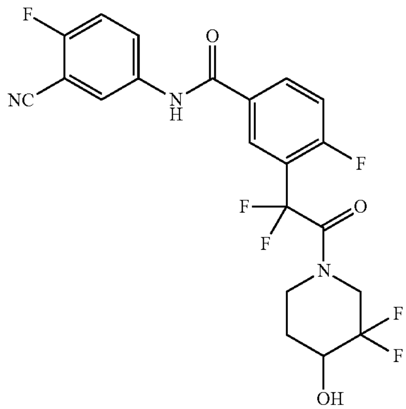 [SMILES: N#Cc1cc(NC(=O)c2ccc(F)c(C(F)(F)C(=O)N3CCC(O)C(F)(F)C3)c2)ccc1F] | N-(3-cyano-4-fluorophenyl)-3-(2-(3,3-difluoro-4-hydroxypiperidin-1-yl)-1,1-difluoro-2-oxoethyl)-4-fluorobenzamide |
| 192 | 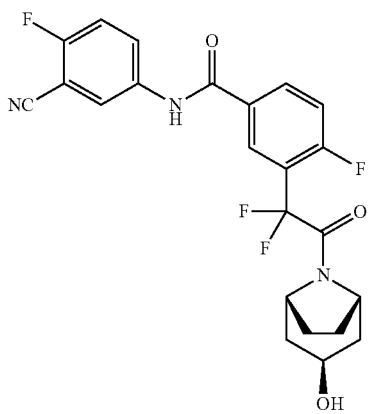 [SMILES: N#Cc1cc(NC(=O)c2ccc(F)c(C(F)(F)C(=O)N3[C@@H]4CC[C@H]3C[C@@H](O)C4)c2)ccc1F] | N-(3-cyano-4-fluorophenyl)-3-(1,1-difluoro-2-((1R,3r,5S)-3-hydroxy-8-azabicyclo[3.2.1]octan-8-yl)-2-oxoethyl)-4-fluorobenzamide |
| 193 | 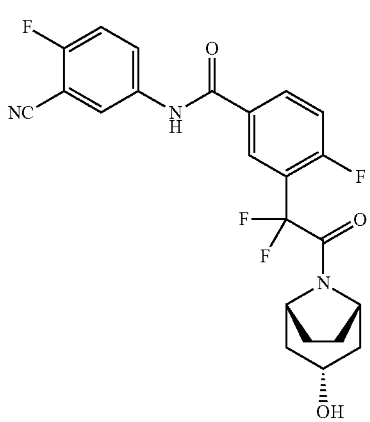 [SMILES: N#Cc1cc(NC(=O)c2ccc(F)c(C(F)(F)C(=O)N3[C@@H]4CC[C@H]3C[C@H](O)C4)c2)ccc1F] | N-(3-cyano-4-fluorophenyl)-3-(1,1-difluoro-2-((1R,3s,5S)-3-hydroxy-8-azabicyclo[3.2.1]octan-8-yl)-2-oxoethyl)-4-fluorobenzamide |

TABLE 1-continued

Exemplary compounds.

| Example | Structure | Chemical Name |
|---|---|---|
| 194 | 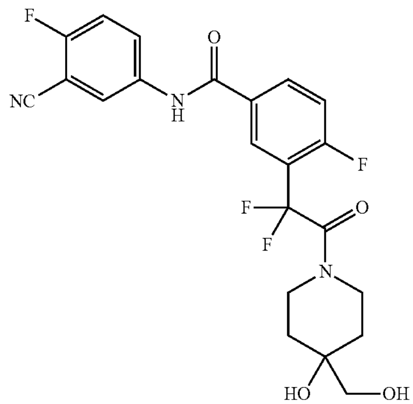 [SMILES: N#Cc1cc(NC(=O)c2ccc(F)c(C(F)(F)C(=O)N3CCC(O)(CO)CC3)c2)ccc1F] | N-(3-cyano-4-fluorophenyl)-3-(1,1-difluoro-2-(4-hydroxy-4-(hydroxymethyl)piperidin-1-yl)-2-oxoethyl)-4-fluorobenzamide |
| 195 | 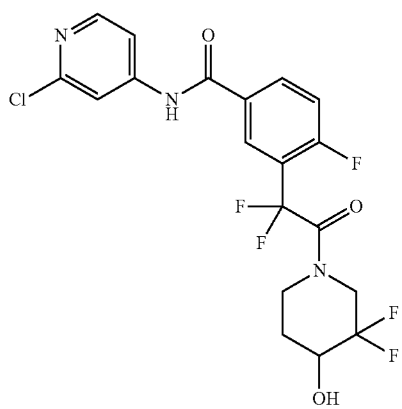 [SMILES: O=C(Nc1ccnc(Cl)c1)c1ccc(F)c(C(F)(F)C(=O)N2CCC(O)C(F)(F)C2)c1] | N-(2-chloropyridin-4-yl)-3-(2-(3,3-difluoro-4-hydroxypiperidin-1-yl)-1,1-difluoro-2-oxoethyl)-4-fluorobenzamide |
| 196 | 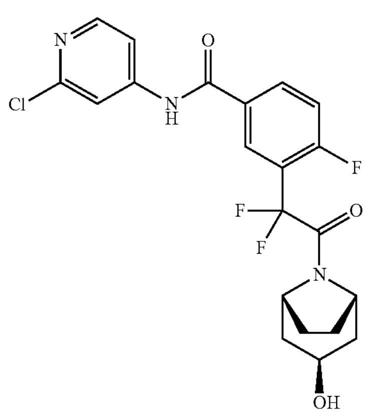 [SMILES: O=C(Nc1ccnc(Cl)c1)c1ccc(F)c(C(F)(F)C(=O)N2[C@@H]3CC[C@H]2C[C@@H](O)C3)c1] | N-(2-chloropyridin-4-yl)-3-(1,1-difluoro-2-((1R,3r,5S)-3-hydroxy-8-azabicyclo[3.2.1]octan-8-yl)-2-oxoethyl)-4-fluorobenzamide |

TABLE 1-continued

Exemplary compounds.

| Example | Structure | Chemical Name |
|---|---|---|
| 197 | 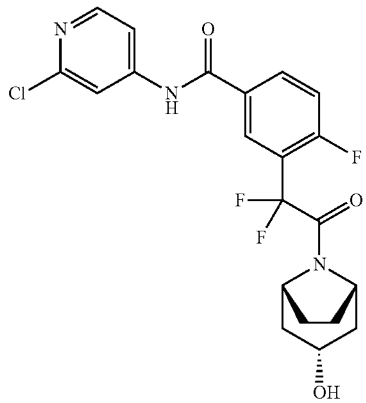 [SMILES: O=C(Nc1ccnc(Cl)c1)c1ccc(F)c(C(F)(F)C(=O)N2[C@@H]3CC[C@H]2C[C@H](O)C3)c1] | N-(2-chloropyridin-4-yl)-3-(1,1-difluoro-2-((1R,3s,5S)-3-hydroxy-8-azabicyclo[3.2.1]octan-8-yl)-2-oxoethyl)-4-fluorobenzamide |
| 198 | 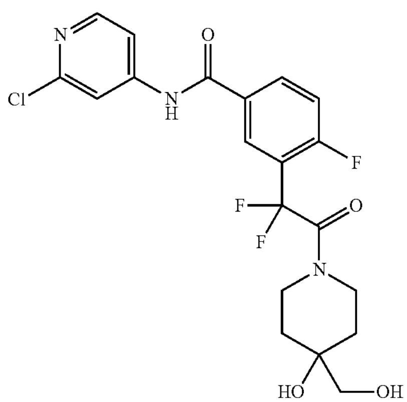 [SMILES: O=C(Nc1ccnc(Cl)c1)c1ccc(F)c(C(F)(F)C(=O)N2CCC(O)(CO)CC2)c1] | N-(2-chloropyridin-4-yl)-3-(1,1-difluoro-2-(4-hydroxy-4-(hydroxymethyl)piperidin-1-yl)-2-oxoethyl)-4-fluorobenzamide |
| 199 | 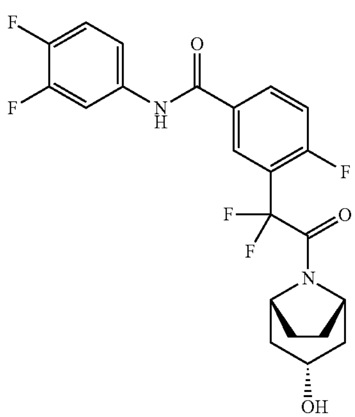 [SMILES: O=C(Nc1ccc(F)c(F)c1)c1ccc(F)c(C(F)(F)C(=O)N2[C@@H]3CC[C@H]2C[C@H](O)C3)c1] | 3-(1,1-difluoro-2-((1R,3s,5S)-3-hydroxy-8-azabicyclo[3.2.1]octan-8-yl)-2-oxoethyl)-N-(3,4-difluorophenyl)-4-fluorobenzamide |

TABLE 1-continued

Exemplary compounds.

| Example | Structure | Chemical Name |
|---|---|---|
| 200 | 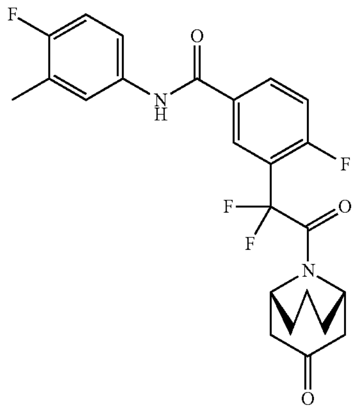 [SMILES: Cc1cc(NC(=O)c2ccc(F)c(C(F)(F)C(=O)N3[C@@H]4CCC[C@H]3CC(=O)C4)c2)ccc1F] | 3-(1,1-difluoro-2-oxo-2-((1R,5S)-3-oxo-9-azabicyclo[3.3.1]nonan-9-yl)ethyl)-4-fluoro-N-(4-fluoro-3-methylphenyl)benzamide |
| 201 | 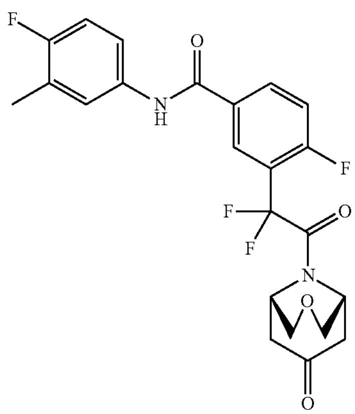 [SMILES: Cc1cc(NC(=O)c2ccc(F)c(C(F)(F)C(=O)N3[C@@H]4COC[C@H]3CC(=O)C4)c2)ccc1F] | 3-(1,1-difluoro-2-oxo-2-((1R,5S)-7-oxo-3-oxa-9-azabicyclo[3.3.1]nonan-9-yl)ethyl)-4-fluoro-N-(4-fluoro-3-methylphenyl)benzamide |
| 202 | 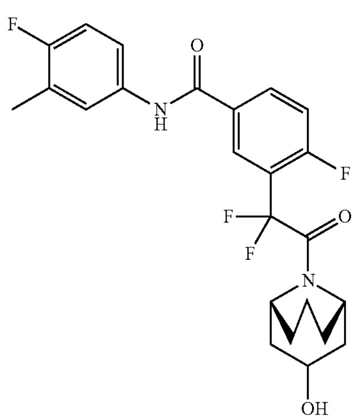 [SMILES: Cc1cc(NC(=O)c2ccc(F)c(C(F)(F)C(=O)N3[C@@H]4CCC[C@H]3CC(O)C4)c2)ccc1F] | 3-(1,1-difluoro-2-((1R,5S)-3-hydroxy-9-azabicyclo[3.3.1]nonan-9-yl)-2-oxoethyl)-4-fluoro-N-(4-fluoro-3-methylphenyl)benzamide |

TABLE 1-continued

Exemplary compounds.

| Example | Structure | Chemical Name |
|---|---|---|
| 203 | 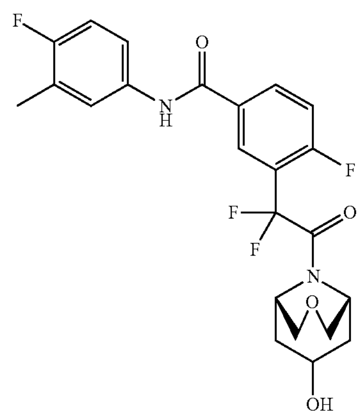 [SMILES: Cc1cc(NC(=O)c2ccc(F)c(C(F)(F)C(=O)N3[C@@H]4COC[C@H]3CC(O)C4)c2)ccc1F] | 3-(1,1-difluoro-2-((1R,5S)-7-hydroxy-3-oxa-9-azabicyclo[3.3.1]nonan-9-yl)-2-oxoethyl)-4-fluoro-N-(4-fluoro-3-methylphenyl)benzamide |
| 204 | 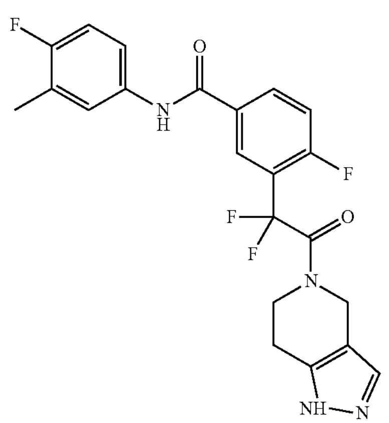 [SMILES: Cc1cc(NC(=O)c2ccc(F)c(C(F)(F)C(=O)N3CCc4[nH]ncc4C3)c2)ccc1F] | 3-(1,1-difluoro-2-oxo-2-(1,4,6,7-tetrahydro-5H-pyrazolo[4,3-c]pyridin-5-yl)ethyl)-4-fluoro-N-(4-fluoro-3-methylphenyl)benzamide |
| 205 | 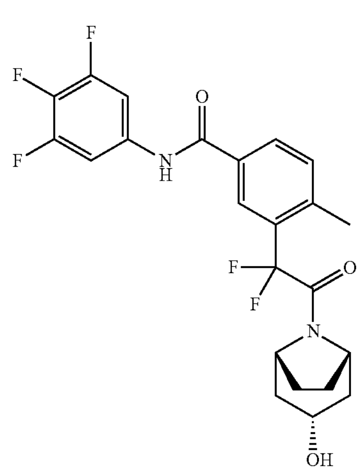 | 3-(1,1-difluoro-2-((1R,3s,5S)-3-hydroxy-8-azabicyclo[3.2.1]octan-8-yl)-2-oxoethyl)-4-methyl-N-(3,4,5-trifluorophenyl)benzamide |

TABLE 1-continued

Exemplary compounds.

| Example | Structure | Chemical Name |
|---|---|---|
| 206 | 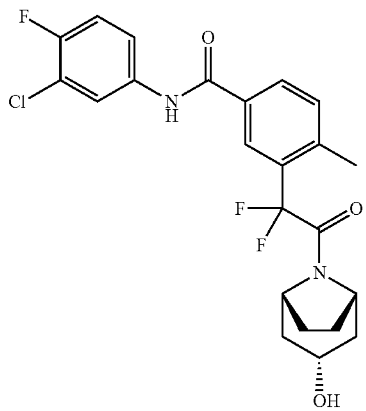 [SMILES: Cc1ccc(C(=O)Nc2ccc(F)c(Cl)c2)cc1C(F)(F)C(=O)N1[C@@H]2CC[C@H]1C[C@H](O)C2] | N-(3-chloro-4-fluorophenyl)-3-(1,1-difluoro-2-((1R,3s,5S)-3-hydroxy-8-azabicyclo[3.2.1]octan-8-yl)-2-oxoethyl)-4-methylbenzamide |
| 207 | 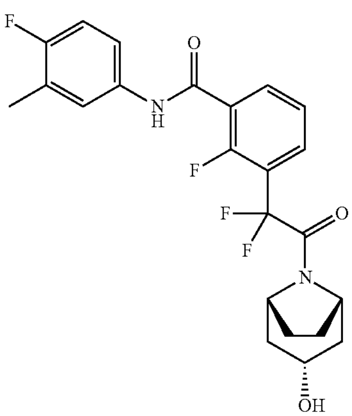 [SMILES: Cc1cc(NC(=O)c2cccc(C(F)(F)C(=O)N3[C@@H]4CC[C@H]3C[C@H](O)C4)c2F)ccc1F] | 3-(1,1-difluoro-2-((1R,3s,5S)-3-hydroxy-8-azabicyclo[3.2.1]octan-8-yl)-2-oxoethyl)-2-fluoro-N-(4-fluoro-3-methylphenyl)benzamide |
| 208 | 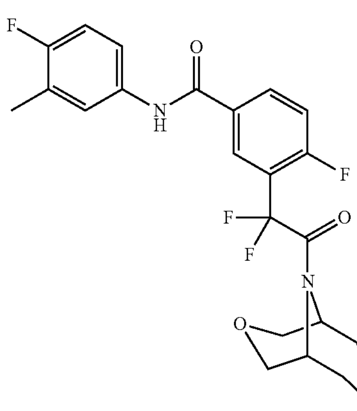 | 3-(2-((1R,5S)-3-oxa-7,9-diazabicyclo[3.3.1]nonan-9-yl)-1,1-difluoro-2-oxoethyl)-4-fluoro-N-(4-fluoro-3-methylphenyl)benzamide |

TABLE 1-continued

Exemplary compounds.

| Example | Structure | Chemical Name |
|---|---|---|
| 209 | 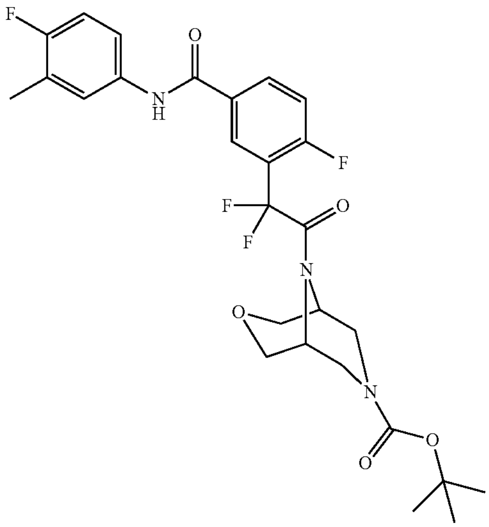 [SMILES: Cc1cc(NC(=O)c2ccc(F)c(C(F)(F)C(=O)N3C4COCC3CN(C(=O)OC(C)(C)C)C4)c2)ccc1F] | tert-butyl (1R,5S)-9-(2,2-difluoro-2-(2-fluoro-5-((4-fluoro-3-methylphenyl)carbamoyl)phenyl)acetyl)-3-oxa-7,9-diazabicyclo[3.3.1]nonane-7-carboxylate |
| 210 | 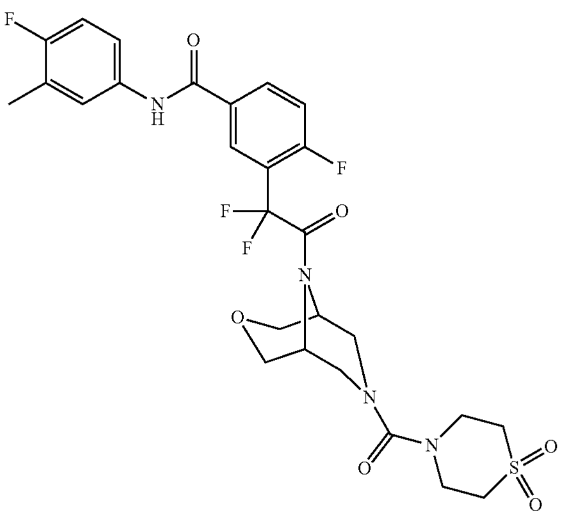 [SMILES: Cc1cc(NC(=O)c2ccc(F)c(C(F)(F)C(=O)N3C4COCC3CN(C(=O)N3CCS(=O)(=O)CC3)C4)c2)ccc1F] | 3-(2-((1R,5S)-7-(1,1-dioxidothiomorpholine-4-carbonyl)-3-oxa-7,9-diazabicyclo[3.3.1]nonan-9-yl)-1,1-difluoro-2-oxoethyl)-4-fluoro-N-(4-fluoro-3-methylphenyl)benzamide |
| 211 | 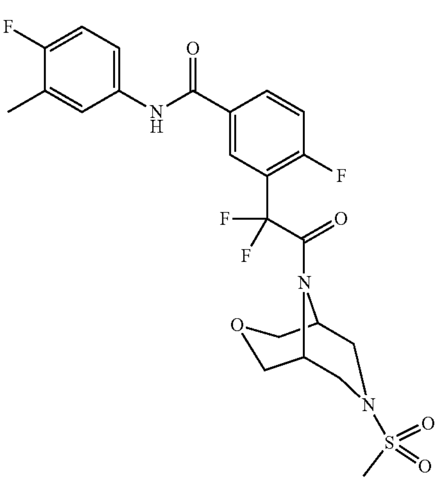 [SMILES: Cc1cc(NC(=O)c2ccc(F)c(C(F)(F)C(=O)N3C4COCC3CN(S(C)(=O)=O)C4)c2)ccc1F] | 3-(1,1-difluoro-2-((1R,5S)-7-(methylsulfonyl)-3-oxa-7,9-diazabicyclo[3.3.1]nonan-9-yl)-2-oxoethyl)-4-fluoro-N-(4-fluoro-3-methylphenyl)benzamide |

TABLE 1-continued

Exemplary compounds.

| Example | Structure | Chemical Name |
|---|---|---|
| 212 | 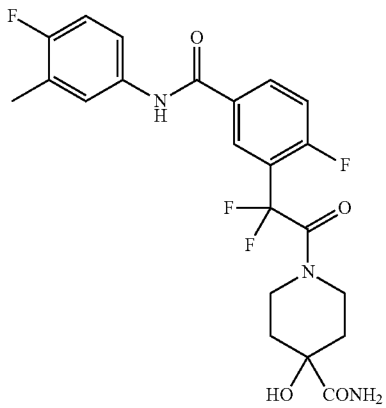 [SMILES: Cc1cc(NC(=O)c2ccc(F)c(C(F)(F)C(=O)N3CCC(O)(C(N)=O)CC3)c2)ccc1F] | 1-(2,2-difluoro-2-(2-fluoro-5-((4-fluoro-3-methylphenyl)carbamoyl)phenyl)acetyl)-4-hydroxypiperidine-4-carboxamide |
| 213 | 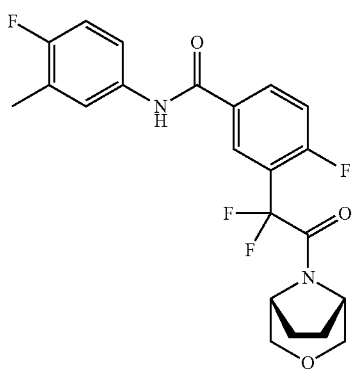 | 3-(2-((1R,5S)-3-oxa-8-azabicyclo[3.2.1]octan-8-yl)-1,1-difluoro-2-oxoethyl)-4-fluoro-N-(4-fluoro-3-methylphenyl)benzamide |
| 214 | 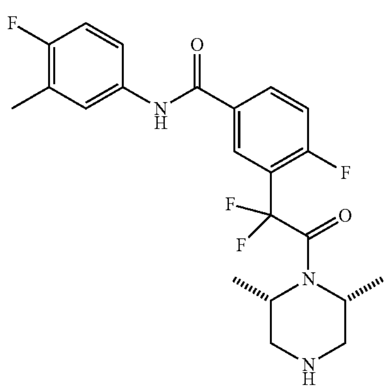 [SMILES: Cc1cc(NC(=O)c2ccc(F)c(C(F)(F)C(=O)N3[C@H](C)CNC[C@@H]3C)c2)ccc1F] | 3-(2-((2S,6R)-2,6-dimethylpiperazin-1-yl)-1,1-difluoro-2-oxoethyl)-4-fluoro-N-(4-fluoro-3-methylphenyl)benzamide |
| 215 | 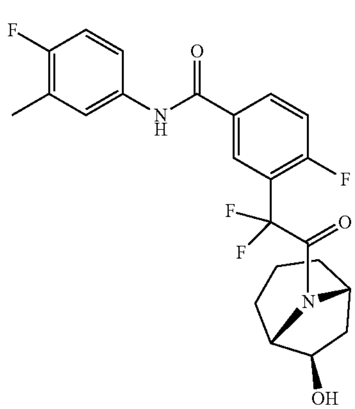 [SMILES: Cc1cc(NC(=O)c2ccc(F)c(C(F)(F)C(=O)N3[C@@H]4CCC[C@H]3[C@H](O)C4)c2)ccc1F] | 3-(1,1-difluoro-2-((1R,5S,6R)-6-hydroxy-8-azabicyclo[3.2.1]octan-8-yl)-2-oxoethyl)-4-fluoro-N-(4-fluoro-3-methylphenyl)benzamide |

TABLE 1-continued

Exemplary compounds.

| Example | Structure | Chemical Name |
|---|---|---|
| 216 | 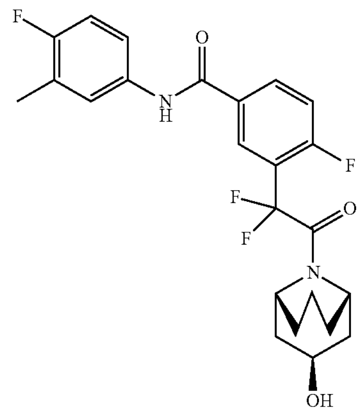 [SMILES: Cc1cc(NC(=O)c2ccc(F)c(C(F)(F)C(=O)N3[C@@H]4CCC[C@H]3C[C@@H](O)C4)c2)ccc1F] | 3-(1,1-difluoro-2-((1R,3r,5S)-3-hydroxy-9-azabicyclo[3.3.1]nonan-9-yl)-2-oxoethyl)-4-fluoro-N-(4-fluoro-3-methylphenyl)benzamide |
| 217 | 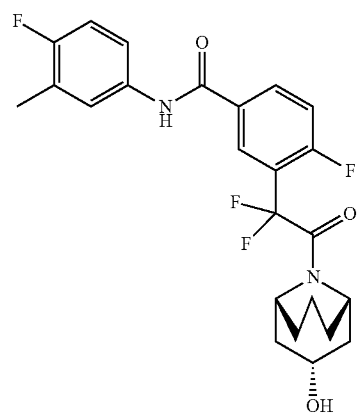 [SMILES: Cc1cc(NC(=O)c2ccc(F)c(C(F)(F)C(=O)N3[C@@H]4CCC[C@H]3C[C@H](O)C4)c2)ccc1F] | 3-(1,1-difluoro-2-((1R,3s,5S)-3-hydroxy-9-azabicyclo[3.3.1]nonan-9-yl)-2-oxoethyl)-4-fluoro-N-(4-fluoro-3-methylphenyl)benzamide |
| 218 | 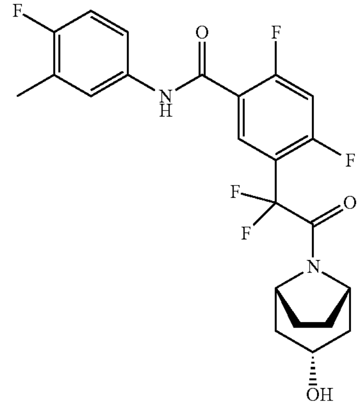 | 5-(1,1-difluoro-2-((1R,3s,5S)-3-hydroxy-8-azabicyclo[3.2.1]octan-8-yl)-2-oxoethyl)-2,4-difluoro-N-(4-fluoro-3-methylphenyl)benzamide |

TABLE 1-continued

Exemplary compounds.

| Example | Structure | Chemical Name |
|---|---|---|
| 219 | 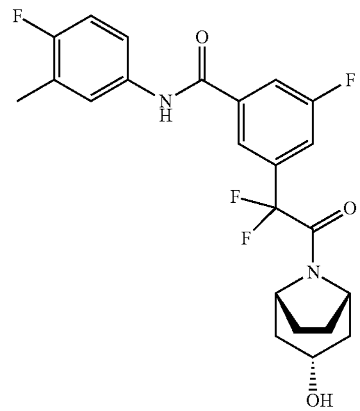 | 3-(1,1-difluoro-2-((1R,3s,5S)-3-hydroxy-8-azabicyclo[3.2.1]octan-8-yl)-2-oxoethyl)-5-fluoro-N-(4-fluoro-3-methylphenyl)benzamide |
| 220 | 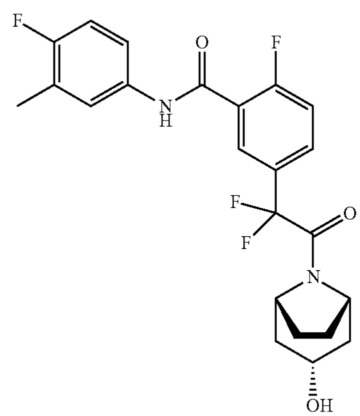 | 5-(1,1-difluoro-2-((1R,3s,5S)-3-hydroxy-8-azabicyclo[3.2.1]octan-8-yl)-2-oxoethyl)-2-fluoro-N-(4-fluoro-3-methylphenyl)benzamide |
| 221 | 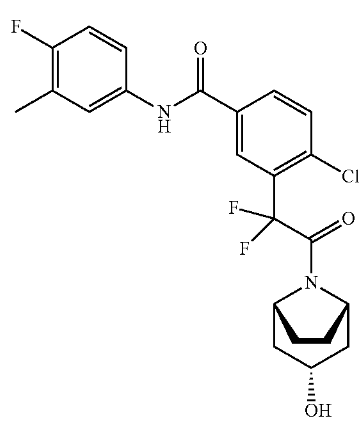 | 4-chloro-3-(1,1-difluoro-2-((1R,3s,5S)-3-hydroxy-8-azabicyclo[3.2.1]octan-8-yl)-2-oxoethyl)-N-(4-fluoro-3-methylphenyl)benzamide |

TABLE 1-continued

Exemplary compounds.

| Example | Structure | Chemical Name |
|---|---|---|
| 222 | 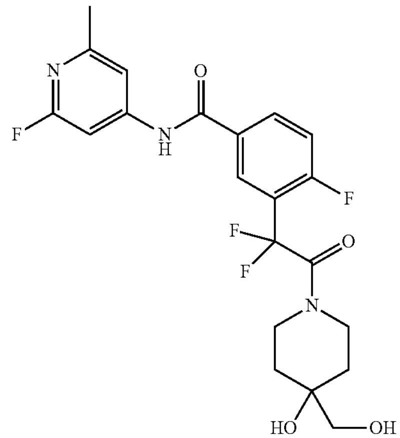 [SMILES: Cc1cc(NC(=O)c2ccc(F)c(C(F)(F)C(=O)N3CCC(O)(CO)CC3)c2)cc(F)n1] | 3-(1,1-difluoro-2-(4-hydroxy-4-(hydroxymethyl)piperidin-1-yl)-2-oxoethyl)-4-fluoro-N-(2-fluoro-6-methylpyridin-4-yl)benzamide |
| 223 | 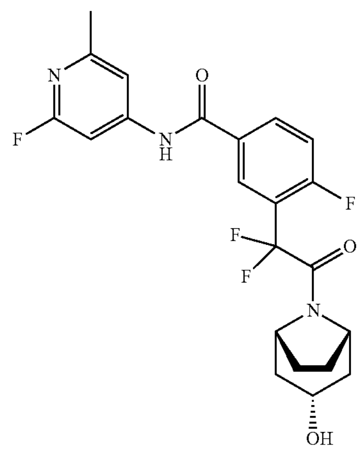 | 3-(1,1-difluoro-2-((1R,3s,5S)-3-hydroxy-8-azabicyclo[3.2.1]octan-8-yl)-2-oxoethyl)-4-fluoro-N-(2-fluoro-6-methylpyridin-4-yl)benzamide |
| 224 | 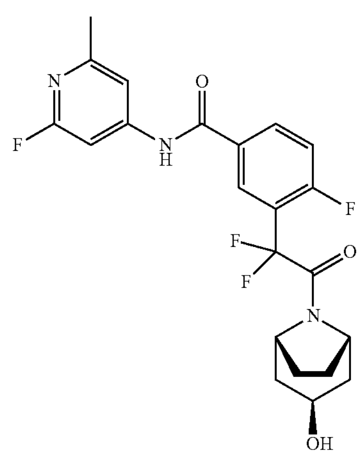 | 3-(1,1-difluoro-2-((1R,3r,5S)-3-hydroxy-8-azabicyclo[3.2.1]octan-8-yl)-2-oxoethyl)-4-fluoro-N-(2-fluoro-6-methylpyridin-4-yl)benzamide |

TABLE 1-continued

Exemplary compounds.

| Example | Structure | Chemical Name |
|---|---|---|
| 225 | 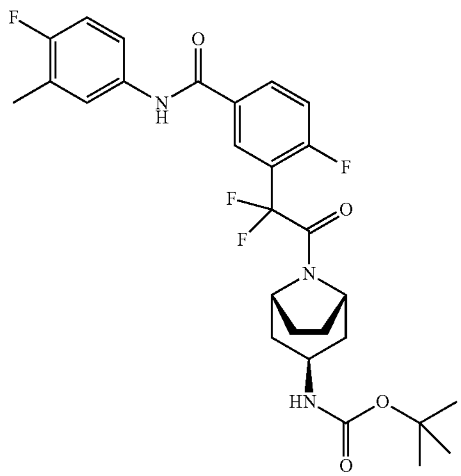 | tert-butyl ((1R,3r,5S)-8-(2,2-difluoro-2-(2-fluoro-5-((4-fluoro-3-methylphenyl)carbamoyl)phenyl)acetyl)-8-azabicyclo[3.2.1]octan-3-yl)carbamate |
| 226 | 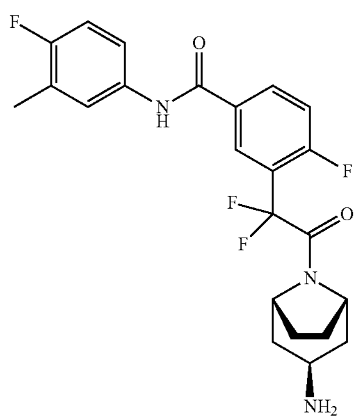 | 3-(2-((1R,3r,5S)-3-amino-8-azabicyclo[3.2.1]octan-8-yl)-1,1-difluoro-2-oxoethyl)-4-fluoro-N-(4-fluoro-3-methylphenyl)benzamide |
| 227 | 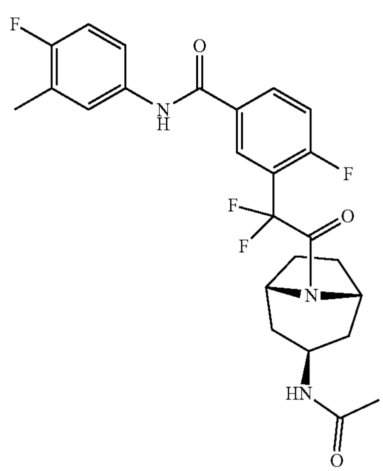 [SMILES: CC(=O)N[C@@H]1C[C@H]2CC[C@@H](C1)N2C(=O)C(F)(F)c1cc(C(=O)Nc2ccc(F)c(C)c2)ccc1F] | 3-(2-((1R,3s,5S)-3-acetamido-8-azabicyclo[3.2.1]octan-8-yl)-1,1-difluoro-2-oxoethyl)-4-fluoro-N-(4-fluoro-3-methylphenyl)benzamide |

TABLE 1-continued

Exemplary compounds.

| Example | Structure | Chemical Name |
|---|---|---|
| 228 | 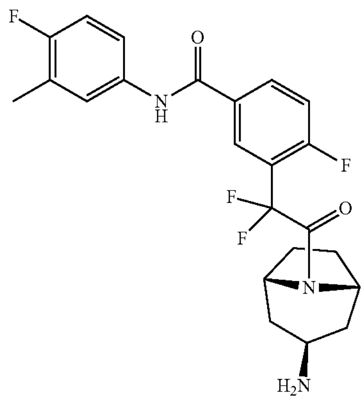 [SMILES: Cc1cc(NC(=O)c2ccc(F)c(C(F)(F)C(=O)N3[C@@H]4CC[C@H]3C[C@H](N)C4)c2)ccc1F] | 3-(2-((1R,3s,5S)-3-amino-8-azabicyclo[3.2.1]octan-8-yl)-1,1-difluoro-2-oxoethyl)-4-fluoro-N-(4-fluoro-3-methylphenyl)benzamide |
| 229 | 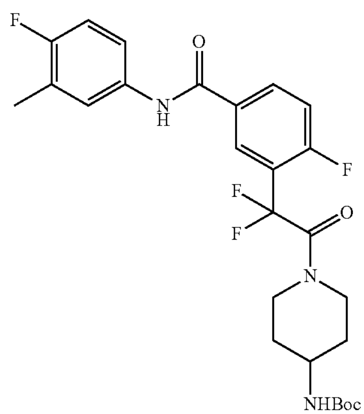 [SMILES: Cc1cc(NC(=O)c2ccc(F)c(C(F)(F)C(=O)N3CCC(NC(=O)OC(C)(C)C)CC3)c2)ccc1F] | tert-butyl (1-(2,2-difluoro-2-(2-fluoro-5-((4-fluoro-3-methylphenyl)carbamoyl)phenyl)acetyl)piperidin-4-yl)carbamate |
| 230 | 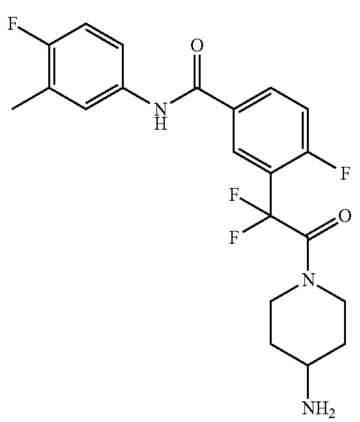 [SMILES: Cc1cc(NC(=O)c2ccc(F)c(C(F)(F)C(=O)N3CCC(N)CC3)c2)ccc1F] | 3-(2-(4-aminopiperidin-1-yl)-1,1-difluoro-2-oxoethyl)-4-fluoro-N-(4-fluoro-3-methylphenyl)benzamide |

TABLE 1-continued

Exemplary compounds.

| Example | Structure | Chemical Name |
|---|---|---|
| 231 | 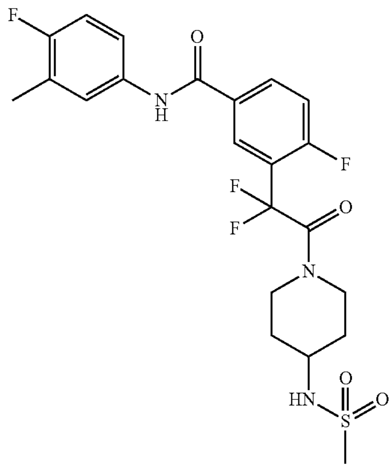 [SMILES: Cc1cc(NC(=O)c2ccc(F)c(C(F)(F)C(=O)N3CCC(NS(C)(=O)=O)CC3)c2)ccc1F] | 3-(1,1-difluoro-2-(4-(methylsulfonamido)piperidin-1-yl)-2-oxoethyl)-4-fluoro-N-(4-fluoro-3-methylphenyl)benzamide |
| 232 | 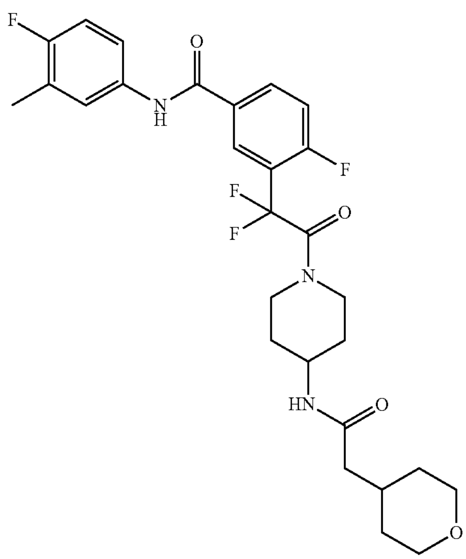 [SMILES: Cc1cc(NC(=O)c2ccc(F)c(C(F)(F)C(=O)N3CCC(NC(=O)CC4CCOCC4)CC3)c2)ccc1F] | 3-(1,1-difluoro-2-oxo-2-(4-(2-(tetrahydro-2H-pyran-4-yl)acetamido)piperidin-1-yl)ethyl)-4-fluoro-N-(4-fluoro-3-methylphenyl)benzamide |
| 233 | 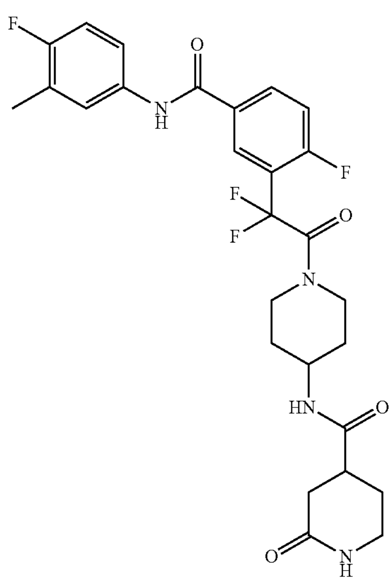 [SMILES: Cc1cc(NC(=O)c2ccc(F)c(C(F)(F)C(=O)N3CCC(NC(=O)C4CCNC(=O)C4)CC3)c2)ccc1F] | N-(1-(2,2-difluoro-2-(2-fluoro-5-((4-fluoro-3-methylphenyl)carbamoyl)phenyl)acetyl)piperidin-4-yl)-2-oxopiperidine-4-carboxamide |

TABLE 1-continued

Exemplary compounds.

| Example | Structure | Chemical Name |
|---|---|---|
| 234 | 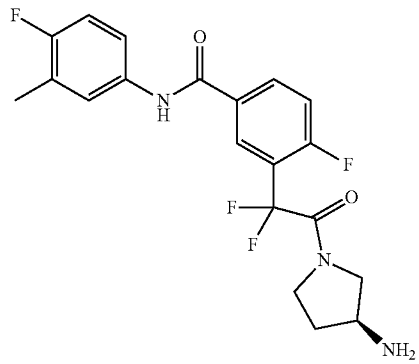 [SMILES: Cc1cc(NC(=O)c2ccc(F)c(C(F)(F)C(=O)N3CC[C@H](N)C3)c2)ccc1F] | (S)-3-(2-(3-aminopyrrolidin-1-yl)-1,1-difluoro-2-oxoethyl)-4-fluoro-N-(4-fluoro-3-methylphenyl)benzamide |
| 235 | 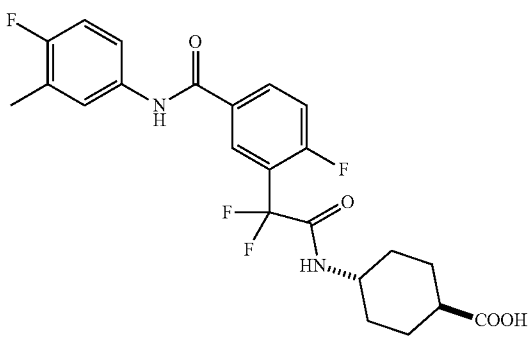 | (1r,4r)-4-(2,2-difluoro-2-(2-fluoro-5-((4-fluoro-3-methylphenyl)carbamoyl)phenyl)acetamido)cyclohexane-1-carboxylic acid |
| 236 | 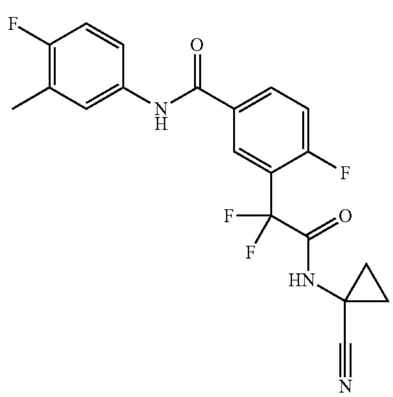 [SMILES: Cc1cc(NC(=O)c2ccc(F)c(C(F)(F)C(=O)NC3(C#N)CC3)c2)ccc1F] | 3-(2-((1-cyanocyclopropyl)amino)-1,1-difluoro-2-oxoethyl)-4-fluoro-N-(4-fluoro-3-methylphenyl)benzamide |
| 237 | 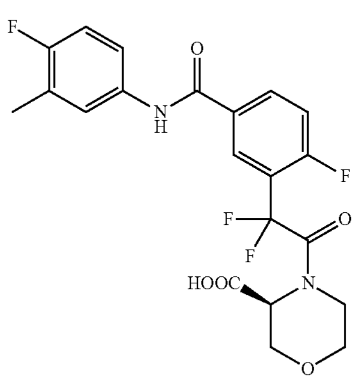 [SMILES: Cc1cc(NC(=O)c2ccc(F)c(C(F)(F)C(=O)N3CCOC[C@H]3C(=O)O)c2)ccc1F] | (S)-4-(2,2-difluoro-2-(2-fluoro-5-((4-fluoro-3-methylphenyl)carbamoyl)phenyl)acetyl)morpholine-3-carboxylic acid |

TABLE 1-continued

Exemplary compounds.

| Example | Structure | Chemical Name |
|---|---|---|
| 238 | 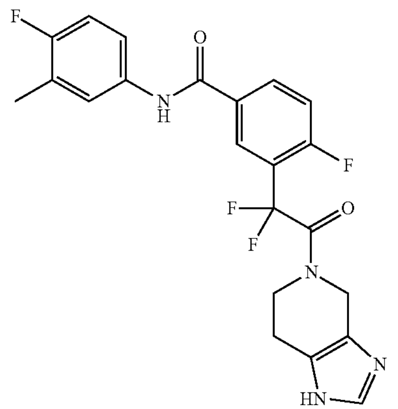 [SMILES: Cc1cc(NC(=O)c2ccc(F)c(C(F)(F)C(=O)N3CCc4[nH]cnc4C3)c2)ccc1F] | 3-(1,1-difluoro-2-oxo-2-(1,4,6,7-tetrahydro-5H-imidazo[4,5-c]pyridin-5-yl)ethyl)-4-fluoro-N-(4-fluoro-3-methylphenyl)benzamide |
| 239 | 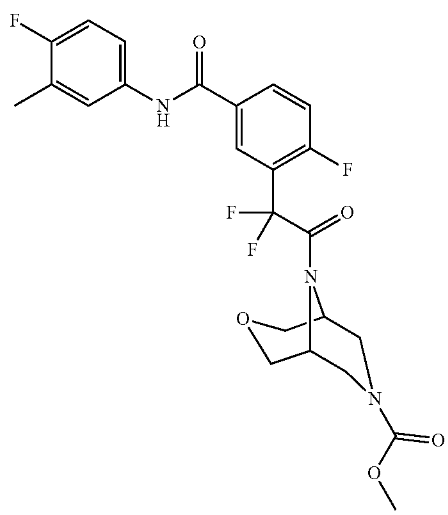 [SMILES: COC(=O)N1CC2COCC(C1)N2C(=O)C(F)(F)c1cc(C(=O)Nc2ccc(F)c(C)c2)ccc1F] | methyl (1R,5S)-9-(2,2-difluoro-2-(2-fluoro-5-((4-fluoro-3-methylphenyl)carbamoyl)phenyl)acetyl)-3-oxa-7,9-diazabicyclo[3.3.1]nonane-7-carboxylate |
| 240 | 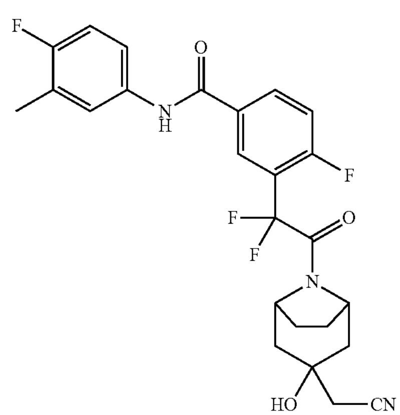 [SMILES: Cc1cc(NC(=O)c2ccc(F)c(C(F)(F)C(=O)N3C4CCC3CC(O)(CC#N)C4)c2)ccc1F] | 3-(2-((1R,5S)-3-(cyanomethyl)-3-hydroxy-8-azabicyclo[3.2.1]octan-8-yl)-1,1-difluoro-2-oxoethyl)-4-fluoro-N-(4-fluoro-3-methylphenyl)benzamide |

TABLE 1-continued

Exemplary compounds.

| Example | Structure | Chemical Name |
|---|---|---|
| 241 | 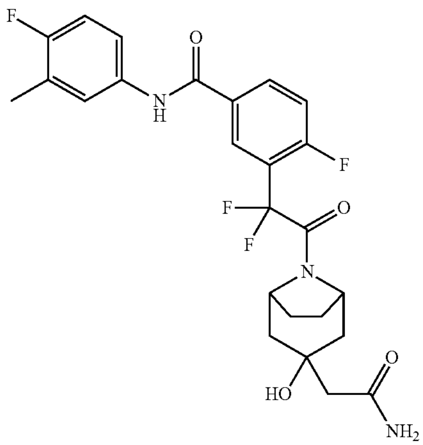 [SMILES: Cc1cc(NC(=O)c2ccc(F)c(C(F)(F)C(=O)N3C4CCC3CC(O)(CC(N)=O)C4)c2)ccc1F] | 3-(2-((1R,5S)-3-(2-amino-2-oxoethyl)-3-hydroxy-8-azabicyclo[3.2.1]octan-8-yl)-1,1-difluoro-2-oxoethyl)-4-fluoro-N-(4-fluoro-3-methylphenyl)benzamide |
| 242 | 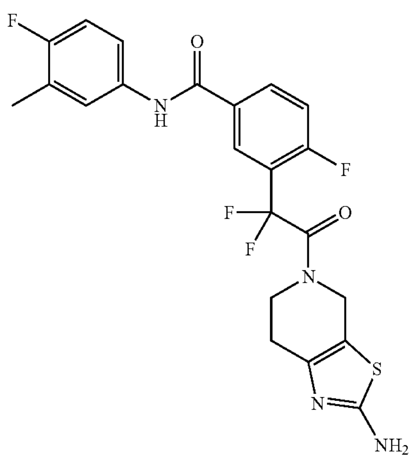 [SMILES: Cc1cc(NC(=O)c2ccc(F)c(C(F)(F)C(=O)N3CCc4nc(N)sc4C3)c2)ccc1F] | 3-(2-(2-amino-6,7-dihydrothiazolo[5,4-c]pyridin-5(4H)-yl)-1,1-difluoro-2-oxoethyl)-4-fluoro-N-(4-fluoro-3-methylphenyl)benzamide |
| 243 | 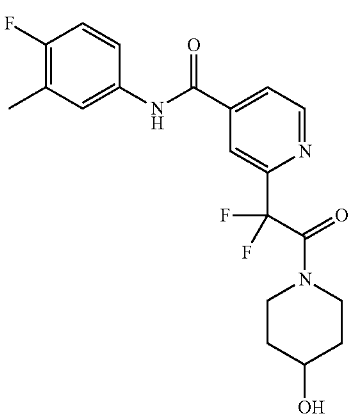 [SMILES: Cc1cc(NC(=O)c2ccnc(C(F)(F)C(=O)N3CCC(O)CC3)c2)ccc1F] | 2-(1,1-difluoro-2-(4-hydroxypiperidin-1-yl)-2-oxoethyl)-N-(4-fluoro-3-methylphenyl)isonicotinamide |

TABLE 1-continued

Exemplary compounds.

| Example | Structure | Chemical Name |
|---------|-----------|---------------|
| 244 | 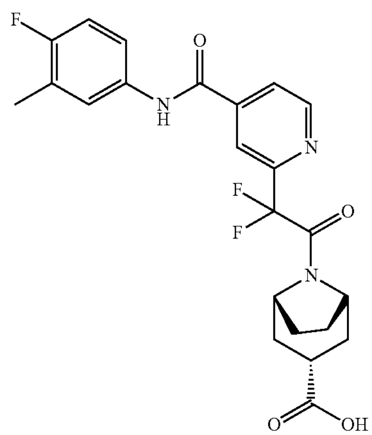 | (1R,3s,5S)-8-(2,2-difluoro-2-(4-((4-fluoro-3-methylphenyl)carbamoyl)pyridin-2-yl)acetyl)-8-azabicyclo[3.2.1]octane-3-carboxylic acid |
| 245 | 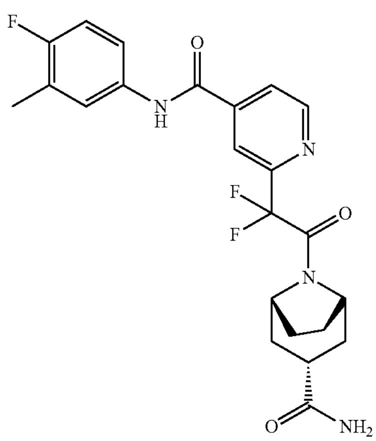 | (1R,3s,5S)-8-(2,2-difluoro-2-(4-((4-fluoro-3-methylphenyl)carbamoyl)pyridin-2-yl)acetyl)-8-azabicyclo[3.2.1]octane-3-carboxamide |
| 246 | 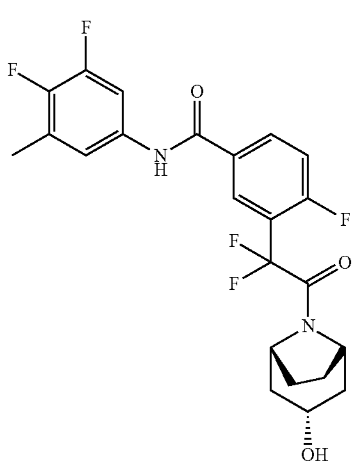 | 3-(1,1-difluoro-2-((1R,3s,5S)-3-hydroxy-8-azabicyclo[3.2.1]octan-8-yl)-2-oxoethyl)-N-(3,4-difluoro-5-methylphenyl)-4-fluorobenzamide |

TABLE 1-continued

Exemplary compounds.

| Example | Structure | Chemical Name |
|---|---|---|
| 247 | 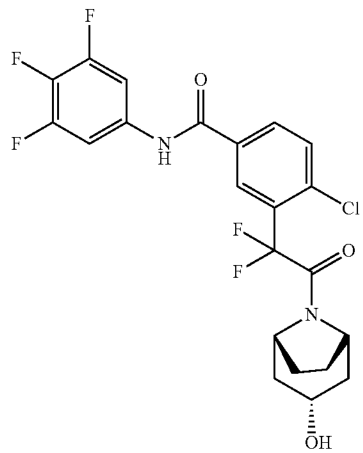 | 4-chloro-3-(1,1-difluoro-2-((1R,3s,5S)-3-hydroxy-8-azabicyclo[3.2.1]octan-8-yl)-2-oxoethyl)-N-(3,4,5-trifluorophenyl)benzamide |
| 248 | 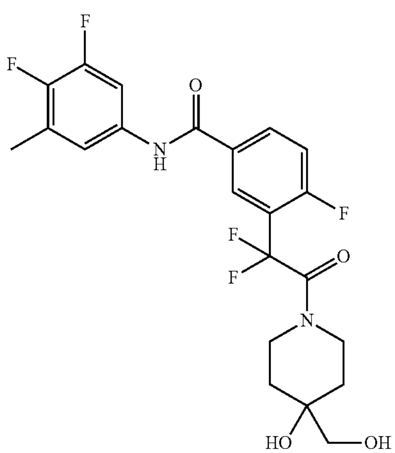 [SMILES: Cc1cc(NC(=O)c2ccc(F)c(C(F)(F)C(=O)N3CCC(O)(CO)CC3)c2)cc(F)c1F] | 3-(1,1-difluoro-2-(4-hydroxy-4-(hydroxymethyl)piperidin-1-yl)-2-oxoethyl)-N-(3,4-difluoro-5-methylphenyl)-4-fluorobenzamide |
| 249 | 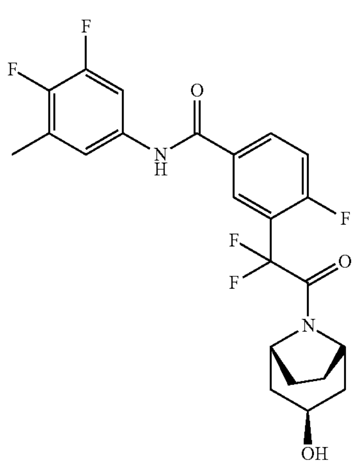 | 3-(1,1-difluoro-2-((1R,3r,5S)-3-hydroxy-8-azabicyclo[3.2.1]octan-8-yl)-2-oxoethyl)-N-(3,4-difluoro-5-methylphenyl)-4-fluorobenzamide |

TABLE 1-continued

Exemplary compounds.

| Example | Structure | Chemical Name |
|---|---|---|
| 250 | 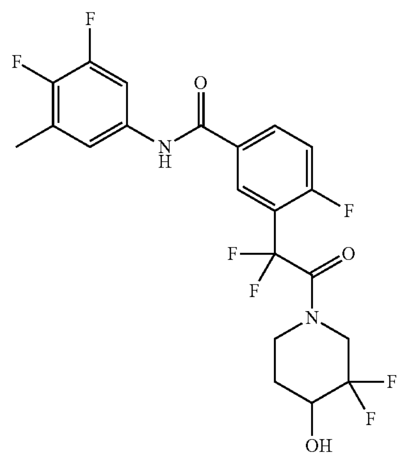 [SMILES: Cc1cc(NC(=O)c2ccc(F)c(C(F)(F)C(=O)N3CCC(O)C(F)(F)C3)c2)cc(F)c1F] | 3-(2-(3,3-difluoro-4-hydroxypiperidin-1-yl)-1,1-difluoro-2-oxoethyl)-N-(3,4-difluoro-5-methylphenyl)-4-fluorobenzamide |
| 251 | 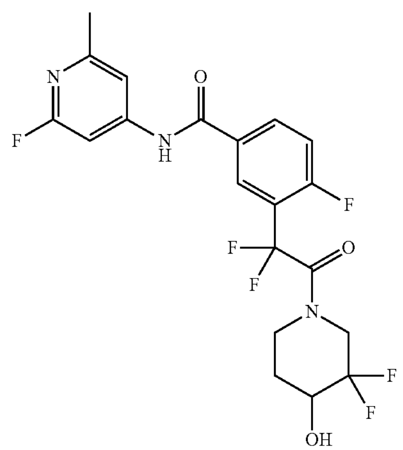 [SMILES: Cc1cc(NC(=O)c2ccc(F)c(C(F)(F)C(=O)N3CCC(O)C(F)(F)C3)c2)cc(F)n1] | 3-(2-(3,3-difluoro-4-hydroxypiperidin-1-yl)-1,1-difluoro-2-oxoethyl)-4-fluoro-N-(2-fluoro-6-methylpyridin-4-yl)benzamide |
| 252 | 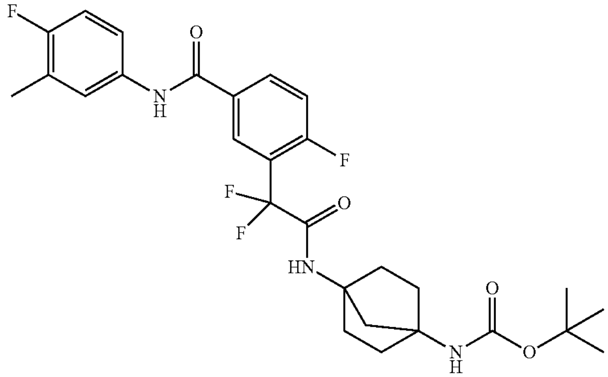 [SMILES: Cc1cc(NC(=O)c2ccc(F)c(C(F)(F)C(=O)NC34CCC(NC(=O)OC(C)(C)C)(CC3)C4)c2)ccc1F] | tert-butyl (4-(2,2-difluoro-2-(2-fluoro-5-((4-fluoro-3-methylphenyl)carbamoyl)phenyl)acetamido)bicyclo[2.2.1]heptan-1-yl)carbamate |

TABLE 1-continued

Exemplary compounds.

| Example | Structure | Chemical Name |
|---|---|---|
| 253 | 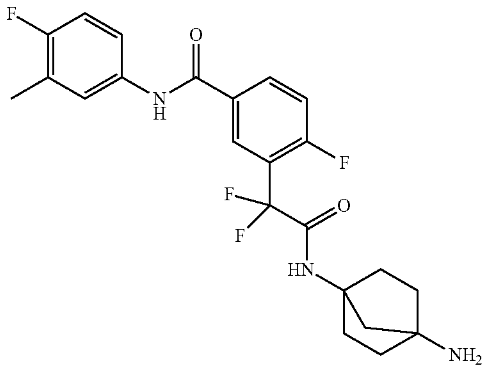 [SMILES: Cc1cc(NC(=O)c2ccc(F)c(C(F)(F)C(=O)NC34CCC(N)(CC3)C4)c2)ccc1F] | 3-(2-((4-aminobicyclo[2.2.1]heptan-1-yl)amino)-1,1-difluoro-2-oxoethyl)-4-fluoro-N-(4-fluoro-3-methylphenyl)benzamide |
| 254 | 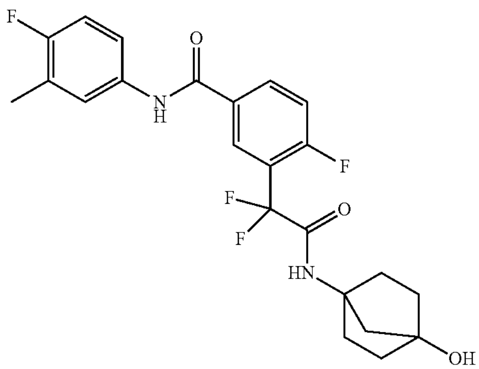 [SMILES: Cc1cc(NC(=O)c2ccc(F)c(C(F)(F)C(=O)NC34CCC(O)(CC3)C4)c2)ccc1F] | 3-(1,1-difluoro-2-((4-hydroxybicyclo[2.2.1]heptan-1-yl)amino)-2-oxoethyl)-4-fluoro-N-(4-fluoro-3-methylphenyl)benzamide |
| 255 | 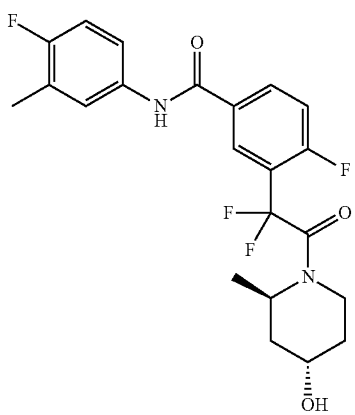 [SMILES: Cc1cc(NC(=O)c2ccc(F)c(C(F)(F)C(=O)N3CC[C@H](O)C[C@H]3C)c2)ccc1F] | 3-(1,1-difluoro-2-((2R,4S)-4-hydroxy-2-methylpiperidin-1-yl)-2-oxoethyl)-N-(4-fluoro-3-methylphenyl)benzamide |
| 256 | 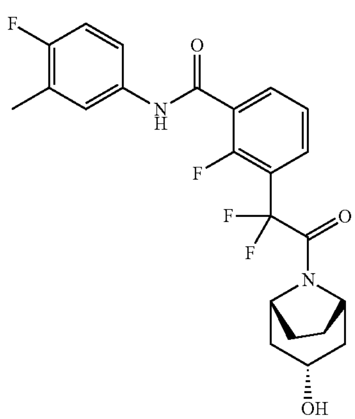 | 3-(1,1-difluoro-2-((1R,3s,5S)-3-hydroxy-8-azabicyclo[3.2.1]octan-8-yl)-2-oxoethyl)-2-fluoro-N-(4-fluoro-3-methylphenyl)benzamide |

TABLE 1-continued

Exemplary compounds.

| Example | Structure | Chemical Name |
|---------|-----------|---------------|
| 257 | 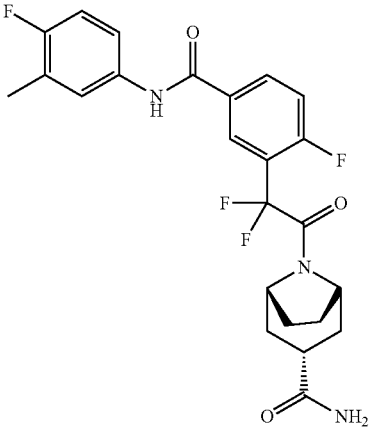 | (1R,3s,5S)-8-(2,2-difluoro-2-(2-fluoro-5-((4-fluoro-3-methylphenyl)carbamoyl)phenyl)acetyl)-8-azabicyclo[3.2.1]octane-3-carboxamide |
| 258 | 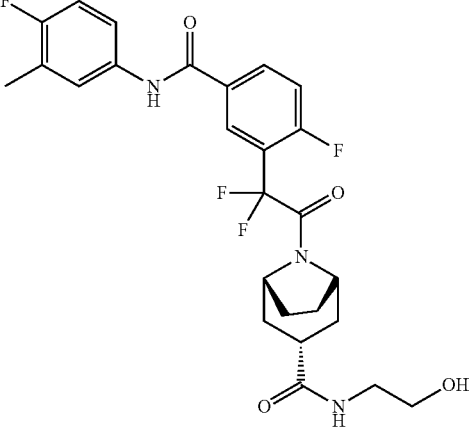 | (1R,3s,5S)-8-(2,2-difluoro-2-(2-fluoro-5-((4-fluoro-3-methylphenyl)carbamoyl)phenyl)acetyl)-N-(2-hydroxyethyl)-8-azabicyclo[3.2.1]octane-3-carboxamide |
| 259 | 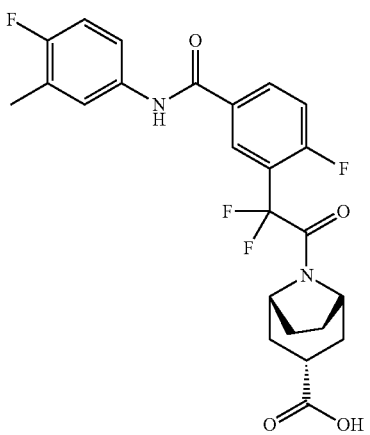 | (1R,3s,5S)-8-(2,2-difluoro-2-(2-fluoro-5-((4-fluoro-3-methylphenyl)carbamoyl)phenyl)acetyl)-8-azabicyclo[3.2.1]octane-3-carboxylic acid |

TABLE 1-continued

Exemplary compounds.

| Example | Structure | Chemical Name |
|---|---|---|
| 260 | 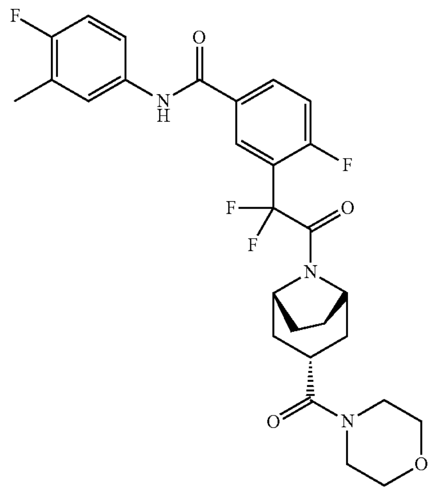 | 3-(1,1-difluoro-2-((1R,3s,5S)-3-(morpholine-4-carbonyl)-8-azabicyclo[3.2.1]octan-8-yl)-2-oxoethyl)-4-fluoro-N-(4-fluoro-3-methylphenyl)benzamide |
| 261 | 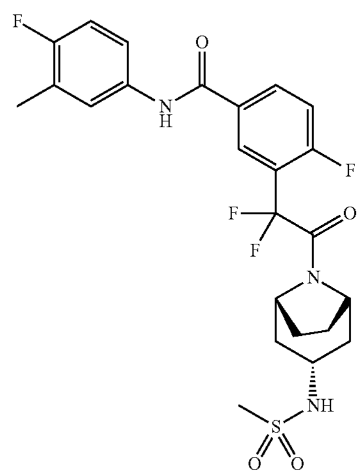 | 3-(1,1-difluoro-2-((1R,3s,5S)-3-(methylsulfonamido)-8-azabicyclo[3.2.1]octan-8-yl)-2-oxoethyl)-4-fluoro-N-(4-fluoro-3-methylphenyl)benzamide |
| 262 | 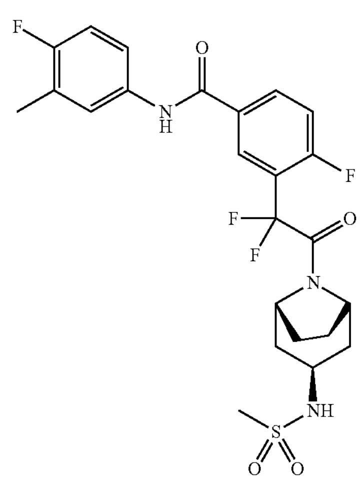 | 3-(1,1-difluoro-2-((1R,3r,5S)-3-(methylsulfonamido)-8-azabicyclo[3.2.1]octan-8-yl)-2-oxoethyl)-4-fluoro-N-(4-fluoro-3-methylphenyl)benzamide |

TABLE 1-continued

Exemplary compounds.

| Example | Structure | Chemical Name |
|---|---|---|
| 263 | 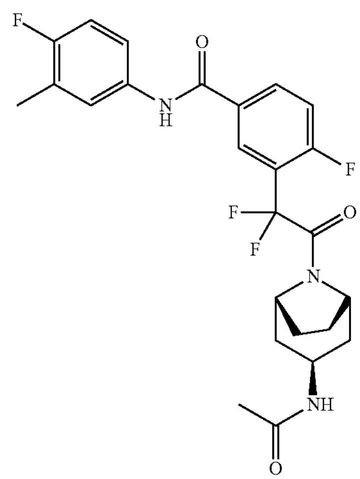 | 3-(2-((1R,3r,5S)-3-acetamido-8-azabicyclo[3.2.1]octan-8-yl)-1,1-difluoro-2-oxoethyl)-4-fluoro-N-(4-fluoro-3-methylphenyl)benzamide |
| 264 | 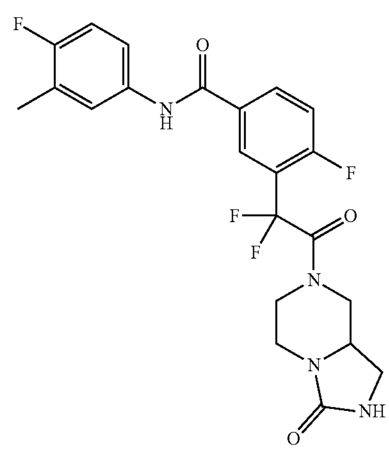 [SMILES: Cc1cc(NC(=O)c2ccc(F)c(C(F)(F)C(=O)N3CCN4C(=O)NCC4C3)c2)ccc1F] | 3-(1,1-difluoro-2-oxo-2-(3-oxohexahydroimidazo[1,5-a]pyrazin-7(1H)-yl)ethyl)-4-fluoro-N-(4-fluoro-3-methylphenyl)benzamide |
| 265 | 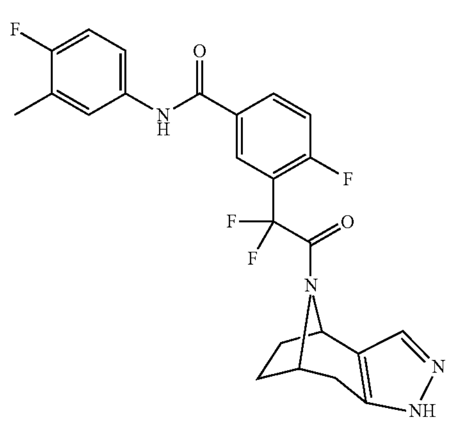 [SMILES: Cc1cc(NC(=O)c2ccc(F)c(C(F)(F)C(=O)N3C4CCC3c3cn[nH]c3C4)c2)ccc1F] | 3-(1,1-difluoro-2-((4R,7S)-1,4,5,6,7,8-hexahydro-4,7-epiminocyclohepta[c]pyrazol-9-yl)-2-oxoethyl)-4-fluoro-N-(4-fluoro-3-methylphenyl)benzamide |

TABLE 1-continued

Exemplary compounds.

| Example | Structure | Chemical Name |
|---|---|---|
| 266 | 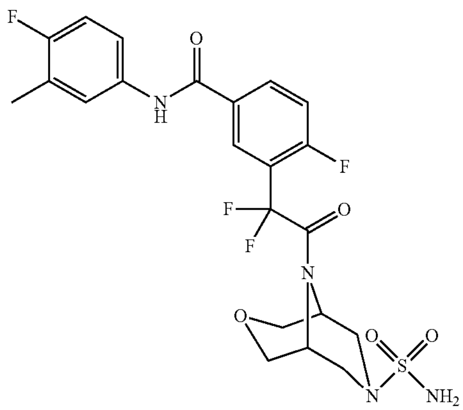 [SMILES: Cc1cc(NC(=O)c2ccc(F)c(C(F)(F)C(=O)N3C4COCC3CN(S(N)(=O)=O)C4)c2)ccc1F] | 3-(1,1-difluoro-2-oxo-2-((1R,5S)-7-sulfamoyl-3-oxa-7,9-diazabicyclo[3.3.1]nonan-9-yl)ethyl)-4-fluoro-N-(4-fluoro-3-methylphenyl)benzamide |
| 267 | 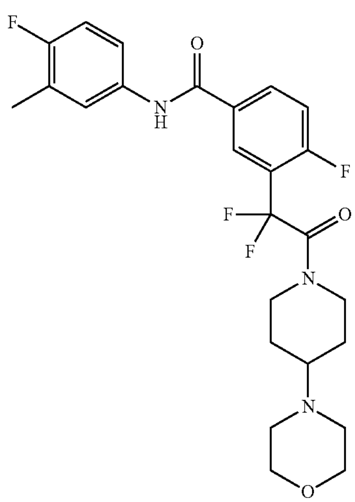 [SMILES: Cc1cc(NC(=O)c2ccc(F)c(C(F)(F)C(=O)N3CCC(N4CCOCC4)CC3)c2)ccc1F] | 3-(1,1-difluoro-2-(4-morpholinopiperidin-1-yl)-2-oxoethyl)-4-fluoro-N-(4-fluoro-3-methylphenyl)benzamide |
| 268 | 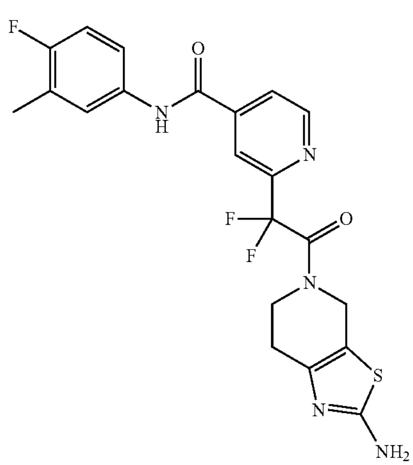 [SMILES: Cc1cc(NC(=O)c2ccnc(C(F)(F)C(=O)N3CCc4nc(N)sc4C3)c2)ccc1F] | 2-(2-(2-amino-6,7-dihydrothiazolo[5,4-c]pyridin-5(4H)-yl)-1,1-difluoro-2-oxoethyl)-N-(4-fluoro-3-methylphenyl)isonicotinamide |

TABLE 1-continued

Exemplary compounds.

| Example | Structure | Chemical Name |
|---------|-----------|---------------|
| 269 | 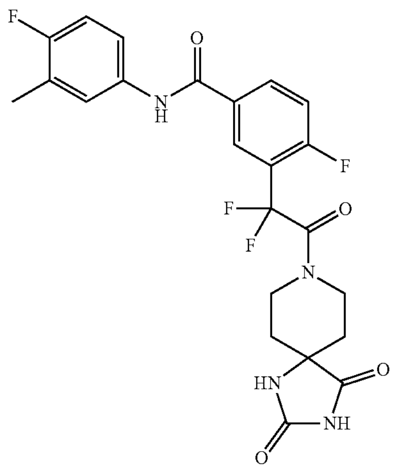 [SMILES: Cc1cc(NC(=O)c2ccc(F)c(C(F)(F)C(=O)N3CCC4(CC3)NC(=O)NC4=O)c2)ccc1F] | 3-(2-(2,4-dioxo-1,3,8-triazaspiro[4.5]decan-8-yl)-1,1-difluoro-2-oxoethyl)-4-fluoro-N-(4-fluoro-3-methylphenyl)benzamide |
| 270 | 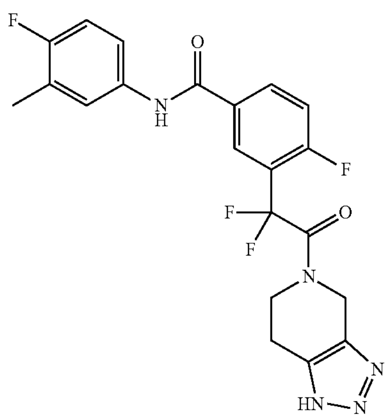 [SMILES: Cc1cc(NC(=O)c2ccc(F)c(C(F)(F)C(=O)N3CCc4[nH]nnc4C3)c2)ccc1F] | 3-(1,1-difluoro-2-oxo-2-(1,4,6,7-tetrahydro-5H-[1,2,3]-triazolo[4,5-c]pyridin-5-yl)ethyl)-4-fluoro-N-(4-fluoro-3-methylphenyl)benzamide |
| 271 | 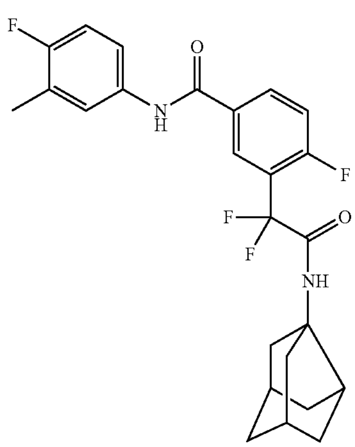 [SMILES: Cc1cc(NC(=O)c2ccc(F)c(C(F)(F)C(=O)NC34CC5CC(CC3C5)C4)c2)ccc1F] | 3-(1,1-difluoro-2-(((2R,3as,5S,6as)-hexahydro-2,5-methanopentalen-3a(1H)-yl)amino)-2-oxoethyl)-4-fluoro-N-(4-fluoro-3-methylphenyl)benzamide |

TABLE 1-continued

Exemplary compounds.

| Example | Structure | Chemical Name |
|---------|-----------|---------------|
| 272 | 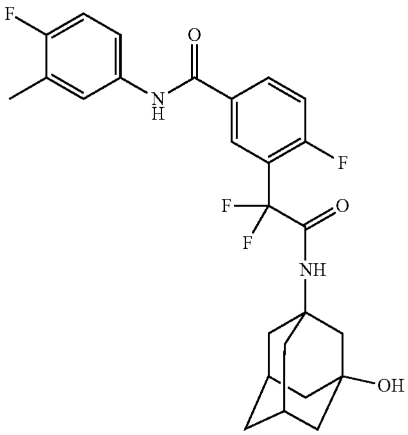 [SMILES: Cc1cc(NC(=O)c2ccc(F)c(C(F)(F)C(=O)NC34CC5CC(CC(O)(C5)C3)C4)c2)ccc1F] | 3-(1,1-difluoro-2-(((1r,3s,5R,7S)-3-hydroxyadamantan-1-yl)amino)-2-oxoethyl)-4-fluoro-N-(4-fluoro-3-methylphenyl)benzamide |
| 273 | 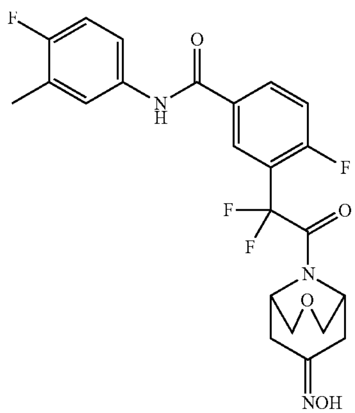 | 3-(1,1-difluoro-2-(7-(hydroxyimino)-3-oxa-9-azabicyclo[3.3.1]nonan-9-yl)-2-oxoethyl)-4-fluoro-N-(4-fluoro-3-methylphenyl)benzamide |
| 274 | 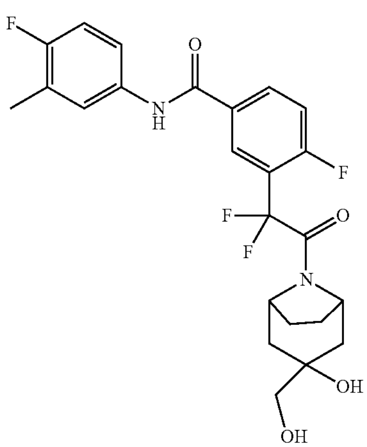 [SMILES: Cc1cc(NC(=O)c2ccc(F)c(C(F)(F)C(=O)N3C4CCC3CC(O)(CO)C4)c2)ccc1F] | 3-(1,1-difluoro-2-((1R,5S)-3-hydroxy-3-(hydroxymethyl)-8-azabicyclo[3.2.1]octan-8-yl)-2-oxoethyl)-4-fluoro-N-(4-fluoro-3-methylphenyl)benzamide-isomer 1 |

TABLE 1-continued

Exemplary compounds.

| Example | Structure | Chemical Name |
|---|---|---|
| 275 | 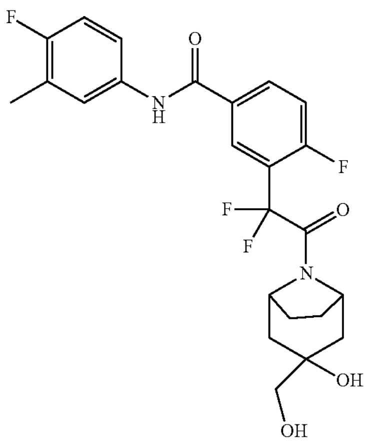 [SMILES: Cc1cc(NC(=O)c2ccc(F)c(C(F)(F)C(=O)N3C4CCC3CC(O)(CO)C4)c2)ccc1F] | 3-(1,1-difluoro-2-((1R,5S)-3-hydroxy-3-(hydroxymethyl)-8-azabicyclo[3.2.1]octan-8-yl)-2-oxoethyl)-4-fluoro-N-(4-fluoro-3-methylphenyl)benzamide-isomer 2 |
| 276 | 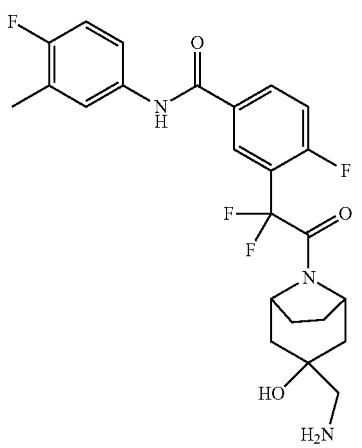 [SMILES: Cc1cc(NC(=O)c2ccc(F)c(C(F)(F)C(=O)N3C4CCC3CC(O)(CN)C4)c2)ccc1F] | 3-(2-((1R,5S)-3-(aminomethyl)-3-hydroxy-8-azabicyclo[3.2.1]octan-8-yl)-1,1-difluoro-2-oxoethyl)-4-fluoro-N-(4-fluoro-3-methylphenyl)benzamide |
| 277 | 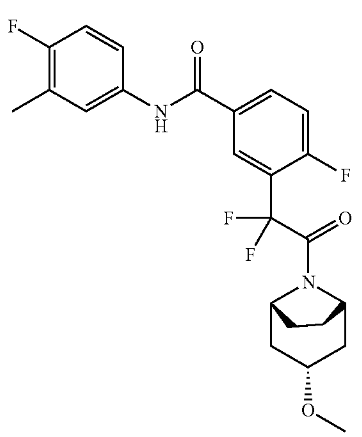 | 3-(1,1-difluoro-2-((1R,3s,5S)-3-methoxy-8-azabicyclo[3.2.1]octan-8-yl)-2-oxoethyl)-4-fluoro-N-(4-fluoro-3-methylphenyl)benzamide |

TABLE 1-continued

Exemplary compounds.

| Example | Structure | Chemical Name |
|---|---|---|
| 278 | 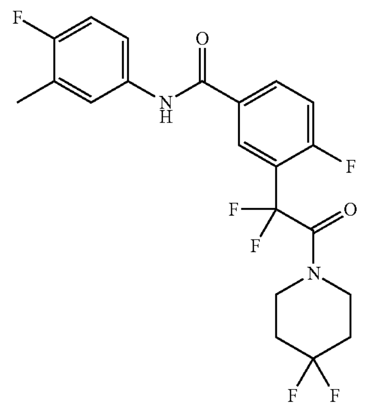 [SMILES: Cc1cc(NC(=O)c2ccc(F)c(C(F)(F)C(=O)N3CCC(F)(F)CC3)c2)ccc1F] | 3-(2-(4,4-difluoropiperidin-1-yl)-1,1-difluoro-2-oxoethyl)-4-fluoro-N-(4-fluoro-3-methylphenyl)benzamide |
| 279 | 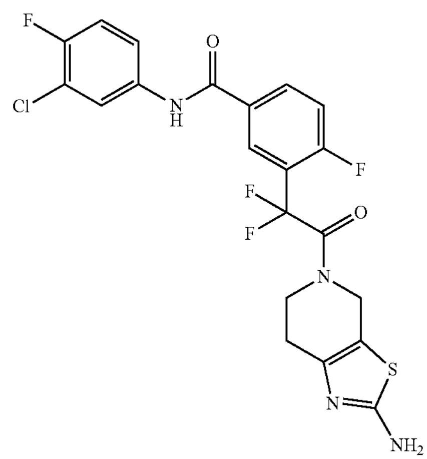 [SMILES: Nc1nc2c(s1)CN(C(=O)C(F)(F)c1cc(C(=O)Nc3ccc(F)c(Cl)c3)ccc1F)CC2] | 3-(2-(2-amino-6,7-dihydrothiazolo[5,4-c]pyridin-5(4H)-yl)-1,1-difluoro-2-oxoethyl)-N-(3-chloro-4-fluorophenyl)-4-fluorobenzamide |
| 280 | 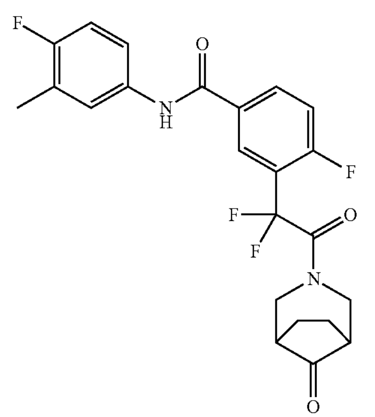 [SMILES: Cc1cc(NC(=O)c2ccc(F)c(C(F)(F)C(=O)N3CC4CCC(C3)C4=O)c2)ccc1F] | 3-(1,1-difluoro-2-oxo-2-((1R,5S)-8-oxo-3-azabicyclo[3.2.1]octan-3-yl)ethyl)-4-fluoro-N-(4-fluoro-3-methylphenyl)benzamide |

TABLE 1-continued

Exemplary compounds.

| Example | Structure | Chemical Name |
|---|---|---|
| 281 | 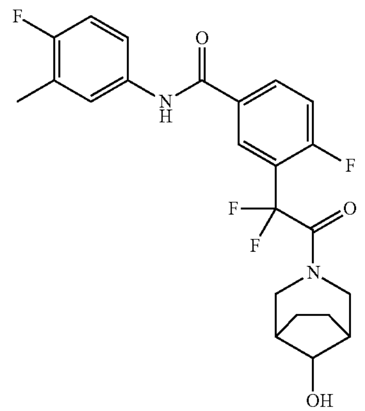 [SMILES: Cc1cc(NC(=O)c2ccc(F)c(C(F)(F)C(=O)N3CC4CCC(C3)C4O)c2)ccc1F] | 3-(1,1-difluoro-2-((1R,5S,8s)-8-hydroxy-3-azabicyclo[3.2.1]octan-3-yl)-2-oxoethyl)-4-fluoro-N-(4-fluoro-3-methylphenyl)benzamide |
| 282 | 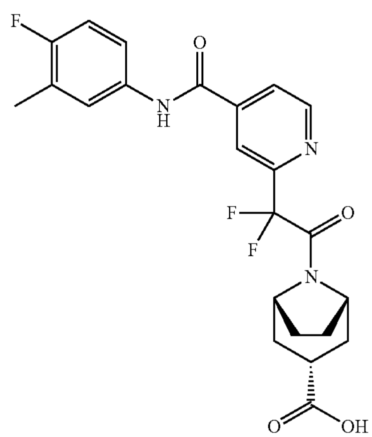 [SMILES: Cc1cc(NC(=O)c2ccnc(C(F)(F)C(=O)N3[C@@H]4CC[C@H]3C[C@H](C(=O)O)C4)c2)ccc1F] | (1R,3s,5S)-8-(2,2-difluoro-2-(4-((4-fluoro-3-methylphenyl)carbamoyl)pyridin-2-yl)acetyl)-8-azabicyclo[3.2.1]octane-3-carboxylic acid |
| 283 | 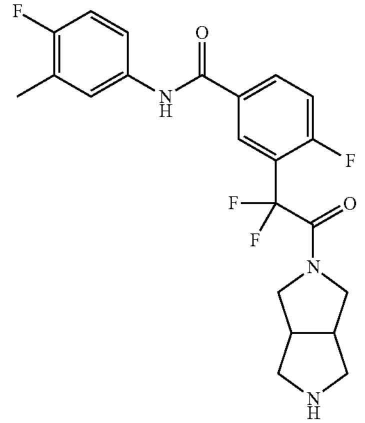 [SMILES: Cc1cc(NC(=O)c2ccc(F)c(C(F)(F)C(=O)N3CC4CNCC4C3)c2)ccc1F] | 3-(1,1-difluoro-2-(hexahydropyrrolo[3,4-c]pyrrol-2(1H)-yl)-2-oxoethyl)-4-fluoro-N-(4-fluoro-3-methylphenyl)benzamide |

TABLE 1-continued

Exemplary compounds.

| Example | Structure | Chemical Name |
|---|---|---|
| 284 | 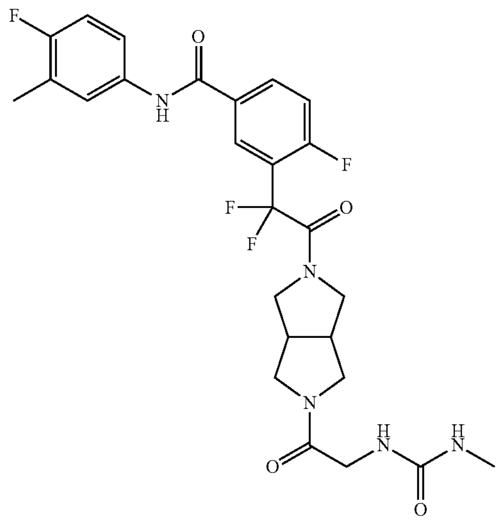 [SMILES: CNC(=O)NCC(=O)N1CC2CN(C(=O)C(F)(F)c3cc(C(=O)Nc4ccc(F)c(C)c4)ccc3F)CC2C1] | 3-(1,1-difluoro-2-(5-((methylcarbamoyl)glycyl)hexahydropyrrolo[3,4-c]pyrrol-2(1H)-yl)-2-oxoethyl)-4-fluoro-N-(4-fluoro-3-methylphenyl)benzamide |
| 285 | 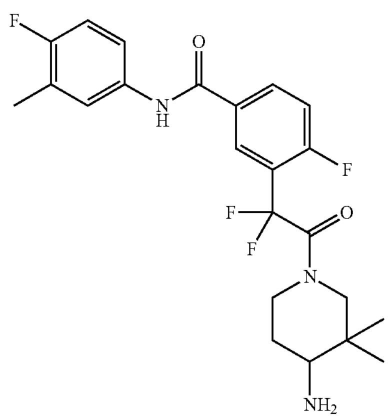 | 3-(2-(4-amino-3,3-dimethylpiperidin-1-yl)-1,1-difluoro-2-oxoethyl)-4-fluoro-N-(4-fluoro-3-methylphenyl)benzamide |
| 286 | 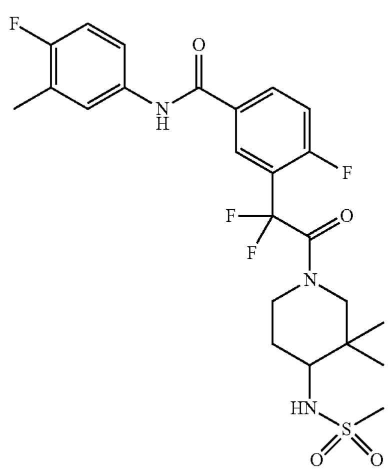 [SMILES: Cc1cc(NC(=O)c2ccc(F)c(C(F)(F)C(=O)N3CCC(NS(C)(=O)=O)C(C)(C)C3)c2)ccc1F] | 3-(2-(3,3-dimethyl-4-(methylsulfonamido)piperidin-1-yl)-1,1-difluoro-2-oxoethyl)-4-fluoro-N-(4-fluoro-3-methylphenyl)benzamide |

TABLE 1-continued

Exemplary compounds.

| Example | Structure | Chemical Name |
|---|---|---|
| 287 | 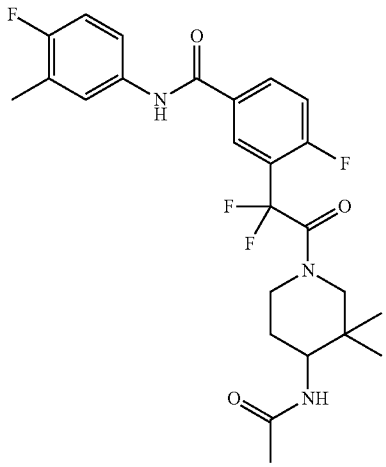 | 3-(2-(4-acetamido-3,3-dimethylpiperidin-1-yl)-1,1-difluoro-2-oxoethyl)-4-fluoro-N-(4-fluoro-3-methylphenyl)benzamide |
| 288 | 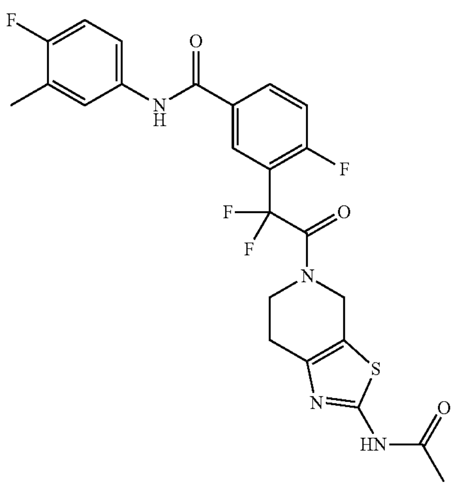 [SMILES: CC(=O)Nc1nc2c(s1)CN(C(=O)C(F)(F)c1cc(C(=O)Nc3ccc(F)c(C)c3)ccc1F)CC2] | 3-(2-(2-acetamido-6,7-dihydrothiazolo[5,4-c]pyridin-5(4H)-yl)-1,1-difluoro-2-oxoethyl)-4-fluoro-N-(4-fluoro-3-methylphenyl)benzamide |
| 289 | 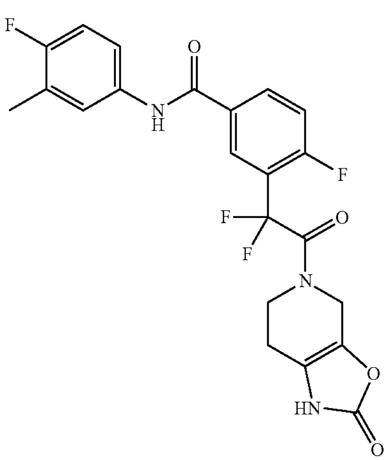 [SMILES: Cc1cc(NC(=O)c2ccc(F)c(C(F)(F)C(=O)N3CCc4[nH]c(=O)oc4C3)c2)ccc1F] | 3-(1,1-difluoro-2-oxo-2-(2-oxo-1,4,6,7-tetrahydrooxazolo[5,4-c]pyridin-5(2H)-yl)ethyl)-4-fluoro-N-(4-fluoro-3-methylphenyl)benzamide |

TABLE 1-continued

Exemplary compounds.

| Example | Structure | Chemical Name |
|---|---|---|
| 290 | 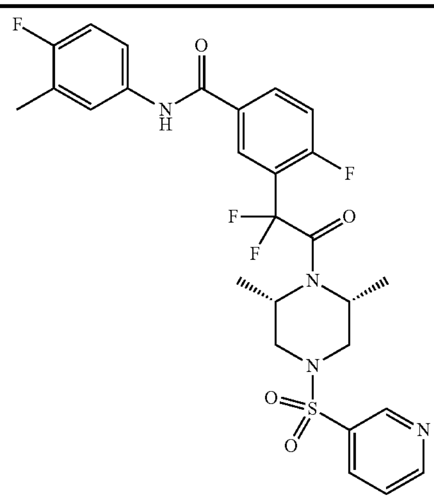 | 3-(2-((2S,6R)-2,6-dimethyl-4-(pyridin-3-ylsulfonyl)piperazin-1-yl)-1,1-difluoro-2-oxoethyl)-4-fluoro-N-(4-fluoro-3-methylphenyl)benzamide |
| 291 | 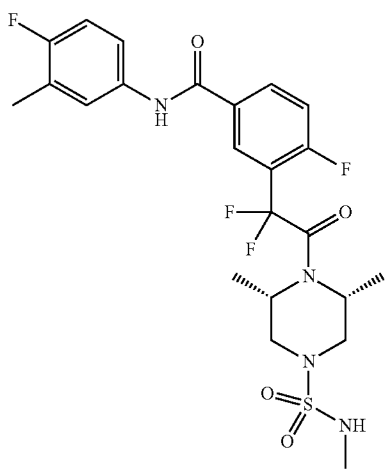 [SMILES: CNS(=O)(=O)N1C[C@@H](C)N(C(=O)C(F)(F)c2cc(C(=O)Nc3ccc(F)c(C)c3)ccc2F)[C@@H](C)C1] | 3-(2-((2S,6R)-2,6-dimethyl-4-(N-methylsulfamoyl)piperazin-1-yl)-1,1-difluoro-2-oxoethyl)-4-fluoro-N-(4-fluoro-3-methylphenyl)benzamide |
| 292 | 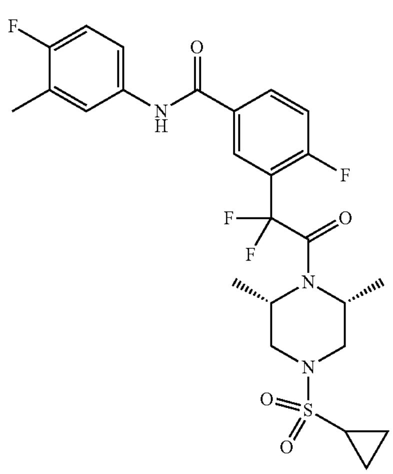 [SMILES: Cc1cc(NC(=O)c2ccc(F)c(C(F)(F)C(=O)N3[C@H](C)CN(S(=O)(=O)C4CC4)C[C@@H]3C)c2)ccc1F] | 3-(2-((2S,6R)-4-(cyclopropylsulfonyl)-2,6-dimethylpiperazin-1-yl)-1,1-difluoro-2-oxoethyl)-4-fluoro-N-(4-fluoro-3-methylphenyl)benzamide |

TABLE 1-continued

Exemplary compounds.

| Example | Structure | Chemical Name |
|---|---|---|
| 293 | 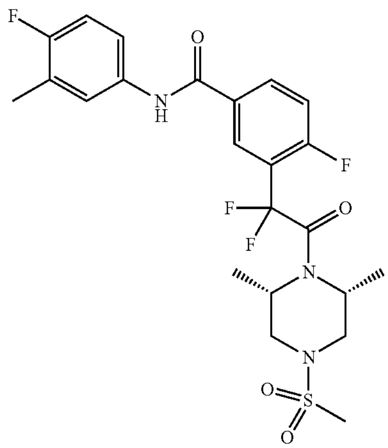 [SMILES: Cc1cc(NC(=O)c2ccc(F)c(C(F)(F)C(=O)N3[C@H](C)CN(S(C)(=O)=O)C[C@@H]3C)c2)ccc1F] | 3-(2-((2S,6R)-2,6-dimethyl-4-(methylsulfonyl)piperazin-1-yl)-1,1-difluoro-2-oxoethyl)-4-fluoro-N-(4-fluoro-3-methylphenyl)benzamide |
| 294 | 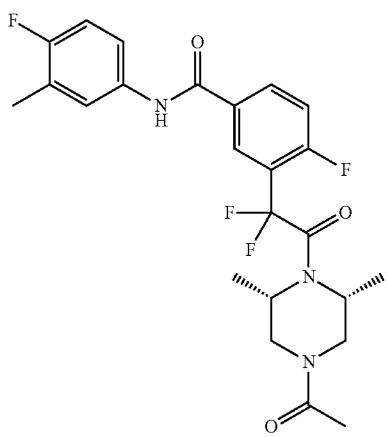 [SMILES: CC(=O)N1C[C@@H](C)N(C(=O)C(F)(F)c2cc(C(=O)Nc3ccc(F)c(C)c3)ccc2F)[C@@H](C)C1] | 3-(2-((2S,6R)-4-acetyl-2,6-dimethylpiperazin-1-yl)-1,1-difluoro-2-oxoethyl)-4-fluoro-N-(4-fluoro-3-methylphenyl)benzamide |
| 295 | 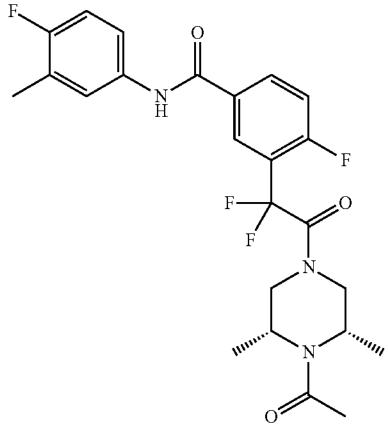 [SMILES: CC(=O)N1[C@H](C)CN(C(=O)C(F)(F)c2cc(C(=O)Nc3ccc(F)c(C)c3)ccc2F)C[C@@H]1C] | 3-(2-((3R,5S)-4-acetyl-3,5-dimethylpiperazin-1-yl)-1,1-difluoro-2-oxoethyl)-4-fluoro-N-(4-fluoro-3-methylphenyl)benzamide |

TABLE 1-continued

Exemplary compounds.

| Example | Structure | Chemical Name |
| --- | --- | --- |
| 296 | 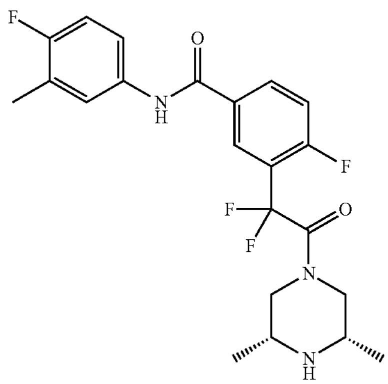 [SMILES: Cc1cc(NC(=O)c2ccc(F)c(C(F)(F)C(=O)N3C[C@@H](C)N[C@@H](C)C3)c2)ccc1F] | 3-(2-((3R,5S)-3,5-dimethylpiperazin-1-yl)-1,1-difluoro-2-oxoethyl)-4-fluoro-N-(4-fluoro-3-methylphenyl)benzamide |
| 297 | 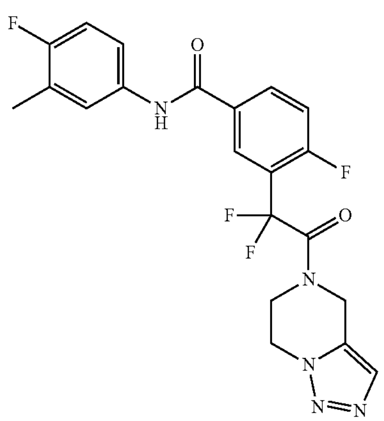 [SMILES: Cc1cc(NC(=O)c2ccc(F)c(C(F)(F)C(=O)N3CCn4nncc4C3)c2)ccc1F] | 3-(2-(6,7-dihydro-[1,2,3]triazolo[1,5-a]pyrazin-5(4H)-yl)-1,1-difluoro-2-oxoethyl)-4-fluoro-N-(4-fluoro-3-methylphenyl)benzamide |
| 298 | 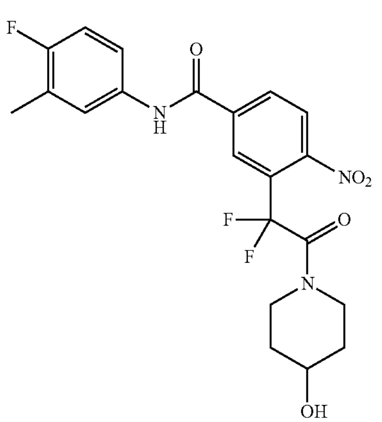 [SMILES: Cc1cc(NC(=O)c2ccc([N+](=O)[O-])c(C(F)(F)C(=O)N3CCC(O)CC3)c2)ccc1F] | 3-(1,1-difluoro-2-(4-hydroxypiperidin-1-yl)-2-oxoethyl)-N-(4-fluoro-3-methylphenyl)-4-nitrobenzamide |

TABLE 1-continued
Exemplary compounds.
| Example | Structure | Chemical Name |
|---|---|---|
| 299 | 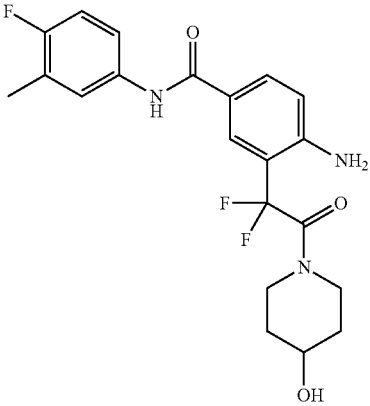 [SMILES: Cc1cc(NC(=O)c2ccc(N)c(C(F)(F)C(=O)N3CCC(O)CC3)c2)ccc1F] | 4-amino-3-(1,1-difluoro-2-(4-hydroxypiperidin-1-yl)-2-oxoethyl)-N-(4-fluoro-3-methylphenyl)benzamide |
| 300 | 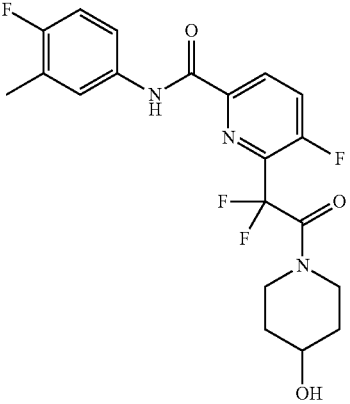 [SMILES: Cc1cc(NC(=O)c2ccc(F)c(C(F)(F)C(=O)N3CCC(O)CC3)n2)ccc1F] | 6-(1,1-difluoro-2-(4-hydroxypiperidin-1-yl)-2-oxoethyl)-5-fluoro-N-(4-fluoro-3-methylphenyl)picolinamide |
| 301 | 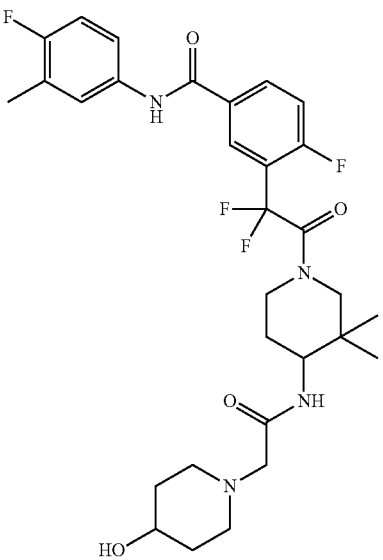 [SMILES: Cc1cc(NC(=O)c2ccc(F)c(C(F)(F)C(=O)N3CCC(NC(=O)CN4CCC(O)CC4)C(C)(C)C3)c2)ccc1F] | 3-(1,1-difluoro-2-(4-(2-(4-hydroxypiperidin-1-yl)acetamido)-3,3-dimethylpiperidin-1-yl)-2-oxoethyl)-4-fluoro-N-(4-fluoro-3-methylphenyl)benzamide |

TABLE 1-continued

Exemplary compounds.

| Example | Structure | Chemical Name |
|---|---|---|
| 302 | 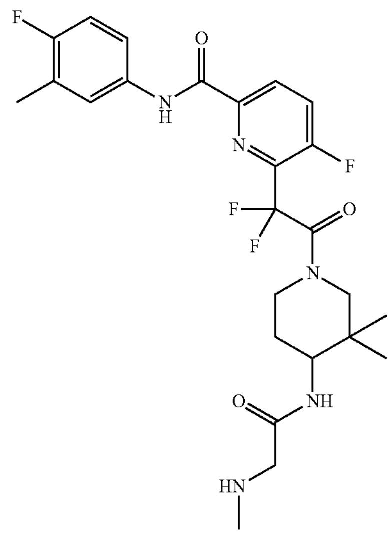 [SMILES: CNCC(=O)NC1CCN(C(=O)C(F)(F)c2nc(C(=O)Nc3ccc(F)c(C)c3)ccc2F)CC1(C)C] | 6-(2-(3,3-dimethyl-4-(2-(methylamino)acetamido)piperidin-1-yl)-1,1-difluoro-2-oxoethyl)-5-fluoro-N-(4-fluoro-3-methylphenyl)picolinamide |
| 303 | 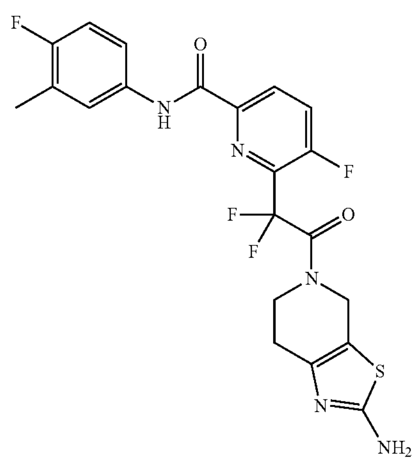 [SMILES: Cc1cc(NC(=O)c2ccc(F)c(C(F)(F)C(=O)N3CCc4nc(N)sc4C3)n2)ccc1F] | 6-(2-(2-amino-6,7-dihydrothiazolo[5,4-c]pyridin-5(4H)-yl)-1,1-difluoro-2-oxoethyl)-5-fluoro-N-(4-fluoro-3-methylphenyl)picolinamide |
| 304 | 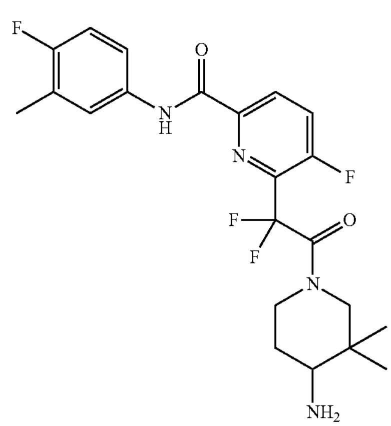 [SMILES: Cc1cc(NC(=O)c2ccc(F)c(C(F)(F)C(=O)N3CCC(N)C(C)(C)C3)n2)ccc1F] | 6-(2-(4-amino-3,3-dimethylpiperidin-1-yl)-1,1-difluoro-2-oxoethyl)-5-fluoro-N-(4-fluoro-3-methylphenyl)picolinamide |

TABLE 1-continued

Exemplary compounds.

| Example | Structure | Chemical Name |
|---|---|---|
| 305 | 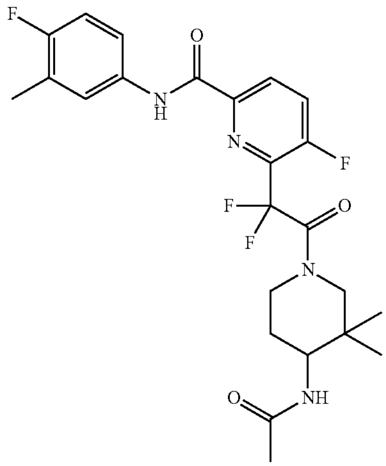 [SMILES: CC(=O)NC1CCN(C(=O)C(F)(F)c2nc(C(=O)Nc3ccc(F)c(C)c3)ccc2F)CC1(C)C] | 6-(2-(4-acetamido-3,3-dimethylpiperidin-1-yl)-1,1-difluoro-2-oxoethyl)-5-fluoro-N-(4-fluoro-3-methylphenyl)picolinamide |
| 306 | 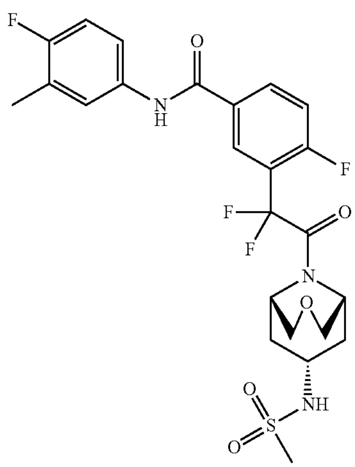 [SMILES: Cc1cc(NC(=O)c2ccc(F)c(C(F)(F)C(=O)N3[C@@H]4COC[C@H]3C[C@H](NS(C)(=O)=O)C4)c2)ccc1F] | 3-(1,1-difluoro-2-((1R,5S,7r)-7-(methylsulfonamido)-3-oxa-9-azabicyclo[3.3.1]nonan-9-yl)-2-oxoethyl)-4-fluoro-N-(4-fluoro-3-methylphenyl)benzamide |
| 307 | 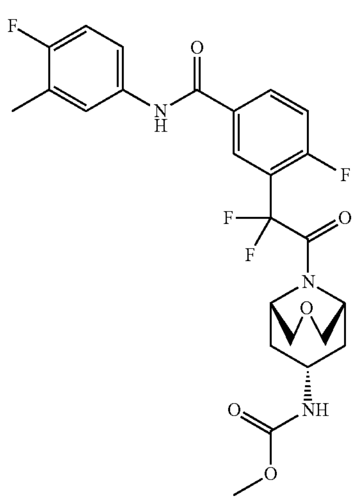 [SMILES: COC(=O)N[C@@H]1C[C@H]2COC[C@@H](C1)N2C(=O)C(F)(F)c1cc(C(=O)Nc2ccc(F)c(C)c2)ccc1F] | methyl ((1R,5S,7r)-9-(2,2-difluoro-2-(2-fluoro-5-((4-fluoro-3-methylphenyl)carbamoyl)phenyl)acetyl)-3-oxa-9-azabicyclo[3.3.1]nonan-7-yl)carbamate |

TABLE 1-continued

Exemplary compounds.

| Example | Structure | Chemical Name |
|---|---|---|
| 308 | 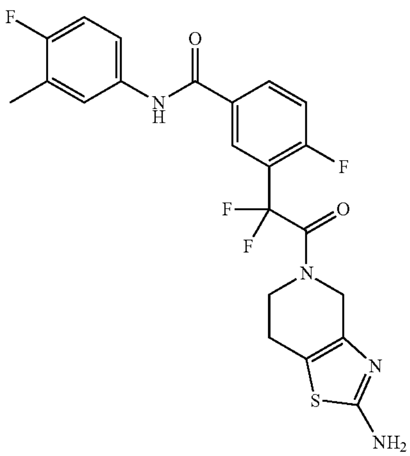 [SMILES: Cc1cc(NC(=O)c2ccc(F)c(C(F)(F)C(=O)N3CCc4sc(N)nc4C3)c2)ccc1F] | 3-(2-(2-amino-6,7-dihydrothiazolo[4,5-c]pyridin-5(4H)-yl)-1,1-difluoro-2-oxoethyl)-4-fluoro-N-(4-fluoro-3-methylphenyl)benzamide |
| 309 | 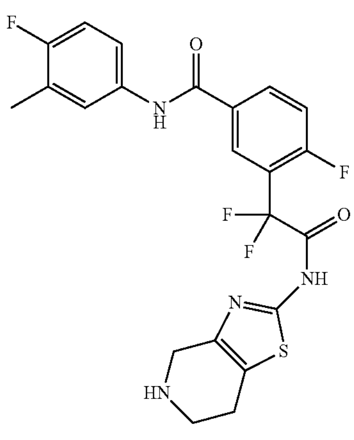 [SMILES: Cc1cc(NC(=O)c2ccc(F)c(C(F)(F)C(=O)Nc3nc4c(s3)CCNC4)c2)ccc1F] | 3-(1,1-difluoro-2-oxo-2-((4,5,6,7-tetrahydrothiazolo[4,5-c]pyridin-2-yl)amino)ethyl)-4-fluoro-N-(4-fluoro-3-methylphenyl)benzamide |
| 310 | 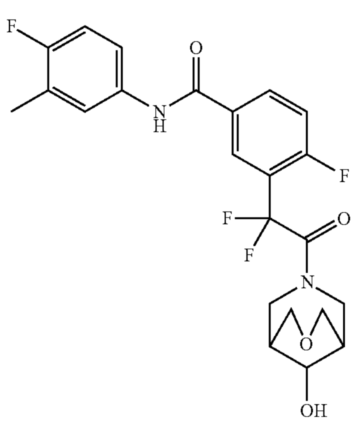 [SMILES: Cc1cc(NC(=O)c2ccc(F)c(C(F)(F)C(=O)N3CC4COCC(C3)C4O)c2)ccc1F] | 3-(1,1-difluoro-2-(9-hydroxy-3-oxa-7-azabicyclo[3.3.1]nonan-7-yl)-2-oxoethyl)-4-fluoro-N-(4-fluoro-3-methylphenyl)benzamide |

TABLE 1-continued

| Exemplary compounds. | | |
|---|---|---|
| Example | Structure | Chemical Name |
| 311 | | 3-(2-(4-acetamido-3,3-dimethylpiperidin-1-yl)-1,1-difluoro-2-oxoethyl)-4-amino-N-(4-fluoro-3-methylphenyl)benzamide |
| 312 | | 3-(1,1-difluoro-2-oxo-2-(3-(trifluoromethyl)-5,6-dihydroimidazo[1,5-a]pyrazin-7(8H)-yl)ethyl)-4-fluoro-N-(4-fluoro-3-methylphenyl)benzamide |
| 313 | | 3-(2-((5R,8S)-2-amino-5,6,7,8-tetrahydro-4H-5,8-epiminocyclohepta[d]thiazol-9-yl)-1,1-difluoro-2-oxoethyl)-4-fluoro-N-(4-fluoro-3-methylphenyl)benzamide |

TABLE 1-continued

Exemplary compounds.

| Example | Structure | Chemical Name |
|---|---|---|
| 314 | 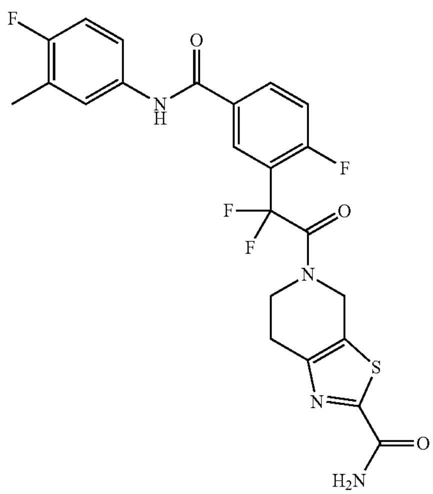 [SMILES: Cc1cc(NC(=O)c2ccc(F)c(C(F)(F)C(=O)N3CCc4nc(C(N)=O)sc4C3)c2)ccc1F] | 5-(2,2-difluoro-2-(2-fluoro-5-((4-fluoro-3-methylphenyl)carbamoyl)phenyl)acetyl)-4,5,6,7-tetrahydrothiazolo[5,4-c]pyridine-2-carboxamide |
| 315 | 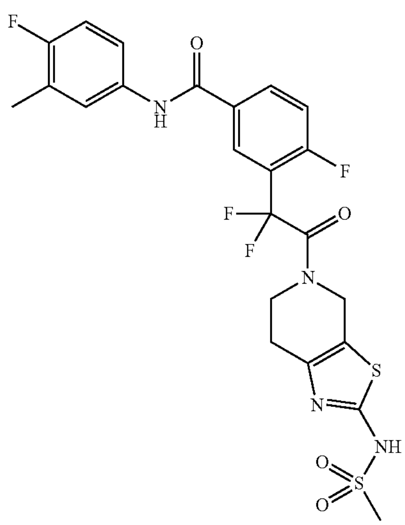 [SMILES: Cc1cc(NC(=O)c2ccc(F)c(C(F)(F)C(=O)N3CCc4nc(NS(C)(=O)=O)sc4C3)c2)ccc1F] | 3-(1,1-difluoro-2-(2-(methylsulfonamido)-6,7-dihydrothiazolo[5,4-c]pyridin-5(4H)-yl)-2-oxoethyl)-4-fluoro-N-(4-fluoro-3-methylphenyl)benzamide |
| 316 | 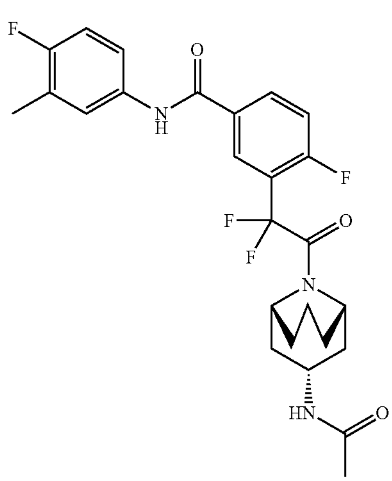 [SMILES: CC(=O)N[C@@H]1C[C@H]2CCC[C@@H](C1)N2C(=O)C(F)(F)c1cc(C(=O)Nc2ccc(F)c(C)c2)ccc1F] | 3-(2-((1R,3s,5S)-3-acetamido-9-azabicyclo[3.3.1]nonan-9-yl)-1,1-difluoro-2-oxoethyl)-4-fluoro-N-(4-fluoro-3-methylphenyl)benzamide |

TABLE 1-continued

Exemplary compounds.

| Example | Structure | Chemical Name |
|---|---|---|
| 317 | 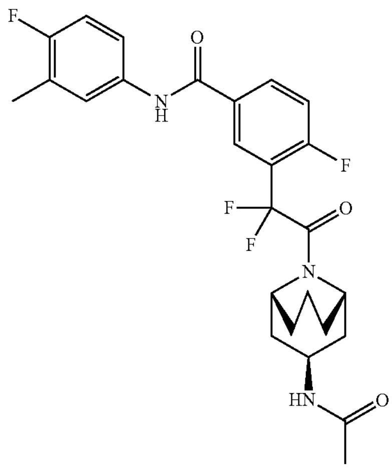 [SMILES: CC(=O)N[C@H]1C[C@H]2CCC[C@@H](C1)N2C(=O)C(F)(F)c1cc(C(=O)Nc2ccc(F)c(C)c2)ccc1F] | 3-(2-((1R,3r,5S)-3-acetamido-9-azabicyclo[3.3.1]nonan-9-yl)-1,1-difluoro-2-oxoethyl)-4-fluoro-N-(4-fluoro-3-methylphenyl)benzamide |
| 318 | 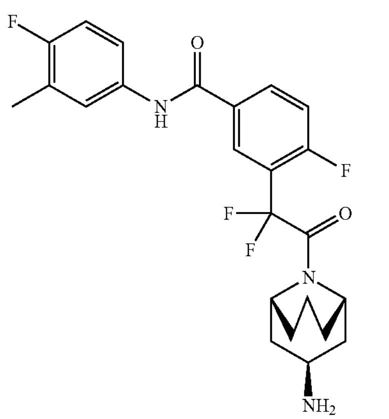 [SMILES: Cc1cc(NC(=O)c2ccc(F)c(C(F)(F)C(=O)N3[C@@H]4CCC[C@H]3C[C@@H](N)C4)c2)ccc1F] | 3-(2-((1R,3r,5S)-3-amino-9-azabicyclo[3.3.1]nonan-9-yl)-1,1-difluoro-2-oxoethyl)-4-fluoro-N-(4-fluoro-3-methylphenyl)benzamide |
| 319 | 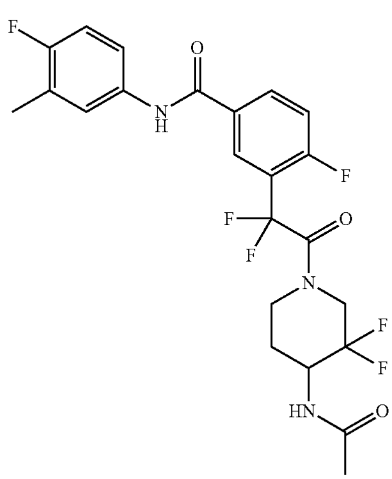 [SMILES: CC(=O)NC1CCN(C(=O)C(F)(F)c2cc(C(=O)Nc3ccc(F)c(C)c3)ccc2F)CC1(F)F] | 3-(2-(4-acetamido-3,3-difluoropiperidin-1-yl)-1,1-difluoro-2-oxoethyl)-4-fluoro-N-(4-fluoro-3-methylphenyl)benzamide |

TABLE 1-continued

Exemplary compounds.

| Example | Structure | Chemical Name |
|---|---|---|
| 320 | 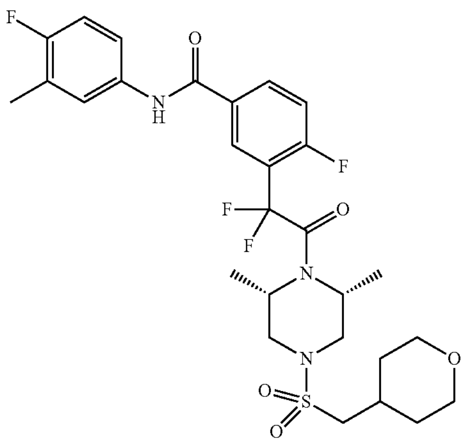 [SMILES: Cc1cc(NC(=O)c2ccc(F)c(C(F)(F)C(=O)N3[C@H](C)CN(S(=O)(=O)CC4CCOCC4)C[C@@H]3C)c2)ccc1F] | 3-(2-((2S,6R)-2,6-dimethyl-4-(((tetrahydro-2H-pyran-4-yl)methyl)sulfonyl)piperazin-1-yl)-1,1-difluoro-2-oxoethyl)-4-fluoro-N-(4-fluoro-3-methylphenyl)benzamide |
| 321 | 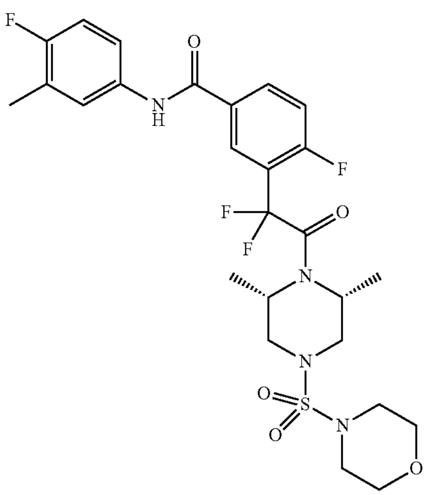 [SMILES: Cc1cc(NC(=O)c2ccc(F)c(C(F)(F)C(=O)N3[C@H](C)CN(S(=O)(=O)N4CCOCC4)C[C@@H]3C)c2)ccc1F] | 3-(2-((2S,6R)-2,6-dimethyl-4-(morpholinosulfonyl)piperazin-1-yl)-1,1-difluoro-2-oxoethyl)-4-fluoro-N-(4-fluoro-3-methylphenyl)benzamide |
| 322 | 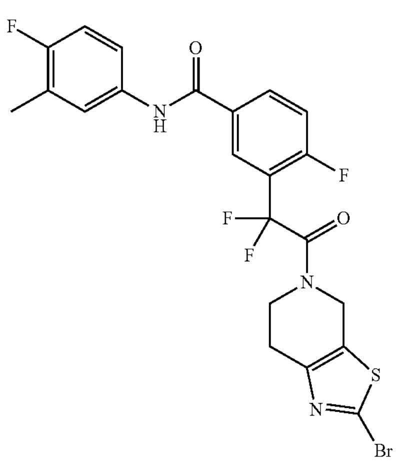 [SMILES: Cc1cc(NC(=O)c2ccc(F)c(C(F)(F)C(=O)N3CCc4nc(Br)sc4C3)c2)ccc1F] | 3-(2-(2-bromo-6,7-dihydrothiazolo[5,4-c]pyridin-5(4H)-yl)-1,1-difluoro-2-oxoethyl)-4-fluoro-N-(4-fluoro-3-methylphenyl)benzamide |

TABLE 1-continued

Exemplary compounds.

| Example | Structure | Chemical Name |
|---|---|---|
| 323 | 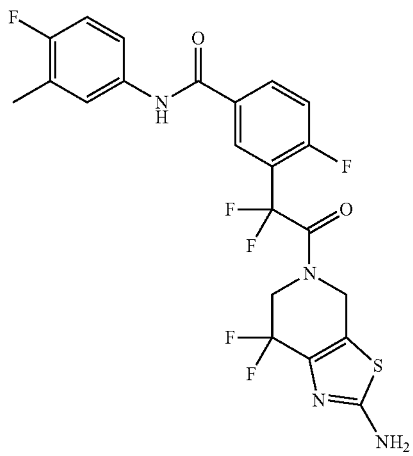 [SMILES: Cc1cc(NC(=O)c2ccc(F)c(C(F)(F)C(=O)N3Cc4sc(N)nc4C(F)(F)C3)c2)ccc1F] | 3-(2-(2-amino-7,7-difluoro-6,7-dihydrothiazolo[5,4-c]pyridin-5(4H)-yl)-1,1-difluoro-2-oxoethyl)-4-fluoro-N-(4-fluoro-3-methylphenyl)benzamide |
| 324 | 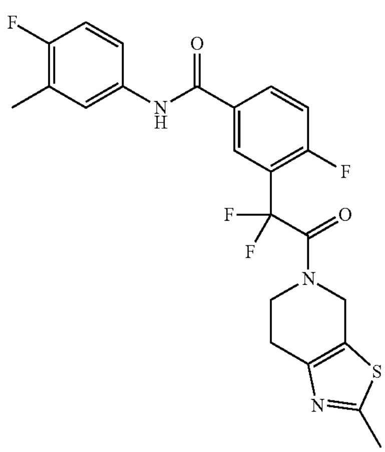 [SMILES: Cc1nc2c(s1)CN(C(=O)C(F)(F)c1cc(C(=O)Nc3ccc(F)c(C)c3)ccc1F)CC2] | 3-(1,1-difluoro-2-(2-methyl-6,7-dihydrothiazolo[5,4-c]pyridin-5(4H)-yl)-2-oxoethyl)-4-fluoro-N-(4-fluoro-3-methylphenyl)benzamide |
| 325 | 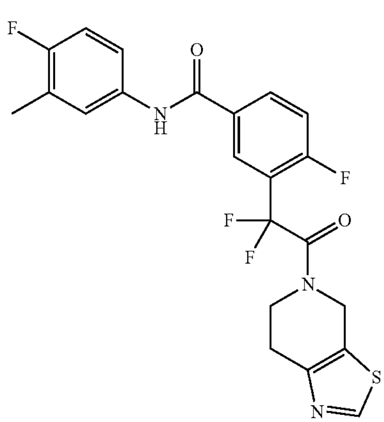 [SMILES: Cc1cc(NC(=O)c2ccc(F)c(C(F)(F)C(=O)N3CCc4ncsc4C3)c2)ccc1F] | 3-(2-(6,7-dihydrothiazolo[5,4-c]pyridin-5(4H)-yl)-1,1-difluoro-2-oxoethyl)-4-fluoro-N-(4-fluoro-3-methylphenyl)benzamide |

TABLE 1-continued

Exemplary compounds.

| Example | Structure | Chemical Name |
|---|---|---|
| 326 | 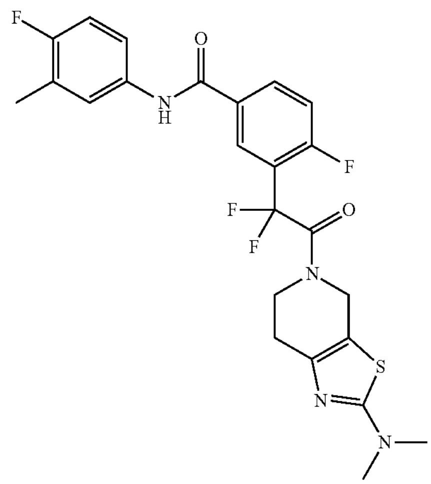 [SMILES: Cc1cc(NC(=O)c2ccc(F)c(C(F)(F)C(=O)N3CCc4nc(N(C)C)sc4C3)c2)ccc1F] | 3-(2-(2-(dimethylamino)-6,7-dihydrothiazolo[5,4-c]pyridin-5(4H)-yl)-1,1-difluoro-2-oxoethyl)-4-fluoro-N-(4-fluoro-3-methylphenyl)benzamide |
| 327 | 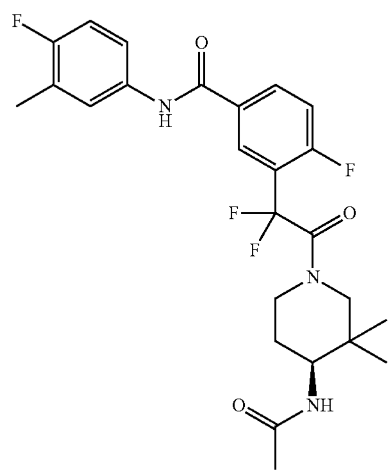 [SMILES: CC(=O)N[C@H]1CCN(C(=O)C(F)(F)c2cc(C(=O)Nc3ccc(F)c(C)c3)ccc2F)CC1(C)C] | (S)-3-(2-(4-acetamido-3,3-dimethylpiperidin-1-yl)-1,1-difluoro-2-oxoethyl)-4-fluoro-N-(4-fluoro-3-methylphenyl)benzamide |
| 328 | 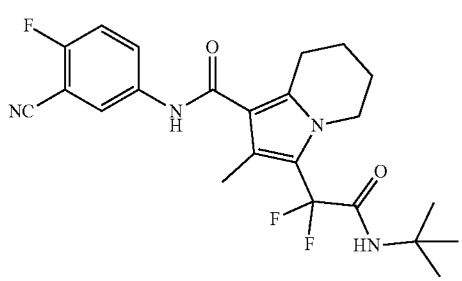 [SMILES: Cc1c(C(=O)Nc2ccc(F)c(C#N)c2)c2n(c1C(F)(F)C(=O)NC(C)(C)C)CCCC2] | 3-(2-(tert-butylamino)-1,1-difluoro-2-oxoethyl)-N-(3-cyano-4-fluorophenyl)-2-methyl-5,6,7,8-tetrahydroindolizine-1-carboxamide |
| 329 | 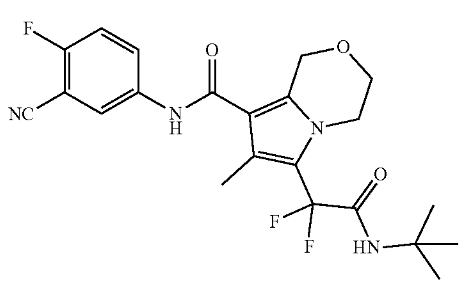 [SMILES: Cc1c(C(=O)Nc2ccc(F)c(C#N)c2)c2n(c1C(F)(F)C(=O)NC(C)(C)C)CCOC2] | 6-(2-(tert-butylamino)-1,1-difluoro-2-oxoethyl)-N-(3-cyano-4-fluorophenyl)-7-methyl-3,4-dihydro-1H-pyrrolo[2,1-c][1,4]oxazine-8-carboxamide |

TABLE 1-continued

Exemplary compounds.

| Example | Structure | Chemical Name |
|---|---|---|
| 330 | 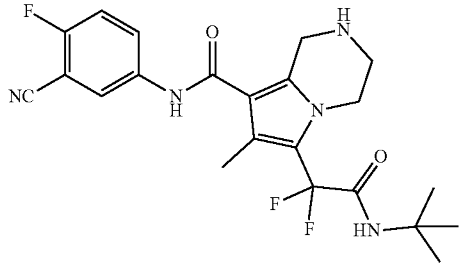 [SMILES: Cc1c(C(=O)Nc2ccc(F)c(C#N)c2)c2n(c1C(F)(F)C(=O)NC(C)(C)C)CCNC2] | 6-(2-(tert-butylamino)-1,1-difluoro-2-oxoethyl)-N-(3-cyano-4-fluorophenyl)-7-methyl-1,2,3,4-tetrahydropyrrolo[1,2-a]pyrazine-8-carboxamide |
| 331 | 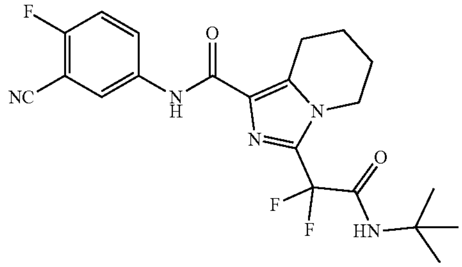 [SMILES: CC(C)(C)NC(=O)C(F)(F)c1nc(C(=O)Nc2ccc(F)c(C#N)c2)c2n1CCCC2] | 3-(2-(tert-butylamino)-1,1-difluoro-2-oxoethyl)-N-(3-cyano-4-fluorophenyl)-5,6,7,8-tetrahydroimidazo[1,5-a]pyridine-1-carboxamide |
| 332 | 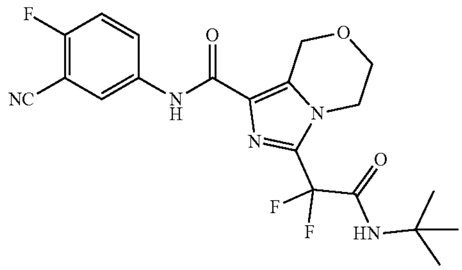 [SMILES: CC(C)(C)NC(=O)C(F)(F)c1nc(C(=O)Nc2ccc(F)c(C#N)c2)c2n1CCOC2] | 3-(2-(tert-butylamino)-1,1-difluoro-2-oxoethyl)-N-(3-cyano-4-fluorophenyl)-5,6-dihydro-8H-imidazo[5,1-c][1,4]oxazine-1-carboxamide |
| 333 | 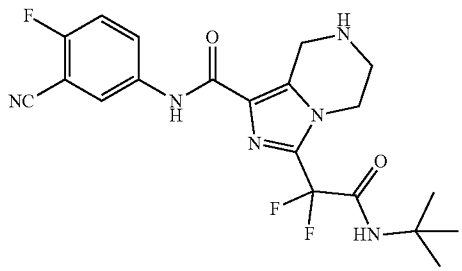 [SMILES: CC(C)(C)NC(=O)C(F)(F)c1nc(C(=O)Nc2ccc(F)c(C#N)c2)c2n1CCNC2] | 3-(2-(tert-butylamino)-1,1-difluoro-2-oxoethyl)-N-(3-cyano-4-fluorophenyl)-5,6,7,8-tetrahydroimidazo[1,5-a]pyrazine-1-carboxamide |
| 334 | 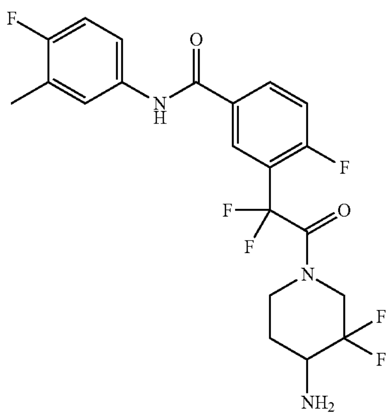 [SMILES: Cc1cc(NC(=O)c2ccc(F)c(C(F)(F)C(=O)N3CCC(N)C(F)(F)C3)c2)ccc1F] | 3-(2-(4-amino-3,3-difluoropiperidin-1-yl)-1,1-difluoro-2-oxoethyl)-4-fluoro-N-(4-fluoro-3-methylphenyl)benzamide |

TABLE 1-continued

Exemplary compounds.

| Example | Structure | Chemical Name |
| --- | --- | --- |
| 335 | 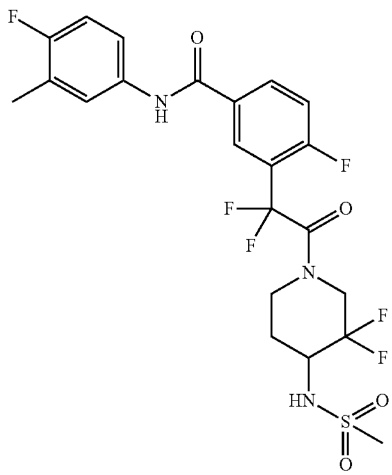 [SMILES: Cc1cc(NC(=O)c2ccc(F)c(C(F)(F)C(=O)N3CCC(NS(C)(=O)=O)C(F)(F)C3)c2)ccc1F] | 3-(2-(3,3-difluoro-4-(methylsulfonamido)piperidin-1-yl)-1,1-difluoro-2-oxoethyl)-4-fluoro-N-(4-fluoro-3-methylphenyl)benzamide |
| 336 | 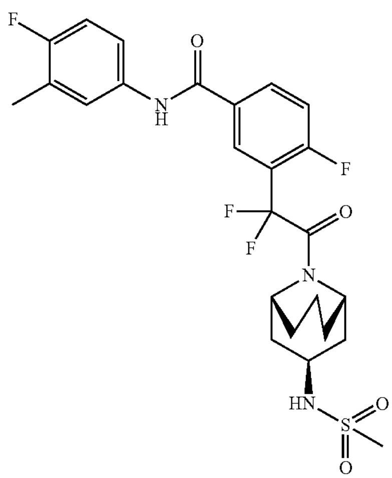 [SMILES: Cc1cc(NC(=O)c2ccc(F)c(C(F)(F)C(=O)N3[C@@H]4CCC[C@H]3C[C@@H](NS(C)(=O)=O)C4)c2)ccc1F] | 3-(1,1-difluoro-2-((1R,3r,5S)-3-(methylsulfonamido)-9-azabicyclo[3.3.1]nonan-9-yl)-2-oxoethyl)-4-fluoro-N-(4-fluoro-3-methylphenyl)benzamide |
| 337 | 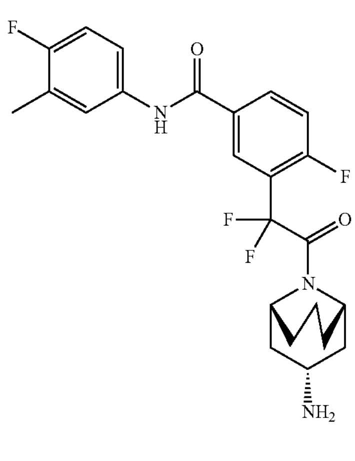 [SMILES: Cc1cc(NC(=O)c2ccc(F)c(C(F)(F)C(=O)N3[C@@H]4CCC[C@H]3C[C@H](N)C4)c2)ccc1F] | 3-(2-((1R,3s,5S)-3-amino-9-azabicyclo[3.3.1]nonan-9-yl)-1,1-difluoro-2-oxoethyl)-4-fluoro-N-(4-fluoro-3-methylphenyl)benzamide |

TABLE 1-continued

Exemplary compounds.

| Example | Structure | Chemical Name |
|---|---|---|
| 338 | 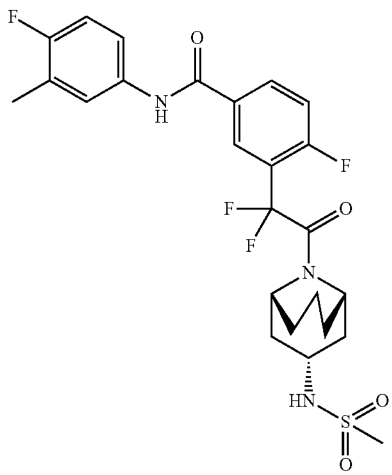 [SMILES: Cc1cc(NC(=O)c2ccc(F)c(C(F)(F)C(=O)N3[C@@H]4CCC[C@H]3C[C@H](NS(C)(=O)=O)C4)c2)ccc1F] | 3-(1,1-difluoro-2-((1R,3s,5S)-3-(methylsulfonamido)-9-azabicyclo[3.3.1]nonan-9-yl)-2-oxoethyl)-4-fluoro-N-(4-fluoro-3-methylphenyl)benzamide |
| 339 | 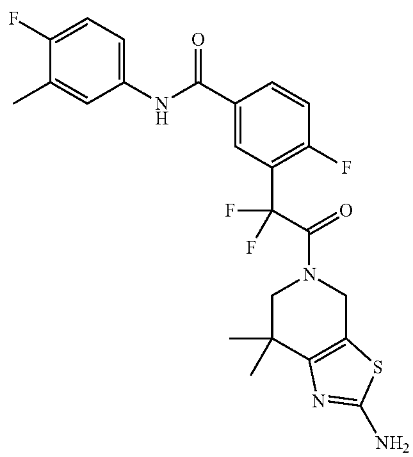 [SMILES: Cc1cc(NC(=O)c2ccc(F)c(C(F)(F)C(=O)N3Cc4sc(N)nc4C(C)(C)C3)c2)ccc1F] | 3-(2-(2-amino-7,7-dimethyl-6,7-dihydrothiazolo[5,4-c]pyridin-5(4H)-yl)-1,1-difluoro-2-oxoethyl)-4-fluoro-N-(4-fluoro-3-methylphenyl)benzamide |
| 340 | 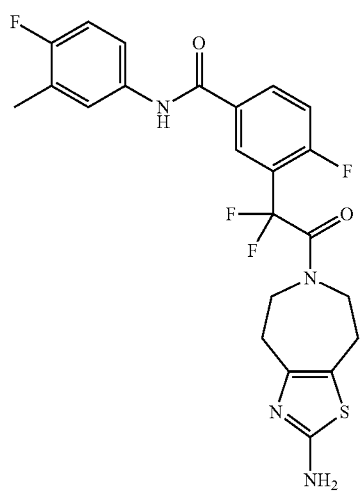 [SMILES: Cc1cc(NC(=O)c2ccc(F)c(C(F)(F)C(=O)N3CCc4nc(N)sc4CC3)c2)ccc1F] | 3-(2-(2-amino-4,5,7,8-tetrahydro-6H-thiazolo[4,5-d]azepin-6-yl)-1,1-difluoro-2-oxoethyl)-4-fluoro-N-(4-fluoro-3-methylphenyl)benzamide |

TABLE 1-continued

Exemplary compounds.

| Example | Structure | Chemical Name |
|---|---|---|
| 341 | 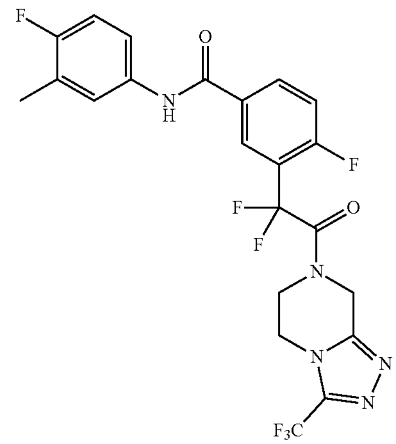 [SMILES: Cc1cc(NC(=O)c2ccc(F)c(C(F)(F)C(=O)N3CCn4c(nnc4C(F)(F)F)C3)c2)ccc1F] | 3-(1,1-difluoro-2-oxo-2-(3-(trifluoromethyl)-5,6-dihydro-[1,2,4]triazolo[4,3-a]pyrazin-7(8H)-yl)ethyl)-4-fluoro-N-(4-fluoro-3-methylphenyl)benzamide |
| 342 | 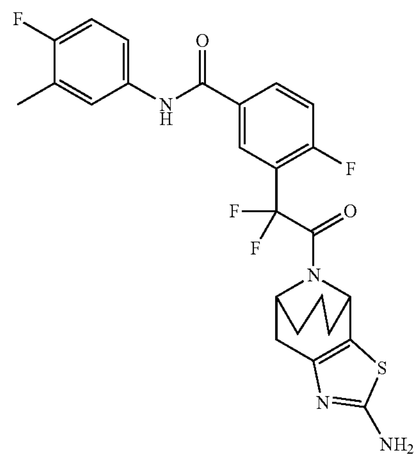 [SMILES: Cc1cc(NC(=O)c2ccc(F)c(C(F)(F)C(=O)N3C4CCCC3c3sc(N)nc3C4)c2)ccc1F] | 3-(2-(2-amino-4,5,6,7,8,9-hexahydro-5,9-epiminocycloocta[d]thiazol-10-yl)-1,1-difluoro-2-oxoethyl)-4-fluoro-N-(4-fluoro-3-methylphenyl)benzamide |

Further Forms of Compounds Disclosed Herein
Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine, and chlorine, such as $^{2}$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein, and the pharmaceutically acceptable salts, solvates, or stereoisomers thereof which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritium, i.e. $^3$H, and carbon-14, i.e. $^{14}$C, isotopes are particularly preferred for their ease of preparation and detectability. Further, substitution with heavy isotopes such as deuterium, i.e. $^2$H, produces certain therapeutic advantages resulting from greater metabolic stability, for example increased in vivo half-life or reduced dosage requirements.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4} \text{ alkyl})_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Preparation of Compounds

Example 1: Synthesis of 3-(2-(sec-butylamino)-1,1-difluoro-2-oxoethyl)-N-(3,4-difluorophenyl)-4-fluorobenzamide

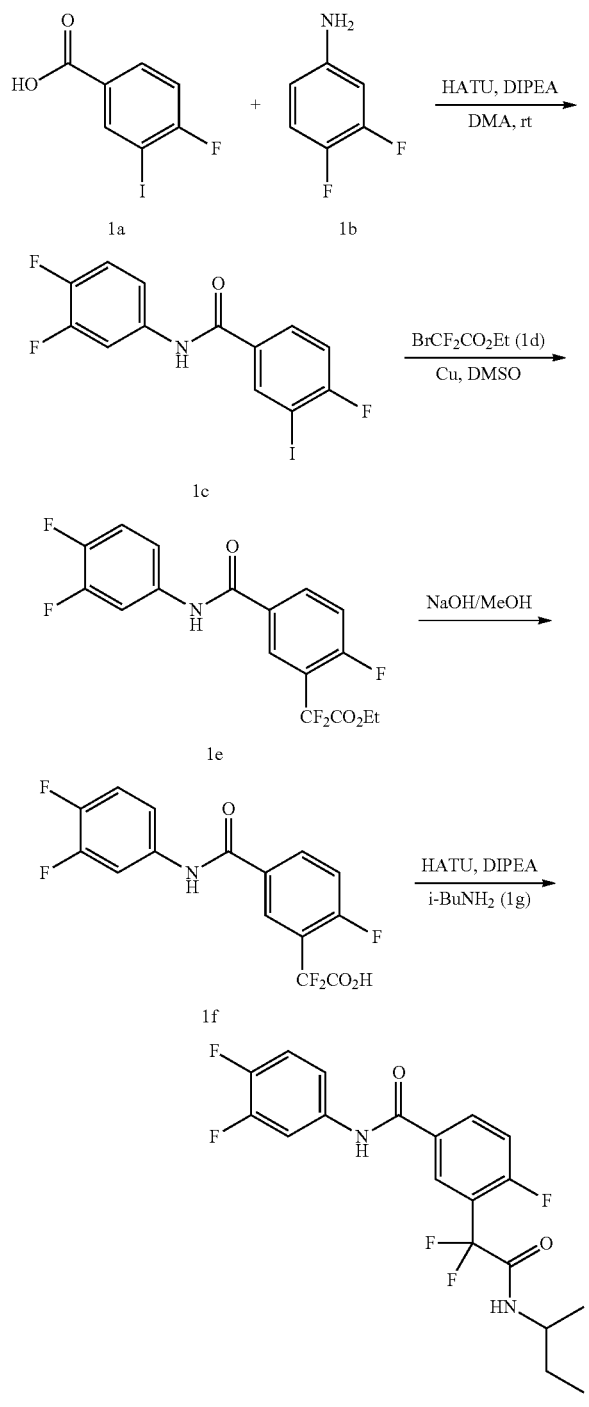

Step 1: Synthesis of N-(3,4-difluorophenyl)-4-fluoro-3-iodobenzamide (1c)

HATU (1.7 g, 4.5 mmol) was added to a solution of 4-fluoro-3-iodobenzoic acid (1 g, 3.8 mmol) in DMF (10 mL) at rt. After 30 min, 3,4-difluoroaniline (0.51 g, 3.9 mmol) and DIPEA (0.5 g, 3.8 mmol) in DMF (2 mL) were added dropwise to it. The resulting mixture was stirred at rt for 20 hrs. The reaction mixture was diluted with EtOAc, washed with water, and brine. The organic layer was dried over $Na_2SO_4$, filtered, concentrated, and purified by flash chromatography on silica gel (EtOAc/Hexanes 0~100%) to afford the product as white solid (1.0 g). ESI-MS, m/z 378 $(MH)^+$.

Step 2: Synthesis of ethyl 2-(5-((3,4-difluorophenyl)carbamoyl)-2-fluorophenyl)-2,2-difluoroacetate (1e)

A mixture of Cu (0.25 g, powder, 4 mmol) and 1c (0.5 g, 1.3 mmol) in DMSO (6 mL) was flushed with argon, then, 1d (0.27 g, 1.3 mmol) was added under argon. After 20 min at rt, the mixture was warmed to 50° C. After 20 hrs, the reaction was cooled to rt, diluted with EtOAc, filtered through celite. The filtrate was washed with saturated $NH_4Cl$, water, and brine. The solvent was evaporated in vacuo, and the residue was purified by flash chromatography on silica gel (EtOAc/Hexanes 0~50%) to afford the product as colorless oil (0.35 g). ESI-MS, m/z 374 $(MH)^+$.

Step 3: Synthesis of 2-(5-((3,4-difluorophenyl)carbamoyl)-2-fluorophenyl)-2,2-difluoroacetic acid (1f)

NaOH (2N, 1.5 mL) was added to a solution of 1e (0.3 g) in MeOH (4 mL) at 0° C. The mixture was warmed to rt. After 2 hrs, the reaction mixture was cooled to 0° C., then, neutralized to pH 2 with aqueous HCl (0.5 N). The mixture was concentrated in vacuo to remove organic solvent. The residue was dissolved in $CH_3CN$/water. After freeze-drying, afforded the crude product as white solid, which was used as such. $^1H$ NMR (300 MHz, DMSO-$d_6$) 10.78 (s, 1H), 8.23-8.28 (m, 2H), 7.91-8.25 (m, 1H), 7.38-7.6 (m, 3H); ESI-MS m/z 346 $(MH)^+$.

Step 4: Synthesis of 3-(2-(sec-butylamino)-1,1-difluoro-2-oxoethyl)-N-(3,4-difluorophenyl)-4-fluorobenzamide HATU (50 mg) was added to a solution of 1f (30 mg) in DMF (0.5 mL) at rt. After 20 min, sec-butylamine (10 mg) and DIPEA (15 mg) DMA (0.2 mL) were added dropwise. The reaction mixture was stirred at rt for 20 hrs. The reaction mixture was quenched with aqueous TFA (4%, 0.4 mL), then, extracted with EtOAc (10 mL). The organic layer was washed with water and brine, then, concentrated in vacuo. The residue was purified by reverse phase chromatography eluted with ACN and water, and dried using lyophilization to afford the title product as white solid. ESI-MS, m/z 401 $(MH)^+$.

Example 2: Synthesis of 3-(1,1-difluoro-2-(4-hydroxypiperidin-1-yl)-2-oxoethyl)-N-(3,4-difluorophenyl)-4-fluorobenzamide

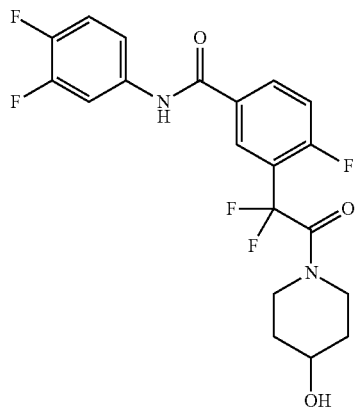 [SMILES: O=C(Nc1ccc(F)c(F)c1)c1ccc(F)c(C(F)(F)C(=O)N2CCC(O)CC2)c1]

The title compound was prepared following the procedure described in Example 1, Step 4, using piperidin-4-ol instead of sec-butylamine. The crude product was purified by reverse phase chromatography eluted with ACN and water and dried using lyophilization to afford the title product as white solid. ESI-MS, m/z 429 (MH)⁺.

Example 3: Synthesis of (S)-3-(1,1-difluoro-2-oxo-2-((tetrahydrofuran-3-yl)amino)ethyl)-N-(3,4-difluorophenyl)-4-fluorobenzamide

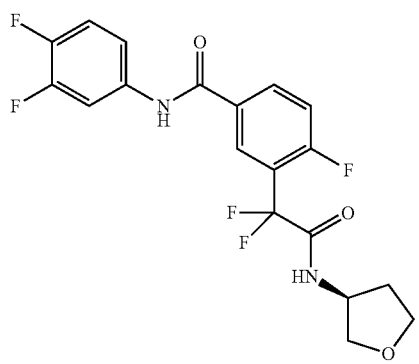 [SMILES: O=C(Nc1ccc(F)c(F)c1)c1ccc(F)c(C(F)(F)C(=O)N[C@H]2CCOC2)c1]

The title compound was prepared following the procedure described in Example 1, Step 4, using (S)-tetrahydrofuran-3-amine instead of sec-butylamine. The crude product was purified by reverse phase chromatography eluted with ACN and water and dried using lyophilization to afford the title product as white solid. ESI-MS, m/z 415 (MH)⁺.

Example 4: Synthesis of 3-(1,1-difluoro-2-morpholino-2-oxoethyl)-N-(3,4-difluorophenyl)-4-fluorobenzamide

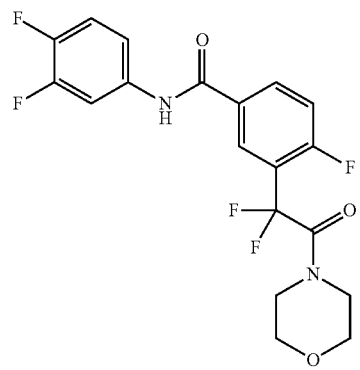 [SMILES: O=C(Nc1ccc(F)c(F)c1)c1ccc(F)c(C(F)(F)C(=O)N2CCOCC2)c1]

The title compound was prepared following the procedure described in Example 1, Step 4, using morpholine instead of sec-butylamine. The crude product was purified by reverse phase chromatography eluted with ACN and water and dried using lyophilization to afford the title product as white solid. ESI-MS, m/z 415 (MH)⁺.

Example 5: Synthesis of 3-(1,1-difluoro-2-oxo-2-((tetrahydro-2H-pyran-4-yl)amino)ethyl)-N-(3,4-difluorophenyl)-4-fluorobenzamide

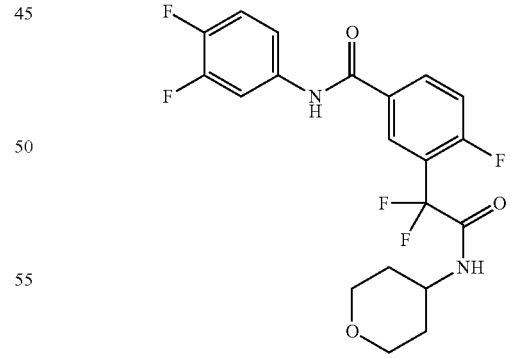

The title compound was prepared following the procedure described in Example 1, Step 4, using tetrahydro-2H-pyran-4-amine instead of sec-butylamine. The crude product was purified by reverse phase chromatography eluted with ACN and water and dried using lyophilization to afford the title product as white solid. ESI-MS, m/z 429 (MH)⁺.

Example 6: Synthesis of 3-(2-(((1,4-dioxan-2-yl)methyl)amino)-1,1-difluoro-2-oxoethyl)-N-(3,4-difluorophenyl)-4-fluorobenzamide

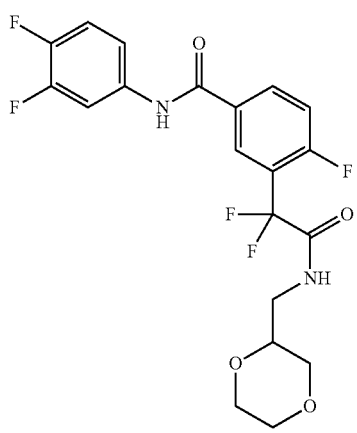 [SMILES: O=C(Nc1ccc(F)c(F)c1)c1ccc(F)c(C(F)(F)C(=O)NCC2COCCO2)c1]

The title compound was prepared following the procedure described in Example 1, Step 4, using (1,4-dioxan-2-yl)methanamine instead of sec-butylamine. The crude product was purified by reverse phase chromatography eluted with ACN and water and dried using lyophilization to afford the title product as white solid. ESI-MS, m/z 445 (MH)$^+$.

Example 7: Synthesis of 3-(1,1-difluoro-2-(isopropylamino)-2-oxoethyl)-N-(3,4-difluorophenyl)-4-fluorobenzamide

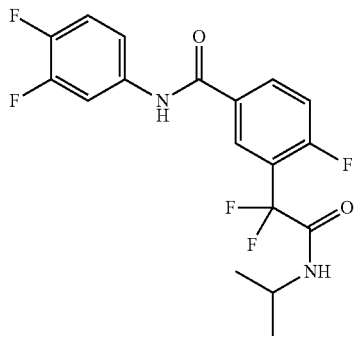 [SMILES: CC(C)NC(=O)C(F)(F)c1cc(C(=O)Nc2ccc(F)c(F)c2)ccc1F]

The title compound was prepared following the procedure described in Example 1, Step 4, using propan-2-amine instead of sec-butylamine. The crude product was purified by reverse phase chromatography eluted with ACN and water and dried using lyophilization to afford the title product as white solid. ESI-MS, m/z 387 (MH)$^+$.

Example 8: Synthesis of 3-(2-(cyclohexylamino)-1,1-difluoro-2-oxoethyl)-N-(3,4-difluorophenyl)-4-fluorobenzamide

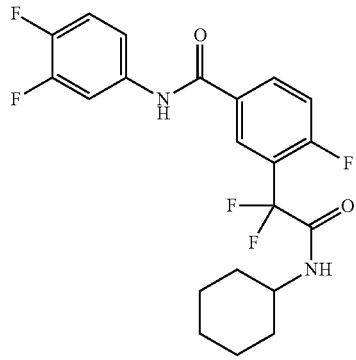

The title compound was prepared following the procedure described in Example 1, Step 4, using cyclohexanamine instead of sec-butylamine. The crude product was purified by reverse phase chromatography eluted with ACN and water and dried using lyophilization to afford the title product as white solid. ESI-MS, m/z 427 (MH)$^+$.

Example 9: Synthesis of 3-(1,1-difluoro-2-(isopropylamino)-2-oxoethyl)-N-(3,4-difluorophenyl)-4-methylbenzamide

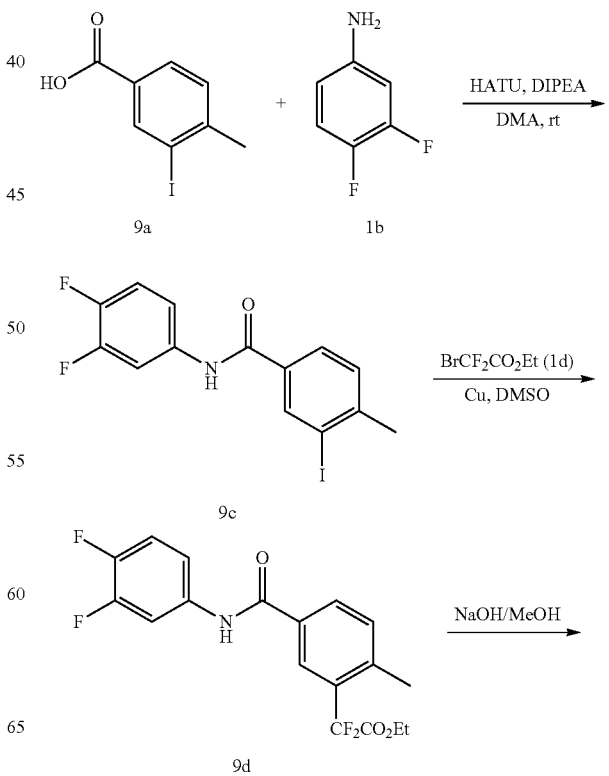

-continued

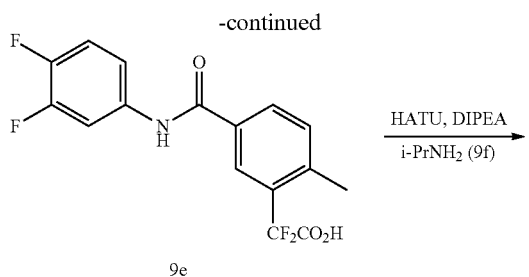

9e

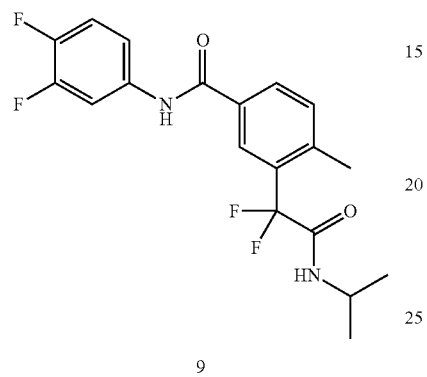

9

The title compound was prepared following the procedures described in Example 1, Steps 1 through 4, using compound 9a and 9f instead of 1a and 1g. The crude product was purified by reverse phase chromatography eluted with ACN and water and dried using lyophilization to afford the title product as white solid. ESI-MS, m/z 383 (MH)$^+$.

Example 10: Synthesis of 3-(1,1-difluoro-2-(4-hydroxypiperidin-1-yl)-2-oxoethyl)-N-(3,4-difluorophenyl)-4-methylbenzamide

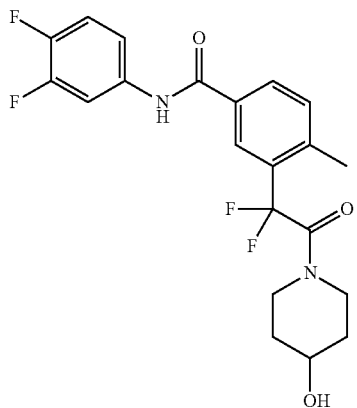

The title compound was prepared following the procedure described in Example 1, Step 4, using compound 9e and piperidin-4-ol. The crude product was purified by reverse phase chromatography eluted with ACN and water and dried using lyophilization to afford the title product as white solid. ESI-MS, m/z 425 (MH)$^+$.

Example 11: Synthesis of 3-(1,1-difluoro-2-oxo-2-(piperidin-1-yl)ethyl)-N-(3,4-difluorophenyl)-4-fluorobenzamide

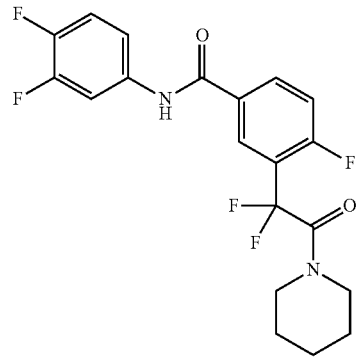 [SMILES: O=C(Nc1ccc(F)c(F)c1)c1ccc(F)c(C(F)(F)C(=O)N2CCCCC2)c1]

The title compound was prepared following the procedure described in Example 1, Step 4, using piperidine instead of sec-butylamine. The crude product was purified by reverse phase chromatography eluted with ACN and water and dried using lyophilization to afford the title product as white solid. ESI-MS, m/z 413 (MH)$^+$.

Example 12: Synthesis of (S)-3-(1,1-difluoro-2-(3-hydroxypyrrolidin-1-yl)-2-oxoethyl)-N-(3,4-difluorophenyl)-4-fluorobenzamide

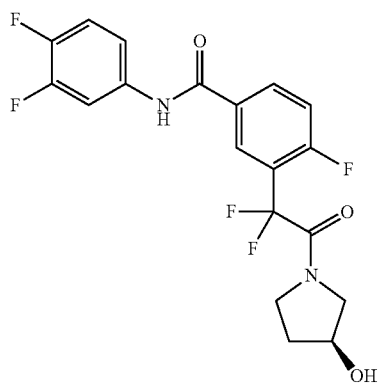 [SMILES: O=C(Nc1ccc(F)c(F)c1)c1ccc(F)c(C(F)(F)C(=O)N2CC[C@H](O)C2)c1]

The title compound was prepared following the procedure described in Example 1, Step 4, using (S)-pyrrolidin-3-ol instead of sec-butylamine. The crude product was purified by reverse phase chromatography eluted with ACN and water and dried using lyophilization to afford the title product as white solid. ESI-MS, m/z 415 (MH)$^+$.

Example 13: Synthesis of (S)-3-(1,1-difluoro-2-(3-(hydroxymethyl)pyrrolidin-1-yl)-2-oxoethyl)-N-(3,4-difluorophenyl)-4-fluorobenzamide

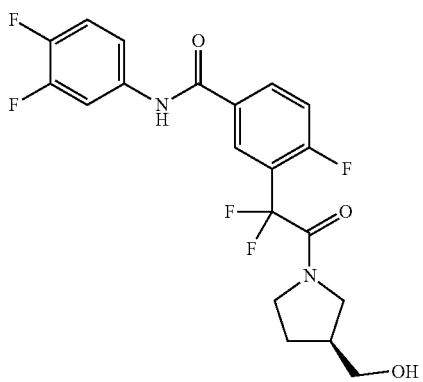 [SMILES: O=C(Nc1ccc(F)c(F)c1)c1ccc(F)c(C(F)(F)C(=O)N2CC[C@H](CO)C2)c1]

The title compound was prepared following the procedure described in Example 1, Step 4, using (S)-pyrrolidin-3-ylmethanol instead of sec-butylamine. The crude product was purified by reverse phase chromatography eluted with ACN and water and dried using lyophilization to afford the title product as white solid. ESI-MS, m/z 429 (MH)+.

Example 14: Synthesis of 3-(1,1-difluoro-2-(4-hydroxypiperidin-1-yl)-2-oxoethyl)-N-(4-fluoro-3-methylphenyl)benzamide

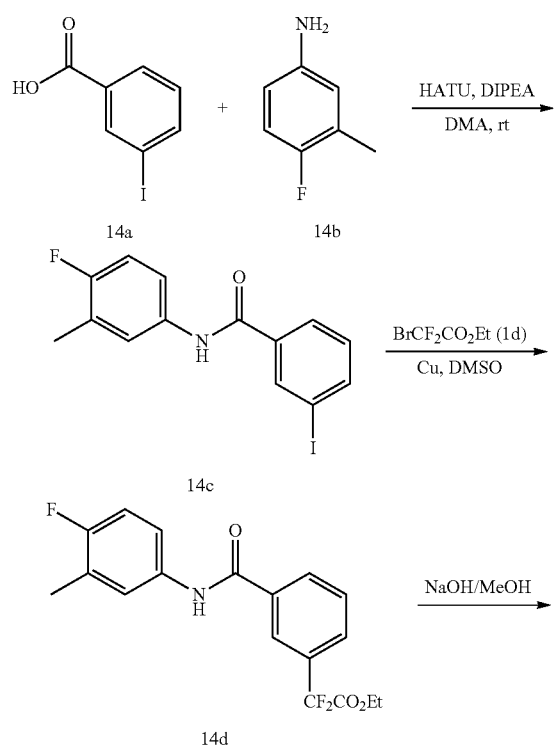

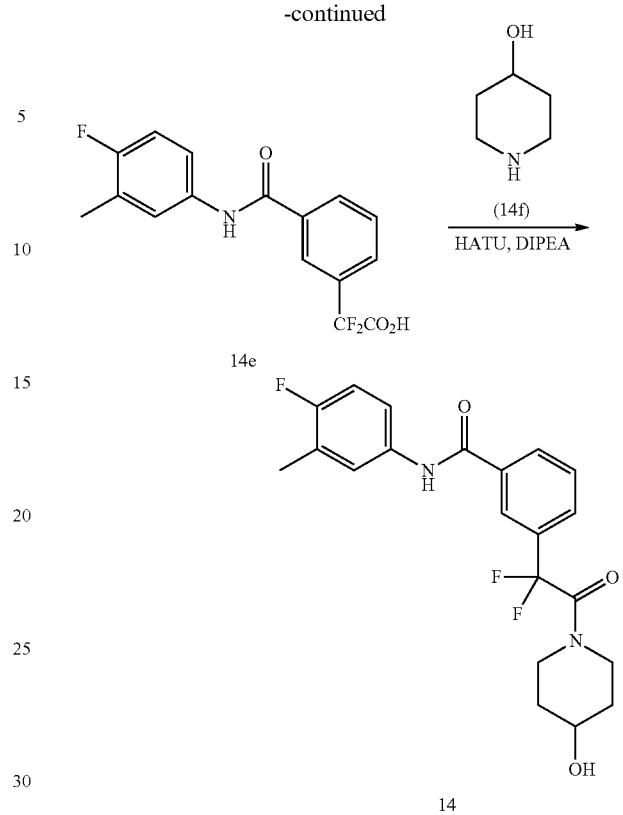

The title compound was prepared from 14a, 14b, and 14f, following the procedure described in Example 1. The crude product was purified by reverse phase chromatography eluted with ACN and water and dried using lyophilization to afford the title product as white solid. ESI-MS, m/z 407 (MH)+.

Example 15: Synthesis of 3-(1,1-difluoro-2-(3-hydroxypiperidin-1-yl)-2-oxoethyl)-N-(3,4-difluorophenyl)-4-fluorobenzamide

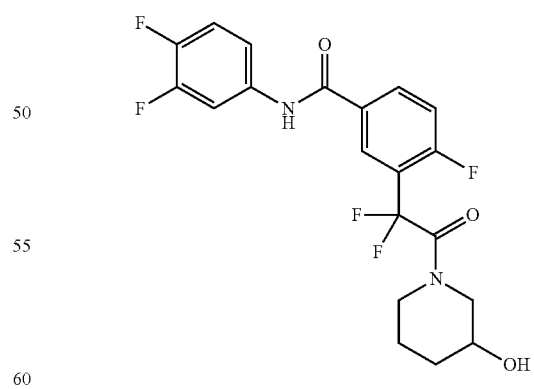

The title compound was prepared following the procedure described in Example 1, Step 4, using piperidin-3-ol instead of sec-butylamine. The crude product was purified by reverse phase chromatography eluted with ACN and water and dried using lyophilization to afford the title product as white solid. ESI-MS, m/z 429 (MH)+.

Example 16: Synthesis of 3-(2-(bis(2-hydroxyethyl)amino)-1,1-difluoro-2-oxoethyl)-N-(3,4-difluorophenyl)-4-fluorobenzamide

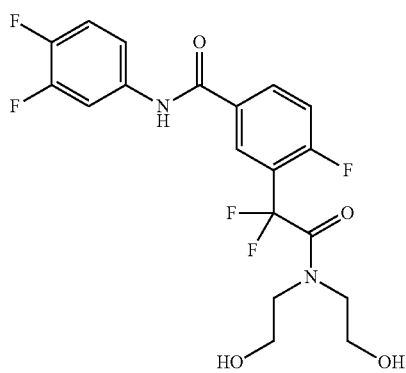 [SMILES: O=C(Nc1ccc(F)c(F)c1)c1ccc(F)c(C(F)(F)C(=O)N(CCO)CCO)c1]

The title compound was prepared following the procedure described in Example 1, Step 4, using 2,2'-azanediylbis(ethan-1-ol) instead of sec-butylamine. The crude product was purified by reverse phase chromatography eluted with ACN and water and dried using lyophilization to afford the title product as white solid. ESI-MS, m/z 433 (MH)+.

Example 17: Synthesis of 4-chloro-3-(1,1-difluoro-2-(4-hydroxypiperidin-1-yl)-2-oxoethyl)-N-(4-fluoro-3-methylphenyl)benzamide

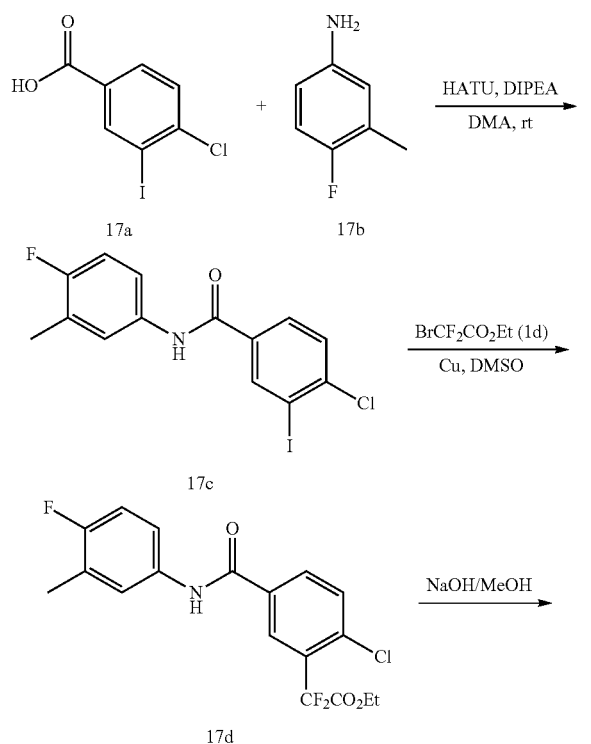

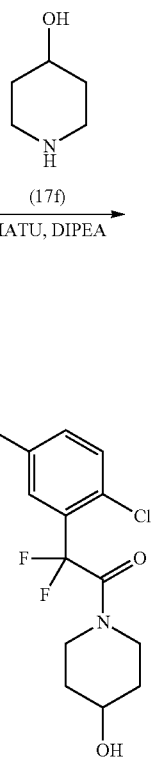

The title compound was prepared from 17a, 17b, and 17f, following the procedure described in Example 1, Steps 1 through 4. The crude product was purified by reverse phase chromatography eluted with ACN and water and dried using lyophilization to afford the title product as white solid. ESI-MS, m/z 441 (MH)+.

Example 18: Synthesis of 3-(2-(tert-butylamino)-1,1-difluoro-2-oxoethyl)-N-(3,4-difluorophenyl)-4-fluorobenzamide

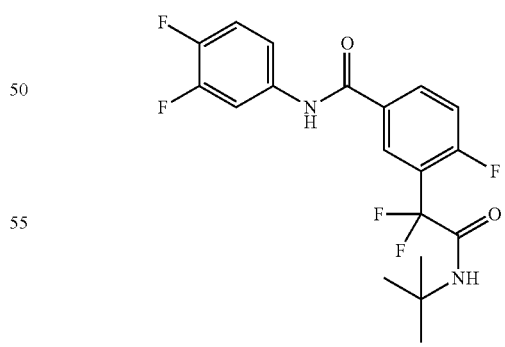

The title compound was prepared following the procedure described in Example 1, Step 4, using tert-butylamine instead of sec-butylamine. The crude product was purified by reverse phase chromatography eluted with ACN and water and dried using lyophilization to afford the title product as white solid. ESI-MS m/z 401 (MH)+.

Example 19: Synthesis of 3-(1,1-difluoro-2-oxo-2-(tert-pentylamino)ethyl)-N-(3,4-difluorophenyl)-4-fluorobenzamide

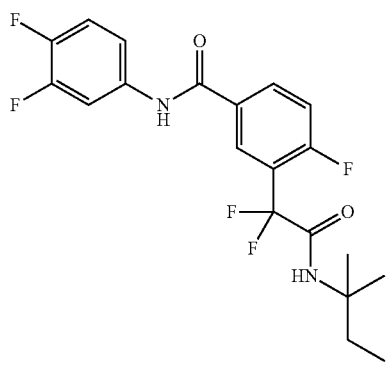 [SMILES: CCC(C)(C)NC(=O)C(F)(F)c1cc(C(=O)Nc2ccc(F)c(F)c2)ccc1F]

The title compound was prepared following the procedure described in Example 1, Step 4, using 2-methylbutan-2-amine instead of sec-butylamine. The crude product was purified by reverse phase chromatography eluted with ACN and water and dried using lyophilization to afford the title product as white solid. ESI-MS, m/z 415 (MH)$^+$.

Example 20: Synthesis of 3-(2-(cyclopentylamino)-1,1-difluoro-2-oxoethyl)-N-(3,4-difluorophenyl)-4-fluorobenzamide

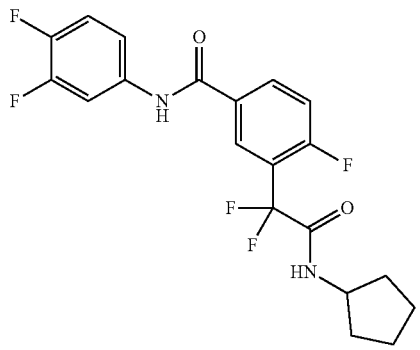 [SMILES: O=C(Nc1ccc(F)c(F)c1)c1ccc(F)c(C(F)(F)C(=O)NC2CCCC2)c1]

The title compound was prepared following the procedure described in Example 1, Step 4, using cyclopentanamine instead of sec-butylamine. The crude product was purified by reverse phase chromatography eluted with ACN and water and dried using lyophilization to afford the title product as white solid. ESI-MS, m/z 413 (MH)$^+$.

Example 21: Synthesis of 3-(1,1-difluoro-2-((2-methoxyphenyl)amino)-2-oxoethyl)-N-(3,4-difluorophenyl)-4-fluorobenzamide

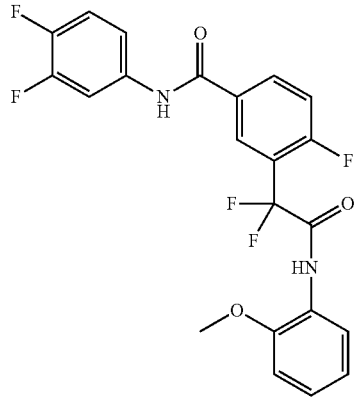 [SMILES: COc1ccccc1NC(=O)C(F)(F)c1cc(C(=O)Nc2ccc(F)c(F)c2)ccc1F]

The title compound was prepared following the procedure described in Example 1, Step 4, using 2-methoxyaniline instead of sec-butylamine. The crude product was purified by reverse phase chromatography eluted with ACN and water and dried using lyophilization to afford the title product as white solid. ESI-MS, m/z 451 (MH)$^+$.

Example 22: Synthesis of 3-(1,1-difluoro-2-((5-fluoropyridin-2-yl)amino)-2-oxoethyl)-N-(3,4-difluorophenyl)-4-fluorobenzamide

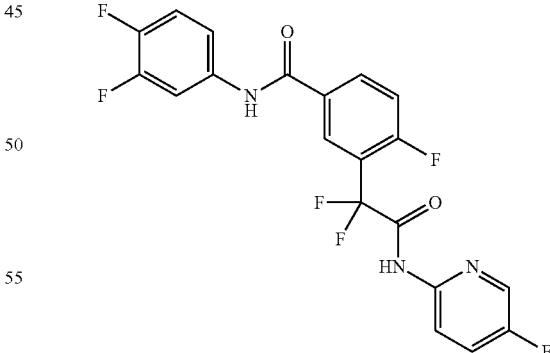

The title compound was prepared following the procedure described in Example 1, Step 4, using 5-fluoropyridin-2-amine instead of sec-butylamine. The crude product was purified by reverse phase chromatography eluted with ACN and water and dried using lyophilization to afford the title product as white solid. ESI-MS, m/z 440 (MH)$^+$.

Example 23: Synthesis of 4-chloro-3-(1,1-difluoro-2-(isopropylamino)-2-oxoethyl)-N-(4-fluoro-3-methylphenyl)benzamide

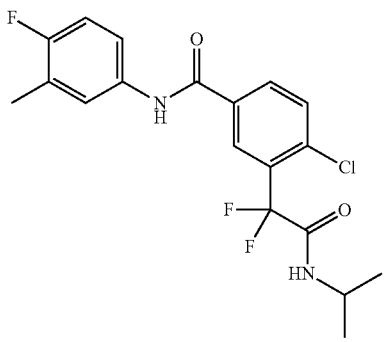

The title compound was prepared following the procedure described in Example 1, Step 4, using compound 17e and propan-2-amine. The crude product was purified by reverse phase chromatography eluted with ACN and water and dried using lyophilization to afford the title product as white solid. ESI-MS, m/z 399 (MH)$^+$.

Example 24: Synthesis of 3-(1,1-difluoro-2-((1-hydroxy-2-methylpropan-2-yl)amino)-2-oxoethyl)-N-(3,4-difluorophenyl)-4-fluorobenzamide

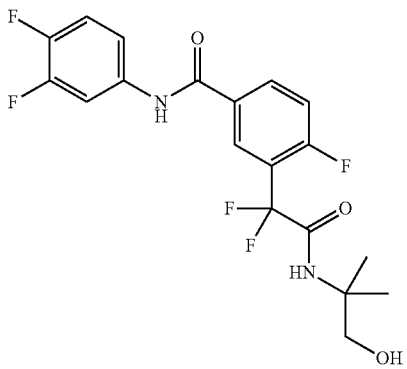 [SMILES: CC(C)(CO)NC(=O)C(F)(F)c1cc(C(=O)Nc2ccc(F)c(F)c2)ccc1F]

The title compound was prepared following the procedure described in Example 1, Step 4, using 2-amino-2-methylpropan-1-ol instead of sec-butylamine. The crude product was purified by reverse phase chromatography eluted with ACN and water and dried using lyophilization to afford the title product as white solid. ESI-MS, m/z 417 (MH)$^+$.

Example 25: Synthesis of 3-(1,1-difluoro-2-(3-hydroxyazepan-1-yl)-2-oxoethyl)-N-(3,4-difluorophenyl)-4-fluorobenzamide

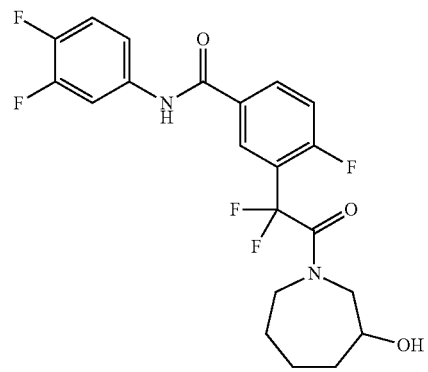 [SMILES: O=C(Nc1ccc(F)c(F)c1)c1ccc(F)c(C(F)(F)C(=O)N2CCCCC(O)C2)c1]

The title compound was prepared following the procedure described in Example 1, Step 4, using azepan-3-ol instead of sec-butylamine. The crude product was purified by reverse phase chromatography eluted with ACN and water and dried using lyophilization to afford the title product as white solid. ESI-MS, m/z 443 (MH)$^+$.

Example 26: Synthesis of 3-(1,1-difluoro-2-(((1r,4r)-4-hydroxycyclohexyl)amino)-2-oxoethyl)-N-(3,4-difluorophenyl)-4-fluorobenzamide

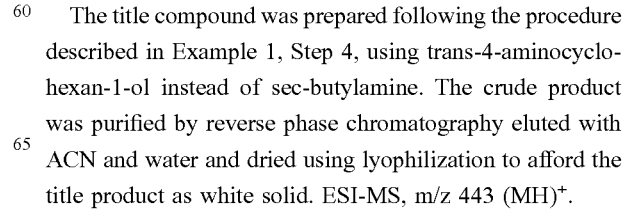

The title compound was prepared following the procedure described in Example 1, Step 4, using trans-4-aminocyclohexan-1-ol instead of sec-butylamine. The crude product was purified by reverse phase chromatography eluted with ACN and water and dried using lyophilization to afford the title product as white solid. ESI-MS, m/z 443 (MH)$^+$.

Example 27: Synthesis of 3-(1,1-difluoro-2-(((1S, 4S)-4-hydroxycyclohexyl)amino)-2-oxoethyl)-N-(3, 4-difluorophenyl)-4-fluorobenzamide

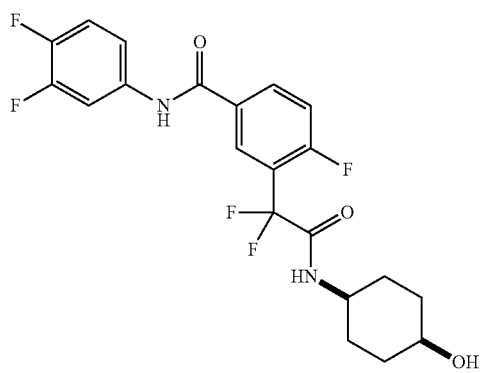

The title compound was prepare following the procedure described in Example 1, Step 4, using cis-4-aminocyclohexan-1-ol instead of sec-butylamine. The crude product was purified by reverse phase chromatography eluted with ACN and water and dried using lyophilization to afford the title product as white solid. ESI-MS, m/z 443 (MH)$^+$.

Example 28: Synthesis of 3-(1,1-difluoro-2-((1-hydroxy-2-methylpropan-2-yl)amino)-2-oxoethyl)-4-fluoro-N-(4-fluoro-3-methylphenyl)benzamide

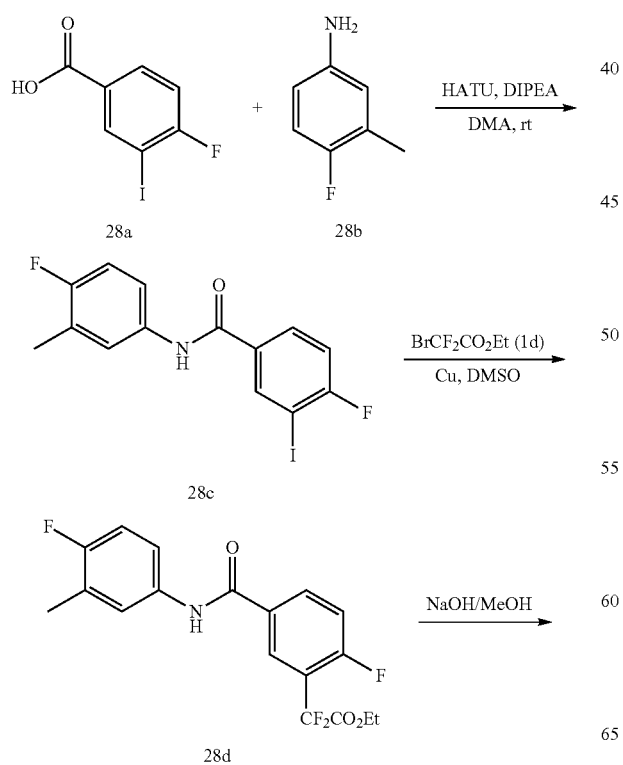

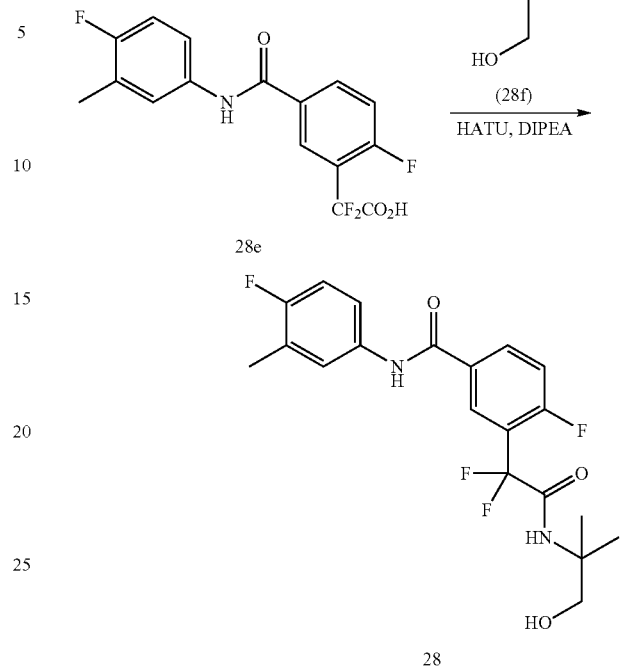

The title compound was prepared from 28a, 28b, and 28f, following the procedure described in Example 1. The product was purified by reverse phase chromatography eluted with ACN and water and dried using lyophilization to afford the title product as white solid. ESI-MS, m/z 413 (MH)$^+$.

Example 29: Synthesis of 3-(1,1-difluoro-2-(4-hydroxypiperidin-1-yl)-2-oxoethyl)-4-fluoro-N-(4-fluoro-3-methylphenyl)benzamide

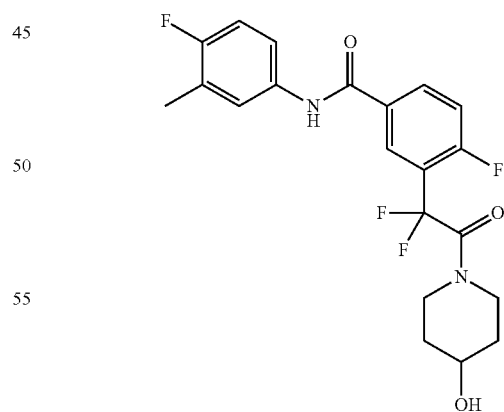

The title compound was prepared following the procedure described in Example 1, Step 4, using piperidin-4-ol and 28e. The crude product was purified by reverse phase chromatography eluted with ACN and water and concentrated using lyophilization to afford the title product as white solid. ESI-MS, m/z 425 (MH)$^+$.

Example 30: Synthesis of 2-(1,1-difluoro-2-(4-hydroxypiperidin-1-yl)-2-oxoethyl)-N-(4-fluoro-3-methylphenyl)thiazole-4-carboxamide

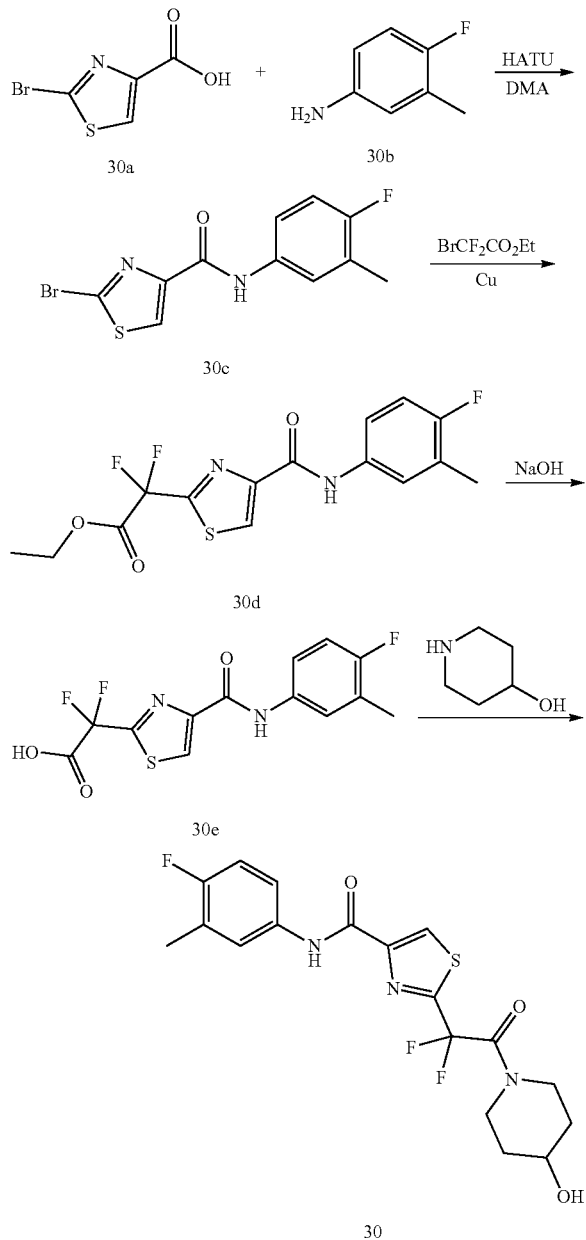

Step 1: Synthesis of 2-bromo-N-(4-fluoro-3-methylphenyl)thiazole-4-carboxamide (30c)

Compound 30c was prepared following the procedure in Example 1, Step 1, using 2-bromothiazole-4-carboxylic acid instead of 1a, to provide the title compound as a white solid: $^1$HNMR (300 MHz, CDCl3) 8.93 (s, 1H), 8.14 (s, 1H), 7.53 (d, 1H, J=6.0 Hz), 7.43-7.46 (m, 1H), 6.99 (dd, 1H, J=8.7 & 9.3 Hz), 2.28 (s, 3H); ESI-MS, m/z 315/317 (MH)$^+$.

Step 2: Synthesis of ethyl 2,2-difluoro-2-(4-((4-fluoro-3-methylphenyl)carbamoyl)thiazol-2-yl)acetate (30d)

A mixture of 30c (0.3 g, 0.95 mmol), and Cu (0.2 g, 3.1 mmol) in DMSO (6 mL) was flushed with argon. Then, ethyl 2-bromo-2,2-difluoroacetate (0.2 g, 0.95 mmol) was added under argon. The mixture was heated at 60° C. for 12 hrs. After cooled to rt, the reaction mixture was diluted with EtOAc, then, washed saturated NH$_4$Cl. The organic layer was separated, washed with water/brine, concentrated and purified by flash chromatography on silica gel (EtOAc/Hexanes 0~100%) to afford the product as yellow oil (0.1 g): $^1$HNMR (300 MHz, CDCl$_3$) 8.92 (s, 1H), 8.41 (s, 1H), 7.52 (d, 1H, J=6.3 Hz), 7.42-7.46 (m, 1H), 6.99 (dd, 1H, J=9.1 & 9.3 Hz), 4.4-4.48 (m, 2H), 2.28 (s, 3H), 1.38 (t, 3H, J=7.2 Hz). ESI-MS, m/z 359 (MH)$^+$.

Step 3: Synthesis of 2,2-difluoro-2-(4-((4-fluoro-3-methylphenyl)carbamoyl)thiazol-2-yl)acetic acid (30e)

The title compound was prepared following the procedure in Example 1, Step 3, isolated as white solid: ESI-MS, m/z 331 (MH)$^+$.

Step 4: Synthesis of 2-(1,1-difluoro-2-(4-hydroxypiperidin-1-yl)-2-oxoethyl)-N-(4-fluoro-3-methylphenyl)thiazole-4-carboxamide The title compound was prepared following the procedure in Example 1, Step 4, using 30e and piperidin-4-ol. The crude product was purified by reverse phase chromatography eluted with ACN and water and dried using lyophilization to afford the title product as white solid. ESI-MS, m/z 414 (MH)$^+$.

Example 31: Synthesis of N-(3,4-difluorophenyl)-4-fluoro-3-(1-fluoro-2-((1-hydroxy-2-methylpropan-2-yl)amino)-2-oxoethyl)benzamide

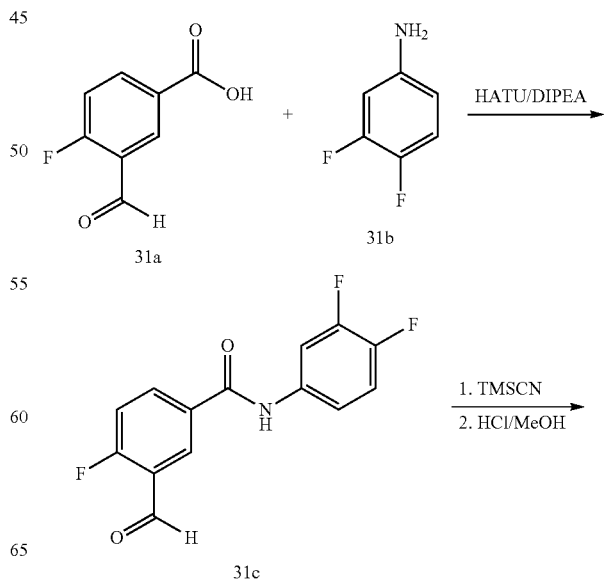

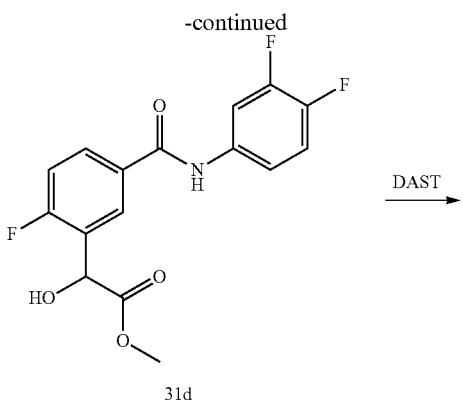

31d

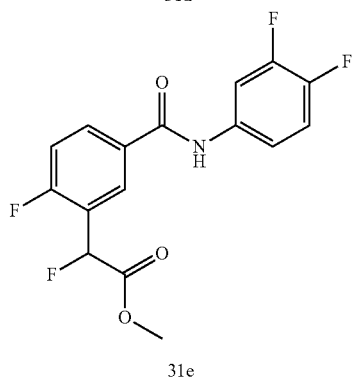

31e

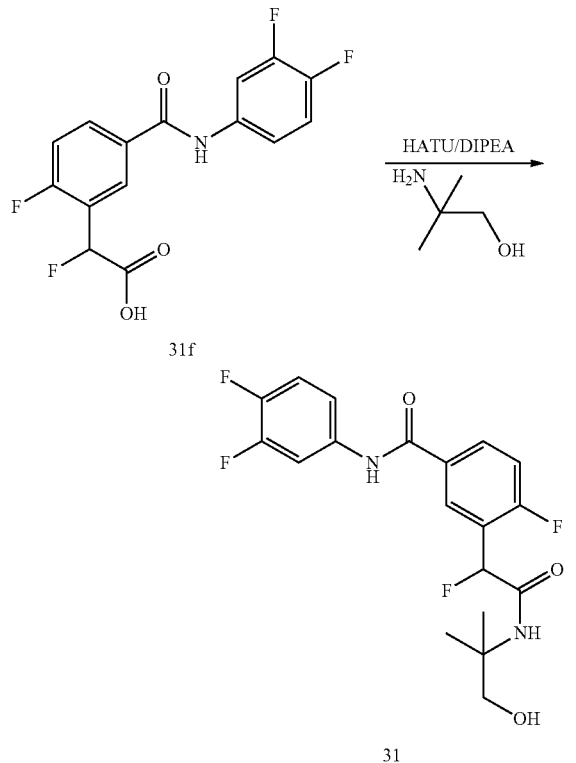

31f

31

Step 1: Synthesis of N-(3,4-difluorophenyl)-4-fluoro-3-formylbenzamide (31c)

Compound (31c) was prepared following the procedure described in Example 1, Step 1, isolated as yellow solid. ESI-MS, m/z 280 (MH)+.

Step 2: Synthesis of methyl 2-(5-((3,4-difluorophenyl)carbamoyl)-2-fluorophenyl)-2-hydroxyacetate (31d)

Trimethylsilyl cyanide (TMSCN, 0.16 g, 1.6 mmol) was added to a solution of 31c (0.3 g, 1 mmol) and DMAP (15 mg) in 20 mL of CH$_3$CN at rt. The reaction mixture was stirred at rt for 4 hrs. The solvent was evaporated in vacuo, and the residue was dissolved in 50 mL of methanolic HC solution (~3 N). The mixture was stirred at rt for 20 hrs, then, the solvent was removed in vacuo. The residues was purified by flash chromatography on silica gel (EtOAc/Hexanes 0~100%) to afford the product as yellow solid (0.25 g): $^1$HNMR (300 MHz, CDCl$_3$) 7.8-7.9 (m, 3H), 7.68-7.74 (m, 1H), 7.1-7.2 (m, 3H), 5.42 (s, 1H), 3.79 (s, 3H), 3.65 (s, 1H); ESI-MS, m/z 340) (MH)+.

Step 3: Synthesis of methyl 2-(5-((3,4-difluorophenyl)carbamoyl)-2-fluorophenyl)-2-fluoroacetate (31e)

(Diethylamino)sulfur trifluoride (DAST, 0.12 g) was added to a solution of 31d (0.2 g, 0.6 mmol) in DCM (2 mL) at −78° C. After 2 hrs, the reaction mixture was warmed to 0° C. for 20 min. The reaction mixture was quenched with saturated NaHCO$_3$ at 0° C. The organic layer was separated and purified by flash chromatography on silica gel (EtOAc/Hexanes 0~100%) to afford the title compound as yellow oil (0.14 g). $^1$HNMR (300 MHz, DMSO-d$_6$) 10.83 (s, 1H), 8.24 (br, 1H), 8.17 (d, 1H, J=7.2 Hz), 7.92-8.02 (m, 1H), 7.62 (d, 1H, J=9.0 Hz), 7.39-7.49 (m, 2H), 6.22 (d, 1H, J=42.9 Hz); ESI-MS, m/z 328 (MH)+.

Step 4: Synthesis of 2-(5-((3,4-difluorophenyl)carbamoyl)-2-fluorophenyl)-2-fluoroacetic acid The title compound was prepared following the procedure of Example 1, Step 3.

Step 5: Synthesis of N-(3,4-difluorophenyl)-4-fluoro-3-(1-fluoro-2-((1-hydroxy-2-methylpropan-2-yl)amino)-2-oxoethyl)benzamide The title compound was prepared following the procedure described in Example 1, Step 4, using 31f. The crude product was purified by reverse phase chromatography eluted with ACN and water and dried using lyophilization to afford the title product as white solid. ESI-MS, m/z 399 (MH)+.

Example 32: Synthesis of N-(3,4-difluorophenyl)-4-fluoro-3-(1-fluoro-2-(4-hydroxypiperidin-1-yl)-2-oxoethyl)benzamide

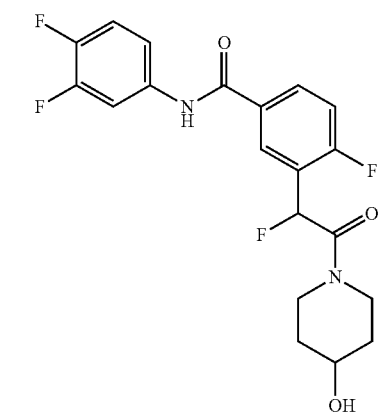 [SMILES: O=C(Nc1ccc(F)c(F)c1)c1ccc(F)c(C(F)C(=O)N2CCC(O)CC2)c1]

The title compound was prepared following the procedure described in Example 1, Step 4, using 31e and piperidin-4-ol. The crude product was purified by reverse phase chromatography eluted with ACN and water and dried using lyophilization to afford the title product as white solid. ESI-MS, m/z 411 (MH)+.

Example 33: Synthesis of 4-chloro-N-(3-cyano-4-fluorophenyl)-3-(1,1-difluoro-2-(4-hydroxypiperidin-1-yl)-2-oxoethyl)benzamide

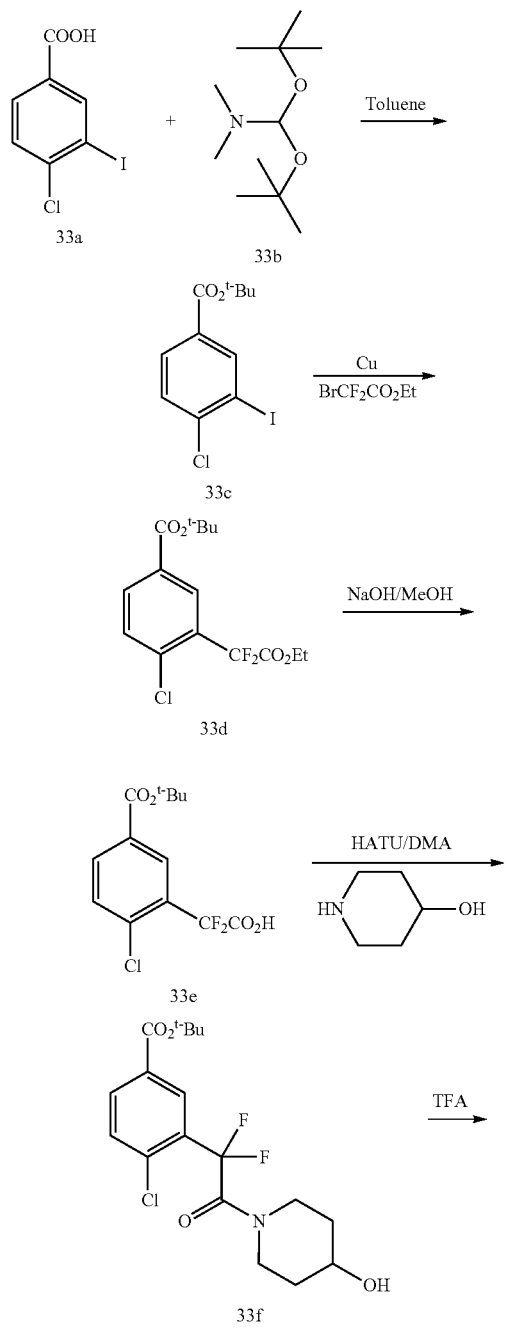

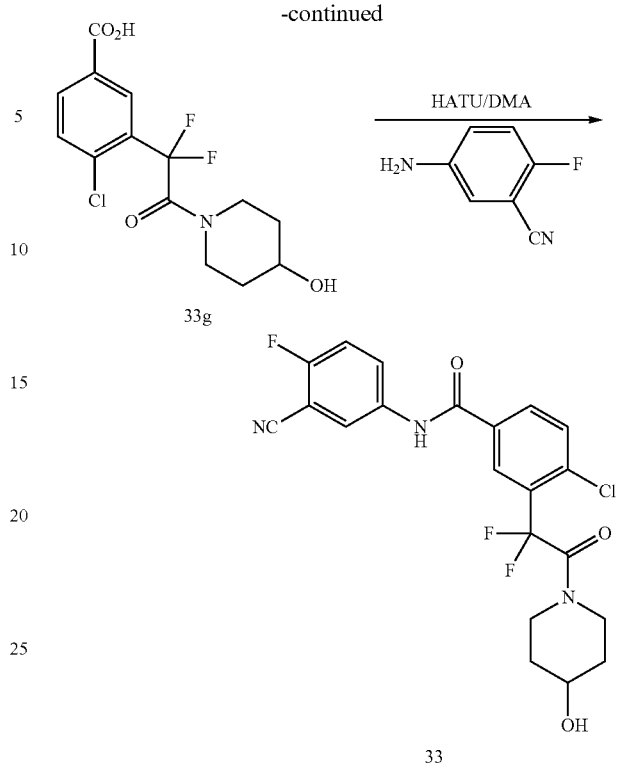

Step 1: Synthesis of tert-butyl 4-chloro-3-iodobenzoate (33c)

Compound 33b (7.2 g, 35.4 mmol) was added in a dropwise fashion to a solution of 33a (2 g, 7.1 mmol) in toluene (100 mL) at 85° C. under argon. After 1 hr at 85° C., the reaction mixture was cooled to rt, and quenched with water (20 mL). The organic layer was separated, washed with saturated NaHCO$_3$ and brine. The solvent was removed in vacuo, and the residue was purified by flash chromatography on silica gel (EtOAc/Hexanes 0~30%) to afford the product as colorless oil (1.8 g, 80%): $^1$H NMR (300 MHz, CDCl$_3$) 8.33 (d, 1H, J=1.8 Hz), 8.04 (dd, 1H, J=1.8 & 8.4 Hz), 7.46 (d, 1H, J=8.1 Hz), 4.35 (q, 2H, J=6.9 Hz), 1.59 (s, 9H), 1.31 (t, 3H, J=6.9 Hz).

Step 2: Synthesis of tert-butyl 4-chloro-3-(2-ethoxy-1,1-difluoro-2-oxoethyl)benzoate (33d)

The title compound was prepared following the procedure described in Example 1, Step 2, using 33c instead of 1c. The crude product was purified flash chromatography on silica gel (EtOAc/Hexanes 0~50%) to afford the product as colorless oil (1.4 g, 72%). $^1$H NMR (300 MHz, DMSO-d$_6$) 8.13 (d, 1H, J=1.8 Hz), 8.05 (dd, 1H, J=1.5 & 8.1 Hz), 7.76 (d, 1H, J=8.1 Hz), 1.52 (s, 9H).

Step 3: Synthesis of 2-(5-(tert-butoxycarbonyl)-2-chlorophenyl)-2,2-difluoroacetic acid (33e)

The title compound was prepared following the procedure described in Example 1, Step 3, using 33d instead of id, and isolated as a white solid. ESI-MS, m/z 307 (MH)+.

Step 4: Synthesis of tert-butyl 4-chloro-3-(1,1-difluoro-2-(4-hydroxypiperidin-1-yl)-2-oxoethyl)benzoate (33f)

The title compound was prepared following the procedure described in Example 1, Step 4, using 33e and piperidin-4-ol. The product was purified by flash chromatography on silica gel (EtOAc/Hexanes 0~100%) as colorless oil. ESI-MS, m/z 390 (MH)+.

Step 5: Synthesis of 4-chloro-3-(1,1-difluoro-2-(4-hydroxypiperidin-1-yl)-2-oxoethyl)benzoic acid (33g)

TFA (4 mL) was added to a solution of 33f (0.8 g) in DCM (6 mL) at 0° C. After 30 min, the reaction mixture was warmed to rt for 2 hrs. The solvent was removed in vacuo, and the residue was lyophilized to dryness to afford crude 33g as white solid, which was used without further purification. ESI-MS, m/z 334 (MH)+.

Step 6: Synthesis of 4-chloro-N-(3-cyano-4-fluorophenyl)-3-(1,1-difluoro-2-(4-hydroxypiperidin-1-yl)-2-oxoethyl)benzamide The title compound was prepared following the procedure described in Example 1, Step 4, using the crude 33g and 5-amino-2-fluorobenzonitrile. The crude product was purified by reverse phase chromatography eluted with ACN and water and dried using lyophilization to afford the title product as white solid. ESI-MS, m/z 452 (MH)+.

Example 34: Synthesis of 4-chloro-3-(1,1-difluoro-2-(4-hydroxypiperidin-1-yl)-2-oxoethyl)-N-(3,4,5-trifluorophenyl)benzamide

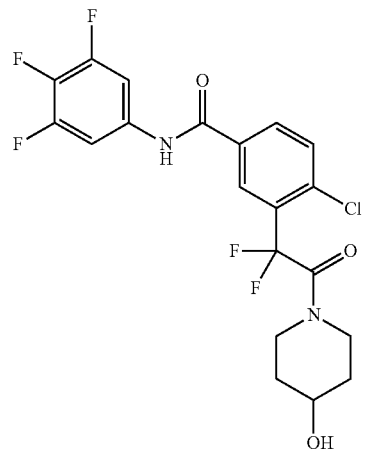 [SMILES: O=C(Nc1cc(F)c(F)c(F)c1)c1ccc(Cl)c(C(F)(F)C(=O)N2CCC(O)CC2)c1]

The title compound was prepared following the procedure described in Example 1, Step 4, using the crude 33g and 3,4,5-trifluoroaniline. The crude product was purified by reverse phase chromatography eluted with ACN and water and dried using lyophilization to afford the title product as white solid. ESI-MS, m/z 463 (MH)+.

Example 35: Synthesis of 4-chloro-N-(3-chloro-4-fluorophenyl)-3-(1,1-difluoro-2-(4-hydroxypiperidin-1-yl)-2-oxoethyl)benzamide

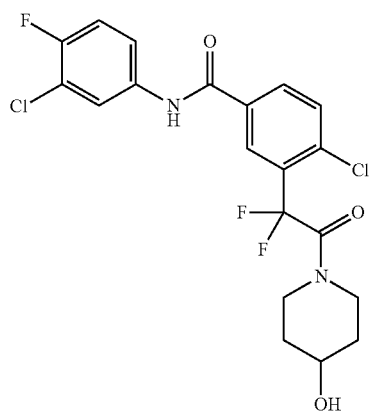 [SMILES: O=C(Nc1ccc(F)c(Cl)c1)c1ccc(Cl)c(C(F)(F)C(=O)N2CCC(O)CC2)c1]

The title compound was prepared following the procedure described in Example 1, Step 4, using the crude 33g and 3-chloro-4-fluoroaniline. The crude product was purified by reverse phase chromatography eluted with ACN and water and dried using lyophilization to afford the title product as white solid. ESI-MS, m/z 462 (MH)+.

Example 36: Synthesis of 4-chloro-3-(1,1-difluoro-2-(4-hydroxypiperidin-1-yl)-2-oxoethyl)-N-(4-fluorophenyl)benzamide

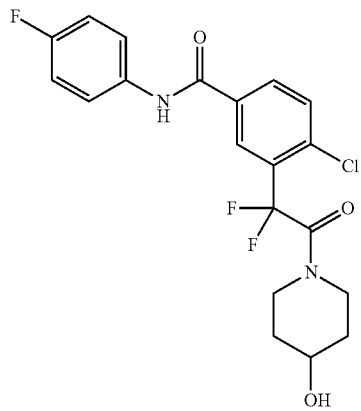

The title compound was prepared following the procedure described in Example 1, Step 4, using the crude 33g and 4-fluoroaniline. The crude product was purified by reverse phase chromatography eluted with ACN and water and dried using lyophilization to afford the title product as white solid. ESI-MS, m/z 427 (MH)+.

Example 37: Synthesis of 4-chloro-N-(4-chloro-2-fluorophenyl)-3-(1,1-difluoro-2-(4-hydroxypiperidin-1-yl)-2-oxoethyl)benzamide

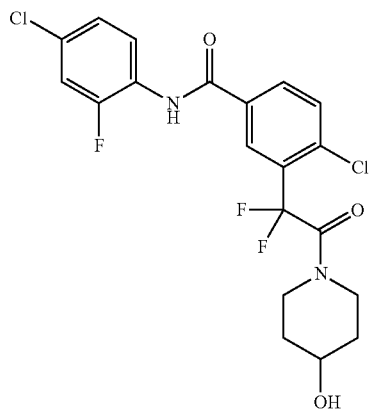 [SMILES: O=C(Nc1ccc(Cl)cc1F)c1ccc(Cl)c(C(F)(F)C(=O)N2CCC(O)CC2)c1]

The title compound was prepared following the procedure described in Example 1, Step 4, using the crude 33g and 4-chloro-2-fluoroaniline. The crude product was purified by reverse phase chromatography eluted with ACN and water and dried using lyophilization to afford the title product as white solid. ESI-MS, m/z 462 (MH)⁺.

Example 38: Synthesis of 4-chloro-3-(1,1-difluoro-2-(4-hydroxypiperidin-1-yl)-2-oxoethyl)-N-(5-fluoropyridin-2-yl)benzamide

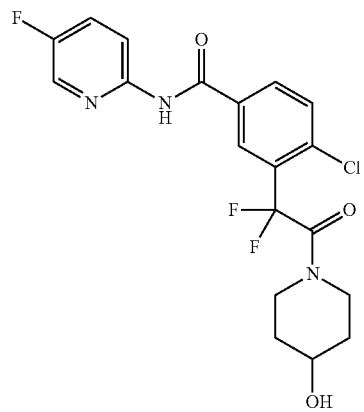 [SMILES: O=C(Nc1ccc(F)cn1)c1ccc(Cl)c(C(F)(F)C(=O)N2CCC(O)CC2)c1]

The title compound was prepared following the procedure described in Example 1, Step 4, using the crude 33g and 5-fluoropyridin-2-amine. The crude product was purified by reverse phase chromatography eluted with ACN and water and dried using lyophilization to afford the title product as white solid. ESI-MS, m/z 428 (MH)⁺.

Example 39: Synthesis of 4-chloro-N-(4-chlorophenyl)-3-(1,1-difluoro-2-(4-hydroxypiperidin-1-yl)-2-oxoethyl)benzamide

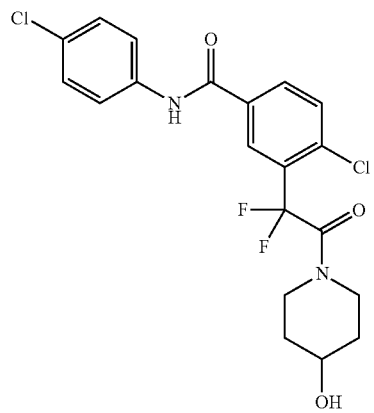 [SMILES: O=C(Nc1ccc(Cl)cc1)c1ccc(Cl)c(C(F)(F)C(=O)N2CCC(O)CC2)c1]

The title compound was prepared following the procedure described in Example 1, Step 4, using the crude 33g and 4-chloroaniline. The crude product was purified by reverse phase chromatography eluted with ACN and water and dried using lyophilization to afford the title product as white solid. ESI-MS, m/z 444 (MH)⁺.

Example 40: Synthesis of 4-chloro-N-(4-chlorophenyl)-3-(1,1-difluoro-2-(4-hydroxypiperidin-1-yl)-2-oxoethyl)-N-methylbenzamide

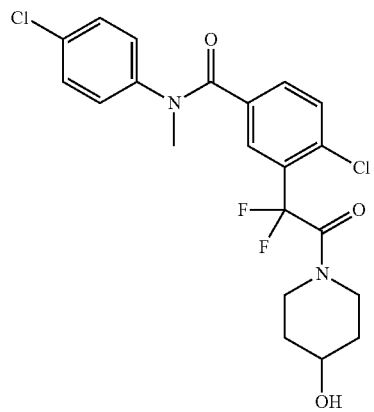 [SMILES: CN(C(=O)c1ccc(Cl)c(C(F)(F)C(=O)N2CCC(O)CC2)c1)c1ccc(Cl)cc1]

The title compound was prepared following the procedure described in Example 1, Step 4, using the crude 33g and 4-chloro-N-methylaniline. The crude product was purified by reverse phase chromatography eluted with ACN and water and dried using lyophilization to afford the title product as white solid. ESI-MS, m/z 458 (MH)⁺.

Example 41: Synthesis of 4-chloro-N-(2-chloro-4-fluorophenyl)-3-(1,1-difluoro-2-(4-hydroxypiperidin-1-yl)-2-oxoethyl)benzamide

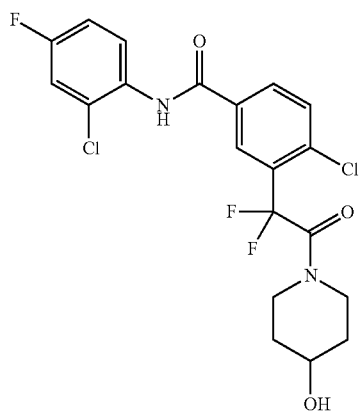 [SMILES: O=C(Nc1ccc(F)cc1Cl)c1ccc(Cl)c(C(F)(F)C(=O)N2CCC(O)CC2)c1]

The title compound was prepare following the procedure described in Example 1, Step 4, using the crude 33g and 2-chloro-4-fluoroaniline. The crude product was purified by reverse phase chromatography eluted with ACN and water and dried using lyophilization to afford the title product as white solid. ESI-MS, m/z 462 (MH)⁺.

Example 42: Synthesis of 4-chloro-3-(1,1-difluoro-2-(4-hydroxypiperidin-1-yl)-2-oxoethyl)-N-(3,4-difluorophenyl)benzamide

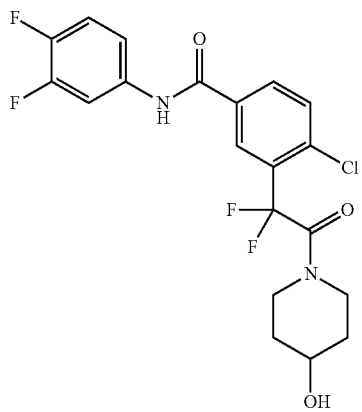 [SMILES: O=C(Nc1ccc(F)c(F)c1)c1ccc(Cl)c(C(F)(F)C(=O)N2CCC(O)CC2)c1]

The title compound was prepared following the procedure described in Example 1, Step 4, using the crude 33g and 3,4-difluoroaniline. The crude product was purified by reverse phase chromatography eluted with ACN and water and dried using lyophilization to afford the title product as white solid. ESI-MS, m/z 445 (MH)⁺.

Example 43: Synthesis of N-(3-bromo-4-fluorophenyl)-4-chloro-3-(1,1-difluoro-2-(4-hydroxypiperidin-1-yl)-2-oxoethyl)benzamide

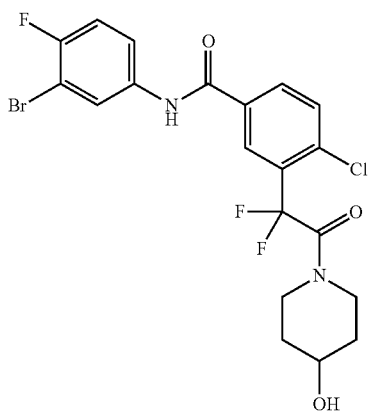

The title compound was prepared following the procedure described in Example 1, Step 4, using the crude 33g and 3-bromo-4-fluoroaniline. The crude product was purified by reverse phase chromatography eluted with ACN and water and dried using lyophilization to afford the title product as white solid. ESI-MS, m/z 505/507 (MH)⁺.

Example 44: Synthesis of 2-(1,1-difluoro-2-(4-hydroxypiperidin-1-yl)-2-oxoethyl)-N-(4-fluoro-3-methylphenyl)thiazole-5-carboxamide

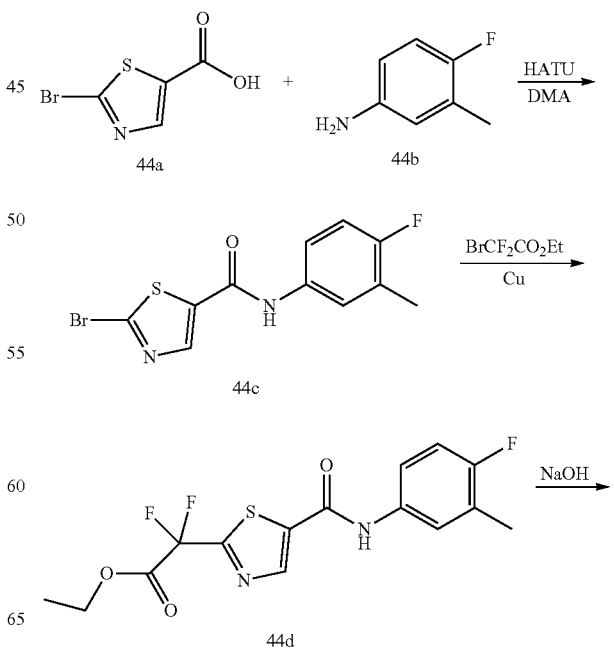

325
-continued

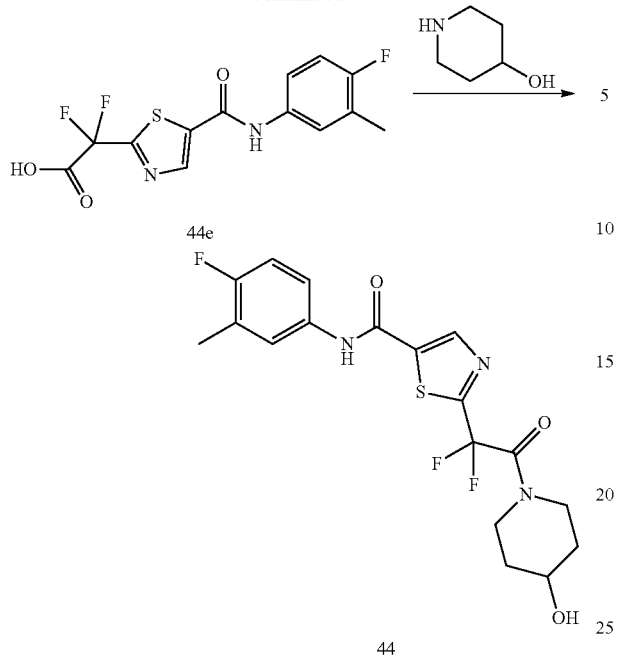

The title compound was prepared following the procedure described in Example 30, using 2-bromothiazole-5-carboxylic acid instead of 30a. The product was purified by reverse phase chromatography eluted with ACN and water and dried using lyophilization to afford the title product as white solid. ESI-MS, m/z 414 (MH)+.

Example 45: Synthesis of 3-(1,1-difluoro-2-((4-hydroxy-2-methylbutan-2-yl)amino)-2-oxoethyl)-N-(3,4-difluorophenyl)-4-fluorobenzamide

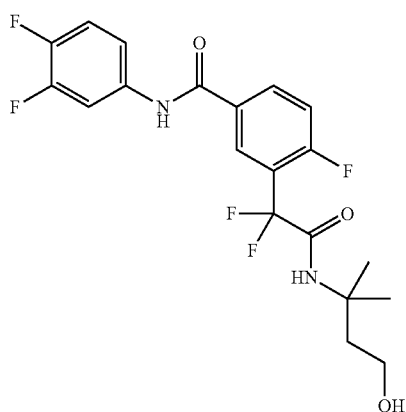 [SMILES: CC(C)(CCO)NC(=O)C(F)(F)c1cc(C(=O)Nc2ccc(F)c(F)c2)ccc1F]

The title compound was prepared following the procedure described in Example 1, Step 4, using 3-amino-3-methylbutan-1-ol instead of sec-butylamine. The crude product was purified by reverse phase chromatography eluted with ACN and water and dried using lyophilization to afford the title product as white solid. ESI-MS, m/z 431 (MH)+.

326
Example 46: Synthesis of N-(3,4-difluorophenyl)-3-(2-(ethyl(3-hydroxypropyl)amino)-1,1-difluoro-2-oxoethyl)-4-fluorobenzamide

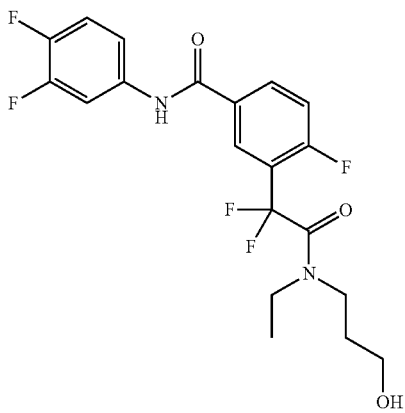 [SMILES: CCN(CCCO)C(=O)C(F)(F)c1cc(C(=O)Nc2ccc(F)c(F)c2)ccc1F]

The title compound was prepared following the procedure described in Example 1, Step 4, using 3-(ethylamino)propan-1-ol instead of sec-butylamine. The crude product was purified by reverse phase chromatography eluted with ACN and water and dried using lyophilization to afford the title product as white solid. ESI-MS, m/z 431 (MH)+.

Example 47: Synthesis of 3-(1,1-difluoro-2-((3-hydroxypropyl)(methyl)amino)-2-oxoethyl)-N-(3,4-difluorophenyl)-4-fluorobenzamide

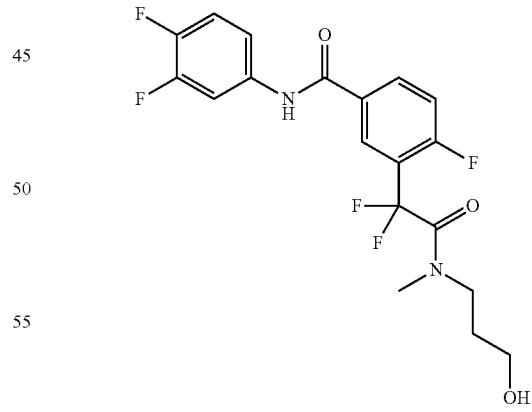

The title compound was prepared following the procedure described in Example 1, Step 4, using 3-(methylamino)propan-1-ol instead of sec-butylamine. The crude product was purified by reverse phase chromatography eluted with ACN and water and dried using lyophilization to afford the title product as white solid. ESI-MS, m/z 417 (MH)+.

Example 48: Synthesis of 3-(1,1-difluoro-2-(4-(hydroxymethyl)piperidin-1-yl)-2-oxoethyl)-N-(3,4-difluorophenyl)-4-fluorobenzamide

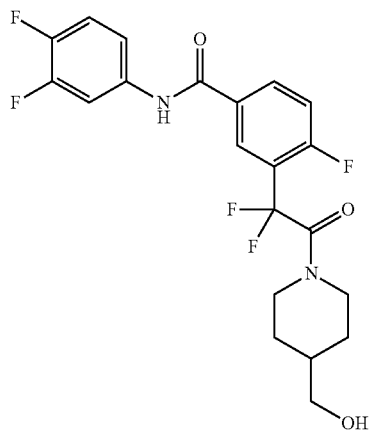 [SMILES: O=C(Nc1ccc(F)c(F)c1)c1ccc(F)c(C(F)(F)C(=O)N2CCC(CO)CC2)c1]

The title compound was prepared following the procedure described in Example 1, Step 4, using piperidin-4-ylmethanol instead of sec-butylamine. The crude product was purified by reverse phase chromatography eluted with ACN and water and dried using lyophilization to afford the title product as white solid. ESI-MS, m/z 443 (MH)⁺.

Example 49: Synthesis of 3-(1,1-difluoro-2-(3-(hydroxymethyl)piperidin-1-yl)-2-oxoethyl)-N-(3,4-difluorophenyl)-4-fluorobenzamide

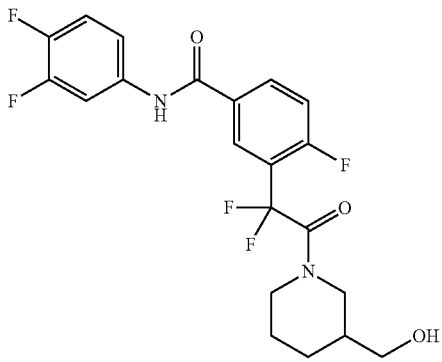 [SMILES: O=C(Nc1ccc(F)c(F)c1)c1ccc(F)c(C(F)(F)C(=O)N2CCCC(CO)C2)c1]

The title compound was prepared following the procedure described in Example 1, Step 4, using piperidin-3-ylmethanol instead of sec-butylamine. The crude product was purified by reverse phase chromatography eluted with ACN and water and dried using lyophilization to afford the title product as white solid. ESI-MS, m/z 443 (MH)⁺.

Example 50: Synthesis of 3-(1,1-difluoro-2-oxo-2-(pyridin-4-ylamino)ethyl)-N-(3,4-difluorophenyl)-4-fluorobenzamide

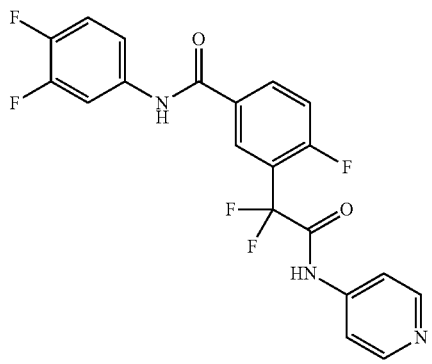 [SMILES: O=C(Nc1ccc(F)c(F)c1)c1ccc(F)c(C(F)(F)C(=O)Nc2ccncc2)c1]

The title compound was prepared following the procedure described in Example 1, Step 4, using pyridin-4-amine instead of sec-butylamine. The crude product was purified by reverse phase chromatography eluted with ACN and water and dried using lyophilization to afford the title product as white solid. ESI-MS, m/z 422 (MH)⁺.

Example 51: Synthesis of 3-(1,1-difluoro-2-oxo-2-((pyridin-4-ylmethyl)amino)ethyl)-N-(3,4-difluorophenyl)-4-fluorobenzamide

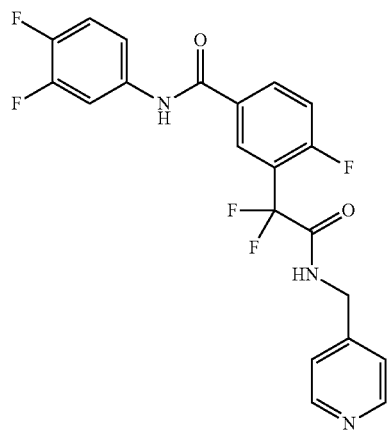 [SMILES: O=C(Nc1ccc(F)c(F)c1)c1ccc(F)c(C(F)(F)C(=O)NCc2ccncc2)c1]

The title compound was prepared following the procedure described in Example 1, Step 4, using pyridin-4-ylmethanamine instead of sec-butylamine. The crude product was purified by reverse phase chromatography eluted with ACN and water and dried using lyophilization to afford the title product as white solid. ESI-MS, m/z 436 (MH)⁺.

Example 52: Synthesis of 3-(1,1-difluoro-2-((2-hydroxyethyl)(propyl)amino)-2-oxoethyl)-N-(3,4-difluorophenyl)-4-fluorobenzamide

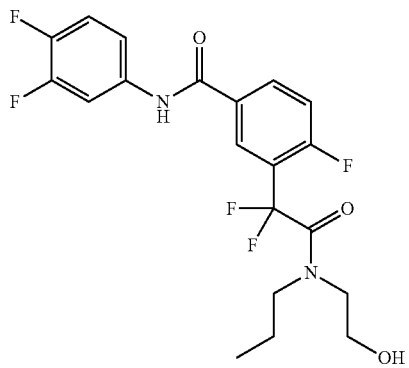 [SMILES: CCCN(CCO)C(=O)C(F)(F)c1cc(C(=O)Nc2ccc(F)c(F)c2)ccc1F]

The title compound was prepared following the procedure described in Example 1, Step 4, using 2-(propylamino) ethan-1-ol instead of sec-butylamine. The crude product was purified by reverse phase chromatography eluted with ACN and water and dried using lyophilization to afford the title product as white solid. ESI-MS, m/z 431 (MH)$^+$.

Example 53: Synthesis of (R)—N-(3,4-difluorophenyl)-3-(2-((2,3-dihydroxypropyl)amino)-1,1-difluoro-2-oxoethyl)-4-fluorobenzamide

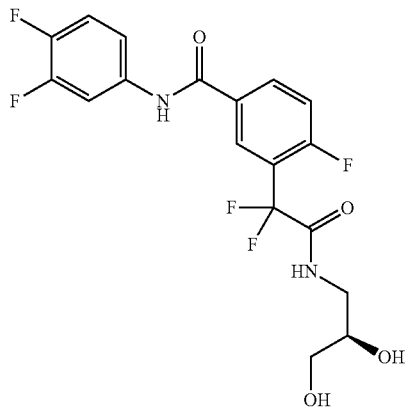 [SMILES: O=C(Nc1ccc(F)c(F)c1)c1ccc(F)c(C(F)(F)C(=O)NC[C@@H](O)CO)c1]

The title compound was prepared following the procedure described in Example 1, Step 4, using (R)-3-aminopropane-1,2-diol instead of sec-butylamine. The crude product was purified by reverse phase chromatography eluted with ACN and water and dried using lyophilization to afford the title product as white solid. ESI-MS, m/z 419 (MH)$^+$.

Example 54: Synthesis of (S)—N-(3,4-difluorophenyl)-3-(2-((2,3-dihydroxypropyl)amino)-1,1-difluoro-2-oxoethyl)-4-fluorobenzamide

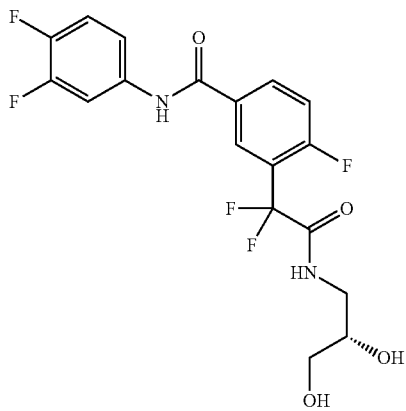 [SMILES: O=C(Nc1ccc(F)c(F)c1)c1ccc(F)c(C(F)(F)C(=O)NC[C@H](O)CO)c1]

The title compound was prepared following the procedure described in Example 1, Step 4, using (S)-3-aminopropane-1,2-diol instead of sec-butylamine. The crude product was purified by reverse phase chromatography eluted with ACN and water and dried using lyophilization to afford the title product as white solid. ESI-MS, m/z 419 (MH)$^+$.

Example 55: Synthesis of N-(3,4-difluorophenyl)-3-(2-(ethyl(2-hydroxyethyl)amino)-1,1-difluoro-2-oxoethyl)-4-fluorobenzamide

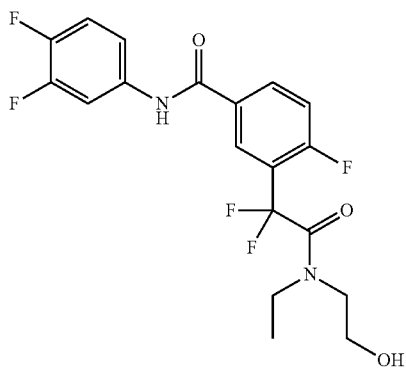

The title compound was prepared following the procedure described in Example 1, Step 4, using 2-(ethylamino)ethan-1-ol instead of sec-butylamine. The crude product was purified by reverse phase chromatography eluted with ACN and water and dried using lyophilization to afford the title product as white solid. ESI-MS, m/z 417 (MH)$^+$.

Example 56: Synthesis of (±)-4-chloro-3-(2-(3,4-dihydroxypiperidin-1-yl)-1,1-difluoro-2-oxoethyl)-N-(4-fluoro-3-methylphenyl)benzamide

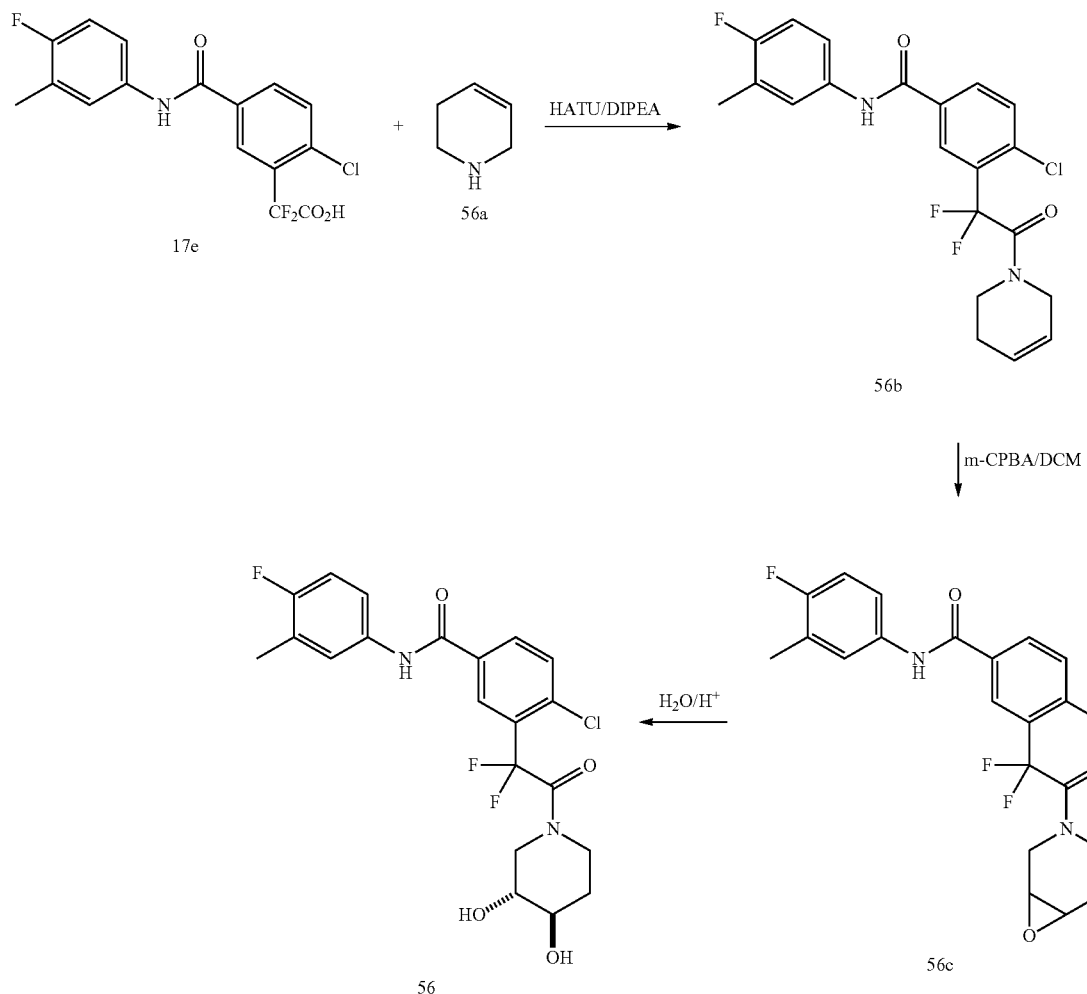

Step 1: Synthesis of 4-chloro-3-(2-(3,6-dihydropyridin-1(2H)-yl)-1,1-difluoro-2-oxoethyl)-N-(4-fluoro-3-methylphenyl)benzamide (56b)

The title compound was prepared following the procedure described in Example 1, Step 4, using 1,2,3,6-tetrahydropyridine instead of sec-butylamine. The crude product was purified by flash chromatography on silica gel (EtOAc/Hexanes 0~100%) to afford the product as white solid. ESI-MS, m/z 423 (MH)+.

Step 2: Synthesis of 3-(2-(7-oxa-3-azabicyclo[4.1.0]heptan-3-yl)-1,1-difluoro-2-oxoethyl)-4-chloro-N-(4-fluoro-3-methylphenyl)benzamide meta-Chloroperoxybenzoic acid (50 mg, m-CPBA, ~77%) was added to a solution of 56b (50 mg) in DCM (2 mL) at 0° C. The reaction mixture was warmed to rt for 20 hrs. The reaction was quenched with aqueous $Na_2S_2O_3$ (1 N, 1 mL) and saturated $NaHCO_3$ (2 mL), then, extracted with DCM. The organic layer was separated, washed with brine, and concentrated in vacuo to afford crude 56c as colorless oil, which was used without further purification. ESI-MS, m/z 439 (MH)+.

Step 3: Synthesis of 4-chloro-3-(2-(3,4-dihydroxypiperidin-1-yl)-1,1-difluoro-2-oxoethyl)-N-(4-fluoro-3-methylphenyl)benzamide $H_2SO_4$ (0.5 N, 0.5 mL) was added to a solution of 56c in 1,4-dioxane (1 mL) at rt. After 3 hrs at rt, the reaction mixture was carefully quenched with aqueous NaOH (2 N) to pH 7, and concentrated in vacuo until only water remained. The residues was purified by reverse phase HPLC and lyophilized to afford the title compound as white solid: ESI-MS, m/z 457 (MH)+.

Example 57: Synthesis of 4-chloro-3-(2-((3S,4R)-3,4-dihydroxypiperidin-1-yl)-1,1-difluoro-2-oxoethyl)-N-(4-fluoro-3-methylphenyl)benzamide

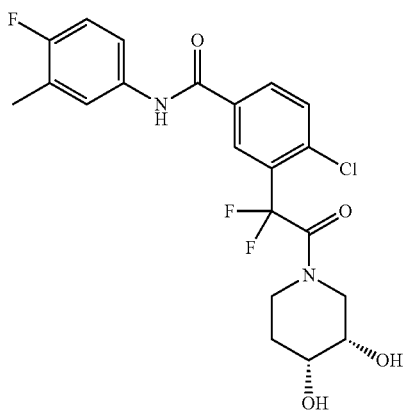

AD-mix-alpha (0.2 g) was added to a mixture of 56b (30 mg) in ʹ-BuOH/H₂O (1/1, 4 mL) at rt. After 20 hrs, aqueous Na₂S₂O₃ (1 N, 1 mL), water (5 mL) and EtOAc (10 mL) were added. The resulting mixture was stirred at rt for 5 min. The organic layer was separated, concentrated in vacuo, and purified by reverse phase HPLC eluted with ACN and water, and lyophilized to afford the title compound as white solid: ESI-MS, m/z 457 (MH)⁺.

Example 58: Synthesis of 4-chloro-3-(2-((3R,4S)-3,4-dihydroxypiperidin-1-yl)-1,1-difluoro-2-oxoethyl)-N-(4-fluoro-3-methylphenyl)benzamide

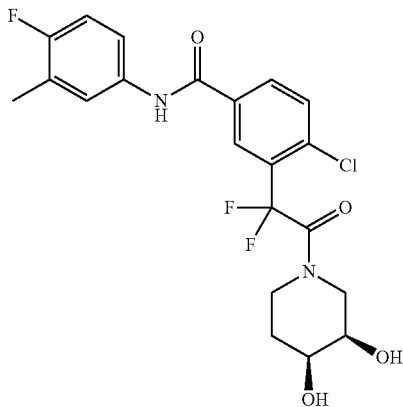 [SMILES: Cc1cc(NC(=O)c2ccc(Cl)c(C(F)(F)C(=O)N3CC[C@H](O)[C@H](O)C3)c2)ccc1F]

The title compound was prepared following the procedure described in Example 57, using AD-mix-beta instead of AD-mix-alpha. The crude product was purified by reverse phase chromatography eluted with ACN and water and dried using lyophilization to afford the title product as white solid. ESI-MS, m/z 457 (MH)⁺.

Example 59: Synthesis of 5-(1,1-difluoro-2-oxo-2-(pyrrolidin-1-yl)ethyl)-N-(4-fluoro-3-methylphenyl)thiophene-3-carboxamide

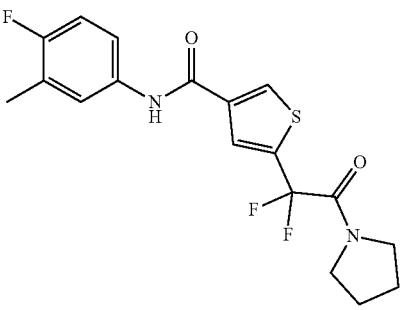 [SMILES: Cc1cc(NC(=O)c2csc(C(F)(F)C(=O)N3CCCC3)c2)ccc1F]

The title compound was prepared following the procedures described in Example 1, Steps 1 through 4, using 5-bromothiophene-3-carboxylic acid and 4-fluoro-3-methylaniline in Step 1 and pyrrolidine in Step 4. The final product was purified by reverse phase chromatography to afford the title compound as off-white solid. ESI-MS m/z 383 (MH)⁺.

Example 60: Synthesis of N-(3-carbamoyl-4-fluorophenyl)-4-chloro-3-(1,1-difluoro-2-(4-hydroxypiperidin-1-yl)-2-oxoethyl)benzamide

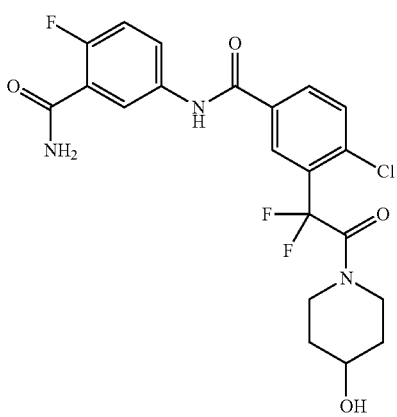 [SMILES: NC(=O)c1cc(NC(=O)c2ccc(Cl)c(C(F)(F)C(=O)N3CCC(O)CC3)c2)ccc1F]

A mixture of Example 33 (10 mg) and hydrido(dimethylphosphinous acid-kP)[hydrogen bis(dimethylphosphinito-kP)]platinum(II) (2 mg, Stream Chemicals, Inc.) in 0.5 mL of EtOH/H₂O (1/1) was flushed with argon, then, heated to 85° C. for 5 hrs. After cooling to rt, the mixture was purified by reverse phase chromatography eluted with ACN and water, and dried using lyophilization to afford the title product as white solid. ESI-MS, m/z 470 (MH)⁺.

Example 61: Synthesis of 4-chloro-3-(1,1-difluoro-2-(4-hydroxypiperidin-1-yl)-2-oxoethyl)-N-(3,4-difluoro-5-methoxyphenyl)benzamide

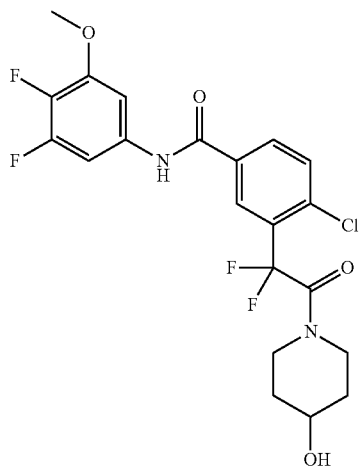 [SMILES: COc1cc(NC(=O)c2ccc(Cl)c(C(F)(F)C(=O)N3CCC(O)CC3)c2)cc(F)c1F]

The title compound was prepared following the procedure described in Example 1, Step 4, using the crude 33g and 3,4-difluoro-5-methoxyaniline. The crude product was purified by reverse phase chromatography eluted with ACN and water and dried using lyophilization to afford the title product as white solid. ESI-MS m/z 475 (MH)+.

Example 62: Synthesis of 4-bromo-3-(1,1-difluoro-2-(4-hydroxypiperidin-1-yl)-2-oxoethyl)-N-(4-fluoro-3-methylphenyl)benzamide

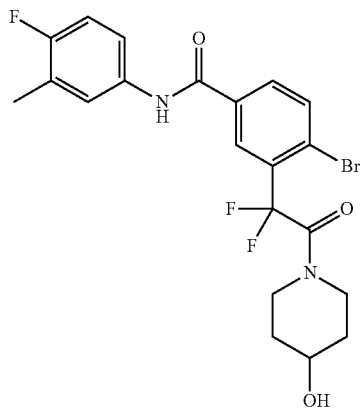

The title compound was prepared following the procedures described in Example 1, Steps 1 through 4, using 4-bromo-3-iodobenzoic acid instead of 3-iodobenzoic acid. The final product was purified by reverse phase chromatography eluted with ACN and water and dried using lyophilization to afford the title product as white solid. ESI-MS, m/z 485/487 (MH)+.

Example 63: Synthesis of 5-(1,1-difluoro-2-(4-hydroxypiperidin-1-yl)-2-oxoethyl)-N-(4-fluoro-3-methylphenyl)thiophene-2-carboxamide

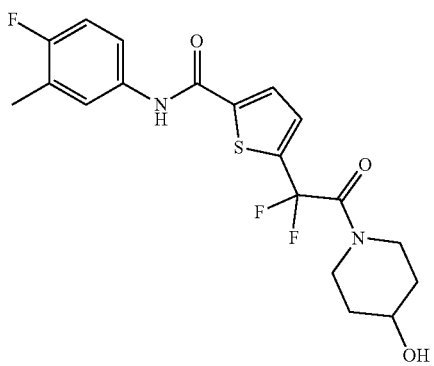 [SMILES: Cc1cc(NC(=O)c2ccc(C(F)(F)C(=O)N3CCC(O)CC3)s2)ccc1F]

The title compound was-prepared following the procedures described in Example 1, Steps 1 through 4. The final product was purified by reverse phase chromatography to afford the title compound as off-white solid. ESI-MS m/z 413 (MH)+.

Example 64: Synthesis of N-(3,4-difluorophenyl)-3-(2-((2,4-dimethoxybenzyl)amino)-1,1-difluoro-2-oxoethyl)-4-fluorobenzamide

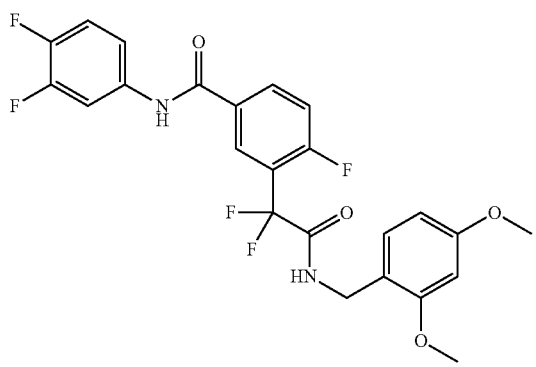 [SMILES: COc1ccc(CNC(=O)C(F)(F)c2cc(C(=O)Nc3ccc(F)c(F)c3)ccc2F)c(OC)c1]

The title compound was prepared following the procedure described in Example 1, Step 4, using (2,4-dimethoxyphenyl)methanamine instead of sec-butylamine. The crude product was purified by reverse phase chromatography eluted with ACN and water and dried using lyophilization to afford the title product as white solid. ESI-MS, m/z 495 (MH)+.

Example 65: Synthesis of 3-(1,1-difluoro-2-((4-hydroxybenzyl)amino)-2-oxoethyl)-N-(3,4-difluorophenyl)-4-fluorobenzamide

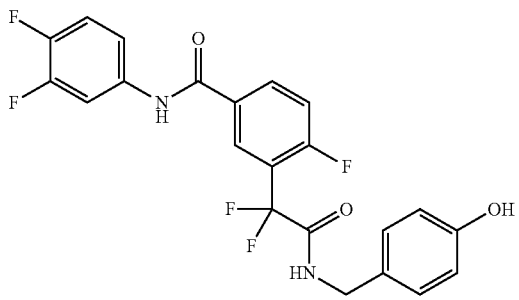 [SMILES: O=C(Nc1ccc(F)c(F)c1)c1ccc(F)c(C(F)(F)C(=O)NCc2ccc(O)cc2)c1]

The title compound was prepared following the procedure described in Example 1, Step 4, using 4-(aminomethyl)phenol instead of sec-butylamine. The crude product was purified by reverse phase chromatography eluted with ACN and water and dried using lyophilization to afford the title product as white solid. ESI-MS, m/z 451 (MH)$^+$.

Example 66: Synthesis of 3-(1,1-difluoro-2-oxo-2-((pyridin-3-ylmethyl)amino)ethyl)-N-(3,4-difluorophenyl)-4-fluorobenzamide

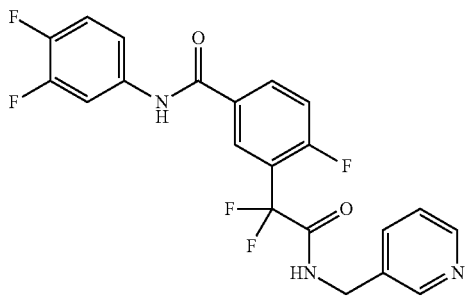 [SMILES: O=C(Nc1ccc(F)c(F)c1)c1ccc(F)c(C(F)(F)C(=O)NCc2cccnc2)c1]

The title compound was prepared following the procedure described in Example 1, Step 4, using pyridin-3-ylmethanamine instead of sec-butylamine. The crude product was purified by reverse phase chromatography eluted with ACN and water and dried using lyophilization to afford the title product as white solid. ESI-MS, m/z 436 (MH)$^+$.

Example 67: Synthesis of 4-chloro-5-(1,1-difluoro-2-(4-hydroxypiperidin-1-yl)-2-oxoethyl)-N-(4-fluoro-3-methylphenyl)-2-methylbenzamide

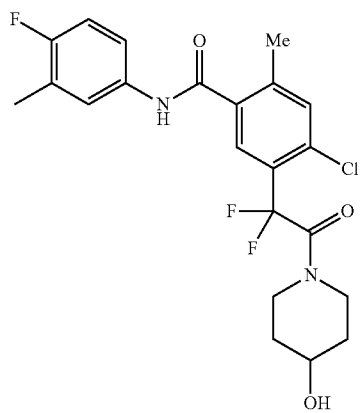 [SMILES: Cc1cc(NC(=O)c2cc(C(F)(F)C(=O)N3CCC(O)CC3)c(Cl)cc2C)ccc1F]

The title compound was prepared following the procedure described in Example 1, Step 1 through step 4, using 4-chloro-5-iodo-2-methylbenzoic acid instead of 4-fluoro-3-iodobenzoic acid. The crude product was purified by reverse phase chromatography eluted with ACN and water and dried using lyophilization to afford the title product as white solid. ESI-MS, m/z 455 (MH)$^+$.

Example 68: Synthesis of 3-(1,1-difluoro-2-oxo-2-((thiazol-2-ylmethyl)amino)ethyl)-4-fluoro-N-(4-fluoro-3-methylphenyl)benzamide

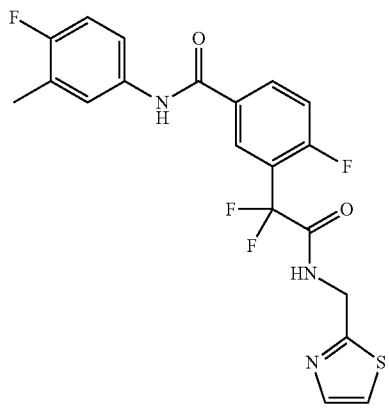 [SMILES: Cc1cc(NC(=O)c2ccc(F)c(C(F)(F)C(=O)NCc3nccs3)c2)ccc1F]

The title compound was prepared following the procedure described in Example 1, Step 4, using thiazol-2-ylmethanamine and 14e. The crude product was purified by reverse phase chromatography eluted with ACN and water and dried using lyophilization to afford the title product as white solid. ESI-MS, m/z 438 (MH)$^+$.

Example 69: Synthesis of 3-(1,1-difluoro-2-(4-hydroxy-3-(hydroxymethyl)piperidin-1-yl)-2-oxoethyl)-4-fluoro-N-(4-fluoro-3-methylphenyl)benzamide

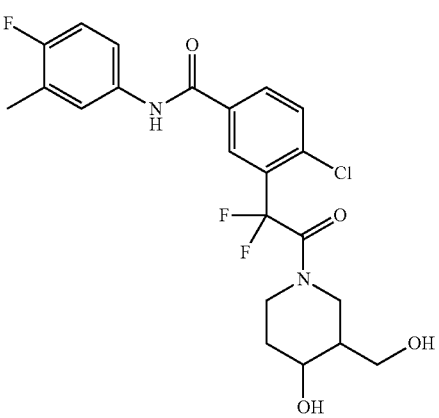

The title compound was prepared following the procedure described in Example 1, Step 4, using 3-(hydroxymethyl)piperidin-4-ol and 14e. The crude product was purified by reverse phase chromatography eluted with ACN and water and dried using lyophilization to afford the title product as white solid. ESI-MS, m/z 455 (MH)$^+$.

Example 70: Synthesis of 3-(1,1-difluoro-2-(4-hydroxy-4-methylpiperidin-1-yl)-2-oxoethyl)-4-fluoro-N-(4-fluoro-3-methylphenyl)benzamide

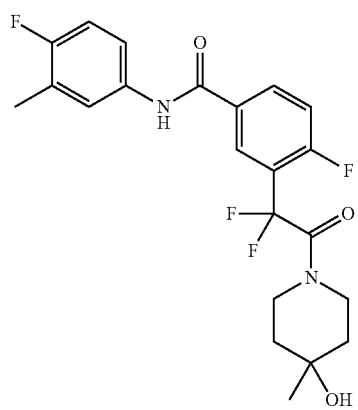 [SMILES: Cc1cc(NC(=O)c2ccc(F)c(C(F)(F)C(=O)N3CCC(C)(O)CC3)c2)ccc1F]

The title compound was prepared following the procedure described in Example 1, Step 4, using 4-methylpiperidin-4-ol and 14e. The crude product was purified by reverse phase chromatography eluted with ACN and water and dried using lyophilization to afford the title product as white solid. ESI-MS, m/z 439 (MH)$^+$.

Example 71: Synthesis of 3-(1,1-difluoro-2-(4-hydroxy-2,2-dimethylpiperidin-1-yl)-2-oxoethyl)-4-fluoro-N-(4-fluoro-3-methylphenyl)benzamide

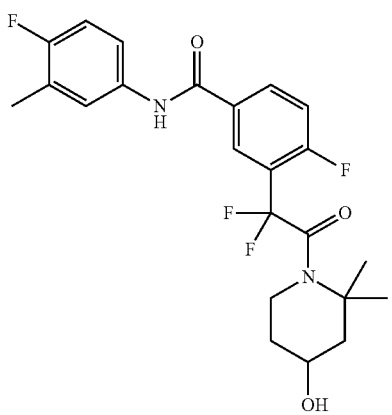 [SMILES: Cc1cc(NC(=O)c2ccc(F)c(C(F)(F)C(=O)N3CCC(O)CC3(C)C)c2)ccc1F]

The title compound was prepared following the procedure described in Example 1, Step 4, using 2,2-dimethylpiperidin-4-ol and 14e. The crude product was purified by reverse phase chromatography eluted with ACN and water and dried using lyophilization to afford the title product as white solid. ESI-MS, m/z 453 (MH)$^+$.

Example 72: Synthesis of 3-(1,1-difluoro-2-(4-hydroxy-2,2-dimethylpiperidin-1-yl)-2-oxoethyl)-4-fluoro-N-(4-fluoro-3-methylphenyl)benzamide

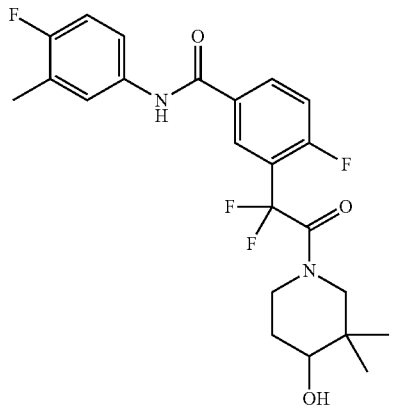 [SMILES: Cc1cc(NC(=O)c2ccc(F)c(C(F)(F)C(=O)N3CCC(O)C(C)(C)C3)c2)ccc1F]

The title compound was prepared following the procedure described in Example 1, Step 4, using 3,3-dimethylpiperidin-4-ol and 14e. The crude product was purified by reverse phase chromatography eluted with ACN and water and dried using lyophilization to afford the title product as white solid. ESI-MS, m/z 453 (MH)$^+$.

Example 73: Synthesis of 3-(2-(3,3-difluoropyrrolidin-1-yl)-1,1-difluoro-2-oxoethyl)-4-fluoro-N-(4-fluoro-3-methylphenyl)benzamide

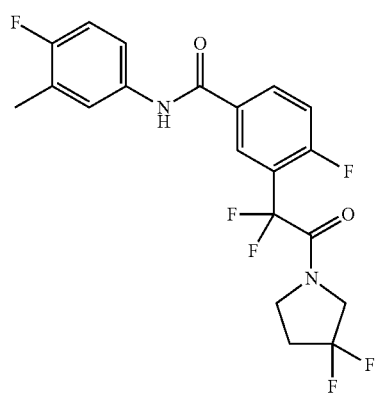 [SMILES: Cc1cc(NC(=O)c2ccc(F)c(C(F)(F)C(=O)N3CCC(F)(F)C3)c2)ccc1F]

The title compound was prepared following the procedure described in Example 1, Step 4, using 3,3-difluoropyrrolidine and 14e. The crude product was purified by reverse phase chromatography eluted with ACN and water and dried using lyophilization to afford the title product as white solid. ESI-MS, m/z 431 (MH)$^+$.

Example 74: Synthesis of 4-chloro-3-(2-(3,6-dihydropyridin-1(2H)-yl)-1,1-difluoro-2-oxoethyl)-N-(4-fluoro-3-methylphenyl)benzamide

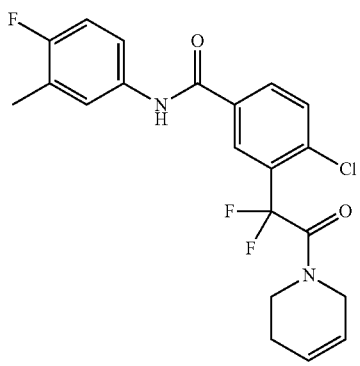 [SMILES: Cc1cc(NC(=O)c2ccc(Cl)c(C(F)(F)C(=O)N3CC=CCC3)c2)ccc1F]

The title compound was prepared following the procedure described in Example 1, Step 4, using 1,2,3,6-tetrahydropyridine and 17e. The crude product was purified by flash chromatography on silica gel (EtOAc/Hexanes 0~100%) to afford the product as white solid. ESI-MS, m/z 423 (MH)$^+$.

Example 75: Synthesis of 3-(1,1-difluoro-2-(4-hydroxy-4-(hydroxymethyl)piperidin-1-yl)-2-oxoethyl)-4-fluoro-N-(4-fluoro-3-methylphenyl)benzamide

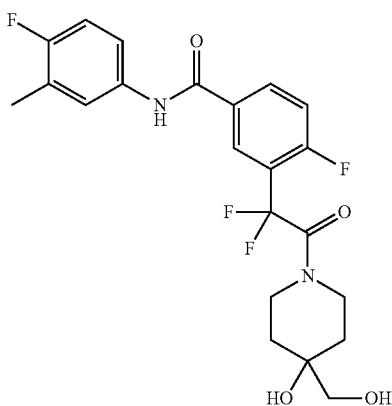 [SMILES: Cc1cc(NC(=O)c2ccc(F)c(C(F)(F)C(=O)N3CCC(O)(CO)CC3)c2)ccc1F]

The title compound was prepared following the procedure described in Example 1, Step 4, using 4-(hydroxymethyl)piperidin-4-ol and 14e. The crude product was purified by reverse phase chromatography eluted with ACN and water and dried using lyophilization to afford the title product as white solid. ESI-MS, m/z 423 (MH)$^+$.

Example 76: Synthesis of 3-(1,1-difluoro-2-oxo-2-(1,4,5,7-tetrahydro-6H-pyrazolo[3,4-c]pyridin-6-yl)ethyl)-4-fluoro-N-(4-fluoro-3-methylphenyl)benzamide

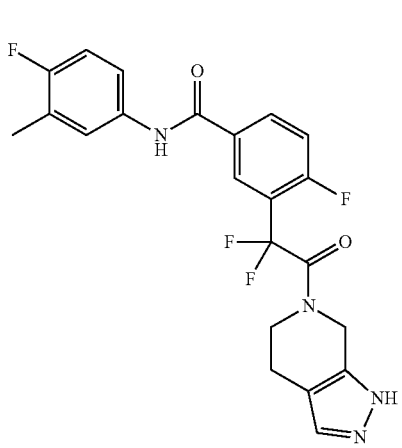 [SMILES: Cc1cc(NC(=O)c2ccc(F)c(C(F)(F)C(=O)N3CCc4cn[nH]c4C3)c2)ccc1F]

The title compound was prepared following the procedure described in Example 1, Step 4, using 4,5,6,7-tetrahydro-1H-pyrazolo[3,4-c]pyridine and 14e. The crude product was purified by reverse phase chromatography eluted with ACN and water and dried using lyophilization to afford the title product as white solid. ESI-MS, m/z 447 (MH)$^+$.

Examples 77-89: Syntheses of Compounds 77-89 Shown in Table 2

Compounds 77-89 shown in Table 2 were prepared in analogy to the procedures described for Example 1. The final products were purified by reverse phase chromatography or preparative TLC to afford the title compounds as solids. Analytical data for the compounds is shown in Table 2.

Examples 90-95: Syntheses of Compounds 90-95 Shown in Table 2

Compounds 90-95 shown in Table 2 were prepared in analogy to the procedures described for Example 33. The final products were purified by reverse phase chromatography or preparative TLC to afford the title compounds as solids. Analytical data for the compounds are shown in Table 2.

TABLE 2

| Analytical data for Exemplary compounds 77-95. | | |
| --- | --- | --- |
| Example | MW | ESI m/z (M + H)$^+$ |
| 77 | 460.4 | 461.0 |
| 78 | 450.4 | 450.9 |
| 79 | 438.4 | 438.9 |
| 80 | 424.4 | 424.7 |
| 81 | 384.4 | 385.1 |
| 82 | 400.4 | 401.1 |

TABLE 2-continued
Analytical data for Exemplary compounds 77-95.
| Example | MW | ESI m/z (M + H)+ |
|---|---|---|
| 83 | 438.4 | 438.9 |
| 84 | 424.4 | 424.8 |
| 85 | 444.8 | 444.9 |
| 86 | 446.4 | 446.6 |
| 87 | 489.3 | 488.5; 490.5 |
| 88 | 435.4 | 436.0 |
| 89 | 396.4 | 396.7 |
| 90 | 424.4 | 424.7 |
| 91 | 436.4 | 437.0 |
| 92 | 424.4 | 424.8 |
| 93 | 424.4 | 424.6 |
| 94 | 436.4 | 436.9 |
| 95 | 440.8 | 440.7 |
Example 96: Synthesis of 2-(1,1-difluoro-2-(4-hydroxypiperidin-1-yl)-2-oxoethyl)-N-(4-fluoro-3-methylphenyl)-1-methyl-1H-pyrrole-3-carboxamide (96), and
Example 97: Synthesis of 5-(1,1-difluoro-2-(4-hydroxypiperidin-1-yl)-2-oxoethyl)-N-(4-fluoro-3-methylphenyl)-1-methyl-1H-pyrrole-3-carboxamide (97)
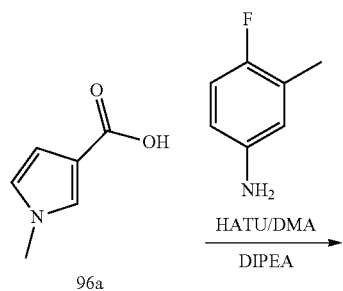
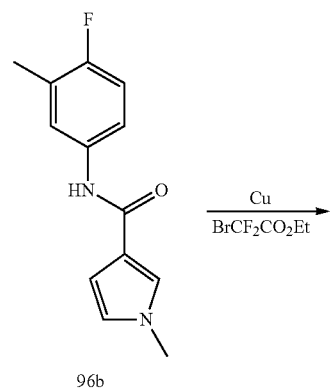
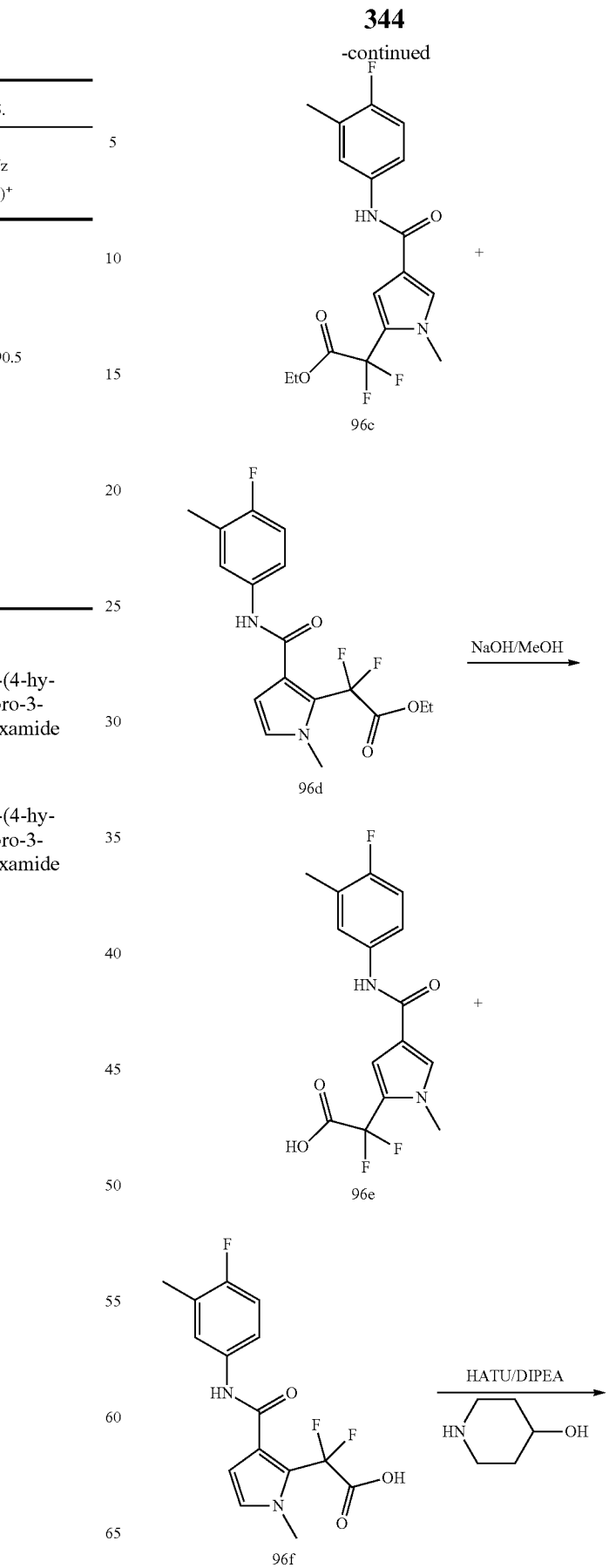

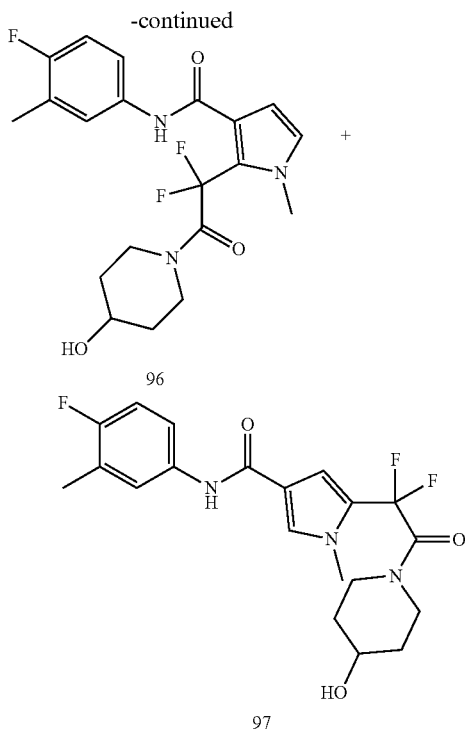

Step 3: Synthesis of 2-(1,1-difluoro-2-(4-hydroxypiperidin-1-yl)-2-oxoethyl)-N-(4-fluoro-3-methylphenyl)-1-methyl-1H-pyrrole-3-carboxamide (96), and 5-(1,1-difluoro-2-(4-hydroxypiperidin-1-yl)-2-oxoethyl)-N-(4-fluoro-3-methylphenyl)-1-methyl-1H-pyrrole-3-carboxamide (97)

The title compounds were prepared following the procedure described in Example 1, Step 4, using the crude 96e/96f and piperidin-4-ol. The crude products were purified by reverse phase chromatography eluted with ACN and water and dried using lyophilization to afford the title products as white solids. ESI-MS, m/z 410 (MH)+ for both compounds.

Example 98: Synthesis of 4-bromo-5-(1,1-difluoro-2-(4-hydroxypiperidin-1-yl)-2-oxoethyl)-N-(4-fluoro-3-methylphenyl)-1-methyl-1H-pyrrole-2-carboxamide

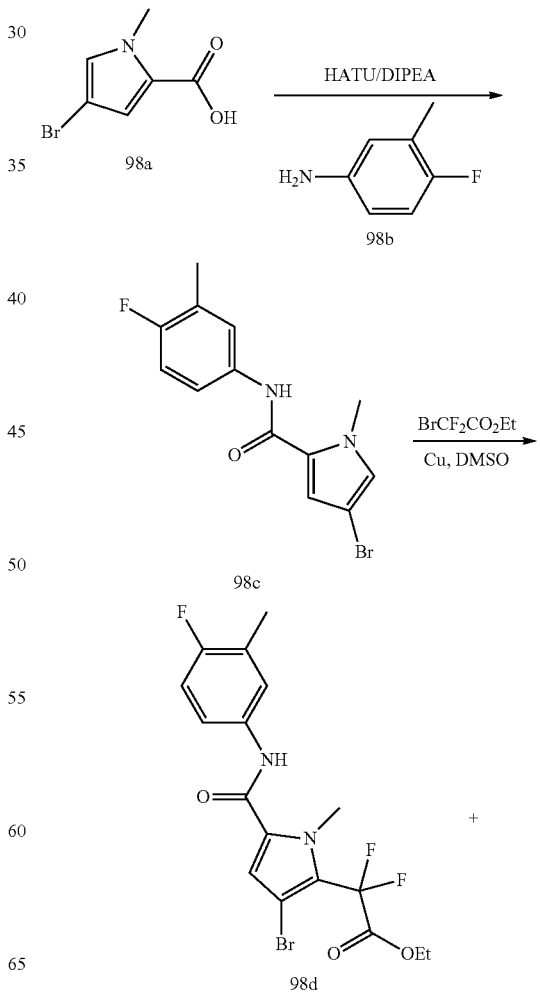

Step 1: Synthesis of N-(4-fluoro-3-methylphenyl)-1-methyl-1H-pyrrole-3-carboxamide (96a)

HATU (3.3 g, 8.9 mmol) was added to a solution of compound 62a (1 g, 8.9 mmol) in DMA (15 mL) at rt. After 20 min, a solution of 4-fluoro-3-methylaniline (1 g, 8 mmol) and DIPEA (1 g, 8 mmol) in DMA (2 mL) were added dropwise. The mixture was stirred at rt for 20 hrs. The reaction was quenched with water, and extracted with EtOAc. The organic layer was separated, washed with water/brine, concentrated, then, purified by flash chromatography on silica gel (EtOAc/Hexanes 0~100%) to afford the product as white solid (0.9 g). ESI-MS, m/z 233 (MH)+.

Step 2: Synthesis of ethyl 2,2-difluoro-2-(4-((4-fluoro-3-methylphenyl)carbamoyl)-1-methyl-1H-pyrrol-2-yl)acetate (96c), and ethyl 2,2-difluoro-2-(3-((4-fluoro-3-methylphenyl)carbamoyl)-1-methyl-1H-pyrrol-2-yl)acetate (96d)

A mixture of 96b (0.25 g, 0.77 mmol), Cu (0.25 g, 3.9 mmol, powder) and ethyl 2-bromo-2,2-difluoroacetate (0.2 g, 1 mmol) in DMSO (5 mL) was flushed with argon, then, heated at 50° C. for 4 hrs. After cooled to rt, EtOAc was added, and the mixture was filtered through celite. The filtration was washed with saturated NH4Cl/brine, concentrated in vacuo, and purified by flash chromatography on silica gel (EtOAc/Hexanes 0~100%) to afford a mixture of 96c and 96d (white solid, 0.1 g). ESI-MS, m/z 355 (MH)+.

Step 2: Synthesis of 2,2-difluoro-2-(4-((4-fluoro-3-methylphenyl)carbamoyl)-1-methyl-1H-pyrrol-2-yl)acetic acid (96e) and 2,2-difluoro-2-(3-((4-fluoro-3-methylphenyl)carbamoyl)-1-methyl-1H-pyrrol-2-yl)acetic acid (96f)

NaOH (2 N, 1 mL) was added to a solution of the above mixture in MeOH (3 mL) at 0° C. After 2 hrs at rt, the reaction mixture was quenched with aqueous HCl (0.5 N to pH ~2) at 0° C. The organic solvent was removed under vacuo, then, lyophilized to dryness to give the crude 96e and 96f as white solid. ESI-MS m/z 327 (MH)+.

347

-continued

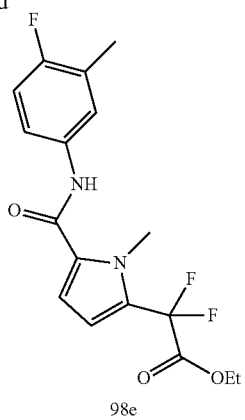

98e

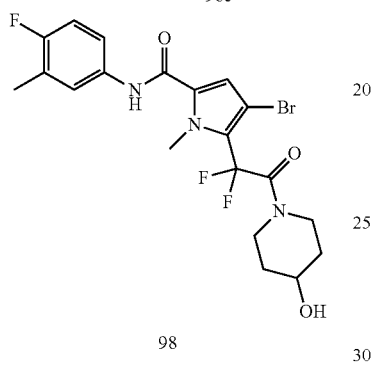

98

Step 1: Synthesis of 4-bromo-N-(4-fluoro-3-methylphenyl)-1-methyl-1H-pyrrole-2-carboxamide (98c)

HATU (1 g, 2.6 mmol) was added to a solution of compound 98a (0.5 g, 2.5 mmol) in DMA (15 mL) at rt. After 20 min, a solution of 4-fluoro-3-methylaniline (0.33 g, 2.6 mmol) and DIPEA (0.4 g) in DMA (2 mL) were added dropwise. The mixture was stirred at rt for 20 hrs. The reaction was quenched with aqueous HCl (0.4 N), and extracted with EtOAc. The organic layer was separated, washed with water/brine, concentrated, then, purified by flash chromatography on silica gel (EtOAc/Hexanes 0~100%) to afford the product as white solid (0.6 g). ESI-MS, m/z 311.0/313.0 (MH)$^+$.

Step 2: Synthesis of ethyl 2-(3-bromo-5-((4-fluoro-3-methylphenyl)carbamoyl)-1-methyl-1H-pyrrol-2-yl)-2,2-difluoroacetate (98d) and ethyl 2,2-difluoro-2-(5-((4-fluoro-3-methylphenyl)carbamoyl)-1-methyl-1H-pyrrol-2-yl)acetate (98e)

A mixture of 98c (0.5 g), Cu (0.32 g, powder) and ethyl 2-bromo-2,2-difluoroacetate (0.4 g) in DMSO (6 mL) was flushed with argon, then, heated at 50° C. for 20 hrs. After cooled to rt, EtOAc was added, and the mixture was filtered through celite. The filtration was washed with saturated NH$_4$Cl/brine, concentrated in vacuo, and purified by flash chromatography on silica gel (EtOAc/Hexanes 0~100%) to afford 98d (0.26 g, ESI-MS, m/z m/z 433.0/435.0) as white solid, and 98e (0.1 g, ESI-MS, m/z 355.1) as colorless oil.

Step 3: Synthesis of 4-bromo-5-(1,1-difluoro-2-(4-hydroxypiperidin-1-yl)-2-oxoethyl)-N-(4-fluoro-3-methylphenyl)-1-methyl-1H-pyrrole-2-carboxamide Compound 98 was prepared following the procedure described in Example 1, Step 3 and Step 4, using 98d and piperidin-4-ol. The crude product was purified by reverse phase chromatography eluted with ACN and water and dried using lyophilization to afford the title product as white solid. ESI-MS, m/z 487/489 (MH)$^+$.

Example 99: Synthesis of 5-(1,1-difluoro-2-(4-hydroxypiperidin-1-yl)-2-oxoethyl)-N-(4-fluoro-3-methylphenyl)-1-methyl-1H-pyrrole-2-carboxamide

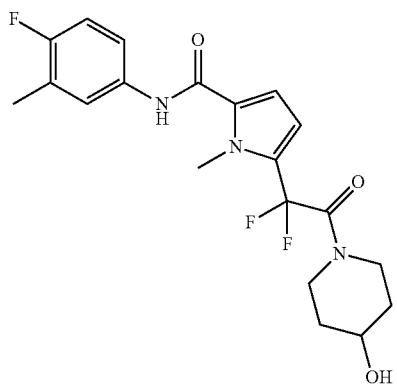 [SMILES: Cc1cc(NC(=O)c2ccc(C(F)(F)C(=O)N3CCC(O)CC3)n2C)ccc1F]

The title compound was prepared following the procedure described in Example 1, Step 3 and Step 4, using 98e and piperidin-4-ol. The crude product was purified by reverse phase chromatography eluted with ACN and water and dried using lyophilization to afford the title product as white solid. ESI-MS, m/z 410 (MH)$^+$.

Example 100: Synthesis of 5-(2-(tert-butylamino)-1,1-difluoro-2-oxoethyl)-N-(4-fluoro-3-methylphenyl)-1-methyl-1H-pyrrole-3-carboxamide

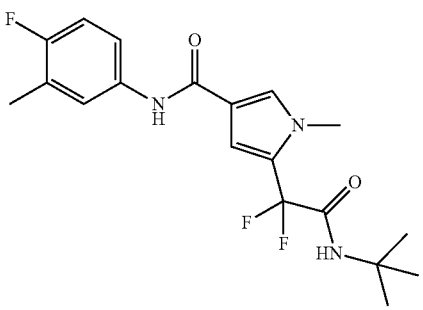 [SMILES: Cc1cc(NC(=O)c2cc(C(F)(F)C(=O)NC(C)(C)C)n(C)c2)ccc1F]

The title compounds were prepared following the procedure described in Example 97, using 2-methylpropan-2-amine instead of piperidin-4-ol. The crude products were purified by reverse phase chromatography eluted with ACN and water and dried using lyophilization to afford the title products as white solids. ESI-MS, m/z 382 (MH)$^+$.

Example 101: Synthesis of 2-(2-(tert-butylamino)-1,1-difluoro-2-oxoethyl)-N-(4-fluoro-3-methylphenyl)-1-methyl-1H-pyrrole-3-carboxamide

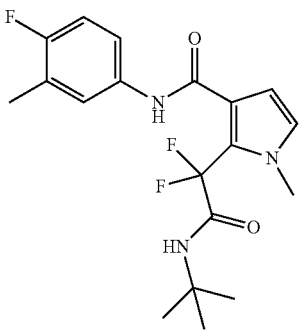 [SMILES: Cc1cc(NC(=O)c2ccn(C)c2C(F)(F)C(=O)NC(C)(C)C)ccc1F]

The title compounds were prepared following the procedure described in Example 96, using 2-methylpropan-2-amine instead of piperidin-4-ol. The crude products were purified by reverse phase chromatography eluted with ACN and water and dried using lyophilization to afford the title products as white solids. ESI-MS, m/z 382 (MH)⁺.

Example 102: Synthesis of 5-(1,1-difluoro-2-(isopropylamino)-2-oxoethyl)-N-(4-fluoro-3-methylphenyl)-1-methyl-1H-pyrrole-3-carboxamide

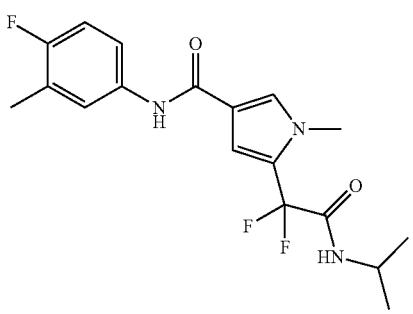 [SMILES: Cc1cc(NC(=O)c2cc(C(F)(F)C(=O)NC(C)C)n(C)c2)ccc1F]

The title compounds were prepared following the procedure described in Example 97, using propan-2-amine instead of piperidin-4-ol. The crude products were purified by reverse phase chromatography eluted with ACN and water and dried using lyophilization to afford the title products as white solids. ESI-MS, m/z 368 (MH)⁺.

Example 103: Synthesis of (S)-5-(2-(sec-butylamino)-1,1-difluoro-2-oxoethyl)-N-(4-fluoro-3-methylphenyl)-1-methyl-1H-pyrrole-3-carboxamide

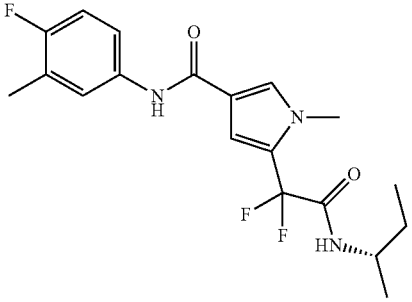 [SMILES: CC[C@H](C)NC(=O)C(F)(F)c1cc(C(=O)Nc2ccc(F)c(C)c2)cn1C]

The title compounds were prepared following the procedure described in Example 97, using (S)-butan-2-amine instead of piperidin-4-ol. The crude products were purified by reverse phase chromatography eluted with ACN and water and dried using lyophilization to afford the title products as white solids. ESI-MS, m/z 382 (MH)⁺.

Example 104: Synthesis of 5-(1,1-difluoro-2-((1-hydroxy-2-methylpropan-2-yl)amino)-2-oxoethyl)-N-(4-fluoro-3-methylphenyl)-1-methyl-1H-pyrrole-3-carboxamide

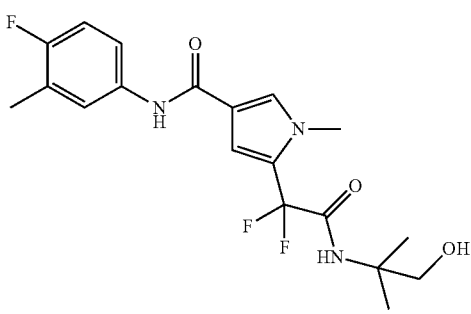 [SMILES: Cc1cc(NC(=O)c2cc(C(F)(F)C(=O)NC(C)(C)CO)n(C)c2)ccc1F]

The title compounds were prepared following the procedure described in Example 97, using 2-amino-2-methylpropan-1-ol instead of piperidin-4-ol. The crude products were purified by reverse phase chromatography eluted with ACN and water and dried using lyophilization to afford the title products as white solids. ESI-MS, m/z 398 (MH)⁺.

Example 105: Synthesis of 2-(1,1-difluoro-2-((1-hydroxy-2-methylpropan-2-yl)amino)-2-oxoethyl)-N-(4-fluoro-3-methylphenyl)-1-methyl-1H-pyrrole-3-carboxamide

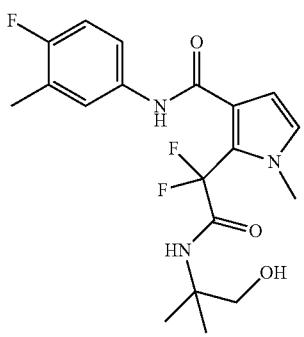 [SMILES: Cc1cc(NC(=O)c2ccn(C)c2C(F)(F)C(=O)NC(C)(C)CO)ccc1F]

The title compounds were prepared following the procedure described in Example 96, using 2-amino-2-methylpropan-1-ol instead of piperidin-4-ol. The crude products were purified by reverse phase chromatography eluted with ACN and water and dried using lyophilization to afford the title products as white solids. ESI-MS, m/z 398 (MH)$^+$.

Example 106: Synthesis of 5-(2-(tert-butylamino)-1,1-difluoro-2-oxoethyl)-N-(4-fluoro-3-methylphenyl)-1,2-dimethyl-1H-pyrrole-3-carboxamide

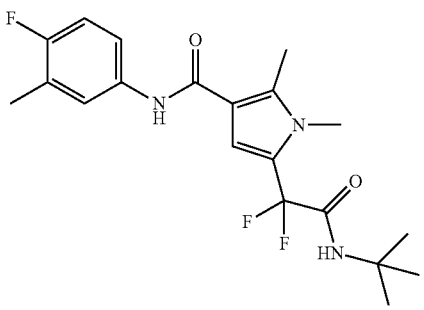 [SMILES: Cc1cc(NC(=O)c2cc(C(F)(F)C(=O)NC(C)(C)C)n(C)c2C)ccc1F]

The title compounds were prepared following the procedure described in Example 97, using 1,2-dimethyl-1H-pyrrole-3-carboxylic acid instead of 1-methyl-1H-pyrrole-3-carboxylic acid. The crude products were purified by reverse phase chromatography eluted with ACN and water and dried using lyophilization to afford the title products as white solids. ESI-MS, m/z 396 (MH)$^+$.

Example 107: Synthesis of 5-(2-(tert-butylamino)-1,1-difluoro-2-oxoethyl)-N-(4-fluoro-3-methylphenyl)-1,2,4-trimethyl-1H-pyrrole-3-carboxamide

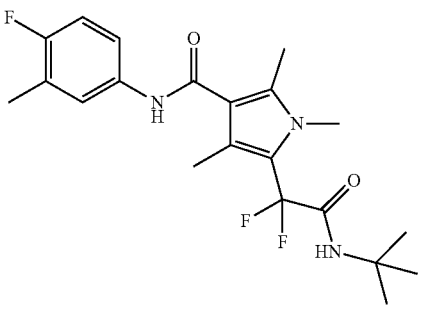 [SMILES: Cc1cc(NC(=O)c2c(C)c(C(F)(F)C(=O)NC(C)(C)C)n(C)c2C)ccc1F]

The title compounds were prepared following the procedure described in Example 97, using 1,2,4-trimethyl-1H-pyrrole-3-carboxylic acid instead of 1-methyl-1H-pyrrole-3-carboxylic acid. The crude products were purified by reverse phase chromatography eluted with ACN and water and dried using lyophilization to afford the title products as white solids. ESI-MS, m/z 410 (MH)$^+$.

Example 108: Synthesis of (S)-2-(2-(sec-butylamino)-1,1-difluoro-2-oxoethyl)-N-(4-fluoro-3-methylphenyl)-1-methyl-1H-pyrrole-3-carboxamide

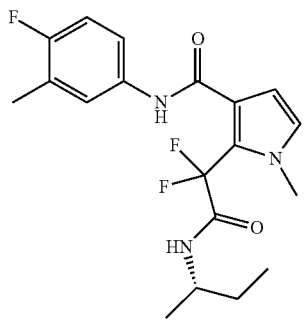 [SMILES: CC[C@H](C)NC(=O)C(F)(F)c1c(C(=O)Nc2ccc(F)c(C)c2)ccn1C]

The title compounds were prepared following the procedure described in Example 96, using (S)-butan-2-amine instead of piperidin-4-ol. The crude products were purified by reverse phase chromatography eluted with ACN and water and dried using lyophilization to afford the title products as white solids. ESI-MS, m/z 382 (MH)$^+$.

Example 109: Synthesis of (R)-5-(2-(sec-buty-lamino)-1,1-difluoro-2-oxoethyl)-N-(4-fluoro-3-methylphenyl)-1-methyl-1H-pyrrole-3-carboxamide

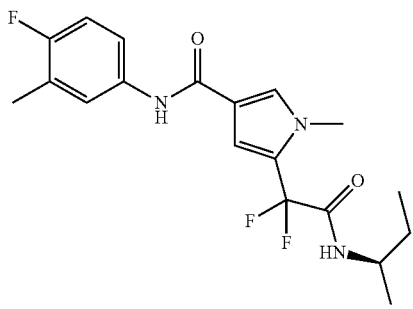 [SMILES: CC[C@@H](C)NC(=O)C(F)(F)c1cc(C(=O)Nc2ccc(F)c(C)c2)cn1C]

The title compounds were prepared following the procedure described in Example 97, using (R)-butan-2-amine instead of piperidin-4-ol. The crude products were purified by reverse phase chromatography eluted with ACN and water and dried using lyophilization to afford the title products as white solids. ESI-MS, m/z 382 (MH)$^+$.

Example 110: Synthesis of (R)-2-(2-(sec-buty-lamino)-1,1-difluoro-2-oxoethyl)-N-(4-fluoro-3-methylphenyl)-1-methyl-1H-pyrrole-3-carboxamide

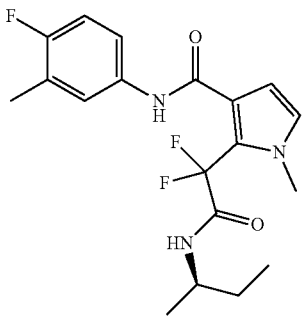 [SMILES: CC[C@@H](C)NC(=O)C(F)(F)c1c(C(=O)Nc2ccc(F)c(C)c2)ccn1C]

The title compounds were prepared following the procedure described in Example 96, using (R)-butan-2-amine instead of piperidin-4-ol. The crude products were purified by reverse phase chromatography eluted with ACN and water and dried using lyophilization to afford the title products as white solids. ESI-MS, m/z 382 (MH)$^+$.

Example 111: Synthesis of 5-(1,1-difluoro-2-oxo-2-((1,1,1-trifluoropropan-2-yl)amino)ethyl)-N-(4-fluoro-3-methylphenyl)-1-methyl-1H-pyrrole-3-carboxamide

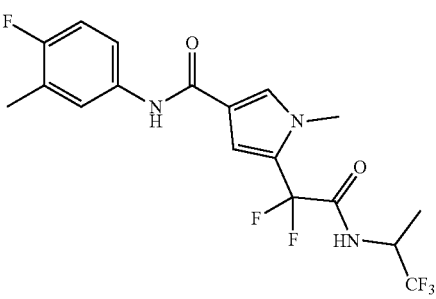 [SMILES: Cc1cc(NC(=O)c2cc(C(F)(F)C(=O)NC(C)C(F)(F)F)n(C)c2)ccc1F]

The title compounds were prepared following the procedure described in Example 97, using 1,1,1-trifluoropropan-2-amine of piperidin-4-ol. The crude products were purified by reverse phase chromatography eluted with ACN and water and dried using lyophilization to afford the title products as white solids. ESI-MS, m/z 422 (MH)$^+$.

Example 112: Synthesis of 2-(1,1-difluoro-2-oxo-2-((1,1,1-trifluoropropan-2-yl)amino)ethyl)-N-(4-fluoro-3-methylphenyl)-1-methyl-1H-pyrrole-3-carboxamide

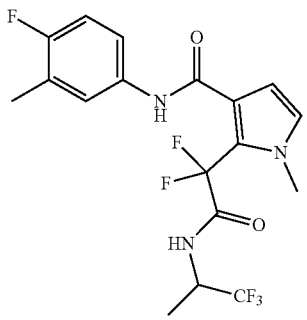 [SMILES: Cc1cc(NC(=O)c2ccn(C)c2C(F)(F)C(=O)NC(C)C(F)(F)F)ccc1F]

The title compounds were prepared following the procedure described in Example 96, using 1,1,1-trifluoropropan-2-amine of piperidin-4-ol. The crude products were purified by reverse phase chromatography eluted with ACN and water and dried using lyophilization to afford the title products as white solids. ESI-MS, m/z 422 (MH)$^+$.

Example 113: Synthesis of 5-(2-(tert-butylamino)-1,1-difluoro-2-oxoethyl)-N-(4-fluoro-3-methylphenyl)-1,4-dimethyl-1H-pyrrole-3-carboxamide (113)

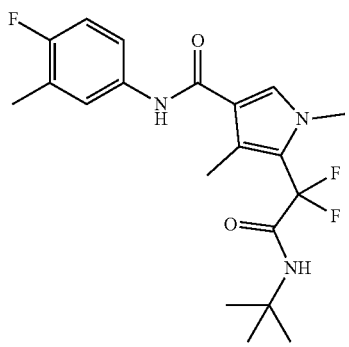 [SMILES: Cc1cc(NC(=O)c2cn(C)c(C(F)(F)C(=O)NC(C)(C)C)c2C)ccc1F]

Example 114: Synthesis of 2-(2-(tert-butylamino)-1,1-difluoro-2-oxoethyl)-N-(4-fluoro-3-methylphenyl)-1,4-dimethyl-1H-pyrrole-3-carboxamide (114)

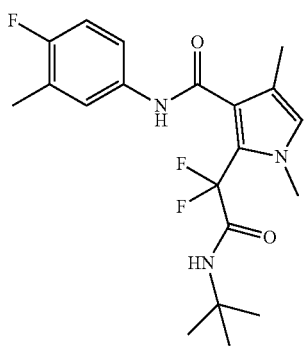 [SMILES: Cc1cc(NC(=O)c2c(C)cn(C)c2C(F)(F)C(=O)NC(C)(C)C)ccc1F]

The title compounds were prepared following the procedure described in Example 96, using 1,4-dimethyl-1H-pyrrole-3-carboxylic acid instead of 1-methyl-1H-pyrrole-3-carboxylic acid. The final products were purified by reverse phase chromatography eluted with ACN and water and dried using lyophilization to afford the title products as white solids. ESI-MS, m/z 396 (MH)$^+$ for both compounds.

Example 115: Synthesis of 3-(1,1-difluoro-2-(4-hydroxypiperidin-1-yl)-2-oxoethyl)-N-(4-fluoro-3-methylphenyl)-4-vinylbenzamide

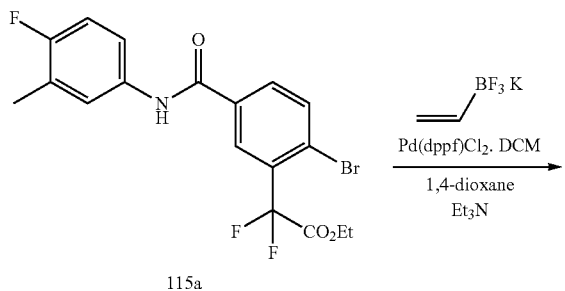

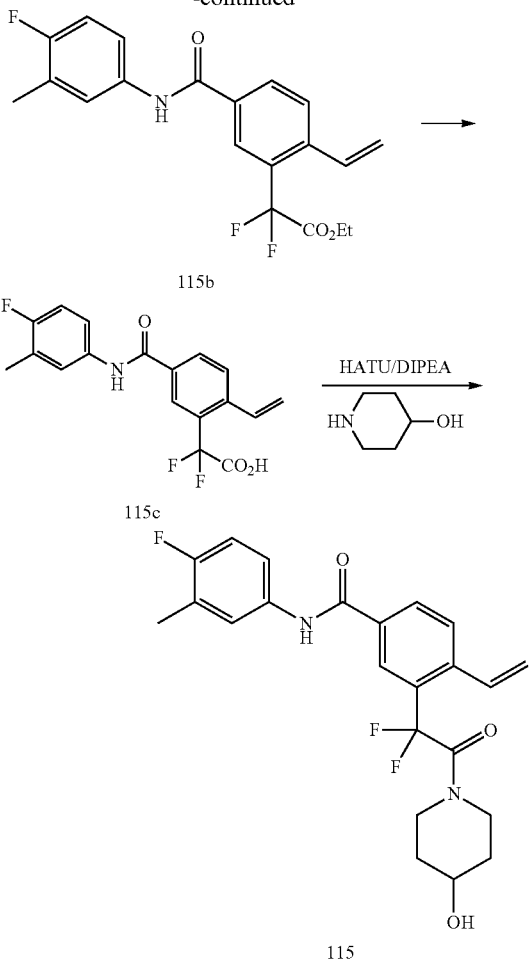

Step 1: Synthesis of ethyl 2-(2-bromo-5-((4-fluoro-3-methylphenyl)carbamoyl)phenyl)-2,2-difluoroacetate (115a)

The title compounds were prepared following the procedure described in Example 1 step 1 and step 2, using 4-bromo-3-iodobenzoic acid. The product was purified by flash chromatography on silica gel (EtOAc/Hexanes 0~50%) to afford the product as white solid. ESI-MS, m/z 430.0/432.0 (MH)$^+$.

Step 2: Synthesis of ethyl 2,2-difluoro-2-(5-((4-fluoro-3-methylphenyl)carbamoyl)-2-vinylphenyl)acetate (115b)

A mixture of 115a (0.5 g, 1.2 mmol), potassium vinyltrifluoroborate (0.2 g), triethylamine (0.25 g), and Pd(dppf)Cl$_2$ in EtOH/THF (4 mL, 1/1) was flushed with argon, then, heated at 85° C. for 20 hrs. After cooling to rt, the reaction mixture was concentrated, and the residue was purified by flash chromatography on silica gel (EtOAc/hexanes 0~70%) to give 115b as a colorless oil (0.3 g): ESI-MS, m/z 378.

Step 3: Synthesis of 2,2-difluoro-2-(5-((4-fluoro-3-methylphenyl)carbamoyl)-2-vinylphenyl)acetic acid (115c)

Aqueous NaOH (2 N, 1 mL) was added to a solution of 115b (0.2 g) in MeOH (3 mL) at 0° C. The reaction mixture was warmed to rt for 2 hrs. The reaction mixture was cooled to 0 C and neutralized to pH ~2 with aqueous HCl (0.5 N). The solvent was removed in vacuo, and the residue was dissolved in CAN/water, and dried using lyophilization to afford the crude products as white solids, which was used without further purification. ESI-MS, m/z 350.

Step 4: Synthesis of 3-(1,1-difluoro-2-(4-hydroxypiperidin-1-yl)-2-oxoethyl)-N-(4-fluoro-3-methylphenyl)-4-vinylbenzamide The title compounds were prepared following the procedure described in Example 1, step 4, using 115c and piperidin-4-ol. The final product was purified by reverse phase chromatography eluted with ACN and water and dried using lyophilization to afford the title products as white solids. ESI-MS, m/z 433 (MH)$^+$.

Example 116: Synthesis of (R)-3-(1,1-difluoro-2-(4-hydroxypiperidin-1-yl)-2-oxoethyl)-4-(1,2-dihydroxyethyl)-N-(4-fluoro-3-methylphenyl)benzamide

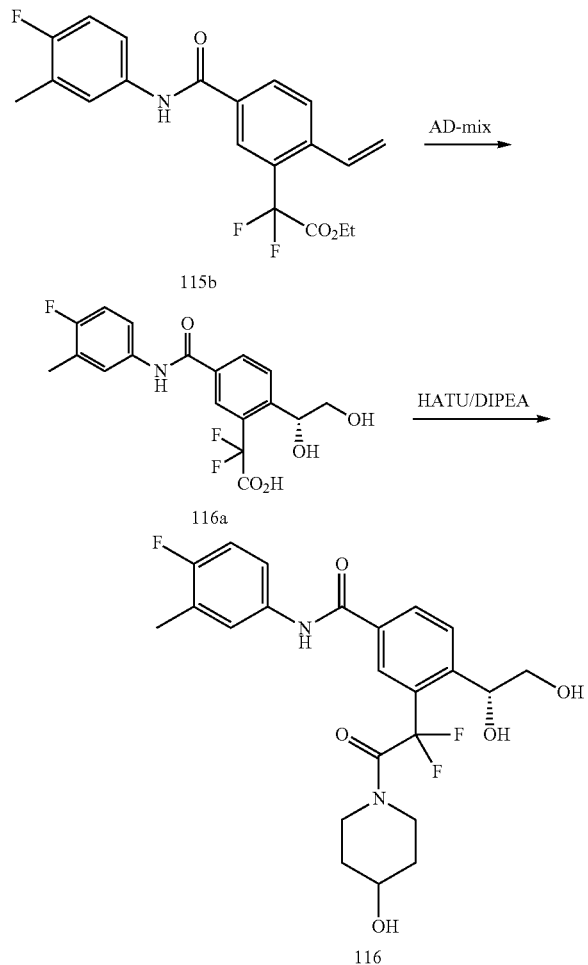

Step 1: Synthesis of (R)-2-(2-(1,2-dihydroxyethyl)-5-((4-fluoro-3-methylphenyl)carbamoyl)phenyl)-2,2-difluoroacetic acid (116a)

A mixture of AD-mix-beta (0.5 g) and 115b (0.12 g) in $^t$-BuOH/water (1/1, 6 mL) was stirred at rt for 3 days. The reaction was quenched with aqueous Na$_2$S$_2$O$_5$ (0.5 N, 4 mL), and extracted with EtOAc. The organic layer was washed with water/brine, and concentrated in vacuo. After lyophilization to afford crude 116a as yellow solid. ESI-MS, m/z 384.

Step 2: Synthesis of (R)-3-(1,1-difluoro-2-(4-hydroxypiperidin-1-yl)-2-oxoethyl)-4-(1,2-dihydroxyethyl)-N-(4-fluoro-3-methylphenyl)benzamide The title compounds were prepared following the procedure described in Example 1, step 4, using 116a and piperidin-4-ol. The final product was purified by reverse phase chromatography eluted with ACN and water and dried using lyophilization to afford the title products as white solids. ESI-MS, m/z 467 (MH)$^+$.

Example 117: Synthesis of (R)-3-(2-(tert-butylamino)-1,1-difluoro-2-oxoethyl)-4-(1,2-dihydroxyethyl)-N-(4-fluoro-3-methylphenyl)benzamide

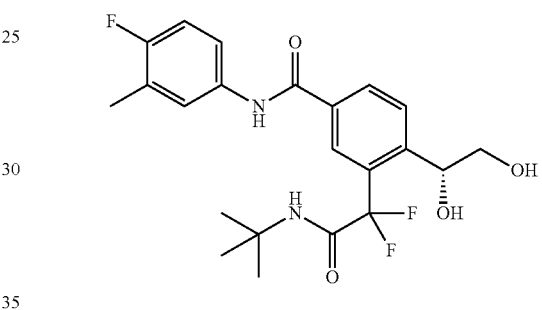

The title compounds were prepared following the procedure described in Example 1, step 4, using 116a and 2-methylpropan-2-amine. The final product was purified by reverse phase chromatography eluted with ACN and water and dried using lyophilization to afford the title products as white solids. ESI-MS, m/z 439 (MH)$^+$.

Example 118: Synthesis of 1-(2,2-difluoro-2-(2-fluoro-5-((4-fluoro-3-methylphenyl)carbamoyl)phenyl)acetyl)piperidine-4-carboxylic acid

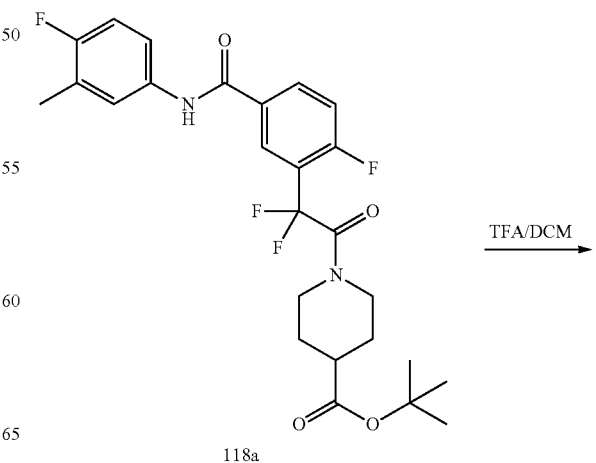

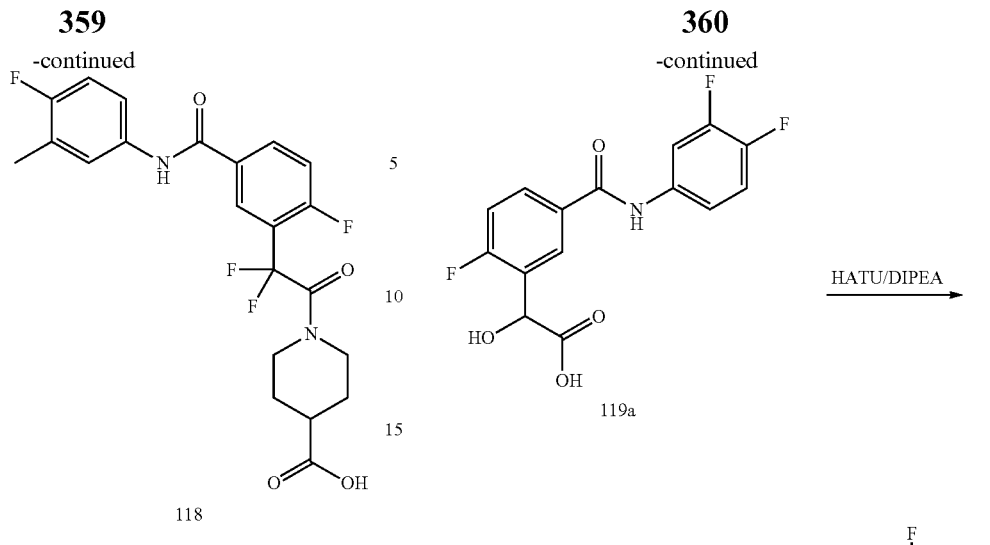

118

Step 1: Synthesis of tert-butyl 1-(2,2-difluoro-2-(2-fluoro-5-((4-fluoro-3-methylphenyl)carbamoyl)phenyl)acetyl)piperidine-4-carboxylate (118a)

The title compounds were prepared following the procedure described in Example 1, step 4, using tert-butyl piperidine-4-carboxylate instead of butan-2-amine. The product was purified by flash chromatography on silica gel (EtOAc/Hexanes 0~100%) to afford 118a as colorless oil. ESI-MS, m/z 509 (MH)+.

Step 2: Synthesis of 1-(2,2-difluoro-2-(2-fluoro-5-((4-fluoro-3-methylphenyl)carbamoyl)phenyl)acetyl)piperidine-4-carboxylic acid. (118)

TFA (0.5 mL) was added to a solution of 118a (20 mg) in DCM (1 mL) at 0° C. The mixture was stirred at rt for 4 hrs. The solvent was removed in vacuo to give crude product, which was purified by reverse phase chromatography eluted with ACN and water and dried using lyophilization to afford the title products as white solids. ESI-MS, m/z 453 (MH)+.

Example 119: Synthesis of 3-(2-(tert-butylamino)-1-hydroxy-2-oxoethyl)-N-(3,4-difluorophenyl)-4-fluorobenzamide

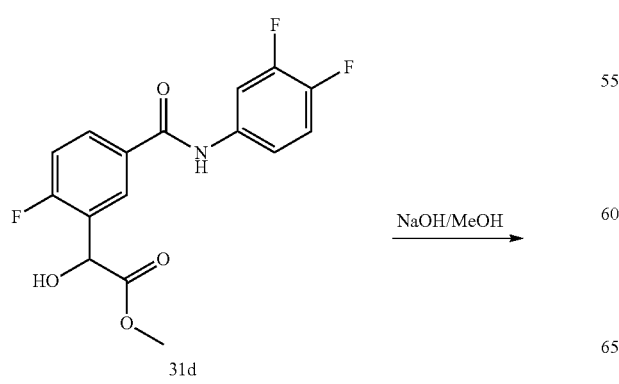

31d

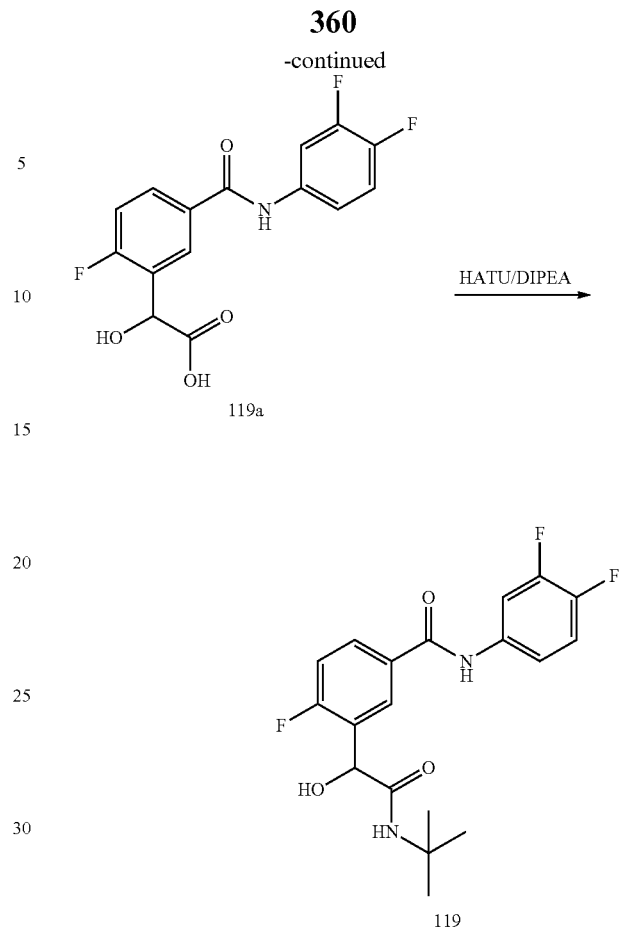

119

Step 1: Synthesis of 3-(2-(tert-butylamino)-1-hydroxy-2-oxoethyl)-N-(3,4-difluorophenyl)-4-fluorobenzamide (119a)

The title compounds were prepared following the procedure described in Example 115, step 3, using 31d instead of 115b. The crude product was used without further purification. ESI-MS, m/z 326.

Step 2: Synthesis of 3-(2-(tert-butylamino)-1-hydroxy-2-oxoethyl)-N-(3,4-difluorophenyl)-4-fluorobenzamide The title compounds were prepared following the procedure described in Example 1, step 4, using 119a and 2-methylpropan-2-amine. The final product was purified by reverse phase chromatography eluted with ACN and water and dried using lyophilization to afford the title products as white solids. ESI-MS, m/z 381 (MH)+.

Example 120: Synthesis of N-(3,4-difluorophenyl)-4-fluoro-3-(1-hydroxy-2-(4-hydroxypiperidin-1-yl)-2-oxoethyl)benzamide

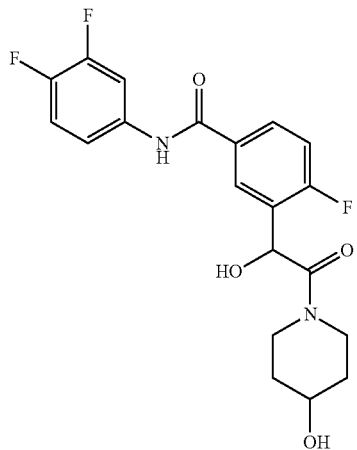 [SMILES: O=C(Nc1ccc(F)c(F)c1)c1ccc(F)c(C(O)C(=O)N2CCC(O)CC2)c1]

The title compounds were prepared following the procedure described in Example 1, step 4, using 119a and piperidin-4-ol. The final product was purified by reverse phase chromatography eluted with ACN and water and dried using lyophilization to afford the title products as white solids. ESI-MS, m/z 409 (MH)$^+$.

Example 121: Synthesis of 4-(2-(tert-butylamino)-1-hydroxy-2-oxoethyl)-N-(4-fluoro-3-methylphenyl)-1-methyl-1H-pyrrole-2-carboxamide

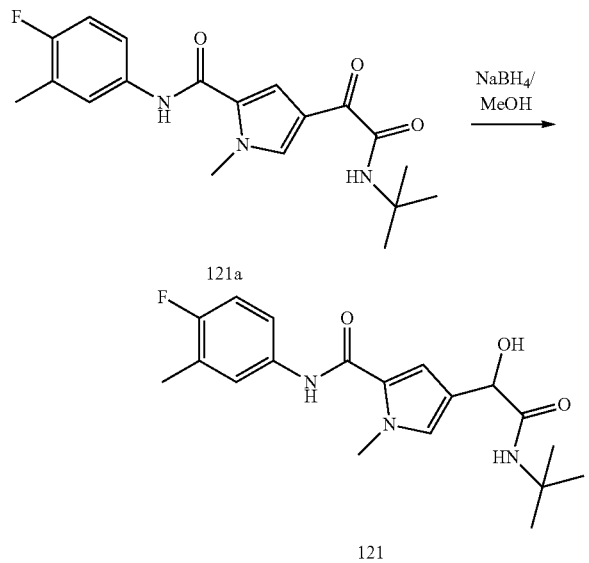

Step 1: Synthesis of 4-(2-(tert-butylamino)-2-oxoacetyl)-N-(4-fluoro-3-methylphenyl)-1-methyl-1H-pyrrole-2-carboxamide (121a)

The title compound was prepared according to the procedures described in Van Dyck, B. R., et al, PCT International Application publication WO 2015/011281. ESI-MS, m/z 360 (MH)$^+$.

Step 2: Synthesis of 4-(2-(tert-butylamino)-1-hydroxy-2-oxoethyl)-N-(4-fluoro-3-methylphenyl)-1-methyl-1H-pyrrole-2-carboxamide NaBH$_4$ (20 mg) was added to a solution of 121a (20 mg) in MeOH/CH$_3$CN (2 mL, 1/1) at rt. After 4 min., the mixture was quenched with water, concentrated and purified by reverse phase chromatography eluted with ACN and water and dried using lyophilization to afford the title products as white solids. ESI-MS, m/z 362 (MH)$^+$.

Examples 122-342

Examples 122-342 (structures shown in Table 1) were prepared in analogy to the procedures described above. The observed ESI-MS data for these Examples are shown in Table 3.

TABLE 3

Analytical data for Exemplary compounds 122-342.

| Example | MW | ESI-MS m/z (M + H)$^+$ |
|---|---|---|
| 122 | 437.2 | 438.1 |
| 123 | 375.4 | 376.2 |
| 124 | 403.5 | 404.2 |
| 125 | 423.4 | 424.1 |
| 126 | 423.4 | 424.1 |
| 127 | 423.4 | 424.1 |
| 128 | 423.4 | 424.1 |
| 129 | 411.4 | 421.1 |
| 131 | 457.5 | 440 (–H$_2$O) |
| 132 | 411.4 | 412.2 |
| 133 | 423.4 | 424.1 |
| 134 | 395.4 | 396.2 |
| 135 | 395.4 | 396.1 |
| 136 | 401.8 | 402.2 |
| 137 | 401.8 | 402.2 |
| 138 | 389.8 | 390.2 |
| 139 | 401.8 | 402.2 |
| 140 | 441.8 | 442.2 |
| 141 | 441.8 | 442.2 |
| 142 | 415.8 | 416.2 |
| 143 | 415.8 | 416.2 |
| 144 | 417.8 | 418.2 |
| 145 | 417.8 | 418.2 |
| 146 | 410.8 | 411.2 |
| 147 | 410.8 | 411.2 |
| 148 | 468.7 | 469.2 |
| 149 | 532.3 | 533.2 |
| 150 | 424.2 | 425.1 |
| 151 | 483.1 | 483.0/485.0 |
| 152 | 452.2 | 452.9 |
| 153 | 438.2 | 439.1 |
| 154 | 450.2 | 451.1 |
| 155 | 457.5 | 458.0 |
| 156 | 398.1 | 399.1 |
| 157 | 384.4 | 385.2 |
| 158 | 463.3 | 464.1 |
| 159 | 442.4 | 442.8 |
| 160 | 425.4 | 425.6 |
| 161 | 474.4 | 474.9 |
| 162 | 442.4 | 442.9 |
| 163 | 450.4 | 451.1 |
| 164 | 451.4 | 452.2 |
| 165 | 382.4 | 383.1 |
| 166 | 382.4 | 383.1 |
| 167 | 427.8 | 427.7 |
| 168 | 440.8 | 440.8 |
| 169 | 480.8 | 480.5 |
| 170 | 470.8 | 470.9 |
| 171 | 470.8 | 470.9 |
| 172 | 474.8 | 474.9 |
| 173 | 472.4 | 472.6 |

TABLE 3-continued

Analytical data for Exemplary compounds 122-342.

| Example | MW | ESI-MS m/z (M + H)+ |
|---|---|---|
| 174 | 476.4 | 476.5 |
| 175 | 525.2 | 524.7 |
| 176 | 515.3 | 514.8 |
| 177 | 471.4 | 471.9 |
| 178 | 461.4 | 461.9 |
| 179 | 432.4 | 432.7 |
| 180 | 422.4 | 422.9 |
| 181 | 422.4 | 422.9 |
| 182 | 426.4 | 426.9 |
| 183 | 460.4 | 461.0 |
| 184 | 450.5 | 450.8 |
| 185 | 450.5 | 450.8 |
| 186 | 454.5 | 454.9 |
| 187 | 482.3 | 482.5 |
| 188 | 472.4 | 472.9 |
| 189 | 515.3 | 514.7 |
| 190 | 519.3 | 519.0 |
| 191 | 471.4 | 471.9 |
| 192 | 461.4 | 461.5 |
| 193 | 461.4 | 462.0 |
| 194 | 465.4 | 465.5 |
| 195 | 463.8 | 463.5 |
| 196 | 453.8 | 453.7 |
| 197 | 453.8 | 453.7 |
| 198 | 457.8 | 457.5 |
| 199 | 454.4 | 455.1 |
| 200 | 462.4 | 463.2 |
| 201 | 464.4 | 465.1 |
| 202 | 464.5 | 465.1 |
| 203 | 466.4 | 467.1 |
| 204 | 446.4 | 447.1 |
| 205 | 468.4 | 469.0 |
| 206 | 466.9 | 466.6 |
| 207 | 450.4 | 450.7 |
| 208 | 451.4 | 452.1 |
| 209 | 551.5 | 552.1 |
| 210 | 612.6 | 613.1 |
| 211 | 529.5 | 530.1 |
| 212 | 467.4 | 468.1 |
| 213 | 436.4 | 436.6 |
| 214 | 437.4 | 438.2 |
| 215 | 450.4 | 450.8 |
| 216 | 464.5 | 465.2 |
| 217 | 464.5 | 464.6 |
| 218 | 468.4 | 469.0 |
| 219 | 450.4 | 450.8 |
| 220 | 450.4 | 450.8 |
| 221 | 466.9 | 467.1 |
| 222 | 455.4 | 456.1 |
| 223 | 451.4 | 452.1 |
| 224 | 451.4 | 452.1 |
| 225 | 549.6 | 572.1 (M + Na)+ |
| 226 | 449.4 | 449.8 |
| 227 | 491.5 | 492.2 |
| 228 | 449.4 | 449.8 |
| 229 | 523.5 | 524.2 |
| 230 | 423.4 | 424.2 |
| 231 | 501.5 | 502.2 |
| 232 | 549.6 | 550.1 |
| 233 | 548.5 | 549.2 |
| 234 | 409.4 | 410.1 |
| 235 | 466.4 | 467.2 |
| 236 | 405.4 | 406.2 |
| 237 | 454.4 | 455.2 |
| 238 | 446.4 | 447.1 |
| 239 | 509.5 | 510.1 |
| 240 | 489.5 | 490.2 |
| 241 | 507.5 | 508.2 |
| 242 | 478.5 | 479.1 |
| 243 | 407.4 | 408.2 |
| 244 | 461.4 | 462.1 |
| 245 | 460.5 | 461.2 |
| 246 | 468.4 | 469.1 |
| 247 | 488.8 | 488.7 |
| 248 | 472.4 | 473.1 |
| 249 | 468.4 | 469.1 |
| 250 | 478.4 | 479.0 |
| 251 | 461.4 | 462.0 |
| 252 | 549.6 | 572.1 (M + Na)+ |
| 253 | 449.4 | 450.1 |
| 254 | 450.4 | 451.1 |
| 255 | 438.4 | 439.1 |
| 256 | 450.4 | 451.1 |
| 257 | 477.5 | 477.8 |
| 258 | 521.5 | 521.8 |
| 259 | 478.4 | 478.8 |
| 260 | 547.6 | 547.8 |
| 261 | 527.5 | 527.5 |
| 262 | 527.5 | 527.5 |
| 263 | 491.5 | 492.1 |
| 264 | 464.4 | 465.1 |
| 265 | 472.4 | 473.1 |
| 266 | 530.5 | 531.1 |
| 267 | 493.5 | 494.2 |
| 268 | 461.5 | 462.2 |
| 269 | 492.4 | 493.1 |
| 270 | 447.4 | 448.2 |
| 271 | 460.5 | 461.2 |
| 272 | 490.5 | 491.1 |
| 273 | 479.4 | 480.1 |
| 274 | 480.5 | 480.6 |
| 275 | 480.5 | 480.5 |
| 276 | 479.5 | 479.9 |
| 277 | 464.5 | 465.1 |
| 278 | 444.4 | 445.1 |
| 279 | 498.9 | 499.2 |
| 280 | 448.4 | 449.1 |
| 281 | 450.4 | 451.1 |
| 282 | 461.4 | 462.1 |
| 283 | 435.4 | 436.1 |
| 284 | 549.5 | 550.2 |
| 285 | 451.5 | 452.2 |
| 286 | 529.6 | 530.2 |
| 287 | 493.5 | 494.2 |
| 288 | 520.5 | 520.5 |
| 289 | 463.4 | 463.6 |
| 290 | 578.6 | 578.7 |
| 291 | 530.5 | 530.7 |
| 292 | 541.6 | 541.7 |
| 293 | 515.5 | 515.7 |
| 294 | 479.5 | 479.8 |
| 295 | 479.5 | 480.1 |
| 296 | 437.4 | 438.1 |
| 297 | 447.4 | 447.6 |
| 298 | 451.4 | 452.2 |
| 299 | 421.4 | 422.2 |
| 300 | 425.4 | 426.2 |
| 301 | 592.6 | 593.2 |
| 302 | 523.5 | 524.1 |
| 303 | 479.5 | 480.2 |
| 304 | 452.5 | 453.1 |
| 305 | 494.5 | 495.2 |
| 306 | 543.5 | 544.1 |
| 307 | 523.5 | 524.1 |
| 308 | 478.5 | 479.1 |
| 309 | 478.5 | 479.1 |
| 310 | 466.4 | 467.1 |
| 311 | 490.5 | 491.2 |
| 312 | 514.4 | 515.0 |
| 313 | 504.5 | 505.0 |
| 314 | 506.5 | 506.8 |
| 315 | 556.6 | 557.0 |
| 316 | 505.5 | 505.9 |
| 317 | 505.5 | 505.9 |
| 318 | 463.5 | 464.1 |
| 319 | 501.4 | 501.8 |
| 320 | 599.6 | 599.4 |
| 321 | 586.6 | 684.4 |

TABLE 3-continued

Analytical data for Exemplary compounds 122-342.

| Example | MW | ESI-MS m/z (M + H)+ |
|---|---|---|
| 322 | 542.3 | 541.3 |
| 323 | 514.4 | 514.8 |
| 324 | 477.5 | 477.5 |
| 325 | 463.5 | 464.0 |
| 326 | 506.5 | 507.0 |
| 327 | 493.5 | 494.2 |
| 334 | 459.4 | 459.6 |
| 335 | 537.5 | 537.8 |
| 336 | 541.6 | 541.5 |
| 337 | 463.5 | 463.6 |
| 338 | 541.6 | 541.8 |
| 339 | 506.5 | 506.5 |
| 340 | 492.5 | 493.0 |
| 341 | 515.4 | 516.0 |
| 342 | 518.5 | 518.8 |

Example I: Oral Composition of a Compound of Formula (I) or (II), or a Pharmaceutically Acceptable Salt, Solvate, or Stereoisomer Thereof To prepare a pharmaceutical composition for oral delivery, 400 mg of a compound of Formula (I) or (II), or a pharmaceutically acceptable salt, solvate, or stereoisomer thereof and the following ingredients are mixed intimately and pressed into single scored tablets.

Tablet Formulation

| Ingredient | Quantity per tablet (mg) |
|---|---|
| compound | 400 |
| cornstarch | 50 |
| croscarmellose sodium | 25 |
| lactose | 120 |
| magnesium stearate | 5 |

The following ingredients are mixed intimately and loaded into a hard-shell gelatin capsule.

Capsule Formulation

| Ingredient | Quantity per capsule (mg) |
|---|---|
| compound | 200 |
| lactose spray dried | 148 |
| magnesium stearate | 2 |

Example II: In Vitro Antiviral Assays

The anti-HBV activity of the Capsid Assembly Modulators (CAMs) was evaluated in a cell based assay utilizing the human hepatoma cell line HepAD38 (Ladner, S K., et al., 1998). HepAD38 cells were derived from the parental line, HepG2, that were stably transfected with a construct containing an HBV genome (genotype D, serotype ayw) under the control of a tetracycline repressible CMV promoter. Upon removal of tetracycline, viral pre-genomic RNA (pgRNA) and mRNAs are expressed and infectious viral particles are assembled and secreted into the culture medium providing a reliable, robust system to measure multiple steps of the HBV life cycle. Disruption of capsid formation results in reduced levels of DNA-containing virus particles that are released into the culture supernatant. To quantify the effect of CAMs on HBV replication, we developed a sensitive QPCR-based assay that measures extracellular HBV DNA levels upon treatment of HepAD38 cells with various concentrations of test compounds.

HepAD38 cells were maintained in DMEM/F12 medium containing 10% FBS, 400 μg/mL G418 and 0.3 μg/mL tetracycline (tet+medium) to maintain repression of HBV replication. To evaluate each compound, HepAD38 cells were seeded into 24-well collagen coated culture plates (Corning BioCoat) at a density of 200,000 cells per well in 1 mL of tet+medium and allowed to adhere overnight at 37° C., 5% $CO_2$ in a humidified incubator. The following day, test articles were subjected to half-logo serial dilutions, ranging from 30 μM to 10 nM, in 100% DMSO at 200× the desired final assay concentration. Tetracycline was removed from the cells by aspirating the tet+medium and washing the cells once with growth medium lacking tetracycline (tet-). Various concentrations of each compound were added to the appropriate wells (1:200 dilution) and the plates were returned to the incubator. Following 7 days of incubation, culture supernatants were harvested and HBV DNA levels were evaluated by QPCR and compared to the vehicle treated control wells (i.e. DMSO alone).

To quantify HBV DNA levels, cell culture supernatants were diluted 1:10 in sterile, nuclease-free water (Gibco). The diluted supernatants were subsequently added to a PCR master mix containing 1× Roche Light Cycler Master Mix, 0.5 μM forward primer, 0.5 μM reverse primer (Fwd:

(SEQ ID NO: 1)
5'-TTGGTGTCTTTCGGAGTGTG;

Rev:
(SEQ ID NO: 2))
5'-AGGGGCATTTGGTGGTCTAT, 0.2 μM Roche Universal Probe Library Probe 25. The volume was brought to 20 μL with nuclease-free water and amplification of the HBV target sequence was performed using a Roche LightCycler 480 QPCR instrument. PCR extended out to 45 cycles with each cycle consisting of a denaturation step at 95° C. for 10 sec., followed by an annealing step at 60° C. for 10 sec. and a brief extension step at 72° C. for 1 sec.

Extracellular HBV DNA levels, expressed in copies/mL, were determined by comparison to a standard curve ($10^2$-$10^9$ copies/mL) using the Roche LightCycler analysis software. These values were subsequently converted to percent inhibition of HBV replication by dividing the HBV DNA levels in the experimental samples with those obtained from the vehicle control (~1-2×105 copies/mL). Potency, expressed as an $EC_{50}$ (the effective concentration required to inhibit 5000 of HBV replication), was calculated from the dose-response curve using a 4-parameter non-linear regression analysis (GraphPad Prism). The nucleoside analog inhibitor entecavir was used as a positive control to validate each assay run. The $EC_{50}$ value of entecavir in the HepAD38 assay was 0.5 nM, as previously reported in the literature.

Table 4 summarizes the antiviral activity of the exemplary compounds. A: $EC_{50}$>30 μM; B: $EC_{50}$ values between 5 μM and 30 M; C: $EC_{50}$ values K<5 μM. NT=not tested.

TABLE 4

Summary of anti-HBV replication in HepAD38 cells.

| Ex. | Anti-HBV EC$_{50}$ |
|---|---|
| 1 | C |
| 2 | C |
| 3 | B |
| 4 | B |
| 5 | B |
| 6 | B |
| 7 | B |
| 8 | B |
| 9 | A |
| 10 | B |
| 11 | B |
| 12 | B |
| 13 | B |
| 14 | C |
| 15 | C |
| 16 | B |
| 17 | C |
| 18 | B |
| 19 | C |
| 20 | B |
| 21 | B |
| 22 | B |
| 23 | B |
| 24 | B |
| 25 | C |
| 26 | C |
| 27 | C |
| 28 | B |
| 29 | C |
| 30 | B |
| 31 | B |
| 32 | C |
| 33 | C |
| 34 | C |
| 35 | C |
| 36 | C |
| 37 | A |
| 38 | A |
| 39 | B |
| 40 | A |
| 41 | B |
| 42 | C |
| 43 | C |
| 44 | A |
| 45 | C |
| 46 | B |
| 47 | B |
| 48 | C |
| 49 | C |
| 50 | B |
| 51 | C |
| 52 | B |
| 53 | C |
| 54 | C |
| 55 | B |
| 56 | C |
| 57 | C |
| 58 | C |
| 59 | C |
| 60 | B |
| 61 | B |
| 62 | C |
| 63 | A |
| 64 | B |
| 65 | B |
| 66 | B |
| 67 | C |
| 68 | C |
| 69 | C |
| 70 | C |
| 71 | B |
| 72 | C |
| 73 | B |
| 74 | C |
| 75 | C |
| 76 | C |
| 77 | C |
| 78 | C |
| 79 | B |
| 80 | A |
| 81 | B |
| 82 | A |
| 83 | B |
| 84 | A |
| 85 | C |
| 86 | C |
| 87 | C |
| 88 | C |
| 89 | A |
| 90 | C |
| 91 | A |
| 92 | C |
| 93 | C |
| 94 | C |
| 95 | A |
| 96 | B |
| 97 | C |
| 98 | A |
| 99 | A |
| 100 | C |
| 101 | C |
| 102 | C |
| 103 | C |
| 104 | C |
| 105 | B |
| 106 | C |
| 107 | C |
| 108 | C |
| 109 | C |
| 110 | A |
| 111 | C |
| 112 | A |
| 113 | C |
| 114 | A |
| 115 | C |
| 116 | A |
| 117 | A |
| 118 | C |
| 119 | B |
| 120 | A |
| 121 | C |
| 122 | B |
| 123 | B |
| 124 | B |
| 125 | C |
| 126 | B |
| 127 | C |
| 128 | B |
| 129 | C |
| 131 | B |
| 132 | C |
| 133 | C |
| 134 | C |
| 135 | B |
| 136 | B |
| 137 | C |
| 138 | B |
| 139 | C |
| 139 | C |
| 140 | C |
| 141 | B |
| 142 | C |
| 143 | B |
| 144 | C |
| 145 | B |
| 146 | C |

TABLE 4-continued

Summary of anti-HBV replication in HepAD38 cells.

| Ex. | Anti-HBV EC$_{50}$ |
|---|---|
| 147 | B |
| 148 | C |
| 149 | C |
| 150 | C |
| 151 | C |
| 152 | C |
| 153 | C |
| 154 | C |
| 155 | C |
| 156 | B |
| 157 | B |
| 158 | B |
| 159 | C |
| 160 | B |
| 161 | B |
| 162 | C |
| 163 | C |
| 164 | C |
| 165 | B |
| 166 | B |
| 167 | B |
| 168 | C |
| 169 | C |
| 170 | C |
| 171 | C |
| 172 | C |
| 173 | C |
| 174 | C |
| 175 | C |
| 176 | C |
| 177 | C |
| 178 | C |
| 179 | B |
| 180 | B |
| 181 | B |
| 182 | B |
| 183 | B |
| 184 | B |
| 185 | B |
| 186 | B |
| 187 | C |
| 188 | C |
| 189 | C |
| 190 | C |
| 191 | C |
| 192 | C |
| 193 | C |
| 194 | C |
| 195 | C |
| 196 | C |
| 197 | C |
| 198 | C |
| 199 | C |
| 200 | C |
| 201 | C |
| 202 | C |
| 203 | C |
| 204 | C |
| 205 | B |
| 206 | C |
| 207 | C |
| 208 | C |
| 209 | C |
| 210 | C |
| 211 | C |
| 212 | C |
| 213 | C |
| 214 | C |
| 215 | C |
| 216 | C |
| 217 | C |
| 218 | C |
| 219 | B |
| 220 | C |
| 221 | C |
| 222 | B |
| 223 | C |
| 224 | C |
| 225 | C |
| 226 | C |
| 227 | C |
| 228 | C |
| 229 | C |
| 230 | C |
| 231 | C |
| 232 | C |
| 233 | C |
| 234 | B |
| 235 | B |
| 236 | B |
| 237 | B |
| 238 | C |
| 239 | C |
| 240 | C |
| 241 | C |
| 242 | C |
| 243 | B |
| 244 | B |
| 245 | B |
| 246 | C |
| 247 | B |
| 248 | C |
| 249 | C |
| 250 | C |
| 251 | B |
| 252 | B |
| 253 | C |
| 254 | B |
| 255 | C |
| 256 | C |
| 257 | C |
| 258 | C |
| 259 | C |
| 260 | C |
| 261 | C |
| 262 | C |
| 263 | C |
| 264 | C |
| 265 | C |
| 266 | C |
| 267 | B |
| 268 | B |
| 269 | C |
| 270 | C |
| 271 | B |
| 272 | B |
| 273 | C |
| 274 | C |
| 275 | C |
| 276 | C |
| 277 | C |
| 278 | B |
| 279 | C |
| 280 | C |
| 281 | C |
| 282 | B |
| 283 | C |
| 284 | B |
| 285 | C |
| 286 | C |
| 287 | C |
| 288 | C |
| 289 | C |
| 290 | C |
| 291 | C |
| 292 | C |

TABLE 4-continued

Summary of anti-HBV replication in HepAD38 cells.

| Ex. | Anti-HBV $EC_{50}$ |
|---|---|
| 293 | C |
| 294 | C |
| 295 | C |
| 296 | C |
| 297 | C |
| 298 | C |
| 299 | C |
| 300 | C |
| 301 | C |
| 302 | C |
| 303 | C |
| 304 | C |
| 305 | C |
| 306 | C |
| 307 | C |
| 308 | C |
| 309 | B |
| 310 | C |
| 311 | C |
| 312 | C |
| 313 | C |
| 314 | NT |
| 315 | NT |
| 316 | NT |
| 317 | NT |
| 318 | NT |
| 319 | NT |
| 320 | NT |
| 321 | NT |
| 322 | NT |
| 323 | NT |
| 324 | NT |
| 325 | NT |
| 326 | NT |
| 327 | C |
| 334 | C |
| 335 | C |
| 336 | C |
| 337 | C |
| 338 | C |
| 339 | C |
| 340 | C |
| 341 | B |
| 342 | C |

Example III: In Vitro Cytotoxicity Assays

To evaluate antiviral selectivity, the cytotoxic activity of each compound was determined using a standard cell viability assay performed on the parental HepG2 cell line. Cell viability was determined by measuring the conversion of 3-(4,5-dimethylthiazol-2-yl)-2,5-diphenyltetrazolium bromide (MTT) to the insoluble formazan salt crystal that occurs in live cells. Briefly, HepG2 cells were seeded in 96-well plates at a density of 20,000 cells per well in EMEM+10% FBS (complete growth medium) and allowed to adhere overnight in a 37° C., 5% $CO_2$ humidified incubator. The next day, test agents were prepared by performing 8 half-$\log_{10}$ serial dilutions in 100% DMSO at 200× the final desired concentration in the assay. Compounds were tested over a range of concentrations from 30 μM to 1.0 nM in the assay. HepG2 cells were incubated in the presence of various concentrations of CAMs for 7 days in a 37° C., 5% $CO_2$ humidified incubator. At the completion of the 7-day incubation period, MTT reagent was added to each well and the mixture was incubated for an additional 3-4 hours. At the completion of the incubation period, all wells were aspirated to remove the culture medium. The formazan crystals were solubilized from the cell monolayers with 100% DMSO. Plates were briefly mixed on an orbital shaker and absorbance was measured at 492 nm using a Perkin-Elmer EnVision multi-label plate reader. All absorbance values were converted to a percentage of the signal obtained from the vehicle treated controls. Absorbance values at 492 nm are directly proportional to the number of viable cells present in the sample. A $CC_{50}$ value (cytotoxic concentration that results in loss of 50% cell viability) was calculated from the dose-response curve by 4-parameter, non-linear regression analysis using the GraphPad Prism software. The positive control compound, staurosporine, reduced the viability of HepG2 cells in a dose-dependent manner ($CC_{50}$=100 nM).

Table 5 summarizes the cytotoxicity assay data in the hepatocyte cell line HepG2 for the example compounds. A: $CC_{50}$>30 μM; B: $CC_{50}$ values between 5 μM and 30 μM; C: $CC_{50}$ values<5 μM. NT=not tested.

TABLE 5

Summary of cytotoxicity results in HepG2 cells for example compounds.

| Ex. | Cytotoxicity $CC_{50}$ |
|---|---|
| 1 | B |
| 2 | B |
| 3 | B |
| 4 | B |
| 5 | B |
| 6 | B |
| 7 | B |
| 8 | B |
| 9 | A |
| 10 | B |
| 11 | B |
| 12 | B |
| 13 | B |
| 14 | B |
| 15 | B |
| 16 | A |
| 17 | B |
| 18 | B |
| 19 | B |
| 20 | B |
| 21 | B |
| 22 | A |
| 23 | B |
| 24 | B |
| 25 | B |
| 26 | B |
| 27 | B |
| 28 | A |
| 29 | A |
| 30 | B |
| 31 | B |
| 32 | B |
| 33 | A |
| 34 | B |
| 35 | B |
| 36 | A |
| 37 | A |
| 38 | A |
| 39 | B |
| 40 | A |
| 41 | A |
| 42 | B |
| 43 | B |
| 44 | A |
| 45 | B |
| 46 | A |
| 47 | A |
| 48 | B |

TABLE 5-continued

Summary of cytotoxicity results in HepG2 cells for example compounds.

| Ex. | Cytotoxicity $CC_{50}$ |
|---|---|
| 49 | A |
| 50 | B |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | B |
| 64 | B |
| 65 | B |
| 66 | A |
| 67 | A |
| 68 | B |
| 69 | A |
| 70 | B |
| 71 | A |
| 72 | B |
| 73 | B |
| 74 | B |
| 75 | B |
| 76 | B |
| 77 | B |
| 78 | B |
| 79 | A |
| 80 | A |
| 81 | A |
| 82 | A |
| 83 | A |
| 84 | A |
| 85 | B |
| 86 | B |
| 87 | B |
| 88 | A |
| 89 | B |
| 90 | B |
| 91 | A |
| 92 | B |
| 93 | B |
| 94 | A |
| 95 | A |
| 96 | A |
| 97 | A |
| 98 | A |
| 99 | A |
| 100 | A |
| 101 | A |
| 102 | A |
| 103 | B |
| 104 | A |
| 105 | A |
| 106 | B |
| 107 | A |
| 108 | A |
| 109 | A |
| 110 | A |
| 111 | A |
| 112 | A |
| 113 | A |
| 114 | A |
| 115 | A |
| 116 | A |
| 117 | A |
| 118 | A |
| 119 | B |
| 120 | A |
| 121 | A |
| 122 | A |
| 123 | B |
| 124 | A |
| 125 | A |
| 126 | A |
| 127 | A |
| 128 | A |
| 129 | A |
| 131 | B |
| 132 | A |
| 133 | A |
| 134 | A |
| 135 | A |
| 136 | A |
| 137 | A |
| 138 | A |
| 139 | B |
| 139 | A |
| 140 | A |
| 141 | A |
| 142 | A |
| 143 | A |
| 144 | A |
| 145 | A |
| 146 | A |
| 147 | A |
| 148 | A |
| 149 | B |
| 150 | A |
| 151 | A |
| 152 | B |
| 153 | A |
| 154 | B |
| 155 | B |
| 156 | B |
| 157 | B |
| 158 | B |
| 159 | B |
| 160 | B |
| 161 | A |
| 162 | B |
| 163 | B |
| 164 | A |
| 165 | A |
| 166 | A |
| 167 | B |
| 168 | B |
| 169 | B |
| 170 | B |
| 171 | B |
| 172 | B |
| 173 | B |
| 174 | B |
| 175 | B |
| 176 | B |
| 177 | B |
| 178 | A |
| 179 | A |
| 180 | A |
| 181 | A |
| 182 | A |
| 183 | A |
| 184 | A |
| 185 | A |
| 186 | A |
| 187 | B |
| 188 | B |
| 189 | B |
| 190 | B |
| 191 | B |
| 192 | B |
| 193 | B |
| 194 | B |

TABLE 5-continued

Summary of cytotoxicity results in HepG2 cells for example compounds.

| Ex. | Cytotoxicity $CC_{50}$ |
|---|---|
| 195 | C |
| 196 | C |
| 197 | C |
| 198 | B |
| 199 | B |
| 200 | B |
| 201 | B |
| 202 | B |
| 203 | B |
| 204 | B |
| 205 | B |
| 206 | B |
| 207 | B |
| 208 | B |
| 209 | B |
| 210 | A |
| 211 | A |
| 212 | B |
| 213 | A |
| 214 | B |
| 215 | B |
| 216 | B |
| 217 | B |
| 218 | A |
| 219 | B |
| 220 | B |
| 221 | B |
| 222 | A |
| 223 | C |
| 224 | C |
| 225 | B |
| 226 | B |
| 227 | B |
| 228 | B |
| 229 | B |
| 230 | B |
| 231 | B |
| 232 | B |
| 233 | B |
| 234 | A |
| 235 | A |
| 236 | A |
| 237 | A |
| 238 | A |
| 239 | B |
| 240 | C |
| 241 | B |
| 242 | B |
| 243 | A |
| 244 | B |
| 245 | A |
| 246 | B |
| 247 | B |
| 248 | B |
| 249 | B |
| 250 | B |
| 251 | B |
| 252 | C |
| 253 | A |
| 254 | A |
| 255 | B |
| 256 | B |
| 257 | B |
| 258 | A |
| 259 | A |
| 260 | A |
| 261 | C |
| 262 | B |
| 263 | B |
| 264 | A |
| 265 | B |
| 266 | A |
| 267 | B |
| 268 | A |
| 269 | A |
| 270 | B |
| 271 | B |
| 272 | B |
| 273 | B |
| 274 | C |
| 275 | A |
| 276 | B |
| 277 | B |
| 278 | A |
| 279 | B |
| 280 | B |
| 281 | B |
| 282 | A |
| 283 | B |
| 284 | A |
| 285 | B |
| 286 | B |
| 287 | B |
| 288 | B |
| 289 | B |
| 290 | B |
| 291 | B |
| 292 | B |
| 293 | B |
| 294 | B |
| 295 | B |
| 296 | B |
| 297 | B |
| 298 | B |
| 299 | B |
| 300 | B |
| 301 | B |
| 302 | B |
| 303 | B |
| 304 | B |
| 305 | B |
| 306 | B |
| 307 | B |
| 308 | B |
| 309 | B |
| 310 | A |
| 311 | A |
| 312 | NT |
| 313 | NT |
| 314 | NT |
| 315 | NT |
| 316 | NT |
| 317 | NT |
| 318 | NT |
| 319 | NT |
| 320 | NT |
| 321 | NT |
| 322 | NT |
| 323 | NT |
| 324 | NT |
| 325 | NT |
| 326 | NT |
| 327 | A |
| 334 | B |
| 335 | A |
| 336 | A |
| 337 | B |
| 338 | B |
| 339 | B |
| 340 | B |
| 341 | B |
| 342 | A |

What is claimed is:

1. A compound of Formula (II), or a pharmaceutically acceptable salt, solvate, or stereoisomer thereof:

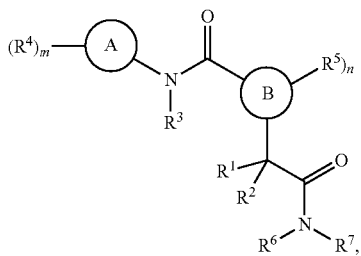

(II)

wherein:
Ring A is aryl, heteroaryl, cycloalkyl, or heterocycloalkyl;
Ring B is;

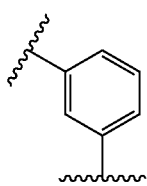 [SMILES: *c1cccc(*)c1]

$R^1$ is —F, —Cl, —OH, or —$OR^a$;
$R^2$ is hydrogen, —F, —Cl, —CN, —$OR^a$, $C_{1-6}$alkyl, $C_{1-6}$haloalkyl, $C_{1-6}$hydroxyalkyl, $C_{1-6}$heteroalkyl, or $C_{3-8}$cycloalkyl;
$R^3$ is hydrogen or $C_{1-6}$alkyl;
each $R^4$ is independently halogen, —CN, —OH, —$OR^a$, —SH, —$SR^a$, —S(=O)$R^a$, —$NO_2$, —$NR^bR^c$, —S(=O)$_2R^a$, —NHS(=O)$_2R^a$, —S(=O)$_2NR^bR^c$, —C(=O)$R^a$, —OC(=O)$R^a$, —C(=O)$OR^b$, —C(=O)$NR^bR^c$, —OC(=O)$NR^bR^c$, —$NR^bC$(=O)$NR^bR^c$, —$NR^bC$(=O)$R^a$, —$NR^bC$(=O)$OR^b$, $C_{1-6}$alkyl, $C_{1-6}$haloalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three $R^{12}$;
or two $R^4$ on adjacent atoms are taken together with the atoms to which they are attached to form a carbocycle ring or a heterocycle ring; each optionally substituted with one, two, or three $R^{12}$;
each $R^5$ is independently hydrogen, halogen, —CN, —OH, —$OR^a$, —SH, —$SR^a$, —S(=O)$R^a$, —$NO_2$, —$NR^bR^c$, —S(=O)$_2R^a$, —NHS(=O)$_2R^a$, —S(=O)$_2NR^bR^c$, —C(=O)$R^a$, —OC(=O)$R^a$, —C(=O)$OR^b$, —OC(=O)$OR^b$, —C(=O)$NR^bR^c$, —OC(=O)$NR^bR^c$, —$NR^bC$(=O)$NR^bR^c$, —$NR^bC$(=O)$R^a$, —$NR^bC$(=O)$OR^b$, $C_{1-6}$alkyl, $C_{1-6}$haloalkyl, $C_{1-6}$hydroxyalkyl, $C_{2-6}$alkenyl, $C_{2-6}$alkynyl, $C_{3-8}$cycloalkyl, $C_{2-7}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkenyl, alkynyl, cycloalkyl, heterocycloalkyl, aryl, and heteroaryl is independently optionally substituted with one, two, or three $R^{13}$;
or two $R^5$ on adjacent atoms are taken together with the atoms to which they are attached to form a carbocycle ring or a heterocycle ring; each optionally substituted with one, two, or three $R^{13}$;
$R^6$ and $R^7$ are each independently hydrogen, $C_{1-6}$alkyl, $C_{1-6}$alkoxy, $C_{2-6}$alkenyl, $C_{2-6}$alkynyl, $C_{3-15}$cycloalkyl, $C_{2-15}$heterocycloalkyl, aryl, heteroaryl, $C_{1-6}$alkyl(aryl), $C_{1-6}$alkyl(heteroaryl), $C_{1-6}$alkyl($C_{3-8}$cycloalkyl), or $C_{1-6}$alkyl($C_{2-7}$heterocycloalkyl); wherein each alkyl, alkoxy, alkenyl, alkynyl, cycloalkyl, heterocycloalkyl, aryl, and heteroaryl is independently optionally substituted with one, two, or three $R^{10}$;
or $R^6$ and $R^7$ are taken together with the nitrogen atom to which they are attached to form a $C_{2-15}$heterocycloalkyl or a $C_{2-15}$heterocycloalkenyl; wherein each heterocycloalkyl and heterocycloalkenyl is independently optionally substituted with one, two, or three $R^{11}$;

m is an integer from 0 to 5;
n is an integer from 0 to 4;
each $R^{10}$ is independently oxo, halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, —B(OR$^d$)$_2$, C$_{1-6}$alkyl, C$_{1-6}$haloalkyl, C$_{1-6}$hydroxyalkyl, C$_{1-6}$heteroalkyl, C$_{2-6}$alkenyl, C$_{2-6}$alkynyl, C$_{3-8}$cycloalkyl, C$_{2-7}$heterocycloalkyl, aryl, heteroaryl, C$_{1-6}$alkyl(aryl), C$_{1-6}$alkyl(heteroaryl), C$_{1-6}$alkyl(C$_{3-8}$cycloalkyl), or C$_{1-6}$alkyl(C$_{2-7}$heterocycloalkyl);
each $R^{11}$ is independently oxo, halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —NR$^b$S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —CH$_2$C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, —NR$^b$C(=O)CH$_2$NR$^b$R$^c$, —C(=O)CH$_2$NR$^b$C(=O)NR$^b$R$^c$, —OP(=O)(OR$^b$)(OR$^b$), —B(OR$^d$)$_2$, C$_{1-6}$alkyl, C$_{1-6}$haloalkyl, C$_{1-6}$hydroxyalkyl, C$_{1-6}$heteroalkyl, C$_{1-6}$cyanoalkyl, C$_{2-6}$alkenyl, C$_{2-6}$alkynyl, C$_{3-8}$cycloalkyl, C$_{2-7}$heterocycloalkyl, aryl, heteroaryl, C$_{1-6}$alkyl(aryl), C$_{1-6}$alkyl(heteroaryl), C$_{1-6}$alkyl(C$_{3-8}$cycloalkyl), or C$_{1-6}$alkyl(C$_{2-7}$heterocycloalkyl);
each $R^{12}$ and $R^{13}$ is independently halogen, —CN, —OH, —OR$^a$, —SH, —SR$^a$, —S(=O)R$^a$, —NO$_2$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_{1-6}$alkyl, C$_{1-6}$haloalkyl, C$_{1-6}$hydroxyalkyl, C$_{1-6}$heteroalkyl, or C$_{3-8}$cycloalkyl;
each $R^a$ is independently C$_{1-6}$alkyl, C$_{2-6}$alkenyl, C$_{2-6}$alkynyl, C$_{1-6}$haloalkyl, C$_{1-6}$hydroxyalkyl, C$_{1-6}$heteroalkyl, C$_{3-8}$cycloalkyl, C$_{2-7}$heterocycloalkyl, aryl, heteroaryl, C$_{1-6}$alkyl(aryl), C$_{1-6}$alkyl(heteroaryl), C$_{1-6}$alkyl(C$_{3-8}$cycloalkyl), or C$_{1-6}$alkyl(C$_{2-7}$heterocycloalkyl); wherein each alkyl, alkenyl, alkynyl, cycloalkyl, heterocycloalkyl, aryl, and heteroaryl is independently optionally substituted with one, two, or three oxo, halogen, —OH, C$_{1-6}$alkyl, or C$_{1-6}$haloalkyl;
each $R^b$ and $R^c$ is independently hydrogen, C$_{1-6}$alkyl, C$_{2-6}$alkenyl, C$_{2-6}$alkynyl, C$_{1-6}$haloalkyl, C$_{1-6}$hydroxyalkyl, C$_{1-6}$heteroalkyl, C$_{3-8}$cycloalkyl, C$_{2-7}$heterocycloalkyl, aryl, heteroaryl, C$_{1-6}$alkyl(aryl), C$_{1-6}$alkyl(heteroaryl), C$_{1-6}$alkyl(C$_{3-8}$cycloalkyl), or C$_{1-6}$alkyl(C$_{2-7}$heterocycloalkyl); wherein each alkyl, alkenyl, alkynyl, cycloalkyl, heterocycloalkyl, aryl, and heteroaryl is independently optionally substituted with one, two, or three oxo, halogen, —OH, C$_{1-6}$alkyl, or C$_{1-6}$haloalkyl;
or $R^b$ and $R^c$ are taken together with the nitrogen atom to which they are attached to form a C$_{2-7}$heterocycloalkyl optionally substituted with one, two, or three oxo, halogen, —OH, C$_{1-6}$alkyl, or C$_{1-6}$haloalkyl; and
each $R^d$ is independently hydrogen or C$_{1-6}$alkyl;
or two $R^d$ are taken together to form a C$_{2-7}$heterocycloalkyl optionally substituted with one, two, or three halogen, —OH, or C$_{1-6}$alkyl.

2. The compound of claim 1, or a pharmaceutically acceptable salt, solvate, or stereoisomer thereof, wherein $R^1$ is —F or —OH.

3. The compound of claim 1, or a pharmaceutically acceptable salt, solvate, or stereoisomer thereof, wherein $R^2$ is hydrogen, —F, or C$_{1-6}$alkyl.

4. The compound of claim 1, or a pharmaceutically acceptable salt, solvate, or stereoisomer thereof, wherein $R^3$ is hydrogen or methyl.

5. The compound of claim 1, or a pharmaceutically acceptable salt, solvate, or stereoisomer thereof, wherein Ring A is aryl or heteroaryl.

6. The compound of claim 1, or a pharmaceutically acceptable salt, solvate, or stereoisomer thereof, wherein each $R^4$ is independently halogen, —CN, —OR$^a$, —NO$_2$, —C(=O)NR$^b$R$^c$, C$_{1-6}$alkyl, C$_{1-6}$haloalkyl, or C$_{3-8}$cycloalkyl.

7. The compound of claim 1, or a pharmaceutically acceptable salt, solvate, or stereoisomer thereof, wherein m is 1 to 3.

8. The compound of claim 1, or a pharmaceutically acceptable salt, solvate, or stereoisomer thereof, wherein each $R^5$ is independently hydrogen, halogen, —CN, —OR$^a$, C$_{1-6}$haloalkyl, C$_{1-6}$hydroxyalkyl, C$_{2-6}$alkenyl, or C$_{1-6}$alkyl.

9. The compound of claim 1, or a pharmaceutically acceptable salt, solvate, or stereoisomer thereof, wherein n is 0 to 2.

10. The compound of claim 1, or a pharmaceutically acceptable salt, solvate, or stereoisomer thereof, wherein $R^6$ is hydrogen or C$_{1-6}$alkyl; wherein the alkyl is optionally substituted with one, two, or three $R^{10}$.

11. The compound of claim 1, or a pharmaceutically acceptable salt, solvate, or stereoisomer thereof, wherein $R^7$ is C$_{1-6}$alkyl, C$_{1-6}$alkoxy, C$_{3-15}$cycloalkyl, C$_{2-15}$heterocycloalkyl, aryl, heteroaryl, C$_{1-6}$alkyl(aryl), C$_{1-6}$alkyl(heteroaryl), C$_{1-6}$alkyl(C$_{3-8}$cycloalkyl), or C$_{1-6}$alkyl(C$_{2-7}$heterocycloalkyl); wherein each alkyl, cycloalkyl, heterocycloalkyl, aryl, and heteroaryl is independently optionally substituted with one, two, or three $R^{10}$.

12. The compound of claim 1, or a pharmaceutically acceptable salt, solvate, or stereoisomer thereof, wherein each $R^{10}$ is independently halogen, —CN, —OH, —OR$^a$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —B(OR$^d$)$_2$, —C$_{1-6}$alkyl, or C$_{1-6}$haloalkyl.

13. The compound of claim 1, or a pharmaceutically acceptable salt, solvate, or stereoisomer thereof, wherein $R^6$ and $R^7$ are taken together with the nitrogen atom to which they are attached to form a C$_{2-15}$heterocycloalkyl optionally substituted with one, two, or three $R^{11}$.

14. The compound of claim 1, or a pharmaceutically acceptable salt, solvate, or stereoisomer thereof, wherein each $R^{11}$ is independently oxo, halogen, —CN, —OH, —OR$^a$, —NR$^b$R$^c$, —S(=O)$_2$R$^a$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —CH$_2$C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, —OP(=O)(OR$^b$)(OR$^b$), —B(OR$^d$)$_2$, C$_{1-6}$alkyl, C$_{1-6}$haloalkyl, C$_{1-6}$hydroxyalkyl, C$_{1-6}$heteroalkyl, C$_{1-6}$cyanoalkyl, or C$_{3-8}$cycloalkyl.

15. The compound of claim 1, or a pharmaceutically acceptable salt, solvate, or stereoisomer thereof, wherein

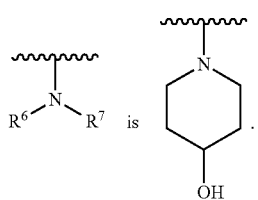

16. A compound, or a pharmaceutically acceptable salt, solvate, or stereoisomer thereof, selected from the group consisting of:
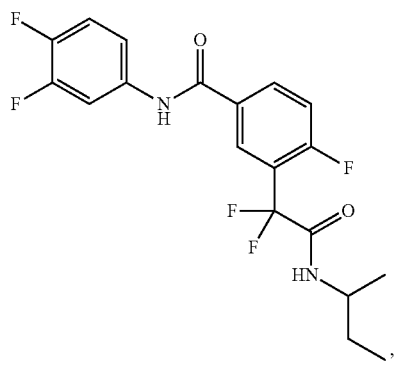
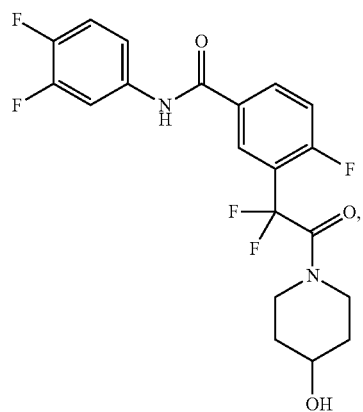
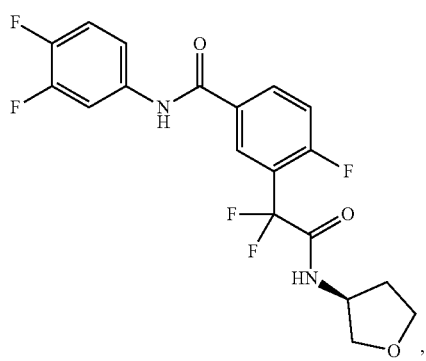
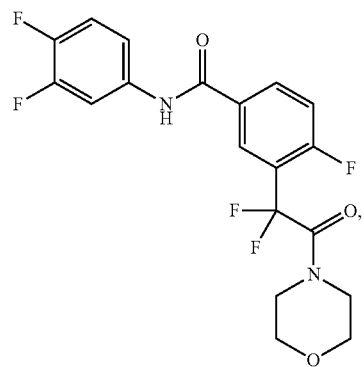
-continued
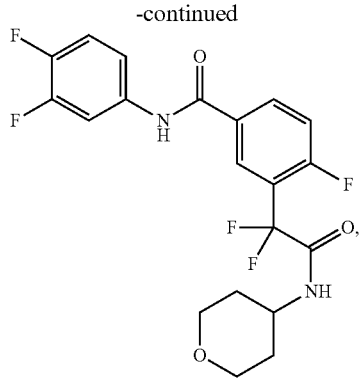
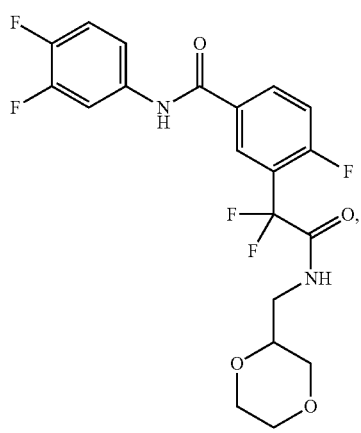
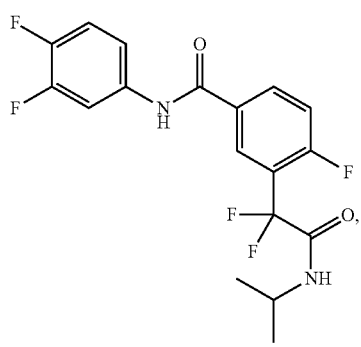
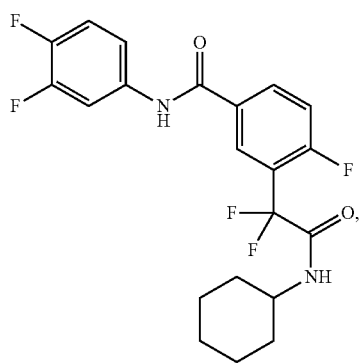

383
-continued
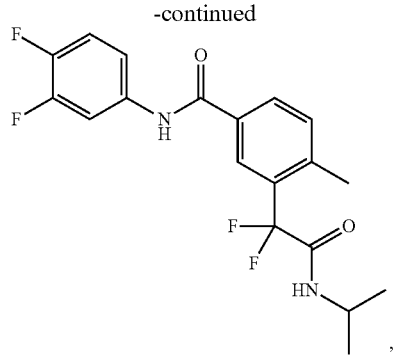
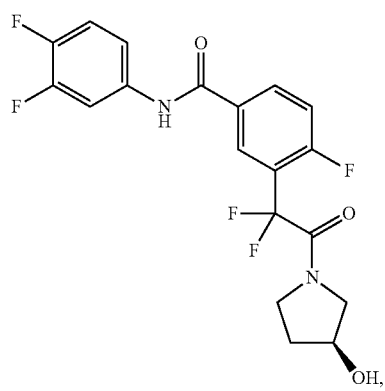
384
-continued
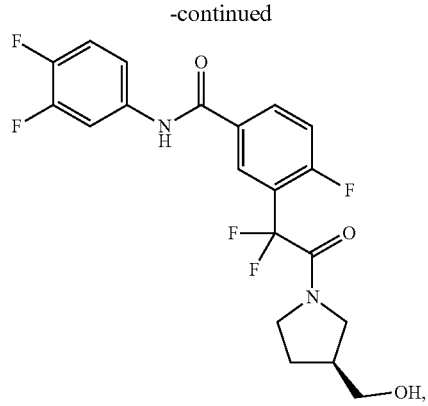
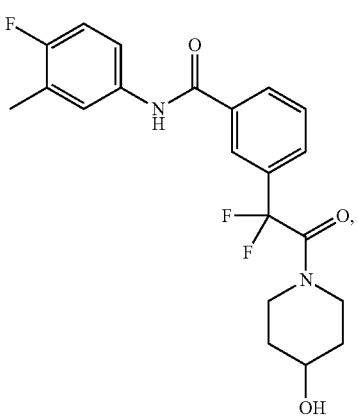
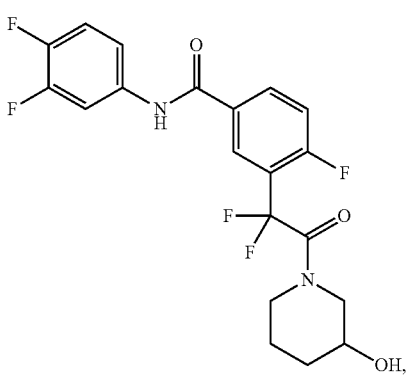
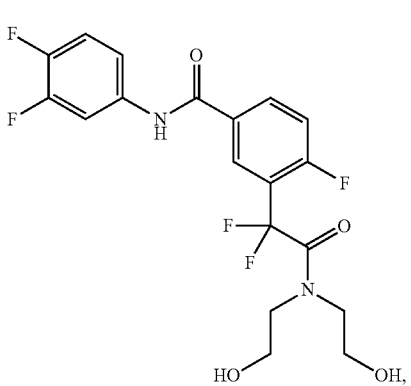

-continued
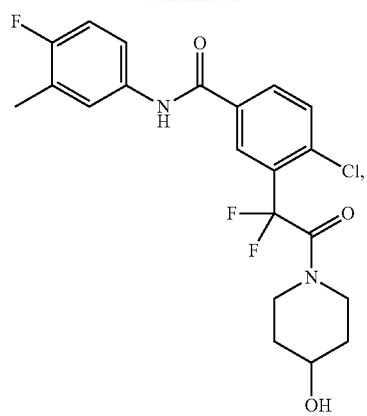
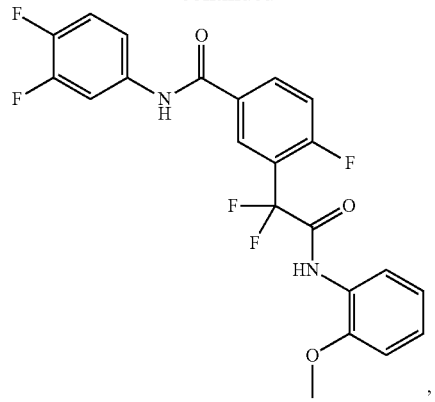
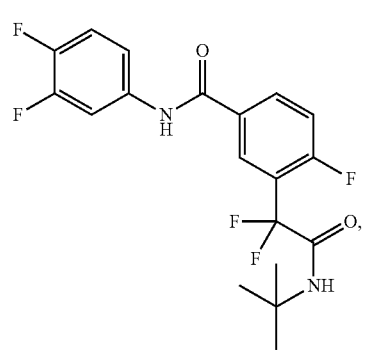
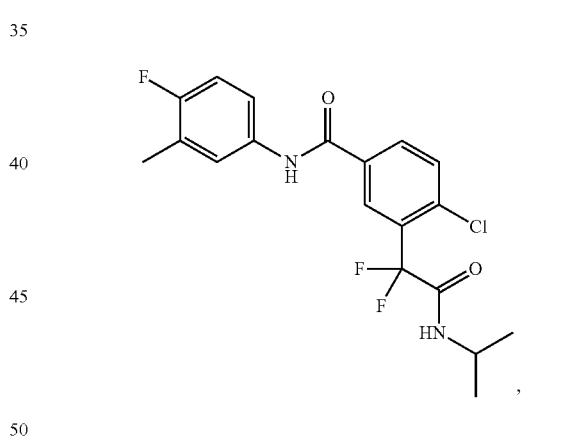
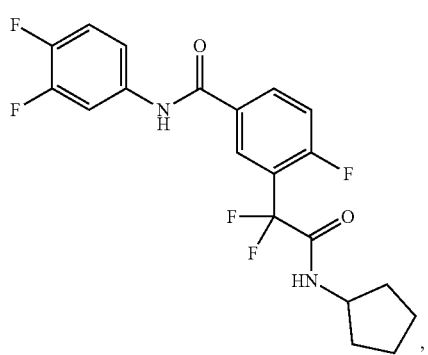
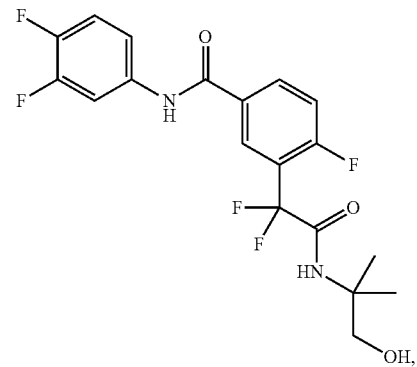

387
-continued
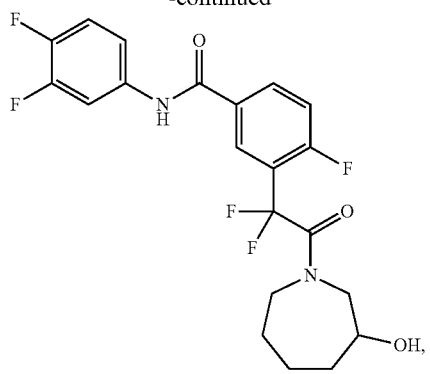
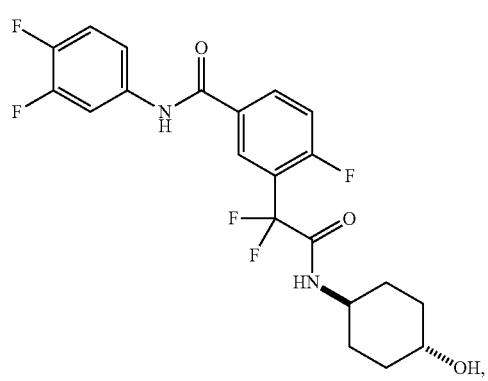
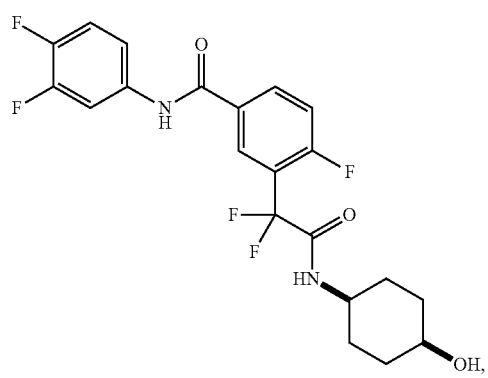
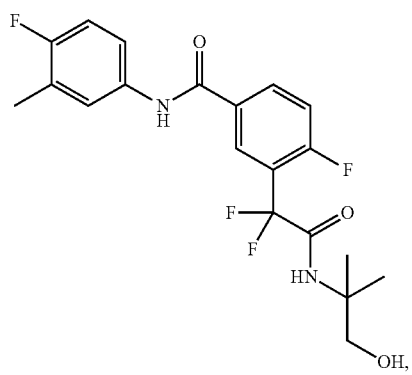
388
-continued
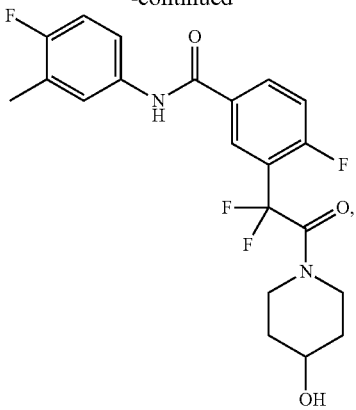
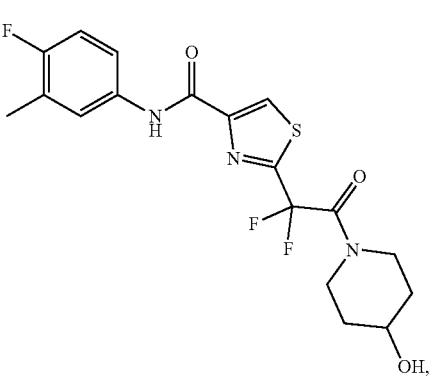
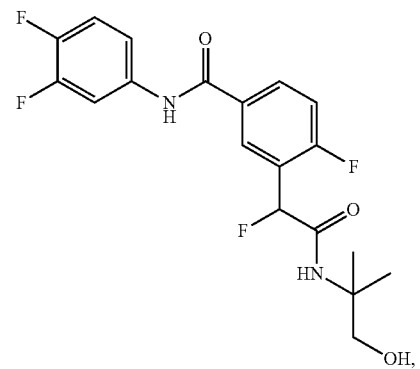
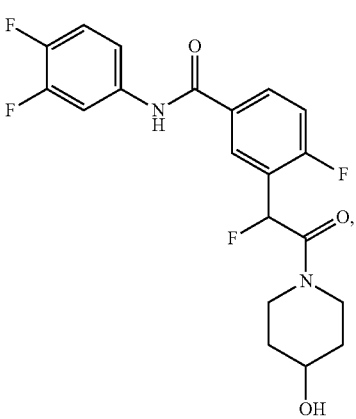

389
-continued
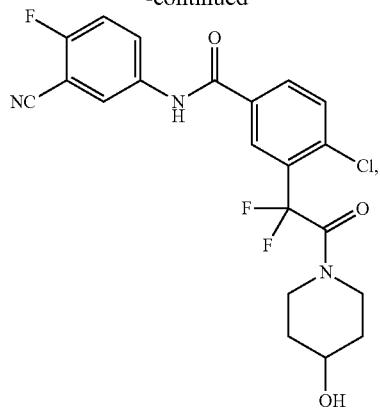
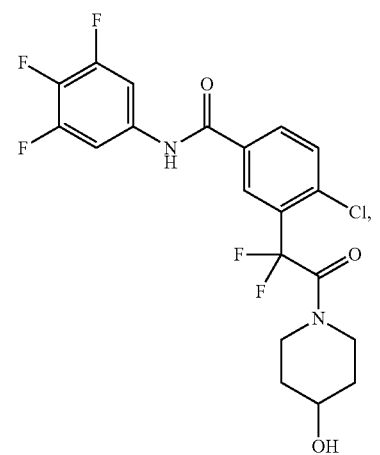
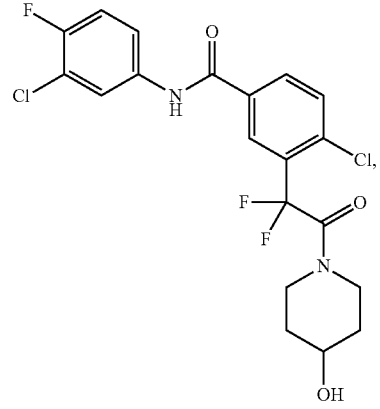
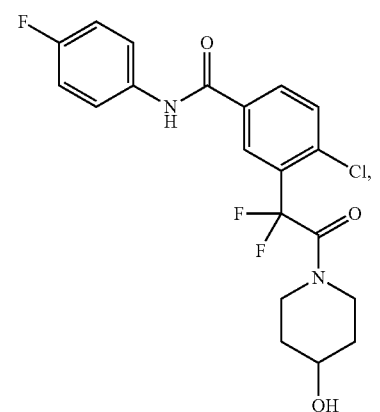
390
-continued
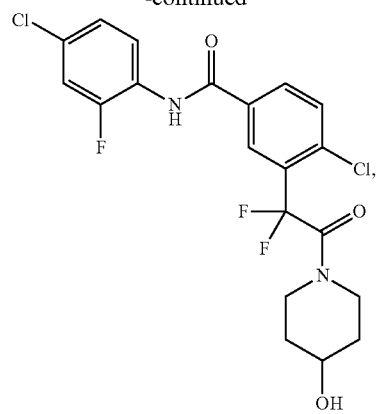
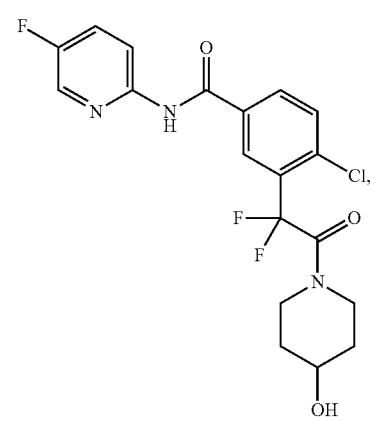
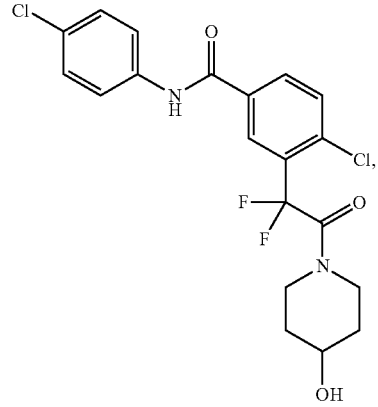
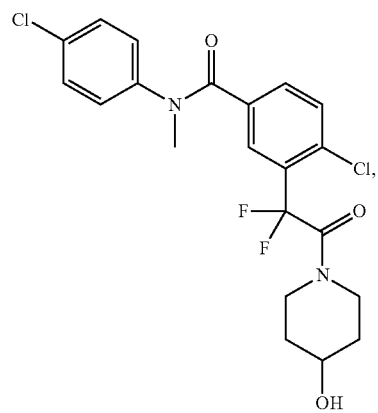

391
-continued
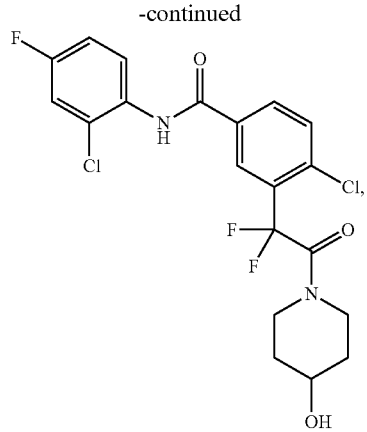
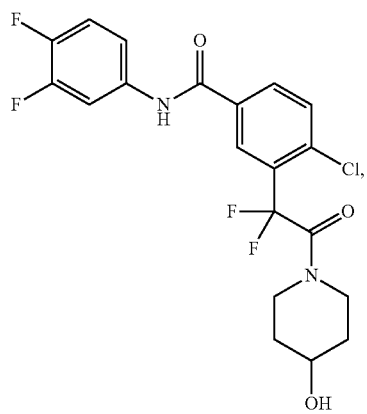
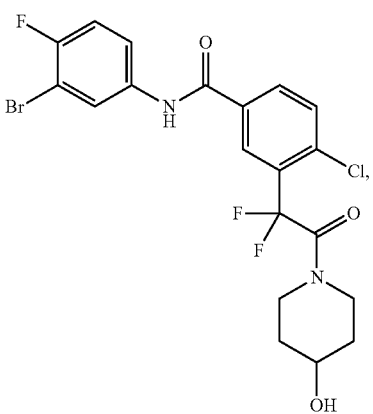
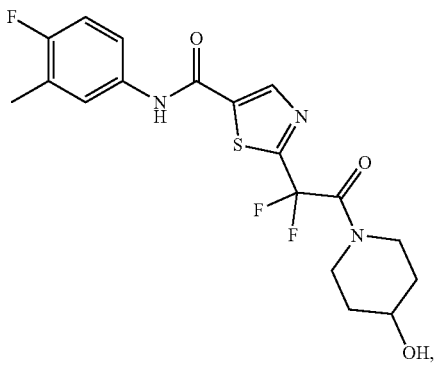
392
-continued
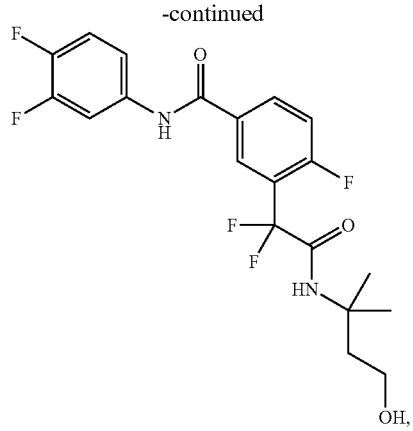
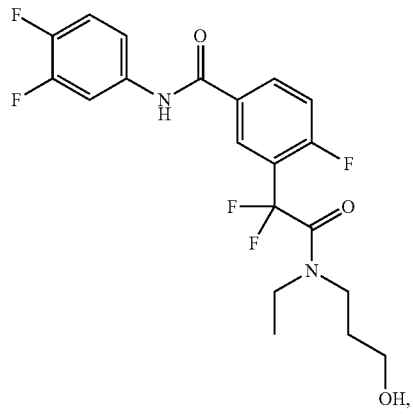
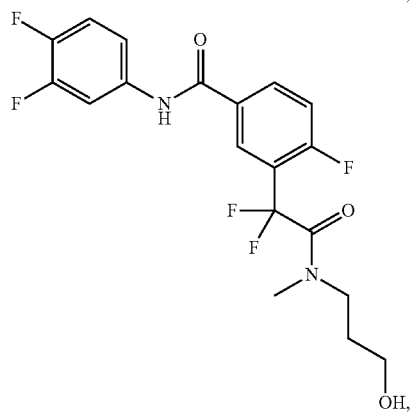
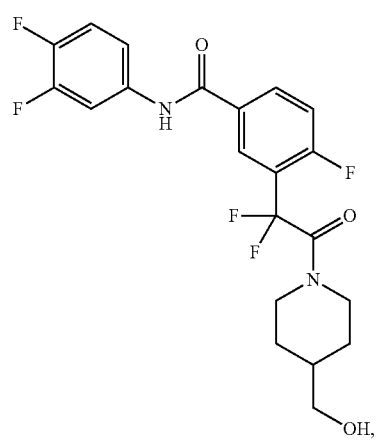

393
-continued
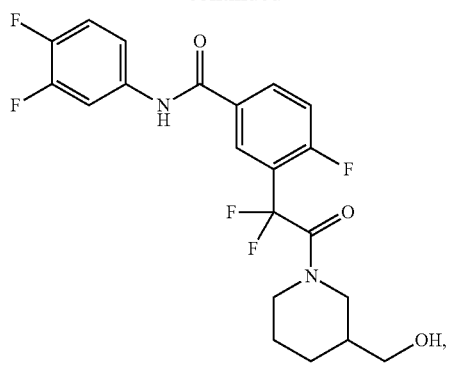
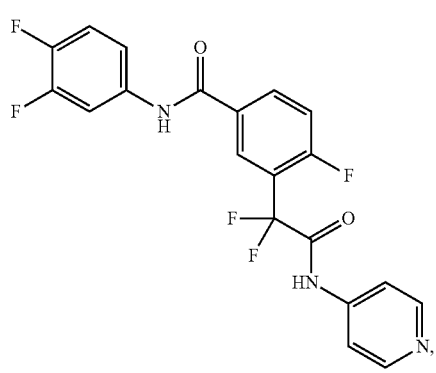
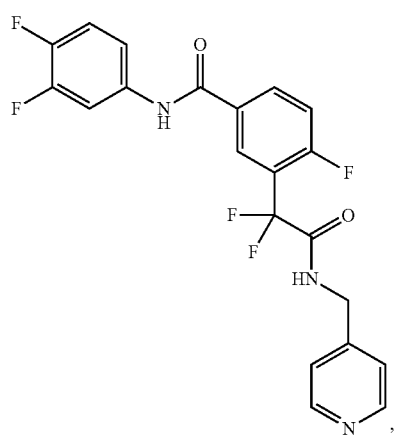
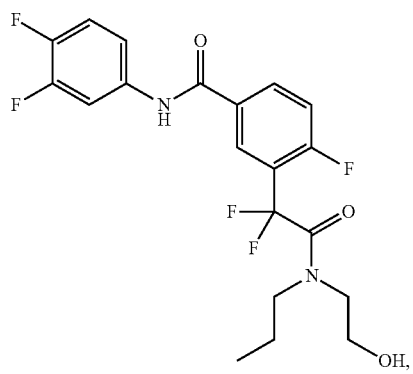
394
-continued
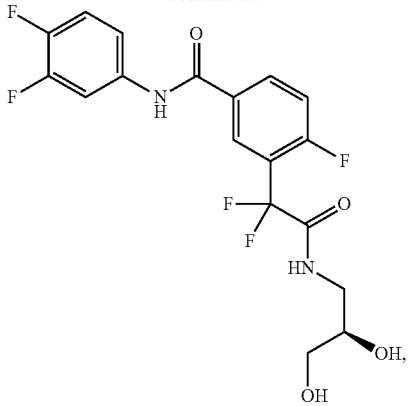
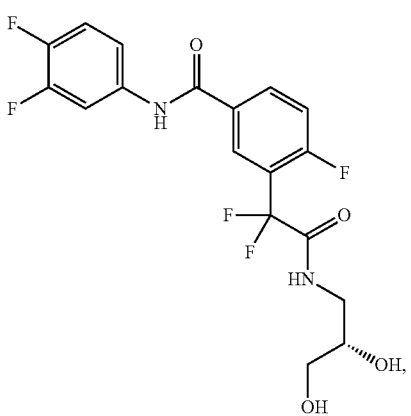
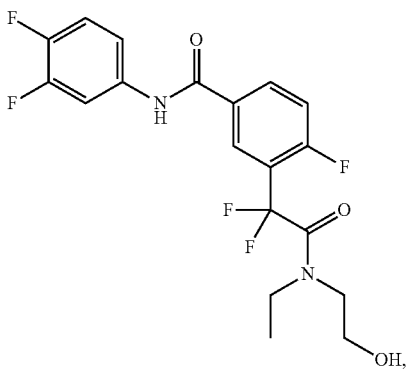
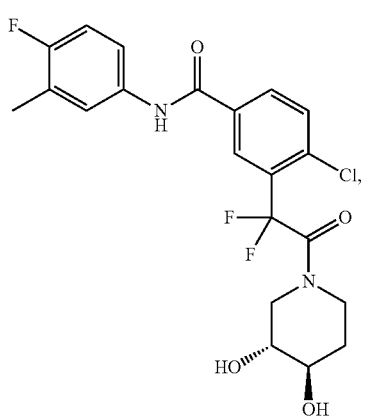

395
-continued
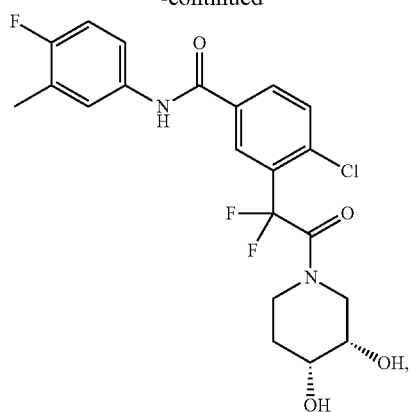
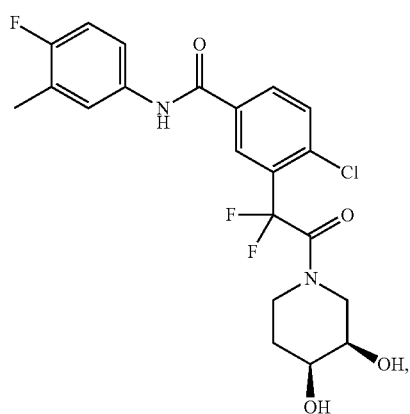
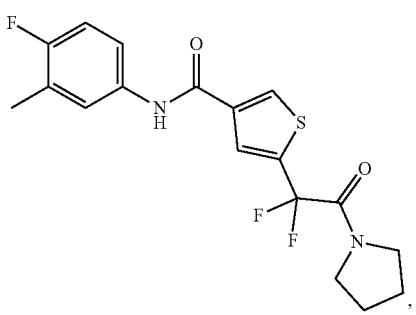
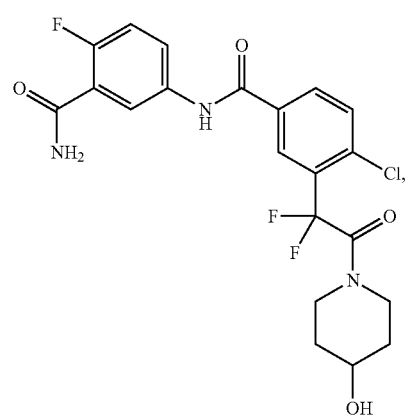
396
-continued
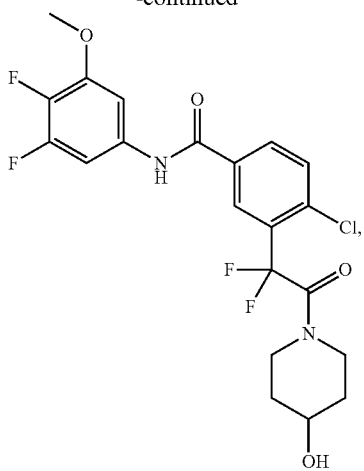
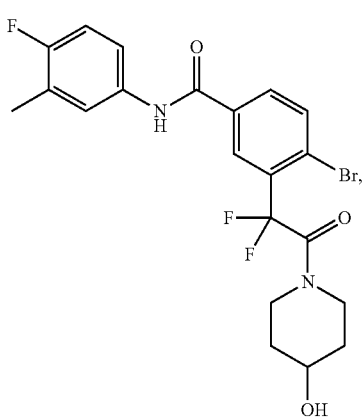
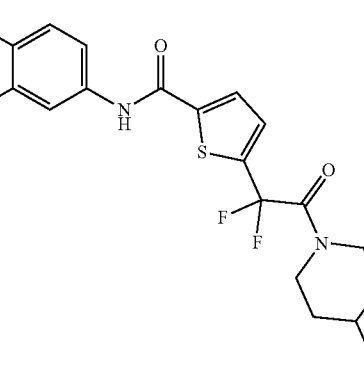
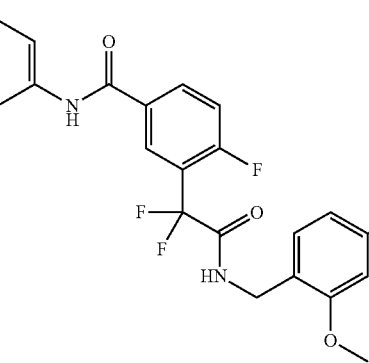

397
-continued
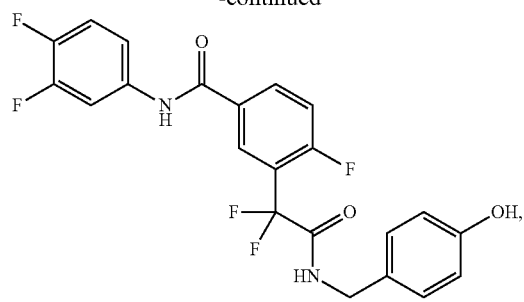
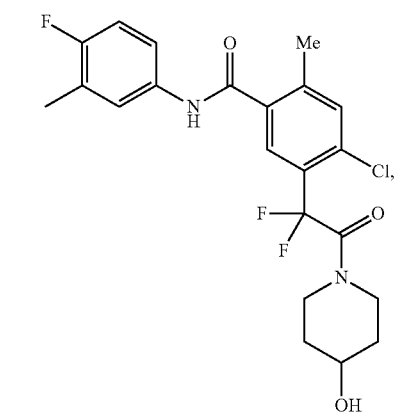
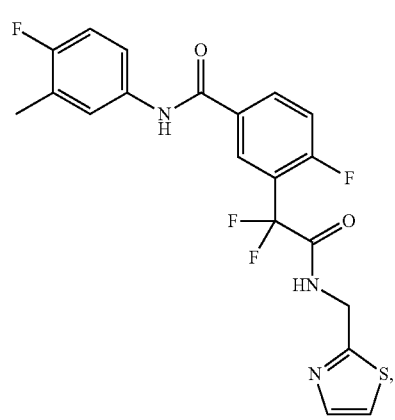
398
-continued
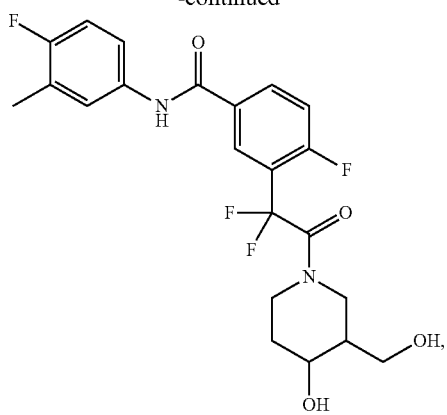
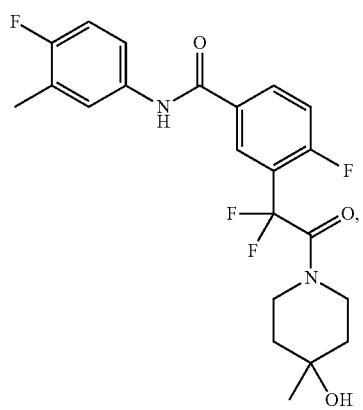
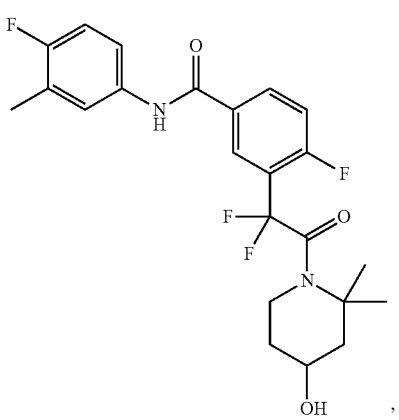
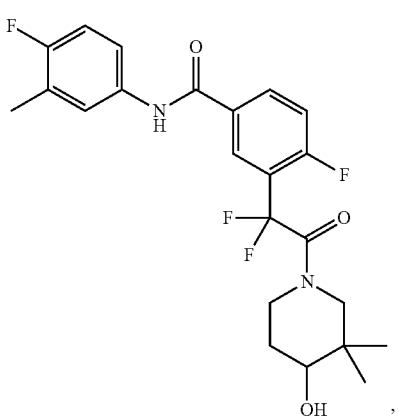

399
-continued
400
-continued
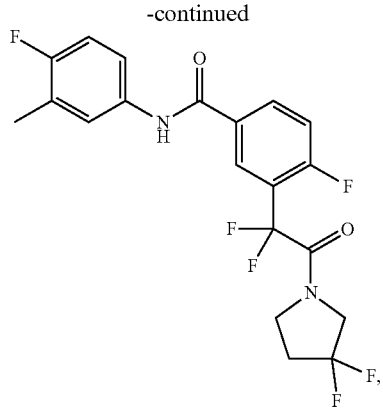
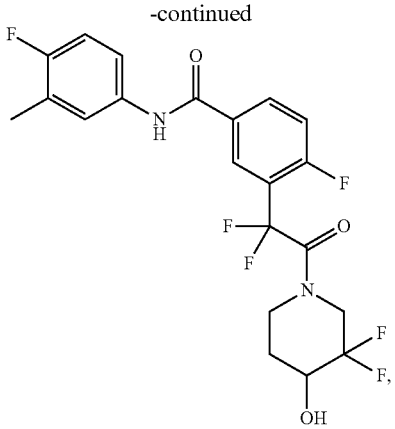
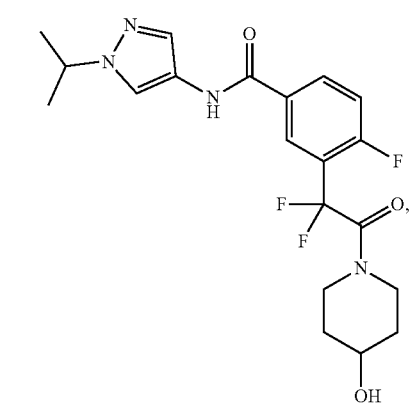

-continued
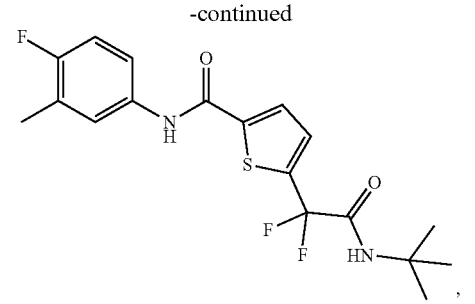
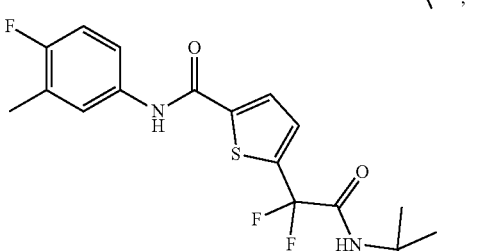
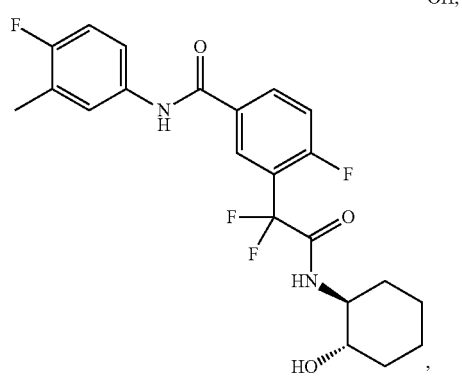
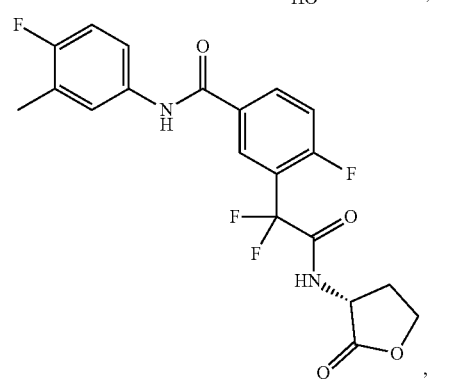
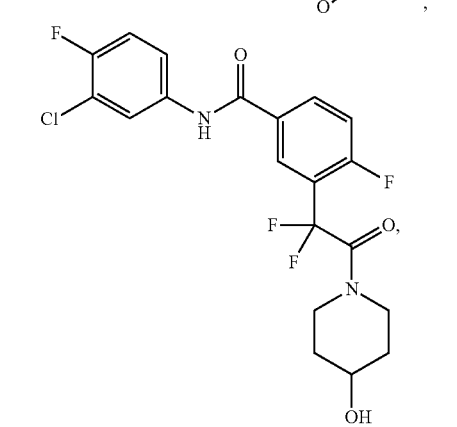
-continued
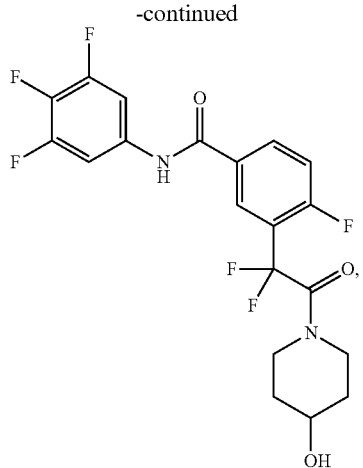
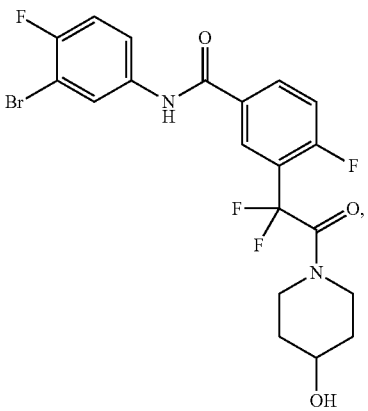
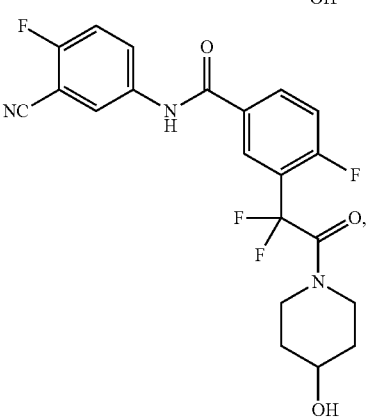
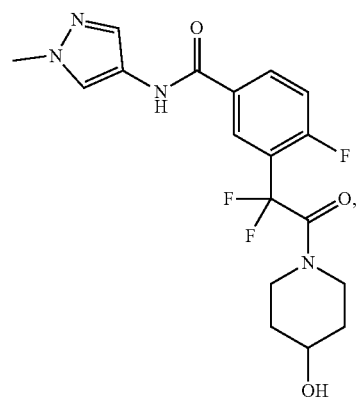

403
-continued
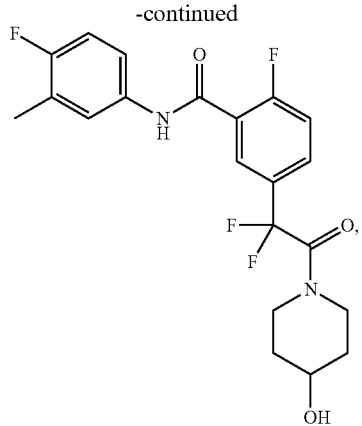
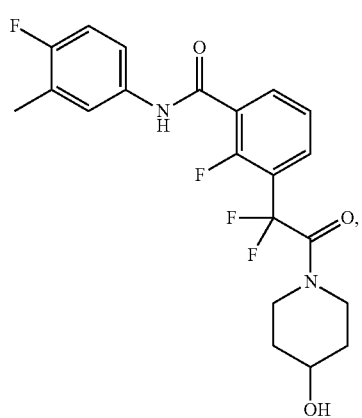
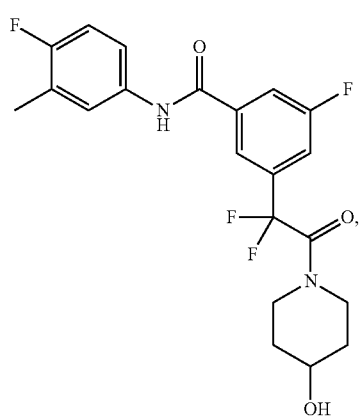
404
-continued
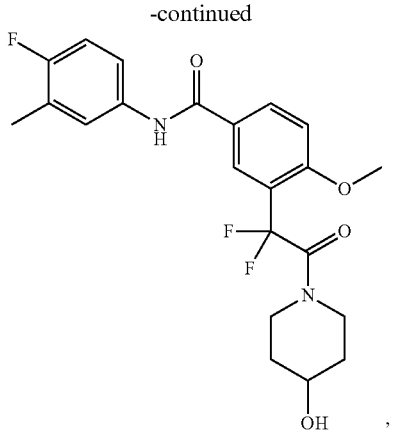
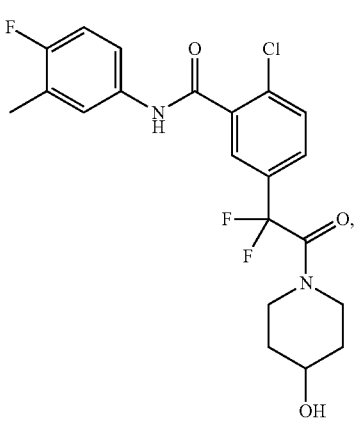
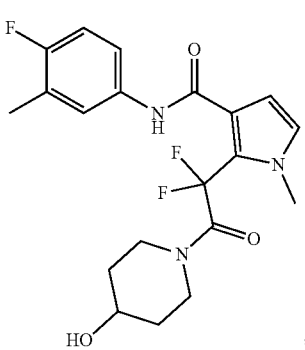
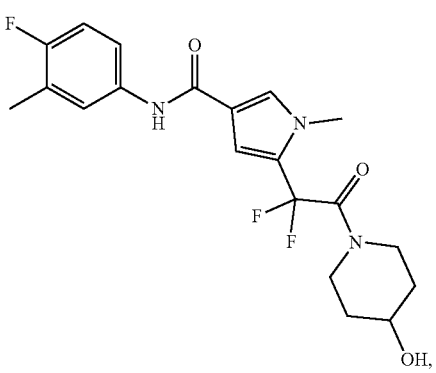

-continued
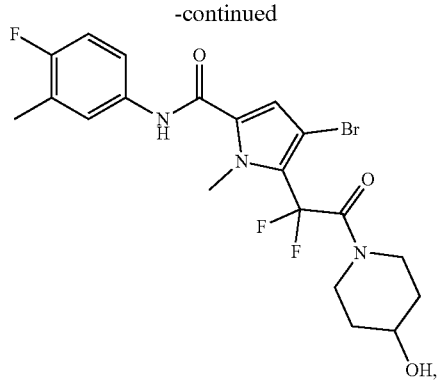
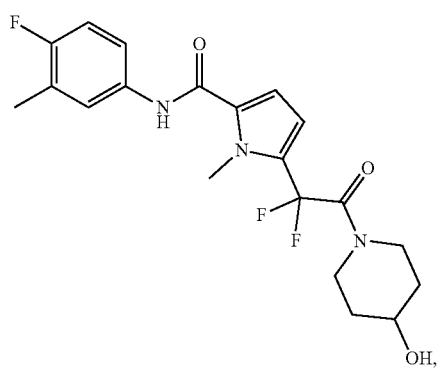
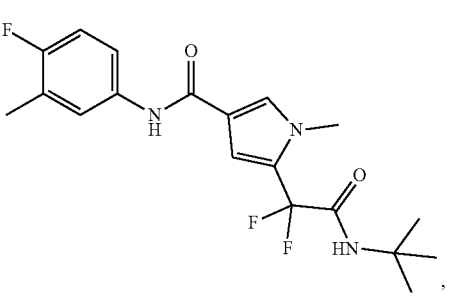
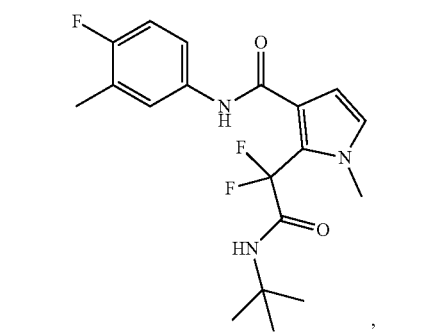
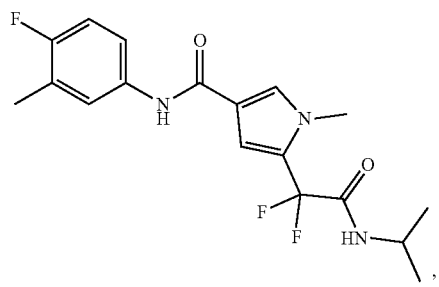
-continued
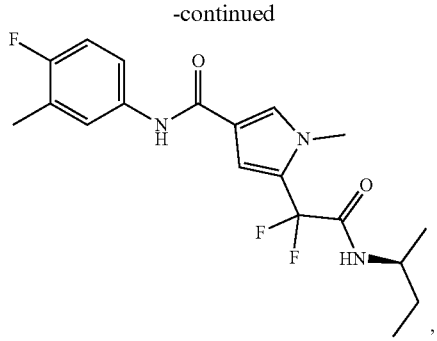
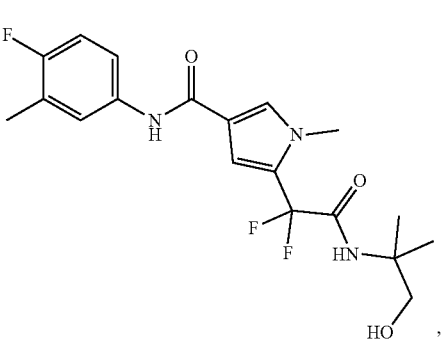
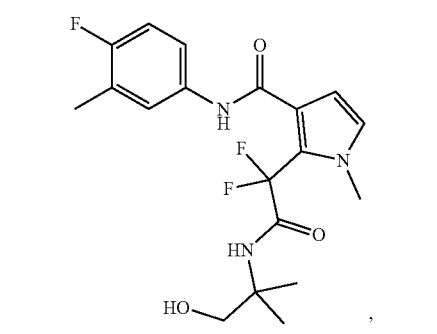
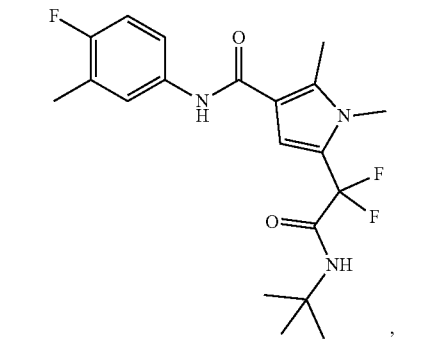
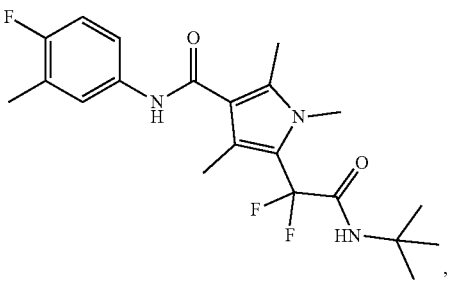

407
-continued
408
-continued
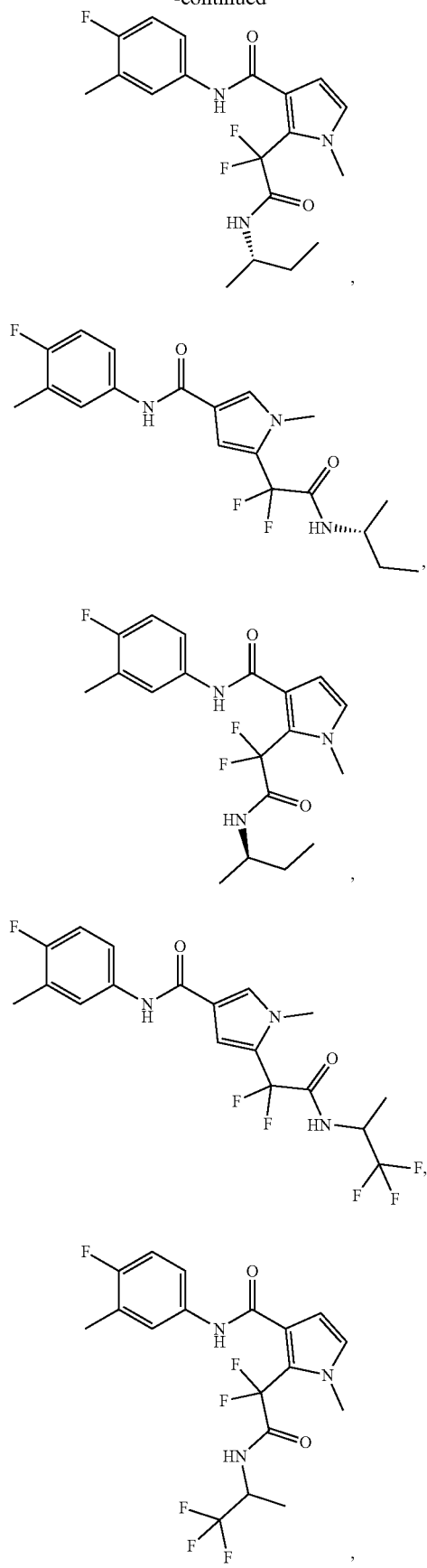
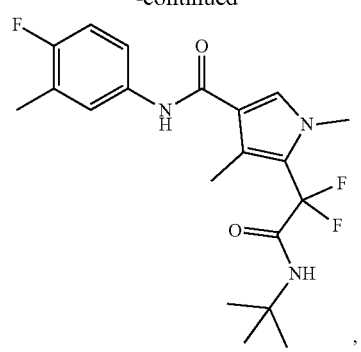
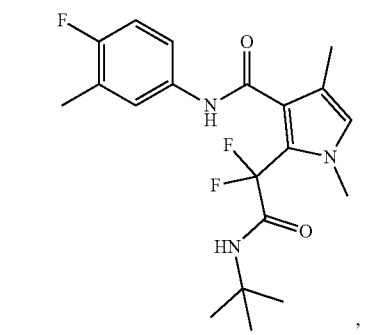
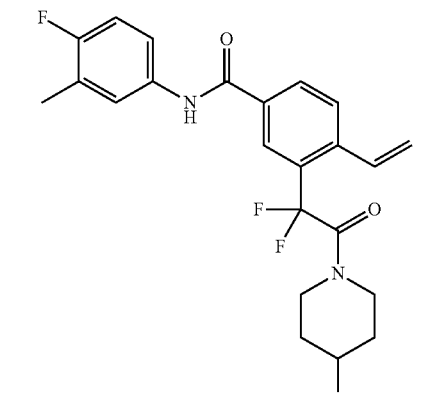

409
-continued
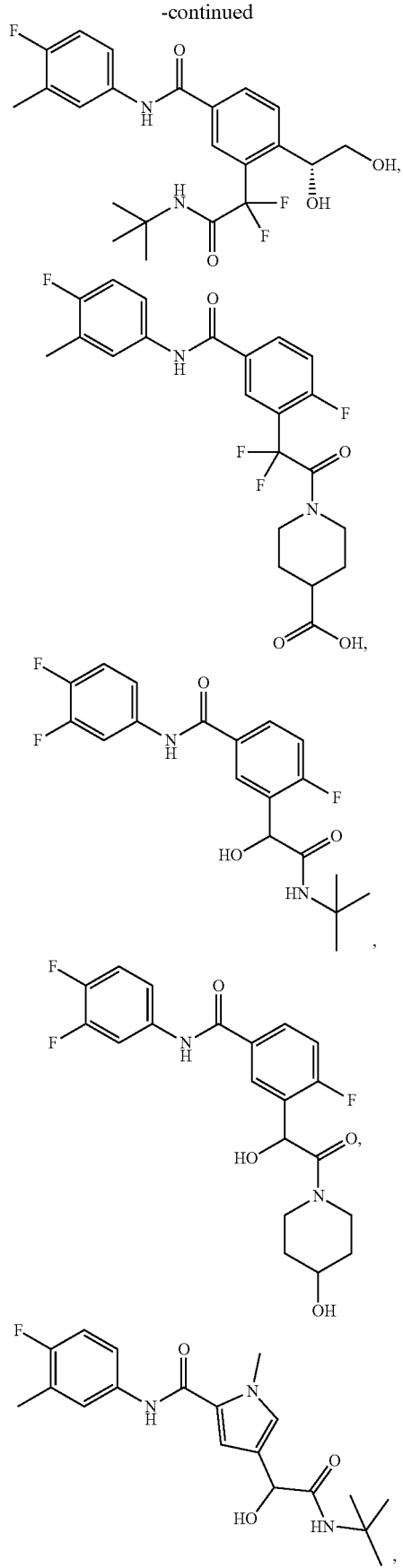
410
-continued
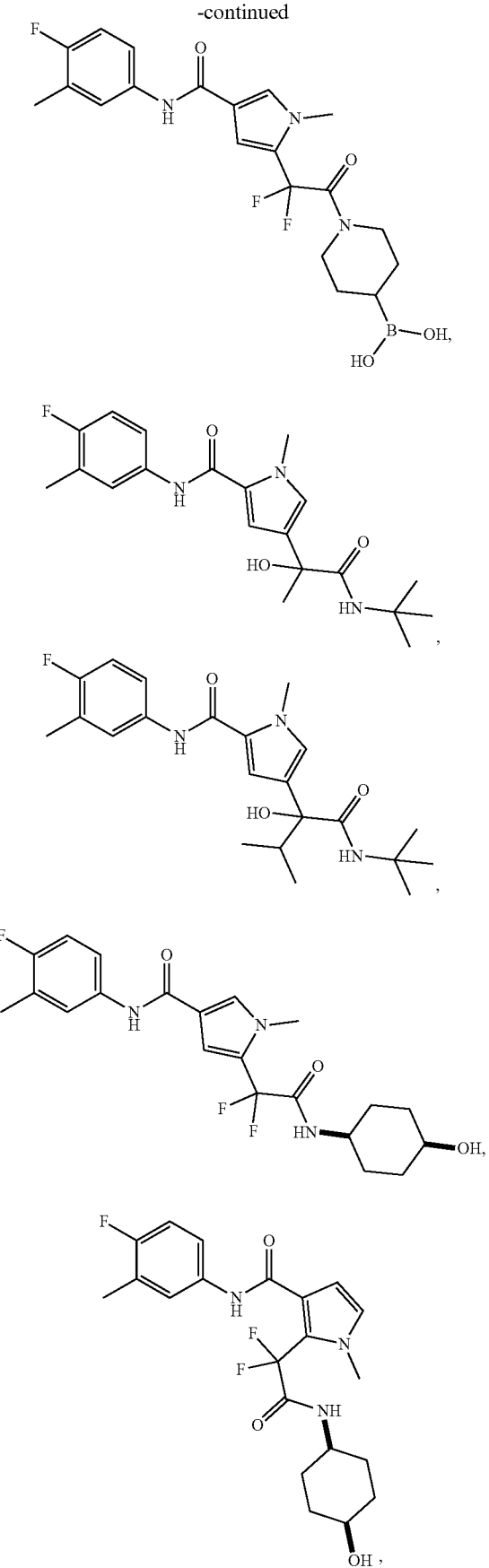

411
-continued
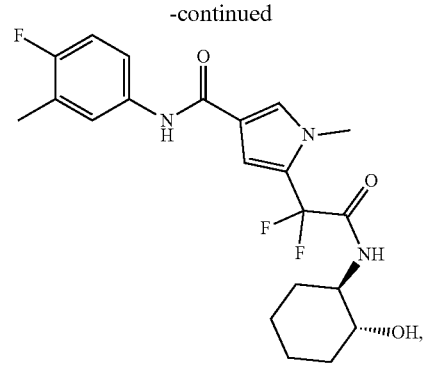
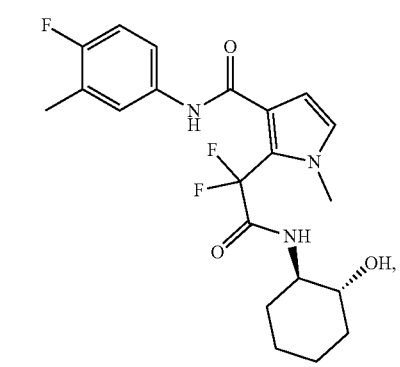
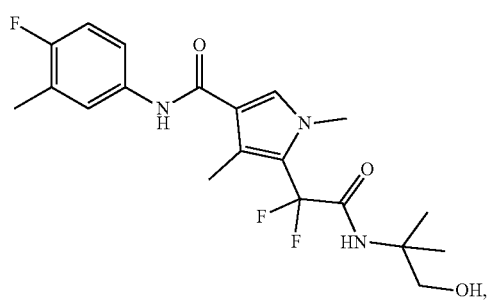
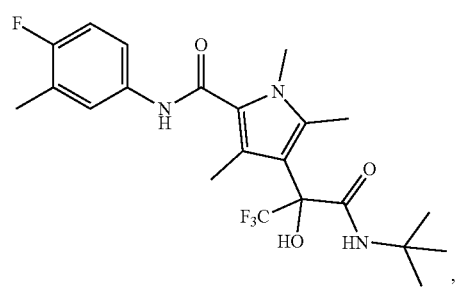
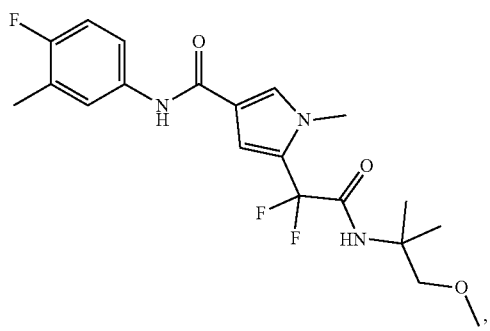
412
-continued
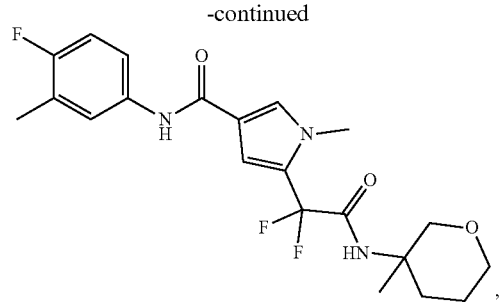
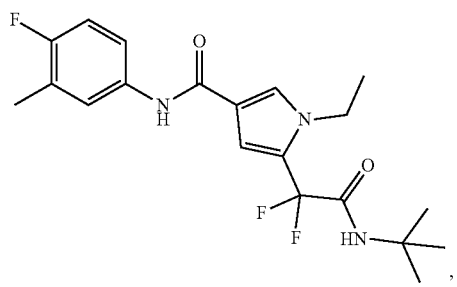
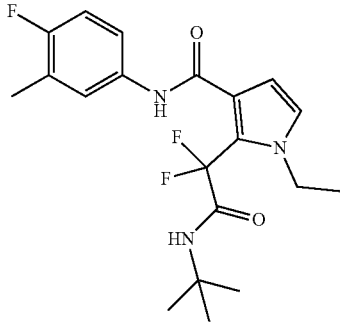
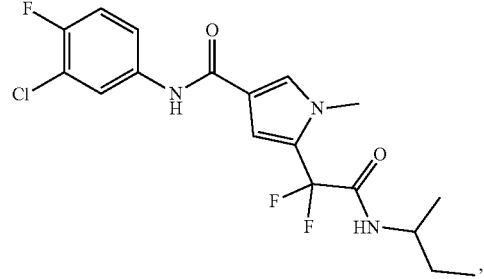
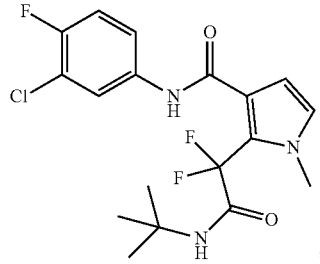
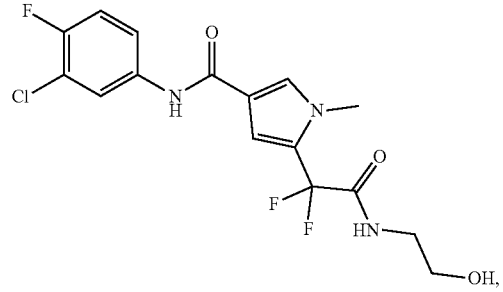

413
-continued
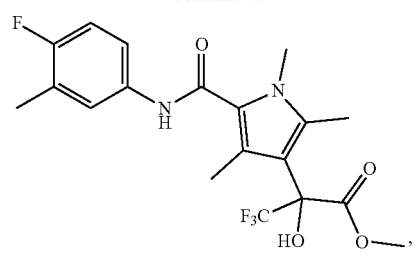
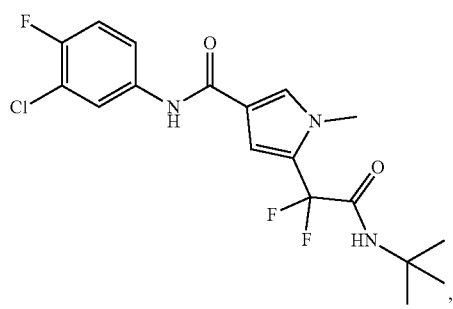
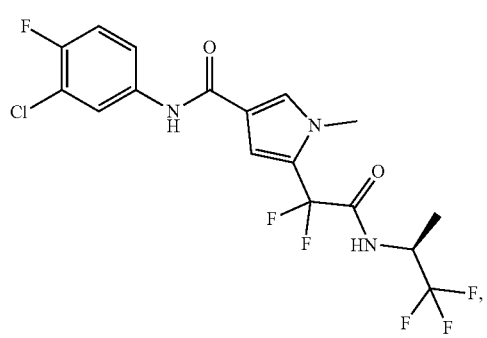
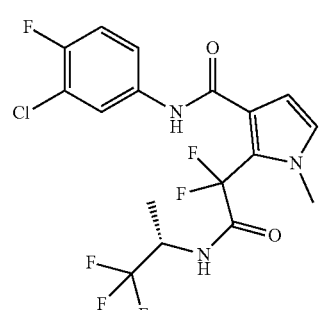
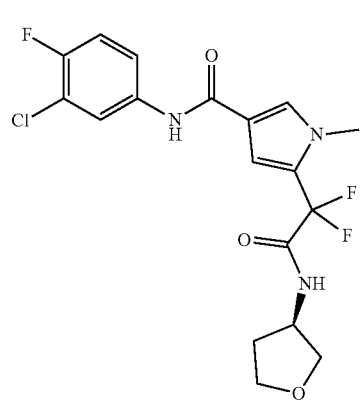
414
-continued
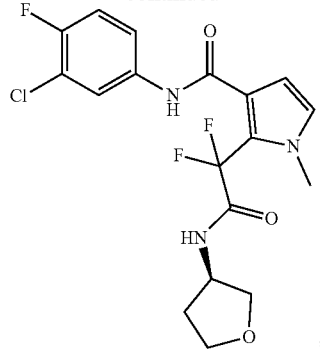
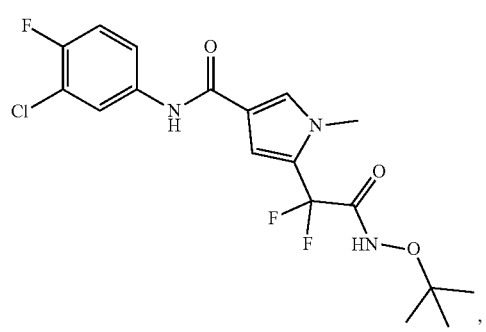
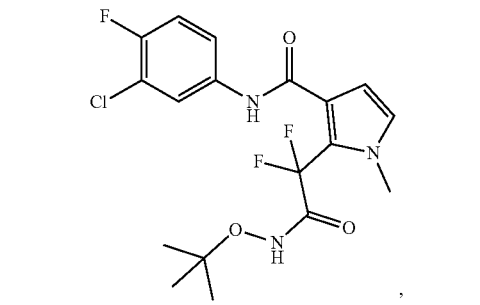
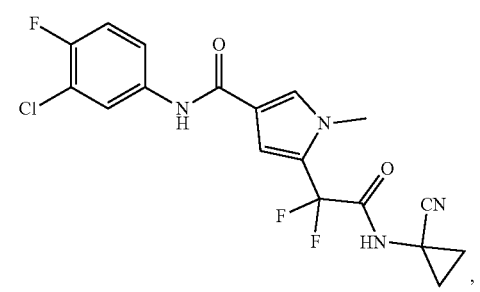
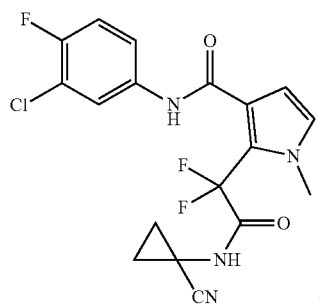

415
-continued
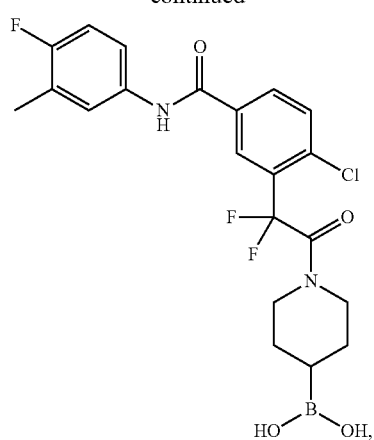
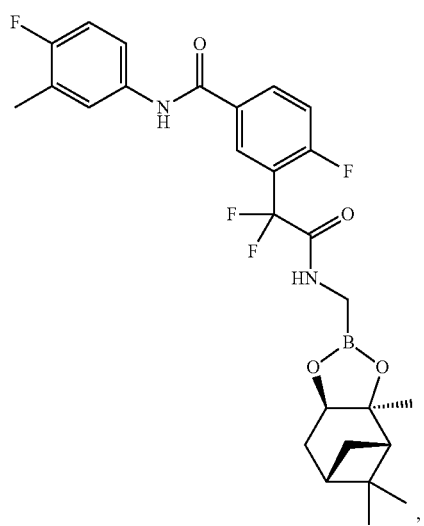
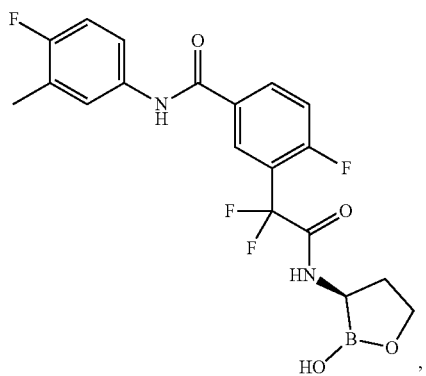
416
-continued
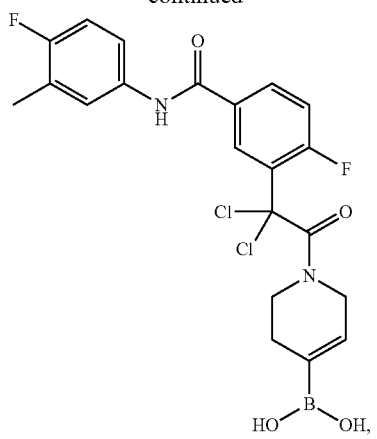
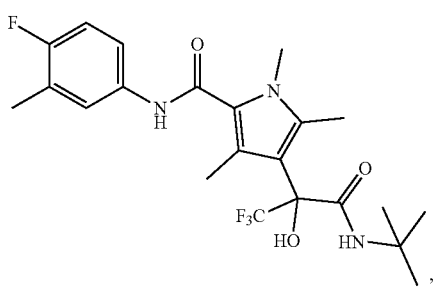
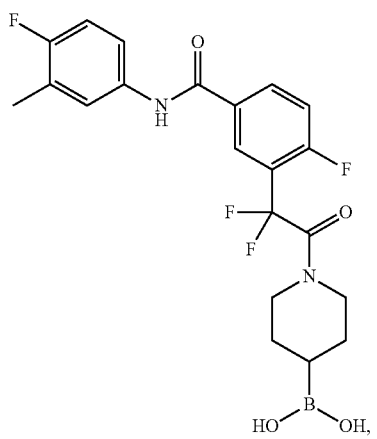
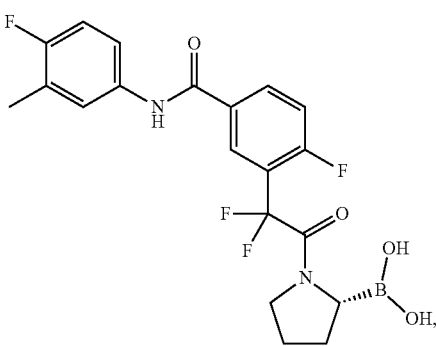

417
-continued
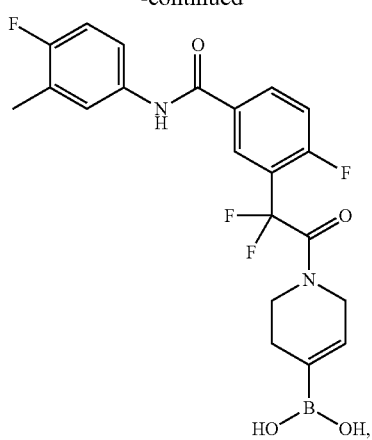
418
-continued
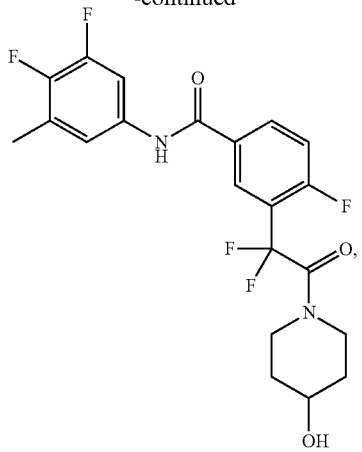
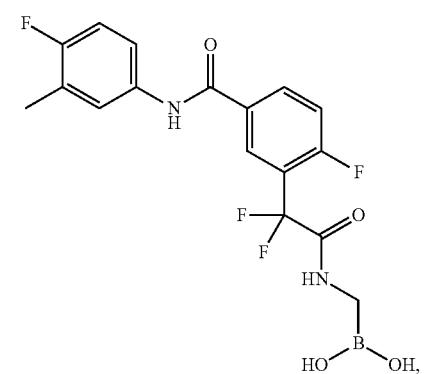
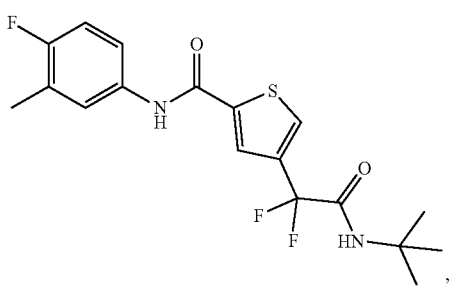
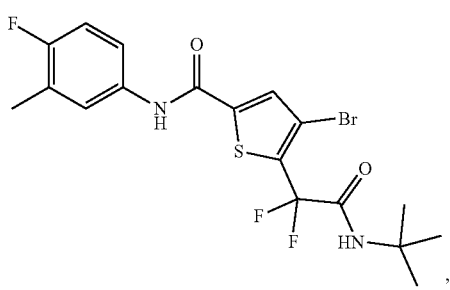

419
-continued
420
-continued
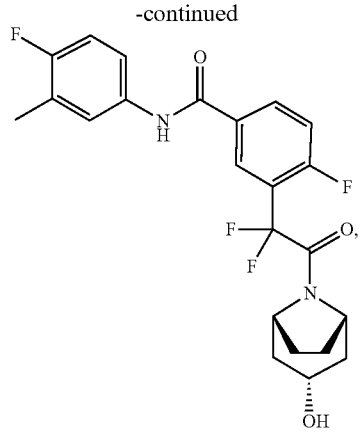
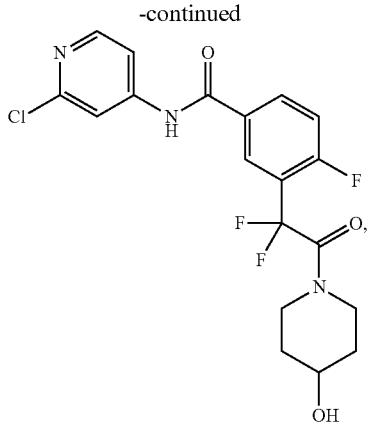

421
-continued
422
-continued
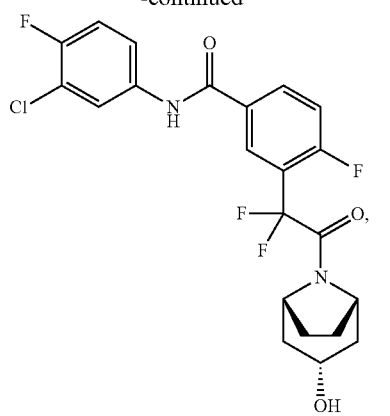
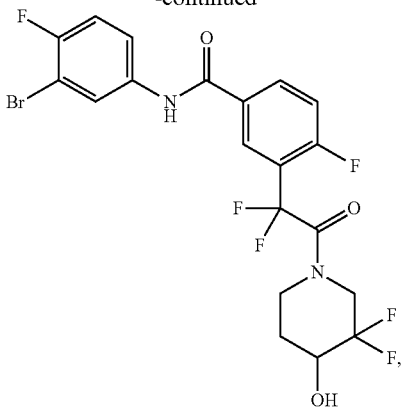
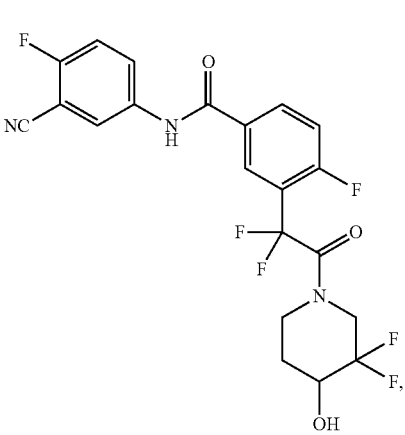
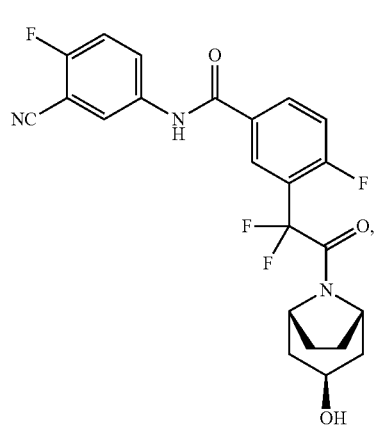

423
-continued
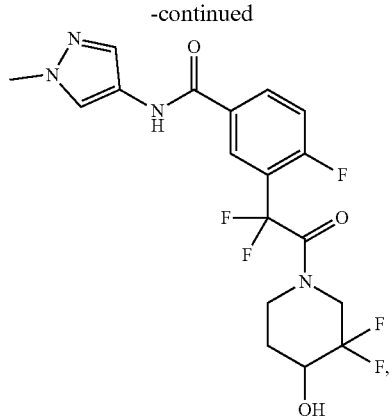
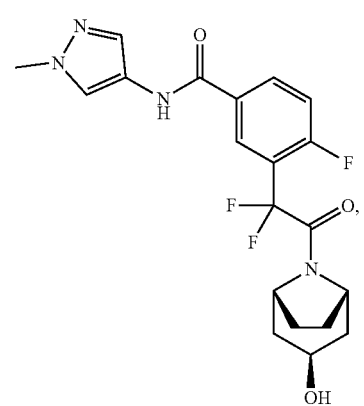
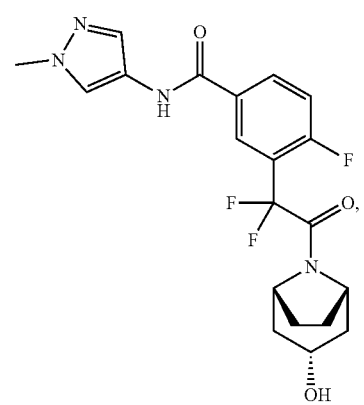
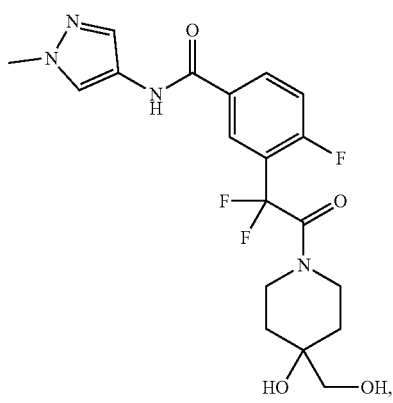
424
-continued
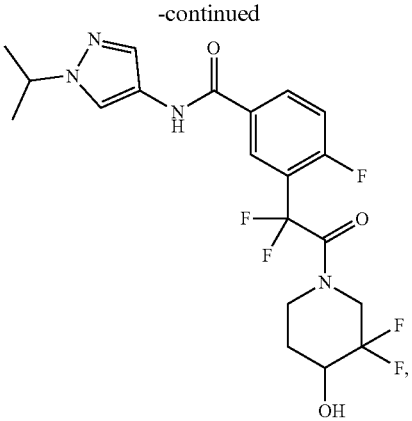
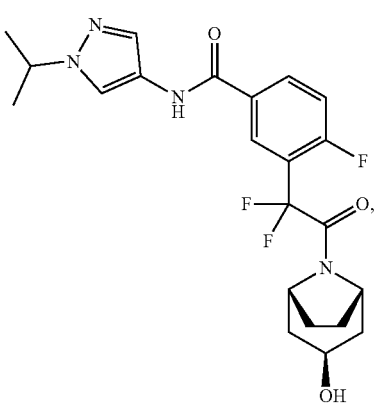
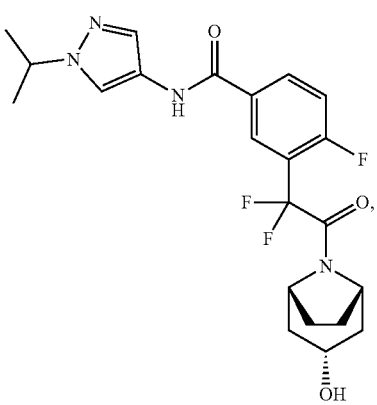
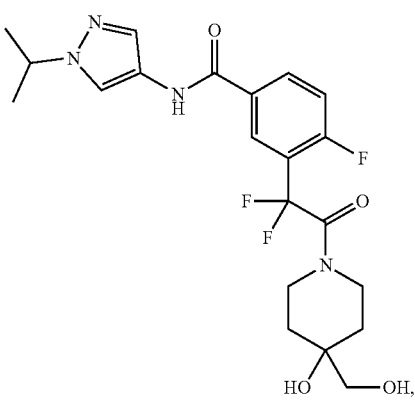

425

426

427
-continued
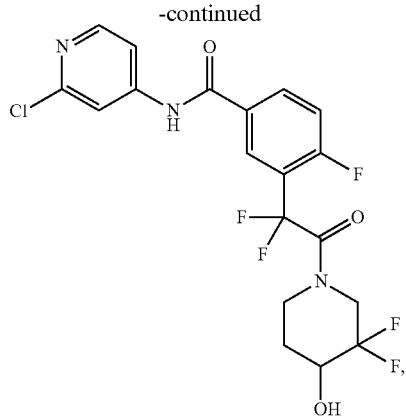
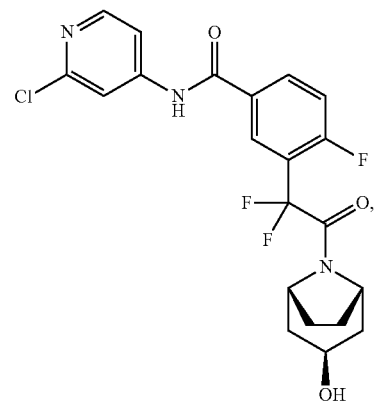
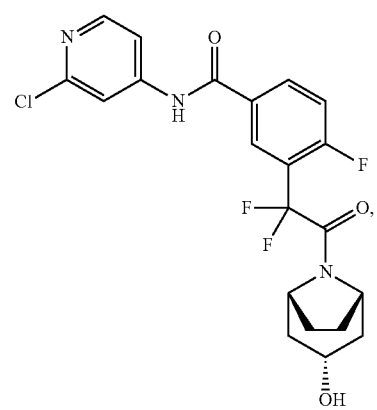
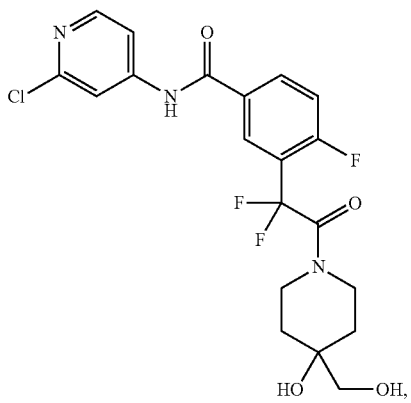
428
-continued
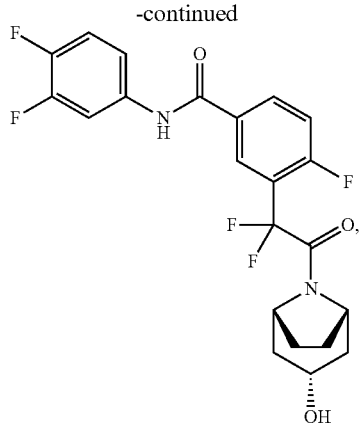
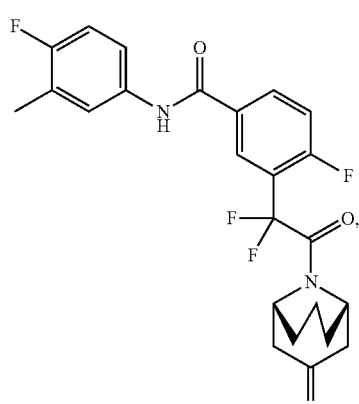
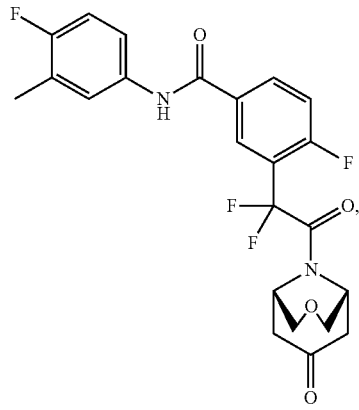
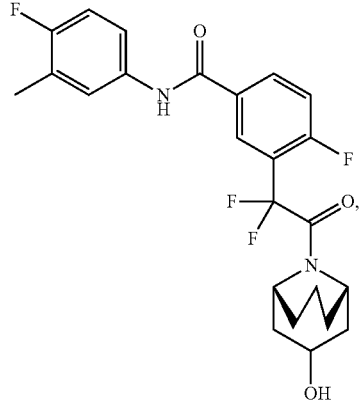

429
-continued
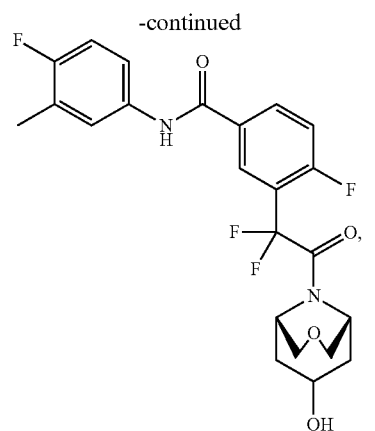
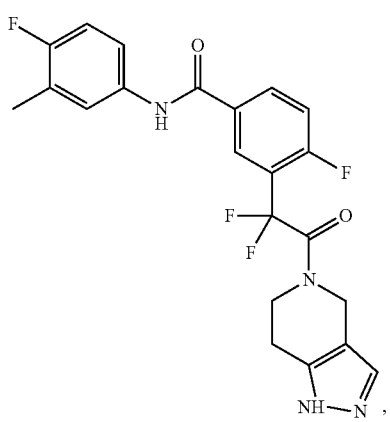
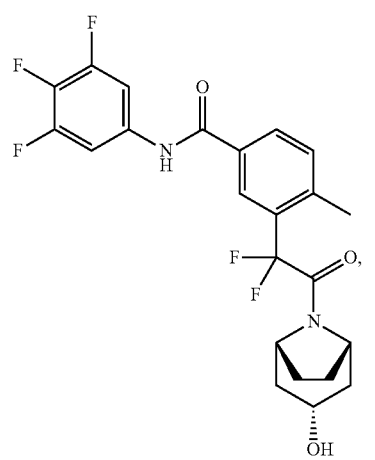
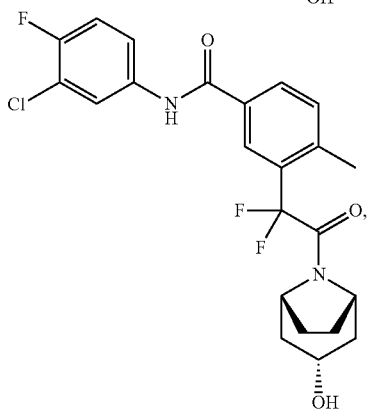
430
-continued
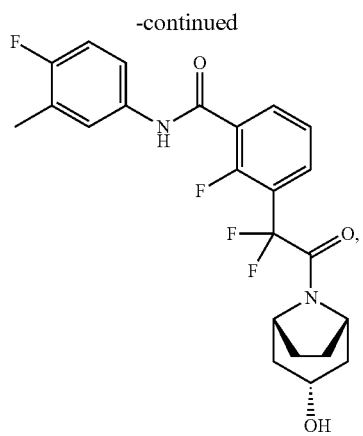
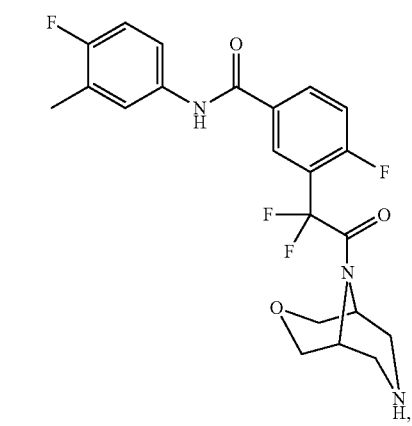
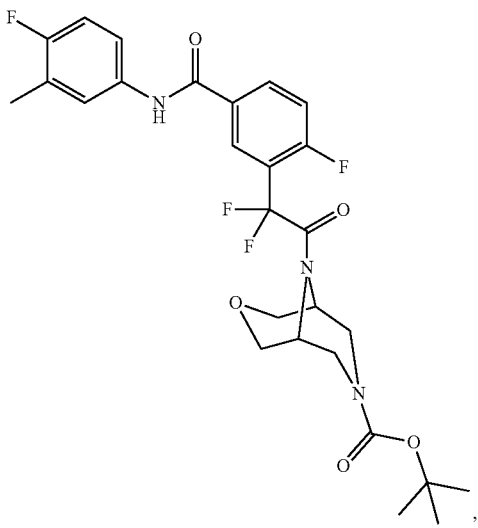

431
-continued
432
-continued
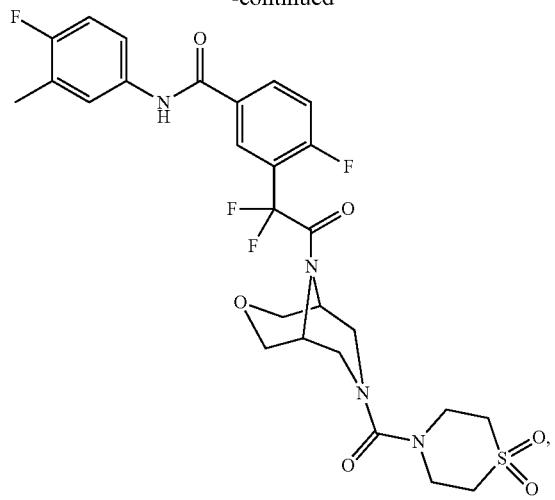
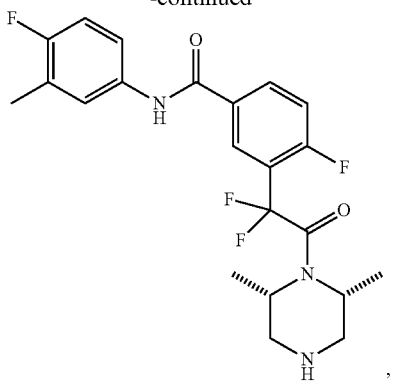
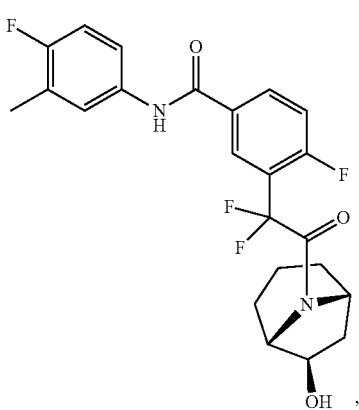
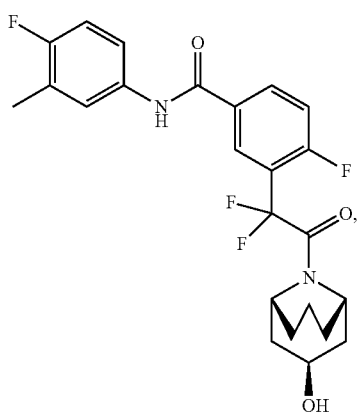
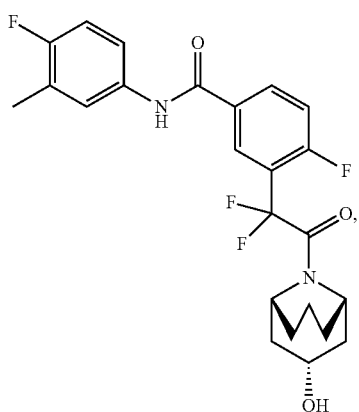

433
-continued
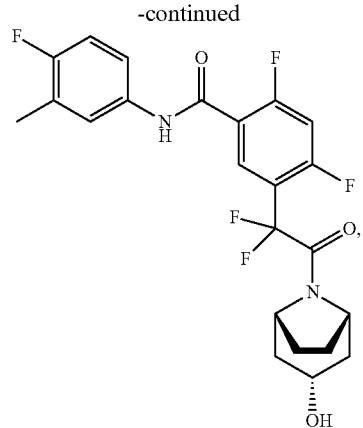
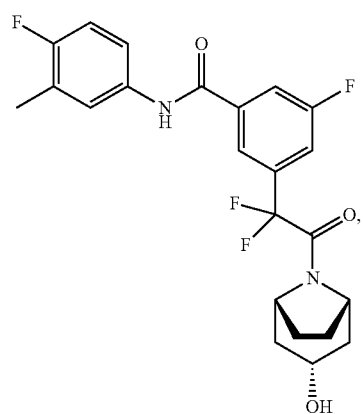
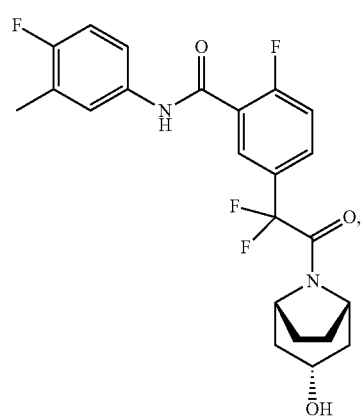
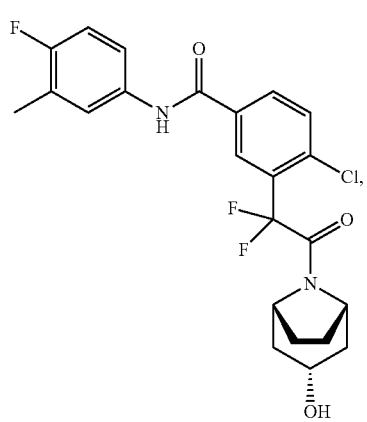
434
-continued
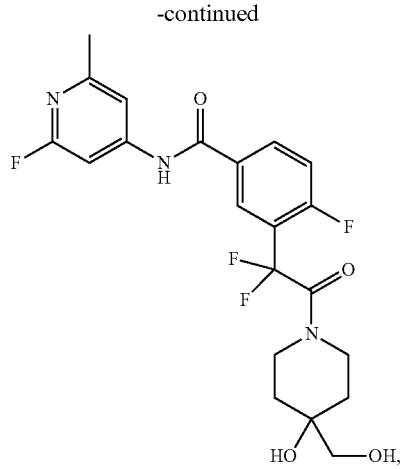
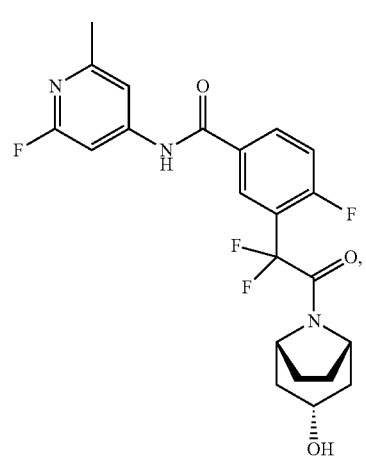
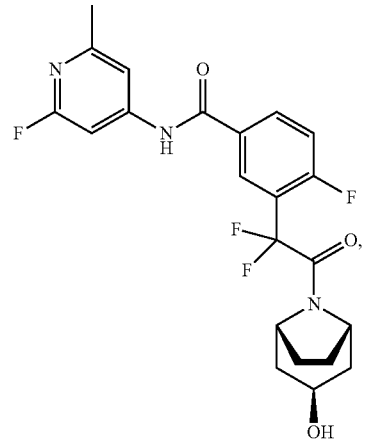

435
-continued
436
-continued
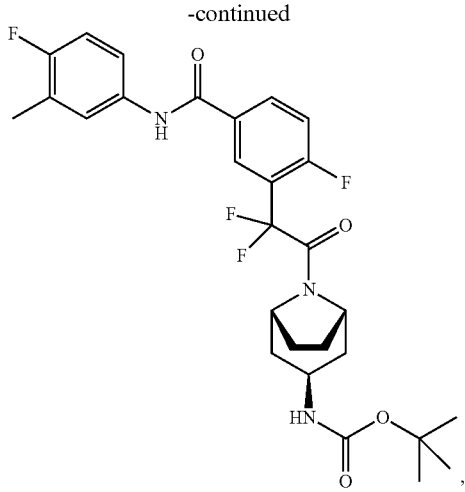
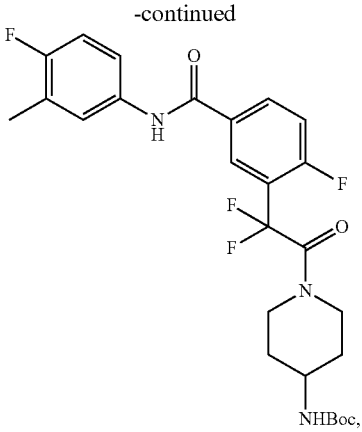
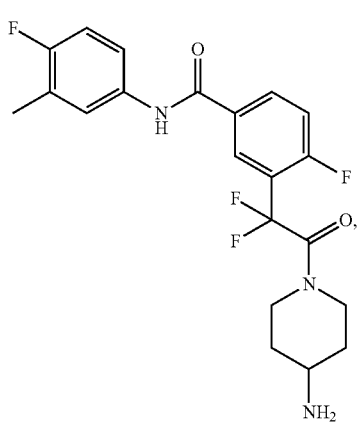
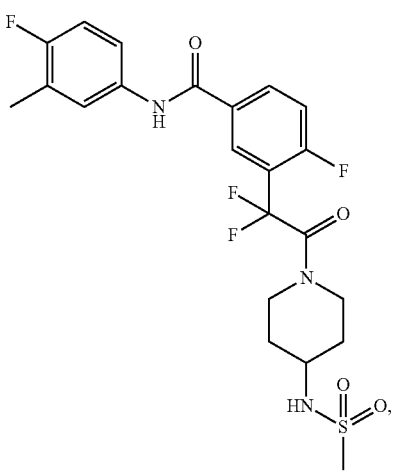

437
-continued
438
-continued
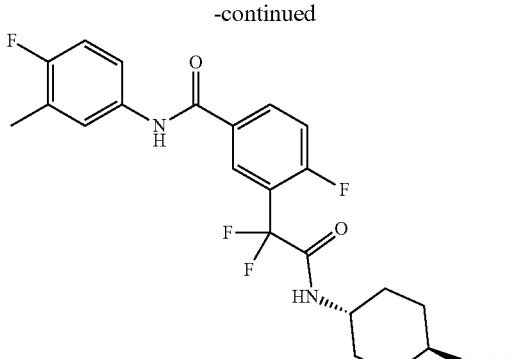
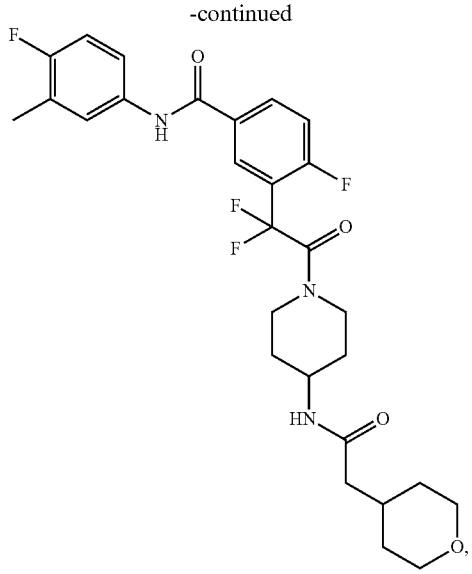
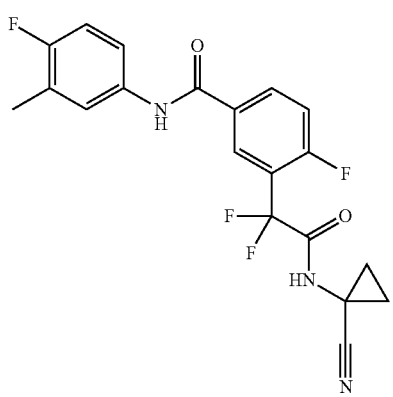
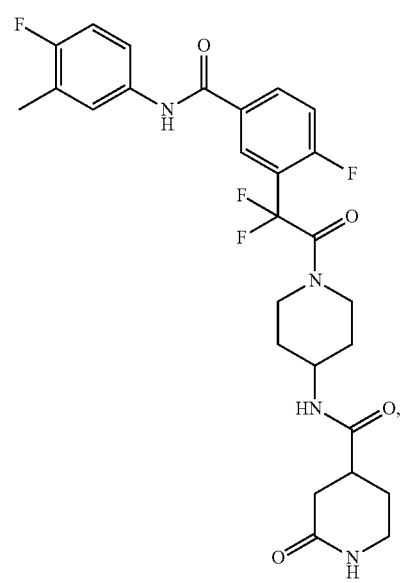
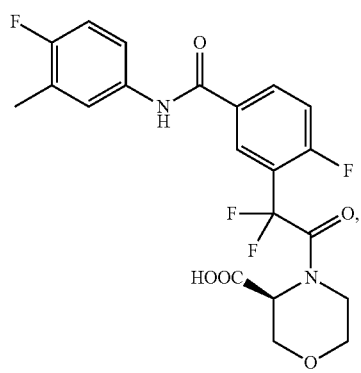
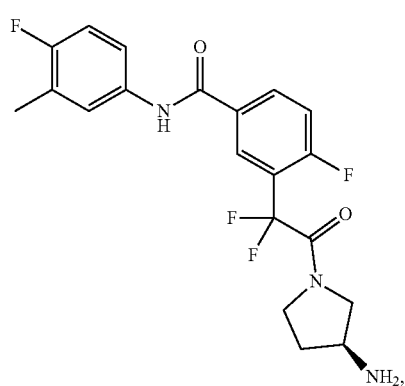

439
-continued
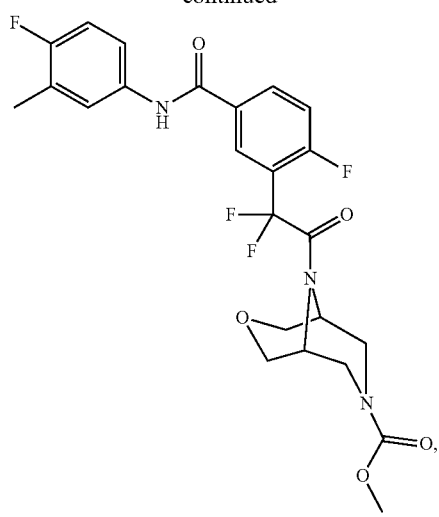
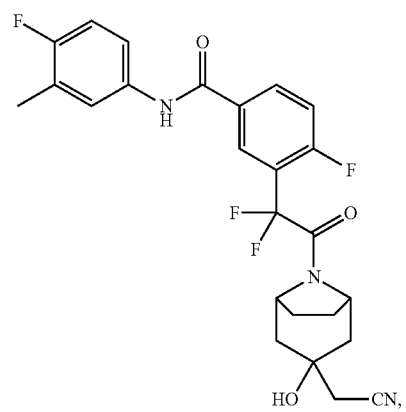
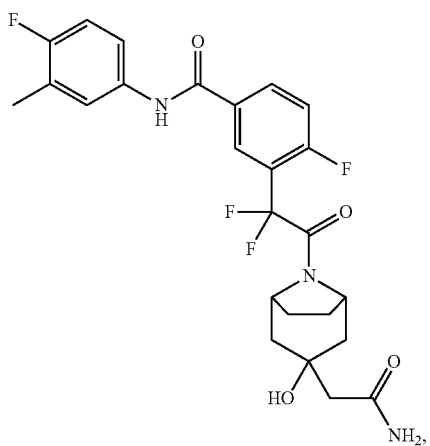
440
-continued
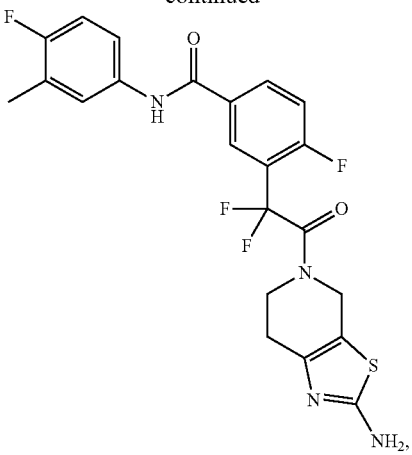
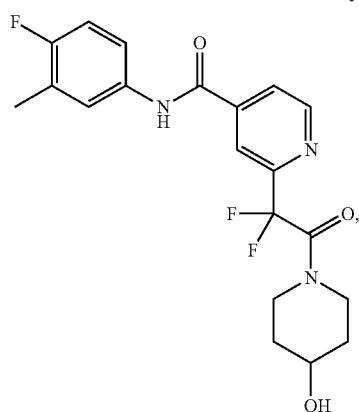
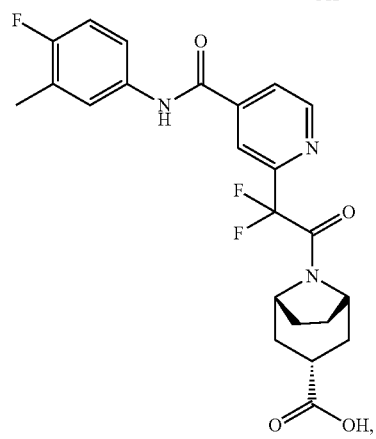
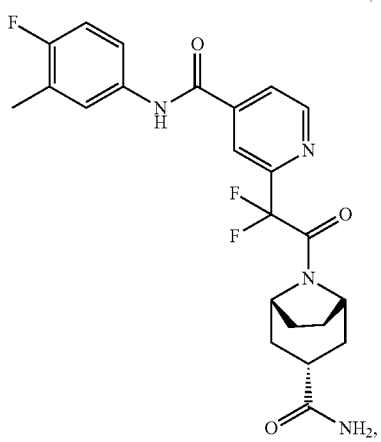

441
-continued
442
-continued
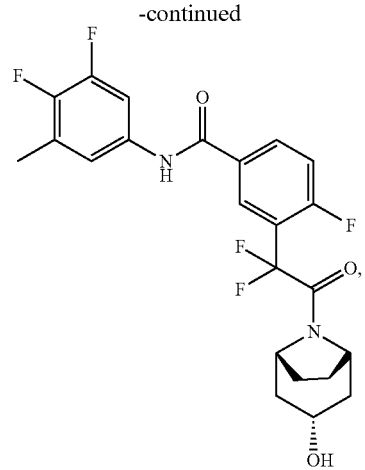
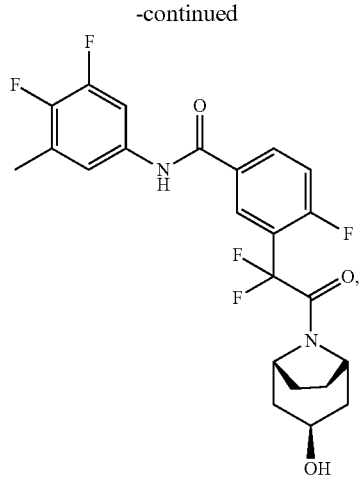
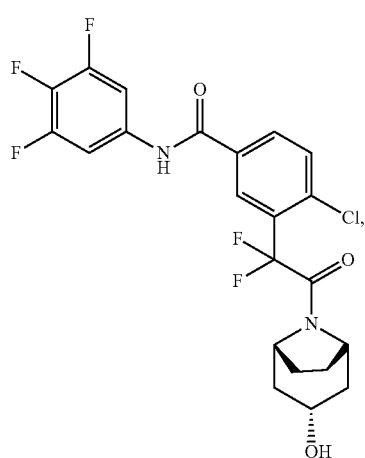
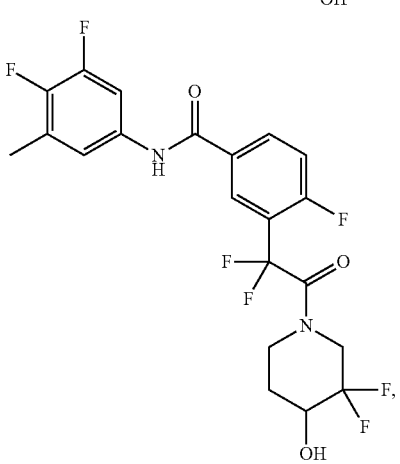
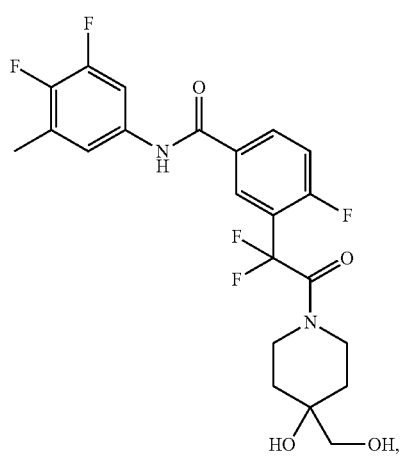
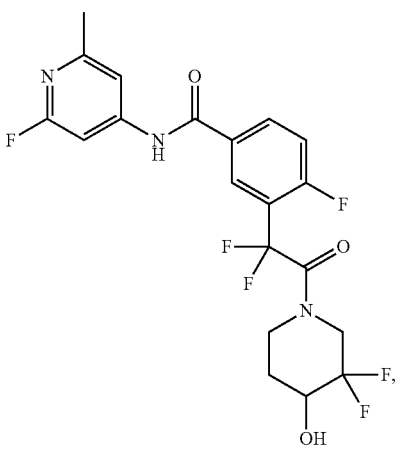
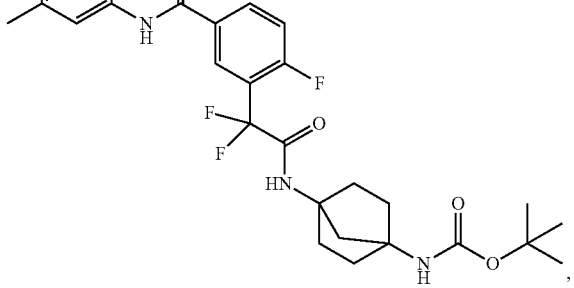

443
-continued
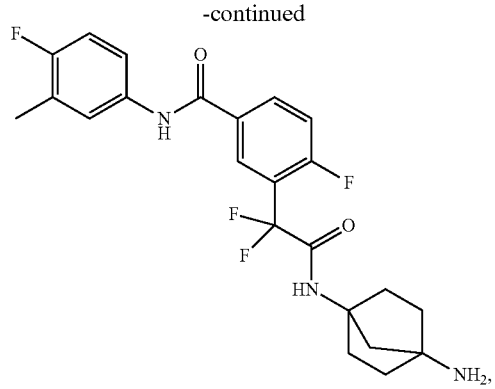
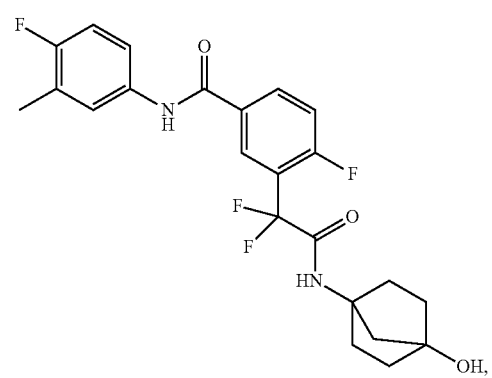
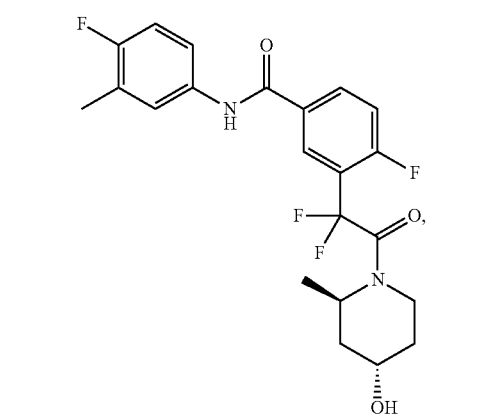
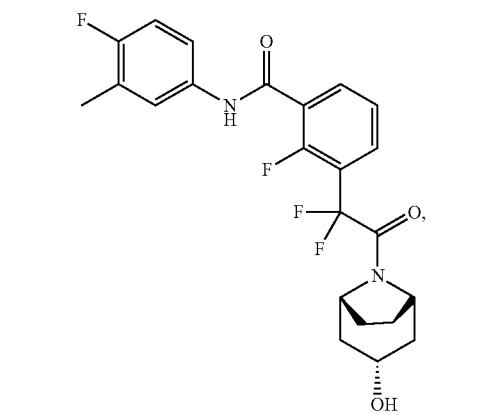
444
-continued
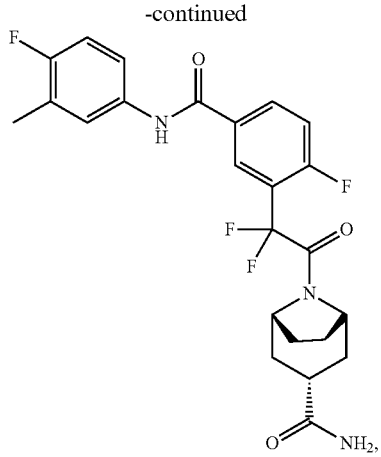
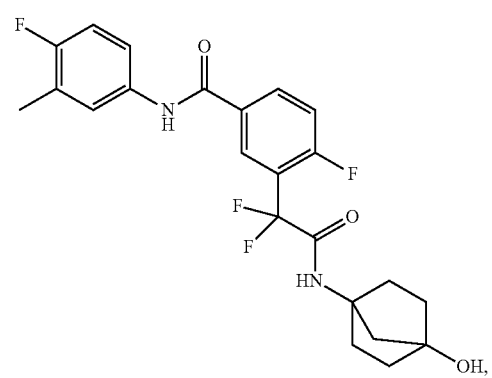
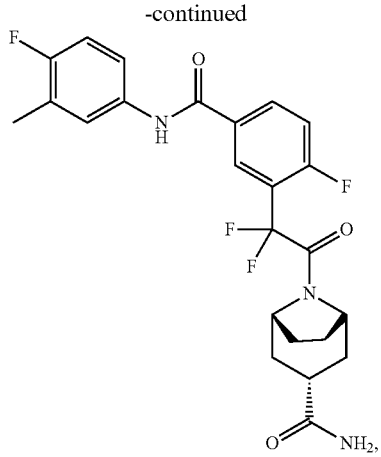

445
-continued
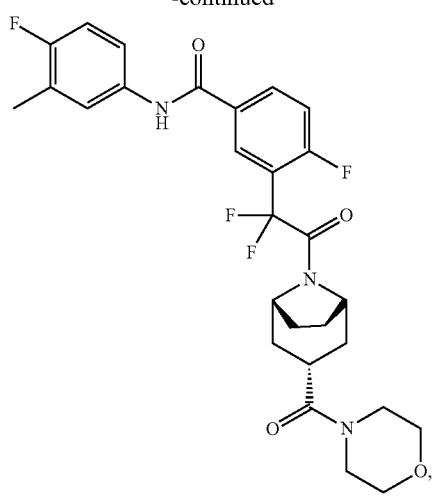
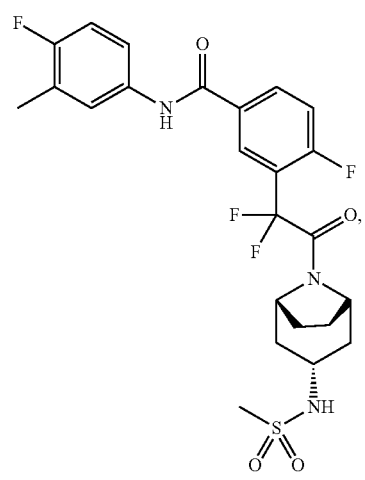
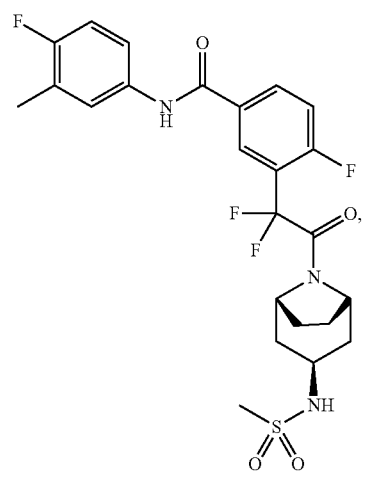
446
-continued
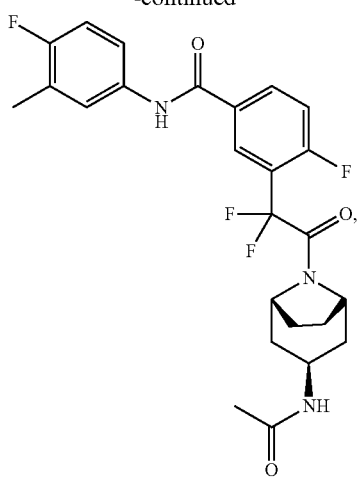
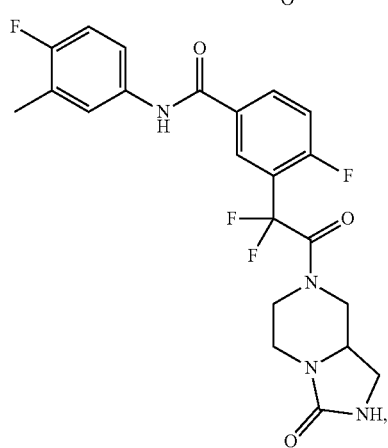
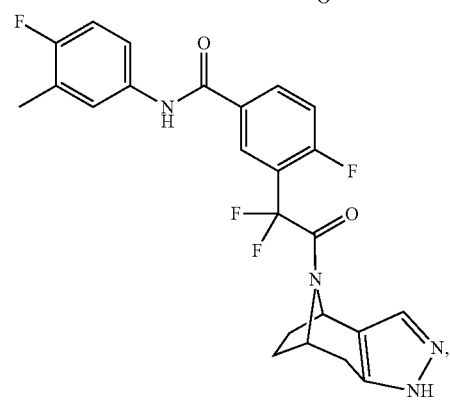
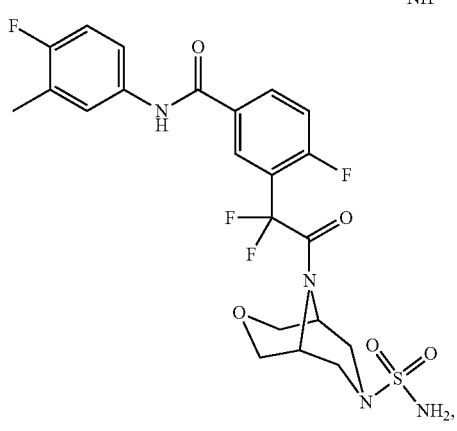

447
-continued
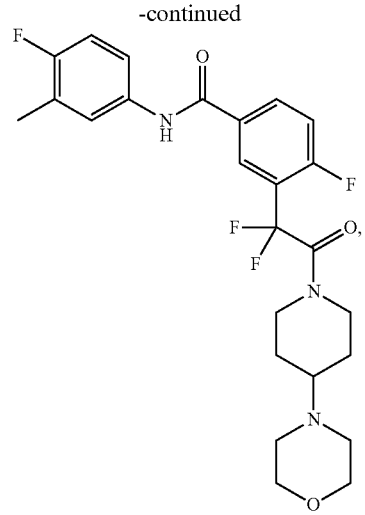
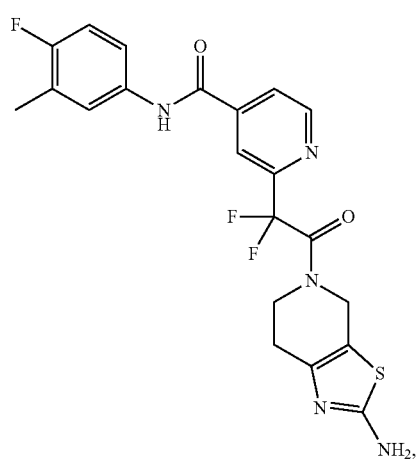
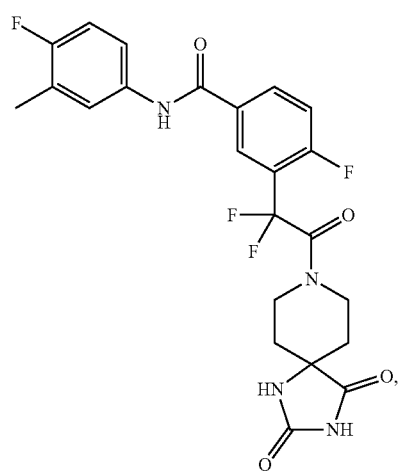
448
-continued
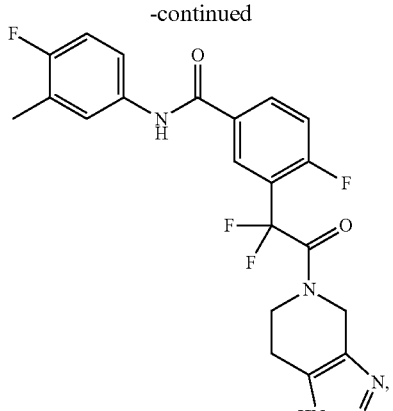
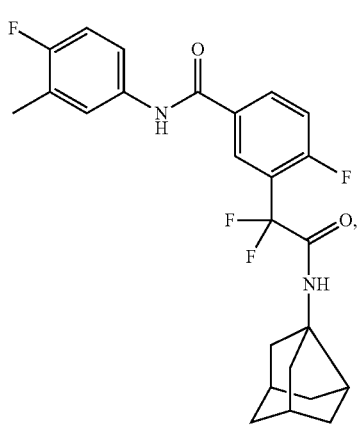
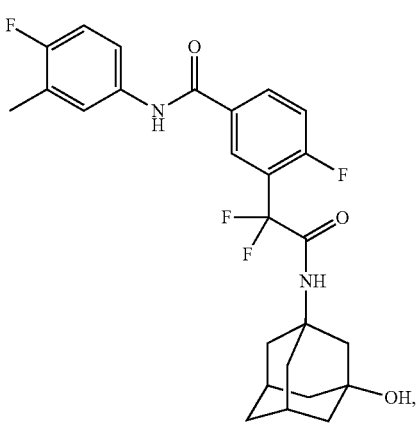
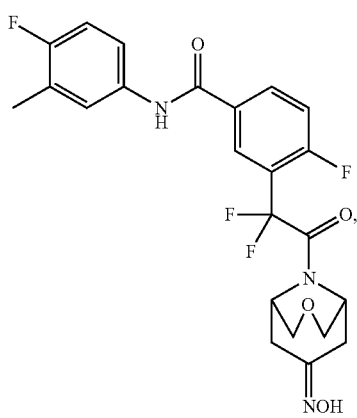

449
-continued
450
-continued
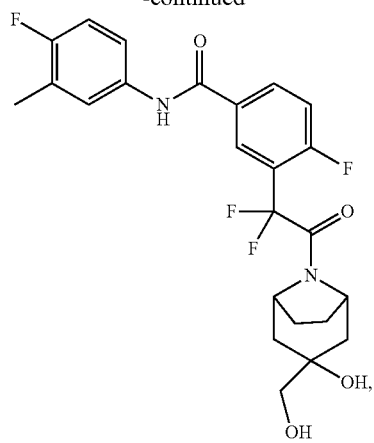
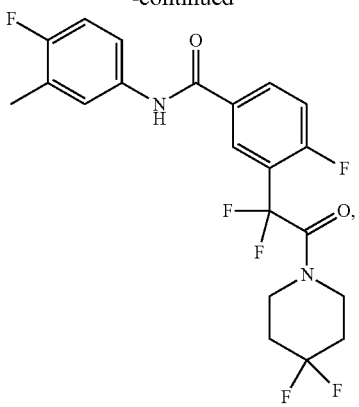
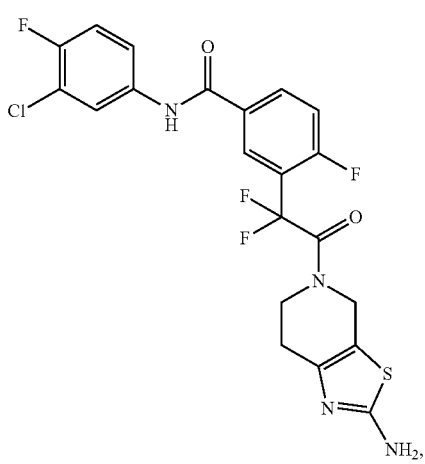
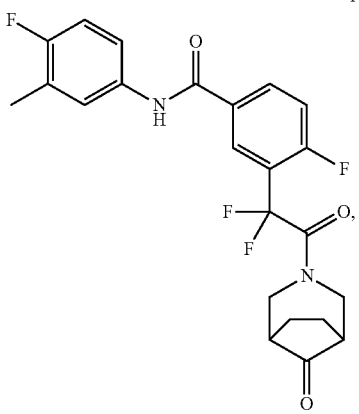
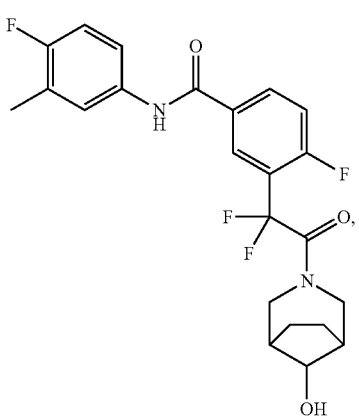

451
-continued
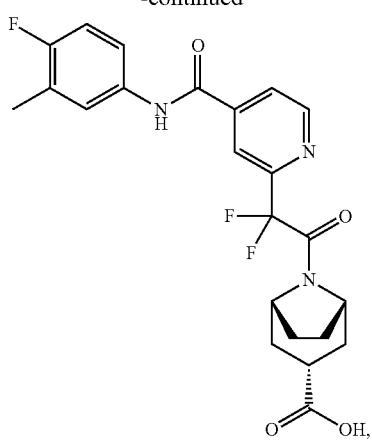
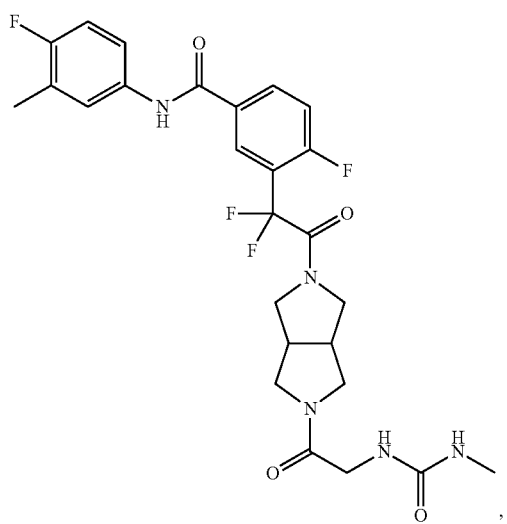
452
-continued
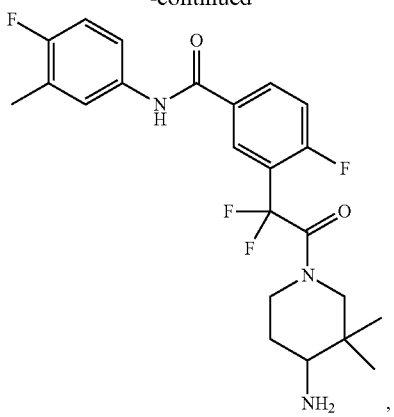
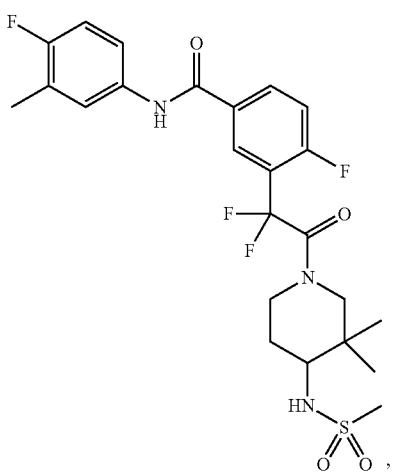
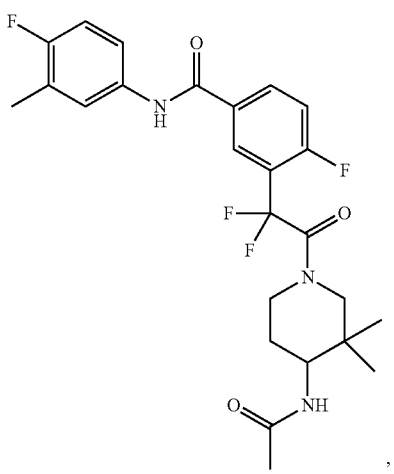

453
-continued
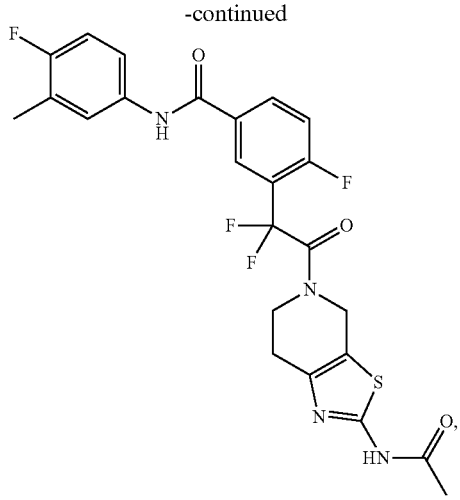
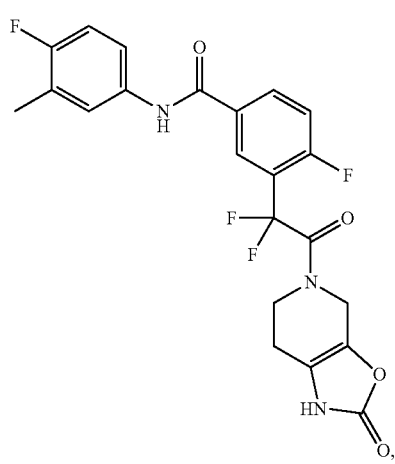
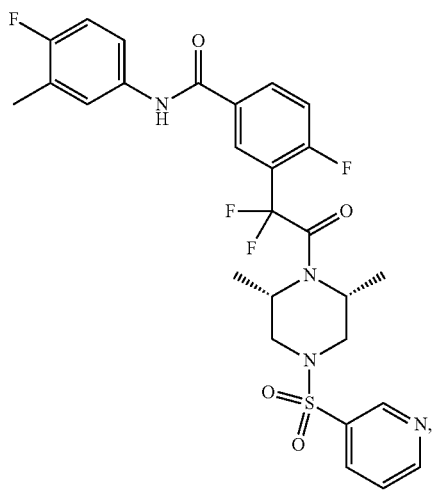
454
-continued
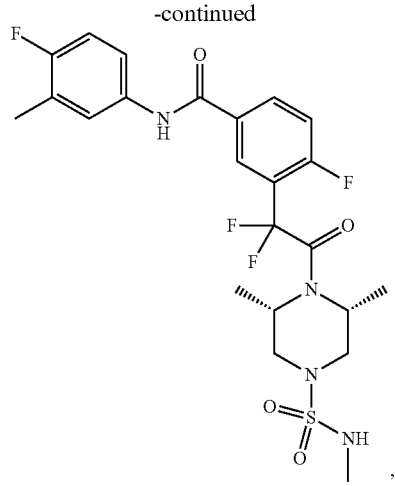
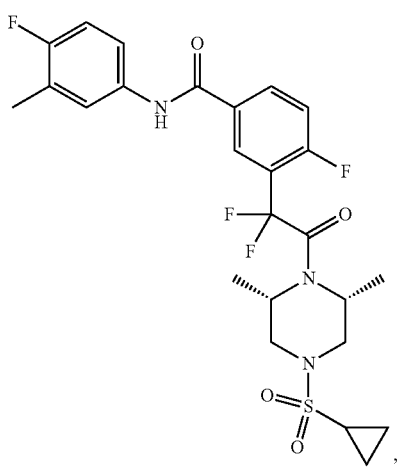
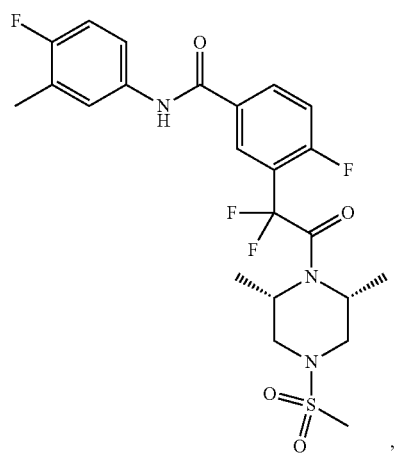

455
-continued
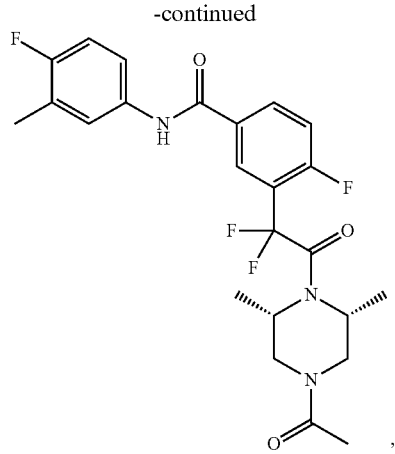
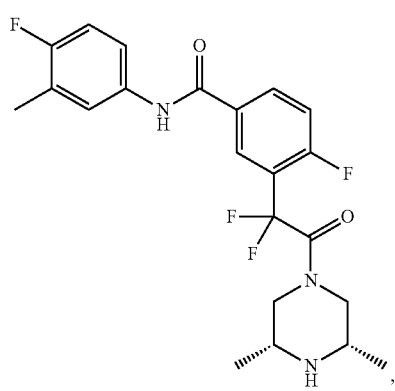
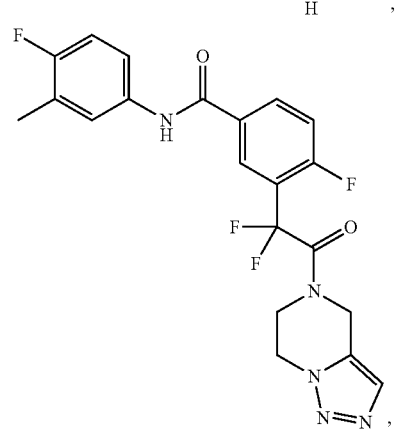
456
-continued
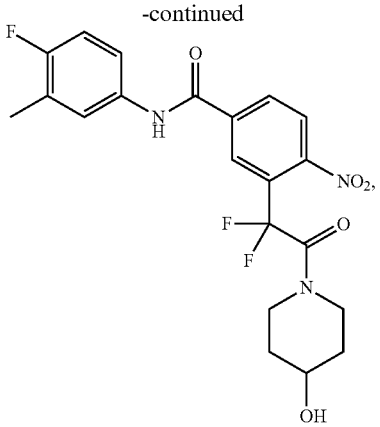
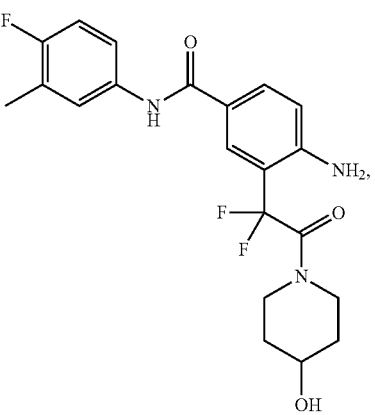
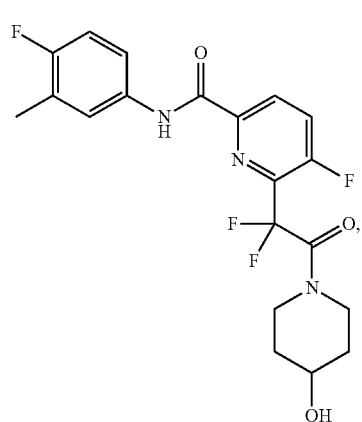

457
-continued
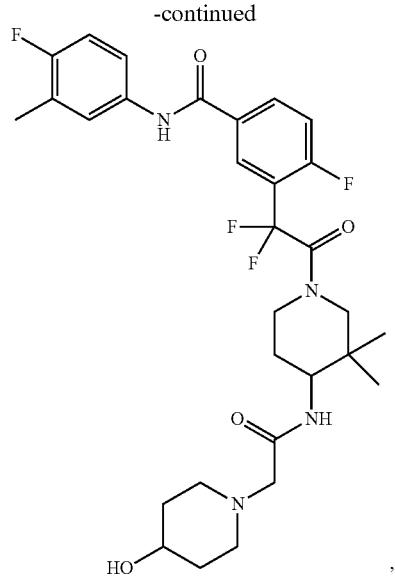
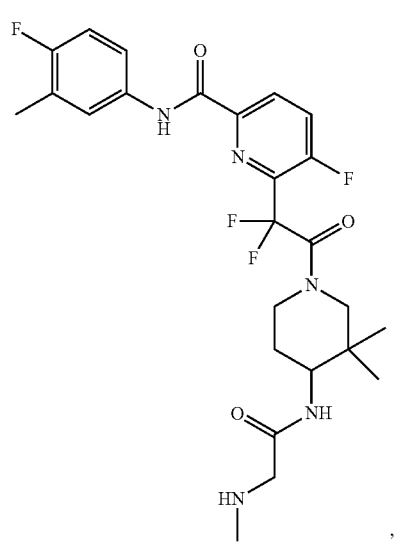
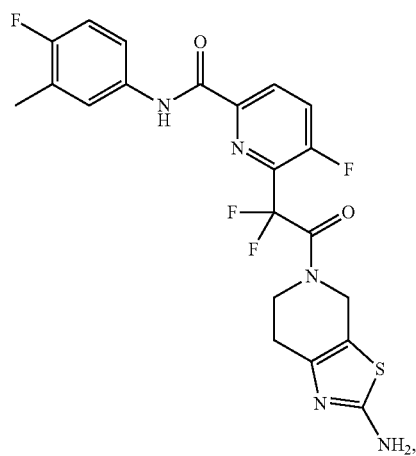 [SMILES: Cc1cc(NC(=O)c2ccc(F)c(C(F)(F)C(=O)N3CCc4nc(N)sc4C3)n2)ccc1F]
458
-continued
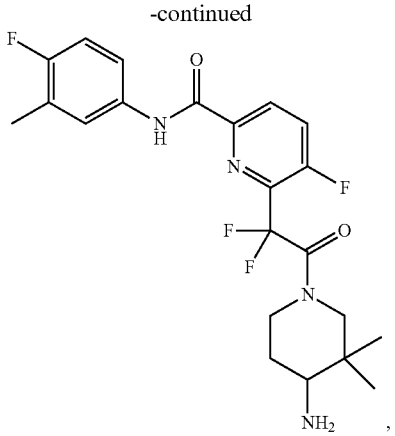
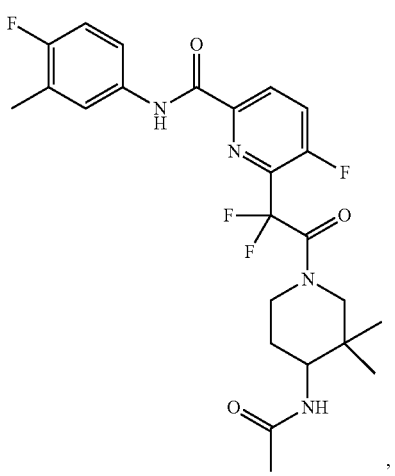
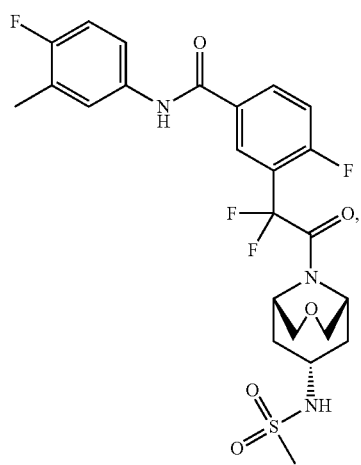

459
-continued
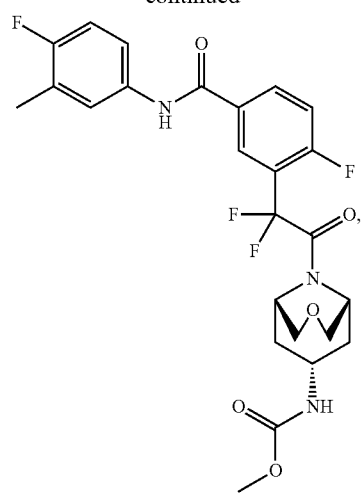
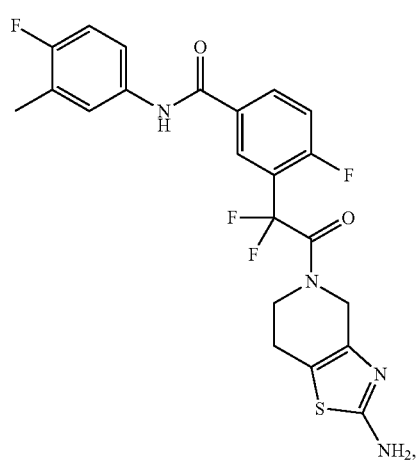
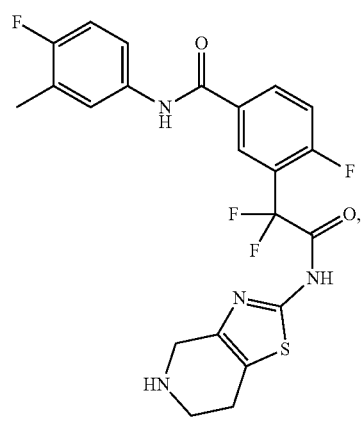
460
-continued
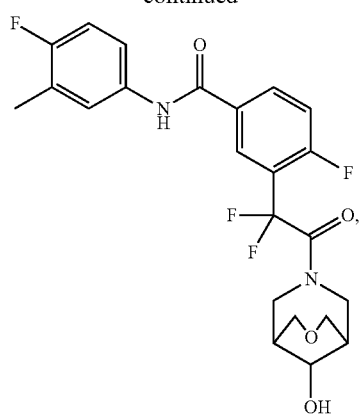
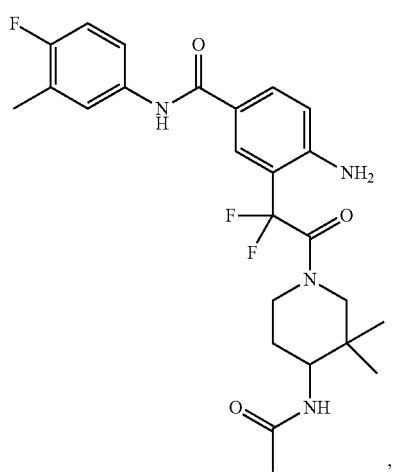
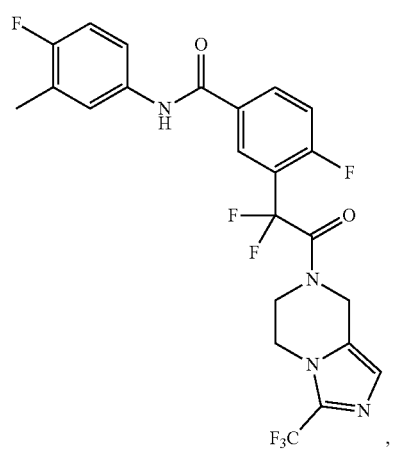

461
-continued
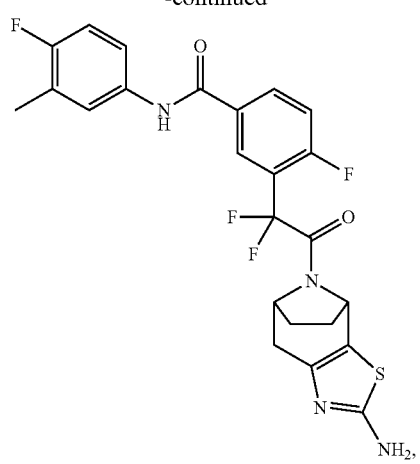
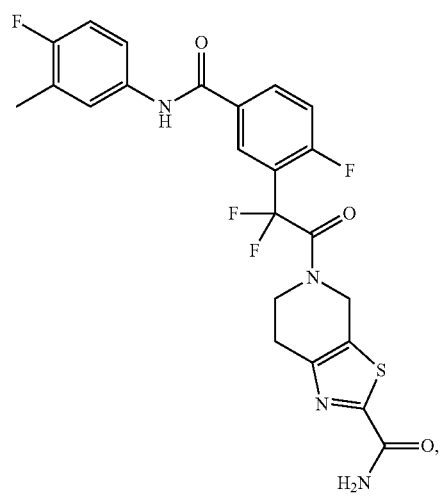
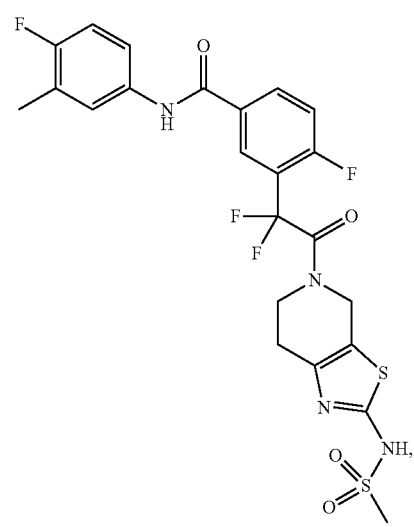 [SMILES: Cc1cc(NC(=O)c2ccc(F)c(C(F)(F)C(=O)N3CCc4nc(NS(C)(=O)=O)sc4C3)c2)ccc1F]
462
-continued
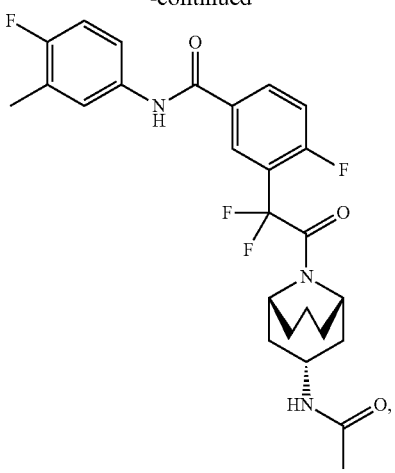
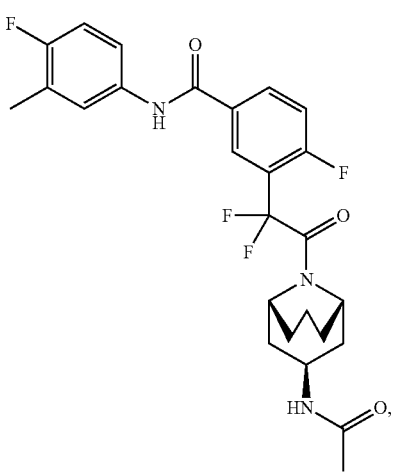
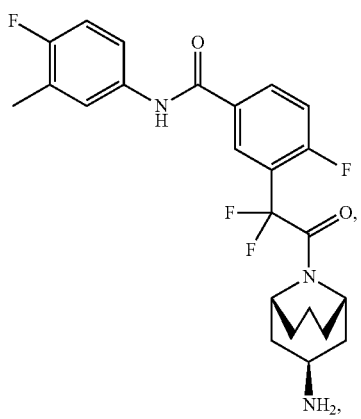

463
-continued
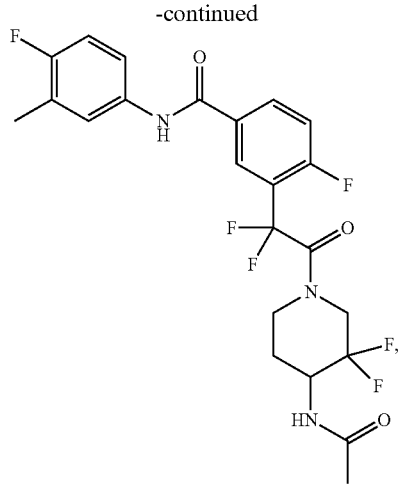
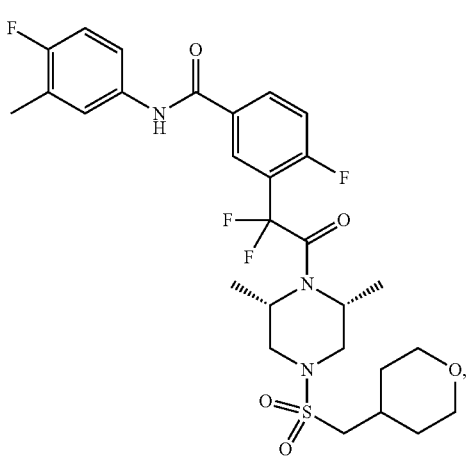
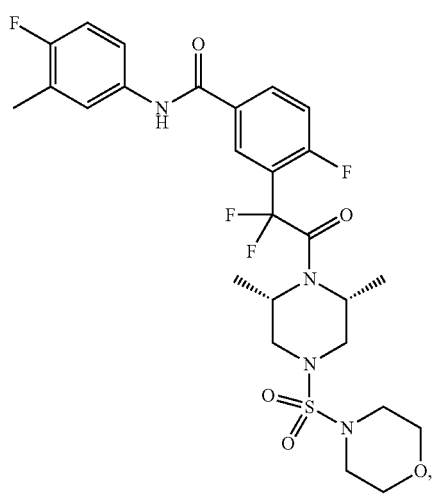
464
-continued
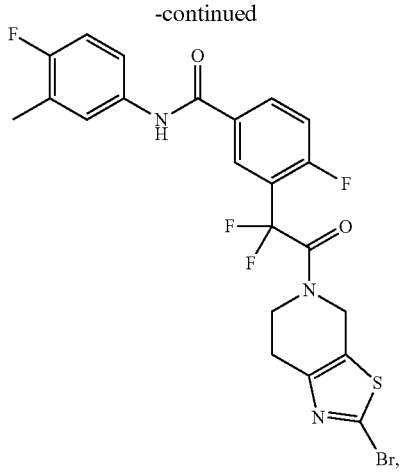
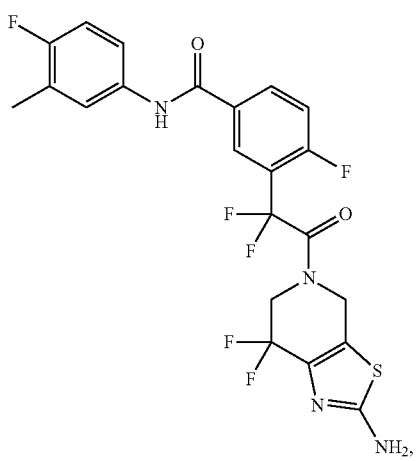
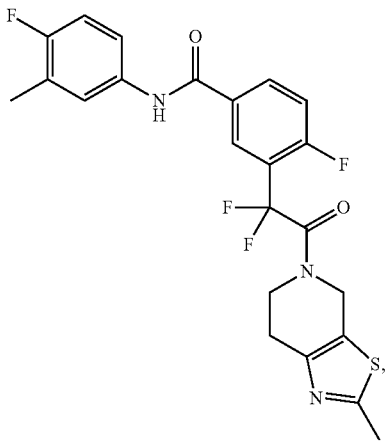

465
-continued
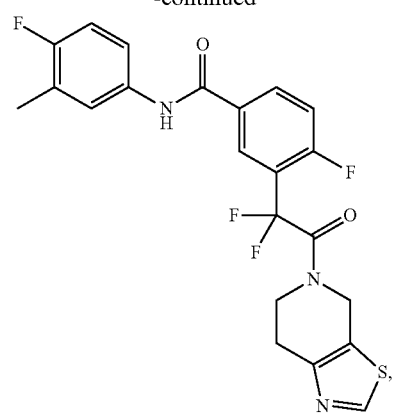
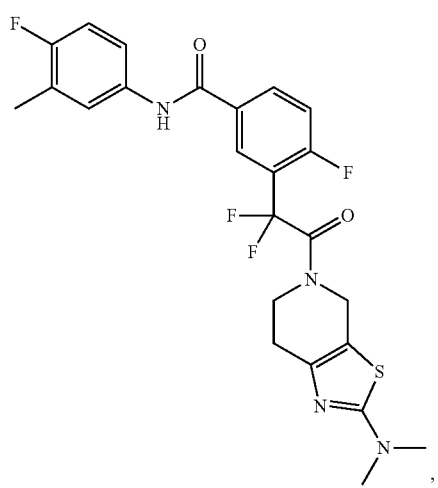
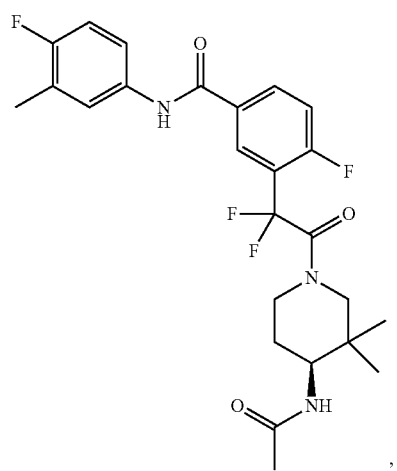
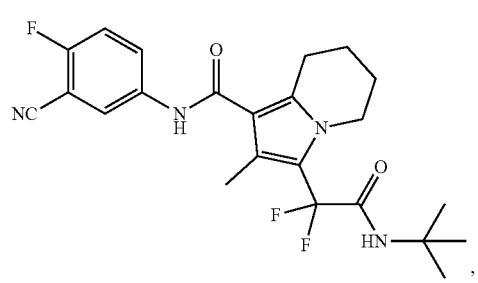
466
-continued
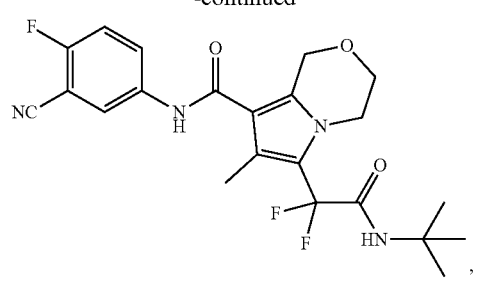
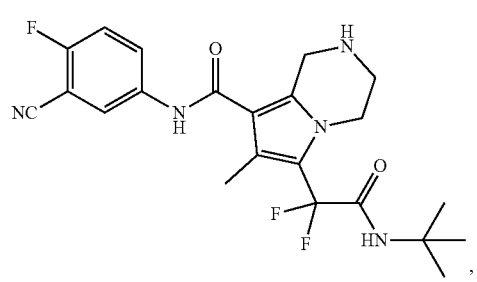
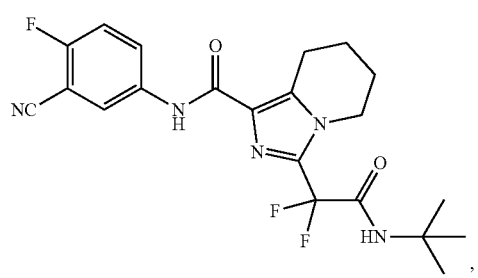
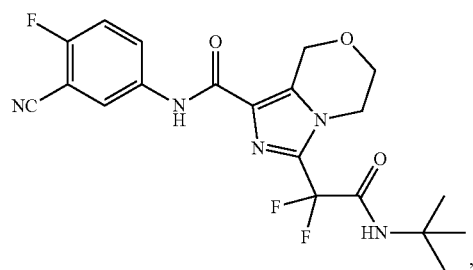
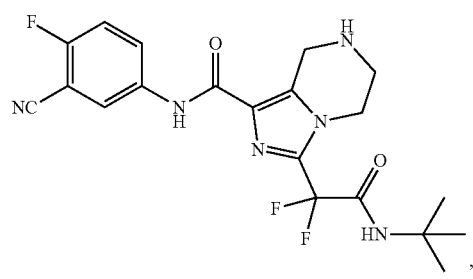

467
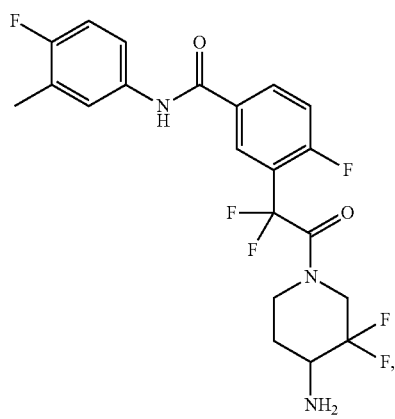
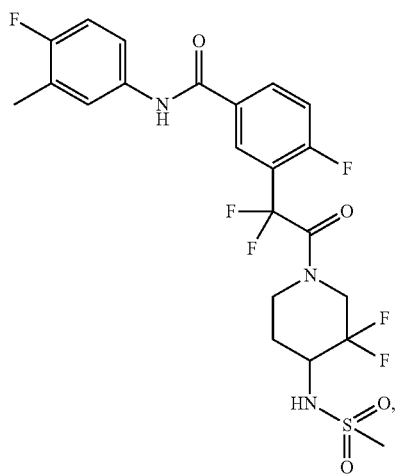
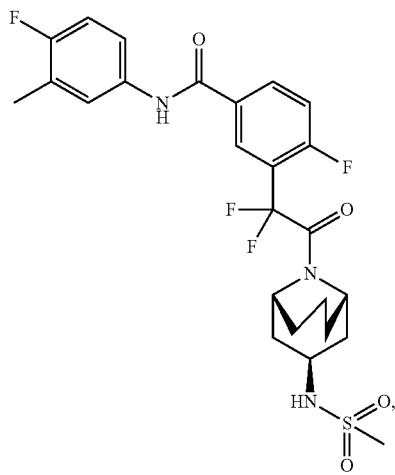
468
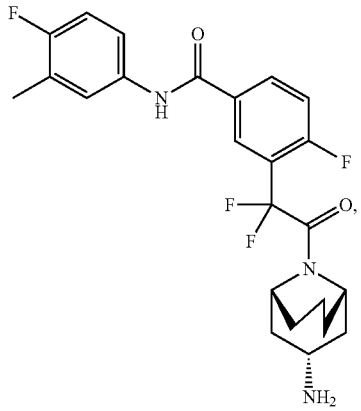
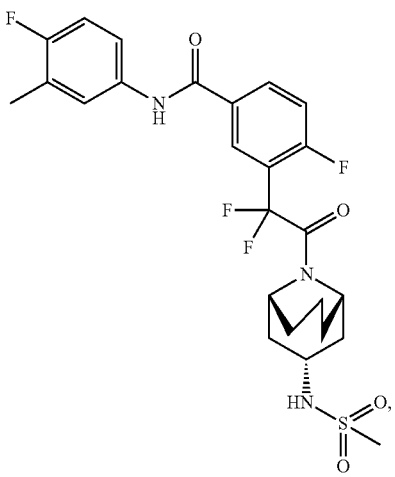
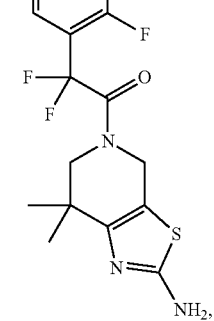

469
-continued

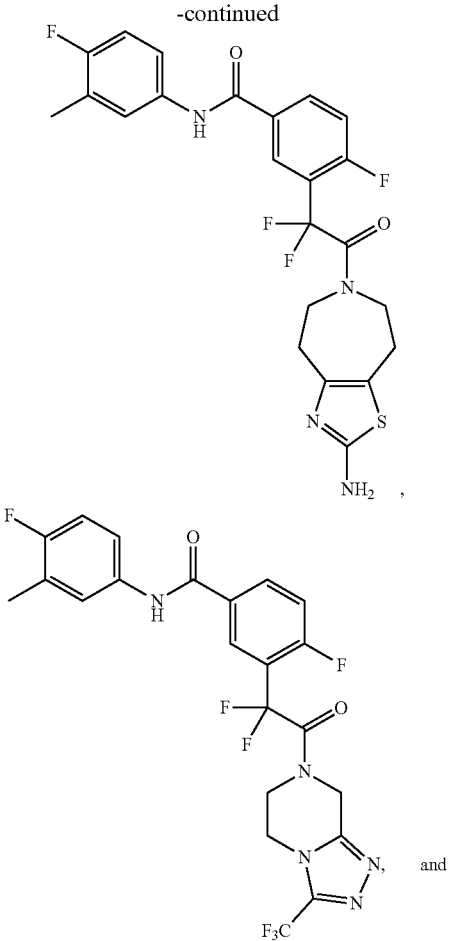

470
-continued

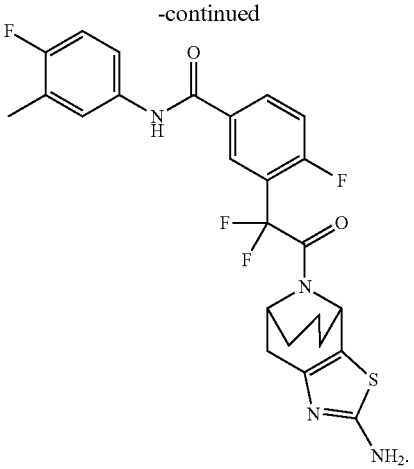

17. A pharmaceutical composition comprising a compound of claim 1, or a pharmaceutically acceptable salt, solvate, or stereoisomer thereof, and a pharmaceutically acceptable excipient.

18. A method of treating an infection that is a hepatitis B infection in a subject, comprising administering to the subject a compound of claim 1, or a pharmaceutically acceptable salt, solvate, or stereoisomer thereof.

* * * * *